United States Patent
Shiraishi et al.

(10) Patent No.: US 7,001,887 B2
(45) Date of Patent: Feb. 21, 2006

(54) PEPTIDE DERIVATIVES

(75) Inventors: Takuya Shiraishi, Shizuoka (JP); Shojiro Kadono, Shizuoka (JP); Masayuki Haramura, Shizuoka (JP); Haruhiko Sato, Shizuoka (JP); Toshiro Kozono, Shizuoka (JP); Takaki Koga, Shizuoka (JP); Akihisa Sakamoto, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 90 days.

(21) Appl. No.: 10/470,801
(22) PCT Filed: Feb. 4, 2002
(86) PCT No.: PCT/JP02/00883
§ 371 (c)(1), (2), (4) Date: Aug. 1, 2003
(87) PCT Pub. No.: WO02/062829
PCT Pub. Date: Aug. 15, 2002

(65) Prior Publication Data
US 2004/0087511 A1 May 6, 2004

(30) Foreign Application Priority Data
Feb. 2, 2001 (JP) .................................. 2001-027474

(51) Int. Cl.
C07K 5/06 (2006.01)
C07D 213/02 (2006.01)
C07D 235/04 (2006.01)
C07D 239/86 (2006.01)
C07D 401/04 (2006.01)

(52) U.S. Cl. .................. 514/19; 514/18; 514/258.1; 514/277; 514/311; 514/314; 514/345; 514/395; 530/331; 544/283; 546/113; 546/134; 546/250; 548/305.1

(58) Field of Classification Search .............. 514/18, 514/19, 258.1, 277, 311, 314, 395; 530/331; 544/283; 546/113, 134, 250; 548/305.1
See application file for complete search history.

(56) References Cited

U.S. PATENT DOCUMENTS

| 5,744,487 | A | 4/1998 | Ohshima et al. |
| 6,287,794 | B1 | 9/2001 | Safar et al. |
| 6,358,960 | B1 | 3/2002 | Senokuchi et al. |
| 6,365,617 | B1 * | 4/2002 | McComsey et al. ........ 514/403 |
| 6,472,393 | B1 | 10/2002 | Aliagas-Martin et al. |
| 6,586,405 | B1 * | 7/2003 | Semple et al. ............... 514/19 |

FOREIGN PATENT DOCUMENTS

| EP | 0669317 | 8/1995 |
| EP | 0921116 | 6/1999 |
| EP | 1078917 | 2/2001 |
| FR | 2791683 A1 * | 10/2000 |
| WO | WO 00/15658 | 3/2000 |
| WO | WO 00/30646 | 6/2000 |
| WO | WO 00/35886 | 6/2000 |
| WO | WO 00/41531 | 7/2000 |
| WO | WO 00/58346 | 10/2000 |

OTHER PUBLICATIONS

Banner, et al. *The Crystal Structure of the Complex of Blood Coagulation factor VIIa with Soluble Tissue Factor Nature*, vol. 380, No. 7 (Mar. 1996), pp. 41–46.

Banner, David. *The Factor VIIa/Tissue Factor Complex, Thrombosis and Haemostasis*, vol. 78, No. 1, (1997), pp. 512–515.

Böhm, Hans–Joachim. *LUDI: Rule–Based Automatic Design of New Substituents for Enzyme Inhibitor Leads, Journal of Computer–Aided Molecular Design*, vol. 6, (1992), pp. 593–606.

Dennis, et al. *Peptide Exosite Inhibitors of Factor VIIa as Anticoagulants, Nature*, vol. 404, (Mar. 2000), pp. 465–470.

Johnson, et al. *Crystallization and Preliminary X–Ray Analysis of Active Site–Inhibited Human Coagulation Factor VIIa (des–GIa), Journal of Structural Biology*, vol. 125, (1999), pp. 90–93.

(Continued)

Primary Examiner—Joseph K. McKane
Assistant Examiner—Susannah E. Lee
(74) Attorney, Agent, or Firm—Browdy and Neimark, P.L.L.C.

(57) ABSTRACT

A compound of Formula (1):

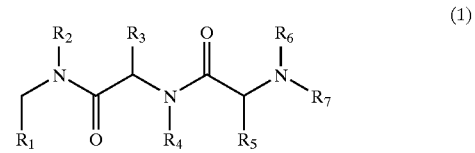

wherein
$R_1$ represents an amidinophenyl group, etc.;
$R_2$ represents a hydrogen atom, etc.;
$R_3$ represents a carbamoylalkyl group, etc.;
$R_4$ represents a hydrogen atom, etc.;
$R_5$ represents a benzyl group, etc.;
$R_6$ represents a hydrogen atom, etc.; and
$R_7$ represents an alkylsulfonyl group, etc.

A crystal of a complex between factor VIIa/human soluble tissue factor and a low-molecular weight reversible factor VIIa inhibitor. A medium carrying a part or all of structure coordinate data of a complex between human factor VIIa/human soluble tissue factor and a low-molecular weight reversible factor VIIa inhibitor, obtainable by X-ray crystal structure analysis of the crystal. A method for computationally designing a low-molecular weight reversible factor VIIa inhibitor using the coordinate data.

13 Claims, 3 Drawing Sheets

OTHER PUBLICATIONS

Kemball–Cook, et al. *Crystal Structure of Active Site–Inhibited Human Coagulation Factor VIIa (des–Gla)*, Journal of Structural Biology, vol. 127, (1999), pp. 213–223.

Kirchhofer, et al. *Activation of Blood Coagulation Factor VIIa with Cleaved Tissue Factor Extracellular Domain and Crystallization of the Active Complex*, PROTEINS, vol. 22, (1995), pp. 419–425.

MacKerell Jr. et al. "CHARMM: The Energy Function and its Parameterization." in *Encyclopedia of Computational Chemistry*. (1998), vol. 1 A–D., pp. 271–277. ISBN: 047196588x.w.set.

Pike, et al. *Structure of Human Factor VIIa and its Implications for the Triggering of Blood Coagulation*, Proc. Natl. Acad. Sci. USA, vol. 96, (Aug. 1999), pp. 8925–8930.

Zhang, et al. *Structure of Extracellular Tissue Factor Complexed with Factor VIIa Inhibited with a BPTI Mutant*, J. Mol. Biol., vol. 285, (1999), pp. 2089–2104.

* cited by examiner

PEPTIDE DERIVATIVES

TECHNICAL FIELD

The present invention relates to peptide derivatives having an inhibitory activity against blood coagulation factor VIIa.

BACKGROUND ART

Blood coagulation is a host defense mechanism provoked in response to vascular injury and/or foreign stimulation. Blood coagulation involves 15 factors including 12 proteinaceous coagulation factors in plasma, along with calcium ion, tissue factor and phospholipid (platelet-derived). This reaction is mediated by a cascade mechanism, in which a series of protease activations occurs successively on the membrane of platelets aggregated at a site of injury or damaged endothelial cells.

The blood coagulation cascade is divided into intrinsic and extrinsic pathways. It is called extrinsic blood coagulation when it occurs with the aid of tissue factor present in tissues, while it is called intrinsic blood coagulation when it occurs without the aid of tissue factor.

Intrinsic blood coagulation is initiated by the contact of blood coagulation factor XII in plasma with the surface of a negatively-charged solid phase or the like. Upon adsorption onto the surface, factor XII is converted through limited hydrolysis into activated factor XII (XIIa), an active protease. In turn, factor XIIa causes the limited hydrolysis of factor XI into activated factor XI (XIa), an active protease. After such a cascade of protease activations, the final protease thrombin causes the limited hydrolysis of fibrinogen into fibrin, leading to the completion of blood coagulation. In downstream reactions after the activation of factor XI, a number of coagulation factors are assembled into complexes to facilitate coagulation factor localization at a site of hemostasis and to ensure efficient activation reactions. Namely, a tenase complex is assembled from phospholipids, factor VIIIa, factor IXa, factor X and $Ca^{2+}$, while a prothrombinase complex is assembled from phospholipids, factor Va, factor Xa, prothrombin and $Ca^{2+}$, resulting in significant promotion of prothrombin activation.

Extrinsic blood coagulation is initiated by the formation of a complex between factor VIIa and tissue factor. This complex between factor VIIa and tissue factor will join the intrinsic pathway at the stage of factor X and IX activation.

In general, extrinsic blood coagulation is reported to be important for hypercoagulation and physiological coagulation under pathological conditions.

Examples of known anticoagulants include a thrombin inhibitor such as heparin, as well as warfarin. However, since a thrombin inhibitor acts on downstream reactions of the blood coagulation cascade and hence cannot control the consumption of coagulation factors that lead to thrombin generation upon excess inhibition of coagulation, such a thrombin inhibitor involves a problem of hemorrhage tendency in clinical use. Likewise, warfarin inhibits the production of many blood coagulation factors and also involves a problem of hemorrhage tendency in clinical use, as in the case of a thrombin inhibitor.

As mentioned above, factor VIIa is located upstream in the extrinsic pathway and hence an inhibitor against factor VIIa will not affect the intrinsic coagulation pathway. That is, such an inhibitor will be able to leave the resistance against hemorrhage. This suggests that a factor VIIa inhibitor is expected to reduce the hemorrhage tendency, a side effect of existing anticoagulants. Thus, a factor VIIa inhibitor is expected to be effective in preventing or treating pathological conditions associated with the extrinsic coagulation pathway, e.g., chronic thrombosis (more specifically, postoperative deep vein thrombosis, post-PTCA restenosis, DIC (disseminated intravascular coagulation), cardioembolic strokes, cardiac infarction and cerebral infarction).

To date, some compounds have been reported as factor VIIa inhibitors (see, e.g., WO00/41531, WO00/35886, WO99/41231, EP921116A, WO00/15658, WO00/30646, WO00/58346).

However, all of these compounds are insufficient to have an inhibitory activity against factor VIIa or a selective inhibitory activity against extrinsic blood coagulation; there is a need to develop an agent having an improved inhibitory activity or an improved selective inhibitory activity.

Recent studies on enzyme inhibitors have tended to employ computational procedures, in which a three-dimensional enzyme model based on X-ray crystal structure analysis or the like is displayed on the screen of a computer to design a candidate compound which may have an inhibitory activity or to perform computer-aided virtual screening. Factor VIIa (hereinafter also referred to as "FVIIa") has also been studied by X-ray structure analysis to determine its three-dimensional structure in free form, in complex with soluble tissue factor (this complex being hereinafter also referred to as "factor VIIa/soluble tissue factor" or "FVIIa/sTF), and in complex with a protein inhibitor (Nature, 380, 41–46, 1996; J. Mol. Biol, 285, 2089–2104, 1999; Proc Natl Acad Sci USA., 96, 8925–8930; J Struct Biol., 127, 213–223, 1999; Nature, 404, 465–470, 2000).

However, computational virtual docking techniques result in inaccurate estimation at present (Guidebook on Molecular Modeling Drug Design, 129–133, 1996, ACADEMIC PRESS); on the other hand, an enzyme molecule frequently undergoes an inhibitor brinding-induced conformational change called induced fit (Guidebook on Molecular Modeling Drug Design, 133–134, 1996, ACADEMIC PRESS). For computer-aided design of inhibitors, it is therefore most desirable to perform X-ray structure analysis on each inhibitor or its structurally similar inhibitor in complex with an enzyme to clarify the details of the binding mode between inhibitor and enzyme at the atomic level. In all previously reported crystals containing factor VIIa, however, irreversible inhibitors or protein inhibitors occupy the active sites of factor VIIa, which may be used as inhibitor-binding sites. Such crystals cannot be used for X-ray crystal structure analysis of a complex between factor VIIa and a low-molecular weight reversible inhibitor (e.g., having a molecular weight less than 1000). Generally, protein crystallization usually requires high purity. A problem of protease cleavage often arises in purifying such high-purity proteins (Crystallization of Nucleic Acids and Proteins, A Practical Approach, 34, 1992, IRL PRESS). In particular, a problem of self-cleavage arises in purifying and crystallizing a protease such as factor VIIa. For this reason, an irreversible inhibitor is often used in purification and crystallization because once binding occurs, the irreversible inhibitor will not be released from the protease and allows complete prevention of self-cleavage during purification and crystallization. However, in the case of a complex with a low-molecular weight reversible inhibitor, it involves technical difficulties because there is no guarantee that self-cleavage is completely prevented during crystallization. Indeed, there has been no report showing the crystallization or three-dimensional structure of a complex between factor VIIa and a low-molecular weight reversible factor VIIa inhibitor.

DISCLOSURE OF THE INVENTION

An object of the present invention is to provide a peptide derivative useful as a medicament, which has an inhibitory activity against blood coagulation factor VIIa or which has an excellent selective inhibitory effect on extrinsic blood coagulation.

Another object of the present invention is to provide a crystal which can be used for X-ray crystal analysis to clarify the three-dimensional structure of a complex between factor VIIa/soluble tissue factor and a low-molecular weight reversible factor VIIa inhibitor, as well as a method for preparing the crystal. Yet another object of the present invention is to provide a method for designing a novel low-molecular weight reversible factor VIIa inhibitor having an excellent specific or selective inhibitory activity for factor VIIa by using three-dimensional structure information of the complex crystal, as well as a low-molecular weight reversible factor VIIa inhibitor designed by the method.

As a result of extensive and intensive efforts, the inventors of the present invention found that a peptide derivative of Formula (1) had an inhibitory activity against factor VIIa or a selective inhibitory effect on extrinsic blood coagulation, which led to the completion of the invention.

Namely, the present invention provides a compound of Formula (1):

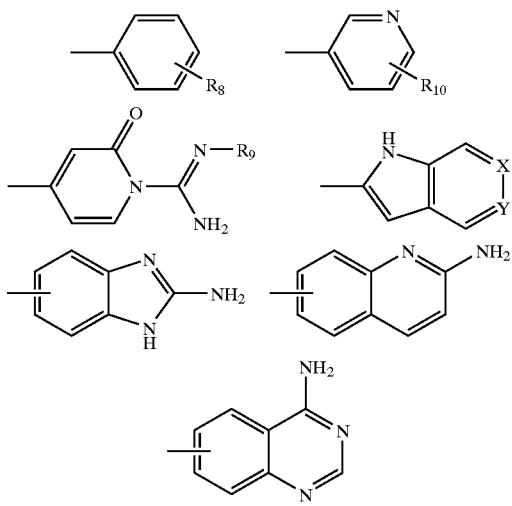

(1)

wherein $R_1$ represents a group selected from the following formulae:

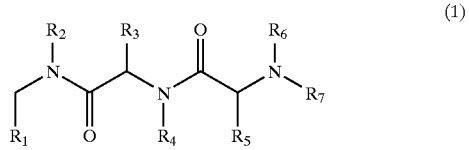

[wherein $R_8$ represents an amino group, an aminomethyl group or

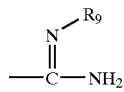

(wherein $R_9$ represents a hydrogen atom, an amino group, a hydroxy group, an acyl group or an alkoxycarbonyl group having an optionally substituted linear or branched $C_1$–$C_6$ alkyl as its alkyl moiety, $R_{10}$ represents an amino group, one of X and Y represents =CH— and the other represents =N—)];

$R_2$ represents a hydrogen atom or a linear or branched $C_1$–$C_6$ alkyl group;

$R_3$ represents:

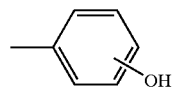

—(CH$_2$)$_m$—R$_{11}$

[wherein m represents an integer of 1 to 6, and $R_{11}$ represents:

—CONH$_2$,

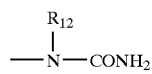

(wherein $R_{12}$ represents a hydrogen atom or a linear or branched $C_1$–$C_3$ alkyl group) or

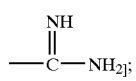

$R_4$ represents a hydrogen atom or a linear or branched $C_1$–$C_6$ alkyl group;

$R_5$ represents a linear or branched $C_1$–$C_6$ alkyl group or —CH$_2$—R$_{13}$ (wherein $R_{13}$ represents an optionally substituted aryl group or an optionally substituted heterocyclic group);

$R_6$ represents a hydrogen atom or a linear or branched $C_1$–$C_6$ alkyl group; and $R_7$ represents an optionally substituted linear or branched $C_1$–$C_6$ alkyl group or —SO$_2$—R$_{14}$ (wherein $R_{14}$ represents an optionally substituted linear or branched $C_1$–$C_8$ alkyl group)

or a tautomer or enantiomer of the compound, or a hydrate or pharmaceutically acceptable salt thereof.

The present invention also provides a pharmaceutical composition comprising a compound of Formula (1). Further, the present invention provides an antithrombotic agent comprising the compound. Furthermore, the present invention provides a blood coagulation factor VIIa inhibitor comprising the compound.

In addition, the present invention provides a crystal of a complex between human factor VIIa/human soluble tissue factor and a low-molecular weight reversible factor VIIa inhibitor. In one embodiment, the low-molecular weight reversible factor VIIa inhibitor is a compound of Formula (1) (wherein each symbol is as defined above).

Further, the present invention provides a method for preparing a crystal of a complex between human factor VIIa/human soluble tissue factor and a low-molecular weight reversible factor VIIa inhibitor, which comprises the following steps (i) to (iii):

(i) preparing human factor VIIa/human soluble tissue factor, which is co-crystallizable with the low-molecular weight reversible factor VIIa inhibitor;

(ii) preparing a concentrated sample for crystallization to add the low-molecular weight reversible factor VIIa inhibitor, and (iii) obtaining the crystal of the complex between human factor VIIa/human soluble tissue factor and the low-molecular weight reversible factor VIIa inhibitor from the concentrated sample for crystallization prepared in (ii) to add a seed crystal of a complex between a low-molecular weight irreversible or reverdible factor VIIa inhibitor and human factor VIIa/human soluble tissue factor. In one embodiment, the low-molecular weight reversible factor VIIa inhibitor is a compound of Formula (1) (wherein each symbol is as defined above).

In addition, the present invention provides a medium carrying a part or all of structure coordinate data of a complex between human factor VIIa/human soluble tissue factor and a low-molecular weight reversible factor VIIa inhibitor, wherein said data are obtainable by performing X-ray crystal structure analysis on the above crystal prepared for the complex between human factor VIIa/human soluble tissue factor and the low-molecular weight reversible factor VIIa inhibitor.

Further, the present invention provides a method for computationally designing a low-molecular weight reversible factor VIIa inhibitor using the above coordinate data. In one embodiment, the low-molecular weight reversible factor VIIa inhibitor is designed to have a substituent capable of interacting with at least one of Asp60 side chain, Tyr94 side chain and Thr98 main chain of the human factor VIIa H chain. In another embodiment, the low-molecular weight reversible factor VIIa inhibitor is designed to have a substituent capable of interacting with Lys192 side chain of the human factor VIIa H chain. In yet another embodiment, the low-molecular weight reversible factor VIIa inhibitor is designed to have a substituent capable of interacting with at least one of Val170E, Gly170F, Asp170G, Ser170H, Pro170I and Gln217 of the human factor VIIa H chain. In yet another embodiment, the low-molecular weight reversible factor VIIa inhibitor is designed to have a substituent capable of interacting with the S4 subsite of the human factor VIIa H chain through a hole extending from the S4 site to the S4 subsite.

Furthermore, the present invention provides a low-molecular weight reversible factor VIIa inhibitor designed by the above method. In one embodiment, the low-molecular weight reversible factor VIIa inhibitor comprises any one of the partial structures shown in the following Class [A-1] or [A-2] as a partial structure capable of interacting with the S2 site of human factor VIIa:

Class [A-1]:

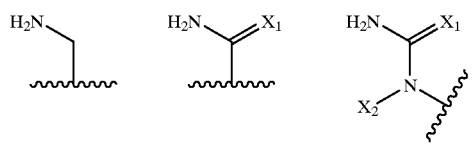

(wherein $X_1$ represents O or NH, and $X_2$ represents a hydrogen atom or a methyl group) or Class [A-2]:

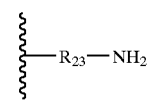

(wherein $R_{23}$ represents a 6 or 5-membered aromatic ring containing a heteroatom(s)).

In another embodiment, the low-molecular weight reversible factor VIIa inhibitor comprises any one of the partial structures shown in the following Class [B-1], [B-2], [B-3] or [B-4] as a partial structure capable of interacting with the S1 subsite of human factor VIIa:

Class [B-1]:

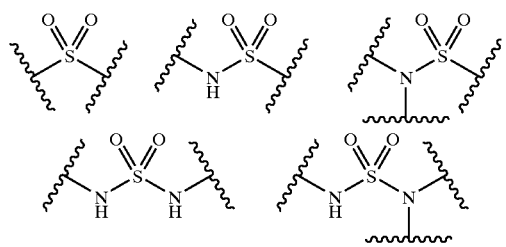

Class [B-2]:

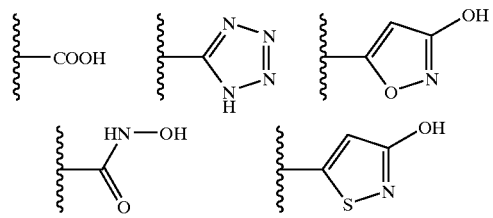

Class [B-3]:

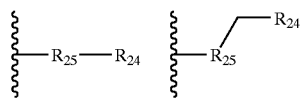

(wherein $R_{24}$ represents the same partial structures defined as Class [B-2], and $R_{25}$ represents a 6 or 5-membered aromatic ring containing a heteroatom(s)) or Class [B-4]:

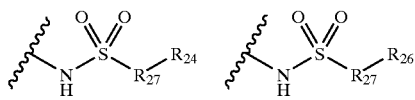

(wherein $R_{27}$ represents a $C_1$–$C_3$ alkylene group, $R_{24}$ represents the same partial structures defined as Class [B-2], and $R_{26}$ represents the same partial structures defined as Class [B-3]).

In yet another embodiment, the low-molecular weight reversible factor VIIa inhibitor comprises any one of the partial structures shown in the following Class [C-1] or [C-2] as a partial structure capable of interacting with the S4 site of human factor VIIa:

Class [C-1]:

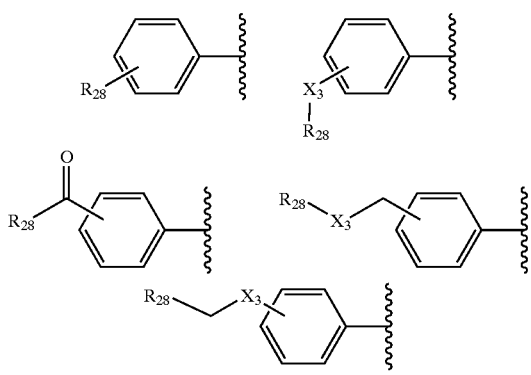

(wherein $X_3$ represents O, NH or $CH_2$, and $R_{28}$ represents a 6 or 5-membered aromatic ring containing a heteroatom(s)) or Class [C-2]:

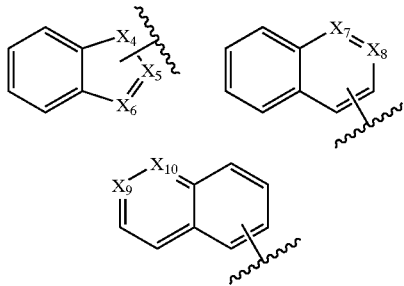

(wherein $X_4$ represents NH, S or O, and $X_5$, $X_6$, $X_7$, $X_8$, $X_9$ and $X_{10}$ each independently represent N or CH).

In yet another embodiment, the low-molecular weight reversible factor VIIa inhibitor comprises any one of the partial structures shown in the above Class [A-1] or [A-2] as a partial structure capable of interacting with the S2 site of human factor VIIa, any one of the partial structures shown in the above Class [B-1], [B-2], [B-3] or [B-4] as a partial structure capable of interacting with the S1 subsite, and any one of the partial structures shown in the above Class [C-1] or [C-2] as a partial structure capable of interacting with the S4 site.

BEST MODE FOR CARRYING OUT THE INVENTION

Figure 1:
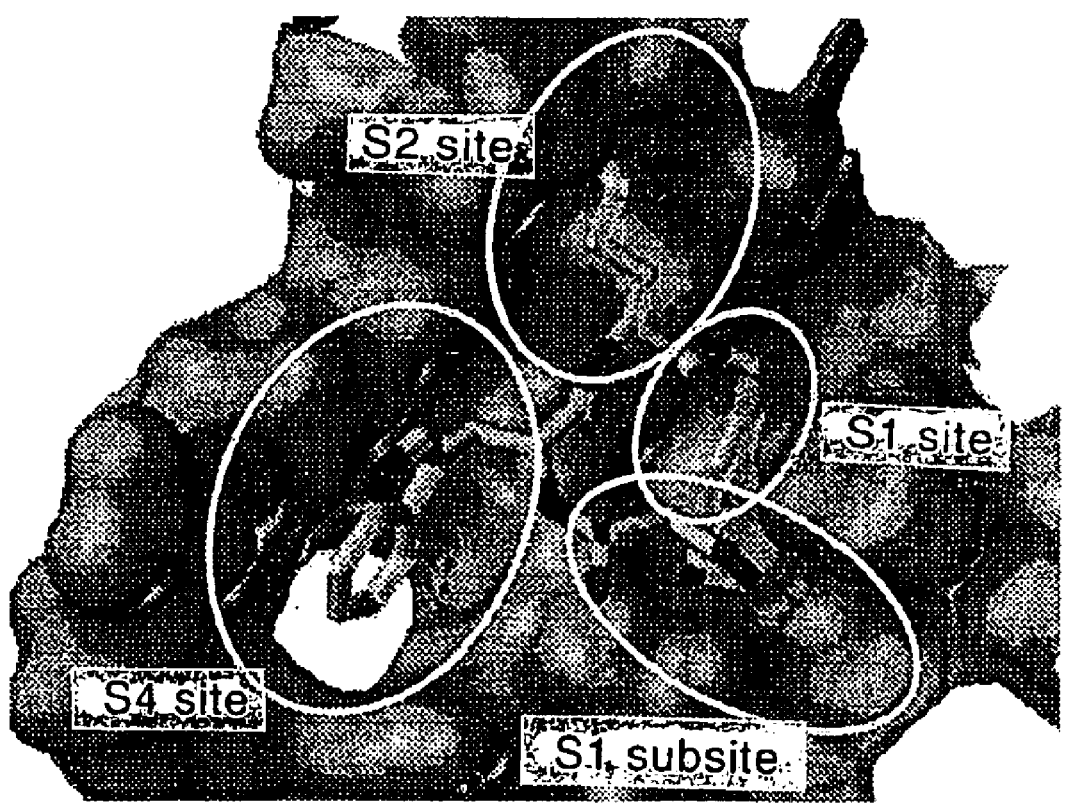
FIG. 1 shows the three-dimensional conformation of the binding sites between human factor VIIa and Compound (1).

In the definition of a compound of Formula (1), the following group defined as $R_1$:

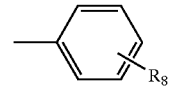

preferably has the following formula:

wherein $R_8$ preferably represents the following formula:

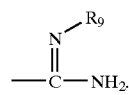

Examples of the acyl group defined as $R_9$ in the formula for $R_8$:

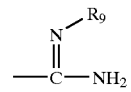

include alkylcarbonyl groups such as a formyl group, an acetyl group, a propionyl group, a butyryl group, an isobutyryl group, a valeryl group, an isovaleryl group, a pivaloyl group, a caproyl group and a phenylacetyl group; alkenylcarbonyl groups such as an acryloyl group, a propioloyl group, a methacryloyl group, a crotonoyl group and an isocrotonoyl group; and arylcarbonyl groups such as a benzoyl group. Preferred is an alkylcarbonyl group having a linear or branched $C_1$–$C_6$ alkyl as its alkyl moiety. Particularly preferred are an acetyl group, a propionyl group, a butyryl group, an isobutyryl group and an isovaleryl group.

The alkoxycarbonyl group having an optionally substituted linear or branched $C_1$–$C_6$ alkyl as its alkyl moiety, defined as $R_9$ in the formula for $R_8$:

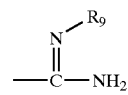

is preferably an alkoxycarbonyl group having an optionally substituted linear or branched $C_1$–$C_4$ alkyl as its alkyl moiety (wherein examples of a substituent include a phenyl group). Particularly preferred are a methoxycarbonyl group, an ethoxycarbonyl group, a t-butoxycarbonyl group and a benzyloxycarbonyl group.

In the present invention, when expressed as "optionally substituted" or when several substitutions are possible for a given group or moiety, it is meant that the group or moiety may be substituted with one or more substituents.

$R_9$ in the formula for $R_8$:

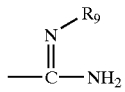

is preferably a hydrogen atom, an amino group, a hydroxy group, an acetyl group, a propionyl group, a butyryl group, an isobutyryl group, an isovaleryl group, a methoxycarbonyl group, an ethoxycarbonyl group, a t-butoxycarbonyl group or a benzyloxycarbonyl group.

The following group defined as $R_1$:

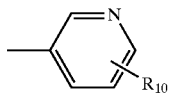

preferably has the following formula:

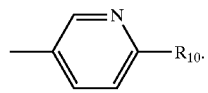

The following group defined as $R_1$:

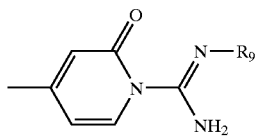

preferably has the following formula:

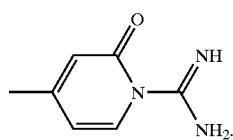

The following group defined as $R_1$:

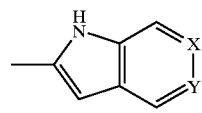

preferably has the following formula:

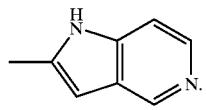

The following group defined as $R_1$:

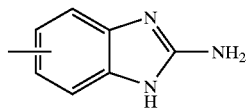

preferably has the following formula:

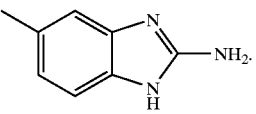

The following group defined as $R_1$:

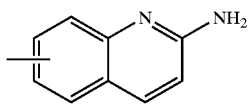

preferably has the following formula:

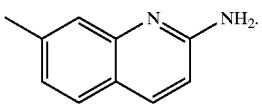

The following group defined as $R_1$:

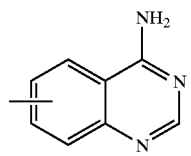

preferably has the following formula:

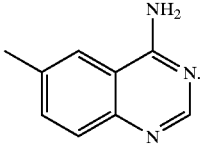

The linear or branched $C_1$–$C_6$ alkyl group defined as $R_2$ is preferably a linear or branched $C_1$–$C_3$ alkyl group, and particularly a methyl group.

The following group defined as $R_3$:

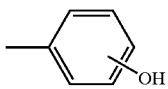

preferably has the following formula:

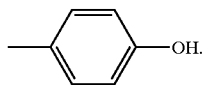

m in the group —$(CH_2)_m$—$R_{11}$ defined as $R_3$ is preferably an integer of 1 to 3, and particularly 2.

$R_{11}$ in the group —$(CH_2)_m$—$R_{11}$ defined as $R_3$ is preferably —$CONH_2$,

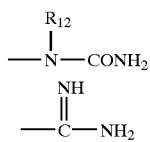

(wherein $R_{12}$ preferably represents a hydrogen atom or a linear or branched $C_1$-$C_3$ alkyl group, and particularly represents a methyl group).

The linear or branched $C_1$-$C_6$ alkyl group defined as $R_4$ is preferably a linear or branched $C_1$-$C_3$ alkyl group, and particularly a methyl group.

The linear or branched $C_1$-$C_6$ alkyl group defined as $R_5$ is preferably a linear or branched $C_1$-$C_4$ alkyl group.

The optionally substituted aryl group as $R_{13}$ in the group —$CH_2$—$R_{13}$ defined as $R_5$ is preferably a group of the following formula:

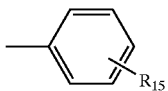

[wherein $R_{15}$ preferably represents a hydrogen atom, an optionally substituted aryl group (wherein examples of the aryl group include a phenyl group and a naphthyl group, with a phenyl group being preferred, and examples of a substituent include a linear or branched $C_1$-$C_3$ alkoxy group, a linear or branched $C_1$-$C_3$ alkyl group which may be substituted with a halogen atom, a nitro group and an amino group), a $C_1$-$C_3$ alkyl group which may be substituted with a halogen atom, a linear or branched $C_1$-$C_3$ alkoxy group, a halogen atom, an arylcarbonyl group (wherein examples of the aryl group include a phenyl group and a naphthyl group, with a phenyl group being preferred), an alkylcarbonyl group having a linear or branched $C_1$-$C_3$ alkyl as its alkyl moiety, a nitro group, or an amino group, and particularly represents a hydrogen atom, a t-butyl group, a methoxy group, a bromine atom, a chlorine atom, a benzoyl group, or a phenyl group which may be substituted with a methoxy group or a trifluoromethyl group or a nitro group or an amino group] or

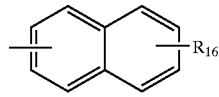

(wherein $R_{16}$ preferably represents a hydrogen atom or a linear or branched $C_1$-$C_6$ alkyl group, and particularly represents a hydrogen atom).

The optionally substituted heterocyclic group as $R_{13}$ in the group —$CH_2$—$R_{13}$ defined as $R_5$ contains a 5- to 10-membered monocyclic or condensed ring having at least one nitrogen atom, oxygen atom and/or sulfur atom as a ring member. Examples include furan, thiophene, pyran, pyrrole, pyridine, indole, benzofuran, benzothiophene, benzopyran and benzothiopyran. Examples of a substituent on the optionally substituted heterocyclic group include those listed below for $R_{17}$ and $R_{18}$.

The optionally substituted heterocyclic group as $R_{13}$ in the group —$CH_2$—$R_{13}$ defined as $R_5$ is preferably a group of the following formula:

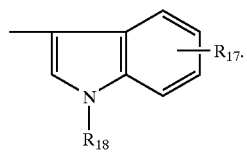

In the above formula, $R_{17}$ preferably represents a hydrogen atom, a hydroxy group, a linear or branched $C_1$-$C_6$ alkyl group, a linear or branched $C_1$-$C_6$ alkoxy group, —O—$(CH_2)_n$—OH (wherein n represents an integer of 1 to 5), —O—$(CH_2)_p$—COOH (wherein p represents an integer of 1 to 5), —O—$(CH_2)_q$—$NH_2$ (wherein q represents an integer of 1 to 5),

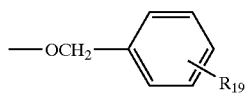

(wherein $R_{19}$ represents a hydrogen atom, a hydroxy group, a carboxyl group, a linear or branched $C_1$-$C_6$ alkyl group, a halogen atom, a linear or branched $C_1$-$C_6$ alkoxy group, or an alkoxycarbonyl group having a linear or branched $C_1$-$C_3$ alkyl as its alkyl moiety), or —$OSO_2$—$R_{20}$ (wherein $R_{20}$ represents a linear or branched $C_1$-$C_6$ alkyl group or a benzyl group).

Above all, $R_{17}$ is preferably a hydrogen atom, a hydroxy group, a methyl group, a linear or branched $C_1$-$C_3$ alkoxy group, —O—$(CH_2)_n$—OH (wherein n represents an integer of 1 to 3), —O—$(CH_2)_p$—COOH (wherein p represents an integer of 1 to 3), —O—$(CH_2)_q$—$NH_2$ (wherein p represents an integer of 1 to 3), —$OSO_2$—$R_{20}$ (wherein $R_{20}$ particularly represents an ethyl group, an n-propyl group, an i-propyl group or a benzyl group), a benzyloxy group, a 3- or 4-hydroxybenzyloxy group, or a 3- or 4-carboxybenzyloxy group.

$R_{18}$ preferably represents a hydrogen atom, a linear or branched $C_1$-$C_6$ alkyl group, a linear or branched $C_1$-$C_6$ alkylsulfonyl group, or an optionally substituted arylsulfonyl group (wherein the aryl group is preferably a phenyl group, and examples of a substituent include a linear or branched $C_1$–$C_3$ alkoxy group, a linear or branched $C_1$–$C_3$ alkyl group which may be substituted with a halogen atom, a nitro group and an amino group), and particularly represents a hydrogen atom, a methyl group, a methanesulfonyl group or a benzenesulfonyl group.

The linear or branched $C_1$–$C_6$ alkyl group defined as $R_6$ is preferably a linear or branched $C_1$–$C_3$ alkyl group.

Examples of a substituent on the optionally substituted linear or branched $C_1$–$C_6$ alkyl group defined as $R_7$ include a carboxyl group, an amino group, a mono- or di-substituted alkylamino group having a $C_1$–$C_6$ alkyl as its alkyl moiety, and an alkylcarbonylamino group having a $C_1$–$C_6$ alkyl as its alkyl moiety.

The alkyl moiety of the optionally substituted linear or branched $C_1$–$C_6$ alkyl group defined as $R_7$ is preferably a linear or branched $C_1$–$C_4$ alkyl group.

The optionally substituted linear or branched, $C_1$–$C_6$ alkyl group defined as $R_7$ is preferably a linear or branched $C_1$–$C_4$ alkyl group or a group of the following formula:

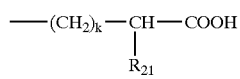

[wherein k represents an integer of 0 to 3, and $R_{21}$ represents a hydrogen atom or —$NHR_{22}$ (wherein $R_{22}$ represents a linear or branched $C_1$–$C_3$ alkyl group or an alkylcarbonyl group having a linear or branched $C_1$–$C_3$ alkyl as its alkyl moiety)].

Above all, in the formula:

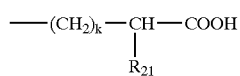

k is particularly an integer of 0 to 2, and $R_{21}$ is preferably a hydrogen atom or —$NHR_{22}$ (wherein $R_{22}$ represents a methyl group or an acetyl group).

Examples of a substituent on the optionally substituted linear or branched $C_1$–$C_8$ alkyl group defined as $R_{14}$ in the group —$SO_2$—$R_{14}$ defined as $R_7$ include (a) a carboxyl group, (b) an alkoxycarbonyl group having a linear or branched $C_1$–$C_3$ alkyl as its alkyl moiety, and (c) a phenyl group which may be substituted with a carboxyl group or the like.

The alkyl moiety of the optionally substituted linear or branched $C_1$–$C_8$ alkyl group defined as $R_{14}$ is preferably a linear or branched $C_1$–$C_6$ alkyl group.

The optionally substituted linear or branched $C_1$–$C_8$ alkyl group defined as $R_{14}$ is preferably (a) an optionally substituted linear or branched $C_1$–$C_6$ alkyl group (wherein said alkyl group may be substituted with a carboxyl group or an alkoxycarbonyl group having a linear or branched $C_1$–$C_3$ alkyl as its alkyl moiety), or (b) —$CH_2$—$R_{23}$ (wherein $R_{23}$ represents an optionally substituted phenyl group, which may be substituted with a carboxyl group or the like).

In particular, $R_{14}$ is preferably a benzyl group, a 2-, 3- or 4-carboxybenzyl group, or an optionally substituted linear or branched $C_1$–$C_4$ alkyl group (wherein said alkyl group may be substituted with a carboxyl group or an alkoxycarbonyl group having a linear or branched $C_1$–$C_3$ alkyl as its alkyl moiety).

$R_1$ is preferably selected from the following formulae:

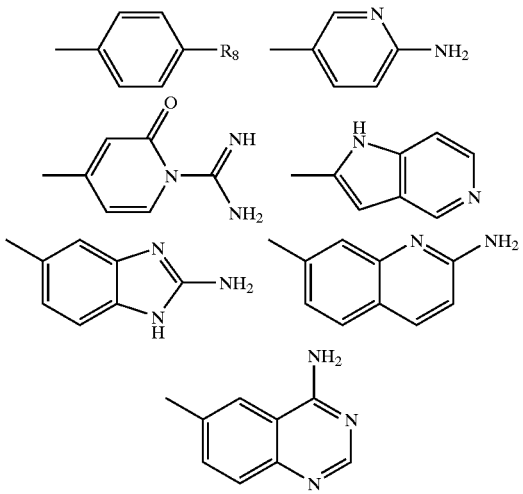

[wherein $R_8$ represents:

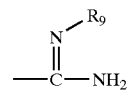

(wherein $R_9$ represents a hydrogen atom, an amino group, a hydroxy group, an acyl group, or an alkoxycarbonyl group having an optionally substituted linear or branched $C_1$–$C_6$ alkyl as its alkyl moiety)].

Above all, $R_1$ is particularly selected from the following formulae:

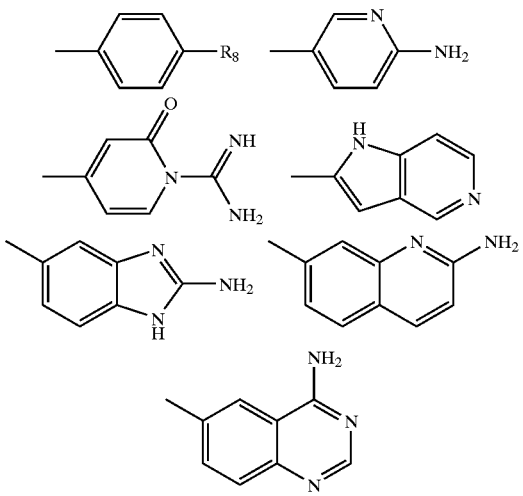

[wherein $R_8$ represents:

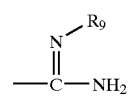

(wherein $R_9$ represents a hydrogen atom, an amino group, a hydroxy group, an acetyl group, a propionyl group, a butyryl group, an isobutyryl group, an isovaleryl group, a methoxycarbonyl group, an ethoxycarbonyl group, a t-butoxycarbonyl group or a benzyloxycarbonyl group)].

$R_2$ is preferably a hydrogen atom or a linear or branched $C_1$–$C_3$ alkyl group, and particularly a hydrogen atom or a methyl group.

$R_3$ is preferably a group of the following formula:

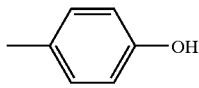

or

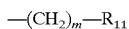

[wherein m represents an integer of 1 to 3, and $R_{11}$ represents:

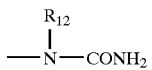

(wherein $R_{12}$ represents a hydrogen atom or a methyl group) or

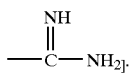

Also preferred is a compound, in which $R_3$ represents a linear or branched $C_1$–$C_6$ alkyl group or —$(CH_2)_m$—$R_{11}$ (wherein m and $R_{11}$ are as defined above).

Also preferred is a compound, in which $R_3$ represents:

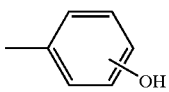

and $R_7$ represents —$SO_2$—$R_{14}$ (wherein $R_{14}$ is as defined above).

In particular, $R_3$ is preferably a group of the following formula:

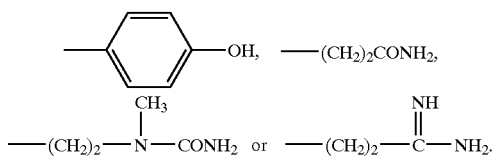

$R_4$ is preferably a hydrogen atom or a linear or branched $C_1$–$C_3$ alkyl group, and particularly a hydrogen atom or a methyl group.

$R_5$ is preferably a linear or branched $C_1$–$C_6$ alkyl group or —$CH_2$—$R_{13}$ [wherein $R_{13}$ represents a group selected from the following formulae:

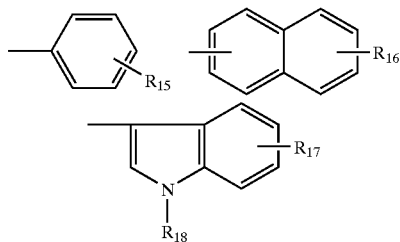

(wherein $R_{15}$ represents a hydrogen atom, an optionally substituted aryl group, a $C_1$–$C_3$ alkyl group which may be substituted with a halogen atom, a linear or branched $C_1$–$C_3$ alkoxy group, a halogen atom, an arylcarbonyl group, an alkylcarbonyl group having a linear or branched $C_1$–$C_3$ alkyl as its alkyl moiety, a nitro group, or an amino group;

$R_{16}$ represents a hydrogen atom or a linear or branched $C_1$–$C_6$ alkyl group;

$R_{17}$ represents a hydrogen atom, a hydroxy group, a linear or branched $C_1$–$C_6$ alkyl group, a linear or branched $C_1$–$C_6$ alkoxy group, —O—$(CH_2)_n$—OH (wherein n represents an integer of 1 to 5), —O—$(CH_2)_p$—COOH (wherein p represents an integer of 1 to 5), —O—$(CH_2)_q$—$NH_2$ (wherein q represents an integer of 1 to 5),

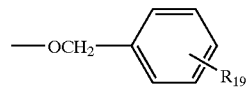

(wherein $R_{19}$ represents a hydrogen atom, a hydroxy group, a carboxyl group, a linear or branched $C_1$–$C_6$ alkyl group, a halogen atom, a linear or branched $C_1$–$C_6$ alkoxy group, or an alkoxycarbonyl group having a linear or branched $C_1$–$C_3$ alkyl as its alkyl moiety), or —$OSO_2$—$R_{20}$ (wherein $R_{20}$ represents a linear or branched $C_1$–$C_6$ alkyl group or a benzyl group); and $R_{18}$ represents a hydrogen atom, a linear or branched $C_1$–$C_6$ alkyl group, a linear or branched $C_1$–$C_6$ alkylsulfonyl group, or an optionally substituted-arylsulfonyl group)].

In particular, $R_5$ is preferably a linear or branched $C_1$–$C_4$ alkyl group or —$CH_2$—$R_{13}$ [wherein $R_{13}$ represents a group selected from the following formulae:

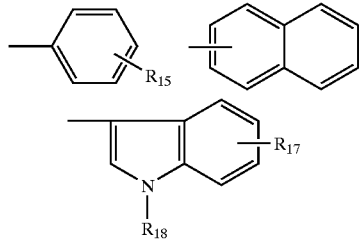

(wherein $R_{15}$ represents a hydrogen atom, a t-butyl group, a methoxy group, a bromine atom, a chlorine atom, a benzoyl group, or a phenyl group which may be substituted with a methoxy group or a trifluoromethyl group or a nitro group or an amino group;

$R_{17}$ represents a hydrogen atom, a hydroxy group, a methyl group, a linear or branched $C_1$–$C_3$ alkoxy group, —O—(CH$_2$)$_n$—OH (wherein n represents an integer of 1 to 3), —O—(CH$_2$)$_p$—COOH (wherein p represents an integer of 1 to 3), —O—(CH$_2$)$_q$NH$_2$ (wherein q represents an integer of 1 to 3), —OSO$_2$—R$_{20}$ (wherein R$_{20}$ represents an ethyl group, an n-propyl group, an i-propyl group or a benzyl group), a benzyloxy group, a 3- or 4-hydroxybenzyloxy group, or a 3- or 4-carboxybenzyloxy group; and R$_{18}$ represents a hydrogen atom, a methyl group, a methanesulfonyl group or a benzenesulfonyl group)].

R$_6$ is preferably a hydrogen atom or a linear or branched C$_1$–C$_3$ alkyl group, and particularly a hydrogen atom or a methyl group.

R$_7$ is preferably a linear or branched C$_1$–C$_6$ alkyl group or a group of the following formula:

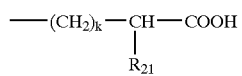

[wherein k represents an integer of 0 to 3, and R$_{21}$ represents a hydrogen atom or —NHR$_{22}$ (wherein R$_{22}$ represents a linear or branched C$_1$–C$_3$ alkyl group or an alkylcarbonyl group having a linear or branched C$_1$–C$_3$ alkyl as its alkyl moiety)] or

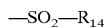

[wherein R$_{14}$ represents:

(i) an optionally substituted linear or branched C$_1$–C$_6$ alkyl group (wherein said alkyl group may be substituted with a carboxyl group or an alkoxycarbonyl group having a linear or branched C$_1$–C$_3$ alkyl as its alkyl moiety); or (ii) —CH$_2$—R$_{23}$ (wherein R$_{23}$ represents an optionally substituted phenyl group)].

Above all, R$_7$ is particularly a linear or branched C$_1$–C$_4$ alkyl group or a group of the following formula:

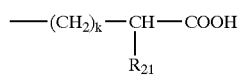

[wherein k represents an integer of 0 to 2, and R$_{21}$ represents a hydrogen atom or —NHR$_{22}$ (wherein R$_{22}$ represents a methyl group or an acetyl group)] or

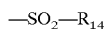

[wherein R$_{14}$ represents a benzyl group, a 2-, 3- or 4-carboxybenzyl group, or an optionally substituted linear or branched C$_1$–C$_4$ alkyl group (wherein said alkyl group may be substituted with a carboxyl group or an alkoxycarbonyl group having a linear or branched C$_1$–C$_3$ alkyl as its alkyl moiety)].

Having the definition given above for each symbol, preferred is a compound of Formula (1) wherein R$_1$ is a group selected from the following formulae:

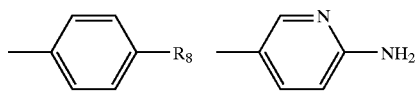

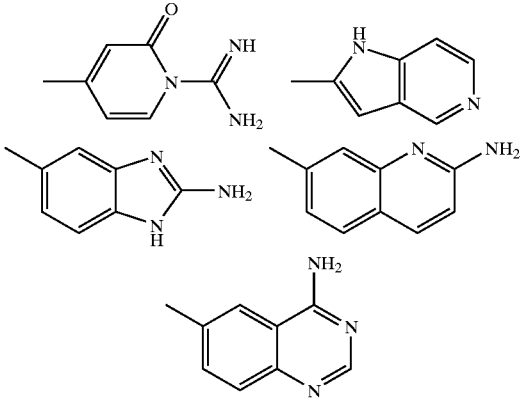

[wherein R$_8$ represents:

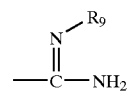

(wherein R$_9$ represents a hydrogen atom, an amino group, a hydroxy group, an acetyl group, a propionyl group, a butyryl group, an isobutyryl group, an isovaleryl group, a methoxycarbonyl group, an ethoxycarbonyl group, a t-butoxycarbonyl group or a benzyloxycarbonyl group)];

R$_2$ is a hydrogen atom or a methyl group;

R$_3$ is a group of the following formula:

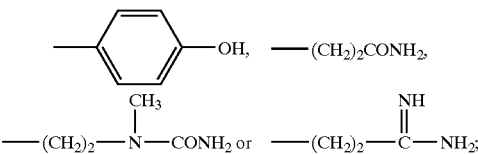

R$_4$ is a hydrogen atom or a methyl group;

R$_5$ is a linear or branched C$_1$–C$_4$ alkyl group or —CH$_2$—R$_{13}$ [wherein R$_{13}$ represents a group selected from the following formulae:

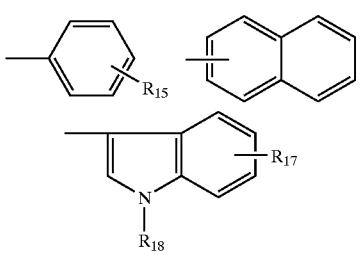

(wherein

R$_{15}$ represents a hydrogen atom, a t-butyl group, a methoxy group, a bromine atom, a chlorine atom, a benzoyl group, or a phenyl group which may be substituted with a methoxy group or a trifluoromethyl group or a nitro group or an amino group;

R$_{17}$ represents a hydrogen atom, a hydroxy group, a methyl group, a linear or branched C$_1$–C$_3$ alkoxy group, —O—(CH$_2$)$_n$—OH (wherein n represents an integer of 1 to 3), —O—(CH$_2$)$_p$—COOH (wherein p represents an integer of 1 to 3), —O—(CH$_2$)$_q$—NH$_2$ (wherein q represents an integer of 1 to 3), —OSO$_2$—R$_{20}$ (wherein R$_{20}$ represents an ethyl group, an n-propyl group, an i-propyl group or a benzyl group), a benzyloxy group, a 3- or 4-hydroxybenzyloxy group, or a 3- or 4-carboxybenzyloxy group; and R$_{18}$ represents a hydrogen atom, a methyl group, a methanesulfonyl group or a benzenesulfonyl group)];

R$_6$ is a hydrogen atom or a methyl group; and

R$_7$ is a linear or branched C$_1$–C$_4$ alkyl group or a group of the following formula:

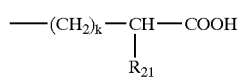

[wherein k represents an integer of 0 to 2, and R$_{21}$ represents a hydrogen atom or —NHR$_{22}$ (wherein R$_{22}$ represents a methyl group or an acetyl group)] or

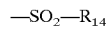

[wherein R$_{14}$ represents a benzyl group, a 2-, 3- or 4-carboxybenzyl group, or an optionally substituted linear or branched C$_1$–C$_4$ alkyl group (wherein said alkyl group may be substituted with a carboxyl group or an alkoxycarbonyl group having a linear or branched C$_1$–C$_3$ alkyl as its alkyl moiety)].

Above all, particularly preferred is a compound selected from the following formulae:

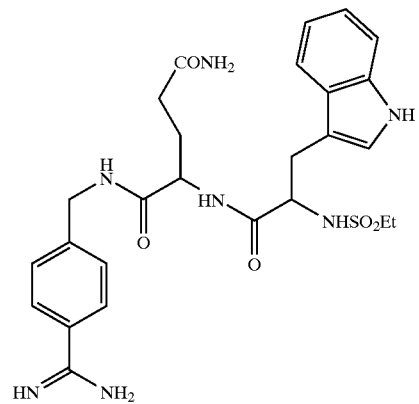

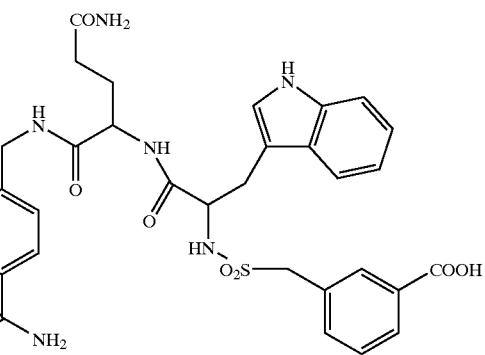

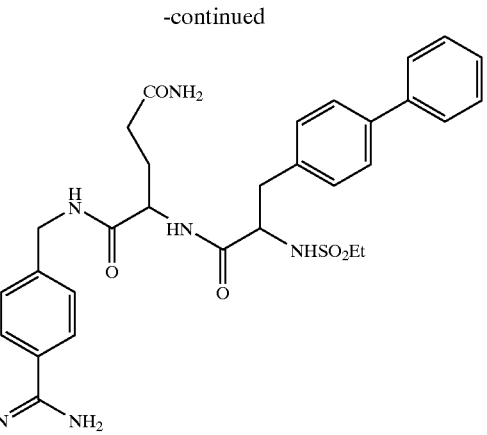

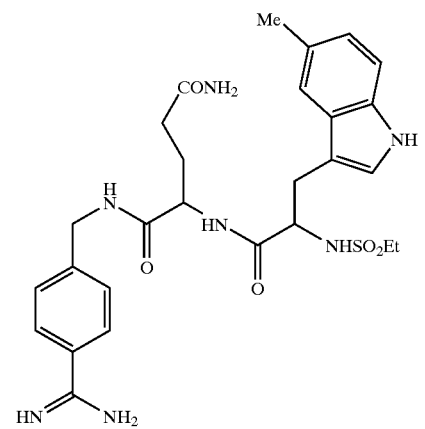

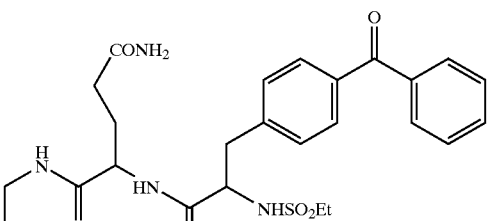

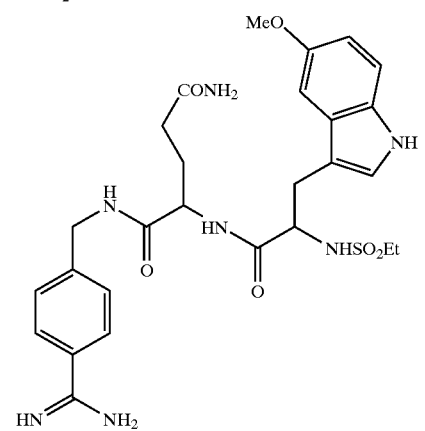

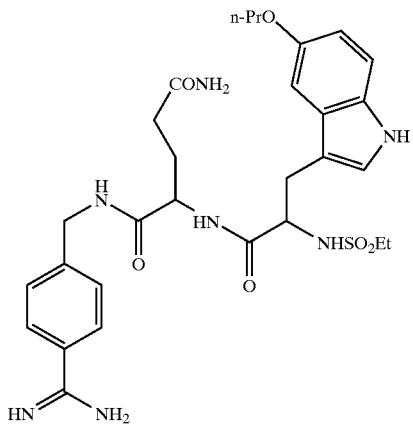

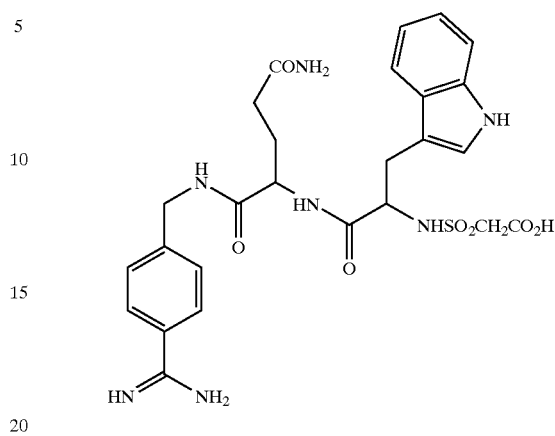

Compounds of Formula (1) have enantiomers; all individual enantiomers and mixtures thereof are intended to be within the scope of the present invention. Above all, preferred are compounds having the S-configuration at the carbon atom attached to $R_3$ and having the R-configuration at the carbon atom attached to $R_5$ in Formula (1).

The compounds of the present invention may also be obtained as hydrates.

Examples of a salt-forming acid include inorganic acids such as hydrochloric acid, hydrobromic acid, hydroiodic acid, sulfuric acid and phosphoric acid, as well as organic acids such as acetic acid, oxalic acid, maleic acid, fumaric acid, citric acid, tartaric acid, methanesulfonic acid and trifluoroacetic acid.

Each compound of Formula (1) may be administered as a pharmaceutical composition in any dosage form suitable for the intended route of administration, in combination with one or more pharmaceutically acceptable diluents, wetting agents, emulsifiers, dispersants, auxiliary agents, preservatives, buffers, binders, stabilizers and the like. It may be administered parenterally or orally.

The dose of the compound can be determined as appropriate for the physique, age and physical condition of a patient, severity of the disease to be treated, elapsed time after onset of the disease, etc. For example, it is usually used at a dose of 1 to 1000 mg/day/person for oral administration and at a dose of 0.1 to 100 mg/day/person for parenteral administration (by intravenous, intramuscular or subcutaneous route).

The compounds of Formula (1) can be prepared as shown in the following Reaction Schemes 1 to 6.

Reaction Scheme 1
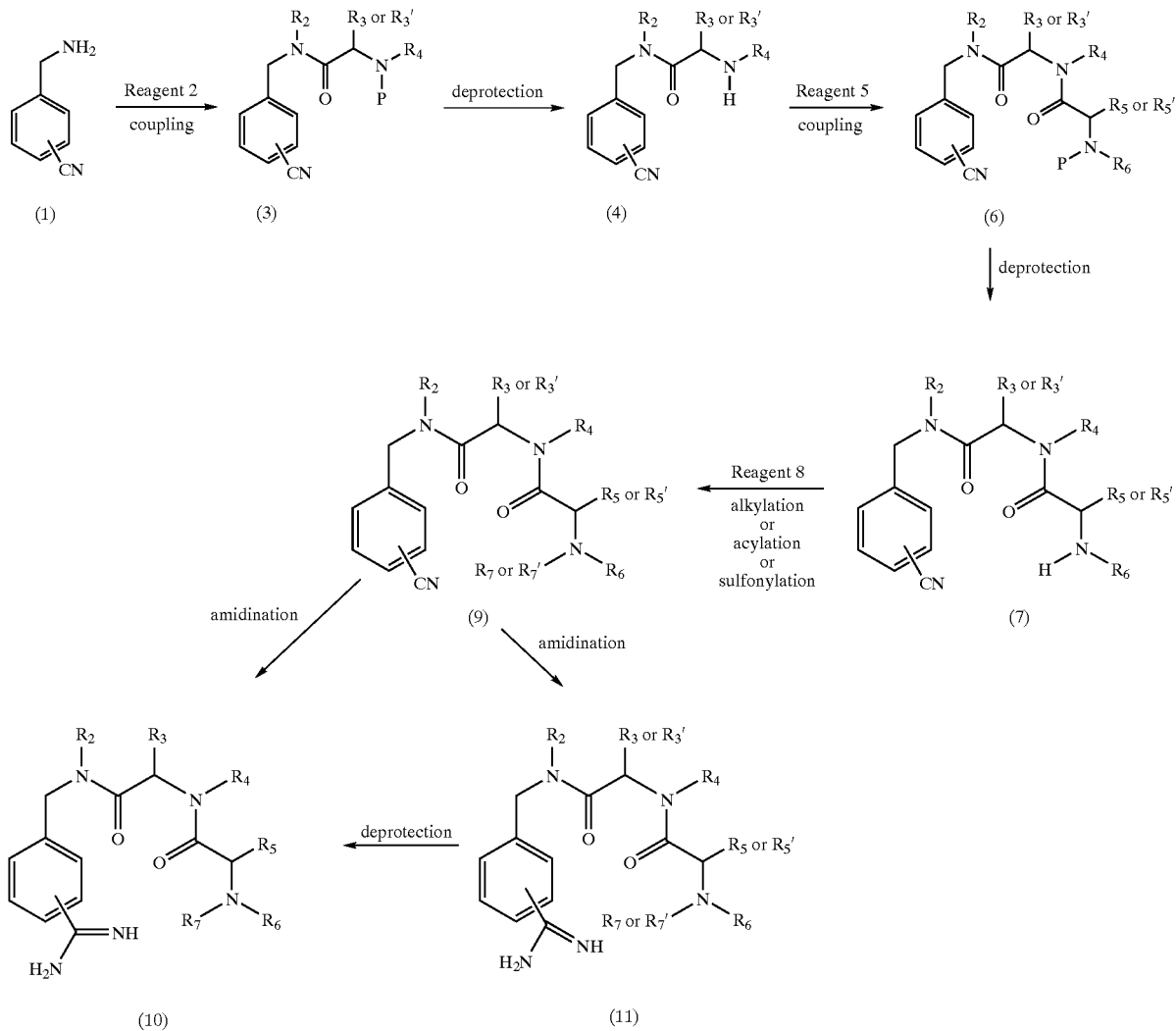
Reaction Scheme 2
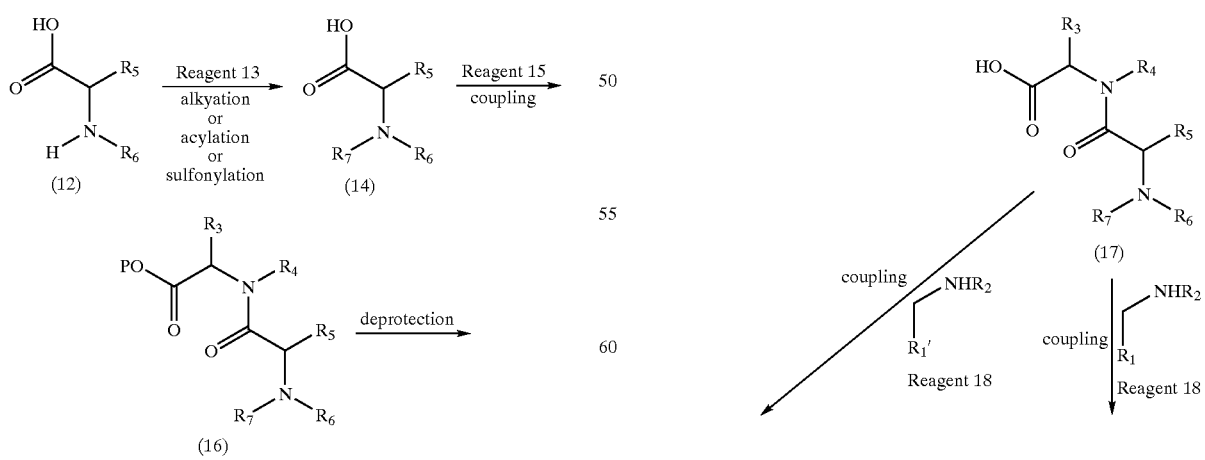

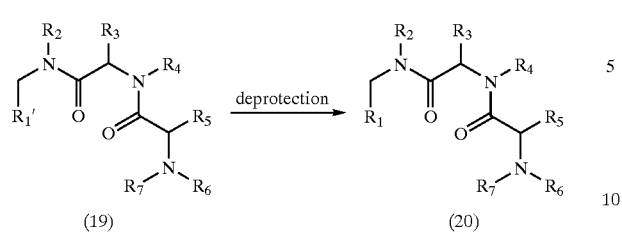
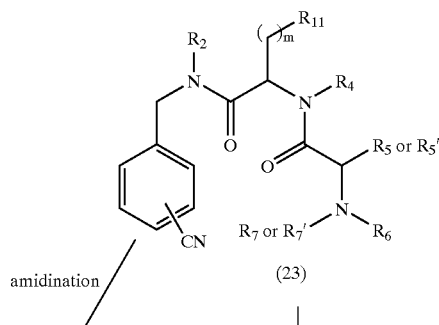
Reaction Scheme 3
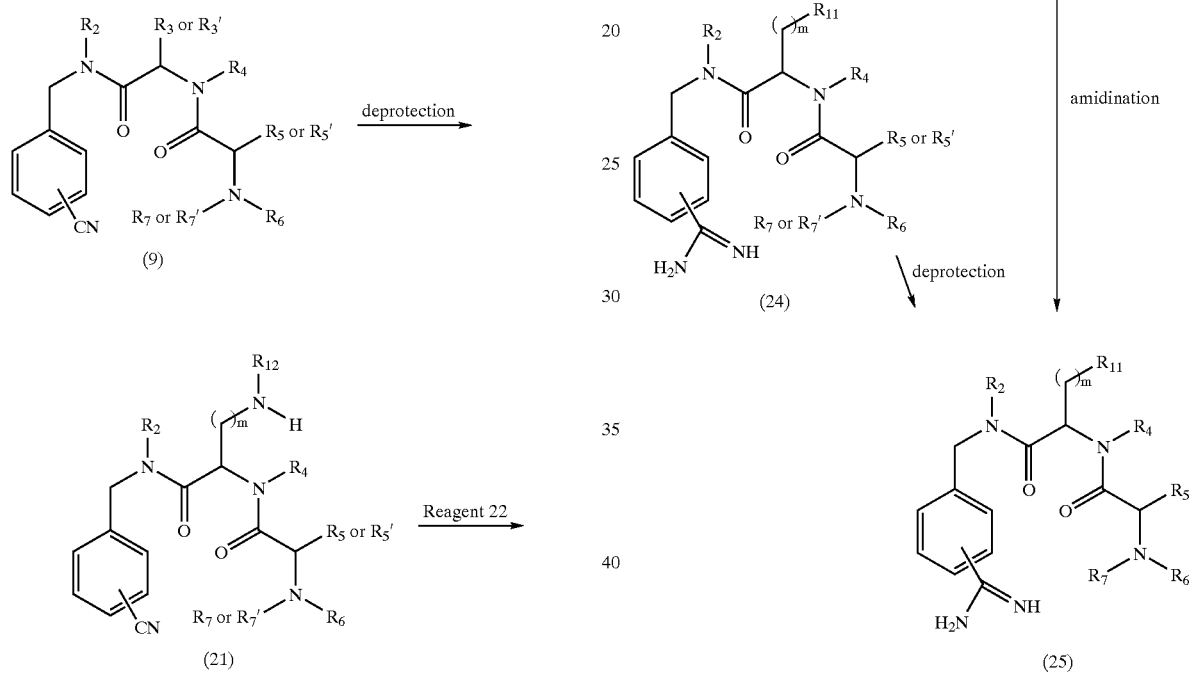
Reaction Scheme 4
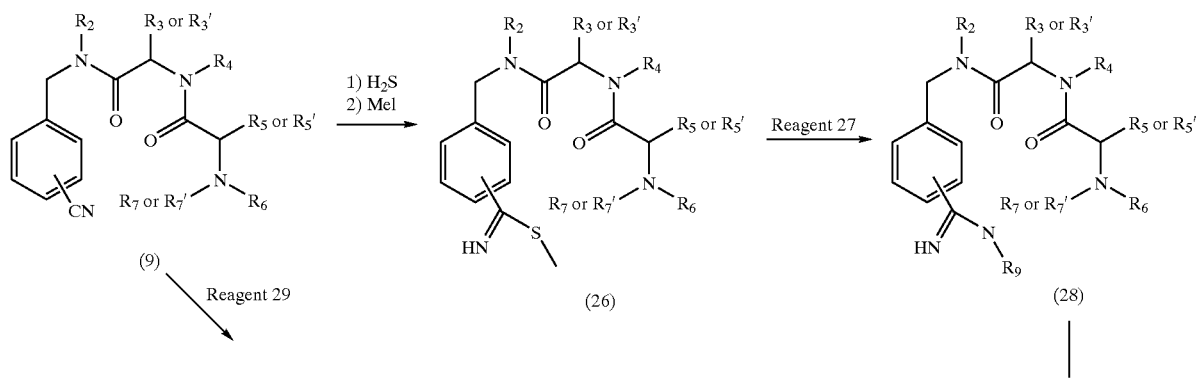

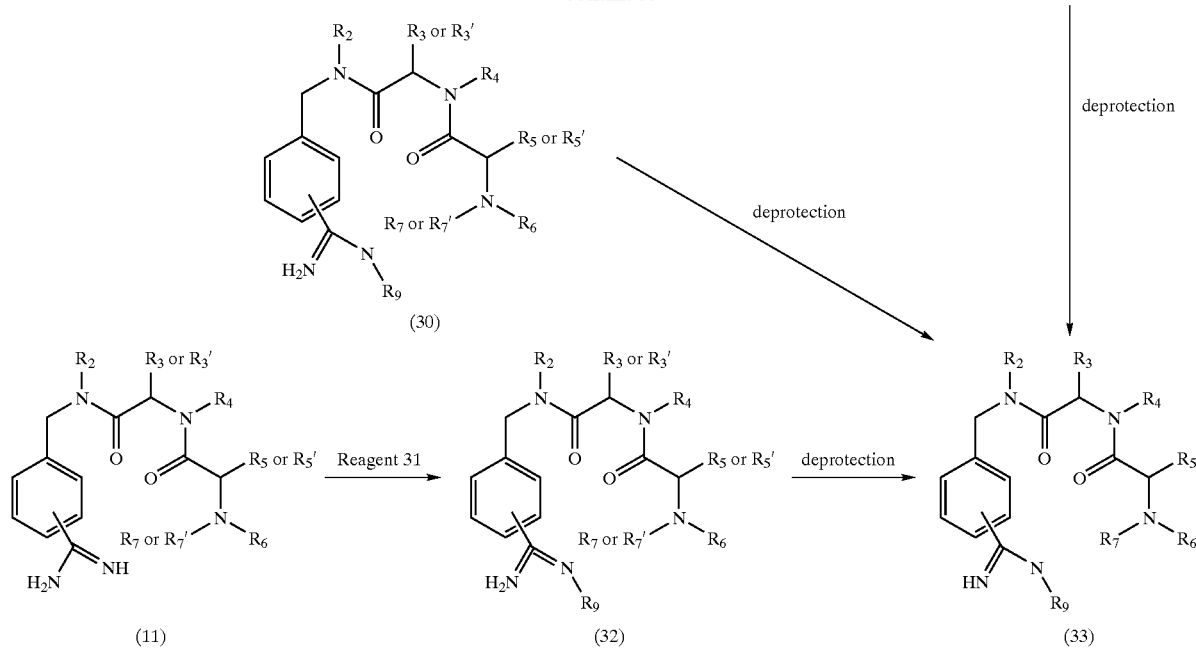
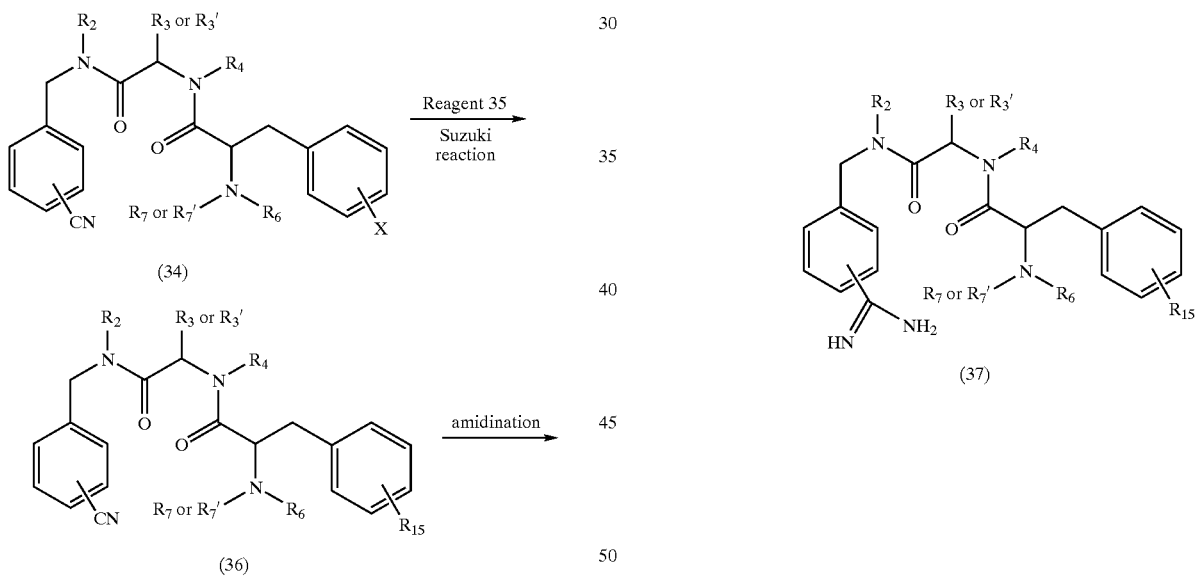
Reaction Scheme 5
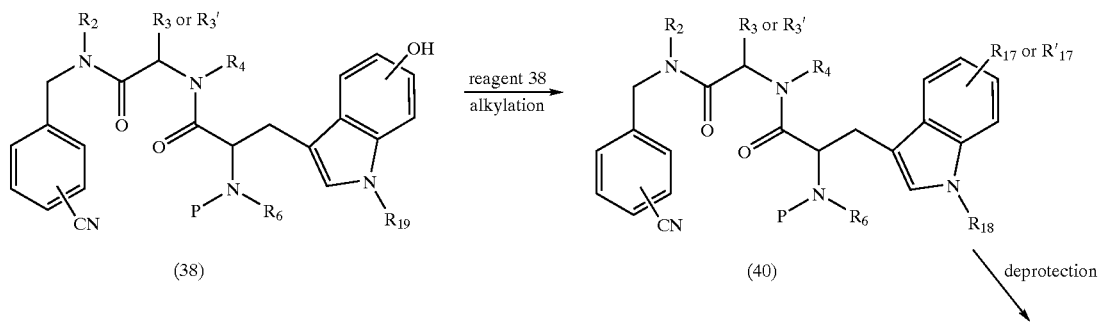
Reaction Scheme 6

-continued

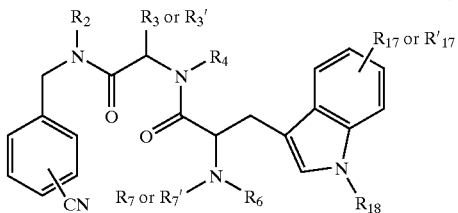

(42)

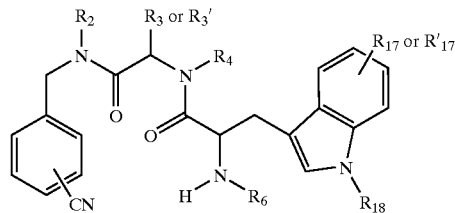

(41)

reagent 8
alkylation
or
acylation
or
sulfonation amidination

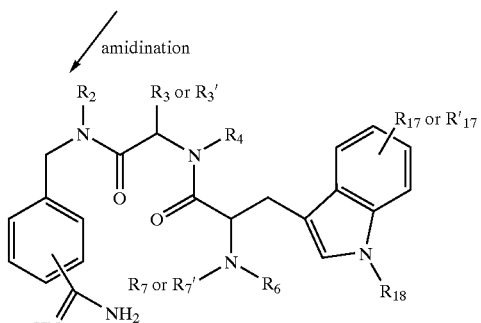

(43)

deprotection

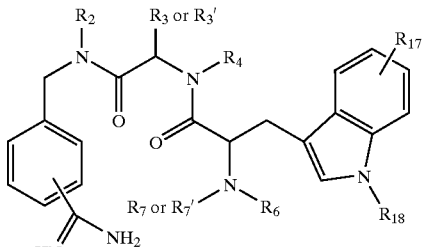

(44)

In Reaction Schemes 1 to 6, the substituents $R_1$, $R_2$, . . . and $R_n$ are each as defined above, and $R_1'$, $R_2'$, . . . and $R_n'$ represent the respective corresponding protected forms of $R_1$, $R_2$, . . . and $R_n$. Examples of protecting groups include those described in Principle and Experiments of Peptide Synthesis (Maruzen Co., Ltd., 1985) or PROTECTING GROUP IN ORGANIC SYNTHESIS SECOND EDITION (JOHN WILEY & SONS, INC, 1991), e.g., a t-butoxycarbonyl (Boc) group, a benzyloxycarbonyl (Cbz) group, a 9-fluorenylmethoxycarbonyl (Fmoc) group.

Likewise, P represents a commonly-used protecting group, such as those described in Principle and Experiments of Peptide Synthesis (Maruzen Co., Ltd., 1985) or PROTECTING GROUP IN ORGANIC SYNTHESIS SECOND EDITION (JOHN WILEY & SONS, INC 1991).

X represents a halogen atom such as chloride, bromide or iodide.

Starting materials in the individual reaction steps are known per se or cat be prepared in a known manner.

All reactions in the individual reaction steps can be performed in a known manner.

Likewise, other starting materials and individual reagents used here are also known per se or can be prepared in a known manner.

The preparation of the compounds according to the present invention will be illustrated in more detail, in line with the above-mentioned reaction schemes.

Reaction Scheme 1

Intermediate (3) may be obtained through condensation between Starting material (1) and Reagent 2 (listed in Table A-1 to Table A-34; this reagent being commercially available or easy to synthesize by known synthesis procedures).

The condensation used here may be accomplished as described in Principle and Experiments of Peptide Synthesis (Maruzen Co., Ltd., 1985), for example, by commonly-used active ester method, acid anhydride method, azide method or acid chloride method, or using various condensing agents. Examples of a condensing agent available for use include commonly-used reagents such as those described in Peptide Synthesis Handbook (Novabiochem, 1998), e.g., N,N'-dicyclohexylcarbodiimide (DCC), water-soluble carbodiimide (WSCI), carbonyldiimidazole (CDI), diphenylphosphorylazide (DPPA), Bop reagent, Pybop reagent, 2-(1H-benzotriazol-1-yl)-1,1,3,3-tetramethyluronium hexafluorophosphate (HBTU), 2-(1H-benzotriazol-1-yl)-1,1,3,3-tetramethyluronium tetrafluoroborate (TBTU) and 2-(7-azabenzotriazol-1-yl)-1,1,3,3-tetramethyluronium hexafluorophosphate (HATU). The reaction may be carried out in a routine manner with an appropriate solvent (e.g., dimethylformamide, dichloromethane) at room temperature or under cooling or heating conditions.

Intermediate (4) may be obtained from Intermediate (3) through appropriate amino deprotection, for example, as described in Principle and Experiments of Peptide Synthesis (Maruzen Co., Ltd., 1985). The reaction may be carried out in a routine manner with or without an appropriate solvent (e.g., dichloromethane, dimethylformamide) at room temperature or under cooling or heating conditions.

Intermediate (6) may be obtained through condensation between Intermediate (4) and Reagent 5 (listed in Table A-1 to Table A-34; this reagent being commercially available or easy to synthesize by known synthesis procedures) in the same manner as described above.

Intermediate (7) may be obtained from Intermediate (6) through amino deprotection as described above. The reaction may be carried out in a routine manner with or without an appropriate solvent (e.g., dichloromethane, dimethylformamide) at room temperature or under cooling or heating conditions.

Intermediate (9) may be obtained from Intermediate (7) through commonly-used alkylation, acylation or sulfonylation with Reagent 8 (listed in Table A-1 to Table A-34; this reagent being commercially available or easy to synthesize by known synthesis procedures). The reaction may be carried out in a routine manner with an appropriate solvent (e.g., dimethylformamide, dichloromethane) at room temperature or under cooling or heating conditions.

Compound (10) and Intermediate (11) may be derived from Intermediate (9) in a known manner as described in JP 09-509937 A, the Chemistry of Amidines and Imidates (JOHN WILEY & SONS, INC, 1991), etc.

For example, Compound (10) may be obtained by treating Intermediate (9) with a strong acid and then reacting it with an ammonium salt or ammonia. The reaction may be carried out in a routine manner with an appropriate solvent (e.g., methanol, ethanol) at room temperature or under cooling or heating conditions.

Compound (10) may also be obtained from Intermediate (11) through appropriate deprotection, for example, as described in Principle and Experiments of Peptide Synthesis (Maruzen Co., Ltd., 1985). The reaction may be carried out in a routine manner with or without an appropriate solvent (e.g., dichloromethane, dimethylformamide, water, ethanol) at room temperature or under cooling or heating conditions.

Reaction Scheme 2

Intermediate (14) may be obtained from Starting material (12) through commonly-used alkylation, acylation or sulfonylation with Reagent 13 (this reagent being an alkyl halide, an acyl chloride or sulfonyl chloride, which is commercially available or easy to synthesize by known synthesis procedures). The reaction may be carried out in a routine manner with an appropriate solvent (e.g., dimethylformamide, dichloromethane) at room temperature or under cooling or heating conditions.

Intermediate (16) may be obtained through condensation between Intermediate (14) and Reagent 15 (this reagent being a naturally-occurring or modified amino acid, which is commercially available or easy to synthesize by known synthesis procedures) in the same manner as described above.

Intermediate (17) may be obtained from Intermediate (16) through appropriate deprotection. The reaction may be carried out in a routine manner with an appropriate solvent (e.g., water, methanol, ethanol) at room temperature or under cooling or heating conditions.

Intermediate (19) may be obtained through condensation between Intermediate (17) and Reagent 18 (listed in Table A-27; this reagent being commercially available or easy to synthesize by known synthesis procedures), while Compound (20) may be obtained through condensation between Intermediate (17) and Reagent 18 in the same manner as described above.

Compound (20) may also be obtained from Intermediate (19) through appropriate deprotection.

Reaction Scheme 3

Compound (21) may be obtained from Intermediate (9) through appropriate deprotection.

Compound (23) may be obtained through reaction between Intermediate (21) and Reagent 22 (listed in Tables A-28 to 29; this reagent being commercially available or easy to synthesize by known synthesis procedures). The reaction may be carried out in a routine manner with an appropriate solvent (e.g., dichloromethane, dimethylformamide, water, tetrahydrofuran) at room temperature or under cooling or heating conditions.

Intermediate (24) and Compound (25) may be obtained through amidination as described above.

Intermediate (25) may also be obtained from Intermediate (24) through appropriate deprotection.

Reaction Scheme 4

Intermediate (26) may be obtained from Intermediate (9) in a known manner, for example, according to the method of Lee, et al. (Bioorg. Med. Chem. Lett. 869–876, 6, 1998).

Intermediate (28) may be obtined from Intermediate (26) and Reagent 27 (this reagent being a compound of Formula: $NH_2—R_9$ (wherein $R_9$ is as defined above), which is commercially available or easy to synthesize by known synthesis procedures) in a known manner, for example, according to the method of Lee, et al. (Bioorg. Med. Chem. Lett. 869–876, 6, 1998).

Intermediate (30) may be obtined from Intermediate (9) and Reagent 29 (this reagent being a compound of Formula: $NH_2—R_9$ (wherein $R_9$ is as defined above), which is commercially available or easy to synthesize by known synthesis procedures) in a known manner, for example, according to the method of Trucker, et al. (Bioorg. Med. Chem. 601–616, 8, 2000).

Intermediate (32) may be obtained from Intermediate (11) and Reagent 31 (this reagent being an amine protecting group, such as a Boc group or a Cbz group), as described in Principle and Experiments of Peptide Synthesis (Maruzen Co., Ltd., 1985) or PROTECTING GROUP IN ORGANIC SYNTHESIS SECOND EDITION (JOHN WILEY & SONS, INC 1991). Examples of Reagent (31) include a t-butyloxycarbonyl group, a benzyloxycarbonyl group, an acetyl group and a 9-fluorenylmethyloxycarbonyl group. The reaction may be carried out in a routine manner with an appropriate solvent (e.g., dichloromethane, dimethylformamide) at room temperature or under cooling or heating conditions.

Compound (33) may be obtained from Intermediate (28), (30) or (32) through appropriate deprotection.

Reaction Scheme 5

Intermediate (34) may be obtained in the same manner as described above for Intermediate (9).

Intermediate (36) may be obtained from Intermediate (34) and Reagent 35 (listed in Tables A-30 to 31; this reagent being commercially available or easy to synthesize by known synthesis procedures) through the Suzuki reaction in the presence of a palladium catalyst, for example, according to the method of Ellman, et al. (J. Am. Chem. Soc. 11171–11172, 161, 1994). This reaction may be carried out in a solvent commonly used for the Suzuki reaction, e.g., an ether solvent, an aromatic hydrocarbon solvent, acetonitrile, dimethylformamide, or a mixed solvent thereof with water, preferably in tetrahydrofuran, more preferably in a mixed solvent of tetrahydrofuran with water. Examples of a reagent available for use as a palladium catalyst include tetrakis(triphenylphosphine)palladium, palladium acetate, dichlorobis(benzonitrile)palladium and tris(dibenzylideneacetone)dipalladium, with tetrakis(triphenylphosphine)palladium and tris(dibenzylideneacetone)dipalladium being preferred.

Compound (37) may be obtained from Intermediate (36) through amidination as described above.

Reaction Scheme 6

Intermediate (38) may be obtained according to the above Reaction Scheme 1.

Intermediate (40) may be obtained from Intermediate (38) through commonly-used alkylation with Reagent 39 (listed in Tables A-32 to 34). The reaction may be carried out in a routine manner in the presence of an appropriate base (e.g., sodium hydride, cesium carbonate, potassium carbonate, sodium hydroxide) using an appropriate solvent (e.g., dimethylformamide, tetrahydrofuran) at room temperature or under cooling or heating conditions.

Intermediate (41) may be obtained from Intermediate (40) through deprotection as described above.

Intermediate (42) may be obtained from Intermediate (41) through alkylation, acylation or sulfonylation with Reagent 8, as described above.

Intermediate (43) may be obtained from Intermediate (42) through amidination as described above.

Compound (44) may be obtained from Intermediate (43) through appropriate deprotection.

As used herein, the term "low-molecular weight factor VIIa inhibitor" refers to an agent having an inhibitory activity against factor VIIa. This term encompasses every compound having such a property, above all, synthetic or natural low-molecular weight compounds or peptide derivatives with a molecular weight less than 1000. The inhibitory activity against factor VIIa may be determined, for example, as described below in the Test Example.

The term "irreversible factor VIIa inhibitor" refers to a factor VIIa inhibitor having a group capable of reacting with factor VIIa, which makes covalent bond with the factor VIIa. In the case of a serine protease such as factor VIIa, a chloromethylketone group may be used as a group capable of reacting with the protease to form a covalent bond with the Ser residue at the active center of the enzyme, resulting in irreversible inhibition. The term "reversible factor VIIa inhibitor" refers to a factor VIIa inhibitor whose binding to factor VIIa is not irreversible. The term "low-molecular weight reversible factor VIIa inhibitor" refers to a low-molecular weight factor VIIa inhibitor whose binding to factor VIIa is not irreversible.

To overcome the problems, the inventors of the present invention have established a method for preparing a crystal of a complex between a low-molecular weight reversible factor VIIa inhibitor and human factor VIIa/human soluble tissue factor. The resulting crystal can be used for X-ray crystal structure analysis to provide accurate three-dimensional structure information about the binding mode between the low-molecular weight reversible factor VIIa inhibitor and human factor VIIa. Upon processing by a computer, this three-dimensional structure information allows a visual and numerical representation of the binding mode between the low-molecular weight reversible inhibitor and factor VIIa. This is advantageous in evaluating interactions important for binding to factor VIIa.

Starting from the structure of the complex between the low-molecular weight reversible VIIa inhibitor and factor VIIa, which is determined by X-ray structure analysis, it is further possible to design a low-molecular weight reversible inhibitor highly specific to factor VIIa by making virtual modifications to the inhibitor molecule. Such computational virtual evaluation is advantageous in facilitating the molecular design of low-molecular weight reversible inhibitors because it requires much less time than actual compound synthesis.

It is also possible to identify accurate sites allowing interactions important for the improvement of specificity to factor VIIa, upon analyzing the relationship between factor VIIa-inhibiting activity or selectivity and the binding mode between a low-molecular weight reversible VIIa inhibitor and factor VIIa. Based on the thus confirmed information about interactions important for the specificity to factor VIIa, the low-molecular weight reversible inhibitor molecule can further be modified on a computer to have interactions important for the specificity to factor VIIa in a case where the binding mode between the inhibitor molecule and factor VIIa or its structurally similar serine protease (e.g., thrombin, trypsin, factor Xa) has been identified or estimated by X-ray crystal structure analysis and/or computer modeling. Although inhibitor-enzyme interactions are very complex processes and there is a limit to accuracy in now-available computational virtual evaluation alone, more efficient molecular design can be accomplished using such interactions whose effectiveness has been confirmed experimentally.

[Crystal of a Complex Between Human Factor VIIa/Human Soluble Tissue Factor and a Low-molecular Weight Reversible Factor VIIa Inhibitor]

This refers to a crystal composed of human factor VIIa/human soluble tissue factor and a low-molecular weight reversible factor VIIa inhibitor, which belongs to the orthorhombic system of space group $P2_12_12_1$ with unit cell parameters a=71.4 Å±5%, b=82.5 Å±5%, c=123.3 Å±5% and $\alpha=\beta=\gamma=90°$ and which contains one complex between human factor VIIa/human soluble tissue factor and the reversible factor VIIa inhibitor in the asymmetric unit.

In such a complex crystal, the low-molecular weight reversible factor VIIa inhibitor is preferably a compound of Formula (1) (wherein each symbol is as defined above).

[Method for Crystallizing a Complex Between Human Factor VIIa/Human Soluble Tissue Factor and a Reversible Factor VIIa Inhibitor]

Human factor VIIa used for crystallization may be prepared as follows. Human factor VII is expressed in cells transformed with a vector encoding human factor VII, purified by column chromatography and then converted into the active form, factor VIIa, which is further purified by column chromatography. Instead of this recombinant factor VIIa, a human FVIIa formulation (NovoSeven, Novo Nordisk Pharma Ltd.) may also be used after purification by column chromatography.

Human soluble tissue factor used for crystallization may be prepared by expression in appropriate cells or microorganism cells (particularly, *E. coli* cells) transformed with a vector encoding the extracellular domain of human tissue factor, and subsequent purification by column chromatography.

The thus prepared human factor VIIa and human soluble tissue factor may be mixed in the presence of benzamidine at an excess ratio of human soluble tissue factor to human factor VIIa, and then purified by gel filtration column chromatography with a benzamidine-free buffer to give a human factor VIIa/human soluble tissue factor complex. To this complex, a low-molecular weight reversible factor VIIa inhibitor of interest for structure analysis may be added at a concentration of around 0.5 mM or at saturation concentration (if less soluble), followed by ultrafiltration to give a concentrated sample for crystallization.

To prepare a crystal, the concentrated sample for crystallization may be subjected to vapor diffusion methods at a temperature of 25° C. in a solution of 100 mM sodium cacodylate buffer (pH 5.0), 6% to 7.5% PEG4000, 5 mM $CaCl_2$ and 5% glycerol (Crystallization of Nucleic Acids and Proteins: A practical Approach, 82–90, 1992, IRL PRESS). During crystallization, it is necessary to add a seed solution prepared by crushing and diluting a crystal of a complex between a low-molecular weight irreversible or reversible factor VIIa inhibitor and human factor VIIa/human soluble tissue factor in 100 mM sodium cacodylate buffer (pH 5.0), 9% PEG4000 and 5 mM $CaCl_2$ using a homogenizer. About a month later, long rod crystals (maximum size: about 1.0 mm long×0.05 mm diameter) may be obtained for a complex between the low-molecular weight reversible factor VIIa inhibitor and human factor VIIa/human soluble tissue factor. Crystallization procedures and solution conditions are not limited to those described above only. For example, crystallization may also be accomplished by static batch methods, free interface diffusion methods or dialysis methods, in addition to vapor diffusion methods.

In such a crystallization method, the low-molecular weight reversible factor VIIa inhibitor is preferably a compound of Formula (1) (wherein each symbol is as defined above).

[Medium Carrying a Part or all of Structure Coordinate Data of a Complex Between Human Factor VIIa/Human Soluble Tissue Factor and a Low-molecular Weight Reversible Factor VIIa Inhibitor]

The coordinates of a complex between a low-molecular weight reversible factor VIIa inhibitor and human factor VIIa/human soluble tissue factor may be obtained by revealing the three-dimensional structure of this complex crystal using X-ray crystal structure analysis, one of the three-dimensional structure determination techniques. In this technique, a crystal is irradiated with monochromatized X-ray beams to collect the intensity data of diffraction spots, based on which the electron density in the crystal unit is calculated to determine the positions of individual atoms. The three-dimensional positions of individual atoms and a variable parameter representing atomic thermal vibration called the temperature factor are refined to minimize the difference between calculated (Fc) and observed (Fo) diffraction intensity data, thereby giving the final coordinate data of the crystal structure. By way of illustration, the above-mentioned procedures is applied to the following compounds disclosed herein as examples for a low-molecular weight reversible factor VIIa inhibitor to prepare crystals of their respective complexes with factor VIIa/human soluble tissue factor, followed by X-ray crystal structure analysis to clarify their binding modes with factor VIIa.

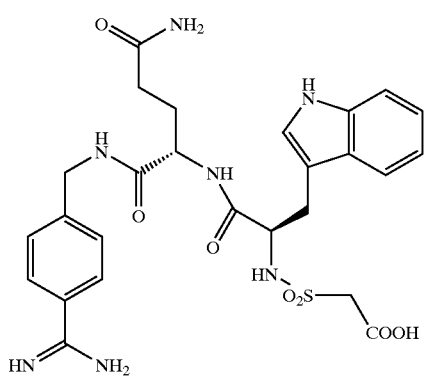

Example 146  (1)

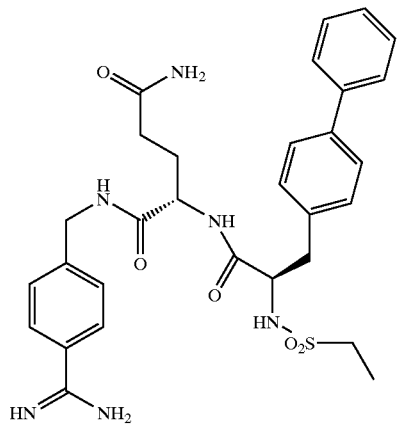

Example 65  (2)

Table 36 shows the coordinate data of a complex between Compound (1) and human factor VIIa/human soluble tissue factor, given in PDB format commonly used in the art for recording three-dimensional coordinates of proteins. In Table 36, the first line denotes the lattice type and symmetry of the crystal. The second and subsequent lines contain the structure coordinate data, including, from the left, atomic number, atom name, amino acid residue name, chain ID, amino acid residue number, X, Y, Z, occupancy, temperature factor, segment ID (equal to chain ID in this case) and atom type. The unit of coordinates is in Å. Amino acid residues are numbered on the basis of the residue number of the corresponding chymotrypsin amino acid residue, as described in Nature, vol. 380, pages 41–46, 1996. Factor VIIa are composed of two polypeptide chains: the longer one is herein referred to as the H chain and the shorter one as the L chain. In Table 36, chain ID indicates the following: H: factor VIIa H chain; L: factor VIIa L chain; T: soluble tissue factor; C: calcium ion; W: water molecule or I: low-molecular weight reversible factor VIIa inhibitor.

In the present invention, a part of coordinate data is intended to mean partial data of structure coordinates obtained by X-ray crystal structure analysis, particularly the coordinate data covering a low-molecular weight reversible factor VIIa inhibitor and its surrounding residues, expressed in three-dimensional form. Likewise, Table 37 shows the coordinate data of a complex between Compound (2) and human factor VIIa/human soluble tissue factor, obtained by X-ray crystal structure analysis. The coordinate data shown in Table 37 is given in PDB format for residues located exclusively within 10 Å of Compound (2).

A medium containing a part or all of coordinate data is intended to mean a computer memory or any disk device carrying a part or all of coordinate data in PDB format or equivalent information.

[Method for Computationally Designing a Novel Low-molecular Weight Reversible Factor VIIa Inhibitor using the Analyzed Coordinate Data]

Figure 2:
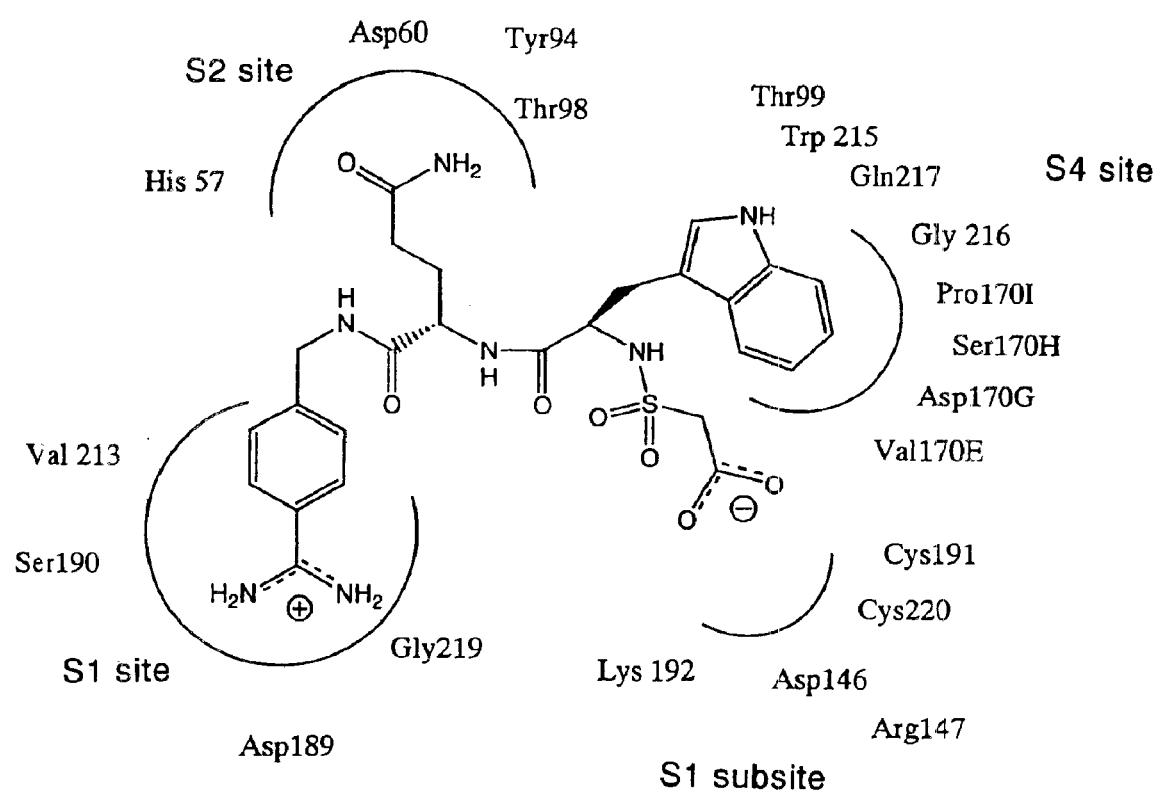
FIG. 2 shows a schematic view of the binding sites between human factor VIIa and Compound (1).

There are many computer programs for representing the three-dimensional structure of molecules such as proteins. When these software programs are combined with the structure coordinates obtained by X-ray crystal structure analysis, it is possible to make computer-aided visual representation of the structure of a complex between a low-molecular weight reversible VIIa inhibitor and human factor VIIa/human soluble tissue factor, particularly the structure surrounding the low-molecular weight reversible factor VIIa inhibitor. This allows visual recognition of interactions between the low-molecular weight reversible factor VIIa inhibitor and human FVIIa. FIG. 1 shows a three-dimensional view of Compound (1) bound to active site pockets of human factor VIIa. The peptide compound of the present invention including Compound (1) will bind to human factor VIIa at 4 sites, which are designated as S1 site, S2 site, S4 site and S1 subsite, respectively. Each active site pocket is composed of amino acid residues from the human factor VIIa H chain. Hereinafter, it is not specifically noted that amino acid residues constituting active sites are found in H chain. FIG. 2 shows a schematic view of the binding mode, along with main amino acid residues of human factor VIIa used for constituting the individual sites. The peptide compound including Compound (1) will bind to these residues via hydrogen bonding, ionic bonding, as well as van der Waals interaction. As used herein, the term "hydrogen bonding" refers to an electric dipole-electric dipole interaction in the form of X—H . . . Y, established by sandwiching hydrogen between a X—H group (wherein X represents an electronegative group) and other electronegative group Y having an unshared electron pair. This term also encompasses an interaction between ion and dipole, one of which is positively or negatively charged at physiological pH. Typically, such an interaction occurs when X and Y are N or O. The term "ionic bonding" refers to an electrostatic interaction established between a group negatively charged at physiological pH (e.g., carboxylic acid) and a group positively charged at physiological pH (e.g., amidino or amine). The term "van der Waals interaction" refers to an interaction between any atoms, which serves as a weak attraction at an appropriate distance apart, whereas it serves as a strong repulsion at a distance less than a threshold. Every atomic species has a value called the van der Waals radius. The strongest attraction is established when a distance between two atoms is the sum of their van der Waals radii.

In these software programs, it is also possible to make virtual modification of the structure of an inhibitor molecule and to make a rough energy estimation for the influence of the modified inhibitor molecule on its binding by calculating a value called the molecular force field energy. Starting from the structure coordinates determined by X-ray crystal structure analysis, it is further possible to design a novel inhibitor capable of establishing a stronger binding to human factor VIIa by making virtual modification of the inhibitor using such programs. Such strategy is advantageous in designing low-molecular weight reversible inhibitors specific to factor VIIa because it requires much less time for evaluation than actual compound synthesis. Examples of such computer programs include, but are not limited to, QUANTA, InsightII, CHARMM, Discover and Ludi (Accelrys Inc) as well as Sybyl (Tripos Inc).

In this way, virtual modifications and evaluations can be made on inhibitors using three-dimensional structure information. However, inhibitor-enzyme binding is a very complex process and there is a limit to accuracy in now-available virtual evaluation. For this reason, a plurality of low-molecular weight reversible factor VIIa inhibitors may be analyzed for the relationship between their factor VIIa-inhibiting activity or selectivity and their binding modes determined by X-ray crystal structure analysis in order to identify sites and interactions important for binding and specificity to human factor VIIa. The thus identified sites and interactions will in turn allow computer-aided design of a low-molecular weight reversible inhibitor specific to human factor VIIa. In this way, a problem of accuracy in computational virtual evaluation of the binding activity can be overcome using such experimentally confirmed information on binding modes.

Table 41 shows the hydrogen bonding between Compound (1) and S2 site of human factor VIIa. Compound (1) has an amide group at a position where it binds to the S2 site, through which hydrogen bonds are formed between its amino moiety and the side chain carboxylic acid of Asp60, the side chain hydroxy group of Tyr94 and the main chain carbonyl oxygen of Thr98. In addition, data in Table 38 indicate that the selectivity against thrombin is higher in low-molecular weight reversible factor VIIa inhibitors capable of hydrogen bonding with these amino acid residues at the S2 site than in factor VIIa inhibitors incapable of hydrogen bonding. These findings suggest that the establishment of such hydrogen bonding is advantageous in providing the specificity to human factor VIIa. Since Asp60 is negatively charged at physiological pH, the establishment of ionic bonding is also advantageous in providing the specificity to factor VIIa.

In view of the foregoing, efficient design can be achieved for an inhibitor highly specific to human factor VIIa by modifying the inhibitor structure to include a hydrogen-bearing nitrogen atom (e.g., an amide group, an amidino group, a guanidino group, aniline, amine) or a hydrogen-bearing oxygen atom (e.g., a hydroxy group) at a position capable of hydrogen bonding or ionic bonding with all or some of the side chain carboxylic acid of Asp60, the side chain hydroxy group of Tyr94 and the main chain carbonyl oxygen of Thr98, particularly with the side chain of Asp60. The molecular design may be accomplished such that a hydrogen-bondable atom of the introduced substituent is located at a distance of 2.5 to 3.5 Å from at least one of the side chain oxygen atom of Asp60, the side chain oxygen atom of Tyr94 and the main chain oxygen atom of Thr98. Likewise, an ionic bond may be introduced such that a positively-charged atom of the introduced substituent is located at a distance of 2.5 to 4.5 Å from the side chain oxygen atom of Asp60. Alternatively, after a structure coordinate of a complex between a molecule to be modified and factor VIIa or its structurally similar protease (e.g., thrombin, trypsin, factor Xa) by modeling or X-ray crystal structure analysis is fitted to the factor VIIa part of the structure coordinates of the complex between Compound (1) or (2) and human factor VIIa/human soluble tissue factor, it may allow to introduce a substituent, which has the atoms capable of hydrogen bonding at the overlap position of the amide group of Compound (1) or (2), into the molecule to be modified.

Tables 42 and 43 show the hydrogen and/or ionic bonding between Compound (1) or (2) and S1 subsite of human factor VIIa, respectively. Each of these inhibitors has a sulfonamide group and/or carboxylic acid at a position where it binds to the S1 subsite, through which a hydrogen or ionic bond is formed with the side chain amine group of Lys192. In addition, data in Table 39 indicate that higher selectivity against thrombin is given by factor VIIa inhibitors capable of hydrogen or ionic bonding with these amino acid residues at the S1 subsite, particularly by those having carboxylic acid. These findings suggest that the establishment of such hydrogen or ionic bonding is advantageous in providing the specificity to human factor VIIa.

In view of the foregoing, efficient design can be achieved for an inhibitor highly specific to human factor VIIa by modifying the inhibitor structure to include carboxylic acid or a biological equivalent thereof (e.g., sulfonic acid, sulfonamide, sulfonurea, tetrazole) at a position capable of hydrogen or ionic bonding with the side chain amino group of Lys192. The molecular design may be accomplished such that a hydrogen-bondable atom of the introduced substituent is located at a distance of 2.5 to 3.5 Å from the side chain nitrogen atom of Lys192. Likewise, an ionic bond may be introduced such that a negatively-charged atom of the introduced substituent is located at a distance of 2.5 to 4.5 Å from the side chain nitrogen atom of Lys192. Alternatively, after a structure coordinate of a complex between a molecule to be modified and factor VIIa or its structurally similar protease (e.g., thrombin, trypsin, factor Xa) by modeling or X-ray crystal structure analysis is fitted to the factor VIIa part of the structure coordinates of the complex between Compound (1) or (2) and human factor VIIa/human soluble tissue factor, it may allow to introduce a substituent, which has the atoms capable of hydrogen or ionic bonding at the overlap position of the sulfonamide group of Compound (2) or the carboxylic acid moiety of Compound (1), into the molecule to be modified. Since the position of Lys192 will vary depending on the structure of a compound bound thereto, the molecule may also be modified to establish hydrogen or ionic bonding with each position of Lys192 when the Compound (1) or the Compound (2) is bounded.

Furthermore, taking into account the flexibility of Lys192, the above strategy may also be applied to the structure adjusted to ensure a stable position of the Lys192 side chain in light of molecular force field energy.

Tables 44 and 45 show the van der Waals interaction between Compound (1) or (2) and S4 site of human factor VIIa, respectively. These compounds establish van der Waals interactions and hydrophobic interactions with the Trp215 side chain, the Gly216 main chain, the Gln217 side chain, the Val170E side chain, the Gly170F main chain, the Asp170G main chain, the Ser170H main and side chains, as well as the Pro170I side chain, among amino acid residues constituting the S4 site. In addition, data in Table 40 indicate that the selectivity against thrombin is higher in Compounds (1) and (2) than in compounds modified to have a smaller area for interactions with these amino acid residues. These findings suggest that the establishment of van der Waals and hydrophobic interactions with these amino acid residues, particularly with Val170E, Gly170F, Asp170G, Ser170H, Pro170I and Gln217, is advantageous in providing the specificity to human factor VIIa. As used herein, the term "hydrophobic interaction" refers to a phenomenon in which nonpolar groups (e.g., an alkyl group, a benzene ring) are associated in water. Water molecules surrounding such nonpolar groups are in low-entropy state and hence energetically unstable. For this reason, the nonpolar groups are associated and interacted with each other to give a smaller surface area in contact with water.

In view of the foregoing, efficient design can be achieved for an inhibitor highly specific to human factor VIIa by modifying the inhibitor structure to include a more hydrophobic group (e.g., a Bi-Phe group, a naphthyl group, an indole group) at a position capable of van der Waals and hydrophobic interactions with these amino acid residues. The molecular design may be accomplished such that atoms in the introduced substituent are located at a distance of 3.5 to 4.2 Å from atoms in these amino acid residues. Alternatively, after a structure coordinate of a complex between a molecule to be modified and factor VIIa or its structurally similar protease (e.g., thrombin, trypsin, factor Xa) by modeling or X-ray crystal structure analysis is fitted to the factor VIIa part of the structure coordinates of the complex between Compound (1) or (2) and human factor VIIa/human soluble tissue factor, it may allow to introduce a substituent, which has the hydrophobic atoms at the overlap position of the indole moiety of Compound (1) or the biphenyl moiety of Compound (2), into the molecule to be modified.

Figure 3:
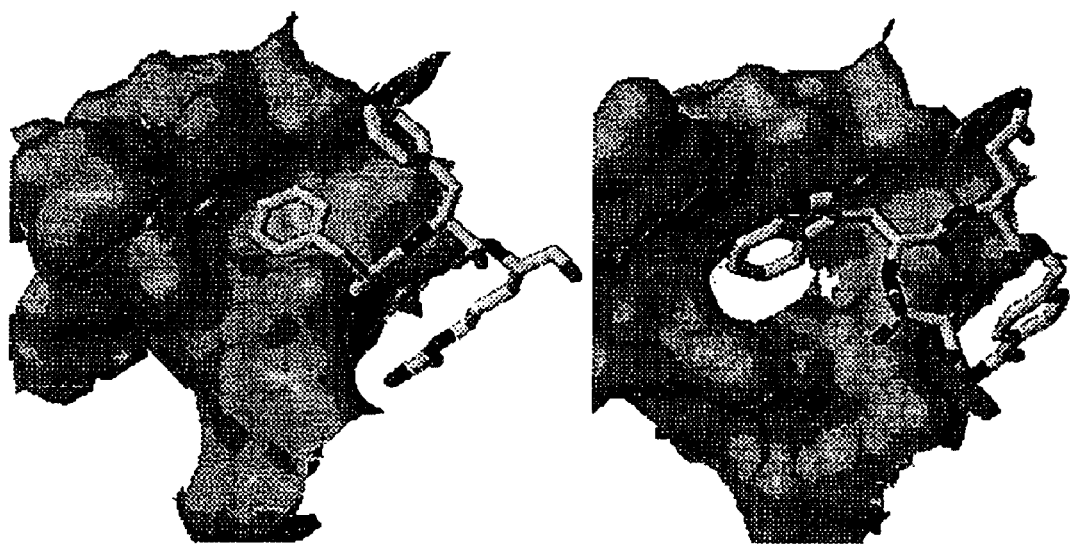
FIG. 3 shows the S4 site of human factor VIIa upon binding to D-Phe-Phe-Arg-cmk (left) or Compound (1) (right).

FIG. 3 shows the molecular surface of the S4 site in factor VIIa upon binding to D-Phe-Phe-Arg chloromethylketone (Nature, 380, 41–46, 1996, PDB=1DAN) or Compound (1). Upon binding to Compound (1), there appears a hole extendable to a space under the S4 site, which is not observed upon binding to D-Phe-Phe-Arg chloromethylketone. There has been no report showing such a hole or a compound resulting in such a hole. This behavior is caused by a change in the position of the Gln217 side chain when the indole ring of Compound (1) binds to a specific position in the S4 site. Under this hole, there is a space surrounded by the Cys168 side chain, the Ser170B side chain, the Ile176 side chain, the Cys182 side chain, the Trp 215 side chain, the Gly 216 main chain, the Gln 217 main and side chains, the His 224 main and side chains, the Phe225 main and side chains, the Gly 226 main chain, as well as the Val227 side chain. This space is hereinafter referred to as S4 subsite. By allowing a substituent to protrude through this hole, it is possible to establish hydrogen bonding, van der Waals interactions and hydrophobic interactions with these S4 subsite residues. When a comparison of three-dimensional structure is made with known blood coagulation-related serine proteases including thrombin, none of these proteases has a space corresponding to the S4 subsite; the establishment of interactions with the S4 subsite is advantageous in providing the specificity to human factor VIIa. For example, in a case where Compound (1) is used as an initial model for molecular design, a substituent introduced at the 5-position of the indole moiety may be allowed to protrude through this hole toward the direction of the S4 subsite.

In view of the foregoing, the compound structure can be modified to include a hydrophobic group (e.g., a benzene ring) at the position corresponding to the indole ring of Compound (1), thereby resulting in a hole extending to the S4 subsite. In addition, a substituent may be introduced in such a way as to protrude through this hole to establish hydrogen bonding, van der Waals interaction and hydrophobic interaction with the S4 subsite. These allow the design of an inhibitor highly specific to human factor VIIa.

In summary, a preferred low-molecular weight reversible factor VIIa inhibitor will interact with at least one of the S2 site, S1 subsite, S4 site and S4 subsite of human factor VIIa. More specifically, a preferred low-molecular weight reversible factor VIIa inhibitor comprises at least one of the partial structures shown in the following Class [A-1], [A-2], [B-1], [B-2], [B-3], [B-4], [C-1] or [C-2].

(A) The Partial Structures Shown in the Following Class [A-1] or [A-2] are Preferred for Interaction with the S2 Site:

Class [A-1]:

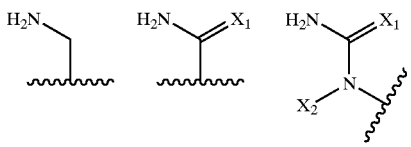

(wherein $X_1$ represents O or NH, and $X_2$ represents a hydrogen atom or a methyl group) or Class [A-2]:

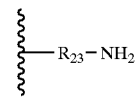

(wherein $R_{23}$ represents a 6 or 5-membered aromatic ring containing a heteroatom(s)).

In Class [A-2], particularly preferred is a partial structure wherein $R_{23}$ is a benzene ring, a pyridine ring or an imidazole ring.

(B) The Partial Structures Shown in the Following Class [B-1], [B-2], [B-31 or [B-4] are Preferred for Interaction with the S1 Subsite:

Class [B-1]:

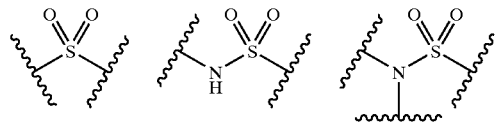

-continued

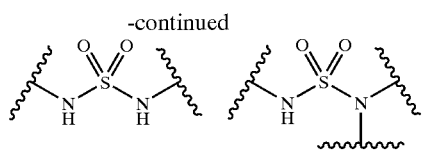

Class [B-2]:

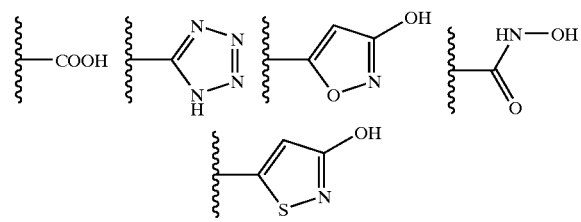

Class [B-3]:

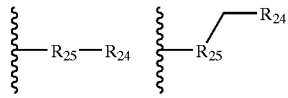

(wherein $R_{24}$ represents the same partial structures defined as Class [B-2], and $R_{25}$ represents a 6 or 5-membered aromatic ring containing a heteroatom(s), preferably represents a benzene ring) or Class [B-4]:

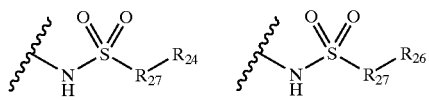

(wherein $R_{27}$ represents a $C_1$–$C_3$ alkylene group, $R_{24}$ represents the same partial structures defined as Class [B-2], and $R_{26}$ represents the same partial structures defined as Class [B-3]).

(C) The Partial Structures Shown in the Following Class [C-1] or [C-2] are Preferred for Interaction with the S4 Site:

Class [C-1]:

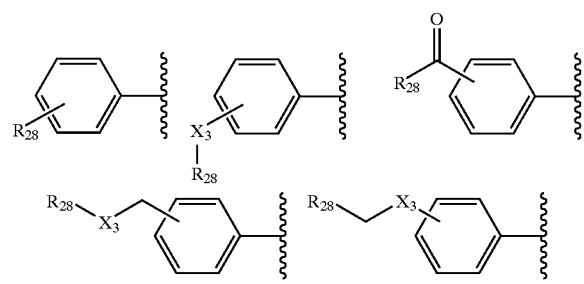

(wherein $X_3$ represents O, NH or $CH_2$, and $R_{28}$ represents a 6 or 5-membered aromatic ring containing a heteroatom(s)

Class [C-2]:

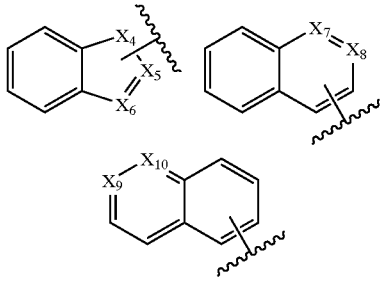

(wherein $X_4$ represents NH, S or O, and $X_5$, $X_6$, $X_7$, $X_8$, $X_9$ and $X_{10}$ each independently represent N or CH).

In Class [C-1], preferred are partial structures wherein $R_{28}$ is a benzene ring.

More specifically, a preferred low-molecular weight reversible factor VIIa inhibitor comprises: (1) any one of the partial structures shown in the above Class [A-1] or [A-2] as a partial structure capable of interacting with the S2 site as well as any one of the partial structures shown in the above Class [B-1], [B-2], [B-3] or [B-4] as a partial structure capable of interacting with the S1 subsite; (2) any one of the partial structures shown in the above Class [A-1] or [A-2] as a partial structure capable of interacting with the S2 site as well as any one of the partial structures shown in the above Class [C-1] or [C-2] as a partial structure capable of interacting with the S4 site; or (3) any one of the partial structures shown in the above Class [B-1], [B-2], [B-3] or [B-4] as a partial structure capable of interacting with the S1 subsite as well as any one of the partial structures shown in the above Class [C-1] or [C-2] as a partial structure capable of interacting with the S4 site.

A particularly preferred low-molecular weight reversible factor VIIa inhibitor comprises any one of the partial structures shown in the above Class [A-1] or [A-2] as a partial structure capable of interacting with the S2 site, any one of the partial structures shown in the above Class [B-1], [B-2], [B-3] or [B-4] as a partial structure capable of interacting with the S1 subsite, and any one of the partial structures shown in the above Class [C-1] or [C-2] as a partial structure capable of interacting with the S4 site.

EXAMPLES

The present invention will be further described in the following Examples, which are not intended to limit the scope of the invention. To explain the utility of the compounds according to the present invention, some representative compounds are tested for their biological activities including FVIIa-inhibiting activity in the Test Example.

In the following Examples, conventional abbreviations are used, as shown below:
DMF=N,N-dimethylformamide;
HOBt=1-hydroxybenzotriazole;
EDC HCl=1-(3-dimethylaminopropyl)-3-ethylcarbodiumide hydrochloride;
Boc=tertiary-butoxycarbonyl;
Ac=acetyl;
Fmoc=9-fluorenylmethoxycarbonyl; and
HPLC=high performance liquid chromatography.

NMR found in the physical property data refers to a nuclear magnetic resonance spectrum. The results are expressed as δ (delta) values in units of ppm, which are commonly used to represent chemical shifts. The measurement was carried out in the presence or absence of an internal standard (TMS; tetramethylsilane). Numerals in parentheses found next to the δ values indicate the number of hydrogen atoms, followed by the symbols s, d, t, q, m and br which represent singlet, doublet, triplet, quartet, multiplet and a broad absorption peak, respectively. Likewise, J represents a coupling constant.

MS refers to mass spectrometry. FAB and ESI are abbreviations for-ionization techniques, Fast-Atom Bombardment Ionization and ElectroSpray Ionization, respectively.

Example 1

$N^1$-4-Cyanobenzyl-$N^2$-t-butoxycarbonyl-L-glutamide

To a solution of 4-cyanobenzylamine (1.6 g, 12.2 mmol) in DMF (20 ml), t-butoxycarbonyl-L-glutamine (2.0 g, 8.1 mmol), HOBt (1.4 g, 8.9 mmol) and EDC HCl (1.7 g, 8.9 mmol) were added and stirred at room temperature under a nitrogen stream. After 12 hours, water was added to the reaction mixture, which was then extracted with ethyl acetate. The ethyl acetate layer was washed sequentially with 10% aqueous citric acid, saturated aqueous sodium bicarbonate and saturated brine, and then dried over anhydrous magnesium sulfate. Magnesium sulfate was filtered off and the filtrate was concentrated under reduced pressure to give $N^1$-4-cyanobenzyl-$N^2$-t-butoxycarbonyl-L-glutamide (2.9 g, 8.1 mmol; yield 100%).

H-NMR (CDCl$_3$) δ: 1.42 (9H, s), 1.87–2.55 (4H, m), 4.14–4.27 (1H, m), 4.49 (2H, d, J=6 Hz), 5.47–6.02 (2H, m), 7.38 (2H, d, J=8 Hz), 7.60 (2H, d, J=8 Hz).

Example 2

$N^1$-4-Cyanobenzyl-L-glutamide

To $N^1$-4-cyanobenzyl-$N^2$-t-butoxycarbonyl-L-glutamide (2.9 g, 8.1 mmol), a 4N hydrochloric acid/ethyl acetate solution (20 ml) was added and stirred at room temperature under a nitrogen stream. After 1 hour, the solvent was distilled off under reduced pressure and the residue was applied to column chromatography (Fuji Silysia NH-DM-1020; mobile phase: dichloromethane:methanol=1:1) to give $N^1$-4-cyanobenzyl-L-glutamide (2.1 g, 8.1 mmol; yield 100%).

H-NMR (CD$_3$OD) δ: 1.77–2.12 (2H, m), 2.32 (3H, t, J=7 Hz), 3.29–3.45 (4H, m), 4.49 (2H, s), 7.50 (2H, d, J=8 Hz), 7.71 (2H, d, J=8 Hz).

Example 3

1-(t-Butoxycarbonyl)-D-tryptophyl-$N^1$-(4-cyanobenzyl)-L-glutamide

To a solution of $N^1$-4-cyanobenzyl-L-glutamide (300 mg, 1.2 mmol) and N-(9-fluorenylmethoxycarbonyl)-1-(t-butoxycarbonyl)-D-tryptophan (606 mg, 1.2 mmol) in DMF (5 ml), HOBt (176 mg, 1.2 mmol) and EDC HCl (221 mg, 1.2 mmol) were added and stirred at room temperature under a nitrogen stream. After 12 hours, water was added to the reaction mixture to precipitate N-(9-fluorenylmethoxycarbonyl)-1-(t-butoxycarbonyl)-D-tryptophyl-$N^1$-(4-cyanobenzyl)-L-glutamide, which was then collected by filtration, washed with water and dried. The resulting N-(9-fluorenylmethoxycarbonyl)-1-(t-butoxycarbonyl)-D-tryptophyl-$N^1$-(4-cyanobenzyl)-L-glutamide was dissolved in dichloromethane (40 ml), to which piperidine (10 ml) was then added and stirred at room temperature under a nitrogen stream. After 5 minutes, the solvent was distilled off under reduced pressure and the residue was applied to column chromatography (Fuji Silysia NH-DM-1020; mobile phase: dichloromethane:methanol=1:0, 10:1) to give 1-(t-butoxycarbonyl)-D-tryptophyl-$N^1$-(4-cyanobenzyl)-L-glutamide (650 mg, 1.2 mmol; yield 100%).

H-NMR (CDCl$_3$) δ: 1.67 (9H, s), 1.80–2.49 (4H, m), 3.13–3.33 (2H, m), 3.70–3.79 (1H, dd, J=4, 9 Hz), 4.40 (2H, d, J=6 Hz), 4.39–4.55 (1H, m), 5.62 (1H, brs), 6.14 (1H, brs), 7.20–7.67 (9H, m), 8.07–8.17 (2H, m).

Example 4

N-(Ethylsulfonyl)-1-(t-butoxycarbonyl)-D-tryptophyl-$N^1$-(4-cyanobenzyl)-L-glutamide To a solution of 1-(t-butoxycarbonyl)-D-tryptophyl-$N^1$-(4-cyanobenzyl)-L-glutamide (300 mg, 0.55 mmol) in DMF (10 ml), triethylamine (162 mg, 1.6 mmol) and ethanesulfonyl chloride (206 mg, 1.6 mmol) were added and stirred at room temperature under a nitrogen stream. After 12 hours, the solvent was distilled off under reduced pressure and the residue was applied to flash column chromatography (Merck Silicagel 60; mobile phase: dichloromethane:methanol=10:1) to give N-(ethylsulfonyl)-1-(t-butoxycarbonyl)-D-tryptophyl-$N^1$-(4-cyanobenzyl)-L-glutamide (135 mg, 0.21 mmol; yield 38%).

H-NMR (CD$_3$OD) δ: 1.08 (3H, t, J=7 Hz), 1.70 (9H, s), 1.60–2.12 (4H, m), 2.75–3.34 (4H, m), 4.13–4.55 (4H, m), 7.24–7.78 (9H, m).

Example 5

N-(Ethylsulfonyl)-D-tryptophyl-$N^1$-(4-amidinobenzyl)-L-glutamide

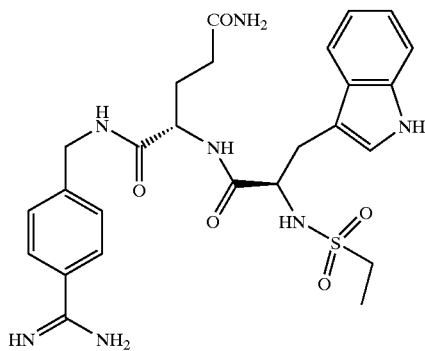

N-(Ethylsulfonyl)-1-(t-butoxycarbonyl)-D-tryptophyl-$N^1$-(4-cyanobenzyl)-L-glutamide (135 mg, 0.21 mmol) was dissolved in saturated hydrogen chloride/ethanol solution (10 ml) and allowed to stand at room temperature for 20 hours. After the solvent was removed under reduced pressure, the resulting N-(ethylsulfonyl)-D-tryptophyl-$N^1$-(4-ethoxyimino-carbonylbenzyl)-L-glutamide was dissolved in ethanol (8 ml) and further dissolved in ammonium acetate (500 mg, 6.4 mmol) and saturated ammonia/ethanol solution (1.3 ml), followed by heating at reflux. After 1 hour, the solvent was distilled off under reduced pressure and the residue was applied to column chromatography (Fuji Silysia NH-DM-1020; mobile phase: dichloromethane:methanol=1:1) to give 4-amidino-[(S)-N-[(R)-N'- ethylsulfonyltryptophyl]glutaminyl]-aminomethylbenzene (94 mg, 0.17 mmol; yield 81%).

ESI+ 556 (M++1).

H-NMR (DMSO-d6) δ: 0.85 (3H, t, J=7 Hz), 1.65–2.03 (2H, m), 2.48–3.54 (6H, m), 4.12–4.43 (4H, m), 6.70–7.75 (9H, m), 7.95 (1H, brs), 8.43 (2H, brs).

Example 6

N-{[3-(Methoxycarbonyl)benzyl]sulfonyl}-1-(t-butoxy-carbonyl)-D-tryptophyl-$N^1$-(4-cyanobenzyl)-L-glutamide To a solution of 1-(t-butoxycarbonyl)-D-tryptophyl-$N^1$-(4-cyanobenzyl)-L-glutamide (350 mg, 0.64 mmol) in DMF (10 ml), triethylamine (194 mg, 1.9 mmol) and [3-(methoxycarbonyl)benzyl]sulfonyl chloride (477 mg, 1.9 mmol) were added and stirred at room temperature under a nitrogen stream. After 12 hours, the solvent was distilled off under reduced pressure and the residue was applied to flash column chromatography (Merck Silicagel 60; mobile phase: dichloromethane:methanol=10:1) to give N-{[3-(methoxycarbonyl)benzyl]sulfonyl}-1-(t-butoxycarbonyl)-D-tryptophyl-$N^1$-(4-cyanobenzyl)-L-glutamide (407 mg, 0.21 mmol; yield 84%).

H-NMR (CD$_3$OD) δ: 1.70 (9H, s), 1.75–2.15 (4H, m), 2.65–3.42 (2H, m), 3.92 (3H, s), 3.88–4.54 (6H, m), 7.23–8.21 (13H, m).

Example 7

N-[(3-(Carboxybenzyl)sulfonyl]-D-tryptophyl-$N^1$-(4-amidinobenzyl)-L-glutamide

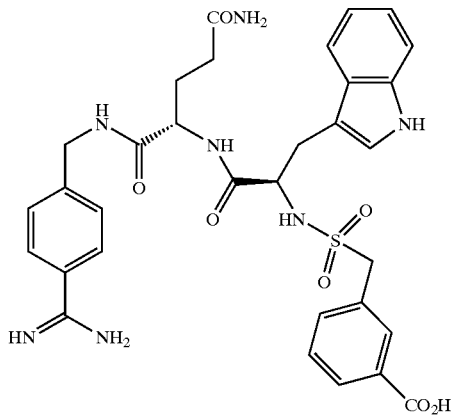

N-{[3-(Methoxycarbonyl)benzyl]sulfonyl}-1-(t-butoxycarbonyl)-D-tryptophyl-$N^1$-(4-cyanobenzyl)-L-glutamide (407 mg, 0.21 mmol) was dissolved in saturated hydrogen chloride/ethanol solution (15 ml) and allowed to stand at room temperature for 20 hours. After the solvent was removed under reduced pressure, the resulting crude product was dissolved in ethanol (16 ml) and further dissolved in ammonium acetate (1 g, 12.8 mmol) and saturated ammonia/ethanol solution (2.4 ml), followed by heating at reflux. After 1 hour, the solvent was distilled off under reduced pressure and the residue was applied to column chromatography (Fuji Silysia NH-DM-1020; mobile phase: dichloromethane:methanol=4:1, 1:1) to give a mixture of N-{[3-(methoxycarbonyl)benzyl]sulfonyl}-D-tryptophyl-$N^1$-(4-amidinobenzyl)-L-glutamide and N-{[3-(ethoxycarbonyl)-benzyl]sulfonyl}-D-tryptophyl-$N^1$-(4-amidinobenzyl)-L-glutamide. This mixture was dissolved in ethanol (2 ml), to which 2N aqueous sodium hydroxide (2 ml) was then added and stirred at room temperature. After 1 hour, the reaction mixture was adjusted to pH 6 with 1N aqueous hydrogen chloride and the precipitated product was collected by filtration. The resulting crude product was applied to preparative HPLC (YMC-pack ODS; gradient of 95% A/B to 45% A/B over 25 min, A=0.1% TFA-H$_2$O, B=0.1% TFA-CH$_3$CN) to give N-[(3-(carboxybenzyl)sulfonyl]-D-tryptophyl-$N^1$-(4-amidino-benzyl)-L-glutamide trifluoroacetate (68 mg, 0.088 mmol; yield 16%).

ESI+ 662 (M++1).

H-NMR (DMSO-d6) δ: 1.64–2.02 (4H, m), 2.90–3.21 (2H, m), 3.89–4.41 (6H, m), 6.75–7.95 (13H, m).

Example 8

N-(Benzylsulfonyl)-D-isoleucine

To a solution of D-isoleucine (3 g, 22.9 mmol) in dioxane (184 ml), 1N aqueous sodium hydroxide (23 ml) and then benzylsulfonyl chloride (6 g, 34.4 mmol) were added and stirred at room temperature. After 3 hours, the reaction mixture was adjusted to pH 2 with 2N aqueous hydrogen chloride and then extracted with ethyl acetate. The ethyl acetate layer was dried over anhydrous magnesium sulfate. After magnesium sulfate was filtered off, the filtrate was concentrated under reduced pressure and the residue was applied to flash column chromatography (Merck Silicagel 60; mobile phase: dichloromethane:methanol=10:1, 4:1) to give N-(benzyl-sulfonyl)-D-isoleucine (6.3 g, 22.2 mmol; yield 97%).

H-NMR (CDCl$_3$) δ: 0.78–1.02 (6H, m), 1.05–1.60 (2H, m), 1.68–1.92 (1H, m), 3.85 (1H, dd, J=4, 7 Hz), 4.22–4.38 (2H, m), 5.17 (1H, d, J=9 Hz), 5.97 (1H, brs), 7.26–7.48 (5H, m).

Example 9

N-(Benzylsulfonyl)-D-isoleucyl-L-methionine methyl ester

To a solution of N-(benzylsulfonyl)-D-isoleucine (6.3 g, 22.2 mmol) and L-methionine methyl ester hydrochloride (6.7 g, 33.3 mmol) in dichloromethane (100 ml), HOBt (4.1 g, 26.6 mmol), EDC HCl (5.1 g, 1.2 mmol) and N-methylmorpholine (3.4 g, 33.3 mmol) were added and stirred at room temperature under a nitrogen stream. After 12 hours, water was added to the reaction mixture, which was then extracted with ethyl acetate. The ethyl acetate layer was washed sequentially with 10% aqueous citric acid, saturated aqueous sodium bicarbonate and saturated brine, and then dried over anhydrous magnesium sulfate. After magnesium sulfate was filtered off, the filtrate was concentrated under reduced pressure and the residue was applied to flash column chromatography (Merck Silicagel 60; mobile phase: dichloromethane) to give N-(benzylsulfonyl)-D-isoleucyl-L-methionine methyl ester (6.4 g, 14.9 mmol; yield 67%).

H-NMR (CD$_3$OD) δ: 0.92–1.02 (6H, m), 1.18–1.36 (1H, m), 1.62–1.88 (2H, m), 2.00–2.28 (2H, m), 2.12 (3H, s), 2.51–2.77 (2H, m), 3.71 (3H, s), 3.83 (1H, d, J=8 Hz), 4.32 (2H, q, J=13 Hz), 4.68 (1H, dd, J=5, 9 Hz), 7.32–7.51 (5H, m).

Example 10

N-(Benzylsulfonyl)-D-tryptophyl-$N^1$-(4-aminobenzyl)-L-methioninamide

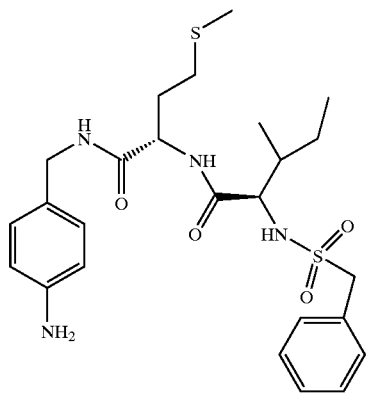

To a solution of N-(benzylsulfonyl)-D-isoleucyl-L-methionine methyl ester (6.4 g, 14.9 mmol) in ethanol (30 ml), 2N aqueous sodium hydroxide (30 ml) was added and stirred at room temperature. After 1 hour, the reaction mixture was adjusted to pH 2 with 2N aqueous hydrogen chloride and then extracted with ethyl acetate. The ethyl acetate layer was washed with saturated brine and then dried over anhydrous magnesium sulfate. Magnesium sulfate was filtered off and the filtrate was concentrated under reduced pressure to give N-(benzylsulfonyl)-D-isoleucyl-L-methionine (6.2 g, 14.9 mmol; yield 100%).

To a solution of N-(benzylsulfonyl)-D-isoleucyl-L-methionine (100 mg, 0.24 mmol) and 4-aminobenzylamine (59 mg, 0.48 mmol) in dichloromethane (5 ml), HOBt (44 mg, 0.29 mmol) and EDC HCl (56 mg, 0.29 mmol) were added and stirred at room temperature under a nitrogen stream. After 12 hours, the reaction mixture was concentrated under reduced pressure and water was added to the residue. The precipitated product was collected by filtration, washed with water and then dried. The resulting crude product was applied to column chromatography (Fuji Silysia NH-DM-1020; mobile phase: dichloromethane:methanol= 10:1) to give N-(benzyl-sulfonyl)-D-tryptophyl-$N^1$-(4-aminobenzyl)-L-methioninamide (108 mg, 0.21 mmol; yield 86%).

ESI+ 521 ($M^+$+1).

H-NMR (CD$_3$OD) δ: 0.87–1.00 (6H, m), 1.09–1.28 (1H, m), 1.57–1.83 (2H, m), 1.86–2.26 (2H, m), 2.09 (3H, s), 2.43–2.69 (2H, m), 3.71 (3H, s), 4.13–4.32 (4H, m), 4.50–4.68 (2H, m), 6.64 (2H, d, J=8 Hz), 7.01 (2H, d, J=8 Hz), 7.32–7.49 (5H, m).

Example 11

N-(Propylsulfonyl)-D-isoleucyl-3-(methylamino)-$N^1$-(4-cyanobenzyl)-L-alaninamide To N-(propylsulfonyl)-D-isoleucyl-3-[(t-butoxycarbonyl) (methyl)amino]-$N^1$-(4-cyanobenzyl)-L-alaninamide (1.6 g, 3 mmol), trifluoroacetic acid (10 ml) was added and stirred at room temperature under a nitrogen stream. After 1 hour, the reaction mixture was concentrated under reduced pressure and the residue was applied to column chromatography (Fuji Silysia NH-DM-1020; mobile phase: dichloromethane:methanol=1:0, 4:1) to give N-(propylsulfonyl)-D-isoleucyl-3-(methylamino)-$N^1$-(4-cyanobenzyl)-L-alaninamide (1.3 g, 2.9 mmol; yield 96%).

ESI+ 452 ($M^+$+1).

H-NMR (CDCl$_3$) δ: 0.79–1.23 (10H, m), 1.46–1.95 (4H, m), 2.41 (3H, s), 2.52–3.81 (4H, m), 4.33–4.52 (4H, m), 7.36 (2H, d, J=8 Hz), 7.59 (2H, d, J=8 Hz).

Example 12

N-(Propylsulfonyl)-D-isoleucyl-3-[(aminocarbonyl)(methyl)-aminol-$N^1$-(4-amidinobenzyl)-L-alaninamide

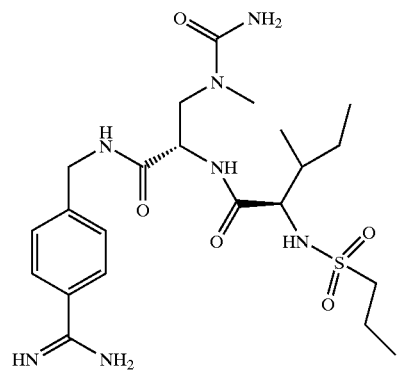

To a solution of N-(propylsulfonyl)-D-isoleucyl-3-(methylamino)-$N^1$-(4-cyanobenzyl)-L-alaninamide (500 mg, 1.0 mmol) in water (1.3 ml)/tetrahydrofuran (3 ml), potassium cyanate (243 mg, 3 mmol) was added under stirring at 50° C. and then further stirred under the same conditions. After stirring for 3 hours, water was added to the reaction mixture, which was then extracted with ethyl acetate. The ethyl acetate layer was dried over anhydrous magnesium sulfate. Magnesium sulfate was filtered off and the filtrate was concentrated under reduced pressure to give N-(propylsulfonyl)-D-isoleucyl-3-[(aminocarbonyl)(methyl)amino]-$N^1$-(4-cyanobenzyl)-L-alaninamide (430 mg, 0.87 mmol; yield 87%).

The resulting product was dissolved in saturated hydrogen chloride/ethanol solution (10 ml) and allowed to stand at room temperature for 20 hours. After the solvent was removed under reduced pressure, the resulting crude product was dissolved in saturated ammonia/ethanol solution (10 ml) and allowed to stand at room temperature for 20 hours. The solvent was distilled off under reduced pressure and the residue was applied to preparative HPLC (YMC-pack ODS: gradient of 95% A/B to 25% A/B over 10 min, A=0.1% TFA-H$_2$O, B=0.1% TFA-CH$_3$CN) to give N-(propylsulfonyl)-D-isoleucyl-3-[(aminocarbonyl)-(methyl)amino]-$N^1$-(4-amidinobenzyl)-L-alaninamide trifluoroacetate (27 mg, 0.004 mmol; yield 5%).

ESI+ 512 ($M^+$+1).

H-NMR (CD3OD) δ: 0.87–1.10 (9H, m), 1.12–1.88 (5H, m), 2.92 (3H, s), 2.87–3.12 (2H, m), 3.52 (1H, dd, J=4, 15 Hz), 3.65 (1H, d, J=8 Hz), 3.82 (1H, dd, J=9, 14 Hz), 4.43–4.67 (3H, m), 7.54 (2H, d, J=8 Hz), 7.76 (2H, d, J=8 Hz).

Example 13

N-(Benzylsulfonyl)-D-isoleucyl-$N^1$-{4-[imino(methylthio)-methyl]benzyl}-L-methioninamide N-(Benzylsulfonyl)-D-isoleucyl-$N^1$-(4-cyanobenzyl)-L-methioninamide (100 mg, 0.19 mmol) was dissolved in pyridine (5 ml) and triethylamine (0.5 ml), bubbled with a hydrogen sulfide gas for 5 minutes, and then stirred for 24 hours. After addition of ethyl acetate to the reaction mixture, the organic layer was washed sequentially with 0.5 N hydrochloric acid, saturated aqueous sodium bicarbonate and saturated brine, and then dried over sodium sulfate. The solvent was distilled off under reduced pressure and the residue was dissolved in acetonitrile, followed by addition of methyl iodide (0.14 ml, 0.94 mmol) and heating at reflux for 2 hours under a nitrogen atmosphere. The solvent was distilled off under reduced pressure and the residue was purified on a silica gel column (dichloromethane:methanol= 10:1) to give N-(benzyl-sulfonyl)-D-isoleucyl-N$^1$-{4-[imino (methylthio)methyl]benzyl}-L-methioninamide (109 mg, 0.19 mmol; yield 100%).

ESI+ 579 (M$^+$+1).

H-NMR (CD$_3$OD) δ: 0.85–0.90 (6H, m), 2.03 (3H, s), 2.40 (3H, s), 3.69 (1H, t, J=6 Hz), 4.50–4.60 (1H, m), 7.21–7.39 (8H, m), 7.60–7.64 (1H, m).

Example 14

N-(Benzylsulfonyl)-D-isoleucyl-N$^1$-{4-[hydrazino (imino)-methyl]benzyl}-L-methioninamide

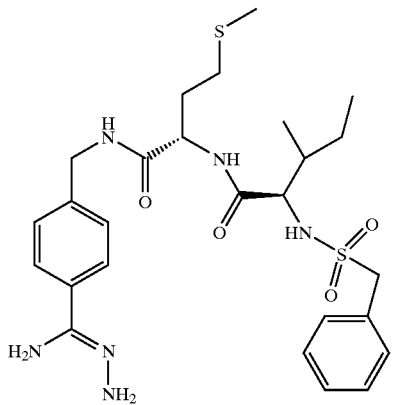

N-(Benzylsulfonyl)-D-isoleucyl-N$^1$-{4-[imino-(methylthio)methyl]benzyl}-L-methioninamide (49 mg, 0.084 mmol) was dissolved in dichloromethane (2 ml) and methanol (2 ml), to which hydrazine (0.020 ml, 0.624 mmol) was then added and stirred for 18 hours. The solvent was distilled off under reduced pressure and the residue was purified by preparative HPLC to give N-(benzylsulfonyl)-D-isoleucyl-N$^1$-{4-[hydrazino(imino)methyl]benzyl}-L-methioninamide (29 mg, 0.051 mmol; yield 61%).

ESI+ 563 (M$^+$+1).

H-NMR (CD$_3$OD) δ: 0.85–0.90 (6H, m), 1.58–1.78 (2H, m), 2.42–2.58 (2H, m), 3.63 (1H, d, J=7 Hz), 4.21 (2H, s), 4.53 (1H, brs), 7.25–7.57 (9H, m).

Example 15

N-(Benzylsulfonyl)-D-isoleucyl-N$^1$-[4-(E)-amino-(hydroxyimino)methyl]benzyl]-L-methioninamide

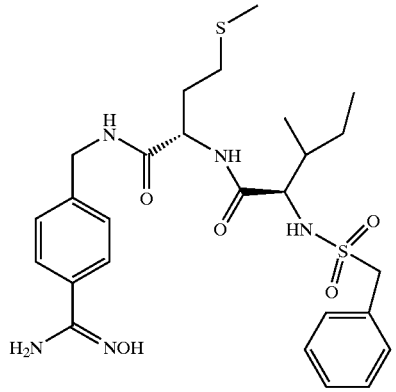

N-(Benzylsulfonyl)-D-isoleucyl-N$^1$-(4-cyanobenzyl)-L-methioninamide (100 mg, 0.19 mmol) was dissolved in ethanol (6 ml) and pyridine (0.6 ml), to which hydroxyamine hydrochloride (120 mg) was then added and stirred for 16 hours. After the solvent was distilled off under reduced pressure, the residue was dissolved in ethanol, filtered and then purified by preparative HPLC to give N-(benzylsulfonyl)-D-isoleucyl-N$^1$-[4-(E)-amino (hydroxyimino)methyl]benzyl]-L-methioninamide (1.6 mg, 0.00003 mmol; yield 1.5%).

ESI+ 564 (M$^+$+1).

H-NMR (CD$_3$OD) δ: 0.85–0.90 (6H, m), 1.50–1.70 (2H, m), 2.05 (3H, s), 2.43–2.60 (2H, m), 3.60 (1H, d, J=8 Hz), 4.20 (1H, s), 7.25–7.45 (9H, m).

Example 16

N-(Benzylsulfonyl)-D-isoleucyl-N$^1$-[4-((E)-amino{ [(t-butyloxy)carbonyl]imino}methyl)benzyl]-L-methioninamide

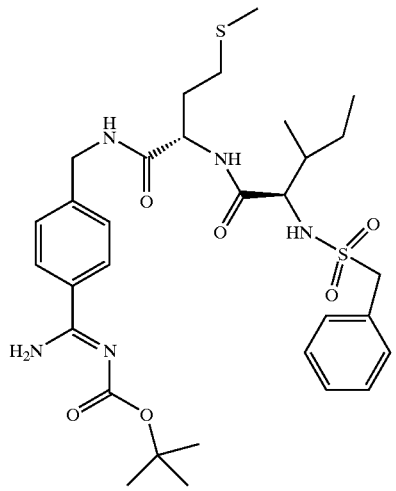

N-(Benzylsulfonyl)-D-isoleucyl-N$^1$-{4-[amino(imino)-methyl]benzyl}-L-methioninamide (20 mg, 0.032 mmol) was dissolved in dimethylformamide (0.5 ml), to which triethylamine (0.018 ml, 0.13 mmol) and di-t-butyl carbonate (14 mg, 0.065 mnol) were then added and stirred for 16 hours. After addition of ethyl acetate to the reaction mixture, the organic layer was washed with water and dried over sodium sulfate. The solvent was distilled off under reduced pressure and the residue was purified by preparative TLC (dichloromethane:methanol=10:1) to give N-(benzylsulfonyl)-D-isoleucyl-$N^1$-[4-((E)-amino-[[(t-butyloxy)carbonyl]imino]methyl)benzyl]-L-methioninamide (16 mg, 0.024 mmol; yield 76%).

ESI+ 648 ($M^+$+1).

H-NMR (CD$_3$OD) δ: 0.85–0.90 (6H, m), 1.50 (9H, s), 2.03 (3H, s), 3.68 (1H, d, J=8 Hz), 4.20 (2H, s), 7.20–7.38 (7H, m), 7.64–7.70 (2H, m).

Example 17

N-(Ethylsulfonyl)-3,5-bis(trifluoromethyl)-D-phenylalanyl-$N^1$-(4-cyanobenzyl)-L-glutamide 4-Bromo-N-(ethylsulfonyl)-D-phenylalanyl-$N^1$-(4-cyanobenzyl)-L-glutamide (30 mg, 0.052 mmol) was dissolved in tetrahydrofuran (4 ml) and water (0.4 ml). Subsequently, 3,5-bistrifluoromethylphenylboronic acid (40.2 mg, 0.156 mmol), sodium carbonate (50 mg) and tetrakis(triphenylphosphine)-palladium (30 mg, 0.026 mmol) were added to the solution, followed by heating at reflux for 2 hours under a nitrogen atmosphere. After addition of ethyl acetate to the reaction mixture, the organic layer was washed with water and dried over sodium sulfate. The solvent was distilled off under reduced pressure and the residue was purified by preparative TLC (dichloromethane:methanol=10:1) and then preparative HPLC to give N-(ethylsulfonyl)-3,5-bis(trifluoromethyl)-D-phenylalanyl-$N^1$-(4-cyanobenzyl)-L-glutamide (24 mg, 0.034 mmol; yield 65%).

ESI+ 712 ($M^+$+1).

H-NMR (CD$_3$OD) δ: 1.10 (3H, t, J=7 Hz), 1.75–1.87 (2H, m), 1.88–2.07 (2H, m), 2.82–3.10 (4H, m), 4.10–4.30 (2H, m), 4.40–4.50 (2H, m), 7.10–7.62 (9H, m), 8.10 (1H, s).

Example 18

N-(Ethylsulfonyl)-3,5-bis(trifluoromethyl)-D-phenylalanyl-$N^1$-{4-amidinobenzyl}-L-glutamide

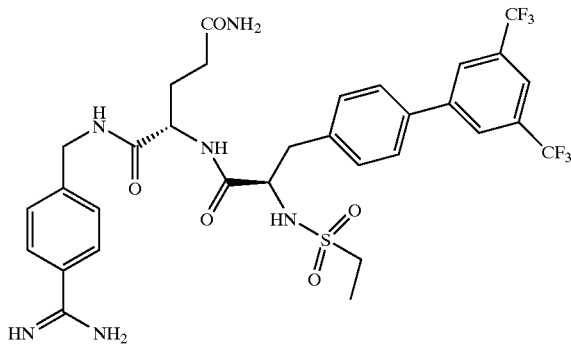

Starting with N-(ethylsulfonyl)-3,5-bis(trifluoromethyl)-D-phenylalanyl-N'-(4-cyanobenzyl)-L-glutamide, the same procedure as shown in Example 5 was repeated to give the compound of interest.

ESI+ 729 ($M^+$+1).

H-NMR (CD$_3$OD) δ: 1.05 (3H, t, J=7 Hz), 1.75–1.85 (2H, m), 1.97–2.05 (2H, m), 2.82–3.10 (4H, m), 4.15–4.22 (2H, m), 4.45 (1H, s), 7.40–7.51 (4H, m), 7.62–7.70 (3H, m), 7.90 (1H, s), 8.13 (2H, s).

Example 19

N-(t-Butoxycarbonyl)-5-{[3-(methoxycarbonyl)benzyl]oxy}-D-tryptophyl-$N^1$-(4-cyanobenzyl)-L-glutamide To a solution of N-(t-butoxycarbonyl)-5-hydroxy-D-tryptophyl-$N^1$-(4-cyanobenzyl)-L-glutamide (327 mg, 0.58 mmol) in acetone (4 ml), 3-(methoxycarbonyl)benzylbromide (267 mg, 1.2 mmol) and cesium carbonate (378 mg, 1.2 mmol) were added and stirred at reflux under a nitrogen stream. After 4 hours, the reaction mixture was filtered and the filtrate was concentrated under reduced pressure. The residue was applied to flash column chromatography (Merck Silicagel 60; mobile phase: dichloromethane:methanol=10:1) to give N-(t-butoxycarbonyl)-5-{[3-(methoxycarbonyl)benzyl]oxy}-D-tryptophyl-$N^1$-(4-cyanobenzyl)-L-glutamide (347 mg, 0.5 mmol; yield 84%).

ESI+ 711 ($M^+$+1).

H-NMR (CD$_3$OD) δ: 1.30 (9H, s), 1.50–2.08 (4H, m), 3.02–3.22 (2H, m), 3.93 (3H, s), 4.02–4.27 (2H, m), 4.39–4.55 (1H, m), 5.20 (2H, s), 6.88 (1H, dd, J=2, 9 Hz), 7.12 (1H, s), 7.19 (1H, d, J=2 Hz), 7.26 (1H, d, J=9 Hz), 7.42 (2H, d, J=8 Hz), 7.51 (1H, t, J=7 Hz), 7.66 (2H, d, J=8 Hz), 7.75 (1H, d, J=6 Hz), 7.97 (1H, d, J=6 Hz), 8.17 (1H, s).

Example 20

5-{[3-(Methoxycarbonyl)benzyl]oxy}-N-(ethylsulfonyl)-D-tryptophyl-$N^1$-(4-cyanobenzyl)-L-glutamide To a solution of N-(t-butoxycarbonyl)-5-{[3-(methoxycarbonyl)benzyl]oxy}-D-tryptophyl-$N^1$-(4-cyanobenzyl)-L-glutamide (347 mg, 0.5 mmol) in dichloromethane (10 ml), trifluoroacetic acid (10 ml) was added and stirred at room temperature under a nitrogen stream. After 1 hour, the solvent was distilled off under reduced pressure. The residue was applied to column chromatography (Fuji Silysia NH-DM-1020; mobile phase: dichloromethane:methanol=1:1) to give 5-{[3-(methoxycarbonyl)benzyl]oxy}-D-tryptophyl-N-(4-cyanobenzyl)-L-glutamide (277 mg, 0.45 mmol; yield 93%).

To a solution of 5-{[3-(methoxycarbonyl)benzyl]oxy}-D-tryptophyl-$N^1$-(4-cyanobenzyl)-L-glutamide (0.45 mmol) in DMF (10 ml), triethylamine (137 mg, 1.4 mmol) and ethanesulfonyl chloride (174 mg, 1.4 mmol) were added and stirred at room temperature under a nitrogen stream. After 2 hours, the solvent was distilled off under reduced pressure and the residue was applied to flash column chromatography (Merck Silicagel 60; mobile phase: dichloromethane:methanol=8:1) to give 5-{[3-(methoxycarbonyl)benzyl]oxy}-N-(ethylsulfonyl)-D-tryptophyl-$N^1$-(4-cyanobenzyl)-L-glutamide (158 mg, 0.22 mmol; yield 50%).

ESI+ 703 ($M^+$+1).

H-NMR (CD$_3$OD) δ: 0.94 (3H, t, J=7 Hz), 1.60–2.08 (4H, m), 2.58–3.30 (4H, m), 3.91 (3H, s), 4.02–4.27 (2H, m), 4.35–4.48 (2H, m), 5.20 (2H, s), 6.89 (1H, dd, J=2, 9 Hz), 7.12 (1H, s), 7.19 (1H, d, J=2 Hz), 7.27 (1H, d, J=9 Hz), 7.42–7.53 (3H, m), 7.65 (2H, d, J=8 Hz), 7.73 (1H, d, J=6 Hz), 7.98 (1H, d, J=6 Hz), 8.16 (1H, s).

Example 21

5-{[3-(Methoxycarbonyl)benzyl]oxy}-N-(ethylsulfonyl)-D-tryptophyl-$N^1$-{4-[amino(imino)methyl]benzyl}-L-glutamide

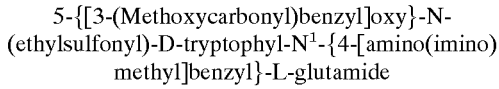

A solution of 5-{[3-(methoxycarbonyl)benzyl]oxy}-N-(ethylsulfonyl)-D-tryptophyl-$N^1$-(4-cyanobenzyl)-L-glutamide (158 mg, 0.22 mmol) in pyridine (10 ml) and triethylamine (2 ml) was bubbled with a hydrogen sulfide gas. After bubbling for 30 minutes, the solution was allowed to stand. After 12 hours, water/ethyl acetate was added to the reaction mixture and the aqueous layer was adjusted to pH 4 with 2N aqueous hydrogen chloride, followed by extraction. The organic layer was washed with saturated brine and then dried over anhydrous magnesium sulfate. Magnesium sulfate was filtered off and the filtrate was concentrated under reduced pressure.

The residue was dissolved in acetone (10 ml), to which methyl iodide (312 mg, 2.2 mmol) was then added and stirred at 50° C. under a nitrogen stream. After 1 hour, the reaction mixture was concentrated under reduced pressure.

The residue was dissolved again in methanol (10 ml), followed by addition of ammonium acetate (170 mg, 2.2 mmol) and heating at reflux under a nitrogen stream. After 4 hours, the solvent was distilled off under reduced pressure and the residue was applied to column chromatography (Fuji Silysia NH-DM-1020; mobile phase: dichloromethane:methanol=4:1, 2:1) to give 5-{[3-(methoxycarbonyl)benzyl]oxy}-N-(ethylsulfonyl)-D-tryptophyl-$N^1$-{4-[amino(imino)methyl]benzyl}-L-glutamide (124 mg, 0.17 mmol; yield 78%).

ESI+ 720 ($M^+$+1).

H-NMR (CD$_3$OD) δ: 0.94 (3H, t, J=7 Hz), 1.64–2.10 (4H, m), 2.55–3.30 (4H, m), 3.89 (3H, s), 4.08–4.42 (4H, m), 5.18 (2H, s), 6.87 (1H, dd, J=2, 9 Hz), 7.15 (1H, s), 7.20–7.76 (8H, m), 7.95 (1H, d, J=6 Hz), 8.14 (1H, s).

Example 22

5-[(3-Carboxybenzyl)oxy]-N-(ethylsulfonyl)-D-tryptophyl-$N^1$-{4-[amino(imino)methyl]benzyl}-L-glutamide

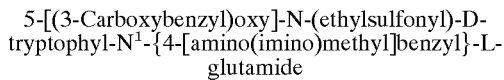

To a solution of 5-{[3-(methoxycarbonyl)benzyl]oxy}-N-(ethylsulfonyl)-D-tryptophyl-$N^1$-{4-[amino(imino)methyl]benzyl}-L-glutamide (124 mg, 0.17 mmol) in ethanol (3 ml), 1N aqueous sodium hydroxide (3 ml) was added and stirred at room temperature. After 2 hours, the reaction mixture was adjusted to pH 6 with 1N aqueous hydrogen chloride and then concentrated under reduced pressure. The residue was applied to preparative HPLC (YMC-pack ODS: gradient of 95% A/B to 25% A/B over 10 min, A=0.1% TFA-H$_2$O, B=0.1% TFA-CH$_3$CN) to give 5-[(3-carboxybenzyl)oxy]-N-(ethylsulfonyl)-D-tryptophyl-$N^1$-{4-[amino(imino)methyl]benzyl}-L-glutamide (85 mg, 0.1 mmol; yield 61%).

ESI+ 706 ($M^+$+1).

H-NMR (CD$_3$OD) δ: 0.97 (3H, t, J=7 Hz), 1.59–2.07 (4H, m), 2.55–3.28 (4H, m), 3.89 (3H, s), 4.10–4.54 (4H, m), 5.19 (2H, s), 6.90 (1H, dd, J=2, 9 Hz), 7.16 (1H, s), 7.23 (1H, d, J=2 Hz), 7.27 (1H, d, J=9 Hz), 7.50–8.00 (7H, m), 8.16 (1H, s).

Examples 23 to 182

The compounds of Examples 23 to 182 were prepared according to Examples 1 to 22 and the reaction schemes mentioned above. Tables 1 to 34 summarize the chemical structures and instrumental analysis data of these compounds. In the tables, Reagent 2, Reagent 5, Intermediate 9 and others are the same as the corresponding reagents and intermediates shown in the above reaction schemes.

TABLE 1

| Example | Reagent 2 | Reagent 5 | Reagent 8 | Structure MS |
|---|---|---|---|---|
| 23 | | | | 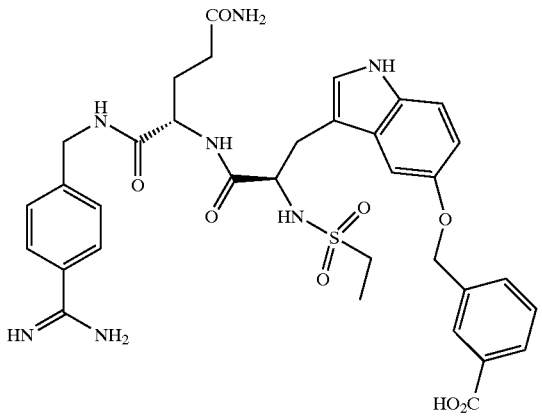<br>ESI+ 394 ($M^+$ + 1) |

TABLE 1-continued

| Example | Reagent 2 | Reagent 5 | Reagent 8 | Structure MS |
|---------|-----------|-----------|-----------|--------------|
| 24 | | | | FAB+ 560 (M+ + 1) |
| 25 | | | | FAB+ 532 (M+ + 1) |
| 26 | | | | ESI+ 504 (M+ + 1) |

TABLE 1-continued

| Example | Reagent 2 | Reagent 5 | Reagent 8 | Structure MS |
|---|---|---|---|---|
| 27 | (structure: HO2C—C(NHBoc)—CH2CH2CH2—OAc) | (structure: HO2C—C(NHBoc)—CH(CH3)2, valine-like) | (structure: benzyl-CH2-SO2-Cl) | (product structure) FAB+ 518 (M⁺ + 1) |

TABLE 2

| Example | Reagent 2 | Reagent 5 | Reagent 8 | Structure MS |
|---|---|---|---|---|
| 28 | (structure: HO2C—C(NHBoc)—CH2CH(CH3)2, leucine) | (structure: HO2C—C(NHFmoc)—CH(OtBu)CH3, threonine derivative) | | (product structure) FAB+ 364 (M⁺ + 1) |
| 29 | (structure: HO2C—C(NHBoc)—(4-hydroxyphenyl)) | (structure: HO2C—C(NHBoc)—CH(CH3)2, valine) | | (product structure) ESI+ 398 (M⁺) |

TABLE 2-continued

| Example | Reagent 2 | Reagent 5 | Reagent 8 | Structure MS |
|---|---|---|---|---|
| 30 | | | | ESI+ 554 (M⁺ + 1) |
| 31 | | | | ESI+ 583 (M⁺ + 1) |
| 32 | | | | ESI+ 518 (M⁺ + 1) |

TABLE 3

| Example | Reagent 2 | Reagent 5 | Reagent 8 | Structure MS |
|---|---|---|---|---|
| 33 | | | | ESI+ 518 (M⁺ + 1) |
| 34 | | | | ESI+ 504 (M⁺ + 1) |
| 35 | | | | ESI+ 561 (M⁺ + 1) |

TABLE 3-continued

| Example | Reagent 2 | Reagent 5 | Reagent 8 | Structure MS |
|---|---|---|---|---|
| 36 | (L-Leu-NHBoc) | (Thr(tBu)-NHFmoc) | propylsulfonyl chloride | ESI+ 470 (M⁺ + 1) |
| 37 | (L-Leu-NHBoc) | (Thr(tBu)-NHFmoc) | ethylsulfonyl chloride | ESI+ 456 (M⁺ + 1) |

TABLE 4

| Example | Reagent 2 | Reagent 5 | Reagent 8 | Structure MS |
|---|---|---|---|---|
| 38 | (L-Leu-NHBoc) | (Thr(tBu)-NHFmoc) | methylsulfonyl chloride | ESI+ 442 (M⁺ + 1) |

TABLE 4-continued

| Example | Reagent 2 | Reagent 5 | Reagent 8 | Structure MS |
|---------|-----------|-----------|-----------|--------------|
| 39 | | | | FAB+ 500 (M⁺ + 1) |
| 40 | | | | FAB+ 548 (M⁺ + 1) |
| 41 | | | | FAB+ 394 (M⁺ + 1) |

TABLE 4-continued

| Example | Reagent 2 | Reagent 5 | Reagent 8 | Structure MS |
|---------|-----------|-----------|-----------|--------------|
| 42 | | | | FAB+ 391 (M⁺ + 1) |

TABLE 5

| Example | Reagent 2 | Reagent 5 | Reagent 8 | Structure MS |
|---------|-----------|-----------|-----------|--------------|
| 43 | | | | FAB+ 483 (M⁺ + 1) |
| 44 | | | | FAB+ 531 (M⁺ + 1) |

TABLE 5-continued

| Example | Reagent 2 | Reagent 5 | Reagent 8 | Structure MS |
|---|---|---|---|---|
| 45 | (H₂NOC-CH₂-C(NHBoc)-CO₂H) | (iBu-C(NHBoc)-CO₂H) | | ESI+ 377 (M⁺ + 1) |
| 46 | (4-HO-C₆H₄-C(NHBoc)-CO₂H) | (iBu-C(NHBoc)-CO₂H) | | FAB+ 412 (M⁺ + 1) |
| 47 | (H₂NOC-CH₂CH₂-C(NHBoc)-CO₂H) | (iBu-C(NHBoc)-CO₂H) | propylsulfonyl chloride | FAB+ 497 (M⁺ + 1) |

TABLE 6

| Example | Reagent 2 | Reagent 5 |
|---|---|---|
| 48 | (H₂NOC-CH₂CH₂-C(NHBoc)-CO₂H) | (iBu-C(NHBoc)-CO₂H) |

TABLE 6-continued
| | | |
|---|---|---|
| 49 | 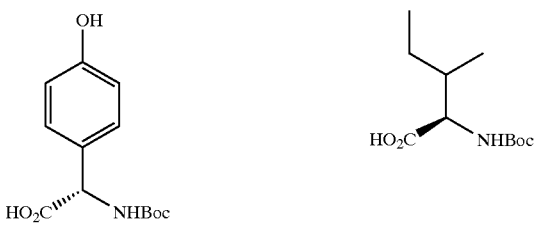 | 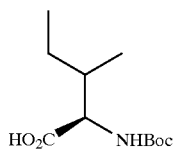 |
| 50 | 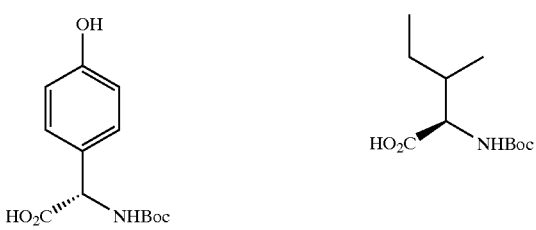 | 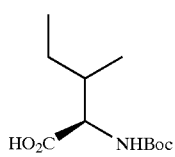 |
| 51 |  | 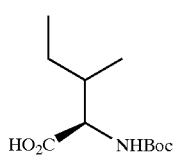 |
| 52 |  | 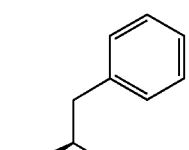 |
| Example | Reagent 8 | Structure MS |
|---|---|---|
| 48 | 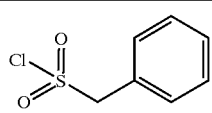 | 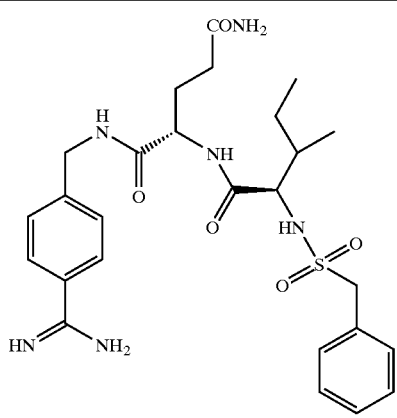<br>FAB+ 526 (M⁺ + 1) |

TABLE 6-continued
49 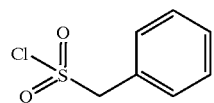 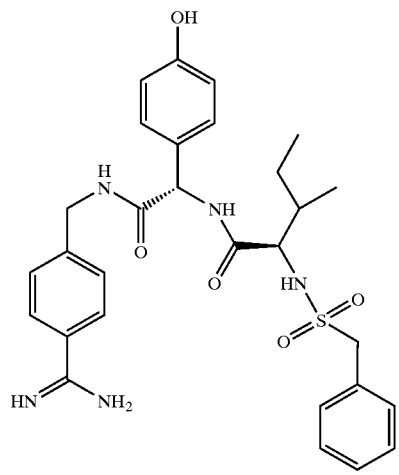
FAB+ 566 (M⁺ + 1)
50 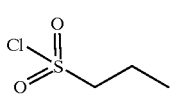 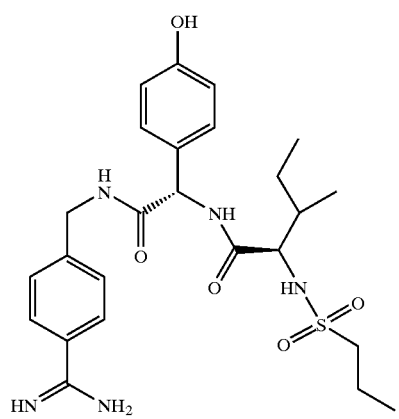
ESI+ 518 (M⁺ + 1)
51 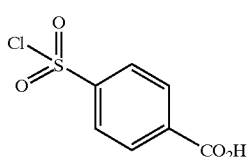 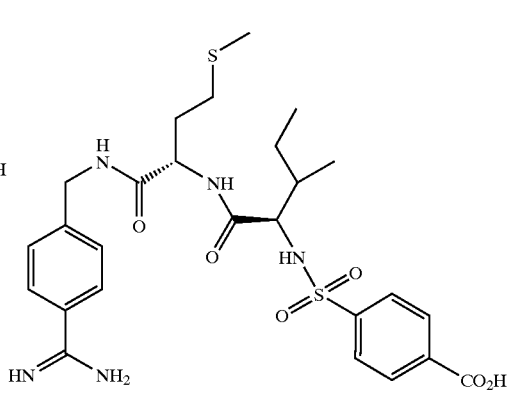
ESI+ 578 (M⁺ + 1)

TABLE 6-continued
52 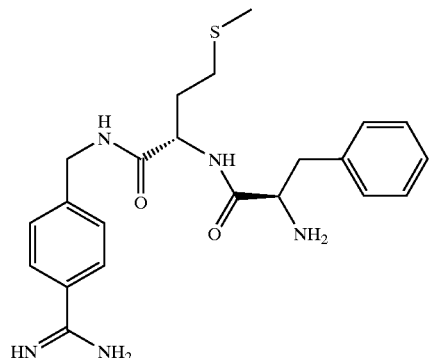
FAB+ 428 (M⁺ + 1)
TABLE 7
| Example | Reagent 2 | Reagent 5 |
| --- | --- | --- |
| 53 | HO₂C(NHBoc)–CH–(CH₂)₃–CONH₂ | HO₂C–CH(NHBoc)–CH(CH₃)₂ (Val-Boc) |
| 54 | HO₂C–CH(NHBoc)–CH₂CH₂SCH₃ (Met-Boc) | HO₂C–CH(NHBoc)–CH₂Ph (Phe-Boc) |
| 55 | HO₂C–CH(NHBoc)–CH₂CH₂SCH₃ | HO₂C–CH(NHBoc)–CH₂Ph |
| 56 | HO₂C–CH(NHBoc)–CH₂CH₂SCH₃ | HO₂C–CH(NHBoc)–CH₂Ph |
| 57 | HO₂C–CH(NHBoc)–CH₂CH₂SCH₃ | HO₂C–CH(NHBoc)–CH₂Ph |

TABLE 7-continued

| Example | Reagent 8 | Structure MS |
|---|---|---|
| 53 | propane-1-sulfonyl chloride | FAB+ 497 (M⁺ + 1) |
| 54 | phenylmethanesulfonyl chloride | FAB+ 582 (M⁺ + 1) |
| 55 | propane-1-sulfonyl chloride | FAB+ 534 (M⁺ + 1) |

TABLE 7-continued
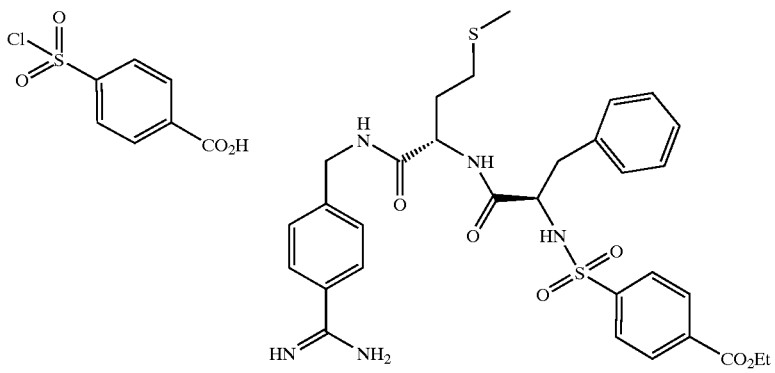
TABLE 8
| Example | Reagent 2 | Reagent 5 |
|---------|-----------|-----------|
| 58 | | |
| 59 | | |
| 60 | | |
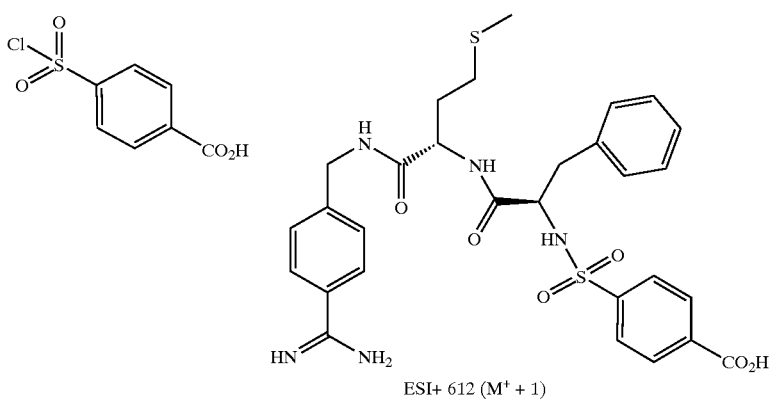

TABLE 8-continued
| | | |
|---|---|---|
| 61 |  | |
| 62 | 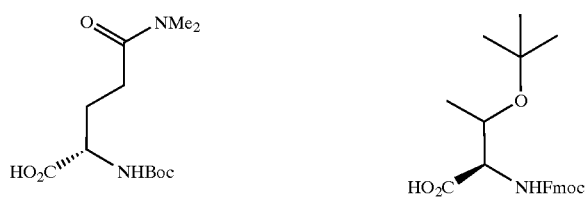 | |
| Example | Reagent 8 | Structure MS |
|---|---|---|
| 58 | 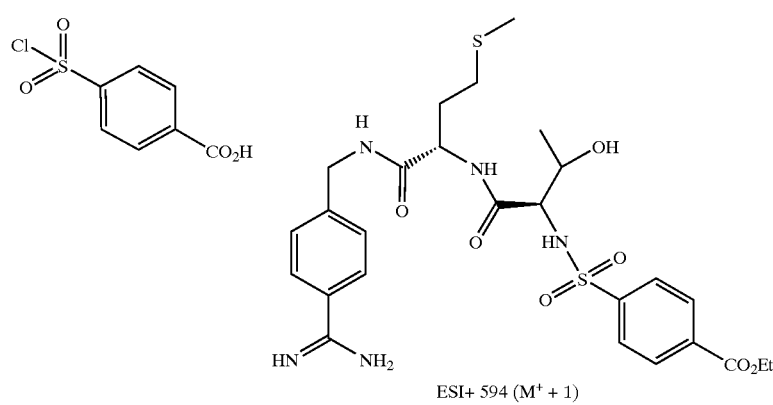 | ESI+ 594 (M⁺ + 1) |
| 59 | 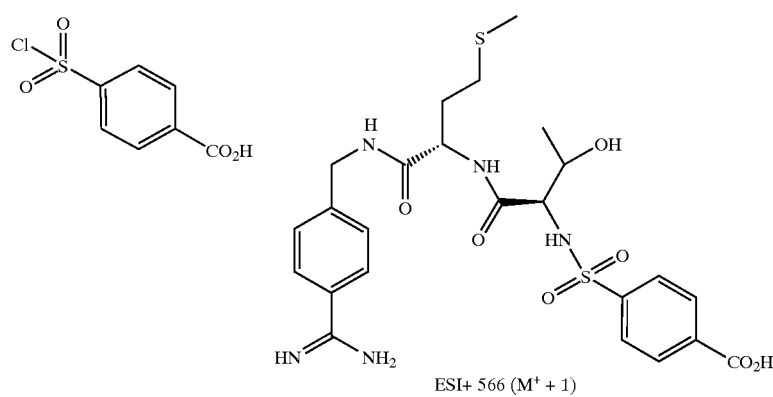 | ESI+ 566 (M⁺ + 1) |

TABLE 8-continued
| 60 | 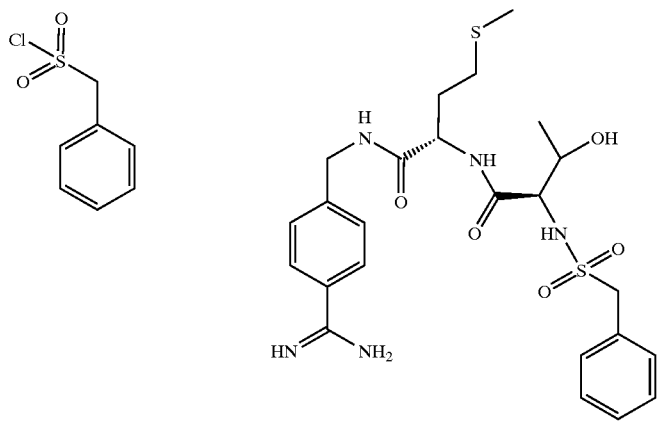 |
ESI+ 536 (M⁺ + 1)
| 61 | 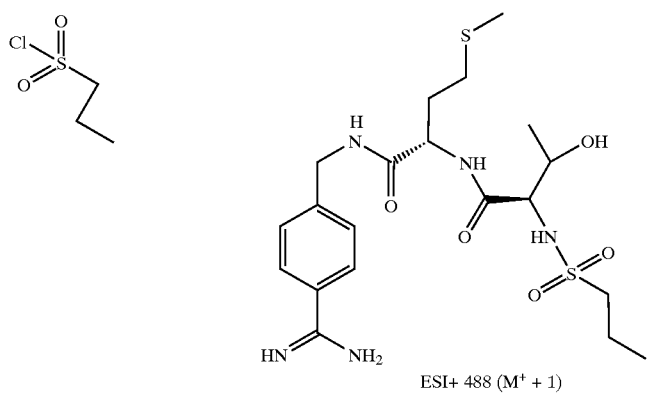 |
ESI+ 488 (M⁺ + 1)
| 62 | 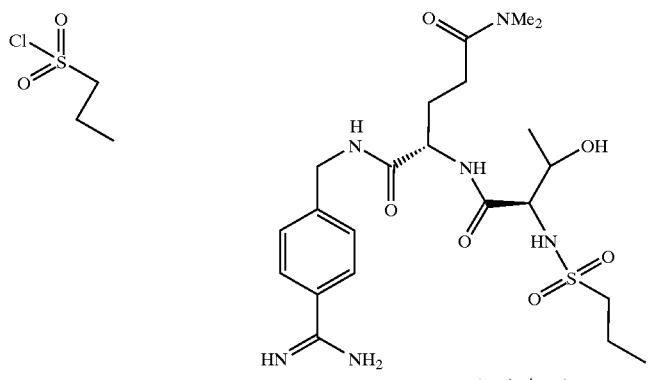 |
FAB+ 513 (M⁺ + 1)

TABLE 9
| Example | Reagent 2 | Reagent 5 |
|---|---|---|
| 63 | 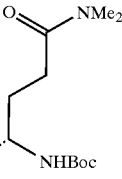 | 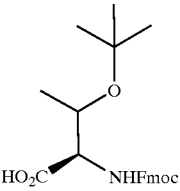 |
| 64 | 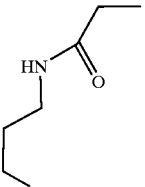 | 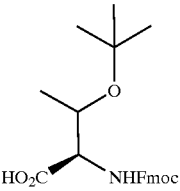 |
| 65 | 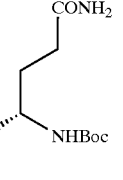 | 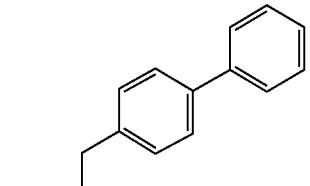 |
| 66 | 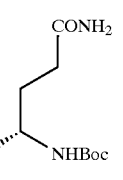 | 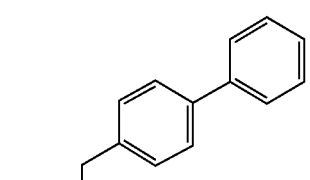 |
| 67 | 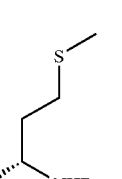 | 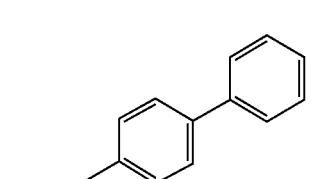 |

TABLE 9-continued

| Example | Reagent 8 | Structure MS |
|---|---|---|
| 63 | benzylsulfonyl chloride | FAB+ 561 (M$^+$ + 1) |
| 64 | propanesulfonyl chloride | ESI+ 512 (M$^+$ + 1) |
| 65 | ethanesulfonyl chloride | ESI+ 593 (M$^+$ + 1) |

TABLE 9-continued
66 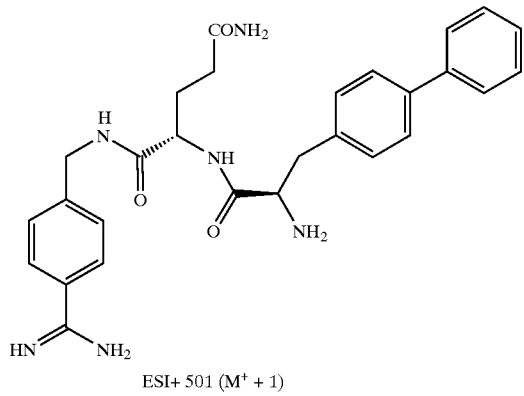
ESI+ 501 (M⁺ + 1)
67 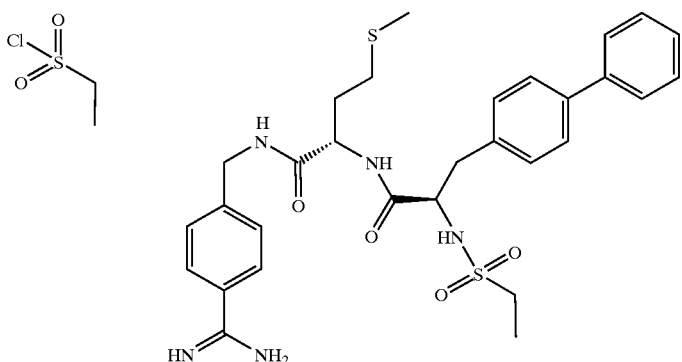
ESI+ 596 (M⁺ + 1)
TABLE 10
| Example | Reagent 2 | Reagent 5 |
| --- | --- | --- |
| 68 | | |
| 69 | | |

TABLE 10-continued

| Example | Reagent 8 | Structure MS |
|---|---|---|
| 70 | (L-glutamine, Boc-protected: CONH2, HO2C, NHBoc) | (Boc-protected biphenylalanine: HO2C, NHBoc, 4-biphenyl) |
| 71 | (L-asparagine, Boc-protected: CONH2, HO2C, NHBoc) | (Boc-protected 1-naphthylalanine: HO2C, NHBoc) |
| 72 | (L-asparagine, Boc-protected: CONH2, HO2C, NHBoc) | (Boc-protected 2-naphthylalanine: HO2C, NHBoc) |
| 68 | propanesulfonyl chloride | ESI+ 610 (M+ + 1) |
| 69 | | ESI+ 438 (M+ + 1) |

TABLE 10-continued
| 70 | 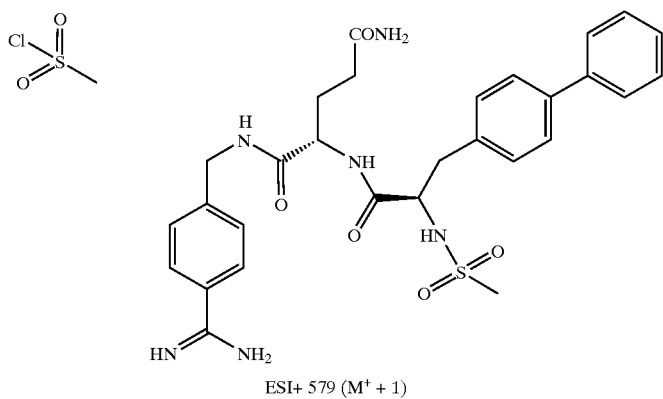 |
|---|---|
| | ESI+ 579 (M⁺ + 1) |
| 71 | 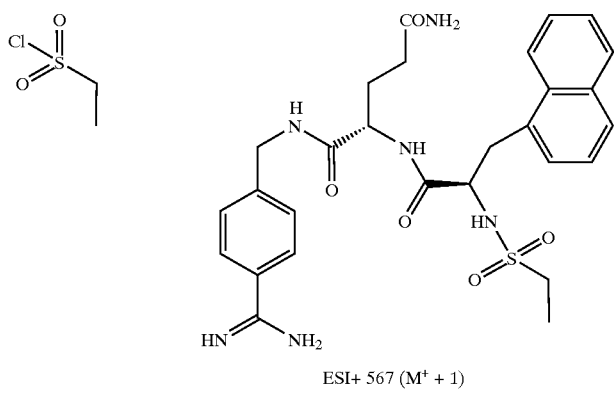 |
|---|---|
| | ESI+ 567 (M⁺ + 1) |
| 72 | 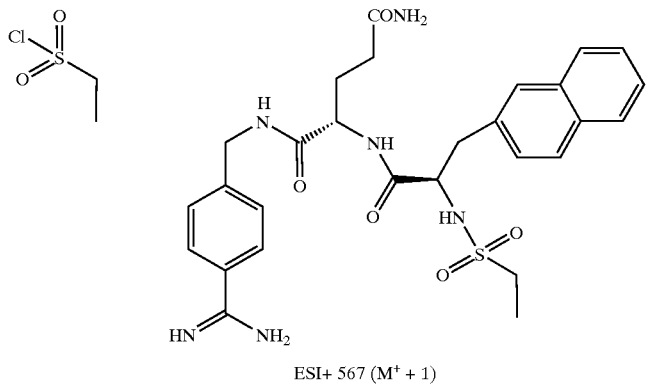 |
|---|---|
| | ESI+ 567 (M⁺ + 1) |
TABLE 11
| Example | Reagent 2 | Reagent 5 | Reagent 8 |
|---|---|---|---|
| 73 | 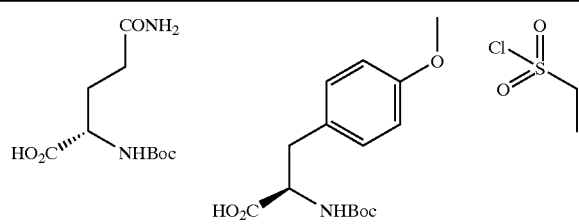 | | |

TABLE 11-continued
| | | | |
|---|---|---|---|
| 74 | 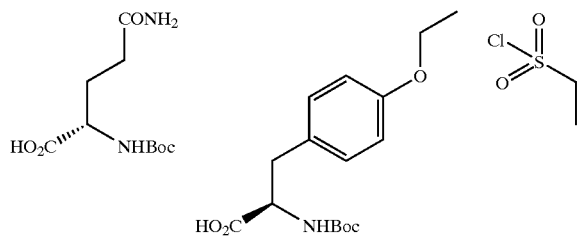 | | |
| 75 | 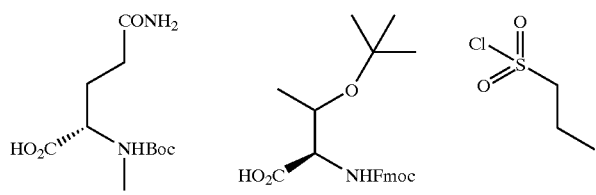 | | |
| 76 | 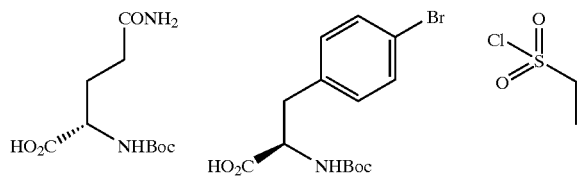 | | |
| 77 | 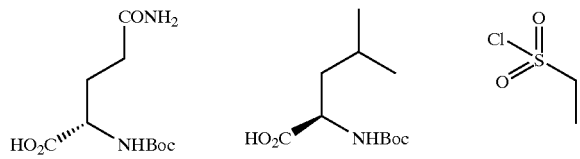 | | |
| Example | Structure MS |
|---|---|
| 73 | 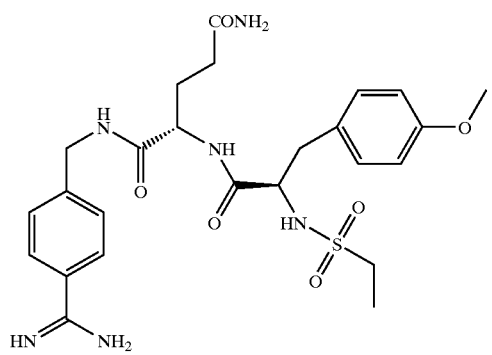<br>ESI + 547 (M⁺+ 1) |

TABLE 11-continued
| 74 | 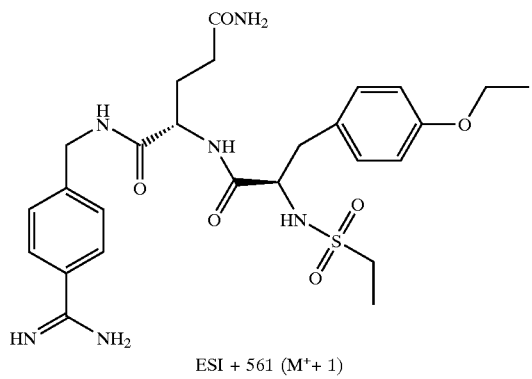 ESI + 561 (M$^+$+ 1) |
| --- | --- |
| 75 | 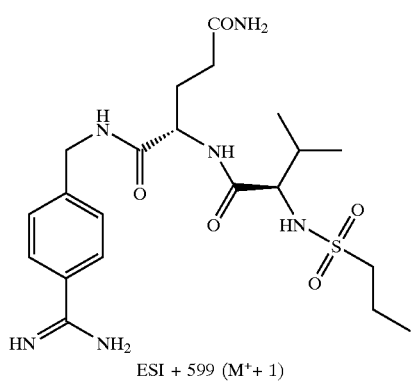 ESI + 599 (M$^+$+ 1) |
| 76 | 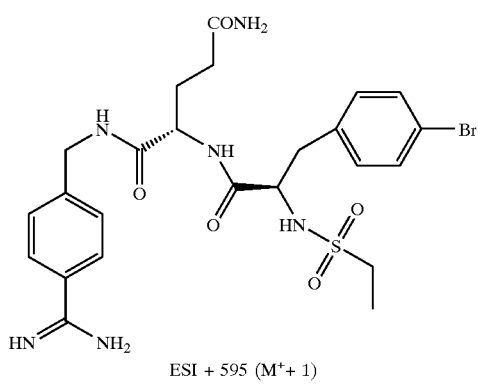 ESI + 595 (M$^+$+ 1) |
| 77 | 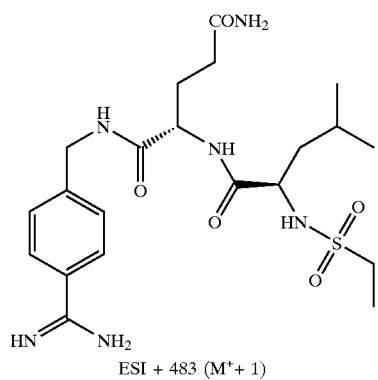 ESI + 483 (M$^+$+ 1) |

TABLE 12

| Example | Reagent 2 | Reagent 5 | Reagent 8 | Structure MS |
|---|---|---|---|---|
| 78 | (Glu-CONH2, NHBoc) | 4-tert-butylphenyl-Ala, NHBoc | ethanesulfonyl chloride | ESI + 573 (M⁺ + 1) |
| 79 | (Glu-CONH2, NHBoc) | homophenyl-Ala, NHBoc | ethanesulfonyl chloride | ESI + 531 (M⁺ + 1) |
| 80 | (Glu-CONH2, NHBoc) | 1-methyl-Trp, NHBoc | ethanesulfonyl chloride | ESI + 570 (M⁺ + 1) |
| 81 | (Glu-CONH2, NHBoc) | 4-benzoylphenyl-Ala, NHBoc | ethanesulfonyl chloride | ESI + 621 (M⁺ + 1) |

TABLE 12-continued

| Example | Reagent 2 | Reagent 5 | Reagent 8 | Structure MS |
|---|---|---|---|---|
| 82 | (L-glutamine derivative, HO₂C–CH(NHBoc)–CH₂CH₂–CONH₂) | (5-methyl tryptophan derivative, HO₂C–CH(NHBoc)–CH₂–(5-methylindol-3-yl)) | ethanesulfonyl chloride (Cl–SO₂–CH₂CH₃) | (product structure) ESI + 570 (M⁺ + 1) |

TABLE 13

| Example | Reagent 2 | Reagent 5 | Reagent 8 |
|---|---|---|---|
| 83 | HO₂C–CH(NHBoc)–CH₂CH₂–CONH₂ | 5-propoxy tryptophan derivative (HO₂C–CH(NHBoc)–CH₂–(5-propoxyindol-3-yl)) | ethanesulfonyl chloride |
| 84 | HO₂C–CH(NHBoc)–CH₂CH₂–CONH₂ | N-(phenylsulfonyl)tryptophan derivative | ethanesulfonyl chloride |
| 85 | HO₂C–CH(NHBoc)–CH₂CH₂–CO₂Et | HO₂C–CH(NHBoc)–CH(CH₃)₂ (valine derivative) | benzylsulfonyl chloride |

TABLE 13-continued
| | | | |
|---|---|---|---|
| 86 | 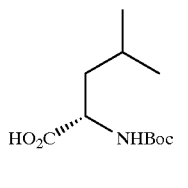 | 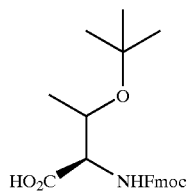 | 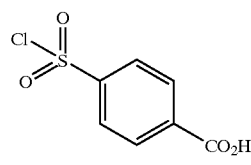 |
| 87 | 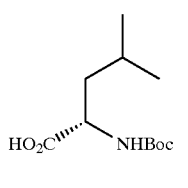 | 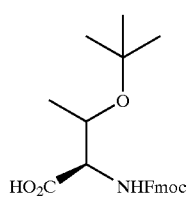 | 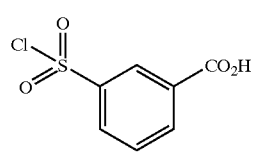 |
| Example | Structure MS |
|---|---|
| 83 | 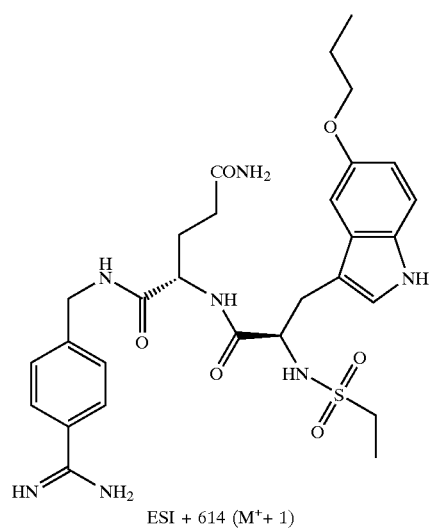<br>ESI + 614 (M⁺+ 1) |
| 84 | 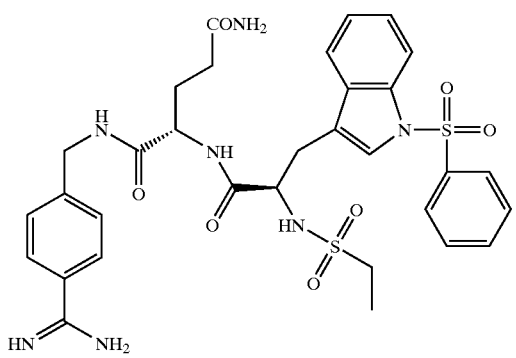<br>ESI + 696 (M⁺+ 1) |

TABLE 13-continued
85
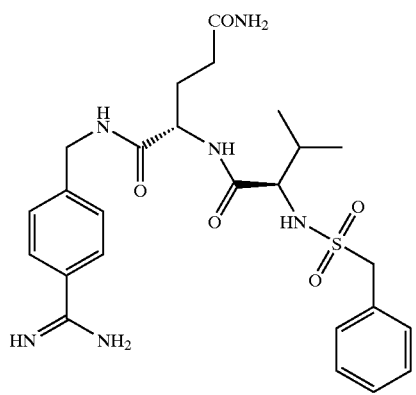
FAB + 532 (M⁺+ 1)
86
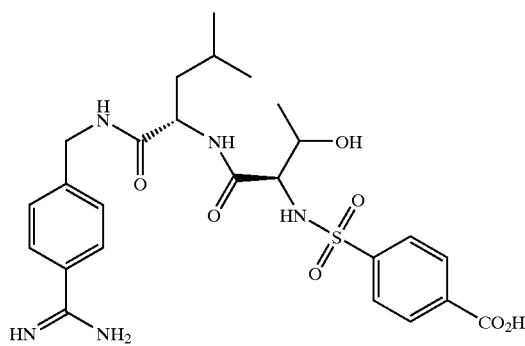
FAB + 548 (M⁺+ 1)
87
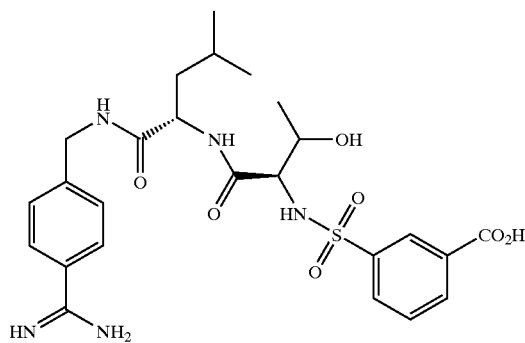
FAB + 548 (M⁺+ 1)

TABLE 14

| Example | Reagent 2 | Reagent 5 | Reagent 8 | Structure MS |
|---------|-----------|-----------|-----------|--------------|
| 88 | | | | ESI + 469 (M$^+$+ 1) |
| 89 | | | | ESI + 471 (M$^+$+ 1) |
| 90 | | | | ESI + 550 (M$^+$+ 1) |

TABLE 14-continued

| Example | Reagent 2 | Reagent 5 | Reagent 8 | Structure MS |
|---|---|---|---|---|
| 91 | | | | ESI + 550 (M⁺+ 1) |
| 92 | | | | ESI + 550 (M⁺+ 1) |

TABLE 15

| Example | Reagent 2 | Reagent 5 | Reagent 8 | Structure MS |
|---|---|---|---|---|
| 93 | | | | ES1+ 608 (M⁺+ 1) |

TABLE 15-continued

| Example | Reagent 2 | Reagent 5 | Reagent 8 | Structure MS |
|---|---|---|---|---|
| 94 | | | | ESI + 594 (M⁺ + 1) |
| 95 | | | | ESI + 580 (M⁺ + 1) |
| 96 | | | | ESI + 502 (M⁺ + 1) |

TABLE 15-continued

| Example | Reagent 2 | Reagent 5 | Reagent 8 | Structure MS |
|---|---|---|---|---|
| 97 | | | | ESI + 592 (M⁺ + 1) |

TABLE 16

| Example | Reagent 2 | Reagent 5 | Reagent 8 |
|---|---|---|---|
| 98 | | | |
| 99 | | | |
| 100 | | | |

TABLE 16-continued
| 101 | 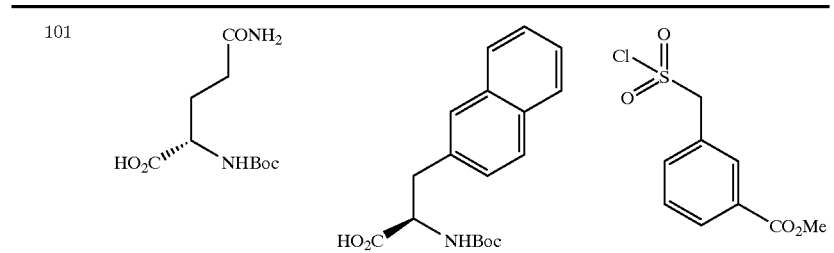 |
| 102 | 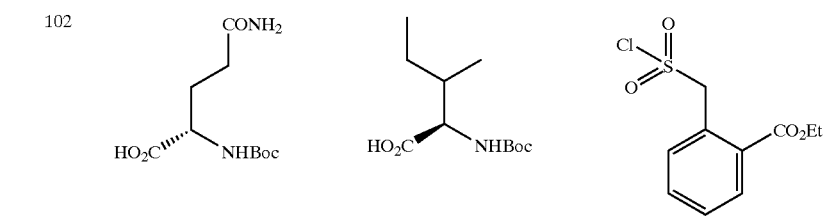 |
| Example | Structure MS |
|---|---|
| 98 | 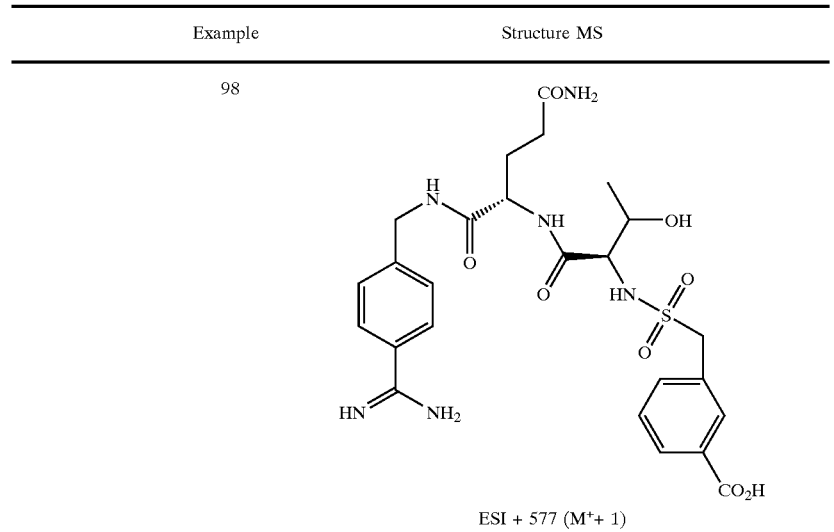<br>ESI + 577 (M⁺+ 1) |
| 99 | 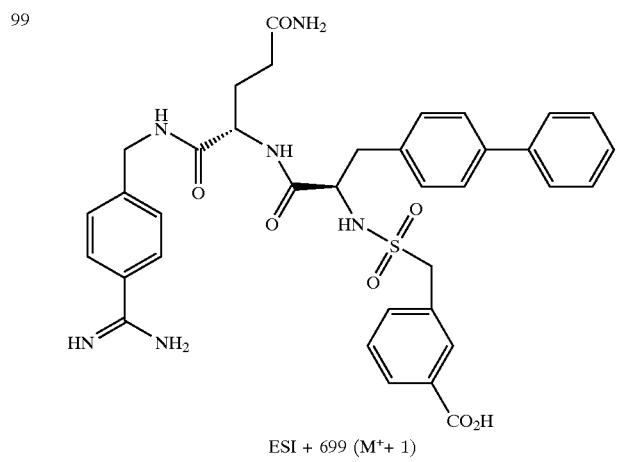<br>ESI + 699 (M⁺+ 1) |

TABLE 16-continued
100
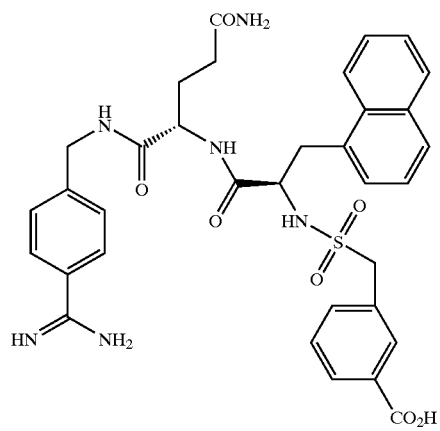
ESI + 673 (M+ + 1)
101
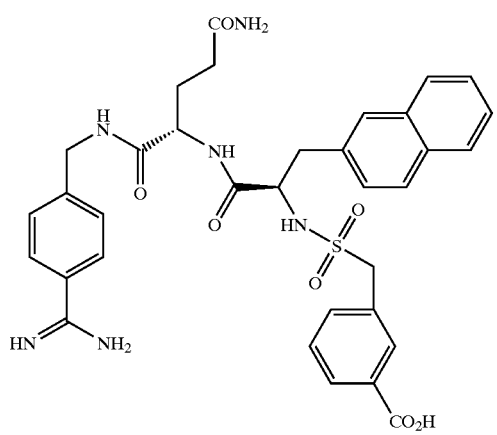
ESI + 673 (M+ + 1)
102
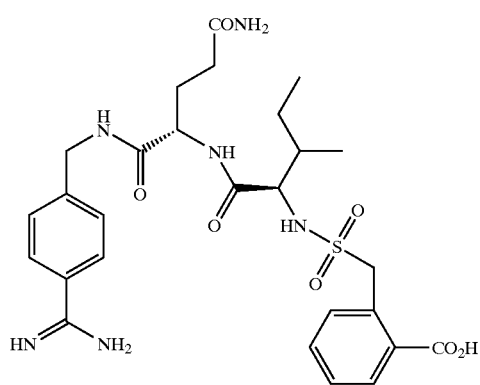
ESI + 589 (M+ + 1)

TABLE 17

| Example | Reagent 2 | Reagent 5 | Reagent 8 |
| --- | --- | --- | --- |
| 103 | Boc-protected amino acid with CONH₂ side chain | Fmoc-Thr(tBu) | ethanesulfonyl chloride |
| 104 | Boc-protected amino acid with CONH₂ side chain | Boc-Ile | 4-(ethoxycarbonyl)phenylmethanesulfonyl chloride |
| 105 | Boc-Met | Boc-4-phenyl-Phe | 3-(methoxycarbonyl)phenylmethanesulfonyl chloride |
| 106 | Boc-protected amino acid with S(O)Me side chain | Fmoc-Thr(tBu) | 3-(methoxycarbonyl)phenylmethanesulfonyl chloride |
| 107 | Boc-protected amino acid with SO₂Me side chain | Fmoc-Thr(tBu) | 3-(methoxycarbonyl)phenylmethanesulfonyl chloride |

TABLE 17-continued
| Example | Structure MS |
|---|---|
| 103 | 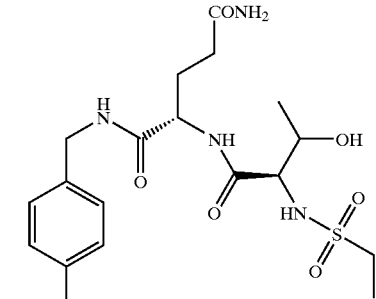
ESI + 471 (M⁺+ 1) |
| 104 | 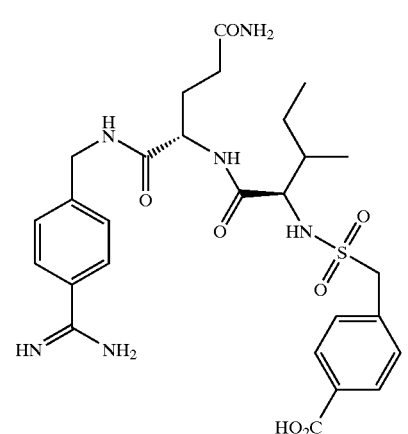
ESI + 589 (M⁺+ 1) |
| 105 | 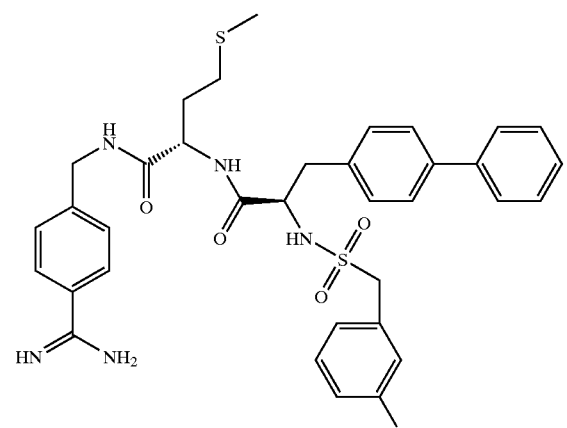
ESI + 702 (M⁺+ 1) |

TABLE 17-continued
106
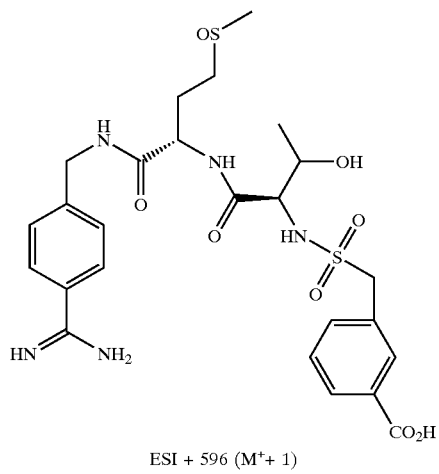
ESI + 596 (M⁺+ 1)
107
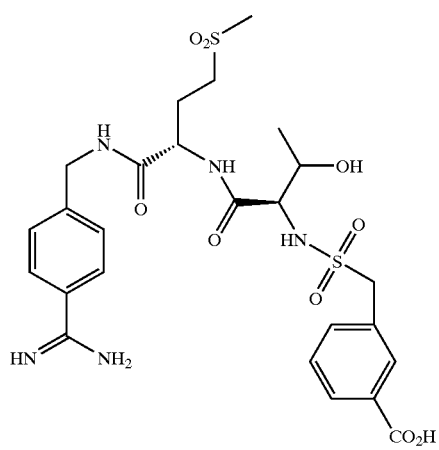
ESI + 612 (M⁺+ 1)
TABLE 18
| Example | Reagent 2 | Reagent 5 | Reagent 8 | Structure MS |
|---|---|---|---|---|
| 108 | | | | ESI + 574 (M⁺+ 1) |

TABLE 18-continued

| Example | Reagent 2 | Reagent 5 | Reagent 8 | Structure MS |
|---------|-----------|-----------|-----------|--------------|
| 109 | | | | ESI + 589 (M⁺+ 1) |
| 110 | | | | ESI + 503 (M⁺+ 1) |
| 111 | | | | ESI + 517 (M⁺+ 1) |

TABLE 18-continued

| Example | Reagent 2 | Reagent 5 | Reagent 8 | Structure MS |
|---|---|---|---|---|
| 112 | | | | ESI + 593 (M⁺+ 1) |

TABLE 19

| Example | Reagent 2 | Reagent 5 | Reagent 8 | Structure MS |
|---|---|---|---|---|
| 113 | | | | ESI + 520 (M⁺+ 1) |
| 114 | | | | ESI + 548 (M⁺+ 1) |

TABLE 19-continued

| Example | Reagent 2 | Reagent 5 | Reagent 8 | Structure MS |
|---------|-----------|-----------|-----------|--------------|
| 115 | | | | ESI + 658 (M⁺+ 1) |
| 116 | | | | ESI + 472 (M⁺+ 1) |
| 117 | | | | ESI + 486 (M⁺+ 1) |

TABLE 20

| Example | Reagent 2 | Reagent 5 | Reagent 8 | Structure MS |
|---------|-----------|-----------|-----------|--------------|
| 113 | | | | ESI + 520 (M⁺+ 1) |
| 114 | | | | ESI + 548 (M⁺+ 1) |
| 115 | | | | ESI + 658 (M⁺+ 1) |

TABLE 20-continued

| Example | Reagent 2 | Reagent 5 | Reagent 8 | Structure MS |
|---|---|---|---|---|
| 116 | | | | ESI + 472 (M⁺+ 1) |
| 117 | | | | ESI + 486 (M⁺+ 1) |

TABLE 21

| Example | Reagent 2 | Reagent 5 | Reagent 8 | Structure MS |
|---|---|---|---|---|
| 123 | | | | ESI + 486 (M⁺+ 1) |

TABLE 21-continued

| Example | Reagent 2 | Reagent 5 | Reagent 8 | Structure MS |
|---|---|---|---|---|
| 124 | | | | ESI + 506 (M⁺+ 1) |
| 125 | | | | ESI + 520 (M⁺+ 1) |
| 126 | | | | ESI + 596 (M⁺+ 1) |

TABLE 21-continued

| Example | Reagent 2 | Reagent 5 | Reagent 8 | Structure MS |
|---|---|---|---|---|
| 127 | | | | ESI + 503 (M⁺+ 1) |

TABLE 22

| Example | Reagent 2 | Reagent 5 | Reagent 8 | Structure MS |
|---|---|---|---|---|
| 128 | | | | ESI + 517 (M⁺+ 1) |
| 129 | | | | ESI + 531 (M⁺+ 1) |

TABLE 22-continued

| Example | Reagent 2 | Reagent 5 | Reagent 8 | Structure MS |
|---|---|---|---|---|
| 130 | | | | ESI + 533 (M⁺+ 1) |
| 131 | | | | ESI + 545 (M⁺+ 1) |
| 132 | | | | ESI + 565 (M⁺+ 1) |

TABLE 23

| Example | Reagent 2 | Reagent 5 | Reagent 8 |
|---|---|---|---|
| 133 | H₂NOC-CH₂CH₂-C*H(NHBoc)-CO₂H | PhCH₂-C*H(NHBoc)-CO₂H | PhCH₂SO₂Cl |
| 134 | H₂NOC-CH₂CH₂-C*H(NHBoc)-CO₂H | (4-biphenyl)CH₂-C*H(NHBoc)-CO₂H | PhCH₂SO₂Cl |
| 135 | H₂NOC-CH₂CH₂-C*H(NHBoc)-CO₂H | Ph₂CH-C*H(NHBoc)-CO₂H | PhCH₂SO₂Cl |
| 136 | H₂NOC-CH₂CH₂-C*H(NHBoc)-CO₂H | CH₃-C*H(NHBoc)-CO₂H | n-PrSO₂Cl |
| 137 | H₂NOC-CH₂CH₂-C*H(NHBoc)-CO₂H | CH₃CH₂-C*H(NHBoc)-CO₂H | n-PrSO₂Cl |

| Example | Structure / MS |
|---|---|
| 133 | 4-amidinobenzyl-NH-C(O)-C*H(CH₂CH₂CONH₂)-NH-C(O)-C*H(CH₂Ph)-NH-SO₂-CH₂Ph<br>ESI+ 579 (M⁺ + 1) |

TABLE 23-continued
134
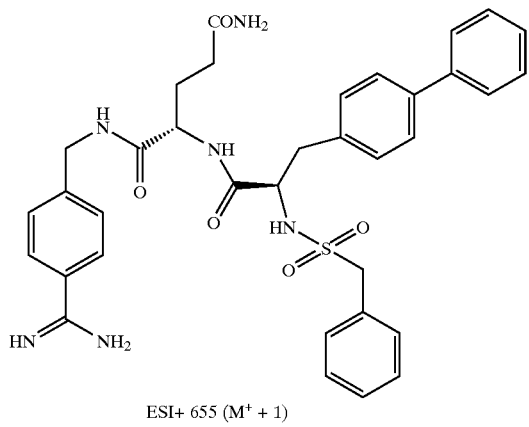
ESI+ 655 (M⁺ + 1)
135
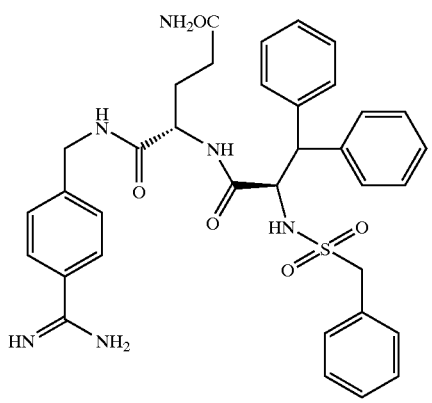
ESI+ 655 (M⁺ + 1)
136
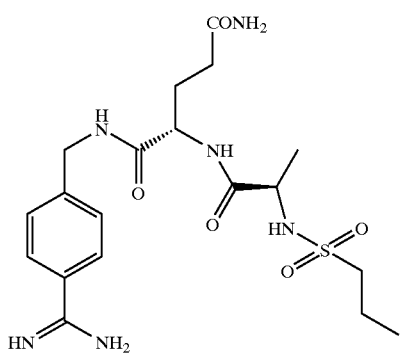
ESI+ 455 (M⁺ + 1)

TABLE 23-continued

| 137 | [Structure: benzylamine with para-amidino group, connected via CH2-NH-C(=O)-CH(CH2CH2CONH2)-NH-C(=O)-CH(CH2CH3)-NH-SO2-CH2CH2CH3] |

ESI+ 469 (M⁺ + 1)

TABLE 24

| Example | Reagent 2 | Reagent 5 | Reagent 8 |
|---------|-----------|-----------|-----------|
| 138 | HO₂C-CH(NHBoc)-CH₂CH₂-CONH₂ | HO₂C-CH(NHFmoc)-CH(CH₃)-O-tBu | Cl-SO₂-CH₂CH₂CH₃ |
| 139 | HO₂C-CH(NHBoc)-CH₂CH₂-CONH₂ | HO₂C-CH(NHBoc)-CH₂-CH(CH₃)₂ | Cl-SO₂-CH₂CH₂CH₃ |
| 140 | HO₂C-CH(NHBoc)-CH₂CH₂-CONH₂ | HO₂C-CH(NHBoc)-CH₂-Ph | Cl-SO₂-CH₂CH₂CH₃ |
| 141 | HO₂C-CH(NHBoc)-CH₂CH₂-CONH₂ | HO₂C-CH(NHBoc)-CH₂-(4-biphenyl) | Cl-SO₂-CH₂CH₂CH₃ |
| 142 | HO₂C-CH(NHBoc)-CH₂CH₂-CONH₂ | HO₂C-CH(NHBoc)-CH(Ph)₂ | Cl-SO₂-CH₂CH₂CH₃ |

TABLE 24-continued
| Example | Structure MS |
|---|---|
| 138 | 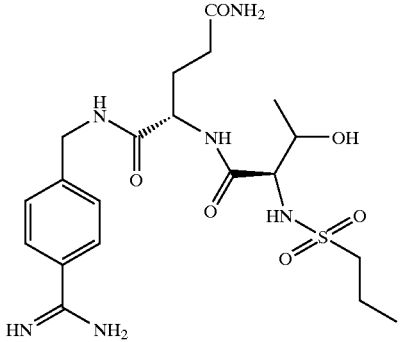<br>ESI+ 485 (M⁺ + 1) |
| 139 | 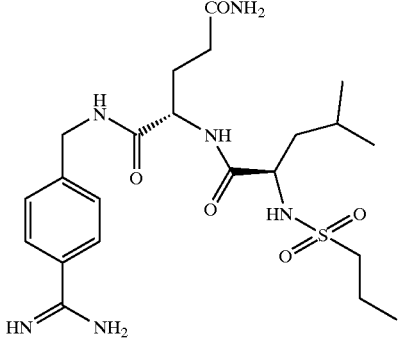<br>ESI+ 497 (M⁺ + 1) |
| 140 | 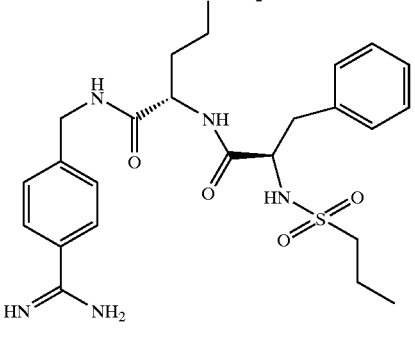<br>ESI+ 531 (M⁺ + 1) |

TABLE 24-continued
141
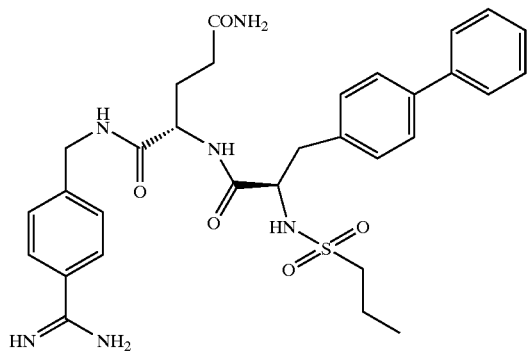
ESI+ 607 (M⁺ + 1)
142
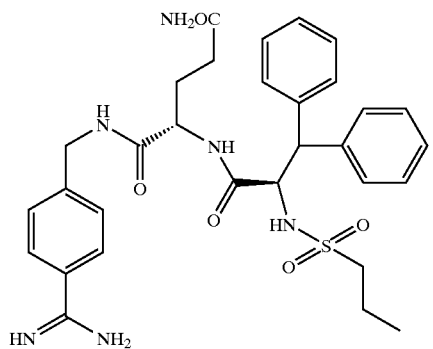
ESI+ 607 (M⁺ + 1)
TABLE 25
| Example | Reagent 2 | Reagent 5 | Reagent 8 | Structure MS |
|---|---|---|---|---|
| 143 | | | | |
ESI+ 455 (M⁺ + 1)

TABLE 25-continued

| Example | Reagent 2 | Reagent 5 | Reagent 8 | Structure MS |
|---|---|---|---|---|
| 144 | | | | ESI+ 469 (M⁺ + 1) |
| 145 | | | | ESI+ 614 (M⁺ + 1) |
| 146 | | | | ESI+ 586 (M⁺ + 1) |

TABLE 25-continued

| Example | Reagent 2 | Reagent 5 | Reagent 8 | Structure MS |
|---|---|---|---|---|
| 147 | (structure with CN, HO₂C, NHBoc) | (structure with HO₂C, NHBoc) | (benzyl sulfonyl chloride with CO₂Me) | (product structure) ESI+ 588 (M⁺ + 1) |

TABLE 26

| Example | Reagent 2 | Reagent 5 | Reagent 8 | Structure MS |
|---|---|---|---|---|
| 148 | (structure with CONH₂, HO₂C, NHBoc) | (methoxy indole structure with HO₂C, NHBoc) | (ethanesulfonyl chloride) | (product structure) ESI+ 586 (M⁺ + 1) |
| 149 | (structure with CONH₂, HO₂C, NHBoc) | (methyl indole structure with HO₂C, NHBoc) | (ethanesulfonyl chloride) | (product structure) ESI+ 570 (M⁺ + 1) |

TABLE 26-continued

| Example | Reagent 2 | Reagent 5 | Reagent 8 | Structure MS |
|---------|-----------|-----------|-----------|--------------|
| 150 | | | | ESI+ 550 (M⁺ + 1) |
| 151 | | | | ESI+ 552 (M⁺ + 1) |
| 152 | | | | ESI+ 600 (M⁺ + 1) |

TABLE 27
| Example | Intermediate 17 | Reagent 18 | Structure MS |
|---|---|---|---|
| 153 | 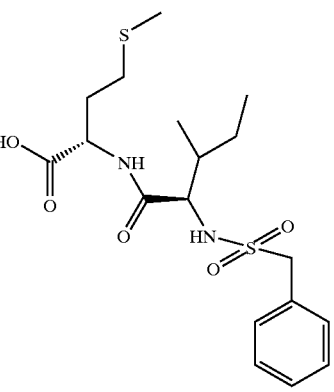 | 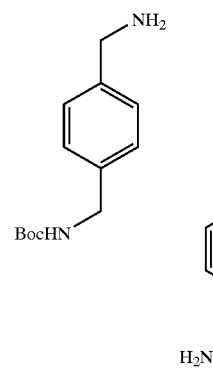 | 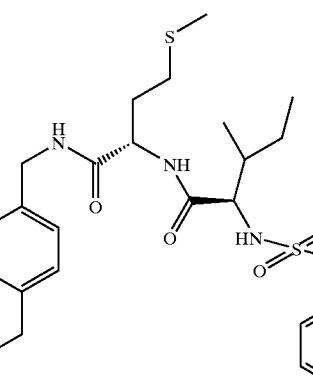<br>ESI+ 535 (M⁺ + 1) |
| 154 | 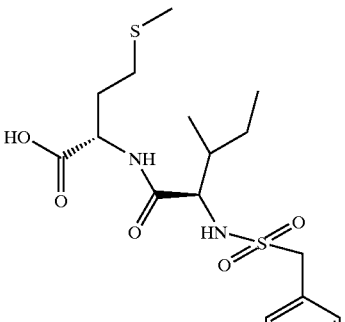 | 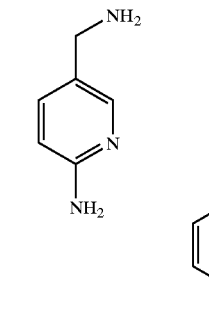 | 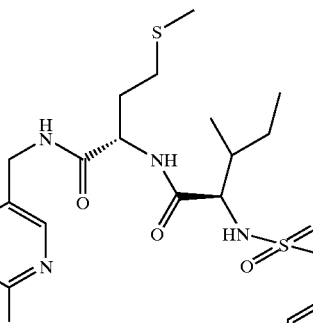<br>ESI+ 522 (M⁺ + 1) |
TABLE 28
| Example | Intermediate 9 | Reagent 22 | Structure MS |
|---|---|---|---|
| 155 | 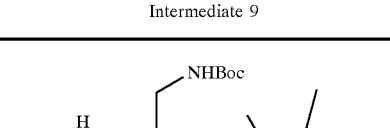 | KNCO | 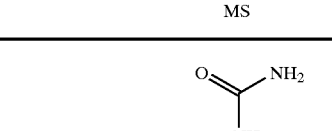<br>ESI+ 498 (M⁺ + 1) |

TABLE 28-continued

| Example | Intermediate 9 | Reagent 22 | Structure MS |
|---|---|---|---|
| 156 | | KNCO | ESI+ 608 (M+ + 1) |
| 157 | | CH3COCl | ESI+ 511 (M+ + 1) |
| 158 | | KNCO | ESI+ 500 (M+ + 1) |

TABLE 28-continued

| Example | Intermediate 9 | Reagent 22 | Structure MS |
|---------|----------------|------------|--------------|
| 159 | | KNCO | FAB+ 548 (M⁺ + 1) |

TABLE 29

| Example | Intermediate 9 | Reagent 22 | Structure MS |
|---------|----------------|------------|--------------|
| 160 | | KNCO | ESI+ 514 (M⁺ + 1) |
| 161 | | KNCO | ESI+ 498 (M⁺ + 1) |

TABLE 29-continued

| Example | Intermediate 9 | Reagent 22 | Structure MS |
|---|---|---|---|
| 162 | (structure) | KNCO | (structure) ESI+ 540 (M⁺ + 1) |
| 163 | (structure) | KNCO | (structure) ESI+ 526 (M⁺ + 1) |

TABLE 30

| Example | Intermediate 34 | Reagent 35 |
|---|---|---|
| 164 | (structure) | (HO)₂B—⟨phenyl⟩—O— |

TABLE 30-continued
| 165 | 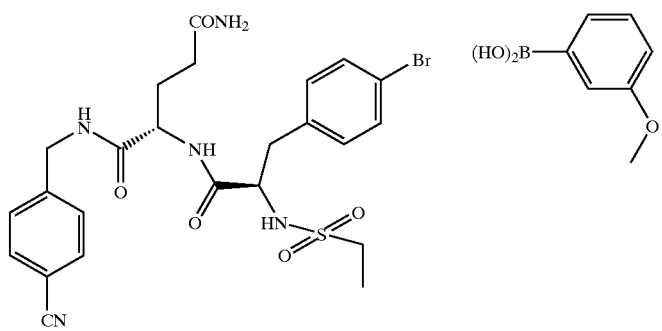 |
| 166 | 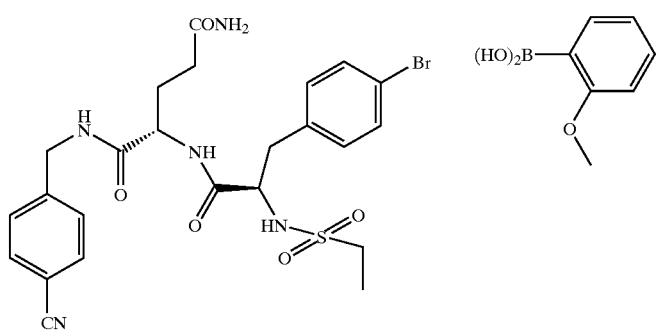 |
| 167 | 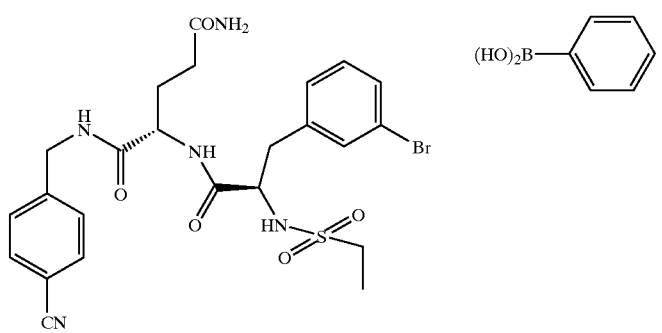 |
| 168 | 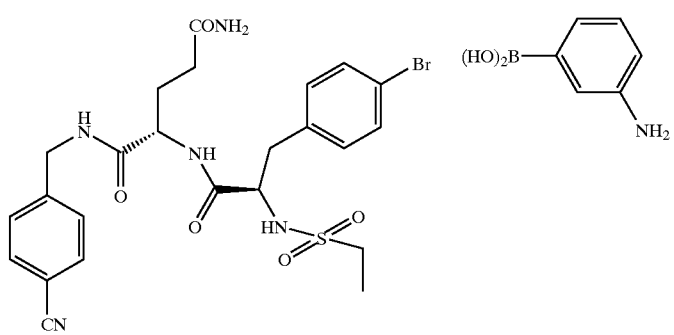 |

TABLE 30-continued
| Example | Structure MS |
|---|---|
| 164 | 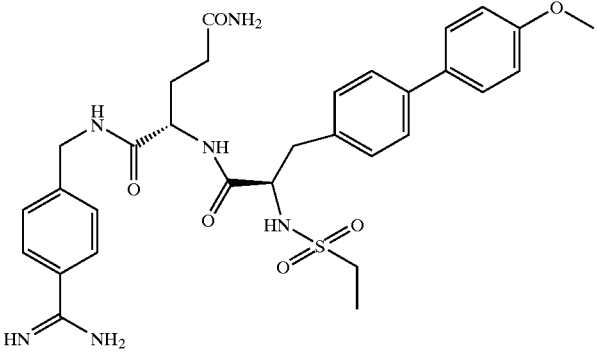<br>ESI+ 623 (M+ + 1) |
| 165 | 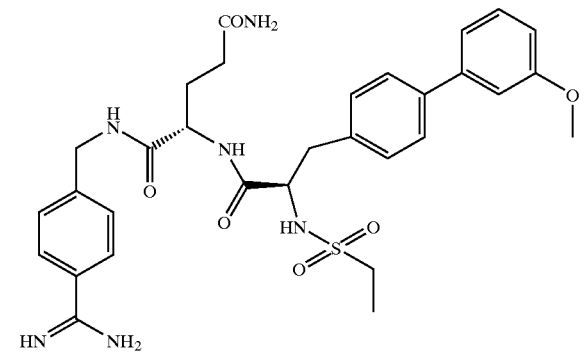<br>ESI+ 623 (M+ + 1) |
| 166 | 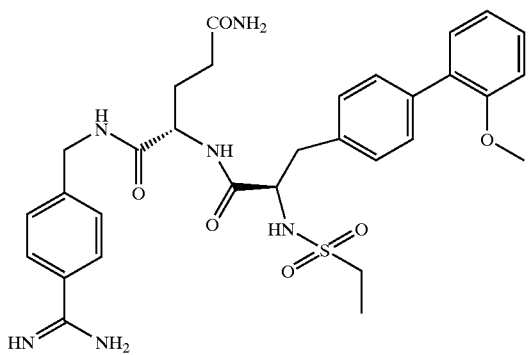<br>ESI+ 623 (M+ + 1) |

TABLE 30-continued
167
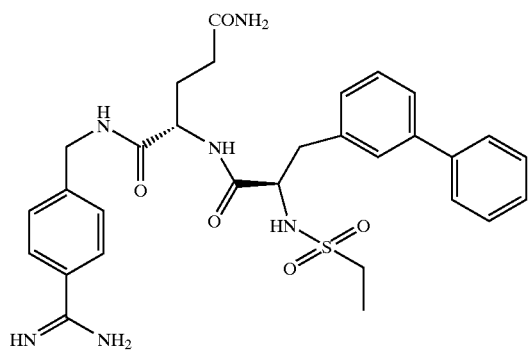
ESI+ 593 (M$^+$ + 1)
168
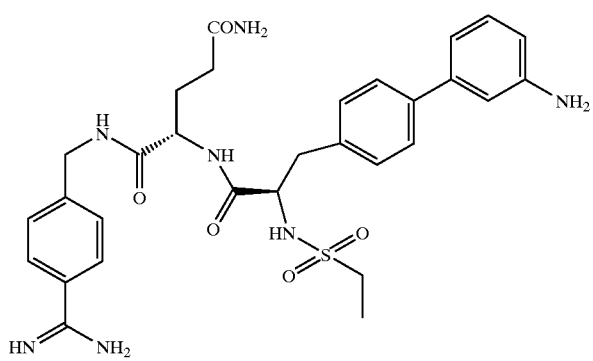
ESI+ 608 (M$^+$ + 1)
TABLE 31
| Example | Intermediate 34 | Reagent 35 |
|---------|-----------------|------------|
| 169 | 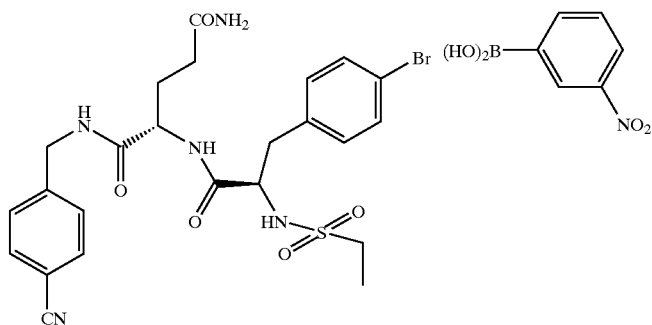 | |

TABLE 31-continued
| Example | Structure MS |
|---------|--------------|
| 169 | 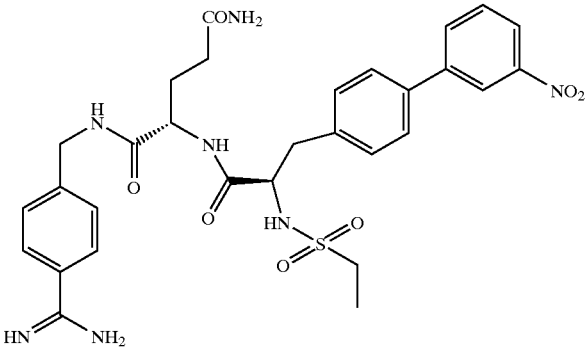 ESI+ 638 (M⁺ + 1) |
TABLE 32
| Example | Intermediate 38 | Reagent 39 | Reagent 8 |
|---------|-----------------|------------|-----------|
| 170 | 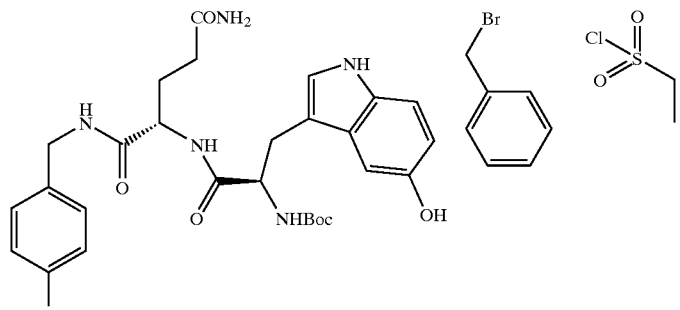 | 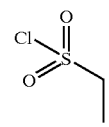 | 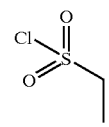 |
| 171 | 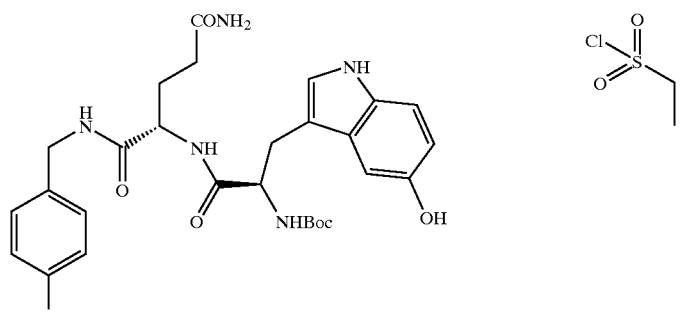 |  | 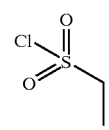 |
| 172 | 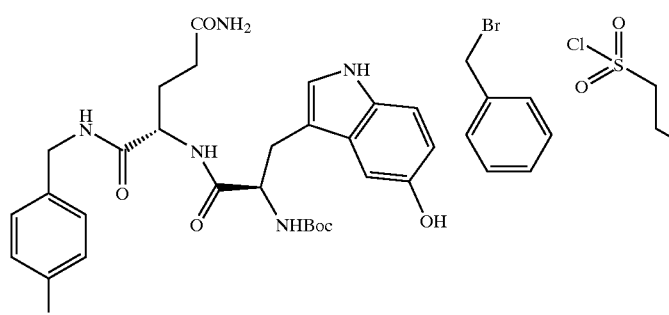 | 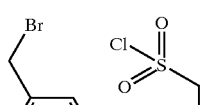 | 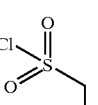 |

TABLE 32-continued
| | | |
|---|---|---|
| 173 | 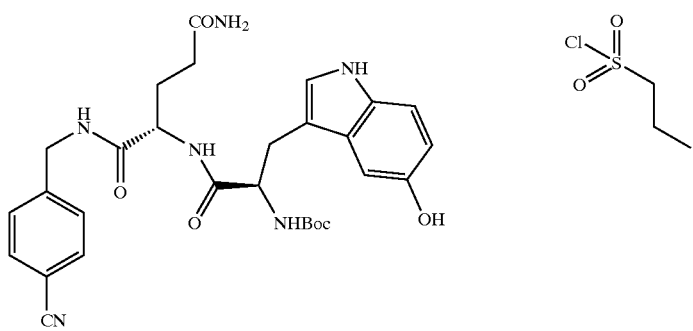 | |
| 174 | 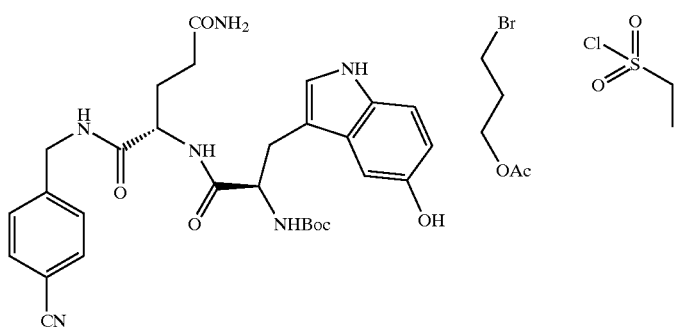 | |
| Example | Structure<br>MS |
|---|---|
| 170 | 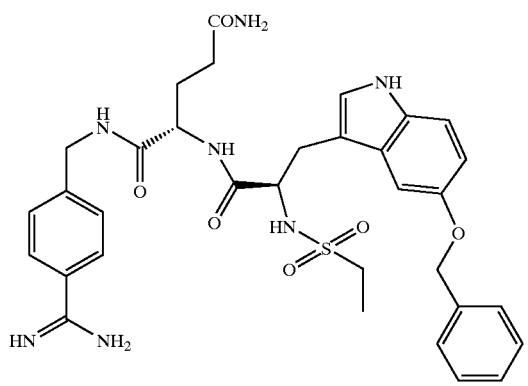<br>ESI+ 662 (M⁺ + 1) |
| 171 | 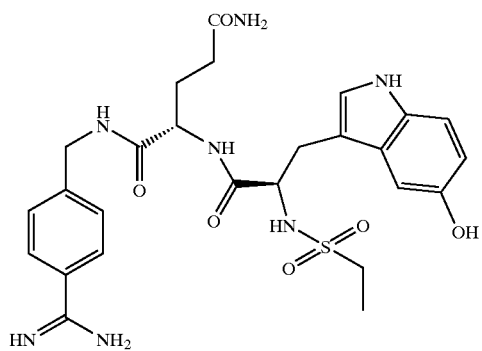<br>ESI+ 572 (M⁺ + 1) |

TABLE 32-continued
172
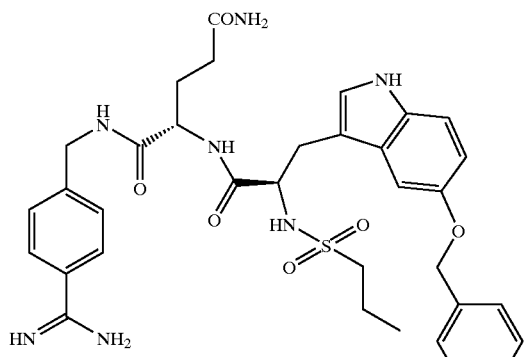
ESI+ 676 (M⁺ + 1)
173
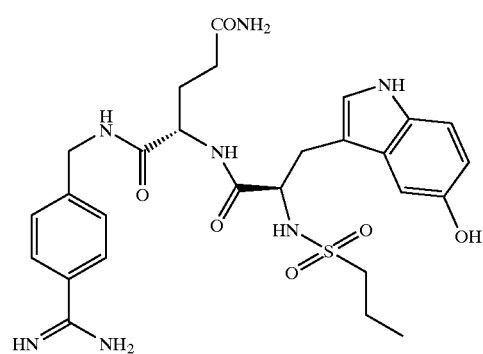
ESI+ 586 (M⁺ + 1)
174
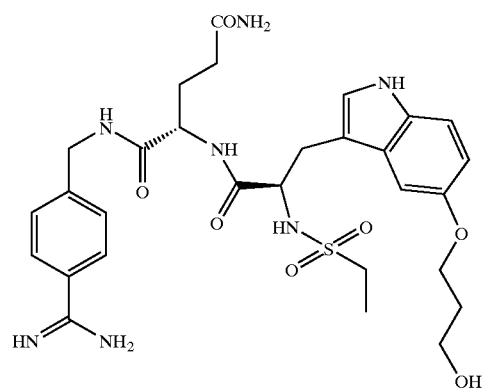
ESI+ 629 (M⁺ + 1)

TABLE 33

| Example | Intermediate 38 | Reagent 39 | Reagent 8 | Structure MS |
|---|---|---|---|---|
| 175 | | | | ESI+ 657 (M⁺ + 1) |
| 176 | | | | ESI+ 643 (M⁺ + 1) |
| 177 | | | | ESI+ 615 (M⁺ + 1) |

TABLE 33-continued

| Example | Intermediate 38 | Reagent 39 | Reagent 8 | Structure MS |
|---|---|---|---|---|
| 178 | | | | ESI+ 630 (M⁺ + 1) |
| 179 | | | | ESI+ 658 (M⁺ + 1) |

TABLE 34

| Example | Intermediate 38 | Reagent 39 |
|---|---|---|
| 180 | | |

TABLE 34-continued
| | | |
|---|---|---|
| 181 | 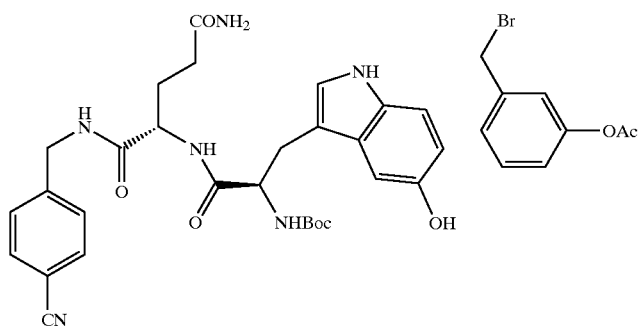 | |
| 182 | 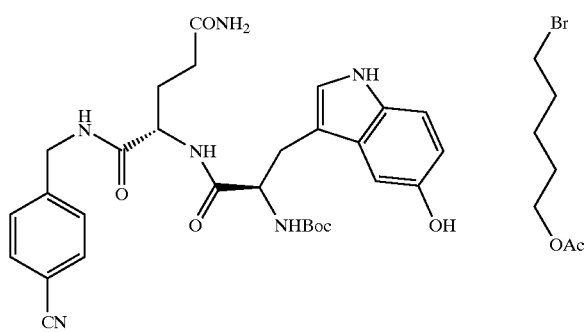 | |
| Example | Reagent 8 | Structure MS |
|---|---|---|
| 180 | | 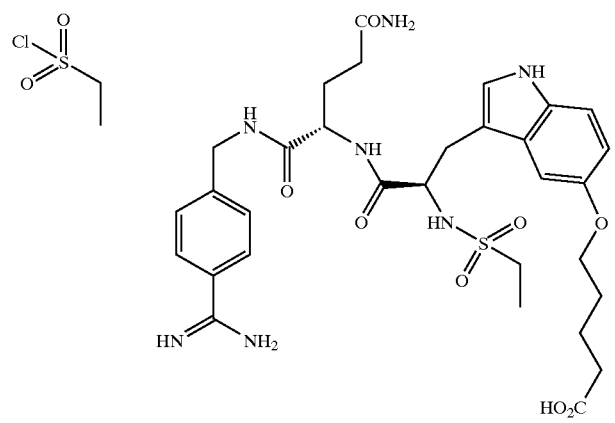
ESI+ 671 (M⁺ + 1) |
| 181 | | 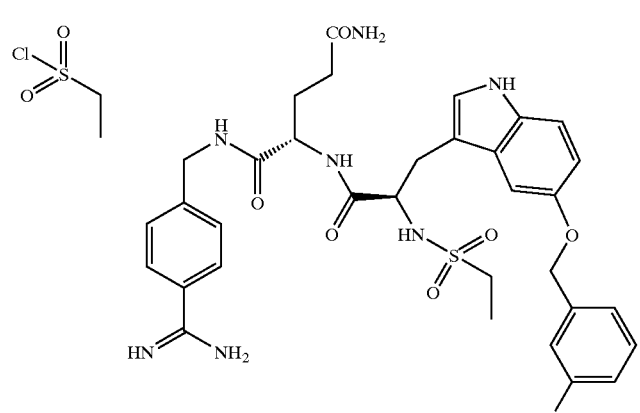
ESI+ 678 (M⁺ + 1) |

TABLE 34-continued

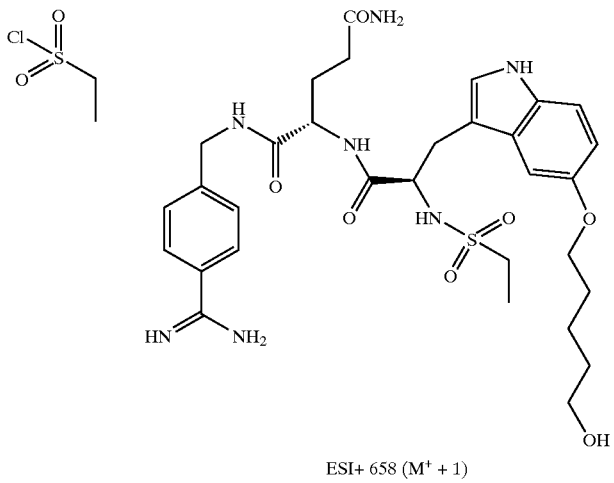

182

ESI+ 658 (M⁺ + 1)

Example 183

Expression and Purification of Human Factor VIIa

Human factor VII cDNA was obtained from a human liver cDNA library (CLONTECH) by PCR. The primer sequences used are as follows:

```
GTCTGGATCCACCATGGTCTCCCAGGCCCTCAG

TGTTGAATTCTACTAGGGAAATGGGGCTCGCA.
```

The human factor VII gene was integrated into a Double One expression vector (IDEC), subcloned and digested with the restriction enzyme SspI. The linearized fragment was then introduced into the CHO cell line DG44 by electroporation to create human factor VII-expressing transformants. The transformants were then grown in the presence of 5 nM methotrexate (Sigma) for gene amplification. The resulting methotrexate-resistant human factor VII-expression transformants were further grown in a CHO-S-SFMII medium (GIBCO BRL) supplemented with 5 nmol/L methotrexate and 0.5 μg/ml vitamin K (Sigma) to express human factor VII.

The culture supernatant of human factor VII-expressing CHO transformants was concentrated through a hollow fiber dialyzer (PAN-130F, Asahi Medical Co., Ltd.) and supplemented with benzamidine at a final concentration of 5 mM for frozen storage. This frozen-stored culture supernatant was used, as appropriate, in purifying human factor VIIa. For purification, reference was made to Methods Enzymol., vol. 80, pages 228–237, 1981 and Biochemistry, vol. 27, pages 7785–7793, 1988. The concentrated culture supernatant was diluted 10-fold in 20 mM Tris-HCl buffer (pH 8.0) containing 5 mM benzamidine and 5 mM EDTA, and then applied to a Q Sepharose Fast Flow column equilibrated with the same buffer. Proteins adsorbed to the column were eluted with a stepwise gradient of NaCl (0.1, 0.2, 0.3 M) in the same buffer. The 0.3 M NaCl fractions containing human factor VII were concentrated by ultrafiltration, diluted 10-fold in 20 mM Tris-HCl buffer (pH 8.0) containing 5 mM benzamidine and 5 mM EDTA, and then applied to a Q Sepharose Fast Flow column equilibrated with the same buffer. After washing with the same buffer, human factor VII was eluted from the column with a linear $CaCl_2$ gradient up to 50 mM. The resulting fractions were analyzed by SDS/PAGE to collect human factor VII-containing fractions, which were then allowed to stand at room temperature for 2 days to facilitate self-digestion for activation into human factor VIIa. The reaction mixture was diluted 10-fold in 20 mM Tris-HCl buffer (pH 7.0) and then applied to a Q Sepharose Fast Flow column equilibrated with the same buffer. Human factor VIIa was eluted with a linear NaCl gradient of 150 to 350 mM in the same buffer. The resulting fractions were analyzed by SDS/PAGE to collect human factor VIIa-containing fractions, thus giving a purified human VIIa fraction.

Example 184

Expression and Purification of Human Soluble Tissue Factor

A gene fragment encoding human soluble tissue factor (amino acids 1–218) was inserted downstream of the tac promoter and the M13 signal peptide sequence to create a secretory expression vector, which was then transformed into *E. coli* JM109 cells. The resulting transformants were grown to express human soluble tissue factor into the culture supernatant.

Purification was performed as described in Biochemistry, vol. 31, pages 3998–4003, 1992, with some modifications. The culture supernatant was concentrated by ultrafiltration and then treated with 65% saturated ammonium sulfate to precipitate the protein of interest. The precipitated product was collected by centrifugation (18000 g, 10 minutes), dissolved in PBS and then dialyzed against 25 mM acetate buffer (pH 5.2). The dialyzed solution was centrifuged (8000 g, 20 minutes) to remove insoluble products and the resulting supernatant was applied to an SP Sepharose Fast Flow column equilibrated with 25 mM acetate buffer (pH 5.2). Human soluble tissue factor was eluted from the column with a linear NaCl gradient up to 500 mM in the same buffer. The resulting fractions were analyzed by SDS/PAGE to collect fractions containing human soluble tissue factor, followed by dialysis against 25 mM Tris-HCl buffer (pH 7.5). The dialyzed fractions were applied to a Q Sepharose Fast Flow column equilibrated with 25 mM Tris-HCl buffer (pH 7.5) and human soluble tissue factor was eluted from the column with a linear NaCl gradient up to 500 mM in the same buffer, thus giving a purified human soluble tissue factor fraction.

Example 185

Preparation of a Human Factor VIIa/Human Soluble Tissue Factor Seed Crystal

As described in Proteins, vol. 22, pages 419–425, 1995, crystallization was performed on a complex between human factor VIIa and human soluble tissue factor, irreversibly inhibited with D-Phe-Phe-Arg chloromethylketone. This crystal is necessary as a seed crystal for crystallization of a complex between reversible factor VIIa inhibitor and human factor VIIa/human soluble tissue factor. The purified human factor VIIa was mixed with a 10-fold molar excess of D-Phe-Phe-Arg chloromethylketone (BACHEM) and allowed to stand at 4° C. for 3 hours. To this mixture, an excess amount of the purified human soluble tissue factor was added and allowed to stand at 37° C. for 30 minutes, followed by ultrafiltration for concentration. The concentrated fraction was applied to a gel filtration column (Superdex 75) equilibrated with 50 mM Tris-HCl buffer (pH 7.5) containing 5 mM $CaCl_2$ and 100 mM NaCl, and then eluted with the same buffer to give a purified fraction of the human factor VIIa/human soluble tissue factor complex irreversibly inhibited with D-Phe-Phe-Arg chloromethylketone. This fraction was concentrated by ultrafiltration for crystallization to prepare a sample with a protein concentration of 10 mg/ml in 50 mM Tris-HCl buffer (pH 7.5), 100 mM NaCl and 5 mM $CaCl_2$. This sample was then allowed to stand at a temperature of 20° C. using hanging drop vapor diffusion methods-under reservoir conditions of 100 mM sodium cacodylate buffer (pH 5.0), 24% PEG4000 and 5 mM $CaCl_2$, yielding a large amount of needle crystal.

Example 186

Preparation of a Human Factor VIIa/Human Soluble Tissue Factor Sample for Crystallization After addition of 1/10 volumes of 1M benzamidine, the purified human factor VIIa was mixed with a molar excess of the purified human soluble tissue factor. This mixture was concentrated by ultrafiltration and then applied to a gel filtration column (Superdex 75) equilibrated with 50 mM Tris-HCl buffer (pH 7.5) containing 5 mM $CaCl_2$ and 100 mM NaCl. A human factor VIIa/human soluble tissue factor complex was eluted from the column with the same buffer to give a purified fraction of the human factor VIIa/human soluble tissue factor complex.

Example 187

Crystallization of a Complex Between a Low-molecular Weight Reversible Factor VIIa Inhibitor and Human Factor VIIa/Human Soluble Tissue Factor The purified human factor VIIa/human soluble tissue factor complex was mixed with Compound (1) or (2) and then concentrated by ultrafiltration for crystallization to prepare a sample with a protein concentration of 12–13 mg/ml in 50 mM Tris-HCl buffer (pH 7.5), 100 mM NaCl and 5 mM $CaCl_2$. Compounds (1) and (2) were used at the concentrations indicated in Table 35.

TABLE 35

|  | Compound (1) | Compound (2) |
|---|---|---|
| Concentration | 0.5 mM | <0.5 mM |

Since spontaneous crystallization will not occur for a complex between a low-molecular weight reversible factor VIIa inhibitor and human factor VIIa/human soluble tissue factor, it is necessary to add a seed crystal during. crystallization. The seed crystal was prepared as follows. In a solution of 100 mM sodium cacodylate buffer (pH 5.0), 9% PEG4000 and 5 mM $CaCl_2$, the crystal of the human factor VIIa/human soluble tissue factor complex irreversibly inhibited with D-Phe-Phe-Arg chloromethylketone was crushed with a homogenizer and then diluted to prepare a series of 10-fold dilutions from $10^{-1}$ to $10^{-6}$. Likewise, a crystal of a complex between a low-molecular weight reversible factor VIIa inhibitor and human factor VIIa/human soluble tissue factor was also available as a seed crystal.

Crystallization was performed by hanging drop vapor diffusion methods at a temperature of 25° C. under reservoir conditions of 100 mM sodium cacodylate buffer (pH 5.0), 6% to 7.5% PEG4000, 5 mM $CaCl_2$ and 5% glycerol. The complex sample prepared from the low-molecular weight reversible factor VIIa inhibitor and human factor VIIa/human soluble tissue factor was mixed with the reservoir and the seed dilutions at a ratio of 1.5 μl:1.5 μl:0.5 μl (sample:reservoir:seed) to prepare a crystallization drop. About a month later, long rod crystals (maximum size: about 1.0 mm long×0.05 mm diameter) were obtained for the complex between the low-molecular weight reversible inhibitor and human factor VIIa/human soluble tissue factor.

Example 188

Measurement of X-ray Diffraction Data (A) Crystal of the Complex Between Compound (1) and Human Factor VIIa/Human Soluble Tissue Factor The crystal was soaked in 100 mM sodium cacodylate buffer (pH 5.0), 9% PEG4000 and 5 mM $CaCl_2$ with a 5% stepwise gradient of glycerol from 10% up to 30%. This crystal together with its surrounding solution was picked by a nylon loop (cryo-loop, Hampton research) and frozen in a nitrogen stream at −170° C. The crystal was maintained in a nitrogen stream at −170° C. during measurement. X-ray diffraction data were collected using an R-axis IV imaging plate detector (Rigaku) under CuKa radiation from a rotating anode X-ray generator with a fine focus filament (Ultrax18, Rigaku) at 44 kV×100 mA through OSMIC X-ray focusing mirrors (Rigaku). The DENZO/SCALEPACK program (Mac Science) was used for cell parameter and crystal orientation determination, diffraction spot indexing, as well as diffraction data processing, thereby obtaining diffraction intensity data up to 2.2 Å resolution. This crystal was found to be isomorphous to the Protein Data Bank complex of human factor VIIa/human soluble tissue factor, irreversibly inhibited with D-Phe-Phe-Arg chloromethylketone (PDB code: 1DAN). This crystal had space group $P2_12_12_1$ with unit cell parameters a=71.40 Å, b=82.22 Å, c=123.47 Å, α=90.0°, β=90.0° and γ=90.0°.

(B) Crystal of the Complex Between Compound (2) and Human Factor VIIa/Human Soluble Tissue Factor The crystal was soaked in 100 mM sodium cacodylate buffer (pH 5.0), 9% PEG4000 and 5 mM $CaCl_2$ with a 5% stepwise gradient of glycerol from 10% up to 30%. This crystal together with its surrounding solution was picked by a nylon loop (cryo-loop, Hampton research) and frozen in a nitrogen stream at −170° C. The crystal was maintained in a nitrogen stream at −170° C. during measurement. X-ray diffraction data were collected using an R-axis IV imaging plate detector (Rigaku) under CuKa radiation from a rotating anode X-ray generator with a fine focus filament (Ultrax18, Rigaku) at 40 kV×100 mA through Yale mirrors (Rigaku). The DENZO/SCALEPACK program (Mac Science) was used for cell parameter and crystal orientation determination, diffraction spot indexing, as well as diffraction data processing, thereby obtaining diffraction intensity data up to 2.2 Å resolution. This crystal was found to be isomorphous to the Protein Data Bank complex of human factor VIIa/human soluble tissue factor, irreversibly inhibited with D-Phe-Phe-Arg chloromethylketone (PDB code: 1DAN). This crystal had space group $P2_12_12_1$ with unit cell parameters a=71.28 Å, b=82.32 Å, c=123.38 Å, α=90.0°, β=90.0° and γ=90.0°.

Example 189

Structure Analysis
(A) Crystal of the Complex Between Compound (1) and Human Factor VIIa/Human Soluble Tissue Factor Water molecules and D-Phe-Phe-Arg chloromethylketone were removed from the coordinate data of the factor VIIa/tissue factor complex irreversibly inhibited with D-Phe-Phe-Arg chloromethylketone (PDB code: 1DAN) in the Protein Data Bank to create an initial model, followed by structure refinement using the CNX2000.1 program (Accerlys Inc). After rigid body refinement and energy minimization refinement, a Fourier map was calculated using coefficients 2Fo-Fc and Fo-Fc, where Fo was the structure factor observed experimentally and Fc was the structure factor calculated from the refined model. The map was then displayed on QUANTA to give a continuous electron density peak around the catalytic active center of factor VIIa. An atomic model for Compound (1) was fitted to this electron density peak, followed by several rounds of refinement by simulated annealing and energy minimization. The locations of water molecules were then determined based on the Fourier map with coefficients 2Fo-Fc and Fo-Fc, followed by simulated annealing refinement and energy minimization refinement. This procedure was repeated to give the final structure coordinates. The refined parameters were xyz coordinates and an isotropic temperature factor for each atom. The occupancy was set to 1.0 for each atom. The final structure contains cordinates of 5142 atoms (including 4688 protein atoms, 9 ion atoms, 404 water atoms and 41 inhibitor atoms), giving a reduction of crystallographic R factor to 22.59% for the 30.0–2.2 Å resolution data (34775 reflections). Meanwhile, the Free R value was 26.72% for 2627 reflections.

(B) Crystal of the Complex Between Compound (2) and Human Factor VIIa/Human Soluble Tissue Factor Water molecules and D-Phe-Phe-Arg chloromethylketone were removed from the coordinate data of the factor VIIa/tissue factor complex irreversibly inhibited with D-Phe-Phe-Arg chloromethylketone (PDB code: 1DAN) in the Protein Data Bank to create an initial model, followed by structure refinement using the CNX2000.1 program. After rigid body refinement and energy minimization refinement, a Fourier map was calculated using coefficients 2Fo-Fc and Fo-Fc, where Fo was the structure factor observed experimentally and Fc was the structure factor calculated from the refined model. The map was then displayed on QUANTA to give a continuous electron density peak around the catalytic active center of factor VIIa. An atomic model for Compound (2) was fitted to this electron density peak, followed by several rounds of refinement by simulated annealing and energy minimization. The locations of water molecules were then determined based on the Fourier map with coefficients 2Fo-Fc and Fo-Fc, followed by simulated annealing refinement and energy minimization refinement. This procedure was repeated to give the final structure coordinates. The refined parameters were xyz coordinates and an isotropic temperature factor for each atom. The occupancy was set to 1.0 for each atom. The final structure contains cordinates of 5193 atoms (including 4688 protein atoms, 9 ion atoms, 454 water atoms and 42 inhibitor atoms), giving a reduction of crystallographic R factor to 21.13% for the 30.0–2.2 Å resolution data (33708 reflections). Meanwhile, the Free R value was 25.08% for 2530 reflections.

Example 190

Structure Coordinates (A) Crystal Structure Coordinates of the Complex Between Compound (1) and Human Factor VIIa/Human Soluble Tissue Factor The coordinates of all atoms were shown in PDB format in Table 36 (found at the end of the specification).

(B) Crystal Structure Coordinates of the Complex Between Compound (2) and Human Factor VIIa/Human Soluble Tissue Factor The coordinates of Compound (2) and amino acid residues within 10 Å of Compound (2) were shown in PDB format in Table 37 (found at the end of the specification).

TABLE 38

Relationship between S2 site-binding moiety and human factor VIIa specificity

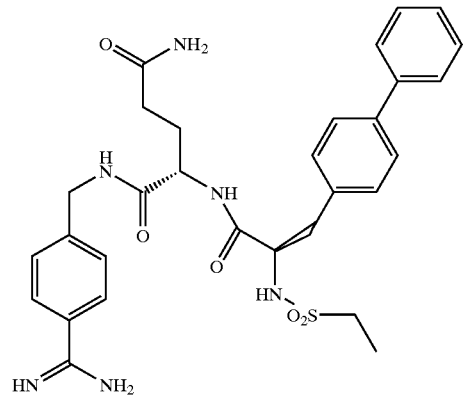

(2)
Example 65

TABLE 38-continued
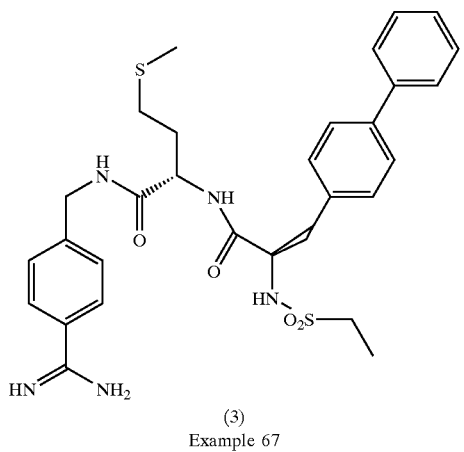
(3)
Example 67
| Compound | Example | IC50 Factor VIIa (nM) | IC50 Thrombin (nM) | Thrombin selectivity |
|---|---|---|---|---|
| (2) | 65 | 93 | 9415 | 101 |
| (3) | 67 | 341 | 2275 | 1 |
TABLE 39
Relationship between S1 subsite-binding moiety and human factor VIIa specificity
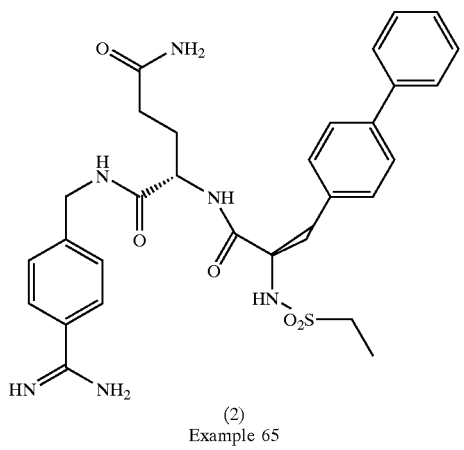
(2)
Example 65
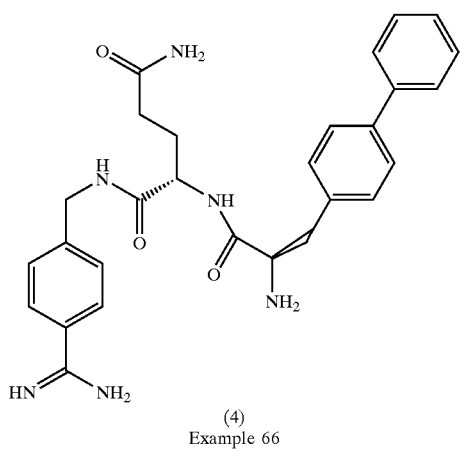
(4)
Example 66
TABLE 39-continued
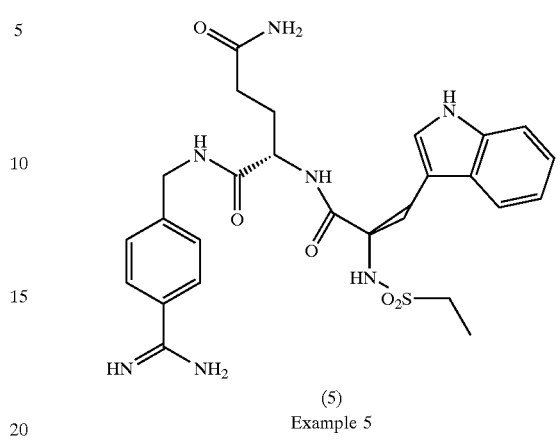
(5)
Example 5
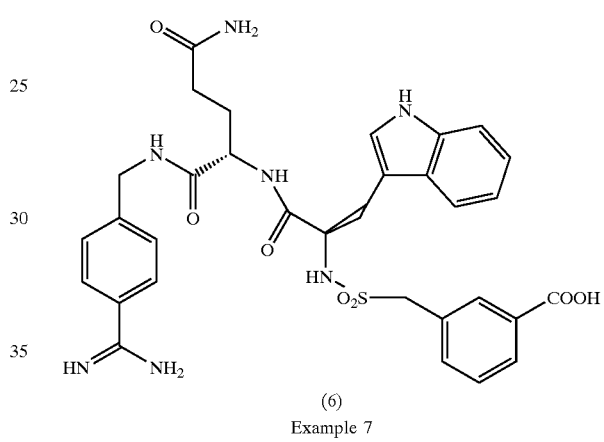
(6)
Example 7
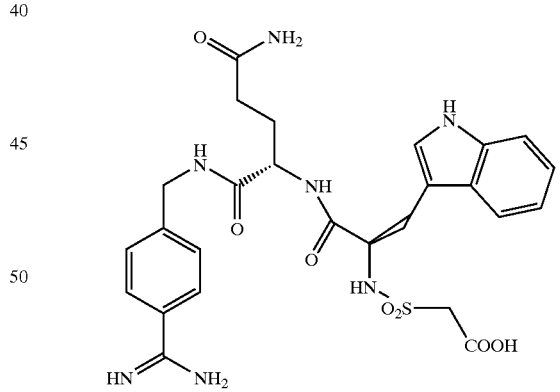
(1)
Example 146
| Compound | Example | IC50 Factor VIIa (nM) | IC50 Thrombin (nM) | Thrombin selectivity |
|---|---|---|---|---|
| (2) | 65 | 93 | 9415 | 101 |
| (4) | 66 | 2945 | 59051 | 20 |
| (5) | 5 | 62 | 5880 | 95 |
| (6) | 7 | 37 | 17870 | 483 |
| (1) | 146 | 153 | 80175 | 524 |

TABLE 40

Relationship between S4 site-binding moiety and human factor VIIa specificity

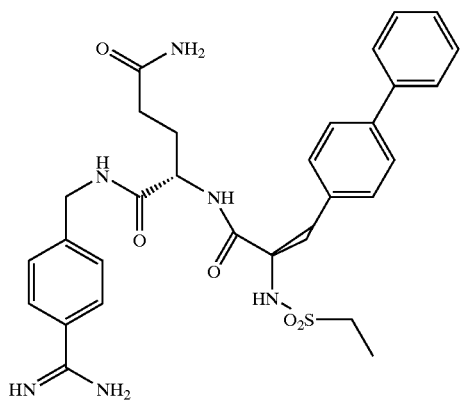

(2)
Example 65

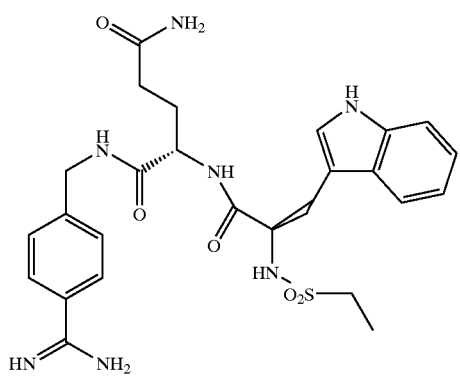

(5)
Example 5

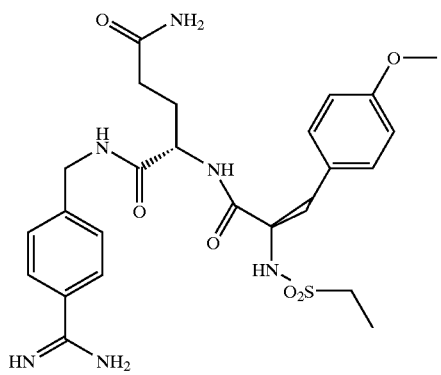

(7)
Example 73

| Compound | Example | IC50 Factor VIIa (nM) | IC50 Thrombin (nM) | Thrombin selectivity |
|---|---|---|---|---|
| (2) | 65 | 93 | 9415 | 101 |
| (5) | 5 | 62 | 5880 | 95 |
| (7) | 73 | 81 | 397 | 5 |

TABLE 41

Hydrogen bonding between Compound (1) and human factor VIIa S2 site

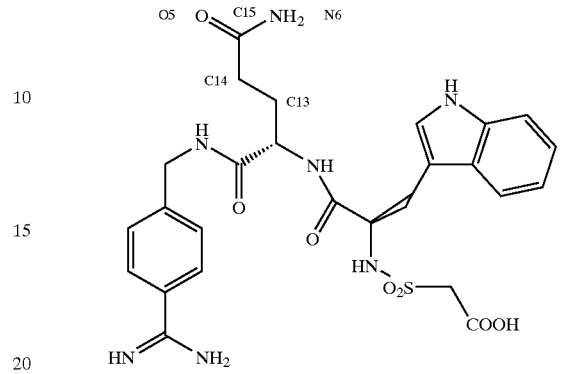

| Inhibitor | Factor VIIa | Distance |
|---|---|---|
| Hydrogen bonding | | |
| N6 | Asp60_OD2 | 3.0 Å |
| N6 | Tyr94_OH | 3.0 Å |
| N6 | Thr98_O | 2.8 Å |
| O5 | Asp60_OD2 | 3.2 Å |

TABLE 42

Hydrogen and ionic bonding between Compound (1) and human factor VIIa S1 subsite

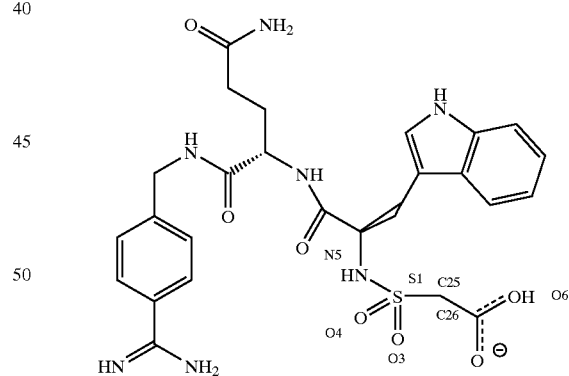

| Inhibitor | Factor VIIa | Distance |
|---|---|---|
| Hydrogen bonding | | |
| N5 | Gly216_O | 2.9 Å |
| O4 | Gly219_N | 2.8 Å |
| Ionic bonding | | |
| O7 | Lys192_NZ | 4.2 Å |

TABLE 43

Hydrogen bonding between Compound (2) and human factor VIIa S1 subsite

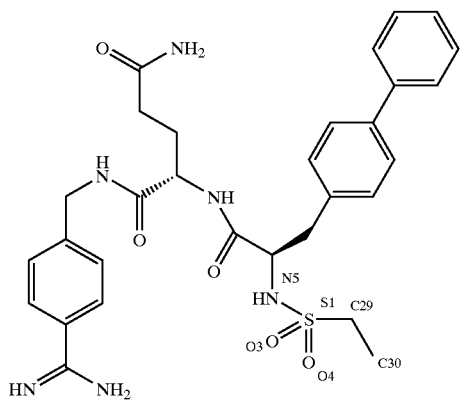

Hydrogen bonding

| Inhibitor | Factor VIIa | Distance |
|---|---|---|
| N5 | Gly216_O | 2.8 Å |
| O3 | Gly219_N | 2.8 Å |
| O4 | Lys192_NZ | 3.2 Å |

TABLE 44

Van der Waals interaction between Compound (1) and human factor VIIa S4 site

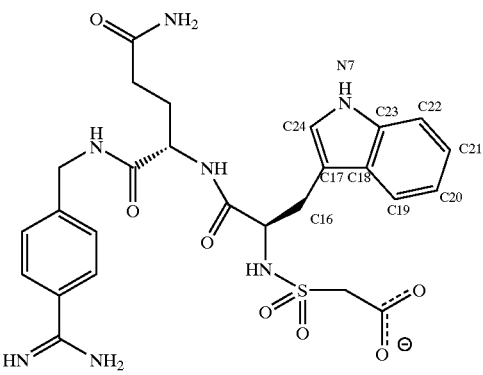

| Ligand atom | Factor VIIa | Minimum distance | Factor VIIa | Minimum distance | Factor VIIa | Minimum distance |
|---|---|---|---|---|---|---|
| C16 | Pro170I | 3.9 Å | | | | |
| C17 | Pro170I | 3.7 Å | | | | |
| C18 | Pro170I | 3.4 Å | | | | |
| C19 | Pro170I | 3.5 Å | | | | |
| C20 | Gln217 | 3.8 Å | Val170E | 4.2 Å | Ser170H | 4.1 Å |
| C20 | Pro170I | 4.0 Å | | | | |
| C21 | Val_170E | 4.0 Å | Asp170G | 4.2 Å | Ser170H | 3.8 Å |
| C22 | Asp170G | 3.5 Å | Ser170H | 4.1 Å | | |
| C23 | Asp170G | 3.8 Å | Pro170I | 3.8 Å | | |
| C24 | Pro170I | 4.1 Å | | | | |
| N7 | Asp170G | 4.0 Å | | | | |

*The above table exclusively shows ligand atoms located within a minimum distance of 4.2 Å from amino acid residues in human factor VIIa.

TABLE 45

Van der Waals interaction between Compound (2) and human factor VIIa S4 site

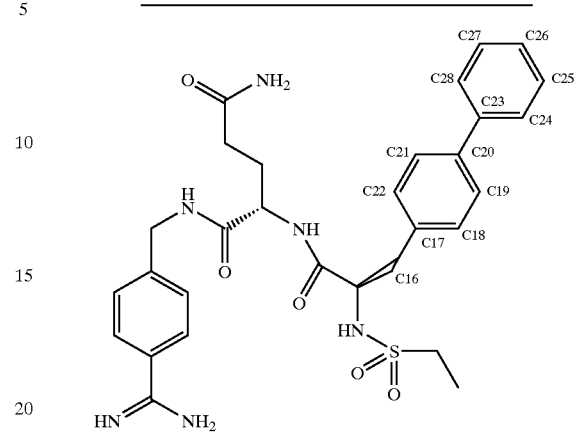

| Ligand atom | Factor VIIa | Minimum distance | Factor VIIa | Minimum distance | Factor VIIa | Minimum distance |
|---|---|---|---|---|---|---|
| C16 | Trp215 | 3.9 Å | Gly216 | 4.2 Å | Pro170I | 4.0 Å |
| C17 | Pro170I | 3.6 Å | | | | |
| C18 | Pro170I | 3.6 Å | Trp215 | 4.2 Å | Gln217 | 4.2 Å |
| C19 | Ser170H | 3.8 Å | Pro170I | 3.6 Å | Gln217 | 3.9 Å |
| C20 | Ser170H | 3.9 Å | Pro170I | 3.7 Å | | |
| C21 | Pro170I | 3.7 Å | | | | |
| C22 | Pro170I | 3.7 Å | | | | |
| C23 | Ser170H | 3.7 Å | | | | |
| C24 | Ser170H | 4.2 Å | Gln217 | 3.9 Å | | |
| C25 | Gln217 | 4.2 Å | | | | |
| C26 | Gly170F | 4.2 Å | | | | |
| C27 | Asp170G | 3.9 Å | Ser170H | 3.9 Å | | |
| C28 | Asp170G | 3.8 Å | Ser170H | 3.6 Å | | |

*The above table exclusively shows ligand atoms located within a minimum distance of 4.2 Å from amino acid residues in human factor VIIa.

Test Example

Biological Activity Test

Method

1. Assay for FVIIa-inhibiting Activity

The assay was carried out with 96-well microplates (Falcon, No. 3072) at room temperature.

A 10 vol % DMSO solution of a test compound (20 μL) was mixed with 40 μL Thromborel®S (50 mg/mL, Dade Behring, GTS-200A), 20 μL Spectrozyme®fVIIa (5 mmol/L, American Diagnostica Inc., #217L), 20 μL Tris buffer (500 mmol/L Tris/HCl, pH 7.5, 1500 mmol/L NaCl, 50 mmol/L $CaCl_2$) and 80 μL distilled water, followed by stirring. The reaction was initiated by addition of 20 μL FVIIa (20 nmol/L, Enzyme Research Laboratories, HF VIIa) and then monitored over time for absorbance at 405 nm using a microplate reader (Biorad, Model 3550) to determine the initial velocity of the reaction for each test compound. The initial reaction velocity was set to 100% in the case of adding 10 vol % DMSO alone, instead of a test compound. A concentration-reaction curve was prepared for FVIIa-inhibiting activity of each test compound to calculate a concentration at which the compound causes 50% inhibition of initial reaction velocity. This concentration was defined as an IC50 value.

2. Assay for Thrombin-inhibiting Activity

The assay was carried out with 96-well microplates (Falcon, No. 3072) at room temperature.

A 10 vol % DMSO solution of a test compound (20 μL) was mixed with 40 μL Tris buffer (200 mmol/L Tris/HCl, pH 8.0), 20 μL NaCl solution (1 mol/L), 20 μL FVR-pNa (2 mmol/L, SIGMA, B 7632) and 80 μL distilled water, followed by stirring. The reaction was initiated by addition of 20 μ2L human thrombin (5 U/mL, SIGMA, T 1063) and then monitored over time for absorbance at 405 nm using a microplate reader (Biorad, Model 3550) to determine the initial velocity of the reaction for each test compound. The same procedure as shown in assay for FVIIa-inhibiting activity was repeated to calculate an IC50 value for each test compound.

Result

The results obtained are shown in Table 46 below.

TABLE 46

| Example No. | IC50 Factor VIIa (nM) | IC50 Thrombin (nM) |
|---|---|---|
| 5 | 62 | 5880 |
| 7 | 37 | 17870 |
| 65 | 93 | 9415 |
| 81 | 177 | 5691 |
| 82 | 131 | 12544 |
| 170 | 37 | 9422 |
| 22 | 39 | 17544 |
| 146 | 153 | 80175 |
| 148 | 65 | 8325 |
| 83 | 55 | 14374 |

INDUSTRIAL APPLICABILITY

The compound of the present invention can have an excellent inhibitory activity against FVIIa or a selective inhibitory activity against extrinsic blood coagulation. This suggests that the compound of the present invention is expected to have pharmaceutical utility such as an antithrombotic agent with higher safety and fewer side effects (e.g., hemorrhage tendency). In particular, it is expected to have prophylactic or therapeutic utility for pathological conditions associated with the extrinsic coagulation pathway. More specifically, it is expected to be effective as a therapeutic or prophylactic agent for chronic thrombosis (e.g., postoperative deep vein thrombosis, post-PTCA restenosis, chronic DIC), cardioembolic strokes, cardiac infarction, cerebral infarction, etc.

In addition, it is not only possible to provide a crystal which can be used for X-ray crystal structure analysis with the aim of three-dimensional structure analysis of a complex between human factor VIIa/human soluble tissue factor and a low-molecular weight reversible factor VIIa inhibitor, but it is also possible to computationally design a low-molecular weight reversible factor VIIa inhibitor using X-ray crystal structure analysis data. Therefore, such a design procedure enables the development of a low-molecular weight reversible factor VIIa inhibitor.

Table 36 Coordinate data of the complex between Compound (1) and human factor VIIa/soluble tissue factor (all data)

```
CRYST1   71.400   82.220  123.470   90.00   90.00   90.00 P212121
ATOM     1   N    ALA  L   1    43.006  30.236  87.010  1.00  26.90  L  N
ATOM     2   CA   ALA  L   1    44.063  31.220  87.381  1.00  27.37  L  C
ATOM     3   C    ALA  L   1    44.489  30.945  88.817  1.00  28.56  L  C
ATOM     4   O    ALA  L   1    43.801  30.238  89.541  1.00  27.63  L  O
ATOM     5   CB   ALA  L   1    43.527  32.638  87.252  1.00  27.26  L  C
ATOM     6   N    ASN  L   2    45.618  31.505  89.233  1.00  29.16  L  N
ATOM     7   CA   ASN  L   2    46.105  31.273  90.585  1.00  29.83  L  C
ATOM     8   C    ASN  L   2    46.263  32.541  91.402  1.00  30.42  L  C
ATOM     9   O    ASN  L   2    46.985  33.456  91.018  1.00  32.56  L  O
ATOM    10   CB   ASN  L   2    47.444  30.533  90.546  1.00  27.10  L  C
ATOM    11   CG   ASN  L   2    47.320  29.133  89.989  1.00  27.19  L  C
ATOM    12   OD1  ASN  L   2    46.579  28.312  90.519  1.00  26.29  L  O
ATOM    13   ND2  ASN  L   2    48.049  28.851  88.917  1.00  27.22  L  N
ATOM    14   N    ALA  L   3    45.565  32.592  92.528  1.00  31.86  L  N
ATOM    15   CA   ALA  L   3    45.652  33.724  93.438  1.00  31.70  L  C
ATOM    16   C    ALA  L   3    46.428  33.192  94.641  1.00  32.24  L  C
ATOM    17   O    ALA  L   3    46.627  31.980  94.764  1.00  31.48  L  O
ATOM    18   CB   ALA  L   3    44.266  34.179  93.853  1.00  31.84  L  C
ATOM    19   N    PHE  L   4    46.864  34.085  95.524  1.00  32.19  L  N
ATOM    20   CA   PHE  L   4    47.636  33.676  96.697  1.00  31.55  L  C
ATOM    21   C    PHE  L   4    46.917  32.656  97.574  1.00  29.19  L  C
ATOM    22   O    PHE  L   4    45.798  32.893  98.025  1.00  30.82  L  O
ATOM    23   CB   PHE  L   4    48.003  34.897  97.548  1.00  33.52  L  C
ATOM    24   CG   PHE  L   4    48.900  34.574  98.715  1.00  35.99  L  C
ATOM    25   CD1  PHE  L   4    50.180  34.067  98.506  1.00  36.15  L  C
ATOM    26   CD2  PHE  L   4    48.464  34.768 100.021  1.00  36.15  L  C
ATOM    27   CE1  PHE  L   4    51.012  33.759  99.580  1.00  38.17  L  C
ATOM    28   CE2  PHE  L   4    49.289  34.464 101.103  1.00  38.45  L  C
ATOM    29   CZ   PHE  L   4    50.567  33.957 100.881  1.00  37.74  L  C
ATOM    30   N    LEU  L   5    47.569  31.519  97.796  1.00  27.82  L  N
ATOM    31   CA   LEU  L   5    47.044  30.442  98.640  1.00  26.01  L  C
ATOM    32   C    LEU  L   5    45.864  29.624  98.122  1.00  26.56  L  C
ATOM    33   O    LEU  L   5    45.505  28.619  98.730  1.00  27.40  L  O
ATOM    34   CB   LEU  L   5    46.682  30.985 100.027  1.00  24.14  L  C
ATOM    35   CG   LEU  L   5    47.816  31.543 100.891  1.00  24.48  L  C
ATOM    36   CD1  LEU  L   5    47.248  31.998 102.231  1.00  22.64  L  C
ATOM    37   CD2  LEU  L   5    48.886  30.479 101.102  1.00  21.31  L  C
ATOM    38   N    CGU  L   6    45.252  30.027  97.016  1.00  26.55  L  N
ATOM    39   CA   CGU  L   6    44.120  29.256  96.516  1.00  26.75  L  C
```

|      |     |     |     |   |    |        |        |         |      |       |   |   |
|------|-----|-----|-----|---|----|--------|--------|---------|------|-------|---|---|
| ATOM | 40  | CB  | CGU | L | 6  | 43.497 | 29.921 | 95.289  | 1.00 | 26.18 | L | C |
| ATOM | 41  | CG  | CGU | L | 6  | 42.283 | 29.117 | 94.819  | 1.00 | 25.49 | L | C |
| ATOM | 42  | CD1 | CGU | L | 6  | 42.608 | 28.386 | 93.520  | 1.00 | 23.72 | L | C |
| ATOM | 43  | CD2 | CGU | L | 6  | 41.068 | 30.027 | 94.667  | 1.00 | 26.90 | L | C |
| ATOM | 44  | OE1 | CGU | L | 6  | 43.364 | 28.939 | 92.739  | 1.00 | 19.08 | L | O |
| ATOM | 45  | OE2 | CGU | L | 6  | 42.108 | 27.273 | 93.323  | 1.00 | 22.25 | L | O |
| ATOM | 46  | OE3 | CGU | L | 6  | 40.524 | 30.434 | 95.688  | 1.00 | 27.43 | L | O |
| ATOM | 47  | OE4 | CGU | L | 6  | 40.690 | 30.308 | 93.557  | 1.00 | 26.50 | L | O |
| ATOM | 48  | C   | CGU | L | 6  | 44.499 | 27.819 | 96.178  | 1.00 | 25.52 | L | C |
| ATOM | 49  | O   | CGU | L | 6  | 43.666 | 26.915 | 96.256  | 1.00 | 24.58 | L | O |
| ATOM | 50  | N   | CGU | L | 7  | 45.760 | 27.607 | 95.813  | 1.00 | 24.67 | L | N |
| ATOM | 51  | CA  | CGU | L | 7  | 46.245 | 26.273 | 95.478  | 1.00 | 24.21 | L | C |
| ATOM | 52  | CB  | CGU | L | 7  | 47.622 | 26.392 | 94.817  | 1.00 | 23.05 | L | C |
| ATOM | 53  | CG  | CGU | L | 7  | 47.330 | 27.007 | 93.446  | 1.00 | 25.83 | L | C |
| ATOM | 54  | CD1 | CGU | L | 7  | 46.490 | 26.029 | 92.643  | 1.00 | 25.89 | L | C |
| ATOM | 55  | CD2 | CGU | L | 7  | 48.590 | 27.400 | 92.679  | 1.00 | 27.73 | L | C |
| ATOM | 56  | OE1 | CGU | L | 7  | 45.505 | 26.442 | 92.115  | 1.00 | 24.48 | L | O |
| ATOM | 57  | OE2 | CGU | L | 7  | 46.845 | 24.866 | 92.591  | 1.00 | 23.44 | L | O |
| ATOM | 58  | OE3 | CGU | L | 7  | 49.041 | 28.527 | 92.846  | 1.00 | 28.58 | L | O |
| ATOM | 59  | OE4 | CGU | L | 7  | 49.090 | 26.585 | 91.922  | 1.00 | 28.37 | L | O |
| ATOM | 60  | C   | CGU | L | 7  | 46.249 | 25.303 | 96.672  | 1.00 | 23.79 | L | C |
| ATOM | 61  | O   | CGU | L | 7  | 46.558 | 24.120 | 96.529  | 1.00 | 25.13 | L | O |
| ATOM | 62  | N   | LEU | L | 8  | 45.896 | 25.811 | 97.848  | 1.00 | 24.29 | L | N |
| ATOM | 63  | CA  | LEU | L | 8  | 45.789 | 24.983 | 99.049  | 1.00 | 24.16 | L | C |
| ATOM | 64  | C   | LEU | L | 8  | 44.458 | 24.235 | 98.963  | 1.00 | 25.54 | L | C |
| ATOM | 65  | O   | LEU | L | 8  | 44.285 | 23.180 | 99.565  | 1.00 | 26.65 | L | O |
| ATOM | 66  | CB  | LEU | L | 8  | 45.790 | 25.851 | 100.311 | 1.00 | 23.41 | L | C |
| ATOM | 67  | CG  | LEU | L | 8  | 47.117 | 26.250 | 100.968 | 1.00 | 24.22 | L | C |
| ATOM | 68  | CD1 | LEU | L | 8  | 48.042 | 26.938 | 99.969  | 1.00 | 19.80 | L | C |
| ATOM | 69  | CD2 | LEU | L | 8  | 46.817 | 27.166 | 102.148 | 1.00 | 23.24 | L | C |
| ATOM | 70  | N   | ARG | L | 9  | 43.520 | 24.798 | 98.203  | 1.00 | 27.13 | L | N |
| ATOM | 71  | CA  | ARG | L | 9  | 42.198 | 24.213 | 98.027  | 1.00 | 27.75 | L | C |
| ATOM | 72  | C   | ARG | L | 9  | 42.226 | 23.132 | 96.949  | 1.00 | 27.08 | L | C |
| ATOM | 73  | O   | ARG | L | 9  | 42.930 | 23.255 | 95.948  | 1.00 | 27.06 | L | O |
| ATOM | 74  | CB  | ARG | L | 9  | 41.192 | 25.300 | 97.625  | 1.00 | 29.68 | L | C |
| ATOM | 75  | CG  | ARG | L | 9  | 41.292 | 26.593 | 98.427  | 1.00 | 33.48 | L | C |
| ATOM | 76  | CD  | ARG | L | 9  | 40.264 | 27.619 | 97.964  | 1.00 | 34.05 | L | C |
| ATOM | 77  | NE  | ARG | L | 9  | 38.914 | 27.246 | 98.370  | 1.00 | 37.69 | L | N |
| ATOM | 78  | CZ  | ARG | L | 9  | 38.254 | 27.781 | 99.395  | 1.00 | 38.57 | L | C |
| ATOM | 79  | NH1 | ARG | L | 9  | 38.806 | 28.734 | 100.136 | 1.00 | 38.38 | L | N |
| ATOM | 80  | NH2 | ARG | L | 9  | 37.037 | 27.349 | 99.689  | 1.00 | 40.53 | L | N |
| ATOM | 81  | N   | PRO | L | 10 | 41.465 | 22.050 | 97.144  | 1.00 | 27.28 | L | N |
| ATOM | 82  | CA  | PRO | L | 10 | 41.446 | 20.985 | 96.137  | 1.00 | 27.55 | L | C |
| ATOM | 83  | C   | PRO | L | 10 | 41.008 | 21.551 | 94.780  | 1.00 | 27.58 | L | C |
| ATOM | 84  | O   | PRO | L | 10 | 40.388 | 22.615 | 94.713  | 1.00 | 27.34 | L | O |
| ATOM | 85  | CB  | PRO | L | 10 | 40.433 | 19.999 | 96.708  | 1.00 | 29.14 | L | C |
| ATOM | 86  | CG  | PRO | L | 10 | 40.613 | 20.160 | 98.191  | 1.00 | 27.86 | L | C |
| ATOM | 87  | CD  | PRO | L | 10 | 40.686 | 21.665 | 98.333  | 1.00 | 28.70 | L | C |
| ATOM | 88  | N   | GLY | L | 11 | 41.334 | 20.848 | 93.702  | 1.00 | 26.59 | L | N |
| ATOM | 89  | CA  | GLY | L | 11 | 40.950 | 21.321 | 92.383  | 1.00 | 28.67 | L | C |
| ATOM | 90  | C   | GLY | L | 11 | 39.445 | 21.370 | 92.164  | 1.00 | 29.12 | L | C |
| ATOM | 91  | O   | GLY | L | 11 | 38.709 | 20.499 | 92.628  | 1.00 | 30.35 | L | O |
| ATOM | 92  | N   | SER | L | 12 | 38.985 | 22.398 | 91.459  | 1.00 | 29.23 | L | N |
| ATOM | 93  | CA  | SER | L | 12 | 37.567 | 22.560 | 91.159  | 1.00 | 29.12 | L | C |
| ATOM | 94  | C   | SER | L | 12 | 37.393 | 23.085 | 89.740  | 1.00 | 29.51 | L | C |
| ATOM | 95  | O   | SER | L | 12 | 37.797 | 24.206 | 89.425  | 1.00 | 28.38 | L | O |
| ATOM | 96  | CB  | SER | L | 12 | 36.916 | 23.531 | 92.143  | 1.00 | 30.52 | L | C |
| ATOM | 97  | OG  | SER | L | 12 | 35.555 | 23.749 | 91.803  | 1.00 | 31.56 | L | O |
| ATOM | 98  | N   | LEU | L | 13 | 36.788 | 22.271 | 88.884  | 1.00 | 29.17 | L | N |
| ATOM | 99  | CA  | LEU | L | 13 | 36.575 | 22.660 | 87.497  | 1.00 | 30.18 | L | C |
| ATOM | 100 | C   | LEU | L | 13 | 35.779 | 23.953 | 87.383  | 1.00 | 30.11 | L | C |
| ATOM | 101 | O   | LEU | L | 13 | 36.128 | 24.844 | 86.611  | 1.00 | 32.23 | L | O |
| ATOM | 102 | CB  | LEU | L | 13 | 35.842 | 21.549 | 86.745  | 1.00 | 30.30 | L | C |
| ATOM | 103 | CG  | LEU | L | 13 | 35.630 | 21.832 | 85.260  | 1.00 | 31.24 | L | C |
| ATOM | 104 | CD1 | LEU | L | 13 | 36.982 | 21.877 | 84.558  | 1.00 | 29.56 | L | C |
| ATOM | 105 | CD2 | LEU | L | 13 | 34.743 | 20.756 | 84.654  | 1.00 | 30.75 | L | C |
| ATOM | 106 | N   | CGU | L | 14 | 34.703 | 24.051 | 88.153  | 1.00 | 29.30 | L | N |
| ATOM | 107 | CA  | CGU | L | 14 | 33.851 | 25.230 | 88.130  | 1.00 | 29.52 | L | C |
| ATOM | 108 | CB  | CGU | L | 14 | 32.668 | 25.027 | 89.072  | 1.00 | 31.22 | L | C |
| ATOM | 109 | CG  | CGU | L | 14 | 31.651 | 26.161 | 89.091  | 1.00 | 35.34 | L | C |
| ATOM | 110 | CD1 | CGU | L | 14 | 30.495 | 25.800 | 90.019  | 1.00 | 36.63 | L | C |
| ATOM | 111 | CD2 | CGU | L | 14 | 31.135 | 26.407 | 87.679  | 1.00 | 36.12 | L | C |
| ATOM | 112 | OE1 | CGU | L | 14 | 29.836 | 26.703 | 90.495  | 1.00 | 37.62 | L | O |
| ATOM | 113 | OE2 | CGU | L | 14 | 30.285 | 24.609 | 90.254  | 1.00 | 40.38 | L | O |
| ATOM | 114 | OE3 | CGU | L | 14 | 31.048 | 27.567 | 87.288  | 1.00 | 37.34 | L | O |
| ATOM | 115 | OE4 | CGU | L | 14 | 30.838 | 25.432 | 86.992  | 1.00 | 37.27 | L | O |
| ATOM | 116 | C   | CGU | L | 14 | 34.585 | 26.515 | 88.502  | 1.00 | 28.40 | L | C |
| ATOM | 117 | O   | CGU | L | 14 | 34.616 | 27.463 | 87.725  | 1.00 | 28.45 | L | O |
| ATOM | 118 | N   | ARG | L | 15 | 35.177 | 26.540 | 89.691  | 1.00 | 27.46 | L | N |

-continued

| | | | | | | | | | | | | |
|---|---|---|---|---|---|---|---|---|---|---|---|---|
| ATOM | 119 | CA | ARG | L | 15 | 35.894 | 27.718 | 90.175 | 1.00 | 27.51 | L | C |
| ATOM | 120 | C | ARG | L | 15 | 37.132 | 28.064 | 89.356 | 1.00 | 27.23 | L | C |
| ATOM | 121 | O | ARG | L | 15 | 37.465 | 29.237 | 89.182 | 1.00 | 25.95 | L | O |
| ATOM | 122 | CB | ARG | L | 15 | 36.313 | 27.508 | 91.637 | 1.00 | 27.70 | L | C |
| ATOM | 123 | CG | ARG | L | 15 | 37.003 | 28.707 | 92.288 | 1.00 | 28.99 | L | C |
| ATOM | 124 | CD | ARG | L | 15 | 37.615 | 28.338 | 93.650 | 1.00 | 27.72 | L | C |
| ATOM | 125 | NE | ARG | L | 15 | 38.708 | 27.374 | 93.512 | 1.00 | 23.84 | L | N |
| ATOM | 126 | CZ | ARG | L | 15 | 38.726 | 26.161 | 94.058 | 1.00 | 24.64 | L | C |
| ATOM | 127 | NH1 | ARG | L | 15 | 37.710 | 25.737 | 94.798 | 1.00 | 25.00 | L | N |
| ATOM | 128 | NH2 | ARG | L | 15 | 39.759 | 25.358 | 93.848 | 1.00 | 23.56 | L | N |
| ATOM | 129 | N | CGU | L | 16 | 37.792 | 27.036 | 88.835 | 1.00 | 27.33 | L | N |
| ATOM | 130 | CA | CGU | L | 16 | 39.032 | 27.205 | 88.085 | 1.00 | 27.34 | L | C |
| ATOM | 131 | CB | CGU | L | 16 | 39.967 | 26.045 | 88.431 | 1.00 | 27.36 | L | C |
| ATOM | 132 | CG | CGU | L | 16 | 40.198 | 25.989 | 89.937 | 1.00 | 23.86 | L | C |
| ATOM | 133 | CD1 | CGU | L | 16 | 40.616 | 27.379 | 90.373 | 1.00 | 24.51 | L | C |
| ATOM | 134 | CD2 | CGU | L | 16 | 41.304 | 24.995 | 90.253 | 1.00 | 23.35 | L | C |
| ATOM | 135 | OE1 | CGU | L | 16 | 41.440 | 27.927 | 89.699 | 1.00 | 27.27 | L | O |
| ATOM | 136 | OE2 | CGU | L | 16 | 40.095 | 27.883 | 91.340 | 1.00 | 24.69 | L | O |
| ATOM | 137 | OE3 | CGU | L | 16 | 42.407 | 25.416 | 90.385 | 1.00 | 20.19 | L | O |
| ATOM | 138 | OE4 | CGU | L | 16 | 41.023 | 23.818 | 90.349 | 1.00 | 22.98 | L | O |
| ATOM | 139 | C | CGU | L | 16 | 38.982 | 27.363 | 86.574 | 1.00 | 29.25 | L | C |
| ATOM | 140 | O | CGU | L | 16 | 39.739 | 28.159 | 86.011 | 1.00 | 29.12 | L | O |
| ATOM | 141 | N | CYS | L | 17 | 38.113 | 26.607 | 85.913 | 1.00 | 29.27 | L | N |
| ATOM | 142 | CA | CYS | L | 17 | 38.020 | 26.672 | 84.460 | 1.00 | 30.58 | L | C |
| ATOM | 143 | C | CYS | L | 17 | 36.760 | 27.339 | 83.910 | 1.00 | 30.90 | L | C |
| ATOM | 144 | O | CYS | L | 17 | 36.767 | 27.841 | 82.789 | 1.00 | 31.41 | L | O |
| ATOM | 145 | CB | CYS | L | 17 | 38.143 | 25.268 | 83.870 | 1.00 | 29.03 | L | C |
| ATOM | 146 | SG | CYS | L | 17 | 39.683 | 24.375 | 84.273 | 1.00 | 29.62 | L | S |
| ATOM | 147 | N | LYS | L | 18 | 35.682 | 27.337 | 84.686 | 1.00 | 33.15 | L | N |
| ATOM | 148 | CA | LYS | L | 18 | 34.428 | 27.953 | 84.254 | 1.00 | 33.15 | L | C |
| ATOM | 149 | C | LYS | L | 18 | 34.376 | 29.423 | 84.649 | 1.00 | 33.16 | L | C |
| ATOM | 150 | O | LYS | L | 18 | 34.202 | 30.299 | 83.804 | 1.00 | 33.01 | L | O |
| ATOM | 151 | CB | LYS | L | 18 | 33.229 | 27.210 | 84.855 | 1.00 | 33.20 | L | C |
| ATOM | 152 | CG | LYS | L | 18 | 32.773 | 25.998 | 84.049 | 1.00 | 35.52 | L | C |
| ATOM | 153 | CD | LYS | L | 18 | 33.805 | 24.888 | 84.034 | 1.00 | 38.86 | L | C |
| ATOM | 154 | CE | LYS | L | 18 | 34.139 | 24.448 | 82.610 | 1.00 | 39.72 | L | C |
| ATOM | 155 | NZ | LYS | L | 18 | 32.971 | 23.879 | 81.874 | 1.00 | 40.07 | L | N |
| ATOM | 156 | N | CGU | L | 19 | 34.525 | 29.686 | 85.942 | 1.00 | 33.87 | L | N |
| ATOM | 157 | CA | CGU | L | 19 | 34.510 | 31.048 | 86.459 | 1.00 | 33.17 | L | C |
| ATOM | 158 | CB | CGU | L | 19 | 34.259 | 31.030 | 87.963 | 1.00 | 34.83 | L | C |
| ATOM | 159 | CG | CGU | L | 19 | 32.874 | 30.589 | 88.419 | 1.00 | 37.03 | L | C |
| ATOM | 160 | CD1 | CGU | L | 19 | 31.834 | 31.593 | 87.934 | 1.00 | 37.84 | L | C |
| ATOM | 161 | CD2 | CGU | L | 19 | 32.836 | 30.518 | 89.941 | 1.00 | 39.06 | L | C |
| ATOM | 162 | OE1 | CGU | L | 19 | 30.658 | 31.307 | 88.057 | 1.00 | 36.43 | L | O |
| ATOM | 163 | OE2 | CGU | L | 19 | 32.229 | 32.655 | 87.435 | 1.00 | 39.63 | L | O |
| ATOM | 164 | OE3 | CGU | L | 19 | 32.692 | 29.414 | 90.470 | 1.00 | 38.92 | L | O |
| ATOM | 165 | OE4 | CGU | L | 19 | 32.955 | 31.571 | 90.570 | 1.00 | 41.50 | L | O |
| ATOM | 166 | C | CGU | L | 19 | 35.826 | 31.771 | 86.182 | 1.00 | 32.60 | L | C |
| ATOM | 167 | O | CGU | L | 19 | 35.934 | 32.978 | 86.388 | 1.00 | 33.89 | L | O |
| ATOM | 168 | N | CGU | L | 20 | 36.824 | 31.030 | 85.714 | 1.00 | 31.95 | L | N |
| ATOM | 169 | CA | CGU | L | 20 | 38.128 | 31.607 | 85.422 | 1.00 | 30.77 | L | C |
| ATOM | 170 | CB | CGU | L | 20 | 39.045 | 31.487 | 86.634 | 1.00 | 28.99 | L | C |
| ATOM | 171 | CG | CGU | L | 20 | 38.620 | 31.952 | 88.020 | 1.00 | 30.59 | L | C |
| ATOM | 172 | CD1 | CGU | L | 20 | 38.770 | 33.462 | 88.131 | 1.00 | 31.48 | L | C |
| ATOM | 173 | CD2 | CGU | L | 20 | 39.521 | 31.281 | 89.047 | 1.00 | 30.25 | L | C |
| ATOM | 174 | OE1 | CGU | L | 20 | 38.025 | 34.061 | 88.882 | 1.00 | 33.25 | L | O |
| ATOM | 175 | OE2 | CGU | L | 20 | 39.634 | 34.004 | 87.461 | 1.00 | 33.62 | L | O |
| ATOM | 176 | OE3 | CGU | L | 20 | 39.282 | 31.444 | 90.226 | 1.00 | 29.48 | L | O |
| ATOM | 177 | OE4 | CGU | L | 20 | 40.453 | 30.598 | 88.629 | 1.00 | 30.41 | L | O |
| ATOM | 178 | C | CGU | L | 20 | 38.791 | 30.857 | 84.283 | 1.00 | 29.55 | L | C |
| ATOM | 179 | O | CGU | L | 20 | 38.328 | 29.796 | 83.875 | 1.00 | 29.94 | L | O |
| ATOM | 180 | N | GLN | L | 21 | 39.891 | 31.419 | 83.795 | 1.00 | 30.03 | L | N |
| ATOM | 181 | CA | GLN | L | 21 | 40.680 | 30.808 | 82.739 | 1.00 | 30.36 | L | C |
| ATOM | 182 | C | GLN | L | 21 | 41.690 | 29.913 | 83.454 | 1.00 | 29.74 | L | C |
| ATOM | 183 | O | GLN | L | 21 | 42.484 | 30.388 | 84.276 | 1.00 | 27.73 | L | O |
| ATOM | 184 | CB | GLN | L | 21 | 41.425 | 31.879 | 81.944 | 1.00 | 33.78 | L | C |
| ATOM | 185 | CG | GLN | L | 21 | 40.535 | 32.812 | 81.134 | 1.00 | 40.75 | L | C |
| ATOM | 186 | CD | GLN | L | 21 | 39.865 | 32.115 | 79.966 | 1.00 | 44.61 | L | C |
| ATOM | 187 | OE1 | GLN | L | 21 | 39.029 | 31.228 | 80.150 | 1.00 | 48.21 | L | O |
| ATOM | 188 | NE2 | GLN | L | 21 | 40.235 | 32.510 | 78.752 | 1.00 | 45.88 | L | N |
| ATOM | 189 | N | CYS | L | 22 | 41.659 | 28.621 | 83.159 | 1.00 | 27.02 | L | N |
| ATOM | 190 | CA | CYS | L | 22 | 42.584 | 27.704 | 83.798 | 1.00 | 26.53 | L | C |
| ATOM | 191 | C | CYS | L | 22 | 43.607 | 27.197 | 82.795 | 1.00 | 28.06 | L | C |
| ATOM | 192 | O | CYS | L | 22 | 43.285 | 26.959 | 81.630 | 1.00 | 29.00 | L | O |
| ATOM | 193 | CB | CYS | L | 22 | 41.824 | 26.529 | 84.417 | 1.00 | 26.03 | L | C |
| ATOM | 194 | SG | CYS | L | 22 | 41.127 | 25.347 | 83.224 | 1.00 | 24.58 | L | S |
| ATOM | 195 | N | SER | L | 23 | 44.846 | 27.044 | 83.251 | 1.00 | 28.01 | L | N |
| ATOM | 196 | CA | SER | L | 23 | 45.919 | 26.564 | 82.395 | 1.00 | 29.36 | L | C |
| ATOM | 197 | C | SER | L | 23 | 45.856 | 25.046 | 82.316 | 1.00 | 29.53 | L | C |

-continued

| | | | | | | | | | | | | |
|---|---|---|---|---|---|---|---|---|---|---|---|---|
| ATOM | 198 | O | SER | L | 23 | 45.041 | 24.409 | 82.991 | 1.00 | 28.50 | L | O |
| ATOM | 199 | CB | SER | L | 23 | 47.278 | 26.991 | 82.954 | 1.00 | 30.24 | L | C |
| ATOM | 200 | OG | SER | L | 23 | 47.547 | 26.328 | 84.176 | 1.00 | 32.90 | L | O |
| ATOM | 201 | N | PHE | L | 24 | 46.729 | 24.471 | 81.496 | 1.00 | 28.75 | L | N |
| ATOM | 202 | CA | PHE | L | 24 | 46.774 | 23.030 | 81.325 | 1.00 | 28.22 | L | C |
| ATOM | 203 | C | PHE | L | 24 | 47.044 | 22.340 | 82.659 | 1.00 | 28.31 | L | C |
| ATOM | 204 | O | PHE | L | 24 | 46.373 | 21.370 | 83.019 | 1.00 | 26.88 | L | O |
| ATOM | 205 | CB | PHE | L | 24 | 47.871 | 22.644 | 80.328 | 1.00 | 27.99 | L | C |
| ATOM | 206 | CG | PHE | L | 24 | 47.906 | 21.179 | 80.019 | 1.00 | 27.32 | L | C |
| ATOM | 207 | CD1 | PHE | L | 24 | 47.014 | 20.626 | 79.106 | 1.00 | 27.03 | L | C |
| ATOM | 208 | CD2 | PHE | L | 24 | 48.791 | 20.338 | 80.684 | 1.00 | 27.00 | L | C |
| ATOM | 209 | CE1 | PHE | L | 24 | 47.000 | 19.256 | 78.864 | 1.00 | 25.26 | L | C |
| ATOM | 210 | CE2 | PHE | L | 24 | 48.784 | 18.964 | 80.449 | 1.00 | 25.45 | L | C |
| ATOM | 211 | CZ | PHE | L | 24 | 47.887 | 18.423 | 79.540 | 1.00 | 25.69 | L | C |
| ATOM | 212 | N | CGU | L | 25 | 48.031 | 22.850 | 83.388 | 1.00 | 27.44 | L | N |
| ATOM | 213 | CA | CGU | L | 25 | 48.405 | 22.282 | 84.673 | 1.00 | 28.71 | L | C |
| ATOM | 214 | CB | CGU | L | 25 | 49.570 | 23.068 | 85.262 | 1.00 | 33.43 | L | C |
| ATOM | 215 | CG | CGU | L | 25 | 50.357 | 22.364 | 86.358 | 1.00 | 38.45 | L | C |
| ATOM | 216 | CD1 | CGU | L | 25 | 51.791 | 22.882 | 86.348 | 1.00 | 40.65 | L | C |
| ATOM | 217 | CD2 | CGU | L | 25 | 50.357 | 20.859 | 86.100 | 1.00 | 40.80 | L | C |
| ATOM | 218 | OE1 | CGU | L | 25 | 52.101 | 23.772 | 87.138 | 1.00 | 41.24 | L | O |
| ATOM | 219 | OE2 | CGU | L | 25 | 52.571 | 22.386 | 85.537 | 1.00 | 43.46 | L | O |
| ATOM | 220 | OE3 | CGU | L | 25 | 50.854 | 20.453 | 85.053 | 1.00 | 41.65 | L | O |
| ATOM | 221 | OE4 | CGU | L | 25 | 49.853 | 20.120 | 86.950 | 1.00 | 42.95 | L | O |
| ATOM | 222 | C | CGU | L | 25 | 47.233 | 22.264 | 85.644 | 1.00 | 26.61 | L | C |
| ATOM | 223 | O | CGU | L | 25 | 46.958 | 21.246 | 86.271 | 1.00 | 25.98 | L | O |
| ATOM | 224 | N | CGU | L | 26 | 46.541 | 23.391 | 85.765 | 1.00 | 25.93 | L | N |
| ATOM | 225 | CA | CGU | L | 26 | 45.389 | 23.474 | 86.652 | 1.00 | 26.06 | L | C |
| ATOM | 226 | CB | CGU | L | 26 | 44.770 | 24.870 | 86.576 | 1.00 | 24.81 | L | C |
| ATOM | 227 | CG | CGU | L | 26 | 45.740 | 25.994 | 86.948 | 1.00 | 26.07 | L | C |
| ATOM | 228 | CD1 | CGU | L | 26 | 46.302 | 25.752 | 88.351 | 1.00 | 26.84 | L | C |
| ATOM | 229 | CD2 | CGU | L | 26 | 45.038 | 27.349 | 86.880 | 1.00 | 26.66 | L | C |
| ATOM | 230 | OE1 | CGU | L | 26 | 45.548 | 25.374 | 89.218 | 1.00 | 24.86 | L | O |
| ATOM | 231 | OE2 | CGU | L | 26 | 47.480 | 25.942 | 88.538 | 1.00 | 26.84 | L | O |
| ATOM | 232 | OE3 | CGU | L | 26 | 44.976 | 27.925 | 85.801 | 1.00 | 28.65 | L | O |
| ATOM | 233 | OE4 | CGU | L | 26 | 44.567 | 27.805 | 87.890 | 1.00 | 26.86 | L | O |
| ATOM | 234 | C | CGU | L | 26 | 44.360 | 22.416 | 86.254 | 1.00 | 26.09 | L | C |
| ATOM | 235 | O | CGU | L | 26 | 43.830 | 21.696 | 87.099 | 1.00 | 26.77 | L | O |
| ATOM | 236 | N | ALA | L | 27 | 44.090 | 22.319 | 84.957 | 1.00 | 26.92 | L | N |
| ATOM | 237 | CA | ALA | L | 27 | 43.139 | 21.341 | 84.449 | 1.00 | 26.84 | L | C |
| ATOM | 238 | C | ALA | L | 27 | 43.590 | 19.927 | 84.797 | 1.00 | 26.93 | L | C |
| ATOM | 239 | O | ALA | L | 27 | 42.775 | 19.085 | 85.171 | 1.00 | 27.45 | L | O |
| ATOM | 240 | CB | ALA | L | 27 | 42.999 | 21.486 | 82.938 | 1.00 | 24.94 | L | C |
| ATOM | 241 | N | ARG | L | 28 | 44.891 | 19.669 | 84.678 | 1.00 | 27.54 | L | N |
| ATOM | 242 | CA | ARG | L | 28 | 45.434 | 18.347 | 84.977 | 1.00 | 29.15 | L | C |
| ATOM | 243 | C | ARG | L | 28 | 45.275 | 17.976 | 86.451 | 1.00 | 29.86 | L | C |
| ATOM | 244 | O | ARG | L | 28 | 45.145 | 16.804 | 86.785 | 1.00 | 31.18 | L | O |
| ATOM | 245 | CB | ARG | L | 28 | 46.911 | 18.278 | 84.600 | 1.00 | 30.06 | L | C |
| ATOM | 246 | CG | ARG | L | 28 | 47.457 | 16.859 | 84.531 | 1.00 | 32.65 | L | C |
| ATOM | 247 | CD | ARG | L | 28 | 48.977 | 16.856 | 84.601 | 1.00 | 36.00 | L | C |
| ATOM | 248 | NE | ARG | L | 28 | 49.441 | 17.365 | 85.890 | 1.00 | 37.93 | L | N |
| ATOM | 249 | CZ | ARG | L | 28 | 49.284 | 16.735 | 87.053 | 1.00 | 38.70 | L | C |
| ATOM | 250 | NH1 | ARG | L | 28 | 48.682 | 15.552 | 87.109 | 1.00 | 38.86 | L | N |
| ATOM | 251 | NH2 | ARG | L | 28 | 49.706 | 17.308 | 88.171 | 1.00 | 39.29 | L | N |
| ATOM | 252 | N | CGU | L | 29 | 45.302 | 18.969 | 87.333 | 1.00 | 29.50 | L | N |
| ATOM | 253 | CA | CGU | L | 29 | 45.131 | 18.714 | 88.761 | 1.00 | 29.34 | L | C |
| ATOM | 254 | CB | CGU | L | 29 | 45.529 | 19.947 | 89.559 | 1.00 | 28.96 | L | C |
| ATOM | 255 | CG | CGU | L | 29 | 47.033 | 20.154 | 89.530 | 1.00 | 30.94 | L | C |
| ATOM | 256 | CD1 | CGU | L | 29 | 47.709 | 19.275 | 90.575 | 1.00 | 33.97 | L | C |
| ATOM | 257 | CD2 | CGU | L | 29 | 47.360 | 21.610 | 89.778 | 1.00 | 29.62 | L | C |
| ATOM | 258 | OE1 | CGU | L | 29 | 48.900 | 19.048 | 90.442 | 1.00 | 37.46 | L | O |
| ATOM | 259 | OE2 | CGU | L | 29 | 47.028 | 18.834 | 91.503 | 1.00 | 36.82 | L | O |
| ATOM | 260 | OE3 | CGU | L | 29 | 48.486 | 21.975 | 89.603 | 1.00 | 27.06 | L | O |
| ATOM | 261 | OE4 | CGU | L | 29 | 46.476 | 22.332 | 90.128 | 1.00 | 28.53 | L | O |
| ATOM | 262 | C | CGU | L | 29 | 43.688 | 18.343 | 89.077 | 1.00 | 28.66 | L | C |
| ATOM | 263 | O | CGU | L | 29 | 43.401 | 17.742 | 90.113 | 1.00 | 29.88 | L | O |
| ATOM | 264 | N | ILE | L | 30 | 42.783 | 18.717 | 88.181 | 1.00 | 27.56 | L | N |
| ATOM | 265 | CA | ILE | L | 30 | 41.371 | 18.408 | 88.340 | 1.00 | 27.41 | L | C |
| ATOM | 266 | C | ILE | L | 30 | 41.103 | 17.006 | 87.791 | 1.00 | 28.29 | L | C |
| ATOM | 267 | O | ILE | L | 30 | 40.605 | 16.138 | 88.503 | 1.00 | 28.57 | L | O |
| ATOM | 268 | CB | ILE | L | 30 | 40.492 | 19.428 | 87.570 | 1.00 | 26.20 | L | C |
| ATOM | 269 | CG1 | ILE | L | 30 | 40.685 | 20.830 | 88.156 | 1.00 | 25.87 | L | C |
| ATOM | 270 | CG2 | ILE | L | 30 | 39.035 | 19.014 | 87.626 | 1.00 | 23.37 | L | C |
| ATOM | 271 | CD1 | ILE | L | 30 | 39.890 | 21.910 | 87.444 | 1.00 | 25.78 | L | C |
| ATOM | 272 | N | PHE | L | 31 | 41.454 | 16.794 | 86.525 | 1.00 | 28.80 | L | N |
| ATOM | 273 | CA | PHE | L | 31 | 41.237 | 15.512 | 85.855 | 1.00 | 32.23 | L | C |
| ATOM | 274 | C | PHE | L | 31 | 42.260 | 14.420 | 86.195 | 1.00 | 34.25 | L | C |
| ATOM | 275 | O | PHE | L | 31 | 41.958 | 13.230 | 86.097 | 1.00 | 34.78 | L | O |
| ATOM | 276 | CB | PHE | L | 31 | 41.188 | 15.739 | 84.341 | 1.00 | 30.23 | L | C |

-continued

| | | | | | | | | | | | | |
|---|---|---|---|---|---|---|---|---|---|---|---|---|
| ATOM | 277 | CG | PHE | L | 31 | 40.039 | 16.608 | 83.900 | 1.00 | 28.90 | L | C |
| ATOM | 278 | CD1 | PHE | L | 31 | 38.737 | 16.111 | 83.893 | 1.00 | 29.15 | L | C |
| ATOM | 279 | CD2 | PHE | L | 31 | 40.254 | 17.926 | 83.512 | 1.00 | 25.49 | L | C |
| ATOM | 280 | CE1 | PHE | L | 31 | 37.664 | 16.918 | 83.503 | 1.00 | 27.09 | L | C |
| ATOM | 281 | CE2 | PHE | L | 31 | 39.194 | 18.740 | 83.123 | 1.00 | 25.64 | L | C |
| ATOM | 282 | CZ | PHE | L | 31 | 37.896 | 18.237 | 83.118 | 1.00 | 26.07 | L | C |
| ATOM | 283 | N | LYS | L | 32 | 43.463 | 14.832 | 86.586 | 1.00 | 36.51 | L | N |
| ATOM | 284 | CA | LYS | L | 32 | 44.544 | 13.919 | 86.967 | 1.00 | 39.51 | L | C |
| ATOM | 285 | C | LYS | L | 32 | 45.132 | 13.120 | 85.800 | 1.00 | 40.53 | L | C |
| ATOM | 286 | O | LYS | L | 32 | 46.265 | 13.362 | 85.386 | 1.00 | 41.25 | L | O |
| ATOM | 287 | CB | LYS | L | 32 | 44.064 | 12.958 | 88.064 | 1.00 | 40.66 | L | C |
| ATOM | 288 | CG | LYS | L | 32 | 43.132 | 13.599 | 89.088 | 1.00 | 43.75 | L | C |
| ATOM | 289 | CD | LYS | L | 32 | 43.294 | 13.002 | 90.473 | 1.00 | 45.44 | L | C |
| ATOM | 290 | CE | LYS | L | 32 | 44.566 | 13.514 | 91.136 | 1.00 | 48.55 | L | C |
| ATOM | 291 | NZ | LYS | L | 32 | 44.556 | 15.002 | 91.284 | 1.00 | 49.03 | L | N |
| ATOM | 292 | N | ASP | L | 33 | 44.366 | 12.167 | 85.278 | 1.00 | 41.87 | L | N |
| ATOM | 293 | CA | ASP | L | 33 | 44.811 | 11.343 | 84.161 | 1.00 | 43.56 | L | C |
| ATOM | 294 | C | ASP | L | 33 | 45.103 | 12.193 | 82.922 | 1.00 | 44.09 | L | C |
| ATOM | 295 | O | ASP | L | 33 | 44.322 | 13.073 | 82.562 | 1.00 | 44.53 | L | O |
| ATOM | 296 | CB | ASP | L | 33 | 43.747 | 10.290 | 83.849 | 1.00 | 45.31 | L | C |
| ATOM | 297 | CG | ASP | L | 33 | 44.088 | 9.458 | 82.635 | 1.00 | 47.36 | L | C |
| ATOM | 298 | OD1 | ASP | L | 33 | 43.843 | 9.923 | 81.525 | 1.00 | 45.97 | L | O |
| ATOM | 299 | OD2 | ASP | L | 33 | 44.606 | 8.347 | 82.809 | 1.00 | 49.11 | L | O |
| ATOM | 300 | N | ALA | L | 34 | 46.235 | 11.920 | 82.279 | 1.00 | 44.21 | L | N |
| ATOM | 301 | CA | ALA | L | 34 | 46.666 | 12.657 | 81.092 | 1.00 | 44.90 | L | C |
| ATOM | 302 | C | ALA | L | 34 | 45.679 | 12.572 | 79.932 | 1.00 | 45.63 | L | C |
| ATOM | 303 | O | ALA | L | 34 | 45.350 | 13.583 | 79.309 | 1.00 | 46.43 | L | O |
| ATOM | 304 | CB | ALA | L | 34 | 48.034 | 12.155 | 80.643 | 1.00 | 45.30 | L | C |
| ATOM | 305 | N | CGU | L | 35 | 45.225 | 11.360 | 79.637 | 1.00 | 45.00 | L | N |
| ATOM | 306 | CA | CGU | L | 35 | 44.274 | 11.132 | 78.559 | 1.00 | 44.45 | L | C |
| ATOM | 307 | CB | CGU | L | 35 | 43.892 | 9.646 | 78.502 | 1.00 | 47.50 | L | C |
| ATOM | 308 | CG | CGU | L | 35 | 45.001 | 8.586 | 78.399 | 1.00 | 52.62 | L | C |
| ATOM | 309 | CD1 | CGU | L | 35 | 46.080 | 9.012 | 77.405 | 1.00 | 54.39 | L | C |
| ATOM | 310 | CD2 | CGU | L | 35 | 45.632 | 8.287 | 79.763 | 1.00 | 53.62 | L | C |
| ATOM | 311 | OE1 | CGU | L | 35 | 47.263 | 8.886 | 77.743 | 1.00 | 55.86 | L | O |
| ATOM | 312 | OE2 | CGU | L | 35 | 45.722 | 9.460 | 76.313 | 1.00 | 56.24 | L | O |
| ATOM | 313 | OE3 | CGU | L | 35 | 46.606 | 8.955 | 80.122 | 1.00 | 53.37 | L | O |
| ATOM | 314 | OE4 | CGU | L | 35 | 45.140 | 7.379 | 80.445 | 1.00 | 54.53 | L | O |
| ATOM | 315 | C | CGU | L | 35 | 43.019 | 11.992 | 78.756 | 1.00 | 42.91 | L | C |
| ATOM | 316 | O | CGU | L | 35 | 42.540 | 12.632 | 77.819 | 1.00 | 42.37 | L | O |
| ATOM | 317 | N | ARG | L | 36 | 42.494 | 12.009 | 79.978 | 1.00 | 40.60 | L | N |
| ATOM | 318 | CA | ARG | L | 36 | 41.304 | 12.795 | 80.294 | 1.00 | 38.99 | L | C |
| ATOM | 319 | C | ARG | L | 36 | 41.572 | 14.296 | 80.212 | 1.00 | 36.95 | L | C |
| ATOM | 320 | O | ARG | L | 36 | 40.728 | 15.061 | 79.747 | 1.00 | 36.47 | L | O |
| ATOM | 321 | CB | ARG | L | 36 | 40.797 | 12.447 | 81.696 | 1.00 | 41.08 | L | C |
| ATOM | 322 | CG | ARG | L | 36 | 40.298 | 11.017 | 81.844 | 1.00 | 43.46 | L | C |
| ATOM | 323 | CD | ARG | L | 36 | 39.891 | 10.718 | 83.278 | 1.00 | 45.24 | L | C |
| ATOM | 324 | NE | ARG | L | 36 | 39.441 | 9.337 | 83.441 | 1.00 | 47.54 | L | N |
| ATOM | 325 | CZ | ARG | L | 36 | 39.133 | 8.776 | 84.607 | 1.00 | 48.41 | L | C |
| ATOM | 326 | NH1 | ARG | L | 36 | 39.225 | 9.471 | 85.734 | 1.00 | 46.77 | L | N |
| ATOM | 327 | NH2 | ARG | L | 36 | 38.728 | 7.512 | 84.647 | 1.00 | 50.53 | L | N |
| ATOM | 328 | N | THR | L | 37 | 42.747 | 14.716 | 80.669 | 1.00 | 34.62 | L | N |
| ATOM | 329 | CA | THR | L | 37 | 43.109 | 16.126 | 80.640 | 1.00 | 32.74 | L | C |
| ATOM | 330 | C | THR | L | 37 | 43.201 | 16.637 | 79.204 | 1.00 | 31.75 | L | C |
| ATOM | 331 | O | THR | L | 37 | 42.694 | 17.714 | 78.891 | 1.00 | 30.68 | L | O |
| ATOM | 332 | CB | THR | L | 37 | 44.455 | 16.369 | 81.351 | 1.00 | 32.46 | L | C |
| ATOM | 333 | OG1 | THR | L | 37 | 44.393 | 15.839 | 82.681 | 1.00 | 32.01 | L | O |
| ATOM | 334 | CG2 | THR | L | 37 | 44.759 | 17.861 | 81.427 | 1.00 | 31.14 | L | C |
| ATOM | 335 | N | LYS | L | 38 | 43.844 | 15.860 | 78.336 | 1.00 | 31.24 | L | N |
| ATOM | 336 | CA | LYS | L | 38 | 43.989 | 16.239 | 76.934 | 1.00 | 32.20 | L | C |
| ATOM | 337 | C | LYS | L | 38 | 42.630 | 16.318 | 76.233 | 1.00 | 30.65 | L | C |
| ATOM | 338 | O | LYS | L | 38 | 42.390 | 17.231 | 75.446 | 1.00 | 31.32 | L | O |
| ATOM | 339 | CB | LYS | L | 38 | 44.891 | 15.241 | 76.197 | 1.00 | 34.59 | L | C |
| ATOM | 340 | CG | LYS | L | 38 | 46.332 | 15.182 | 76.711 | 1.00 | 37.74 | L | C |
| ATOM | 341 | CD | LYS | L | 38 | 47.030 | 16.539 | 76.640 | 1.00 | 39.00 | L | C |
| ATOM | 342 | CE | LYS | L | 38 | 47.216 | 17.009 | 75.204 | 1.00 | 41.05 | L | C |
| ATOM | 343 | NZ | LYS | L | 38 | 47.824 | 18.365 | 75.130 | 1.00 | 38.92 | L | N |
| ATOM | 344 | N | LEU | L | 39 | 41.749 | 15.362 | 76.519 | 1.00 | 28.80 | L | N |
| ATOM | 345 | CA | LEU | L | 39 | 40.417 | 15.345 | 75.919 | 1.00 | 28.45 | L | C |
| ATOM | 346 | C | LEU | L | 39 | 39.665 | 16.624 | 76.275 | 1.00 | 27.55 | L | C |
| ATOM | 347 | O | LEU | L | 39 | 38.927 | 17.170 | 75.458 | 1.00 | 27.44 | L | O |
| ATOM | 348 | CB | LEU | L | 39 | 39.619 | 14.134 | 76.410 | 1.00 | 28.33 | L | C |
| ATOM | 349 | CG | LEU | L | 39 | 38.190 | 14.034 | 75.866 | 1.00 | 30.67 | L | C |
| ATOM | 350 | CD1 | LEU | L | 39 | 38.228 | 13.988 | 74.342 | 1.00 | 30.91 | L | C |
| ATOM | 351 | CD2 | LEU | L | 39 | 37.504 | 12.791 | 76.422 | 1.00 | 30.33 | L | C |
| ATOM | 352 | N | PHE | L | 40 | 39.850 | 17.091 | 77.505 | 1.00 | 26.66 | L | N |
| ATOM | 353 | CA | PHE | L | 40 | 39.213 | 18.315 | 77.968 | 1.00 | 26.79 | L | C |
| ATOM | 354 | C | PHE | L | 40 | 39.869 | 19.531 | 77.319 | 1.00 | 26.64 | L | C |
| ATOM | 355 | O | PHE | L | 40 | 39.188 | 20.429 | 76.821 | 1.00 | 27.35 | L | O |

-continued

| | | | | | | | | | | | |
|---|---|---|---|---|---|---|---|---|---|---|---|
| ATOM | 356 | CB | PHE | L | 40 | 39.346 | 18.438 | 79.491 | 1.00 | 25.08 | L | C |
| ATOM | 357 | CG | PHE | L | 40 | 39.028 | 19.810 | 80.020 | 1.00 | 25.21 | L | C |
| ATOM | 358 | CD1 | PHE | L | 40 | 37.707 | 20.208 | 80.225 | 1.00 | 24.16 | L | C |
| ATOM | 359 | CD2 | PHE | L | 40 | 40.052 | 20.718 | 80.291 | 1.00 | 24.18 | L | C |
| ATOM | 360 | CE1 | PHE | L | 40 | 37.411 | 21.488 | 80.692 | 1.00 | 25.10 | L | C |
| ATOM | 361 | CE2 | PHE | L | 40 | 39.767 | 22.003 | 80.758 | 1.00 | 24.75 | L | C |
| ATOM | 362 | CZ | PHE | L | 40 | 38.444 | 22.389 | 80.959 | 1.00 | 25.22 | L | C |
| ATOM | 363 | N | TRP | L | 41 | 41.199 | 19.539 | 77.324 | 1.00 | 25.96 | L | N |
| ATOM | 364 | CA | TRP | L | 41 | 41.990 | 20.648 | 76.795 | 1.00 | 26.28 | L | C |
| ATOM | 365 | C | TRP | L | 41 | 41.866 | 20.970 | 75.301 | 1.00 | 27.29 | L | C |
| ATOM | 366 | O | TRP | L | 41 | 41.988 | 22.131 | 74.906 | 1.00 | 26.04 | L | O |
| ATOM | 367 | CB | TRP | L | 41 | 43.464 | 20.425 | 77.144 | 1.00 | 24.26 | L | C |
| ATOM | 368 | CG | TRP | L | 41 | 44.306 | 21.652 | 77.027 | 1.00 | 25.36 | L | C |
| ATOM | 369 | CD1 | TRP | L | 41 | 45.257 | 21.906 | 76.086 | 1.00 | 25.02 | L | C |
| ATOM | 370 | CD2 | TRP | L | 41 | 44.270 | 22.802 | 77.883 | 1.00 | 25.54 | L | C |
| ATOM | 371 | NE1 | TRP | L | 41 | 45.819 | 23.143 | 76.299 | 1.00 | 27.28 | L | N |
| ATOM | 372 | CE2 | TRP | L | 41 | 45.232 | 23.715 | 77.395 | 1.00 | 26.01 | L | C |
| ATOM | 373 | CE3 | TRP | L | 41 | 43.517 | 23.149 | 79.014 | 1.00 | 26.85 | L | C |
| ATOM | 374 | CZ2 | TRP | L | 41 | 45.464 | 24.954 | 78.000 | 1.00 | 24.01 | L | C |
| ATOM | 375 | CZ3 | TRP | L | 41 | 43.747 | 24.383 | 79.616 | 1.00 | 25.86 | L | C |
| ATOM | 376 | CH2 | TRP | L | 41 | 44.715 | 25.270 | 79.105 | 1.00 | 26.46 | L | C |
| ATOM | 377 | N | ILE | L | 42 | 41.629 | 19.968 | 74.463 | 1.00 | 28.66 | L | N |
| ATOM | 378 | CA | ILE | L | 42 | 41.523 | 20.237 | 73.033 | 1.00 | 30.71 | L | C |
| ATOM | 379 | C | ILE | L | 42 | 40.370 | 21.171 | 72.666 | 1.00 | 29.53 | L | C |
| ATOM | 380 | O | ILE | L | 42 | 40.469 | 21.936 | 71.705 | 1.00 | 30.98 | L | O |
| ATOM | 381 | CB | ILE | L | 42 | 41.429 | 18.925 | 72.209 | 1.00 | 32.87 | L | C |
| ATOM | 382 | CG1 | ILE | L | 42 | 40.350 | 18.004 | 72.771 | 1.00 | 33.91 | L | C |
| ATOM | 383 | CG2 | ILE | L | 42 | 42.769 | 18.217 | 72.217 | 1.00 | 36.59 | L | C |
| ATOM | 384 | CD1 | ILE | L | 42 | 38.982 | 18.321 | 72.269 | 1.00 | 36.99 | L | C |
| ATOM | 385 | N | SER | L | 43 | 39.289 | 21.127 | 73.437 | 1.00 | 28.62 | L | N |
| ATOM | 386 | CA | SER | L | 43 | 38.136 | 21.985 | 73.185 | 1.00 | 28.31 | L | C |
| ATOM | 387 | C | SER | L | 43 | 38.213 | 23.262 | 74.009 | 1.00 | 27.84 | L | C |
| ATOM | 388 | O | SER | L | 43 | 37.980 | 24.356 | 73.499 | 1.00 | 27.48 | L | O |
| ATOM | 389 | CB | SER | L | 43 | 36.839 | 21.247 | 73.517 | 1.00 | 26.23 | L | C |
| ATOM | 390 | OG | SER | L | 43 | 36.679 | 20.123 | 72.671 | 1.00 | 27.51 | L | O |
| ATOM | 391 | N | TYR | L | 44 | 38.541 | 23.115 | 75.289 | 1.00 | 27.54 | L | N |
| ATOM | 392 | CA | TYR | L | 44 | 38.640 | 24.257 | 76.188 | 1.00 | 27.08 | L | C |
| ATOM | 393 | C | TYR | L | 44 | 39.581 | 25.329 | 75.650 | 1.00 | 27.23 | L | C |
| ATOM | 394 | O | TYR | L | 44 | 39.241 | 26.510 | 75.650 | 1.00 | 27.59 | L | O |
| ATOM | 395 | CB | TYR | L | 44 | 39.136 | 23.805 | 77.567 | 1.00 | 26.19 | L | C |
| ATOM | 396 | CG | TYR | L | 44 | 39.140 | 24.898 | 78.614 | 1.00 | 24.94 | L | C |
| ATOM | 397 | CD1 | TYR | L | 44 | 37.949 | 25.366 | 79.164 | 1.00 | 23.63 | L | C |
| ATOM | 398 | CD2 | TYR | L | 44 | 40.337 | 25.457 | 79.064 | 1.00 | 26.53 | L | C |
| ATOM | 399 | CE1 | TYR | L | 44 | 37.949 | 26.362 | 80.142 | 1.00 | 26.54 | L | C |
| ATOM | 400 | CE2 | TYR | L | 44 | 40.348 | 26.455 | 80.043 | 1.00 | 26.05 | L | C |
| ATOM | 401 | CZ | TYR | L | 44 | 39.151 | 26.899 | 80.577 | 1.00 | 26.97 | L | C |
| ATOM | 402 | OH | TYR | L | 44 | 39.150 | 27.865 | 81.560 | 1.00 | 28.80 | L | O |
| ATOM | 403 | N | SER | L | 45 | 40.757 | 24.911 | 75.192 | 1.00 | 27.72 | L | N |
| ATOM | 404 | CA | SER | L | 45 | 41.768 | 25.839 | 74.686 | 1.00 | 30.15 | L | C |
| ATOM | 405 | C | SER | L | 45 | 41.744 | 26.104 | 73.182 | 1.00 | 30.62 | L | C |
| ATOM | 406 | O | SER | L | 45 | 42.604 | 26.820 | 72.671 | 1.00 | 30.63 | L | O |
| ATOM | 407 | CB | SER | L | 45 | 43.165 | 25.340 | 75.061 | 1.00 | 30.16 | L | C |
| ATOM | 408 | OG | SER | L | 45 | 43.497 | 24.166 | 74.339 | 1.00 | 29.88 | L | O |
| ATOM | 409 | N | ASP | L | 46 | 40.771 | 25.543 | 72.472 | 1.00 | 31.14 | L | N |
| ATOM | 410 | CA | ASP | L | 46 | 40.703 | 25.745 | 71.027 | 1.00 | 31.20 | L | C |
| ATOM | 411 | C | ASP | L | 46 | 40.411 | 27.189 | 70.627 | 1.00 | 30.32 | L | C |
| ATOM | 412 | O | ASP | L | 46 | 40.884 | 27.650 | 69.594 | 1.00 | 32.57 | L | O |
| ATOM | 413 | CB | ASP | L | 46 | 39.646 | 24.833 | 70.405 | 1.00 | 31.05 | L | C |
| ATOM | 414 | CG | ASP | L | 46 | 39.742 | 24.784 | 68.892 | 1.00 | 32.56 | L | C |
| ATOM | 415 | OD1 | ASP | L | 46 | 40.634 | 24.106 | 68.375 | 1.00 | 33.28 | L | O |
| ATOM | 416 | OD2 | ASP | L | 46 | 38.941 | 25.428 | 68.242 | 1.00 | 29.30 | L | O |
| ATOM | 417 | N | GLY | L | 47 | 39.636 | 27.899 | 71.442 | 1.00 | 29.23 | L | N |
| ATOM | 418 | CA | GLY | L | 47 | 39.299 | 29.276 | 71.131 | 1.00 | 28.60 | L | C |
| ATOM | 419 | C | GLY | L | 47 | 38.100 | 29.318 | 70.202 | 1.00 | 31.30 | L | C |
| ATOM | 420 | O | GLY | L | 47 | 37.926 | 28.417 | 69.392 | 1.00 | 30.95 | L | O |
| ATOM | 421 | N | ASP | L | 48 | 37.273 | 30.355 | 70.308 | 1.00 | 31.54 | L | N |
| ATOM | 422 | CA | ASP | L | 48 | 36.090 | 30.472 | 69.462 | 1.00 | 32.74 | L | C |
| ATOM | 423 | C | ASP | L | 48 | 36.378 | 31.223 | 68.165 | 1.00 | 33.54 | L | C |
| ATOM | 424 | O | ASP | L | 48 | 36.498 | 32.452 | 68.159 | 1.00 | 32.67 | L | O |
| ATOM | 425 | CB | ASP | L | 48 | 34.970 | 31.168 | 70.240 | 1.00 | 34.96 | L | C |
| ATOM | 426 | CG | ASP | L | 48 | 33.809 | 31.573 | 69.358 | 1.00 | 36.81 | L | C |
| ATOM | 427 | OD1 | ASP | L | 48 | 33.501 | 30.848 | 68.425 | 1.00 | 36.52 | L | O |
| ATOM | 428 | OD2 | ASP | L | 48 | 33.208 | 32.615 | 69.623 | 1.00 | 39.87 | L | O |
| ATOM | 429 | N | GLN | L | 49 | 36.485 | 30.481 | 67.064 | 1.00 | 33.17 | L | N |
| ATOM | 430 | CA | GLN | L | 49 | 36.767 | 31.089 | 65.762 | 1.00 | 33.44 | L | C |
| ATOM | 431 | C | GLN | L | 49 | 35.666 | 32.022 | 65.259 | 1.00 | 33.32 | L | C |
| ATOM | 432 | O | GLN | L | 49 | 35.871 | 32.774 | 64.305 | 1.00 | 34.51 | L | O |
| ATOM | 433 | CB | GLN | L | 49 | 37.046 | 30.009 | 64.713 | 1.00 | 32.45 | L | C |
| ATOM | 434 | CG | GLN | L | 49 | 38.448 | 29.410 | 64.780 | 1.00 | 31.73 | L | C |

-continued

| | | | | | | | | | | | |
|---|---|---|---|---|---|---|---|---|---|---|---|
| ATOM | 435 | CD | GLN | L | 49 | 38.707 | 28.668 | 66.078 | 1.00 | 33.97 | L | C |
| ATOM | 436 | OE1 | GLN | L | 49 | 37.915 | 27.822 | 66.477 | 1.00 | 32.13 | L | O |
| ATOM | 437 | NE2 | GLN | L | 49 | 39.821 | 28.978 | 66.737 | 1.00 | 32.44 | L | N |
| ATOM | 438 | N | CYS | L | 50 | 34.500 | 31.973 | 65.895 | 1.00 | 32.75 | L | N |
| ATOM | 439 | CA | CYS | L | 50 | 33.391 | 32.840 | 65.519 | 1.00 | 32.95 | L | C |
| ATOM | 440 | C | CYS | L | 50 | 33.533 | 34.239 | 66.113 | 1.00 | 34.35 | L | C |
| ATOM | 441 | O | CYS | L | 50 | 32.803 | 35.154 | 65.733 | 1.00 | 33.23 | L | O |
| ATOM | 442 | CB | CYS | L | 50 | 32.062 | 32.249 | 65.988 | 1.00 | 31.79 | L | C |
| ATOM | 443 | SG | CYS | L | 50 | 31.419 | 30.890 | 64.967 | 1.00 | 30.41 | L | S |
| ATOM | 444 | N | ALA | L | 51 | 34.466 | 34.398 | 67.049 | 1.00 | 36.39 | L | N |
| ATOM | 445 | CA | ALA | L | 51 | 34.698 | 35.681 | 67.712 | 1.00 | 38.60 | L | C |
| ATOM | 446 | C | ALA | L | 51 | 34.967 | 36.818 | 66.727 | 1.00 | 39.03 | L | C |
| ATOM | 447 | O | ALA | L | 51 | 34.554 | 37.955 | 66.952 | 1.00 | 39.61 | L | O |
| ATOM | 448 | CB | ALA | L | 51 | 35.861 | 35.554 | 68.695 | 1.00 | 37.84 | L | C |
| ATOM | 449 | N | GSER | L | 52 | 35.657 | 36.507 | 65.636 | 1.00 | 39.50 | L | N |
| ATOM | 450 | CA | GSER | L | 52 | 35.974 | 37.503 | 64.619 | 1.00 | 39.27 | L | C |
| ATOM | 451 | CB | GSER | L | 52 | 37.114 | 36.982 | 63.737 | 1.00 | 40.23 | L | C |
| ATOM | 452 | OG | GSER | L | 52 | 36.756 | 36.974 | 62.365 | 1.00 | 45.10 | L | O |
| ATOM | 453 | C | GSER | L | 52 | 34.756 | 37.859 | 63.760 | 1.00 | 38.60 | L | C |
| ATOM | 454 | O | GSER | L | 52 | 34.854 | 38.667 | 62.835 | 1.00 | 38.29 | L | O |
| ATOM | 455 | C1 | GSER | L | 52 | 37.197 | 35.776 | 61.707 | 1.00 | 45.99 | L | C |
| ATOM | 456 | C2 | GSER | L | 52 | 38.111 | 36.101 | 60.515 | 1.00 | 46.11 | L | C |
| ATOM | 457 | C3 | GSER | L | 52 | 38.477 | 34.801 | 59.788 | 1.00 | 46.60 | L | C |
| ATOM | 458 | C4 | GSER | L | 52 | 39.100 | 33.808 | 60.777 | 1.00 | 46.16 | L | C |
| ATOM | 459 | C5 | GSER | L | 52 | 38.180 | 33.615 | 62.004 | 1.00 | 46.88 | L | C |
| ATOM | 460 | C6 | GSER | L | 52 | 38.849 | 32.688 | 63.024 | 1.00 | 48.42 | L | C |
| ATOM | 461 | O2 | GSER | L | 52 | 37.438 | 36.988 | 59.614 | 1.00 | 47.32 | L | O |
| ATOM | 462 | O3 | GSER | L | 52 | 39.406 | 35.079 | 58.734 | 1.00 | 46.42 | L | O |
| ATOM | 463 | O4 | GSER | L | 52 | 39.302 | 32.549 | 60.123 | 1.00 | 46.46 | L | O |
| ATOM | 464 | O5 | GSER | L | 52 | 37.851 | 34.874 | 62.616 | 1.00 | 47.23 | L | O |
| ATOM | 465 | O6 | GSER | L | 52 | 39.251 | 31.462 | 62.431 | 1.00 | 51.52 | L | O |
| ATOM | 466 | N | SER | L | 53 | 33.610 | 37.263 | 64.085 | 1.00 | 36.60 | L | N |
| ATOM | 467 | CA | SER | L | 53 | 32.367 | 37.488 | 63.354 | 1.00 | 35.81 | L | C |
| ATOM | 468 | C | SER | L | 53 | 32.602 | 37.463 | 61.845 | 1.00 | 33.73 | L | C |
| ATOM | 469 | O | SER | L | 53 | 32.395 | 38.460 | 61.162 | 1.00 | 33.37 | L | O |
| ATOM | 470 | CB | SER | L | 53 | 31.765 | 38.831 | 63.764 | 1.00 | 37.62 | L | C |
| ATOM | 471 | OG | SER | L | 53 | 32.684 | 39.879 | 63.524 | 1.00 | 40.28 | L | O |
| ATOM | 472 | N | PRO | L | 54 | 33.026 | 36.310 | 61.303 | 1.00 | 32.42 | L | N |
| ATOM | 473 | CA | PRO | L | 54 | 33.285 | 36.192 | 59.865 | 1.00 | 31.65 | L | C |
| ATOM | 474 | C | PRO | L | 54 | 32.069 | 36.078 | 58.940 | 1.00 | 30.67 | L | C |
| ATOM | 475 | O | PRO | L | 54 | 32.156 | 36.424 | 57.761 | 1.00 | 30.19 | L | O |
| ATOM | 476 | CB | PRO | L | 54 | 34.172 | 34.956 | 59.788 | 1.00 | 31.82 | L | C |
| ATOM | 477 | CG | PRO | L | 54 | 33.578 | 34.084 | 60.841 | 1.00 | 30.71 | L | C |
| ATOM | 478 | CD | PRO | L | 54 | 33.366 | 35.051 | 61.994 | 1.00 | 30.98 | L | C |
| ATOM | 479 | N | CYS | L | 55 | 30.946 | 35.594 | 59.461 | 1.00 | 29.86 | L | N |
| ATOM | 480 | CA | CYS | L | 55 | 29.752 | 35.422 | 58.635 | 1.00 | 30.36 | L | C |
| ATOM | 481 | C | CYS | L | 55 | 29.033 | 36.733 | 58.343 | 1.00 | 31.54 | L | C |
| ATOM | 482 | O | CYS | L | 55 | 28.455 | 37.358 | 59.230 | 1.00 | 32.38 | L | O |
| ATOM | 483 | CB | CYS | L | 55 | 28.794 | 34.430 | 59.290 | 1.00 | 28.02 | L | C |
| ATOM | 484 | SG | CYS | L | 55 | 29.586 | 32.875 | 59.818 | 1.00 | 28.74 | L | S |
| ATOM | 485 | N | GLN | L | 56 | 29.060 | 37.122 | 57.074 | 1.00 | 31.32 | L | N |
| ATOM | 486 | CA | GLN | L | 56 | 28.456 | 38.365 | 56.607 | 1.00 | 30.45 | L | C |
| ATOM | 487 | C | GLN | L | 56 | 26.983 | 38.271 | 56.217 | 1.00 | 29.58 | L | C |
| ATOM | 488 | O | GLN | L | 56 | 26.387 | 37.195 | 56.205 | 1.00 | 30.14 | L | O |
| ATOM | 489 | CB | GLN | L | 56 | 29.239 | 38.873 | 55.398 | 1.00 | 29.51 | L | C |
| ATOM | 490 | CG | GLN | L | 56 | 30.731 | 38.996 | 55.615 | 1.00 | 27.82 | L | C |
| ATOM | 491 | CD | GLN | L | 56 | 31.463 | 39.252 | 54.321 | 1.00 | 28.65 | L | C |
| ATOM | 492 | OE1 | GLN | L | 56 | 31.054 | 40.098 | 53.526 | 1.00 | 31.65 | L | O |
| ATOM | 493 | NE2 | GLN | L | 56 | 32.551 | 38.526 | 54.098 | 1.00 | 29.31 | L | N |
| ATOM | 494 | N | ASN | L | 57 | 26.415 | 39.429 | 55.897 | 1.00 | 30.03 | L | N |
| ATOM | 495 | CA | ASN | L | 57 | 25.030 | 39.559 | 55.453 | 1.00 | 29.58 | L | C |
| ATOM | 496 | C | ASN | L | 57 | 23.952 | 38.887 | 56.296 | 1.00 | 29.62 | L | C |
| ATOM | 497 | O | ASN | L | 57 | 23.024 | 38.276 | 55.764 | 1.00 | 29.77 | L | O |
| ATOM | 498 | CB | ASN | L | 57 | 24.921 | 39.085 | 53.999 | 1.00 | 29.04 | L | C |
| ATOM | 499 | CG | ASN | L | 57 | 25.762 | 39.924 | 53.054 | 1.00 | 29.56 | L | C |
| ATOM | 500 | OD1 | ASN | L | 57 | 25.568 | 41.134 | 52.945 | 1.00 | 32.62 | L | O |
| ATOM | 501 | ND2 | ASN | L | 57 | 26.702 | 39.287 | 52.367 | 1.00 | 29.28 | L | N |
| ATOM | 502 | N | GLY | L | 58 | 24.059 | 39.019 | 57.610 | 1.00 | 30.01 | L | N |
| ATOM | 503 | CA | GLY | L | 58 | 23.061 | 38.432 | 58.485 | 1.00 | 30.78 | L | C |
| ATOM | 504 | C | GLY | L | 58 | 23.145 | 36.931 | 58.670 | 1.00 | 30.82 | L | C |
| ATOM | 505 | O | GLY | L | 58 | 22.166 | 36.299 | 59.066 | 1.00 | 31.08 | L | O |
| ATOM | 506 | N | GLY | L | 59 | 24.305 | 36.351 | 58.388 | 1.00 | 31.24 | L | N |
| ATOM | 507 | CA | GLY | L | 59 | 24.453 | 34.919 | 58.557 | 1.00 | 31.81 | L | C |
| ATOM | 508 | C | GLY | L | 59 | 24.692 | 34.578 | 60.015 | 1.00 | 31.05 | L | C |
| ATOM | 509 | O | GLY | L | 59 | 24.845 | 35.466 | 60.853 | 1.00 | 31.54 | L | O |
| ATOM | 510 | N | FSER | L | 60 | 24.723 | 33.289 | 60.326 | 1.00 | 30.80 | L | N |
| ATOM | 511 | CA | FSER | L | 60 | 24.959 | 32.852 | 61.690 | 1.00 | 30.86 | L | C |
| ATOM | 512 | CB | FSER | L | 60 | 23.724 | 32.128 | 62.227 | 1.00 | 31.58 | L | C |
| ATOM | 513 | OG | FSER | L | 60 | 22.643 | 33.041 | 62.308 | 1.00 | 32.58 | L | O |

-continued

| | | | | | | | | | | | |
|---|---|---|---|---|---|---|---|---|---|---|---|
| ATOM | 514 | C | FSER | L | 60 | 26.184 | 31.953 | 61.743 | 1.00 | 30.82 | L | C |
| ATOM | 515 | O | FSER | L | 60 | 26.297 | 30.990 | 60.984 | 1.00 | 29.56 | L | O |
| ATOM | 516 | C1 | FSER | L | 60 | 21.375 | 32.378 | 62.268 | 1.00 | 35.22 | L | C |
| ATOM | 517 | C2 | FSER | L | 60 | 20.246 | 33.387 | 62.560 | 1.00 | 36.79 | L | C |
| ATOM | 518 | C3 | FSER | L | 60 | 20.174 | 34.428 | 61.430 | 1.00 | 37.43 | L | C |
| ATOM | 519 | C4 | FSER | L | 60 | 20.031 | 33.715 | 60.084 | 1.00 | 36.10 | L | C |
| ATOM | 520 | C5 | FSER | L | 60 | 21.164 | 32.683 | 59.913 | 1.00 | 35.80 | L | C |
| ATOM | 521 | C6 | FSER | L | 60 | 21.036 | 31.969 | 58.566 | 1.00 | 35.30 | L | C |
| ATOM | 522 | O2 | FSER | L | 60 | 20.509 | 34.051 | 63.802 | 1.00 | 39.97 | L | O |
| ATOM | 523 | O3 | FSER | L | 60 | 19.049 | 35.291 | 61.638 | 1.00 | 39.35 | L | O |
| ATOM | 524 | O4 | FSER | L | 60 | 18.764 | 33.048 | 60.034 | 1.00 | 38.01 | L | O |
| ATOM | 525 | O5 | FSER | L | 60 | 21.172 | 31.739 | 60.996 | 1.00 | 35.11 | L | O |
| ATOM | 526 | N | CYS | L | 61 | 27.103 | 32.284 | 62.644 | 1.00 | 29.76 | L | N |
| ATOM | 527 | CA | CYS | L | 61 | 28.340 | 31.532 | 62.803 | 1.00 | 30.26 | L | C |
| ATOM | 528 | C | CYS | L | 61 | 28.205 | 30.412 | 63.825 | 1.00 | 30.72 | L | C |
| ATOM | 529 | O | CYS | L | 61 | 27.616 | 30.591 | 64.895 | 1.00 | 29.55 | L | O |
| ATOM | 530 | CB | CYS | L | 61 | 29.468 | 32.474 | 63.227 | 1.00 | 29.48 | L | C |
| ATOM | 531 | SG | CYS | L | 61 | 31.145 | 31.764 | 63.150 | 1.00 | 30.89 | L | S |
| ATOM | 532 | N | LYS | L | 62 | 28.754 | 29.254 | 63.477 | 1.00 | 30.27 | L | N |
| ATOM | 533 | CA | LYS | L | 62 | 28.729 | 28.090 | 64.347 | 1.00 | 29.64 | L | C |
| ATOM | 534 | C | LYS | L | 62 | 30.183 | 27.688 | 64.543 | 1.00 | 29.26 | L | C |
| ATOM | 535 | O | LYS | L | 62 | 30.870 | 27.312 | 63.595 | 1.00 | 28.28 | L | O |
| ATOM | 536 | CB | LYS | L | 62 | 27.943 | 26.952 | 63.696 | 1.00 | 30.78 | L | C |
| ATOM | 537 | CG | LYS | L | 62 | 27.561 | 25.826 | 64.642 | 1.00 | 33.70 | L | C |
| ATOM | 538 | CD | LYS | L | 62 | 28.780 | 25.112 | 65.204 | 1.00 | 35.68 | L | C |
| ATOM | 539 | CE | LYS | L | 62 | 28.392 | 23.957 | 66.122 | 1.00 | 34.05 | L | C |
| ATOM | 540 | NZ | LYS | L | 62 | 27.581 | 24.389 | 67.286 | 1.00 | 32.19 | L | N |
| ATOM | 541 | N | ASP | L | 63 | 30.645 | 27.781 | 65.782 | 1.00 | 29.03 | L | N |
| ATOM | 542 | CA | ASP | L | 63 | 32.018 | 27.455 | 66.120 | 1.00 | 28.45 | L | C |
| ATOM | 543 | C | ASP | L | 63 | 32.317 | 25.970 | 65.961 | 1.00 | 27.88 | L | C |
| ATOM | 544 | O | ASP | L | 63 | 31.489 | 25.120 | 66.286 | 1.00 | 26.64 | L | O |
| ATOM | 545 | CB | ASP | L | 63 | 32.310 | 27.909 | 67.546 | 1.00 | 28.61 | L | C |
| ATOM | 546 | CG | ASP | L | 63 | 33.762 | 27.778 | 67.899 | 1.00 | 31.76 | L | C |
| ATOM | 547 | OD1 | ASP | L | 63 | 34.595 | 28.171 | 67.072 | 1.00 | 29.78 | L | O |
| ATOM | 548 | OD2 | ASP | L | 63 | 34.057 | 27.289 | 68.989 | 1.00 | 31.88 | L | O |
| ATOM | 549 | N | GLN | L | 64 | 33.511 | 25.670 | 65.463 | 1.00 | 27.71 | L | N |
| ATOM | 550 | CA | GLN | L | 64 | 33.934 | 24.296 | 65.222 | 1.00 | 29.46 | L | C |
| ATOM | 551 | C | GLN | L | 64 | 35.354 | 24.115 | 65.751 | 1.00 | 29.86 | L | C |
| ATOM | 552 | O | GLN | L | 64 | 35.988 | 25.076 | 66.145 | 1.00 | 29.22 | L | O |
| ATOM | 553 | CB | GLN | L | 64 | 33.894 | 24.014 | 63.715 | 1.00 | 30.77 | L | C |
| ATOM | 554 | CG | GLN | L | 64 | 33.597 | 22.576 | 63.346 | 1.00 | 33.56 | L | C |
| ATOM | 555 | CD | GLN | L | 64 | 32.157 | 22.156 | 63.621 | 1.00 | 33.54 | L | C |
| ATOM | 556 | OE1 | GLN | L | 64 | 31.840 | 20.973 | 63.568 | 1.00 | 36.28 | L | O |
| ATOM | 557 | NE2 | GLN | L | 64 | 31.284 | 23.119 | 63.904 | 1.00 | 31.18 | L | N |
| ATOM | 558 | N | LEU | L | 65 | 35.862 | 22.891 | 65.740 | 1.00 | 32.40 | L | N |
| ATOM | 559 | CA | LEU | L | 65 | 37.206 | 22.633 | 66.242 | 1.00 | 33.87 | L | C |
| ATOM | 560 | C | LEU | L | 65 | 38.292 | 23.203 | 65.332 | 1.00 | 35.15 | L | C |
| ATOM | 561 | O | LEU | L | 65 | 38.688 | 22.574 | 64.349 | 1.00 | 36.47 | L | O |
| ATOM | 562 | CB | LEU | L | 65 | 37.410 | 21.125 | 66.422 | 1.00 | 35.23 | L | C |
| ATOM | 563 | CG | LEU | L | 65 | 38.554 | 20.679 | 67.337 | 1.00 | 36.14 | L | C |
| ATOM | 564 | CD1 | LEU | L | 65 | 38.435 | 21.372 | 68.687 | 1.00 | 36.95 | L | C |
| ATOM | 565 | CD2 | LEU | L | 65 | 38.503 | 19.172 | 67.517 | 1.00 | 35.86 | L | C |
| ATOM | 566 | N | GLN | L | 66 | 38.767 | 24.401 | 65.666 | 1.00 | 35.72 | L | N |
| ATOM | 567 | CA | GLN | L | 66 | 39.820 | 25.072 | 64.903 | 1.00 | 35.89 | L | C |
| ATOM | 568 | C | GLN | L | 66 | 39.293 | 25.586 | 63.561 | 1.00 | 35.00 | L | C |
| ATOM | 569 | O | GLN | L | 66 | 39.998 | 25.562 | 62.547 | 1.00 | 33.68 | L | O |
| ATOM | 570 | CB | GLN | L | 66 | 40.986 | 24.101 | 64.674 | 1.00 | 37.22 | L | C |
| ATOM | 571 | CG | GLN | L | 66 | 42.288 | 24.748 | 64.232 | 1.00 | 40.93 | L | C |
| ATOM | 572 | CD | GLN | L | 66 | 43.040 | 25.456 | 65.356 | 1.00 | 40.68 | L | C |
| ATOM | 573 | OE1 | GLN | L | 66 | 44.109 | 26.017 | 65.128 | 1.00 | 41.86 | L | O |
| ATOM | 574 | NE2 | GLN | L | 66 | 42.488 | 25.431 | 66.566 | 1.00 | 40.50 | L | N |
| ATOM | 575 | N | SER | L | 67 | 38.051 | 26.059 | 63.568 | 1.00 | 31.83 | L | N |
| ATOM | 576 | CA | SER | L | 67 | 37.412 | 26.568 | 62.365 | 1.00 | 31.03 | L | C |
| ATOM | 577 | C | SER | L | 67 | 35.991 | 27.036 | 62.667 | 1.00 | 31.16 | L | C |
| ATOM | 578 | O | SER | L | 67 | 35.613 | 27.197 | 63.829 | 1.00 | 31.27 | L | O |
| ATOM | 579 | CB | SER | L | 67 | 37.389 | 25.477 | 61.288 | 1.00 | 30.23 | L | C |
| ATOM | 580 | OG | SER | L | 67 | 36.946 | 24.239 | 61.817 | 1.00 | 30.96 | L | O |
| ATOM | 581 | N | TYR | L | 68 | 35.210 | 27.265 | 61.618 | 1.00 | 29.96 | L | N |
| ATOM | 582 | CA | TYR | L | 68 | 33.835 | 27.707 | 61.785 | 1.00 | 28.95 | L | C |
| ATOM | 583 | C | TYR | L | 68 | 32.987 | 27.358 | 60.573 | 1.00 | 28.08 | L | C |
| ATOM | 584 | O | TYR | L | 68 | 33.500 | 26.977 | 59.516 | 1.00 | 27.87 | L | O |
| ATOM | 585 | CB | TYR | L | 68 | 33.769 | 29.221 | 62.024 | 1.00 | 30.00 | L | C |
| ATOM | 586 | CG | TYR | L | 68 | 34.288 | 30.061 | 60.876 | 1.00 | 29.99 | L | C |
| ATOM | 587 | CD1 | TYR | L | 68 | 35.650 | 30.332 | 60.743 | 1.00 | 30.22 | L | C |
| ATOM | 588 | CD2 | TYR | L | 68 | 33.417 | 30.574 | 59.912 | 1.00 | 30.26 | L | C |
| ATOM | 589 | CE1 | TYR | L | 68 | 36.135 | 31.090 | 59.682 | 1.00 | 29.23 | L | C |
| ATOM | 590 | CE2 | TYR | L | 68 | 33.892 | 31.331 | 58.844 | 1.00 | 29.58 | L | C |
| ATOM | 591 | CZ | TYR | L | 68 | 35.251 | 31.585 | 58.737 | 1.00 | 29.30 | L | C |
| ATOM | 592 | OH | TYR | L | 68 | 35.733 | 32.320 | 57.683 | 1.00 | 28.26 | L | O |

-continued

| | | | | | | | | | | | | |
|---|---|---|---|---|---|---|---|---|---|---|---|---|
| ATOM | 593 | N | ILE | L | 69 | 31.680 | 27.499 | 60.743 | 1.00 | 25.46 | L | N |
| ATOM | 594 | CA | ILE | L | 69 | 30.720 | 27.220 | 59.691 | 1.00 | 24.21 | L | C |
| ATOM | 595 | C | ILE | L | 69 | 29.732 | 28.374 | 59.657 | 1.00 | 23.58 | L | C |
| ATOM | 596 | O | ILE | L | 69 | 29.233 | 28.800 | 60.698 | 1.00 | 21.31 | L | O |
| ATOM | 597 | CB | ILE | L | 69 | 29.947 | 25.908 | 59.974 | 1.00 | 24.42 | L | C |
| ATOM | 598 | CG1 | ILE | L | 69 | 30.904 | 24.717 | 59.914 | 1.00 | 24.57 | L | C |
| ATOM | 599 | CG2 | ILE | L | 69 | 28.818 | 25.739 | 58.976 | 1.00 | 23.61 | L | C |
| ATOM | 600 | CD1 | ILE | L | 69 | 30.243 | 23.389 | 60.201 | 1.00 | 23.77 | L | C |
| ATOM | 601 | N | CYS | L | 70 | 29.466 | 28.893 | 58.464 | 1.00 | 23.37 | L | N |
| ATOM | 602 | CA | CYS | L | 70 | 28.517 | 29.985 | 58.323 | 1.00 | 23.29 | L | C |
| ATOM | 603 | C | CYS | L | 70 | 27.195 | 29.499 | 57.730 | 1.00 | 24.32 | L | C |
| ATOM | 604 | O | CYS | L | 70 | 27.174 | 28.777 | 56.735 | 1.00 | 22.69 | L | O |
| ATOM | 605 | CB | CYS | L | 70 | 29.084 | 31.091 | 57.427 | 1.00 | 24.87 | L | C |
| ATOM | 606 | SG | CYS | L | 70 | 30.424 | 32.100 | 58.136 | 1.00 | 24.79 | L | S |
| ATOM | 607 | N | PHE | L | 71 | 26.096 | 29.880 | 58.373 | 1.00 | 23.47 | L | N |
| ATOM | 608 | CA | PHE | L | 71 | 24.765 | 29.550 | 57.896 | 1.00 | 24.42 | L | C |
| ATOM | 609 | C | PHE | L | 71 | 24.305 | 30.861 | 57.285 | 1.00 | 25.98 | L | C |
| ATOM | 610 | O | PHE | L | 71 | 24.271 | 31.884 | 57.961 | 1.00 | 26.06 | L | O |
| ATOM | 611 | CB | PHE | L | 71 | 23.840 | 29.148 | 59.051 | 1.00 | 23.72 | L | C |
| ATOM | 612 | CG | PHE | L | 71 | 24.079 | 27.753 | 59.563 | 1.00 | 23.26 | L | C |
| ATOM | 613 | CD1 | PHE | L | 71 | 25.220 | 27.448 | 60.300 | 1.00 | 20.48 | L | C |
| ATOM | 614 | CD2 | PHE | L | 71 | 23.170 | 26.737 | 59.286 | 1.00 | 21.74 | L | C |
| ATOM | 615 | CE1 | PHE | L | 71 | 25.453 | 26.157 | 60.751 | 1.00 | 19.84 | L | C |
| ATOM | 616 | CE2 | PHE | L | 71 | 23.395 | 25.440 | 59.733 | 1.00 | 22.58 | L | C |
| ATOM | 617 | CZ | PHE | L | 71 | 24.537 | 25.149 | 60.467 | 1.00 | 21.41 | L | C |
| ATOM | 618 | N | CYS | L | 72 | 23.964 | 30.838 | 56.004 | 1.00 | 27.38 | L | N |
| ATOM | 619 | CA | CYS | L | 72 | 23.561 | 32.060 | 55.322 | 1.00 | 28.04 | L | C |
| ATOM | 620 | C | CYS | L | 72 | 22.067 | 32.210 | 55.147 | 1.00 | 29.09 | L | C |
| ATOM | 621 | O | CYS | L | 72 | 21.315 | 31.236 | 55.240 | 1.00 | 30.40 | L | O |
| ATOM | 622 | CB | CYS | L | 72 | 24.216 | 32.125 | 53.941 | 1.00 | 27.64 | L | C |
| ATOM | 623 | SG | CYS | L | 72 | 25.997 | 31.758 | 53.929 | 1.00 | 27.84 | L | S |
| ATOM | 624 | N | LEU | L | 73 | 21.645 | 33.446 | 54.896 | 1.00 | 29.28 | L | N |
| ATOM | 625 | CA | LEU | L | 73 | 20.243 | 33.736 | 54.640 | 1.00 | 29.11 | L | C |
| ATOM | 626 | C | LEU | L | 73 | 20.018 | 33.294 | 53.201 | 1.00 | 29.05 | L | C |
| ATOM | 627 | O | LEU | L | 73 | 20.964 | 33.228 | 52.419 | 1.00 | 29.21 | L | O |
| ATOM | 628 | CB | LEU | L | 73 | 19.963 | 35.233 | 54.786 | 1.00 | 29.61 | L | C |
| ATOM | 629 | CG | LEU | L | 73 | 19.999 | 35.764 | 56.221 | 1.00 | 31.06 | L | C |
| ATOM | 630 | CD1 | LEU | L | 73 | 19.802 | 37.274 | 56.220 | 1.00 | 32.08 | L | C |
| ATOM | 631 | CD2 | LEU | L | 73 | 18.913 | 35.075 | 57.043 | 1.00 | 30.65 | L | C |
| ATOM | 632 | N | PRO | L | 74 | 18.766 | 32.991 | 52.833 | 1.00 | 29.36 | L | N |
| ATOM | 633 | CA | PRO | L | 74 | 18.384 | 32.543 | 51.492 | 1.00 | 29.38 | L | C |
| ATOM | 634 | C | PRO | L | 74 | 19.120 | 33.149 | 50.298 | 1.00 | 29.43 | L | C |
| ATOM | 635 | O | PRO | L | 74 | 19.630 | 32.420 | 49.449 | 1.00 | 29.02 | L | O |
| ATOM | 636 | CB | PRO | L | 74 | 16.888 | 32.828 | 51.461 | 1.00 | 30.46 | L | C |
| ATOM | 637 | CG | PRO | L | 74 | 16.486 | 32.477 | 52.854 | 1.00 | 29.08 | L | C |
| ATOM | 638 | CD | PRO | L | 74 | 17.570 | 33.151 | 53.682 | 1.00 | 29.95 | L | C |
| ATOM | 639 | N | ALA | L | 75 | 19.190 | 34.473 | 50.229 | 1.00 | 28.84 | L | N |
| ATOM | 640 | CA | ALA | L | 75 | 19.849 | 35.124 | 49.100 | 1.00 | 28.32 | L | C |
| ATOM | 641 | C | ALA | L | 75 | 21.368 | 35.226 | 49.194 | 1.00 | 27.93 | L | C |
| ATOM | 642 | O | ALA | L | 75 | 21.978 | 36.020 | 48.481 | 1.00 | 29.61 | L | O |
| ATOM | 643 | CB | ALA | L | 75 | 19.257 | 36.508 | 48.893 | 1.00 | 27.56 | L | C |
| ATOM | 644 | N | PHE | L | 76 | 21.987 | 34.418 | 50.047 | 1.00 | 26.68 | L | N |
| ATOM | 645 | CA | PHE | L | 76 | 23.433 | 34.480 | 50.205 | 1.00 | 25.92 | L | C |
| ATOM | 646 | C | PHE | L | 76 | 24.105 | 33.108 | 50.253 | 1.00 | 25.21 | L | C |
| ATOM | 647 | O | PHE | L | 76 | 23.484 | 32.103 | 50.606 | 1.00 | 24.64 | L | O |
| ATOM | 648 | CB | PHE | L | 76 | 23.770 | 35.269 | 51.479 | 1.00 | 26.98 | L | C |
| ATOM | 649 | CG | PHE | L | 76 | 23.308 | 36.705 | 51.447 | 1.00 | 26.03 | L | C |
| ATOM | 650 | CD1 | PHE | L | 76 | 24.009 | 37.660 | 50.717 | 1.00 | 26.24 | L | C |
| ATOM | 651 | CD2 | PHE | L | 76 | 22.161 | 37.094 | 52.128 | 1.00 | 25.56 | L | C |
| ATOM | 652 | CE1 | PHE | L | 76 | 23.570 | 38.986 | 50.665 | 1.00 | 27.46 | L | C |
| ATOM | 653 | CE2 | PHE | L | 76 | 21.713 | 38.416 | 52.083 | 1.00 | 28.29 | L | C |
| ATOM | 654 | CZ | PHE | L | 76 | 22.420 | 39.363 | 51.350 | 1.00 | 27.25 | L | C |
| ATOM | 655 | N | GLU | L | 77 | 25.381 | 33.082 | 49.881 | 1.00 | 23.35 | L | N |
| ATOM | 656 | CA | GLU | L | 77 | 26.171 | 31.861 | 49.896 | 1.00 | 25.22 | L | C |
| ATOM | 657 | C | GLU | L | 77 | 27.636 | 32.260 | 50.022 | 1.00 | 25.48 | L | C |
| ATOM | 658 | O | GLU | L | 77 | 27.947 | 33.446 | 50.102 | 1.00 | 24.93 | L | O |
| ATOM | 659 | CB | GLU | L | 77 | 25.931 | 31.027 | 48.624 | 1.00 | 24.76 | L | C |
| ATOM | 660 | CG | GLU | L | 77 | 26.369 | 31.665 | 47.317 | 1.00 | 26.43 | L | C |
| ATOM | 661 | CD | GLU | L | 77 | 25.929 | 30.854 | 46.102 | 1.00 | 29.36 | L | C |
| ATOM | 662 | OE1 | GLU | L | 77 | 26.332 | 29.708 | 45.975 | 1.00 | 26.59 | L | O |
| ATOM | 663 | OE2 | GLU | L | 77 | 25.177 | 31.379 | 45.287 | 1.00 | 31.26 | L | O |
| ATOM | 664 | N | GLY | L | 78 | 28.525 | 31.273 | 50.045 | 1.00 | 24.82 | L | N |
| ATOM | 665 | CA | GLY | L | 78 | 29.944 | 31.545 | 50.191 | 1.00 | 24.72 | L | C |
| ATOM | 666 | C | GLY | L | 78 | 30.414 | 31.145 | 51.585 | 1.00 | 26.41 | L | C |
| ATOM | 667 | O | GLY | L | 78 | 29.613 | 31.056 | 52.513 | 1.00 | 25.52 | L | O |
| ATOM | 668 | N | ARG | L | 79 | 31.711 | 30.894 | 51.731 | 1.00 | 26.17 | L | N |
| ATOM | 669 | CA | ARG | L | 79 | 32.299 | 30.507 | 53.014 | 1.00 | 26.44 | L | C |
| ATOM | 670 | C | ARG | L | 79 | 31.847 | 31.428 | 54.146 | 1.00 | 27.39 | L | C |
| ATOM | 671 | O | ARG | L | 79 | 31.503 | 30.972 | 55.236 | 1.00 | 27.00 | L | O |

-continued

| | | | | | | | | | | | | |
|---|---|---|---|---|---|---|---|---|---|---|---|---|
| ATOM | 672 | CB | ARG | L | 79 | 33.827 | 30.532 | 52.894 | 1.00 | 25.97 | L | C |
| ATOM | 673 | CG | ARG | L | 79 | 34.596 | 30.145 | 54.138 | 1.00 | 25.27 | L | C |
| ATOM | 674 | CD | ARG | L | 79 | 36.018 | 29.745 | 53.756 | 1.00 | 27.07 | L | C |
| ATOM | 675 | NE | ARG | L | 79 | 36.352 | 28.422 | 54.279 | 1.00 | 29.92 | L | N |
| ATOM | 676 | CZ | ARG | L | 79 | 37.168 | 27.553 | 53.689 | 1.00 | 31.71 | L | C |
| ATOM | 677 | NH1 | ARG | L | 79 | 37.754 | 27.849 | 52.536 | 1.00 | 34.10 | L | N |
| ATOM | 678 | NH2 | ARG | L | 79 | 37.394 | 26.375 | 54.254 | 1.00 | 34.56 | L | N |
| ATOM | 679 | N | ASN | L | 80 | 31.845 | 32.728 | 53.875 | 1.00 | 28.14 | L | N |
| ATOM | 680 | CA | ASN | L | 80 | 31.440 | 33.727 | 54.858 | 1.00 | 27.10 | L | C |
| ATOM | 681 | C | ASN | L | 80 | 30.171 | 34.446 | 54.415 | 1.00 | 27.35 | L | C |
| ATOM | 682 | O | ASN | L | 80 | 29.950 | 35.598 | 54.785 | 1.00 | 27.84 | L | O |
| ATOM | 683 | CB | ASN | L | 80 | 32.561 | 34.750 | 55.038 | 1.00 | 27.74 | L | C |
| ATOM | 684 | CG | ASN | L | 80 | 33.868 | 34.110 | 55.442 | 1.00 | 29.02 | L | C |
| ATOM | 685 | OD1 | ASN | L | 80 | 33.952 | 33.449 | 56.473 | 1.00 | 31.37 | L | O |
| ATOM | 686 | ND2 | ASN | L | 80 | 34.897 | 34.301 | 54.629 | 1.00 | 31.80 | L | N |
| ATOM | 687 | N | CYS | L | 81 | 29.348 | 33.771 | 53.616 | 1.00 | 26.38 | L | N |
| ATOM | 688 | CA | CYS | L | 81 | 28.103 | 34.353 | 53.113 | 1.00 | 26.94 | L | C |
| ATOM | 689 | C | CYS | L | 81 | 28.341 | 35.691 | 52.395 | 1.00 | 27.16 | L | C |
| ATOM | 690 | O | CYS | L | 81 | 27.474 | 36.566 | 52.392 | 1.00 | 26.50 | L | O |
| ATOM | 691 | CB | CYS | L | 81 | 27.115 | 34.563 | 54.263 | 1.00 | 26.45 | L | C |
| ATOM | 692 | SG | CYS | L | 81 | 26.764 | 33.080 | 55.267 | 1.00 | 28.68 | L | S |
| ATOM | 693 | N | GLU | L | 82 | 29.510 | 35.834 | 51.777 | 1.00 | 26.64 | L | N |
| ATOM | 694 | CA | GLU | L | 82 | 29.875 | 37.058 | 51.077 | 1.00 | 27.18 | L | C |
| ATOM | 695 | C | GLU | L | 82 | 29.314 | 37.153 | 49.654 | 1.00 | 27.98 | L | C |
| ATOM | 696 | O | GLU | L | 82 | 29.364 | 38.216 | 49.031 | 1.00 | 28.25 | L | O |
| ATOM | 697 | CB | GLU | L | 82 | 31.408 | 37.199 | 51.028 | 1.00 | 27.27 | L | C |
| ATOM | 698 | CG | GLU | L | 82 | 32.116 | 36.245 | 50.057 | 1.00 | 25.93 | L | C |
| ATOM | 699 | CD | GLU | L | 82 | 32.435 | 34.881 | 50.658 | 1.00 | 27.71 | L | C |
| ATOM | 700 | OE1 | GLU | L | 82 | 31.618 | 34.339 | 51.391 | 1.00 | 26.78 | L | O |
| ATOM | 701 | OE2 | GLU | L | 82 | 33.503 | 34.356 | 50.371 | 1.00 | 29.60 | L | O |
| ATOM | 702 | N | THR | L | 83 | 28.776 | 36.052 | 49.140 | 1.00 | 28.28 | L | N |
| ATOM | 703 | CA | THR | L | 83 | 28.238 | 36.042 | 47.784 | 1.00 | 28.62 | L | C |
| ATOM | 704 | C | THR | L | 83 | 26.762 | 36.405 | 47.698 | 1.00 | 29.44 | L | C |
| ATOM | 705 | O | THR | L | 83 | 25.910 | 35.738 | 48.284 | 1.00 | 28.89 | L | O |
| ATOM | 706 | CB | THR | L | 83 | 28.442 | 34.668 | 47.117 | 1.00 | 26.44 | L | C |
| ATOM | 707 | OG1 | THR | L | 83 | 29.836 | 34.341 | 47.124 | 1.00 | 25.96 | L | O |
| ATOM | 708 | CG2 | THR | L | 83 | 27.941 | 34.692 | 45.675 | 1.00 | 26.81 | L | C |
| ATOM | 709 | N | HIS | L | 84 | 26.475 | 37.472 | 46.958 | 1.00 | 31.51 | L | N |
| ATOM | 710 | CA | HIS | L | 84 | 25.109 | 37.939 | 46.759 | 1.00 | 34.54 | L | C |
| ATOM | 711 | C | HIS | L | 84 | 24.514 | 37.169 | 45.588 | 1.00 | 35.95 | L | C |
| ATOM | 712 | O | HIS | L | 84 | 24.914 | 37.372 | 44.442 | 1.00 | 36.09 | L | O |
| ATOM | 713 | CB | HIS | L | 84 | 25.085 | 39.434 | 46.424 | 1.00 | 36.24 | L | C |
| ATOM | 714 | CG | HIS | L | 84 | 25.439 | 40.328 | 47.572 | 1.00 | 38.81 | L | C |
| ATOM | 715 | ND1 | HIS | L | 84 | 26.701 | 40.373 | 48.126 | 1.00 | 39.64 | L | N |
| ATOM | 716 | CD2 | HIS | L | 84 | 24.697 | 41.231 | 48.256 | 1.00 | 39.06 | L | C |
| ATOM | 717 | CE1 | HIS | L | 84 | 26.721 | 41.264 | 49.100 | 1.00 | 39.38 | L | C |
| ATOM | 718 | NE2 | HIS | L | 84 | 25.518 | 41.799 | 49.200 | 1.00 | 41.56 | L | N |
| ATOM | 719 | N | LYS | L | 85 | 23.561 | 36.290 | 45.871 | 1.00 | 37.90 | L | N |
| ATOM | 720 | CA | LYS | L | 85 | 22.931 | 35.504 | 44.817 | 1.00 | 39.99 | L | C |
| ATOM | 721 | C | LYS | L | 85 | 22.179 | 36.379 | 43.808 | 1.00 | 41.95 | L | C |
| ATOM | 722 | O | LYS | L | 85 | 21.997 | 35.988 | 42.659 | 1.00 | 42.20 | L | O |
| ATOM | 723 | CB | LYS | L | 85 | 21.983 | 34.471 | 45.432 | 1.00 | 40.09 | L | C |
| ATOM | 724 | CG | LYS | L | 85 | 22.673 | 33.492 | 46.380 | 1.00 | 41.01 | L | C |
| ATOM | 725 | CD | LYS | L | 85 | 21.699 | 32.493 | 46.987 | 1.00 | 40.74 | L | C |
| ATOM | 726 | CE | LYS | L | 85 | 21.202 | 31.494 | 45.958 | 1.00 | 42.61 | L | C |
| ATOM | 727 | NZ | LYS | L | 85 | 22.296 | 30.609 | 45.462 | 1.00 | 43.27 | L | N |
| ATOM | 728 | N | ASP | L | 86 | 21.758 | 37.567 | 44.235 | 1.00 | 44.88 | L | N |
| ATOM | 729 | CA | ASP | L | 86 | 21.030 | 38.487 | 43.361 | 1.00 | 47.56 | L | C |
| ATOM | 730 | C | ASP | L | 86 | 21.941 | 39.324 | 42.455 | 1.00 | 47.92 | L | C |
| ATOM | 731 | O | ASP | L | 86 | 21.456 | 40.131 | 41.663 | 1.00 | 48.41 | L | O |
| ATOM | 732 | CB | ASP | L | 86 | 20.159 | 39.433 | 44.196 | 1.00 | 49.53 | L | C |
| ATOM | 733 | CG | ASP | L | 86 | 19.237 | 38.694 | 45.147 | 1.00 | 52.38 | L | C |
| ATOM | 734 | OD1 | ASP | L | 86 | 18.537 | 37.783 | 44.701 | 1.00 | 53.34 | L | O |
| ATOM | 735 | OD2 | ASP | L | 86 | 19.217 | 39.037 | 46.334 | 1.00 | 53.54 | L | O |
| ATOM | 736 | N | ASP | L | 87 | 23.252 | 39.132 | 42.568 | 1.00 | 48.29 | L | N |
| ATOM | 737 | CA | ASP | L | 87 | 24.213 | 39.883 | 41.762 | 1.00 | 48.43 | L | C |
| ATOM | 738 | C | ASP | L | 87 | 24.938 | 39.017 | 40.736 | 1.00 | 48.75 | L | C |
| ATOM | 739 | O | ASP | L | 87 | 26.108 | 39.250 | 40.431 | 1.00 | 48.28 | L | O |
| ATOM | 740 | CB | ASP | L | 87 | 25.244 | 40.550 | 42.673 | 1.00 | 49.27 | L | C |
| ATOM | 741 | CG | ASP | L | 87 | 24.639 | 41.629 | 43.545 | 1.00 | 49.65 | L | C |
| ATOM | 742 | OD1 | ASP | L | 87 | 25.271 | 41.998 | 44.528 | 1.00 | 50.02 | L | O |
| ATOM | 743 | OD2 | ASP | L | 87 | 23.541 | 42.101 | 43.231 | 1.00 | 50.10 | L | O |
| ATOM | 744 | N | GLN | L | 88 | 24.239 | 38.024 | 40.199 | 1.00 | 48.76 | L | N |
| ATOM | 745 | CA | GLN | L | 88 | 24.834 | 37.130 | 39.216 | 1.00 | 48.54 | L | C |
| ATOM | 746 | C | GLN | L | 88 | 24.028 | 37.101 | 37.921 | 1.00 | 47.25 | L | C |
| ATOM | 747 | O | GLN | L | 88 | 23.989 | 36.081 | 37.238 | 1.00 | 47.52 | L | O |
| ATOM | 748 | CB | GLN | L | 88 | 24.925 | 35.716 | 39.796 | 1.00 | 50.51 | L | C |
| ATOM | 749 | CG | GLN | L | 88 | 25.663 | 35.632 | 41.129 | 1.00 | 53.34 | L | C |
| ATOM | 750 | CD | GLN | L | 88 | 27.134 | 35.973 | 41.006 | 1.00 | 54.62 | L | C |

-continued

| | | | | | | | | | | | | |
|---|---|---|---|---|---|---|---|---|---|---|---|---|
| ATOM | 751 | OE1 | GLN | L | 88 | 27.499 | 37.016 | 40.461 | 1.00 | 55.79 | L | O |
| ATOM | 752 | NE2 | GLN | L | 88 | 27.990 | 35.094 | 41.518 | 1.00 | 55.48 | L | N |
| ATOM | 753 | N | LEU | L | 89 | 23.399 | 38.221 | 37.575 | 1.00 | 45.19 | L | N |
| ATOM | 754 | CA | LEU | L | 89 | 22.587 | 38.294 | 36.363 | 1.00 | 42.20 | L | C |
| ATOM | 755 | C | LEU | L | 89 | 23.431 | 38.485 | 35.105 | 1.00 | 39.92 | L | C |
| ATOM | 756 | O | LEU | L | 89 | 23.313 | 39.493 | 34.407 | 1.00 | 39.00 | L | O |
| ATOM | 757 | CB | LEU | L | 89 | 21.564 | 39.429 | 36.487 | 1.00 | 42.79 | L | C |
| ATOM | 758 | CG | LEU | L | 89 | 20.458 | 39.493 | 35.430 | 1.00 | 43.04 | L | C |
| ATOM | 759 | CD1 | LEU | L | 89 | 19.678 | 38.187 | 35.421 | 1.00 | 43.31 | L | C |
| ATOM | 760 | CD2 | LEU | L | 89 | 19.532 | 40.662 | 35.729 | 1.00 | 43.24 | L | C |
| ATOM | 761 | N | ILE | L | 90 | 24.284 | 37.504 | 34.825 | 1.00 | 37.21 | L | N |
| ATOM | 762 | CA | ILE | L | 90 | 25.151 | 37.532 | 33.654 | 1.00 | 34.54 | L | C |
| ATOM | 763 | C | ILE | L | 90 | 24.832 | 36.325 | 32.778 | 1.00 | 33.42 | L | C |
| ATOM | 764 | O | ILE | L | 90 | 24.290 | 35.327 | 33.253 | 1.00 | 34.00 | L | O |
| ATOM | 765 | CB | ILE | L | 90 | 26.643 | 37.503 | 34.057 | 1.00 | 34.63 | L | C |
| ATOM | 766 | CG1 | ILE | L | 90 | 26.934 | 36.263 | 34.905 | 1.00 | 33.21 | L | C |
| ATOM | 767 | CG2 | ILE | L | 90 | 26.997 | 38.778 | 34.819 | 1.00 | 32.30 | L | C |
| ATOM | 768 | CD1 | ILE | L | 90 | 28.372 | 36.154 | 35.356 | 1.00 | 36.32 | L | C |
| ATOM | 769 | N | CYS | L | 91 | 25.181 | 36.415 | 31.501 | 1.00 | 31.20 | L | N |
| ATOM | 770 | CA | CYS | L | 91 | 24.885 | 35.350 | 30.556 | 1.00 | 30.45 | L | C |
| ATOM | 771 | C | CYS | L | 91 | 25.471 | 33.971 | 30.833 | 1.00 | 30.35 | L | C |
| ATOM | 772 | O | CYS | L | 91 | 24.778 | 32.967 | 30.671 | 1.00 | 29.92 | L | O |
| ATOM | 773 | CB | CYS | L | 91 | 25.261 | 35.790 | 29.143 | 1.00 | 26.98 | L | C |
| ATOM | 774 | SG | CYS | L | 91 | 24.204 | 37.118 | 28.480 | 1.00 | 26.22 | L | S |
| ATOM | 775 | N | VAL | L | 92 | 26.732 | 33.902 | 31.245 | 1.00 | 29.06 | L | N |
| ATOM | 776 | CA | VAL | L | 92 | 27.333 | 32.602 | 31.514 | 1.00 | 28.75 | L | C |
| ATOM | 777 | C | VAL | L | 92 | 26.693 | 31.897 | 32.707 | 1.00 | 27.72 | L | C |
| ATOM | 778 | O | VAL | L | 92 | 26.940 | 30.712 | 32.937 | 1.00 | 28.52 | L | O |
| ATOM | 779 | CB | VAL | L | 92 | 28.866 | 32.709 | 31.718 | 1.00 | 31.07 | L | C |
| ATOM | 780 | CG1 | VAL | L | 92 | 29.529 | 33.115 | 30.403 | 1.00 | 29.69 | L | C |
| ATOM | 781 | CG2 | VAL | L | 92 | 29.190 | 33.717 | 32.813 | 1.00 | 31.06 | L | C |
| ATOM | 782 | N | ASN | L | 93 | 25.865 | 32.622 | 33.457 | 1.00 | 25.61 | L | N |
| ATOM | 783 | CA | ASN | L | 93 | 25.174 | 32.050 | 34.605 | 1.00 | 24.28 | L | C |
| ATOM | 784 | C | ASN | L | 93 | 23.753 | 31.651 | 34.213 | 1.00 | 23.30 | L | C |
| ATOM | 785 | O | ASN | L | 93 | 22.850 | 32.487 | 34.183 | 1.00 | 22.74 | L | O |
| ATOM | 786 | CB | ASN | L | 93 | 25.123 | 33.047 | 35.767 | 1.00 | 23.78 | L | C |
| ATOM | 787 | CG | ASN | L | 93 | 24.294 | 32.533 | 36.930 | 1.00 | 25.91 | L | C |
| ATOM | 788 | OD1 | ASN | L | 93 | 24.175 | 31.326 | 37.128 | 1.00 | 28.42 | L | O |
| ATOM | 789 | ND2 | ASN | L | 93 | 23.725 | 33.442 | 37.710 | 1.00 | 24.92 | L | N |
| ATOM | 790 | N | GLU | L | 94 | 23.564 | 30.370 | 33.907 | 1.00 | 22.36 | L | N |
| ATOM | 791 | CA | GLU | L | 94 | 22.257 | 29.862 | 33.511 | 1.00 | 22.33 | L | C |
| ATOM | 792 | C | GLU | L | 94 | 21.654 | 30.701 | 32.383 | 1.00 | 20.87 | L | C |
| ATOM | 793 | O | GLU | L | 94 | 20.472 | 31.047 | 32.412 | 1.00 | 18.77 | L | O |
| ATOM | 794 | CB | GLU | L | 94 | 21.302 | 29.856 | 34.711 | 1.00 | 24.83 | L | C |
| ATOM | 795 | CG | GLU | L | 94 | 21.714 | 28.934 | 35.863 | 1.00 | 27.12 | L | C |
| ATOM | 796 | CD | GLU | L | 94 | 21.684 | 27.462 | 35.488 | 1.00 | 30.61 | L | C |
| ATOM | 797 | OE1 | GLU | L | 94 | 22.593 | 26.997 | 34.794 | 1.00 | 29.23 | L | O |
| ATOM | 798 | OE2 | GLU | L | 94 | 20.741 | 26.783 | 35.891 | 1.00 | 35.59 | L | O |
| ATOM | 799 | N | ASN | L | 95 | 22.482 | 31.035 | 31.400 | 1.00 | 20.59 | L | N |
| ATOM | 800 | CA | ASN | L | 95 | 22.054 | 31.810 | 30.240 | 1.00 | 21.27 | L | C |
| ATOM | 801 | C | ASN | L | 95 | 21.375 | 33.134 | 30.603 | 1.00 | 22.32 | L | C |
| ATOM | 802 | O | ASN | L | 95 | 20.567 | 33.656 | 29.829 | 1.00 | 22.62 | L | O |
| ATOM | 803 | CB | ASN | L | 95 | 21.108 | 30.963 | 29.381 | 1.00 | 19.04 | L | C |
| ATOM | 804 | CG | ASN | L | 95 | 21.028 | 31.451 | 27.956 | 1.00 | 17.99 | L | C |
| ATOM | 805 | OD1 | ASN | L | 95 | 22.040 | 31.546 | 27.270 | 1.00 | 20.44 | L | O |
| ATOM | 806 | ND2 | ASN | L | 95 | 19.827 | 31.757 | 27.499 | 1.00 | 18.44 | L | N |
| ATOM | 807 | N | GLY | L | 96 | 21.716 | 33.674 | 31.773 | 1.00 | 23.58 | L | N |
| ATOM | 808 | CA | GLY | L | 96 | 21.140 | 34.928 | 32.227 | 1.00 | 22.26 | L | C |
| ATOM | 809 | C | GLY | L | 96 | 19.645 | 34.875 | 32.494 | 1.00 | 22.45 | L | C |
| ATOM | 810 | O | GLY | L | 96 | 19.002 | 35.911 | 32.650 | 1.00 | 24.38 | L | O |
| ATOM | 811 | N | GLY | L | 97 | 19.084 | 33.674 | 32.566 | 1.00 | 21.95 | L | N |
| ATOM | 812 | CA | GLY | L | 97 | 17.654 | 33.558 | 32.789 | 1.00 | 20.54 | L | C |
| ATOM | 813 | C | GLY | L | 97 | 16.871 | 33.760 | 31.501 | 1.00 | 20.22 | L | C |
| ATOM | 814 | O | GLY | L | 97 | 15.645 | 33.740 | 31.510 | 1.00 | 22.61 | L | O |
| ATOM | 815 | N | CYS | L | 98 | 17.580 | 33.959 | 30.393 | 1.00 | 19.38 | L | N |
| ATOM | 816 | CA | CYS | L | 98 | 16.956 | 34.161 | 29.086 | 1.00 | 20.02 | L | C |
| ATOM | 817 | C | CYS | L | 98 | 16.477 | 32.833 | 28.508 | 1.00 | 20.61 | L | C |
| ATOM | 818 | O | CYS | L | 98 | 17.165 | 31.818 | 28.623 | 1.00 | 20.27 | L | O |
| ATOM | 819 | CB | CYS | L | 98 | 17.955 | 34.764 | 28.105 | 1.00 | 19.41 | L | C |
| ATOM | 820 | SG | CYS | L | 98 | 18.601 | 36.419 | 28.485 | 1.00 | 22.10 | L | S |
| ATOM | 821 | N | GLU | L | 99 | 15.314 | 32.839 | 27.867 | 1.00 | 20.33 | L | N |
| ATOM | 822 | CA | GLU | L | 99 | 14.794 | 31.611 | 27.277 | 1.00 | 20.72 | L | C |
| ATOM | 823 | C | GLU | L | 99 | 15.625 | 31.164 | 26.076 | 1.00 | 19.15 | L | C |
| ATOM | 824 | O | GLU | L | 99 | 15.827 | 29.974 | 25.877 | 1.00 | 17.11 | L | O |
| ATOM | 825 | CB | GLU | L | 99 | 13.336 | 31.779 | 26.850 | 1.00 | 22.59 | L | C |
| ATOM | 826 | CG | GLU | L | 99 | 12.682 | 30.457 | 26.467 | 1.00 | 29.91 | L | C |
| ATOM | 827 | CD | GLU | L | 99 | 11.178 | 30.564 | 26.302 | 1.00 | 32.54 | L | C |
| ATOM | 828 | OE1 | GLU | L | 99 | 10.738 | 31.204 | 25.370 | 1.00 | 33.67 | L | O |
| ATOM | 829 | OE2 | GLU | L | 99 | 10.458 | 29.999 | 27.122 | 1.00 | 37.34 | L | O |

-continued

| | | | | | | | | | | | |
|---|---|---|---|---|---|---|---|---|---|---|---|
| ATOM | 830 | N | GLN | L | 100 | 16.101 | 32.114 | 25.274 | 1.00 | 18.04 | L | N |
| ATOM | 831 | CA | GLN | L | 100 | 16.911 | 31.763 | 24.112 | 1.00 | 18.31 | L | C |
| ATOM | 832 | C | GLN | L | 100 | 18.281 | 32.459 | 24.118 | 1.00 | 19.20 | L | C |
| ATOM | 833 | O | GLN | L | 100 | 19.223 | 31.951 | 24.724 | 1.00 | 19.26 | L | O |
| ATOM | 834 | CB | GLN | L | 100 | 16.145 | 32.056 | 22.805 | 1.00 | 16.04 | L | C |
| ATOM | 835 | CG | GLN | L | 100 | 14.789 | 31.342 | 22.716 | 1.00 | 15.13 | L | C |
| ATOM | 836 | CD | GLN | L | 100 | 14.182 | 31.366 | 21.321 | 1.00 | 16.10 | L | C |
| ATOM | 837 | OE1 | GLN | L | 100 | 14.478 | 32.245 | 20.520 | 1.00 | 16.54 | L | O |
| ATOM | 838 | NE2 | GLN | L | 100 | 13.314 | 30.403 | 21.034 | 1.00 | 17.14 | L | N |
| ATOM | 839 | N | TYR | L | 101 | 18.408 | 33.610 | 23.465 | 1.00 | 19.40 | L | N |
| ATOM | 840 | CA | TYR | L | 101 | 19.705 | 34.282 | 23.429 | 1.00 | 20.26 | L | C |
| ATOM | 841 | C | TYR | L | 101 | 19.895 | 35.307 | 24.540 | 1.00 | 22.37 | L | C |
| ATOM | 842 | O | TYR | L | 101 | 18.956 | 36.002 | 24.935 | 1.00 | 22.47 | L | O |
| ATOM | 843 | CB | TYR | L | 101 | 19.934 | 34.955 | 22.071 | 1.00 | 18.52 | L | C |
| ATOM | 844 | CG | TYR | L | 101 | 19.838 | 34.017 | 20.880 | 1.00 | 20.18 | L | C |
| ATOM | 845 | CD1 | TYR | L | 101 | 20.215 | 32.673 | 20.982 | 1.00 | 17.62 | L | C |
| ATOM | 846 | CD2 | TYR | L | 101 | 19.387 | 34.481 | 19.643 | 1.00 | 19.56 | L | C |
| ATOM | 847 | CE1 | TYR | L | 101 | 20.140 | 31.822 | 19.884 | 1.00 | 19.81 | L | C |
| ATOM | 848 | CE2 | TYR | L | 101 | 19.315 | 33.640 | 18.541 | 1.00 | 19.48 | L | C |
| ATOM | 849 | CZ | TYR | L | 101 | 19.693 | 32.313 | 18.666 | 1.00 | 18.80 | L | C |
| ATOM | 850 | OH | TYR | L | 101 | 19.641 | 31.489 | 17.564 | 1.00 | 19.13 | L | O |
| ATOM | 851 | N | CYS | L | 102 | 21.127 | 35.387 | 25.032 | 1.00 | 22.05 | L | N |
| ATOM | 852 | CA | CYS | L | 102 | 21.500 | 36.300 | 26.102 | 1.00 | 23.17 | L | C |
| ATOM | 853 | C | CYS | L | 102 | 22.680 | 37.168 | 25.657 | 1.00 | 24.83 | L | C |
| ATOM | 854 | O | CYS | L | 102 | 23.617 | 36.686 | 25.020 | 1.00 | 25.16 | L | O |
| ATOM | 855 | CB | CYS | L | 102 | 21.897 | 35.494 | 27.343 | 1.00 | 22.80 | L | C |
| ATOM | 856 | SG | CYS | L | 102 | 22.308 | 36.468 | 28.827 | 1.00 | 24.11 | L | S |
| ATOM | 857 | N | SER | L | 103 | 22.628 | 38.451 | 25.995 | 1.00 | 26.62 | L | N |
| ATOM | 858 | CA | SER | L | 103 | 23.695 | 39.382 | 25.650 | 1.00 | 28.86 | L | C |
| ATOM | 859 | C | SER | L | 103 | 24.115 | 40.156 | 26.889 | 1.00 | 29.38 | L | C |
| ATOM | 860 | O | SER | L | 103 | 23.277 | 40.759 | 27.558 | 1.00 | 31.61 | L | O |
| ATOM | 861 | CB | SER | L | 103 | 23.225 | 40.377 | 24.584 | 1.00 | 27.37 | L | C |
| ATOM | 862 | OG | SER | L | 103 | 22.975 | 39.733 | 23.350 | 1.00 | 29.37 | L | O |
| ATOM | 863 | N | ASP | L | 104 | 25.405 | 40.125 | 27.205 | 1.00 | 30.25 | L | N |
| ATOM | 864 | CA | ASP | L | 104 | 25.915 | 40.865 | 28.352 | 1.00 | 31.60 | L | C |
| ATOM | 865 | C | ASP | L | 104 | 26.112 | 42.304 | 27.899 | 1.00 | 33.46 | L | C |
| ATOM | 866 | O | ASP | L | 104 | 26.323 | 42.562 | 26.714 | 1.00 | 32.44 | L | O |
| ATOM | 867 | CB | ASP | L | 104 | 27.258 | 40.303 | 28.820 | 1.00 | 30.24 | L | C |
| ATOM | 868 | CG | ASP | L | 104 | 27.124 | 38.978 | 29.537 | 1.00 | 31.11 | L | C |
| ATOM | 869 | OD1 | ASP | L | 104 | 26.369 | 38.909 | 30.503 | 1.00 | 30.36 | L | O |
| ATOM | 870 | OD2 | ASP | L | 104 | 27.788 | 38.022 | 29.129 | 1.00 | 31.46 | L | O |
| ATOM | 871 | N | HIS | L | 105 | 26.045 | 43.241 | 28.835 | 1.00 | 37.03 | L | N |
| ATOM | 872 | CA | HIS | L | 105 | 26.226 | 44.642 | 28.486 | 1.00 | 40.26 | L | C |
| ATOM | 873 | C | HIS | L | 105 | 27.048 | 45.418 | 29.505 | 1.00 | 43.18 | L | C |
| ATOM | 874 | O | HIS | L | 105 | 26.942 | 45.197 | 30.714 | 1.00 | 42.14 | L | O |
| ATOM | 875 | CB | HIS | L | 105 | 24.866 | 45.317 | 28.288 | 1.00 | 38.90 | L | C |
| ATOM | 876 | CG | HIS | L | 105 | 24.151 | 44.878 | 27.048 | 1.00 | 38.94 | L | C |
| ATOM | 877 | ND1 | HIS | L | 105 | 24.678 | 45.051 | 25.786 | 1.00 | 38.12 | L | N |
| ATOM | 878 | CD2 | HIS | L | 105 | 22.955 | 44.267 | 26.875 | 1.00 | 37.83 | L | C |
| ATOM | 879 | CE1 | HIS | L | 105 | 23.838 | 44.565 | 24.890 | 1.00 | 38.48 | L | C |
| ATOM | 880 | NE2 | HIS | L | 105 | 22.785 | 44.083 | 25.524 | 1.00 | 37.45 | L | N |
| ATOM | 881 | N | THR | L | 106 | 27.875 | 46.325 | 28.993 | 1.00 | 46.90 | L | N |
| ATOM | 882 | CA | THR | L | 106 | 28.731 | 47.171 | 29.816 | 1.00 | 49.56 | L | C |
| ATOM | 883 | C | THR | L | 106 | 27.995 | 48.481 | 30.076 | 1.00 | 49.91 | L | C |
| ATOM | 884 | O | THR | L | 106 | 27.876 | 49.319 | 29.182 | 1.00 | 51.77 | L | O |
| ATOM | 885 | CB | THR | L | 106 | 30.061 | 47.482 | 29.093 | 1.00 | 50.44 | L | C |
| ATOM | 886 | OG1 | THR | L | 106 | 30.719 | 46.256 | 28.752 | 1.00 | 52.50 | L | O |
| ATOM | 887 | CG2 | THR | L | 106 | 30.977 | 48.310 | 29.983 | 1.00 | 51.29 | L | C |
| ATOM | 888 | N | GLY | L | 107 | 27.499 | 48.650 | 31.297 | 1.00 | 50.05 | L | N |
| ATOM | 889 | CA | GLY | L | 107 | 26.772 | 49.862 | 31.637 | 1.00 | 50.24 | L | C |
| ATOM | 890 | C | GLY | L | 107 | 25.265 | 49.664 | 31.683 | 1.00 | 50.91 | L | C |
| ATOM | 891 | O | GLY | L | 107 | 24.524 | 50.566 | 32.076 | 1.00 | 51.47 | L | O |
| ATOM | 892 | N | THR | L | 108 | 24.812 | 48.480 | 31.276 | 1.00 | 50.46 | L | N |
| ATOM | 893 | CA | THR | L | 108 | 23.394 | 48.138 | 31.269 | 1.00 | 48.90 | L | C |
| ATOM | 894 | C | THR | L | 108 | 23.244 | 46.633 | 31.482 | 1.00 | 47.11 | L | C |
| ATOM | 895 | O | THR | L | 108 | 24.024 | 45.847 | 30.948 | 1.00 | 47.64 | L | O |
| ATOM | 896 | CB | THR | L | 108 | 22.733 | 48.524 | 29.929 | 1.00 | 50.40 | L | C |
| ATOM | 897 | OG1 | THR | L | 108 | 23.506 | 47.998 | 28.842 | 1.00 | 51.52 | L | O |
| ATOM | 898 | CG2 | THR | L | 108 | 22.639 | 50.038 | 29.793 | 1.00 | 51.68 | L | C |
| ATOM | 899 | N | LYS | L | 109 | 22.244 | 46.238 | 32.266 | 1.00 | 44.24 | L | N |
| ATOM | 900 | CA | LYS | L | 109 | 22.005 | 44.825 | 32.558 | 1.00 | 41.00 | L | C |
| ATOM | 901 | C | LYS | L | 109 | 21.909 | 43.997 | 31.280 | 1.00 | 37.67 | L | C |
| ATOM | 902 | O | LYS | L | 109 | 21.642 | 44.531 | 30.201 | 1.00 | 37.06 | L | O |
| ATOM | 903 | CB | LYS | L | 109 | 20.716 | 44.663 | 33.367 | 1.00 | 42.02 | L | C |
| ATOM | 904 | CG | LYS | L | 109 | 19.450 | 44.860 | 32.555 | 1.00 | 44.84 | L | C |
| ATOM | 905 | CD | LYS | L | 109 | 18.219 | 44.906 | 33.444 | 1.00 | 47.58 | L | C |
| ATOM | 906 | CE | LYS | L | 109 | 18.148 | 46.209 | 34.230 | 1.00 | 49.04 | L | C |
| ATOM | 907 | NZ | LYS | L | 109 | 18.009 | 47.398 | 33.338 | 1.00 | 48.86 | L | N |
| ATOM | 908 | N | ARG | L | 110 | 22.125 | 42.691 | 31.409 | 1.00 | 33.89 | L | N |

-continued

| | | | | | | | | | | | | |
|---|---|---|---|---|---|---|---|---|---|---|---|---|
| ATOM | 909 | CA | ARG | L | 110 | 22.063 | 41.786 | 30.264 | 1.00 | 31.44 | L | C |
| ATOM | 910 | C | ARG | L | 110 | 20.696 | 41.861 | 29.596 | 1.00 | 28.77 | L | C |
| ATOM | 911 | O | ARG | L | 110 | 19.690 | 42.107 | 30.253 | 1.00 | 28.40 | L | O |
| ATOM | 912 | CB | ARG | L | 110 | 22.334 | 40.346 | 30.709 | 1.00 | 29.16 | L | C |
| ATOM | 913 | CG | ARG | L | 110 | 21.206 | 39.704 | 31.515 | 1.00 | 26.40 | L | C |
| ATOM | 914 | CD | ARG | L | 110 | 20.133 | 39.072 | 30.617 | 1.00 | 23.55 | L | C |
| ATOM | 915 | NE | ARG | L | 110 | 19.049 | 38.500 | 31.409 | 1.00 | 23.99 | L | N |
| ATOM | 916 | CZ | ARG | L | 110 | 18.083 | 39.206 | 31.993 | 1.00 | 26.90 | L | C |
| ATOM | 917 | NH1 | ARG | L | 110 | 18.045 | 40.529 | 31.871 | 1.00 | 25.76 | L | N |
| ATOM | 918 | NH2 | ARG | L | 110 | 17.163 | 38.592 | 32.726 | 1.00 | 23.93 | L | N |
| ATOM | 919 | N | SER | L | 111 | 20.666 | 41.652 | 28.287 | 1.00 | 27.46 | L | N |
| ATOM | 920 | CA | SER | L | 111 | 19.416 | 41.683 | 27.545 | 1.00 | 26.40 | L | C |
| ATOM | 921 | C | SER | L | 111 | 19.173 | 40.310 | 26.925 | 1.00 | 25.75 | L | C |
| ATOM | 922 | O | SER | L | 111 | 20.116 | 39.578 | 26.624 | 1.00 | 25.72 | L | O |
| ATOM | 923 | CB | SER | L | 111 | 19.484 | 42.732 | 26.442 | 1.00 | 23.78 | L | C |
| ATOM | 924 | OG | SER | L | 111 | 20.407 | 42.337 | 25.447 | 1.00 | 28.02 | L | O |
| ATOM | 925 | N | CYS | L | 112 | 17.906 | 39.962 | 26.745 | 1.00 | 24.32 | L | N |
| ATOM | 926 | CA | CYS | L | 112 | 17.553 | 38.682 | 26.152 | 1.00 | 24.98 | L | C |
| ATOM | 927 | C | CYS | L | 112 | 17.024 | 38.891 | 24.742 | 1.00 | 24.93 | L | C |
| ATOM | 928 | O | CYS | L | 112 | 16.341 | 39.879 | 24.470 | 1.00 | 26.51 | L | O |
| ATOM | 929 | CB | CYS | L | 112 | 16.480 | 37.985 | 26.980 | 1.00 | 23.15 | L | C |
| ATOM | 930 | SG | CYS | L | 112 | 16.932 | 37.554 | 28.686 | 1.00 | 25.67 | L | S |
| ATOM | 931 | N | ARG | L | 113 | 17.341 | 37.961 | 23.846 | 1.00 | 24.52 | L | N |
| ATOM | 932 | CA | ARG | L | 113 | 16.884 | 38.042 | 22.463 | 1.00 | 23.03 | L | C |
| ATOM | 933 | C | ARG | L | 113 | 16.292 | 36.709 | 22.021 | 1.00 | 22.44 | L | C |
| ATOM | 934 | O | ARG | L | 113 | 16.260 | 35.749 | 22.791 | 1.00 | 20.23 | L | O |
| ATOM | 935 | CB | ARG | L | 113 | 18.038 | 38.457 | 21.543 | 1.00 | 23.44 | L | C |
| ATOM | 936 | CG | ARG | L | 113 | 18.470 | 39.912 | 21.739 | 1.00 | 25.76 | L | C |
| ATOM | 937 | CD | ARG | L | 113 | 19.706 | 40.286 | 20.926 | 1.00 | 25.39 | L | C |
| ATOM | 938 | NE | ARG | L | 113 | 20.882 | 39.525 | 21.349 | 1.00 | 26.05 | L | N |
| ATOM | 939 | CZ | ARG | L | 113 | 21.361 | 38.459 | 20.712 | 1.00 | 22.82 | L | C |
| ATOM | 940 | NH1 | ARG | L | 113 | 20.775 | 38.019 | 19.607 | 1.00 | 19.33 | L | N |
| ATOM | 941 | NH2 | ARG | L | 113 | 22.421 | 37.823 | 21.190 | 1.00 | 19.90 | L | N |
| ATOM | 942 | N | CYS | L | 114 | 15.810 | 36.656 | 20.783 | 1.00 | 21.91 | L | N |
| ATOM | 943 | CA | CYS | L | 114 | 15.208 | 35.439 | 20.268 | 1.00 | 21.36 | L | C |
| ATOM | 944 | C | CYS | L | 114 | 15.653 | 35.122 | 18.847 | 1.00 | 20.52 | L | C |
| ATOM | 945 | O | CYS | L | 114 | 16.153 | 35.979 | 18.120 | 1.00 | 19.97 | L | O |
| ATOM | 946 | CB | CYS | L | 114 | 13.677 | 35.542 | 20.296 | 1.00 | 20.90 | L | C |
| ATOM | 947 | SG | CYS | L | 114 | 12.941 | 36.040 | 21.885 | 1.00 | 22.52 | L | S |
| ATOM | 948 | N | HIS | L | 115 | 15.453 | 33.868 | 18.469 | 1.00 | 20.76 | L | N |
| ATOM | 949 | CA | HIS | L | 115 | 15.786 | 33.367 | 17.147 | 1.00 | 20.81 | L | C |
| ATOM | 950 | C | HIS | L | 115 | 14.684 | 33.850 | 16.199 | 1.00 | 21.18 | L | C |
| ATOM | 951 | O | HIS | L | 115 | 13.556 | 34.098 | 16.627 | 1.00 | 21.61 | L | O |
| ATOM | 952 | CB | HIS | L | 115 | 15.827 | 31.832 | 17.207 | 1.00 | 20.46 | L | C |
| ATOM | 953 | CG | HIS | L | 115 | 16.269 | 31.172 | 15.938 | 1.00 | 19.99 | L | C |
| ATOM | 954 | ND1 | HIS | L | 115 | 15.455 | 31.057 | 14.832 | 1.00 | 19.51 | L | N |
| ATOM | 955 | CD2 | HIS | L | 115 | 17.442 | 30.586 | 15.602 | 1.00 | 18.82 | L | C |
| ATOM | 956 | CE1 | HIS | L | 115 | 16.107 | 30.432 | 13.870 | 1.00 | 17.84 | L | C |
| ATOM | 957 | NE2 | HIS | L | 115 | 17.315 | 30.134 | 14.311 | 1.00 | 19.44 | L | N |
| ATOM | 958 | N | GLU | L | 116 | 15.020 | 34.012 | 14.925 | 1.00 | 21.79 | L | N |
| ATOM | 959 | CA | GLU | L | 116 | 14.050 | 34.429 | 13.924 | 1.00 | 21.88 | L | C |
| ATOM | 960 | C | GLU | L | 116 | 12.845 | 33.503 | 14.053 | 1.00 | 20.86 | L | C |
| ATOM | 961 | O | GLU | L | 116 | 13.002 | 32.306 | 14.288 | 1.00 | 20.19 | L | O |
| ATOM | 962 | CB | GLU | L | 116 | 14.655 | 34.300 | 12.522 | 1.00 | 25.33 | L | C |
| ATOM | 963 | CG | GLU | L | 116 | 13.663 | 34.559 | 11.391 | 1.00 | 32.50 | L | C |
| ATOM | 964 | CD | GLU | L | 116 | 14.201 | 34.154 | 10.027 | 1.00 | 36.87 | L | C |
| ATOM | 965 | OE1 | GLU | L | 116 | 13.412 | 34.107 | 9.075 | 1.00 | 39.33 | L | O |
| ATOM | 966 | OE2 | GLU | L | 116 | 15.405 | 33.890 | 9.916 | 1.00 | 38.85 | L | O |
| ATOM | 967 | N | GLY | L | 117 | 11.646 | 34.051 | 13.900 | 1.00 | 20.27 | L | N |
| ATOM | 968 | CA | GLY | L | 117 | 10.451 | 33.236 | 14.020 | 1.00 | 18.99 | L | C |
| ATOM | 969 | C | GLY | L | 117 | 9.860 | 33.299 | 15.417 | 1.00 | 19.27 | L | C |
| ATOM | 970 | O | GLY | L | 117 | 8.820 | 32.694 | 15.688 | 1.00 | 19.43 | L | O |
| ATOM | 971 | N | TYR | L | 118 | 10.543 | 34.018 | 16.305 | 1.00 | 19.01 | L | N |
| ATOM | 972 | CA | TYR | L | 118 | 10.116 | 34.206 | 17.689 | 1.00 | 19.23 | L | C |
| ATOM | 973 | C | TYR | L | 118 | 10.278 | 35.692 | 18.018 | 1.00 | 20.14 | L | C |
| ATOM | 974 | O | TYR | L | 118 | 11.012 | 36.409 | 17.344 | 1.00 | 19.66 | L | O |
| ATOM | 975 | CB | TYR | L | 118 | 10.999 | 33.417 | 18.671 | 1.00 | 18.12 | L | C |
| ATOM | 976 | CG | TYR | L | 118 | 10.916 | 31.905 | 18.602 | 1.00 | 15.33 | L | C |
| ATOM | 977 | CD1 | TYR | L | 118 | 11.650 | 31.187 | 17.658 | 1.00 | 15.05 | L | C |
| ATOM | 978 | CD2 | TYR | L | 118 | 10.116 | 31.192 | 19.499 | 1.00 | 13.29 | L | C |
| ATOM | 979 | CE1 | TYR | L | 118 | 11.590 | 29.791 | 17.607 | 1.00 | 14.73 | L | C |
| ATOM | 980 | CE2 | TYR | L | 118 | 10.049 | 29.803 | 19.457 | 1.00 | 14.27 | L | C |
| ATOM | 981 | CZ | TYR | L | 118 | 10.790 | 29.109 | 18.507 | 1.00 | 15.35 | L | C |
| ATOM | 982 | OH | TYR | L | 118 | 10.736 | 27.735 | 18.466 | 1.00 | 15.58 | L | O |
| ATOM | 983 | N | SER | L | 119 | 9.595 | 36.150 | 19.058 | 1.00 | 21.39 | L | N |
| ATOM | 984 | CA | SER | L | 119 | 9.710 | 37.538 | 19.481 | 1.00 | 23.14 | L | C |
| ATOM | 985 | C | SER | L | 119 | 9.746 | 37.524 | 21.002 | 1.00 | 21.88 | L | C |
| ATOM | 986 | O | SER | L | 119 | 9.189 | 36.629 | 21.632 | 1.00 | 23.34 | L | O |
| ATOM | 987 | CB | SER | L | 119 | 8.522 | 38.364 | 18.979 | 1.00 | 23.84 | L | C |

-continued

| | | | | | | | | | | | |
|---|---|---|---|---|---|---|---|---|---|---|---|
| ATOM | 988 | OG | SER | L | 119 | 7.312 | 37.905 | 19.556 | 1.00 | 31.34 | L | O |
| ATOM | 989 | N | LEU | L | 120 | 10.413 | 38.510 | 21.585 | 1.00 | 23.21 | L | N |
| ATOM | 990 | CA | LEU | L | 120 | 10.544 | 38.606 | 23.036 | 1.00 | 24.38 | L | C |
| ATOM | 991 | C | LEU | L | 120 | 9.253 | 39.096 | 23.683 | 1.00 | 26.18 | L | C |
| ATOM | 992 | O | LEU | L | 120 | 8.667 | 40.081 | 23.236 | 1.00 | 27.69 | L | O |
| ATOM | 993 | CB | LEU | L | 120 | 11.683 | 39.565 | 23.389 | 1.00 | 23.36 | L | C |
| ATOM | 994 | CG | LEU | L | 120 | 12.119 | 39.619 | 24.855 | 1.00 | 25.06 | L | C |
| ATOM | 995 | CD1 | LEU | L | 120 | 12.801 | 38.311 | 25.230 | 1.00 | 24.68 | L | C |
| ATOM | 996 | CD2 | LEU | L | 120 | 13.080 | 40.789 | 25.063 | 1.00 | 24.21 | L | C |
| ATOM | 997 | N | LEU | L | 121 | 8.817 | 38.410 | 24.736 | 1.00 | 26.79 | L | N |
| ATOM | 998 | CA | LEU | L | 121 | 7.600 | 38.790 | 25.450 | 1.00 | 28.18 | L | C |
| ATOM | 999 | C | LEU | L | 121 | 7.885 | 39.949 | 26.402 | 1.00 | 29.35 | L | C |
| ATOM | 1000 | O | LEU | L | 121 | 9.039 | 40.320 | 26.614 | 1.00 | 28.95 | L | O |
| ATOM | 1001 | CB | LEU | L | 121 | 7.042 | 37.595 | 26.235 | 1.00 | 26.70 | L | C |
| ATOM | 1002 | CG | LEU | L | 121 | 6.491 | 36.417 | 25.418 | 1.00 | 27.20 | L | C |
| ATOM | 1003 | CD1 | LEU | L | 121 | 6.025 | 35.310 | 26.348 | 1.00 | 27.89 | L | C |
| ATOM | 1004 | CD2 | LEU | L | 121 | 5.335 | 36.891 | 24.554 | 1.00 | 28.46 | L | C |
| ATOM | 1005 | N | ALA | L | 122 | 6.825 | 40.512 | 26.979 | 1.00 | 30.71 | L | N |
| ATOM | 1006 | CA | ALA | L | 122 | 6.948 | 41.638 | 27.903 | 1.00 | 30.91 | L | C |
| ATOM | 1007 | C | ALA | L | 122 | 7.865 | 41.379 | 29.097 | 1.00 | 30.79 | L | C |
| ATOM | 1008 | O | ALA | L | 122 | 8.492 | 42.307 | 29.607 | 1.00 | 32.36 | L | O |
| ATOM | 1009 | CB | ALA | L | 122 | 5.566 | 42.058 | 28.397 | 1.00 | 33.12 | L | C |
| ATOM | 1010 | N | ASP | L | 123 | 7.953 | 40.131 | 29.550 | 1.00 | 28.66 | L | N |
| ATOM | 1011 | CA | ASP | L | 123 | 8.811 | 39.826 | 30.687 | 1.00 | 27.44 | L | C |
| ATOM | 1012 | C | ASP | L | 123 | 10.301 | 40.040 | 30.405 | 1.00 | 27.39 | L | C |
| ATOM | 1013 | O | ASP | L | 123 | 11.123 | 39.955 | 31.314 | 1.00 | 28.38 | L | O |
| ATOM | 1014 | CB | ASP | L | 123 | 8.571 | 38.392 | 31.189 | 1.00 | 27.26 | L | C |
| ATOM | 1015 | CG | ASP | L | 123 | 8.951 | 37.324 | 30.168 | 1.00 | 26.53 | L | C |
| ATOM | 1016 | OD1 | ASP | L | 123 | 9.602 | 37.634 | 29.173 | 1.00 | 25.66 | L | O |
| ATOM | 1017 | OD2 | ASP | L | 123 | 8.595 | 36.173 | 30.389 | 1.00 | 25.85 | L | O |
| ATOM | 1018 | N | GLY | L | 124 | 10.645 | 40.318 | 29.150 | 1.00 | 27.75 | L | N |
| ATOM | 1019 | CA | GLY | L | 124 | 12.033 | 40.551 | 28.789 | 1.00 | 27.23 | L | C |
| ATOM | 1020 | C | GLY | L | 124 | 12.937 | 39.329 | 28.721 | 1.00 | 28.17 | L | C |
| ATOM | 1021 | O | GLY | L | 124 | 14.135 | 39.465 | 28.460 | 1.00 | 27.43 | L | O |
| ATOM | 1022 | N | VAL | L | 125 | 12.389 | 38.137 | 28.943 | 1.00 | 28.24 | L | N |
| ATOM | 1023 | CA | VAL | L | 125 | 13.205 | 36.920 | 28.899 | 1.00 | 27.90 | L | C |
| ATOM | 1024 | C | VAL | L | 125 | 12.626 | 35.779 | 28.057 | 1.00 | 26.61 | L | C |
| ATOM | 1025 | O | VAL | L | 125 | 13.373 | 34.954 | 27.533 | 1.00 | 25.92 | L | O |
| ATOM | 1026 | CB | VAL | L | 125 | 13.476 | 36.367 | 30.326 | 1.00 | 28.91 | L | C |
| ATOM | 1027 | CG1 | VAL | L | 125 | 14.182 | 37.421 | 31.173 | 1.00 | 29.31 | L | C |
| ATOM | 1028 | CG2 | VAL | L | 125 | 12.173 | 35.930 | 30.980 | 1.00 | 27.68 | L | C |
| ATOM | 1029 | N | SER | L | 126 | 11.304 | 35.734 | 27.927 | 1.00 | 25.52 | L | N |
| ATOM | 1030 | CA | SER | L | 126 | 10.639 | 34.677 | 27.175 | 1.00 | 23.57 | L | C |
| ATOM | 1031 | C | SER | L | 126 | 10.475 | 34.989 | 25.696 | 1.00 | 23.79 | L | C |
| ATOM | 1032 | O | SER | L | 126 | 10.427 | 36.157 | 25.294 | 1.00 | 21.55 | L | O |
| ATOM | 1033 | CB | SER | L | 126 | 9.266 | 34.393 | 27.788 | 1.00 | 23.48 | L | C |
| ATOM | 1034 | OG | SER | L | 126 | 9.396 | 34.047 | 29.157 | 1.00 | 24.08 | L | O |
| ATOM | 1035 | N | CYS | L | 127 | 10.391 | 33.932 | 24.890 | 1.00 | 21.77 | L | N |
| ATOM | 1036 | CA | CYS | L | 127 | 10.219 | 34.070 | 23.451 | 1.00 | 22.08 | L | C |
| ATOM | 1037 | C | CYS | L | 127 | 8.966 | 33.324 | 23.020 | 1.00 | 22.86 | L | C |
| ATOM | 1038 | O | CYS | L | 127 | 8.698 | 32.214 | 23.482 | 1.00 | 23.36 | L | O |
| ATOM | 1039 | CB | CYS | L | 127 | 11.431 | 33.516 | 22.700 | 1.00 | 21.97 | L | C |
| ATOM | 1040 | SG | CYS | L | 127 | 13.006 | 34.368 | 23.044 | 1.00 | 21.79 | L | S |
| ATOM | 1041 | N | THR | L | 128 | 8.197 | 33.947 | 22.136 | 1.00 | 21.95 | L | N |
| ATOM | 1042 | CA | THR | L | 128 | 6.967 | 33.353 | 21.645 | 1.00 | 21.10 | L | C |
| ATOM | 1043 | C | THR | L | 128 | 7.041 | 33.249 | 20.126 | 1.00 | 20.42 | L | C |
| ATOM | 1044 | O | THR | L | 128 | 7.593 | 34.126 | 19.458 | 1.00 | 18.28 | L | O |
| ATOM | 1045 | CB | THR | L | 128 | 5.735 | 34.210 | 22.063 | 1.00 | 21.74 | L | C |
| ATOM | 1046 | OG1 | THR | L | 128 | 4.530 | 33.513 | 21.732 | 1.00 | 22.91 | L | O |
| ATOM | 1047 | CG2 | THR | L | 128 | 5.743 | 35.554 | 21.353 | 1.00 | 18.95 | L | C |
| ATOM | 1048 | N | PRO | L | 129 | 6.497 | 32.162 | 19.559 | 1.00 | 21.27 | L | N |
| ATOM | 1049 | CA | PRO | L | 129 | 6.514 | 31.960 | 18.107 | 1.00 | 22.20 | L | C |
| ATOM | 1050 | C | PRO | L | 129 | 5.713 | 33.026 | 17.363 | 1.00 | 23.45 | L | C |
| ATOM | 1051 | O | PRO | L | 129 | 4.621 | 33.394 | 17.786 | 1.00 | 25.63 | L | O |
| ATOM | 1052 | CB | PRO | L | 129 | 5.891 | 30.572 | 17.943 | 1.00 | 22.20 | L | C |
| ATOM | 1053 | CG | PRO | L | 129 | 6.213 | 29.888 | 19.247 | 1.00 | 21.77 | L | C |
| ATOM | 1054 | CD | PRO | L | 129 | 5.938 | 30.984 | 20.243 | 1.00 | 20.67 | L | C |
| ATOM | 1055 | N | THR | L | 130 | 6.260 | 33.528 | 16.262 | 1.00 | 23.88 | L | N |
| ATOM | 1056 | CA | THR | L | 130 | 5.556 | 34.525 | 15.465 | 1.00 | 25.00 | L | C |
| ATOM | 1057 | C | THR | L | 130 | 5.164 | 33.923 | 14.122 | 1.00 | 26.32 | L | C |
| ATOM | 1058 | O | THR | L | 130 | 4.762 | 34.639 | 13.206 | 1.00 | 27.47 | L | O |
| ATOM | 1059 | CB | THR | L | 130 | 6.411 | 35.774 | 15.205 | 1.00 | 25.51 | L | C |
| ATOM | 1060 | OG1 | THR | L | 130 | 7.591 | 35.404 | 14.486 | 1.00 | 27.07 | L | O |
| ATOM | 1061 | CG2 | THR | L | 130 | 6.789 | 36.443 | 16.513 | 1.00 | 27.60 | L | C |
| ATOM | 1062 | N | VAL | L | 131 | 5.299 | 32.601 | 14.014 | 1.00 | 24.93 | L | N |
| ATOM | 1063 | CA | VAL | L | 131 | 4.942 | 31.870 | 12.807 | 1.00 | 23.51 | L | C |
| ATOM | 1064 | C | VAL | L | 131 | 4.271 | 30.565 | 13.218 | 1.00 | 24.02 | L | C |
| ATOM | 1065 | O | VAL | L | 131 | 4.369 | 30.139 | 14.372 | 1.00 | 22.94 | L | O |
| ATOM | 1066 | CB | VAL | L | 131 | 6.178 | 31.541 | 11.930 | 1.00 | 25.15 | L | C |

|      |      |     |     |   |     | -continued |        |        |      |       |   |   |
|------|------|-----|-----|---|-----|--------|--------|--------|------|-------|---|---|
| ATOM | 1067 | CG1 | VAL | L | 131 | 6.844  | 32.831 | 11.469 | 1.00 | 24.40 | L | C |
| ATOM | 1068 | CG2 | VAL | L | 131 | 7.163  | 30.673 | 12.705 | 1.00 | 23.42 | L | C |
| ATOM | 1069 | N   | GLU | L | 132 | 3.589  | 29.937 | 12.268 | 1.00 | 22.59 | L | N |
| ATOM | 1070 | CA  | GLU | L | 132 | 2.888  | 28.690 | 12.518 | 1.00 | 22.16 | L | C |
| ATOM | 1071 | C   | GLU | L | 132 | 3.840  | 27.537 | 12.828 | 1.00 | 20.71 | L | C |
| ATOM | 1072 | O   | GLU | L | 132 | 3.567  | 26.720 | 13.711 | 1.00 | 20.40 | L | O |
| ATOM | 1073 | CB  | GLU | L | 132 | 2.004  | 28.340 | 11.308 | 1.00 | 22.29 | L | C |
| ATOM | 1074 | CG  | GLU | L | 132 | 1.352  | 26.972 | 11.390 | 1.00 | 27.79 | L | C |
| ATOM | 1075 | CD  | GLU | L | 132 | 0.327  | 26.730 | 10.286 | 1.00 | 29.81 | L | C |
| ATOM | 1076 | OE1 | GLU | L | 132 | 0.498  | 27.265 | 9.196  | 1.00 | 30.53 | L | O |
| ATOM | 1077 | OE2 | GLU | L | 132 | −0.636 | 25.985 | 10.526 | 1.00 | 30.39 | L | O |
| ATOM | 1078 | N   | TYR | L | 133 | 4.955  | 27.473 | 12.109 | 1.00 | 19.60 | L | N |
| ATOM | 1079 | CA  | TYR | L | 133 | 5.930  | 26.404 | 12.317 | 1.00 | 17.97 | L | C |
| ATOM | 1080 | C   | TYR | L | 133 | 7.320  | 26.925 | 12.654 | 1.00 | 16.71 | L | C |
| ATOM | 1081 | O   | TYR | L | 133 | 8.236  | 26.860 | 11.834 | 1.00 | 16.11 | L | O |
| ATOM | 1082 | CB  | TYR | L | 133 | 5.998  | 25.511 | 11.077 | 1.00 | 17.19 | L | C |
| ATOM | 1083 | CG  | TYR | L | 133 | 4.737  | 24.717 | 10.874 | 1.00 | 19.02 | L | C |
| ATOM | 1084 | CD1 | TYR | L | 133 | 4.412  | 23.673 | 11.735 | 1.00 | 16.92 | L | C |
| ATOM | 1085 | CD2 | TYR | L | 133 | 3.833  | 25.049 | 9.862  | 1.00 | 19.13 | L | C |
| ATOM | 1086 | CE1 | TYR | L | 133 | 3.220  | 22.978 | 11.602 | 1.00 | 18.85 | L | C |
| ATOM | 1087 | CE2 | TYR | L | 133 | 2.632  | 24.358 | 9.719  | 1.00 | 18.71 | L | C |
| ATOM | 1088 | CZ  | TYR | L | 133 | 2.335  | 23.327 | 10.594 | 1.00 | 19.77 | L | C |
| ATOM | 1089 | OH  | TYR | L | 133 | 1.159  | 22.640 | 10.467 | 1.00 | 20.62 | L | O |
| ATOM | 1090 | N   | PRO | L | 134 | 7.499  | 27.440 | 13.878 | 1.00 | 15.85 | L | N |
| ATOM | 1091 | CA  | PRO | L | 134 | 8.804  | 27.963 | 14.291 | 1.00 | 15.14 | L | C |
| ATOM | 1092 | C   | PRO | L | 134 | 9.807  | 26.814 | 14.412 | 1.00 | 15.88 | L | C |
| ATOM | 1093 | O   | PRO | L | 134 | 9.419  | 25.677 | 14.677 | 1.00 | 17.59 | L | O |
| ATOM | 1094 | CB  | PRO | L | 134 | 8.497  | 28.623 | 15.630 | 1.00 | 13.01 | L | C |
| ATOM | 1095 | CG  | PRO | L | 134 | 7.444  | 27.730 | 16.198 | 1.00 | 13.89 | L | C |
| ATOM | 1096 | CD  | PRO | L | 134 | 6.543  | 27.455 | 15.002 | 1.00 | 15.08 | L | C |
| ATOM | 1097 | N   | CYS | L | 135 | 11.086 | 27.108 | 14.206 | 1.00 | 15.52 | L | N |
| ATOM | 1098 | CA  | CYS | L | 135 | 12.125 | 26.084 | 14.291 | 1.00 | 14.64 | L | C |
| ATOM | 1099 | C   | CYS | L | 135 | 12.228 | 25.562 | 15.714 | 1.00 | 14.59 | L | C |
| ATOM | 1100 | O   | CYS | L | 135 | 11.874 | 26.263 | 16.663 | 1.00 | 12.74 | L | O |
| ATOM | 1101 | CB  | CYS | L | 135 | 13.486 | 26.660 | 13.875 | 1.00 | 13.94 | L | C |
| ATOM | 1102 | SG  | CYS | L | 135 | 14.133 | 27.949 | 14.997 | 1.00 | 16.77 | L | S |
| ATOM | 1103 | N   | GLY | L | 136 | 12.709 | 24.328 | 15.852 | 1.00 | 14.02 | L | N |
| ATOM | 1104 | CA  | GLY | L | 136 | 12.902 | 23.737 | 17.167 | 1.00 | 14.41 | L | C |
| ATOM | 1105 | C   | GLY | L | 136 | 11.682 | 23.301 | 17.957 | 1.00 | 15.69 | L | C |
| ATOM | 1106 | O   | GLY | L | 136 | 11.810 | 22.917 | 19.119 | 1.00 | 16.17 | L | O |
| ATOM | 1107 | N   | LYS | L | 137 | 10.501 | 23.358 | 17.352 | 1.00 | 15.50 | L | N |
| ATOM | 1108 | CA  | LYS | L | 137 | 9.284  | 22.935 | 18.036 | 1.00 | 17.12 | L | C |
| ATOM | 1109 | C   | LYS | L | 137 | 8.701  | 21.730 | 17.309 | 1.00 | 17.03 | L | C |
| ATOM | 1110 | O   | LYS | L | 137 | 8.709  | 21.669 | 16.077 | 1.00 | 17.59 | L | O |
| ATOM | 1111 | CB  | LYS | L | 137 | 8.248  | 24.063 | 18.058 | 1.00 | 16.09 | L | C |
| ATOM | 1112 | CG  | LYS | L | 137 | 8.085  | 24.783 | 19.382 | 1.00 | 20.53 | L | C |
| ATOM | 1113 | CD  | LYS | L | 137 | 9.354  | 25.441 | 19.855 | 1.00 | 23.98 | L | C |
| ATOM | 1114 | CE  | LYS | L | 137 | 9.056  | 26.486 | 20.935 | 1.00 | 26.98 | L | C |
| ATOM | 1115 | NZ  | LYS | L | 137 | 8.408  | 25.912 | 22.147 | 1.00 | 27.12 | L | N |
| ATOM | 1116 | N   | ILE | L | 138 | 8.191  | 20.780 | 18.082 | 1.00 | 16.47 | L | N |
| ATOM | 1117 | CA  | ILE | L | 138 | 7.598  | 19.568 | 17.536 | 1.00 | 16.51 | L | C |
| ATOM | 1118 | C   | ILE | L | 138 | 6.072  | 19.699 | 17.623 | 1.00 | 17.05 | L | C |
| ATOM | 1119 | O   | ILE | L | 138 | 5.479  | 19.442 | 18.665 | 1.00 | 17.09 | L | O |
| ATOM | 1120 | CB  | ILE | L | 138 | 8.091  | 18.340 | 18.332 | 1.00 | 16.51 | L | C |
| ATOM | 1121 | CG1 | ILE | L | 138 | 9.630  | 18.329 | 18.335 | 1.00 | 14.34 | L | C |
| ATOM | 1122 | CG2 | ILE | L | 138 | 7.534  | 17.048 | 17.713 | 1.00 | 15.08 | L | C |
| ATOM | 1123 | CD1 | ILE | L | 138 | 10.268 | 17.188 | 19.119 | 1.00 | 12.57 | L | C |
| ATOM | 1124 | N   | PRO | L | 139 | 5.421  | 20.096 | 16.514 | 1.00 | 18.81 | L | N |
| ATOM | 1125 | CA  | PRO | L | 139 | 3.963  | 20.284 | 16.436 | 1.00 | 19.59 | L | C |
| ATOM | 1126 | C   | PRO | L | 139 | 3.016  | 19.231 | 17.016 | 1.00 | 19.28 | L | C |
| ATOM | 1127 | O   | PRO | L | 139 | 2.065  | 19.588 | 17.708 | 1.00 | 20.94 | L | O |
| ATOM | 1128 | CB  | PRO | L | 139 | 3.718  | 20.548 | 14.943 | 1.00 | 19.14 | L | C |
| ATOM | 1129 | CG  | PRO | L | 139 | 4.902  | 19.948 | 14.273 | 1.00 | 22.59 | L | C |
| ATOM | 1130 | CD  | PRO | L | 139 | 6.034  | 20.304 | 15.195 | 1.00 | 18.46 | L | C |
| ATOM | 1131 | N   | ILE | L | 140 | 3.249  | 17.948 | 16.764 | 1.00 | 18.16 | L | N |
| ATOM | 1132 | CA  | ILE | L | 140 | 2.334  | 16.952 | 17.317 | 1.00 | 19.99 | L | C |
| ATOM | 1133 | C   | ILE | L | 140 | 2.398  | 16.843 | 18.844 | 1.00 | 21.32 | L | C |
| ATOM | 1134 | O   | ILE | L | 140 | 1.550  | 16.194 | 19.454 | 1.00 | 21.50 | L | O |
| ATOM | 1135 | CB  | ILE | L | 140 | 2.549  | 15.544 | 16.711 | 1.00 | 20.09 | L | C |
| ATOM | 1136 | CG1 | ILE | L | 140 | 3.953  | 15.034 | 17.030 | 1.00 | 18.72 | L | C |
| ATOM | 1137 | CG2 | ILE | L | 140 | 2.294  | 15.586 | 15.197 | 1.00 | 21.80 | L | C |
| ATOM | 1138 | CD1 | ILE | L | 140 | 4.178  | 13.596 | 16.611 | 1.00 | 20.33 | L | C |
| ATOM | 1139 | N   | LEU | L | 141 | 3.397  | 17.475 | 19.458 | 1.00 | 21.36 | L | N |
| ATOM | 1140 | CA  | LEU | L | 141 | 3.531  | 17.458 | 20.912 | 1.00 | 23.29 | L | C |
| ATOM | 1141 | C   | LEU | L | 141 | 3.115  | 18.806 | 21.505 | 1.00 | 25.19 | L | C |
| ATOM | 1142 | O   | LEU | L | 141 | 2.965  | 18.942 | 22.716 | 1.00 | 25.84 | L | O |
| ATOM | 1143 | CB  | LEU | L | 141 | 4.975  | 17.144 | 21.315 | 1.00 | 21.25 | L | C |
| ATOM | 1144 | CG  | LEU | L | 141 | 5.601  | 15.886 | 20.705 | 1.00 | 21.10 | L | C |
| ATOM | 1145 | CD1 | LEU | L | 141 | 6.998  | 15.706 | 21.268 | 1.00 | 19.02 | L | C |

-continued

| | | | | | | | | | | | |
|---|---|---|---|---|---|---|---|---|---|---|---|
| ATOM | 1146 | CD2 | LEU | L | 141 | 4.732 | 14.665 | 20.998 | 1.00 | 19.82 | L | C |
| ATOM | 1147 | N | GLU | L | 142 | 2.936 | 19.804 | 20.648 | 1.00 | 29.07 | L | N |
| ATOM | 1148 | CA | GLU | L | 142 | 2.534 | 21.131 | 21.093 | 1.00 | 32.74 | L | C |
| ATOM | 1149 | C | GLU | L | 142 | 1.011 | 21.223 | 21.174 | 1.00 | 35.09 | L | C |
| ATOM | 1150 | O | GLU | L | 142 | 0.514 | 21.605 | 22.226 | 1.00 | 37.74 | L | O |
| ATOM | 1151 | CB | GLU | L | 142 | 3.067 | 22.194 | 20.130 | 1.00 | 32.55 | L | C |
| ATOM | 1152 | CG | GLU | L | 142 | 4.577 | 22.381 | 20.166 | 1.00 | 35.63 | L | C |
| ATOM | 1153 | CD | GLU | L | 142 | 5.062 | 23.007 | 21.462 | 1.00 | 37.38 | L | C |
| ATOM | 1154 | OE1 | GLU | L | 142 | 4.494 | 24.028 | 21.871 | 1.00 | 39.09 | L | O |
| ATOM | 1155 | OE2 | GLU | L | 142 | 6.008 | 22.486 | 22.053 | 1.00 | 36.36 | L | O |
| ATOM | 1156 | OT | GLU | L | 142 | 0.349 | 20.913 | 20.180 | 1.00 | 36.04 | L | O |
| ATOM | 1157 | N | ILE | H | 16 | 21.992 | 3.783 | 14.153 | 1.00 | 14.10 | H | N |
| ATOM | 1158 | CA | ILE | H | 16 | 21.860 | 4.032 | 15.614 | 1.00 | 13.89 | H | C |
| ATOM | 1159 | C | ILE | H | 16 | 21.875 | 2.706 | 16.373 | 1.00 | 14.85 | H | C |
| ATOM | 1160 | O | ILE | H | 16 | 21.043 | 1.834 | 16.132 | 1.00 | 14.89 | H | O |
| ATOM | 1161 | CB | ILE | H | 16 | 20.534 | 4.767 | 15.944 | 1.00 | 13.63 | H | C |
| ATOM | 1162 | CG1 | ILE | H | 16 | 20.451 | 6.095 | 15.183 | 1.00 | 12.69 | H | C |
| ATOM | 1163 | CG2 | ILE | H | 16 | 20.436 | 4.989 | 17.450 | 1.00 | 11.22 | H | C |
| ATOM | 1164 | CD1 | ILE | H | 16 | 21.567 | 7.092 | 15.493 | 1.00 | 10.60 | H | C |
| ATOM | 1165 | N | VAL | H | 17 | 22.830 | 2.564 | 17.285 | 1.00 | 16.19 | H | N |
| ATOM | 1166 | CA | VAL | H | 17 | 22.967 | 1.358 | 18.092 | 1.00 | 16.46 | H | C |
| ATOM | 1167 | C | VAL | H | 17 | 22.445 | 1.593 | 19.504 | 1.00 | 15.78 | H | C |
| ATOM | 1168 | O | VAL | H | 17 | 22.861 | 2.536 | 20.178 | 1.00 | 14.50 | H | O |
| ATOM | 1169 | CB | VAL | H | 17 | 24.451 | 0.918 | 18.195 | 1.00 | 17.79 | H | C |
| ATOM | 1170 | CG1 | VAL | H | 17 | 24.581 | −0.259 | 19.145 | 1.00 | 19.06 | H | C |
| ATOM | 1171 | CG2 | VAL | H | 17 | 24.977 | 0.529 | 16.826 | 1.00 | 19.20 | H | C |
| ATOM | 1172 | N | GLY | H | 18 | 21.532 | 0.735 | 19.950 | 1.00 | 15.38 | H | N |
| ATOM | 1173 | CA | GLY | H | 18 | 20.990 | 0.876 | 21.292 | 1.00 | 13.01 | H | C |
| ATOM | 1174 | C | GLY | H | 18 | 19.982 | 1.998 | 21.472 | 1.00 | 12.80 | H | C |
| ATOM | 1175 | O | GLY | H | 18 | 19.768 | 2.468 | 22.583 | 1.00 | 11.44 | H | O |
| ATOM | 1176 | N | GLY | H | 19 | 19.365 | 2.436 | 20.384 | 1.00 | 11.70 | H | N |
| ATOM | 1177 | CA | GLY | H | 19 | 18.368 | 3.487 | 20.483 | 1.00 | 13.29 | H | C |
| ATOM | 1178 | C | GLY | H | 19 | 16.964 | 2.926 | 20.333 | 1.00 | 13.92 | H | C |
| ATOM | 1179 | O | GLY | H | 19 | 16.731 | 1.736 | 20.540 | 1.00 | 13.45 | H | O |
| ATOM | 1180 | N | LYS | H | 20 | 16.016 | 3.783 | 19.977 | 1.00 | 15.81 | H | N |
| ATOM | 1181 | CA | LYS | H | 20 | 14.644 | 3.341 | 19.788 | 1.00 | 17.79 | H | C |
| ATOM | 1182 | C | LYS | H | 20 | 14.064 | 4.033 | 18.567 | 1.00 | 16.64 | H | C |
| ATOM | 1183 | O | LYS | H | 20 | 14.683 | 4.935 | 18.009 | 1.00 | 13.94 | H | O |
| ATOM | 1184 | CB | LYS | H | 20 | 13.794 | 3.668 | 21.024 | 1.00 | 19.44 | H | C |
| ATOM | 1185 | CG | LYS | H | 20 | 14.312 | 3.043 | 22.317 | 1.00 | 26.17 | H | C |
| ATOM | 1186 | CD | LYS | H | 20 | 13.307 | 3.186 | 23.450 | 1.00 | 29.52 | H | C |
| ATOM | 1187 | CE | LYS | H | 20 | 13.918 | 2.824 | 24.806 | 1.00 | 32.88 | H | C |
| ATOM | 1188 | NZ | LYS | H | 20 | 14.426 | 1.423 | 24.867 | 1.00 | 33.23 | H | N |
| ATOM | 1189 | N | VAL | H | 21 | 12.881 | 3.601 | 18.148 | 1.00 | 13.39 | H | N |
| ATOM | 1190 | CA | VAL | H | 21 | 12.228 | 4.213 | 17.007 | 1.00 | 14.10 | H | C |
| ATOM | 1191 | C | VAL | H | 21 | 11.729 | 5.610 | 17.393 | 1.00 | 15.28 | H | C |
| ATOM | 1192 | O | VAL | H | 21 | 11.136 | 5.796 | 18.459 | 1.00 | 15.43 | H | O |
| ATOM | 1193 | CB | VAL | H | 21 | 11.022 | 3.356 | 16.530 | 1.00 | 14.85 | H | C |
| ATOM | 1194 | CG1 | VAL | H | 21 | 10.233 | 4.104 | 15.446 | 1.00 | 15.73 | H | C |
| ATOM | 1195 | CG2 | VAL | H | 21 | 11.517 | 2.018 | 15.982 | 1.00 | 13.11 | H | C |
| ATOM | 1196 | N | CYS | H | 22 | 11.992 | 6.595 | 16.542 | 1.00 | 14.61 | H | N |
| ATOM | 1197 | CA | CYS | H | 22 | 11.518 | 7.944 | 16.805 | 1.00 | 15.34 | H | C |
| ATOM | 1198 | C | CYS | H | 22 | 10.063 | 7.948 | 16.362 | 1.00 | 15.49 | H | C |
| ATOM | 1199 | O | CYS | H | 22 | 9.779 | 7.785 | 15.176 | 1.00 | 16.18 | H | O |
| ATOM | 1200 | CB | CYS | H | 22 | 12.279 | 8.984 | 15.976 | 1.00 | 13.94 | H | C |
| ATOM | 1201 | SG | CYS | H | 22 | 11.768 | 10.666 | 16.438 | 1.00 | 14.65 | H | S |
| ATOM | 1202 | N | PRO | H | 23 | 9.120 | 8.127 | 17.301 | 1.00 | 16.39 | H | N |
| ATOM | 1203 | CA | PRO | H | 23 | 7.710 | 8.134 | 16.898 | 1.00 | 16.45 | H | C |
| ATOM | 1204 | C | PRO | H | 23 | 7.491 | 9.096 | 15.733 | 1.00 | 16.91 | H | C |
| ATOM | 1205 | O | PRO | H | 23 | 7.995 | 10.220 | 15.746 | 1.00 | 17.56 | H | O |
| ATOM | 1206 | CB | PRO | H | 23 | 6.993 | 8.577 | 18.171 | 1.00 | 16.38 | H | C |
| ATOM | 1207 | CG | PRO | H | 23 | 7.863 | 7.993 | 19.250 | 1.00 | 16.66 | H | C |
| ATOM | 1208 | CD | PRO | H | 23 | 9.251 | 8.348 | 18.753 | 1.00 | 15.94 | H | C |
| ATOM | 1209 | N | LYS | H | 24 | 6.746 | 8.647 | 14.730 | 1.00 | 16.37 | H | N |
| ATOM | 1210 | CA | LYS | H | 24 | 6.464 | 9.456 | 13.549 | 1.00 | 16.46 | H | C |
| ATOM | 1211 | C | LYS | H | 24 | 6.117 | 10.895 | 13.915 | 1.00 | 15.64 | H | C |
| ATOM | 1212 | O | LYS | H | 24 | 5.211 | 11.145 | 14.707 | 1.00 | 17.81 | H | O |
| ATOM | 1213 | CB | LYS | H | 24 | 5.314 | 8.836 | 12.757 | 1.00 | 17.93 | H | C |
| ATOM | 1214 | CG | LYS | H | 24 | 5.122 | 9.431 | 11.369 | 1.00 | 19.08 | H | C |
| ATOM | 1215 | CD | LYS | H | 24 | 3.979 | 8.750 | 10.648 | 1.00 | 19.14 | H | C |
| ATOM | 1216 | CE | LYS | H | 24 | 4.144 | 8.839 | 9.143 | 1.00 | 23.91 | H | C |
| ATOM | 1217 | NZ | LYS | H | 24 | 4.196 | 10.230 | 8.631 | 1.00 | 20.21 | H | N |
| ATOM | 1218 | N | GLY | H | 25 | 6.845 | 11.842 | 13.340 | 1.00 | 14.95 | H | N |
| ATOM | 1219 | CA | GLY | H | 25 | 6.586 | 13.239 | 13.638 | 1.00 | 14.04 | H | C |
| ATOM | 1220 | C | GLY | H | 25 | 7.403 | 13.847 | 14.769 | 1.00 | 13.80 | H | C |
| ATOM | 1221 | O | GLY | H | 25 | 7.427 | 15.068 | 14.909 | 1.00 | 13.20 | H | O |
| ATOM | 1222 | N | GLU | H | 26 | 8.076 | 13.026 | 15.573 | 1.00 | 13.01 | H | N |
| ATOM | 1223 | CA | GLU | H | 26 | 8.874 | 13.560 | 16.683 | 1.00 | 15.70 | H | C |
| ATOM | 1224 | C | GLU | H | 26 | 10.331 | 13.897 | 16.348 | 1.00 | 15.14 | H | C |

-continued

| | | | | | | | | | | | | |
|---|---|---|---|---|---|---|---|---|---|---|---|---|
| ATOM | 1225 | O | GLU | H | 26 | 11.078 | 14.380 | 17.196 | 1.00 | 15.40 | H | O |
| ATOM | 1226 | CB | GLU | H | 26 | 8.789 | 12.625 | 17.898 | 1.00 | 15.76 | H | C |
| ATOM | 1227 | CG | GLU | H | 26 | 7.483 | 12.816 | 18.668 | 1.00 | 19.10 | H | C |
| ATOM | 1228 | CD | GLU | H | 26 | 7.346 | 11.908 | 19.874 | 1.00 | 21.34 | H | C |
| ATOM | 1229 | OE1 | GLU | H | 26 | 8.322 | 11.730 | 20.591 | 1.00 | 22.66 | H | O |
| ATOM | 1230 | OE2 | GLU | H | 26 | 6.249 | 11.395 | 20.097 | 1.00 | 22.32 | H | O |
| ATOM | 1231 | N | CYS | H | 27 | 10.716 | 13.641 | 15.103 | 1.00 | 15.31 | H | N |
| ATOM | 1232 | CA | CYS | H | 27 | 12.048 | 13.958 | 14.582 | 1.00 | 14.35 | H | C |
| ATOM | 1233 | C | CYS | H | 27 | 11.749 | 14.611 | 13.217 | 1.00 | 14.44 | H | C |
| ATOM | 1234 | O | CYS | H | 27 | 12.256 | 14.170 | 12.188 | 1.00 | 15.00 | H | O |
| ATOM | 1235 | CB | CYS | H | 27 | 12.873 | 12.663 | 14.404 | 1.00 | 16.45 | H | C |
| ATOM | 1236 | SG | CYS | H | 27 | 13.342 | 11.868 | 15.982 | 1.00 | 16.62 | H | S |
| ATOM | 1237 | N | PRO | H | 28 | 10.935 | 15.693 | 13.204 | 1.00 | 12.78 | H | N |
| ATOM | 1238 | CA | PRO | H | 28 | 10.550 | 16.393 | 11.972 | 1.00 | 12.72 | H | C |
| ATOM | 1239 | C | PRO | H | 28 | 11.596 | 17.135 | 11.142 | 1.00 | 13.51 | H | C |
| ATOM | 1240 | O | PRO | H | 28 | 11.334 | 17.470 | 9.989 | 1.00 | 14.79 | H | O |
| ATOM | 1241 | CB | PRO | H | 28 | 9.414 | 17.300 | 12.443 | 1.00 | 10.56 | H | C |
| ATOM | 1242 | CG | PRO | H | 28 | 9.872 | 17.708 | 13.785 | 1.00 | 12.39 | H | C |
| ATOM | 1243 | CD | PRO | H | 28 | 10.409 | 16.411 | 14.382 | 1.00 | 13.71 | H | C |
| ATOM | 1244 | N | TRP | H | 29 | 12.763 | 17.403 | 11.715 | 1.00 | 13.66 | H | N |
| ATOM | 1245 | CA | TRP | H | 29 | 13.837 | 18.072 | 10.981 | 1.00 | 12.45 | H | C |
| ATOM | 1246 | C | TRP | H | 29 | 14.801 | 17.058 | 10.344 | 1.00 | 13.04 | H | C |
| ATOM | 1247 | O | TRP | H | 29 | 15.741 | 17.447 | 9.651 | 1.00 | 12.14 | H | O |
| ATOM | 1248 | CB | TRP | H | 29 | 14.622 | 19.019 | 11.905 | 1.00 | 10.27 | H | C |
| ATOM | 1249 | CG | TRP | H | 29 | 14.719 | 18.544 | 13.333 | 1.00 | 10.51 | H | C |
| ATOM | 1250 | CD1 | TRP | H | 29 | 15.510 | 17.540 | 13.818 | 1.00 | 9.50 | H | C |
| ATOM | 1251 | CD2 | TRP | H | 29 | 13.935 | 19.009 | 14.441 | 1.00 | 9.92 | H | C |
| ATOM | 1252 | NE1 | TRP | H | 29 | 15.261 | 17.347 | 15.159 | 1.00 | 9.49 | H | N |
| ATOM | 1253 | CE2 | TRP | H | 29 | 14.299 | 18.235 | 15.566 | 1.00 | 9.72 | H | C |
| ATOM | 1254 | CE3 | TRP | H | 29 | 12.961 | 20.004 | 14.590 | 1.00 | 8.87 | H | C |
| ATOM | 1255 | CZ2 | TRP | H | 29 | 13.717 | 18.424 | 16.824 | 1.00 | 9.39 | H | C |
| ATOM | 1256 | CZ3 | TRP | H | 29 | 12.381 | 20.193 | 15.842 | 1.00 | 9.88 | H | C |
| ATOM | 1257 | CH2 | TRP | H | 29 | 12.763 | 19.404 | 16.944 | 1.00 | 9.90 | H | C |
| ATOM | 1258 | N | GLN | H | 30 | 14.566 | 15.765 | 10.573 | 1.00 | 12.37 | H | N |
| ATOM | 1259 | CA | GLN | H | 30 | 15.427 | 14.723 | 10.011 | 1.00 | 11.48 | H | C |
| ATOM | 1260 | C | GLN | H | 30 | 15.253 | 14.653 | 8.496 | 1.00 | 11.76 | H | C |
| ATOM | 1261 | O | GLN | H | 30 | 14.128 | 14.696 | 7.987 | 1.00 | 10.36 | H | O |
| ATOM | 1262 | CB | GLN | H | 30 | 15.090 | 13.363 | 10.622 | 1.00 | 12.28 | H | C |
| ATOM | 1263 | CG | GLN | H | 30 | 15.832 | 12.180 | 9.982 | 1.00 | 13.59 | H | C |
| ATOM | 1264 | CD | GLN | H | 30 | 17.291 | 12.090 | 10.401 | 1.00 | 11.47 | H | C |
| ATOM | 1265 | OE1 | GLN | H | 30 | 18.171 | 11.810 | 9.587 | 1.00 | 15.48 | H | O |
| ATOM | 1266 | NE2 | GLN | H | 30 | 17.548 | 12.306 | 11.675 | 1.00 | 9.74 | H | N |
| ATOM | 1267 | N | VAL | H | 31 | 16.372 | 14.542 | 7.785 | 1.00 | 10.70 | H | N |
| ATOM | 1268 | CA | VAL | H | 31 | 16.369 | 14.468 | 6.327 | 1.00 | 7.92 | H | C |
| ATOM | 1269 | C | VAL | H | 31 | 16.999 | 13.155 | 5.865 | 1.00 | 9.83 | H | C |
| ATOM | 1270 | O | VAL | H | 31 | 17.922 | 12.641 | 6.501 | 1.00 | 12.57 | H | O |
| ATOM | 1271 | CB | VAL | H | 31 | 17.194 | 15.635 | 5.698 | 1.00 | 11.09 | H | C |
| ATOM | 1272 | CG1 | VAL | H | 31 | 17.177 | 15.534 | 4.167 | 1.00 | 9.42 | H | C |
| ATOM | 1273 | CG2 | VAL | H | 31 | 16.641 | 16.996 | 6.142 | 1.00 | 7.29 | H | C |
| ATOM | 1274 | N | LEU | H | 32 | 16.481 | 12.600 | 4.773 | 1.00 | 10.90 | H | N |
| ATOM | 1275 | CA | LEU | H | 32 | 17.034 | 11.384 | 4.193 | 1.00 | 10.82 | H | C |
| ATOM | 1276 | C | LEU | H | 32 | 17.618 | 11.785 | 2.847 | 1.00 | 12.58 | H | C |
| ATOM | 1277 | O | LEU | H | 32 | 16.902 | 12.294 | 1.984 | 1.00 | 13.53 | H | O |
| ATOM | 1278 | CB | LEU | H | 32 | 15.951 | 10.330 | 3.967 | 1.00 | 10.99 | H | C |
| ATOM | 1279 | CG | LEU | H | 32 | 16.394 | 9.157 | 3.082 | 1.00 | 12.15 | H | C |
| ATOM | 1280 | CD1 | LEU | H | 32 | 17.496 | 8.366 | 3.774 | 1.00 | 10.81 | H | C |
| ATOM | 1281 | CD2 | LEU | H | 32 | 15.200 | 8.251 | 2.796 | 1.00 | 12.95 | H | C |
| ATOM | 1282 | N | LEU | H | 33 | 18.916 | 11.575 | 2.669 | 1.00 | 11.95 | H | N |
| ATOM | 1283 | CA | LEU | H | 33 | 19.566 | 11.921 | 1.411 | 1.00 | 13.59 | H | C |
| ATOM | 1284 | C | LEU | H | 33 | 19.777 | 10.668 | 0.585 | 1.00 | 14.19 | H | C |
| ATOM | 1285 | O | LEU | H | 33 | 20.252 | 9.649 | 1.090 | 1.00 | 13.59 | H | O |
| ATOM | 1286 | CB | LEU | H | 33 | 20.915 | 12.611 | 1.663 | 1.00 | 13.43 | H | C |
| ATOM | 1287 | CG | LEU | H | 33 | 20.843 | 13.953 | 2.401 | 1.00 | 13.16 | H | C |
| ATOM | 1288 | CD1 | LEU | H | 33 | 22.246 | 14.429 | 2.718 | 1.00 | 11.72 | H | C |
| ATOM | 1289 | CD2 | LEU | H | 33 | 20.103 | 14.981 | 1.546 | 1.00 | 14.08 | H | C |
| ATOM | 1290 | N | LEU | H | 34 | 19.423 | 10.757 | −0.691 | 1.00 | 16.19 | H | N |
| ATOM | 1291 | CA | LEU | H | 34 | 19.553 | 9.636 | −1.611 | 1.00 | 17.59 | H | C |
| ATOM | 1292 | C | LEU | H | 34 | 20.384 | 10.026 | −2.826 | 1.00 | 18.00 | H | C |
| ATOM | 1293 | O | LEU | H | 34 | 20.372 | 11.177 | −3.261 | 1.00 | 18.90 | H | O |
| ATOM | 1294 | CB | LEU | H | 34 | 18.165 | 9.184 | −2.086 | 1.00 | 19.63 | H | C |
| ATOM | 1295 | CG | LEU | H | 34 | 17.092 | 8.859 | −1.033 | 1.00 | 21.00 | H | C |
| ATOM | 1296 | CD1 | LEU | H | 34 | 15.741 | 8.708 | −1.712 | 1.00 | 22.40 | H | C |
| ATOM | 1297 | CD2 | LEU | H | 34 | 17.457 | 7.595 | −0.288 | 1.00 | 21.37 | H | C |
| ATOM | 1298 | N | VAL | H | 35 | 21.126 | 9.066 | −3.357 | 1.00 | 19.10 | H | N |
| ATOM | 1299 | CA | VAL | H | 35 | 21.915 | 9.294 | −4.553 | 1.00 | 20.91 | H | C |
| ATOM | 1300 | C | VAL | H | 35 | 21.484 | 8.174 | −5.494 | 1.00 | 21.66 | H | C |
| ATOM | 1301 | O | VAL | H | 35 | 21.512 | 7.004 | −5.124 | 1.00 | 22.02 | H | O |
| ATOM | 1302 | CB | VAL | H | 35 | 23.438 | 9.229 | −4.275 | 1.00 | 21.22 | H | C |
| ATOM | 1303 | CG1 | VAL | H | 35 | 23.846 | 7.837 | −3.828 | 1.00 | 23.40 | H | C |

-continued

| | | | | | | | | | | | |
|---|---|---|---|---|---|---|---|---|---|---|---|
| ATOM | 1304 | CG2 | VAL | H | 35 | 24.201 | 9.641 | −5.516 | 1.00 | 23.57 | H | C |
| ATOM | 1305 | N | ASN | H | 37 | 21.049 | 8.539 | −6.694 | 1.00 | 22.76 | H | N |
| ATOM | 1306 | CA | ASN | H | 37 | 20.575 | 7.557 | −7.668 | 1.00 | 24.27 | H | C |
| ATOM | 1307 | C | ASN | H | 37 | 19.473 | 6.695 | −7.049 | 1.00 | 24.89 | H | C |
| ATOM | 1308 | O | ASN | H | 37 | 19.385 | 5.502 | −7.333 | 1.00 | 25.83 | H | O |
| ATOM | 1309 | CB | ASN | H | 37 | 21.721 | 6.650 | −8.130 | 1.00 | 25.18 | H | C |
| ATOM | 1310 | CG | ASN | H | 37 | 22.904 | 7.428 | −8.674 | 1.00 | 27.92 | H | C |
| ATOM | 1311 | OD1 | ASN | H | 37 | 22.757 | 8.269 | −9.563 | 1.00 | 26.24 | H | O |
| ATOM | 1312 | ND2 | ASN | H | 37 | 24.090 | 7.144 | −8.142 | 1.00 | 29.79 | H | N |
| ATOM | 1313 | N | GLY | H | 38 | 18.645 | 7.300 | −6.198 | 1.00 | 25.00 | H | N |
| ATOM | 1314 | CA | GLY | H | 38 | 17.568 | 6.575 | −5.545 | 1.00 | 23.40 | H | C |
| ATOM | 1315 | C | GLY | H | 38 | 17.977 | 5.678 | −4.386 | 1.00 | 23.72 | H | C |
| ATOM | 1316 | O | GLY | H | 38 | 17.126 | 5.033 | −3.777 | 1.00 | 25.41 | H | O |
| ATOM | 1317 | N | ALA | H | 39 | 19.268 | 5.630 | −4.070 | 1.00 | 22.78 | H | N |
| ATOM | 1318 | CA | ALA | H | 39 | 19.757 | 4.791 | −2.981 | 1.00 | 22.39 | H | C |
| ATOM | 1319 | C | ALA | H | 39 | 20.050 | 5.607 | −1.724 | 1.00 | 22.79 | H | C |
| ATOM | 1320 | O | ALA | H | 39 | 20.450 | 6.767 | −1.807 | 1.00 | 23.53 | H | O |
| ATOM | 1321 | CB | ALA | H | 39 | 21.014 | 4.056 | −3.419 | 1.00 | 20.94 | H | C |
| ATOM | 1322 | N | GLN | H | 40 | 19.848 | 4.993 | −0.562 | 1.00 | 22.25 | H | N |
| ATOM | 1323 | CA | GLN | H | 40 | 20.098 | 5.658 | 0.714 | 1.00 | 22.90 | H | C |
| ATOM | 1324 | C | GLN | H | 40 | 21.574 | 6.042 | 0.824 | 1.00 | 22.41 | H | C |
| ATOM | 1325 | O | GLN | H | 40 | 22.456 | 5.192 | 0.716 | 1.00 | 22.51 | H | O |
| ATOM | 1326 | CB | GLN | H | 40 | 19.720 | 4.730 | 1.871 | 1.00 | 22.59 | H | C |
| ATOM | 1327 | CG | GLN | H | 40 | 19.763 | 5.385 | 3.247 | 1.00 | 25.18 | H | C |
| ATOM | 1328 | CD | GLN | H | 40 | 19.409 | 4.415 | 4.363 | 1.00 | 26.21 | H | C |
| ATOM | 1329 | OE1 | GLN | H | 40 | 18.430 | 3.676 | 4.270 | 1.00 | 26.38 | H | O |
| ATOM | 1330 | NE2 | GLN | H | 40 | 20.198 | 4.421 | 5.430 | 1.00 | 26.47 | H | N |
| ATOM | 1331 | N | LEU | H | 41 | 21.837 | 7.324 | 1.052 | 1.00 | 21.11 | H | N |
| ATOM | 1332 | CA | LEU | H | 41 | 23.206 | 7.816 | 1.164 | 1.00 | 19.35 | H | C |
| ATOM | 1333 | C | LEU | H | 41 | 23.585 | 8.285 | 2.570 | 1.00 | 18.35 | H | C |
| ATOM | 1334 | O | LEU | H | 41 | 24.552 | 7.800 | 3.152 | 1.00 | 18.12 | H | O |
| ATOM | 1335 | CB | LEU | H | 41 | 23.419 | 8.978 | 0.184 | 1.00 | 19.30 | H | C |
| ATOM | 1336 | CG | LEU | H | 41 | 24.745 | 9.744 | 0.271 | 1.00 | 17.33 | H | C |
| ATOM | 1337 | CD1 | LEU | H | 41 | 25.890 | 8.880 | −0.246 | 1.00 | 14.99 | H | C |
| ATOM | 1338 | CD2 | LEU | H | 41 | 24.641 | 11.016 | −0.540 | 1.00 | 16.13 | H | C |
| ATOM | 1339 | N | CYS | H | 42 | 22.816 | 9.226 | 3.110 | 1.00 | 16.56 | H | N |
| ATOM | 1340 | CA | CYS | H | 42 | 23.108 | 9.796 | 4.421 | 1.00 | 15.14 | H | C |
| ATOM | 1341 | C | CYS | H | 42 | 21.907 | 10.492 | 5.033 | 1.00 | 13.30 | H | C |
| ATOM | 1342 | O | CYS | H | 42 | 20.851 | 10.595 | 4.418 | 1.00 | 12.64 | H | O |
| ATOM | 1343 | CB | CYS | H | 42 | 24.226 | 10.844 | 4.291 | 1.00 | 15.11 | H | C |
| ATOM | 1344 | SG | CYS | H | 42 | 25.929 | 10.216 | 4.342 | 1.00 | 18.96 | H | S |
| ATOM | 1345 | N | GLY | H | 43 | 22.101 | 10.988 | 6.251 | 1.00 | 11.79 | H | N |
| ATOM | 1346 | CA | GLY | H | 43 | 21.064 | 11.728 | 6.932 | 1.00 | 9.99 | H | C |
| ATOM | 1347 | C | GLY | H | 43 | 21.362 | 13.209 | 6.753 | 1.00 | 10.90 | H | C |
| ATOM | 1348 | O | GLY | H | 43 | 22.362 | 13.580 | 6.138 | 1.00 | 12.00 | H | O |
| ATOM | 1349 | N | GLY | H | 44 | 20.491 | 14.058 | 7.281 | 1.00 | 11.43 | H | N |
| ATOM | 1350 | CA | GLY | H | 44 | 20.690 | 15.493 | 7.183 | 1.00 | 9.27 | H | C |
| ATOM | 1351 | C | GLY | H | 44 | 19.747 | 16.195 | 8.143 | 1.00 | 9.66 | H | C |
| ATOM | 1352 | O | GLY | H | 44 | 18.884 | 15.553 | 8.741 | 1.00 | 8.35 | H | O |
| ATOM | 1353 | N | THR | H | 45 | 19.908 | 17.507 | 8.293 | 1.00 | 10.40 | H | N |
| ATOM | 1354 | CA | THR | H | 45 | 19.062 | 18.286 | 9.186 | 1.00 | 10.32 | H | C |
| ATOM | 1355 | C | THR | H | 45 | 18.500 | 19.512 | 8.470 | 1.00 | 12.51 | H | C |
| ATOM | 1356 | O | THR | H | 45 | 19.247 | 20.315 | 7.914 | 1.00 | 12.61 | H | O |
| ATOM | 1357 | CB | THR | H | 45 | 19.856 | 18.781 | 10.420 | 1.00 | 11.05 | H | C |
| ATOM | 1358 | OG1 | THR | H | 45 | 20.468 | 17.667 | 11.084 | 1.00 | 11.48 | H | O |
| ATOM | 1359 | CG2 | THR | H | 45 | 18.934 | 19.491 | 11.399 | 1.00 | 9.59 | H | C |
| ATOM | 1360 | N | LEU | H | 46 | 17.185 | 19.662 | 8.475 | 1.00 | 12.48 | H | N |
| ATOM | 1361 | CA | LEU | H | 46 | 16.572 | 20.824 | 7.840 | 1.00 | 12.20 | H | C |
| ATOM | 1362 | C | LEU | H | 46 | 16.689 | 21.980 | 8.829 | 1.00 | 12.78 | H | C |
| ATOM | 1363 | O | LEU | H | 46 | 16.377 | 21.818 | 10.006 | 1.00 | 12.83 | H | O |
| ATOM | 1364 | CB | LEU | H | 46 | 15.090 | 20.553 | 7.558 | 1.00 | 14.68 | H | C |
| ATOM | 1365 | CG | LEU | H | 46 | 14.273 | 21.611 | 6.805 | 1.00 | 13.62 | H | C |
| ATOM | 1366 | CD1 | LEU | H | 46 | 14.639 | 21.570 | 5.321 | 1.00 | 12.45 | H | C |
| ATOM | 1367 | CD2 | LEU | H | 46 | 12.783 | 21.326 | 6.973 | 1.00 | 12.25 | H | C |
| ATOM | 1368 | N | ILE | H | 47 | 17.163 | 23.135 | 8.377 | 1.00 | 12.00 | H | N |
| ATOM | 1369 | CA | ILE | H | 47 | 17.252 | 24.288 | 9.275 | 1.00 | 13.26 | H | C |
| ATOM | 1370 | C | ILE | H | 47 | 16.475 | 25.470 | 8.686 | 1.00 | 15.67 | H | C |
| ATOM | 1371 | O | ILE | H | 47 | 16.356 | 26.523 | 9.312 | 1.00 | 17.65 | H | O |
| ATOM | 1372 | CB | ILE | H | 47 | 18.727 | 24.714 | 9.552 | 1.00 | 11.94 | H | C |
| ATOM | 1373 | CG1 | ILE | H | 47 | 19.427 | 25.098 | 8.249 | 1.00 | 12.91 | H | C |
| ATOM | 1374 | CG2 | ILE | H | 47 | 19.476 | 23.575 | 10.248 | 1.00 | 10.11 | H | C |
| ATOM | 1375 | CD1 | ILE | H | 47 | 20.815 | 25.683 | 8.455 | 1.00 | 13.22 | H | C |
| ATOM | 1376 | N | ASN | H | 48 | 15.944 | 25.264 | 7.481 | 1.00 | 17.72 | H | N |
| ATOM | 1377 | CA | ASN | H | 48 | 15.158 | 26.245 | 6.738 | 1.00 | 21.07 | H | C |
| ATOM | 1378 | C | ASN | H | 48 | 14.312 | 25.485 | 5.728 | 1.00 | 20.14 | H | C |
| ATOM | 1379 | O | ASN | H | 48 | 14.506 | 24.288 | 5.536 | 1.00 | 20.62 | H | O |
| ATOM | 1380 | CB | ASN | H | 48 | 16.071 | 27.199 | 5.965 | 1.00 | 27.12 | H | C |
| ATOM | 1381 | CG | ASN | H | 48 | 16.437 | 28.416 | 6.759 | 1.00 | 32.69 | H | C |
| ATOM | 1382 | OD1 | ASN | H | 48 | 15.566 | 29.193 | 7.156 | 1.00 | 37.95 | H | O |

-continued

| | | | | | | | | | | | |
|---|---|---|---|---|---|---|---|---|---|---|---|
| ATOM | 1383 | ND2 | ASN | H | 48 | 17.729 | 28.600 | 6.998 | 1.00 | 33.59 | H | N |
| ATOM | 1384 | N | THR | H | 49 | 13.387 | 26.176 | 5.069 | 1.00 | 18.81 | H | N |
| ATOM | 1385 | CA | THR | H | 49 | 12.562 | 25.521 | 4.055 | 1.00 | 19.09 | H | C |
| ATOM | 1386 | C | THR | H | 49 | 13.421 | 25.187 | 2.838 | 1.00 | 18.19 | H | C |
| ATOM | 1387 | O | THR | H | 49 | 13.065 | 24.315 | 2.044 | 1.00 | 19.04 | H | O |
| ATOM | 1388 | CB | THR | H | 49 | 11.400 | 26.419 | 3.570 | 1.00 | 16.92 | H | C |
| ATOM | 1389 | OG1 | THR | H | 49 | 11.932 | 27.615 | 2.989 | 1.00 | 18.22 | H | O |
| ATOM | 1390 | CG2 | THR | H | 49 | 10.485 | 26.780 | 4.716 | 1.00 | 17.02 | H | C |
| ATOM | 1391 | N | ILE | H | 50 | 14.559 | 25.871 | 2.707 | 1.00 | 18.59 | H | N |
| ATOM | 1392 | CA | ILE | H | 50 | 15.469 | 25.674 | 1.576 | 1.00 | 18.42 | H | C |
| ATOM | 1393 | C | ILE | H | 50 | 16.841 | 25.067 | 1.907 | 1.00 | 18.14 | H | C |
| ATOM | 1394 | O | ILE | H | 50 | 17.499 | 24.507 | 1.025 | 1.00 | 17.04 | H | O |
| ATOM | 1395 | CB | ILE | H | 50 | 15.694 | 27.030 | 0.841 | 1.00 | 22.10 | H | C |
| ATOM | 1396 | CG1 | ILE | H | 50 | 14.481 | 27.357 | −0.030 | 1.00 | 21.65 | H | C |
| ATOM | 1397 | CG2 | ILE | H | 50 | 16.953 | 26.987 | −0.022 | 1.00 | 23.17 | H | C |
| ATOM | 1398 | CD1 | ILE | H | 50 | 14.338 | 26.454 | −1.235 | 1.00 | 23.27 | H | C |
| ATOM | 1399 | N | TRP | H | 51 | 17.274 | 25.160 | 3.161 | 1.00 | 16.05 | H | N |
| ATOM | 1400 | CA | TRP | H | 51 | 18.592 | 24.655 | 3.528 | 1.00 | 15.56 | H | C |
| ATOM | 1401 | C | TRP | H | 51 | 18.659 | 23.436 | 4.438 | 1.00 | 15.82 | H | C |
| ATOM | 1402 | O | TRP | H | 51 | 17.932 | 23.321 | 5.424 | 1.00 | 16.64 | H | O |
| ATOM | 1403 | CB | TRP | H | 51 | 19.423 | 25.775 | 4.149 | 1.00 | 16.33 | H | C |
| ATOM | 1404 | CG | TRP | H | 51 | 19.593 | 26.967 | 3.254 | 1.00 | 15.89 | H | C |
| ATOM | 1405 | CD1 | TRP | H | 51 | 18.847 | 28.111 | 3.261 | 1.00 | 15.94 | H | C |
| ATOM | 1406 | CD2 | TRP | H | 51 | 20.576 | 27.134 | 2.224 | 1.00 | 15.03 | H | C |
| ATOM | 1407 | NE1 | TRP | H | 51 | 19.306 | 28.982 | 2.302 | 1.00 | 16.22 | H | N |
| ATOM | 1408 | CE2 | TRP | H | 51 | 20.367 | 28.409 | 1.651 | 1.00 | 16.38 | H | C |
| ATOM | 1409 | CE3 | TRP | H | 51 | 21.615 | 26.330 | 1.730 | 1.00 | 16.52 | H | C |
| ATOM | 1410 | CZ2 | TRP | H | 51 | 21.163 | 28.904 | 0.606 | 1.00 | 16.04 | H | C |
| ATOM | 1411 | CZ3 | TRP | H | 51 | 22.405 | 26.822 | 0.690 | 1.00 | 16.73 | H | C |
| ATOM | 1412 | CH2 | TRP | H | 51 | 22.173 | 28.100 | 0.142 | 1.00 | 16.02 | H | C |
| ATOM | 1413 | N | VAL | H | 52 | 19.571 | 22.536 | 4.091 | 1.00 | 14.41 | H | N |
| ATOM | 1414 | CA | VAL | H | 52 | 19.794 | 21.306 | 4.831 | 1.00 | 12.34 | H | C |
| ATOM | 1415 | C | VAL | H | 52 | 21.270 | 21.211 | 5.218 | 1.00 | 11.65 | H | C |
| ATOM | 1416 | O | VAL | H | 52 | 22.136 | 21.461 | 4.391 | 1.00 | 9.66 | H | O |
| ATOM | 1417 | CB | VAL | H | 52 | 19.440 | 20.073 | 3.957 | 1.00 | 11.76 | H | C |
| ATOM | 1418 | CG1 | VAL | H | 52 | 19.909 | 18.800 | 4.632 | 1.00 | 8.59 | H | C |
| ATOM | 1419 | CG2 | VAL | H | 52 | 17.935 | 20.022 | 3.700 | 1.00 | 12.24 | H | C |
| ATOM | 1420 | N | VAL | H | 53 | 21.549 | 20.869 | 6.474 | 1.00 | 11.58 | H | N |
| ATOM | 1421 | CA | VAL | H | 53 | 22.925 | 20.706 | 6.944 | 1.00 | 11.42 | H | C |
| ATOM | 1422 | C | VAL | H | 53 | 23.198 | 19.206 | 7.023 | 1.00 | 11.69 | H | C |
| ATOM | 1423 | O | VAL | H | 53 | 22.431 | 18.470 | 7.629 | 1.00 | 12.13 | H | O |
| ATOM | 1424 | CB | VAL | H | 53 | 23.141 | 21.326 | 8.357 | 1.00 | 11.61 | H | C |
| ATOM | 1425 | CG1 | VAL | H | 53 | 24.522 | 20.923 | 8.910 | 1.00 | 6.99 | H | C |
| ATOM | 1426 | CG2 | VAL | H | 53 | 23.037 | 22.850 | 8.284 | 1.00 | 9.62 | H | C |
| ATOM | 1427 | N | SER | H | 54 | 24.280 | 18.757 | 6.397 | 1.00 | 11.72 | H | N |
| ATOM | 1428 | CA | SER | H | 54 | 24.642 | 17.343 | 6.414 | 1.00 | 10.64 | H | C |
| ATOM | 1429 | C | SER | H | 54 | 26.150 | 17.233 | 6.651 | 1.00 | 11.91 | H | C |
| ATOM | 1430 | O | SER | H | 54 | 26.770 | 18.184 | 7.134 | 1.00 | 12.10 | H | O |
| ATOM | 1431 | CB | SER | H | 54 | 24.256 | 16.687 | 5.082 | 1.00 | 10.42 | H | C |
| ATOM | 1432 | OG | SER | H | 54 | 24.369 | 15.274 | 5.154 | 1.00 | 11.65 | H | O |
| ATOM | 1433 | N | ALA | H | 55 | 26.740 | 16.085 | 6.321 | 1.00 | 12.45 | H | N |
| ATOM | 1434 | CA | ALA | H | 55 | 28.178 | 15.888 | 6.507 | 1.00 | 12.19 | H | C |
| ATOM | 1435 | C | ALA | H | 55 | 28.911 | 15.910 | 5.166 | 1.00 | 12.89 | H | C |
| ATOM | 1436 | O | ALA | H | 55 | 28.422 | 15.377 | 4.169 | 1.00 | 12.34 | H | O |
| ATOM | 1437 | CB | ALA | H | 55 | 28.440 | 14.565 | 7.219 | 1.00 | 10.54 | H | C |
| ATOM | 1438 | N | ALA | H | 56 | 30.087 | 16.528 | 5.146 | 1.00 | 11.36 | H | N |
| ATOM | 1439 | CA | ALA | H | 56 | 30.880 | 16.606 | 3.925 | 1.00 | 12.72 | H | C |
| ATOM | 1440 | C | ALA | H | 56 | 31.315 | 15.244 | 3.387 | 1.00 | 13.03 | H | C |
| ATOM | 1441 | O | ALA | H | 56 | 31.283 | 15.021 | 2.172 | 1.00 | 13.79 | H | O |
| ATOM | 1442 | CB | ALA | H | 56 | 32.122 | 17.481 | 4.156 | 1.00 | 12.20 | H | C |
| ATOM | 1443 | N | HIS | H | 57 | 31.720 | 14.327 | 4.266 | 1.00 | 12.47 | H | N |
| ATOM | 1444 | CA | HIS | H | 57 | 32.187 | 13.025 | 3.791 | 1.00 | 14.60 | H | C |
| ATOM | 1445 | C | HIS | H | 57 | 31.136 | 12.203 | 3.039 | 1.00 | 16.39 | H | C |
| ATOM | 1446 | O | HIS | H | 57 | 31.470 | 11.252 | 2.332 | 1.00 | 16.35 | H | O |
| ATOM | 1447 | CB | HIS | H | 57 | 32.798 | 12.200 | 4.937 | 1.00 | 13.36 | H | C |
| ATOM | 1448 | CG | HIS | H | 57 | 31.807 | 11.425 | 5.749 | 1.00 | 11.86 | H | C |
| ATOM | 1449 | ND1 | HIS | H | 57 | 31.362 | 11.849 | 6.983 | 1.00 | 8.73 | H | N |
| ATOM | 1450 | CD2 | HIS | H | 57 | 31.219 | 10.222 | 5.530 | 1.00 | 9.58 | H | C |
| ATOM | 1451 | CE1 | HIS | H | 57 | 30.547 | 10.941 | 7.491 | 1.00 | 9.27 | H | C |
| ATOM | 1452 | NE2 | HIS | H | 57 | 30.443 | 9.945 | 6.630 | 1.00 | 9.58 | H | N |
| ATOM | 1453 | N | CYS | H | 58 | 29.869 | 12.581 | 3.175 | 1.00 | 16.13 | H | N |
| ATOM | 1454 | CA | CYS | H | 58 | 28.789 | 11.887 | 2.485 | 1.00 | 16.63 | H | C |
| ATOM | 1455 | C | CYS | H | 58 | 28.880 | 12.061 | 0.967 | 1.00 | 15.55 | H | C |
| ATOM | 1456 | O | CYS | H | 58 | 28.248 | 11.329 | 0.208 | 1.00 | 14.79 | H | O |
| ATOM | 1457 | CB | CYS | H | 58 | 27.443 | 12.426 | 2.979 | 1.00 | 17.08 | H | C |
| ATOM | 1458 | SG | CYS | H | 58 | 27.023 | 11.898 | 4.670 | 1.00 | 18.19 | H | S |
| ATOM | 1459 | N | PHE | H | 59 | 29.675 | 13.030 | 0.532 | 1.00 | 15.81 | H | N |
| ATOM | 1460 | CA | PHE | H | 59 | 29.826 | 13.327 | −0.883 | 1.00 | 14.61 | H | C |
| ATOM | 1461 | C | PHE | H | 59 | 31.191 | 12.959 | −1.475 | 1.00 | 14.54 | H | C |

-continued

| | | | | | | | | | | | |
|---|---|---|---|---|---|---|---|---|---|---|---|
| ATOM | 1462 | O | PHE | H | 59 | 31.504 | 13.349 | −2.602 | 1.00 | 13.82 | H | O |
| ATOM | 1463 | CB | PHE | H | 59 | 29.517 | 14.816 | −1.094 | 1.00 | 14.40 | H | C |
| ATOM | 1464 | CG | PHE | H | 59 | 28.188 | 15.231 | −0.517 | 1.00 | 15.03 | H | C |
| ATOM | 1465 | CD1 | PHE | H | 59 | 27.008 | 14.984 | −1.210 | 1.00 | 14.65 | H | C |
| ATOM | 1466 | CD2 | PHE | H | 59 | 28.109 | 15.765 | 0.770 | 1.00 | 14.34 | H | C |
| ATOM | 1467 | CE1 | PHE | H | 59 | 25.768 | 15.252 | −0.629 | 1.00 | 15.30 | H | C |
| ATOM | 1468 | CE2 | PHE | H | 59 | 26.875 | 16.033 | 1.358 | 1.00 | 14.77 | H | C |
| ATOM | 1469 | CZ | PHE | H | 59 | 25.703 | 15.774 | 0.657 | 1.00 | 16.63 | H | C |
| ATOM | 1470 | N | ASP | H | 60 | 31.986 | 12.195 | −0.727 | 1.00 | 14.66 | H | N |
| ATOM | 1471 | CA | ASP | H | 60 | 33.313 | 11.761 | −1.179 | 1.00 | 16.60 | H | C |
| ATOM | 1472 | C | ASP | H | 60 | 33.310 | 10.997 | −2.509 | 1.00 | 18.45 | H | C |
| ATOM | 1473 | O | ASP | H | 60 | 34.172 | 11.216 | −3.358 | 1.00 | 17.09 | H | O |
| ATOM | 1474 | CB | ASP | H | 60 | 33.979 | 10.872 | −0.117 | 1.00 | 15.71 | H | C |
| ATOM | 1475 | CG | ASP | H | 60 | 34.633 | 11.668 | 0.998 | 1.00 | 15.52 | H | C |
| ATOM | 1476 | OD1 | ASP | H | 60 | 34.520 | 12.897 | 1.005 | 1.00 | 13.68 | H | O |
| ATOM | 1477 | OD2 | ASP | H | 60 | 35.262 | 11.049 | 1.855 | 1.00 | 15.21 | H | O |
| ATOM | 1478 | N | LYS | H | 60A | 32.357 | 10.089 | −2.687 | 1.00 | 21.04 | H | N |
| ATOM | 1479 | CA | LYS | H | 60A | 32.303 | 9.306 | −3.918 | 1.00 | 23.97 | H | C |
| ATOM | 1480 | C | LYS | H | 60A | 31.110 | 9.568 | −4.830 | 1.00 | 24.27 | H | C |
| ATOM | 1481 | O | LYS | H | 60A | 30.675 | 8.678 | −5.558 | 1.00 | 24.87 | H | O |
| ATOM | 1482 | CB | LYS | H | 60A | 32.372 | 7.813 | −3.599 | 1.00 | 26.20 | H | C |
| ATOM | 1483 | CG | LYS | H | 60A | 33.775 | 7.323 | −3.279 | 1.00 | 32.13 | H | C |
| ATOM | 1484 | CD | LYS | H | 60A | 34.039 | 7.276 | −1.794 | 1.00 | 35.71 | H | C |
| ATOM | 1485 | CE | LYS | H | 60A | 33.231 | 6.169 | −1.128 | 1.00 | 38.10 | H | C |
| ATOM | 1486 | NZ | LYS | H | 60A | 33.565 | 6.052 | 0.323 | 1.00 | 42.45 | H | N |
| ATOM | 1487 | N | ILE | H | 60B | 30.583 | 10.785 | −4.796 | 1.00 | 25.56 | H | N |
| ATOM | 1488 | CA | ILE | H | 60B | 29.454 | 11.132 | −5.642 | 1.00 | 25.53 | H | C |
| ATOM | 1489 | C | ILE | H | 60B | 29.979 | 11.394 | −7.049 | 1.00 | 28.48 | H | C |
| ATOM | 1490 | O | ILE | H | 60B | 30.919 | 12.168 | −7.232 | 1.00 | 28.70 | H | O |
| ATOM | 1491 | CB | ILE | H | 60B | 28.736 | 12.409 | −5.143 | 1.00 | 24.23 | H | C |
| ATOM | 1492 | CG1 | ILE | H | 60B | 28.147 | 12.180 | −3.746 | 1.00 | 22.79 | H | C |
| ATOM | 1493 | CG2 | ILE | H | 60B | 27.647 | 12.807 | −6.132 | 1.00 | 24.21 | H | C |
| ATOM | 1494 | CD1 | ILE | H | 60B | 27.036 | 11.148 | −3.688 | 1.00 | 19.86 | H | C |
| ATOM | 1495 | N | LYS | H | 60C | 29.378 | 10.734 | −8.034 | 1.00 | 29.76 | H | N |
| ATOM | 1496 | CA | LYS | H | 60C | 29.764 | 10.902 | −9.430 | 1.00 | 31.95 | H | C |
| ATOM | 1497 | C | LYS | H | 60C | 28.665 | 11.665 | −10.169 | 1.00 | 31.45 | H | C |
| ATOM | 1498 | O | LYS | H | 60C | 28.942 | 12.513 | −11.015 | 1.00 | 32.26 | H | O |
| ATOM | 1499 | CB | LYS | H | 60C | 29.974 | 9.536 | −10.091 | 1.00 | 35.12 | H | C |
| ATOM | 1500 | CG | LYS | H | 60C | 31.059 | 8.679 | −9.440 | 1.00 | 38.59 | H | C |
| ATOM | 1501 | CD | LYS | H | 60C | 32.462 | 9.191 | −9.753 | 1.00 | 41.77 | H | C |
| ATOM | 1502 | CE | LYS | H | 60C | 33.034 | 8.561 | −11.024 | 1.00 | 43.81 | H | C |
| ATOM | 1503 | NZ | LYS | H | 60C | 32.241 | 8.847 | −12.257 | 1.00 | 46.15 | H | N |
| ATOM | 1504 | N | ASN | H | 60D | 27.415 | 11.360 | −9.834 | 1.00 | 30.75 | H | N |
| ATOM | 1505 | CA | ASN | H | 60D | 26.272 | 12.005 | −10.464 | 1.00 | 29.53 | H | C |
| ATOM | 1506 | C | ASN | H | 60D | 25.675 | 13.073 | −9.549 | 1.00 | 28.25 | H | C |
| ATOM | 1507 | O | ASN | H | 60D | 24.678 | 12.833 | −8.858 | 1.00 | 26.07 | H | O |
| ATOM | 1508 | CB | ASN | H | 60D | 25.203 | 10.963 | −10.803 | 1.00 | 32.77 | H | C |
| ATOM | 1509 | CG | ASN | H | 60D | 25.726 | 9.853 | −11.700 | 1.00 | 35.73 | H | C |
| ATOM | 1510 | OD1 | ASN | H | 60D | 26.355 | 10.111 | −12.727 | 1.00 | 37.75 | H | O |
| ATOM | 1511 | ND2 | ASN | H | 60D | 25.454 | 8.609 | −11.320 | 1.00 | 37.39 | H | N |
| ATOM | 1512 | N | TRP | H | 61 | 26.279 | 14.256 | −9.567 | 1.00 | 25.37 | H | N |
| ATOM | 1513 | CA | TRP | H | 61 | 25.834 | 15.365 | −8.734 | 1.00 | 25.31 | H | C |
| ATOM | 1514 | C | TRP | H | 61 | 24.422 | 15.863 | −9.016 | 1.00 | 26.09 | H | C |
| ATOM | 1515 | O | TRP | H | 61 | 23.849 | 16.582 | −8.203 | 1.00 | 25.00 | H | O |
| ATOM | 1516 | CB | TRP | H | 61 | 26.822 | 16.532 | −8.839 | 1.00 | 24.50 | H | C |
| ATOM | 1517 | CG | TRP | H | 61 | 28.179 | 16.178 | −8.321 | 1.00 | 21.92 | H | C |
| ATOM | 1518 | CD1 | TRP | H | 61 | 29.211 | 15.634 | −9.027 | 1.00 | 21.98 | H | C |
| ATOM | 1519 | CD2 | TRP | H | 61 | 28.615 | 16.247 | −6.961 | 1.00 | 20.82 | H | C |
| ATOM | 1520 | NE1 | TRP | H | 61 | 30.262 | 15.355 | −8.189 | 1.00 | 22.70 | H | N |
| ATOM | 1521 | CE2 | TRP | H | 61 | 29.921 | 15.722 | −6.912 | 1.00 | 20.71 | H | C |
| ATOM | 1522 | CE3 | TRP | H | 61 | 28.025 | 16.703 | −5.772 | 1.00 | 19.10 | H | C |
| ATOM | 1523 | CZ2 | TRP | H | 61 | 30.651 | 15.634 | −5.724 | 1.00 | 17.70 | H | C |
| ATOM | 1524 | CZ3 | TRP | H | 61 | 28.749 | 16.616 | −4.593 | 1.00 | 17.89 | H | C |
| ATOM | 1525 | CH2 | TRP | H | 61 | 30.050 | 16.084 | −4.579 | 1.00 | 17.22 | H | C |
| ATOM | 1526 | N | ARG | H | 62 | 23.858 | 15.492 | −10.160 | 1.00 | 26.23 | H | N |
| ATOM | 1527 | CA | ARG | H | 62 | 22.503 | 15.919 | −10.494 | 1.00 | 28.01 | H | C |
| ATOM | 1528 | C | ARG | H | 62 | 21.432 | 14.938 | −10.009 | 1.00 | 26.66 | H | C |
| ATOM | 1529 | O | ARG | H | 62 | 20.240 | 15.216 | −10.125 | 1.00 | 25.99 | H | O |
| ATOM | 1530 | CB | ARG | H | 62 | 22.365 | 16.136 | −12.007 | 1.00 | 31.33 | H | C |
| ATOM | 1531 | CG | ARG | H | 62 | 22.965 | 17.448 | −12.509 | 1.00 | 36.27 | H | C |
| ATOM | 1532 | CD | ARG | H | 62 | 22.697 | 17.657 | −13.997 | 1.00 | 40.57 | H | C |
| ATOM | 1533 | NE | ARG | H | 62 | 23.530 | 16.804 | −14.844 | 1.00 | 44.43 | H | N |
| ATOM | 1534 | CZ | ARG | H | 62 | 24.787 | 17.078 | −15.190 | 1.00 | 46.30 | H | C |
| ATOM | 1535 | NH1 | ARG | H | 62 | 25.374 | 18.192 | −14.770 | 1.00 | 46.47 | H | N |
| ATOM | 1536 | NH2 | ARG | H | 62 | 25.462 | 16.229 | −15.954 | 1.00 | 45.81 | H | N |
| ATOM | 1537 | N | ASN | H | 63 | 21.854 | 13.802 | −9.459 | 1.00 | 25.42 | H | N |
| ATOM | 1538 | CA | ASN | H | 63 | 20.917 | 12.797 | −8.958 | 1.00 | 25.01 | H | C |
| ATOM | 1539 | C | ASN | H | 63 | 20.829 | 12.745 | −7.431 | 1.00 | 24.39 | H | C |
| ATOM | 1540 | O | ASN | H | 63 | 20.573 | 11.682 | −6.860 | 1.00 | 24.25 | H | O |

-continued

| | | | | | | | | | | | |
|---|---|---|---|---|---|---|---|---|---|---|---|
| ATOM | 1541 | CB | ASN | H | 63 | 21.296 | 11.404 | −9.468 | 1.00 | 27.47 | H | C |
| ATOM | 1542 | CG | ASN | H | 63 | 21.396 | 11.341 | −10.976 | 1.00 | 31.32 | H | C |
| ATOM | 1543 | OD1 | ASN | H | 63 | 20.715 | 12.078 | −11.686 | 1.00 | 31.92 | H | O |
| ATOM | 1544 | ND2 | ASN | H | 63 | 22.238 | 10.442 | −11.476 | 1.00 | 32.46 | H | N |
| ATOM | 1545 | N | LEU | H | 64 | 21.047 | 13.875 | −6.767 | 1.00 | 21.76 | H | N |
| ATOM | 1546 | CA | LEU | H | 64 | 20.966 | 13.910 | −5.309 | 1.00 | 20.28 | H | C |
| ATOM | 1547 | C | LEU | H | 64 | 19.568 | 14.341 | −4.862 | 1.00 | 19.50 | H | C |
| ATOM | 1548 | O | LEU | H | 64 | 19.071 | 15.395 | −5.268 | 1.00 | 18.78 | H | O |
| ATOM | 1549 | CB | LEU | H | 64 | 22.018 | 14.865 | −4.744 | 1.00 | 19.05 | H | C |
| ATOM | 1550 | CG | LEU | H | 64 | 23.464 | 14.363 | −4.771 | 1.00 | 20.72 | H | C |
| ATOM | 1551 | CD1 | LEU | H | 64 | 24.424 | 15.537 | −4.548 | 1.00 | 20.72 | H | C |
| ATOM | 1552 | CD2 | LEU | H | 64 | 23.654 | 13.282 | −3.702 | 1.00 | 18.65 | H | C |
| ATOM | 1553 | N | ILE | H | 65 | 18.938 | 13.520 | −4.027 | 1.00 | 17.67 | H | N |
| ATOM | 1554 | CA | ILE | H | 65 | 17.589 | 13.810 | −3.539 | 1.00 | 18.01 | H | C |
| ATOM | 1555 | C | ILE | H | 65 | 17.541 | 13.931 | −2.015 | 1.00 | 16.76 | H | C |
| ATOM | 1556 | O | ILE | H | 65 | 18.200 | 13.172 | −1.303 | 1.00 | 14.51 | H | O |
| ATOM | 1557 | CB | ILE | H | 65 | 16.592 | 12.692 | −3.980 | 1.00 | 18.70 | H | C |
| ATOM | 1558 | CG1 | ILE | H | 65 | 16.468 | 12.671 | −5.508 | 1.00 | 19.21 | H | C |
| ATOM | 1559 | CG2 | ILE | H | 65 | 15.215 | 12.918 | −3.352 | 1.00 | 19.44 | H | C |
| ATOM | 1560 | CD1 | ILE | H | 65 | 15.788 | 13.897 | −6.089 | 1.00 | 17.74 | H | C |
| ATOM | 1561 | N | ALA | H | 66 | 16.774 | 14.903 | −1.527 | 1.00 | 15.47 | H | N |
| ATOM | 1562 | CA | ALA | H | 66 | 16.603 | 15.111 | −0.097 | 1.00 | 15.47 | H | C |
| ATOM | 1563 | C | ALA | H | 66 | 15.125 | 14.876 | 0.196 | 1.00 | 16.47 | H | C |
| ATOM | 1564 | O | ALA | H | 66 | 14.254 | 15.513 | −0.405 | 1.00 | 16.85 | H | O |
| ATOM | 1565 | CB | ALA | H | 66 | 16.995 | 16.531 | 0.290 | 1.00 | 12.74 | H | C |
| ATOM | 1566 | N | VAL | H | 67 | 14.844 | 13.954 | 1.108 | 1.00 | 14.86 | H | N |
| ATOM | 1567 | CA | VAL | H | 67 | 13.469 | 13.643 | 1.459 | 1.00 | 16.12 | H | C |
| ATOM | 1568 | C | VAL | H | 67 | 13.169 | 14.082 | 2.894 | 1.00 | 16.69 | H | C |
| ATOM | 1569 | O | VAL | H | 67 | 13.895 | 13.732 | 3.832 | 1.00 | 14.62 | H | O |
| ATOM | 1570 | CB | VAL | H | 67 | 13.184 | 12.123 | 1.323 | 1.00 | 17.25 | H | C |
| ATOM | 1571 | CG1 | VAL | H | 67 | 11.695 | 11.856 | 1.492 | 1.00 | 18.41 | H | C |
| ATOM | 1572 | CG2 | VAL | H | 67 | 13.652 | 11.616 | −0.045 | 1.00 | 15.42 | H | C |
| ATOM | 1573 | N | LEU | H | 68 | 12.111 | 14.875 | 3.042 | 1.00 | 14.71 | H | N |
| ATOM | 1574 | CA | LEU | H | 68 | 11.662 | 15.368 | 4.341 | 1.00 | 14.94 | H | C |
| ATOM | 1575 | C | LEU | H | 68 | 10.368 | 14.648 | 4.744 | 1.00 | 14.41 | H | C |
| ATOM | 1576 | O | LEU | H | 68 | 9.639 | 14.144 | 3.888 | 1.00 | 15.50 | H | O |
| ATOM | 1577 | CB | LEU | H | 68 | 11.409 | 16.881 | 4.282 | 1.00 | 11.00 | H | C |
| ATOM | 1578 | CG | LEU | H | 68 | 12.589 | 17.836 | 4.542 | 1.00 | 14.28 | H | C |
| ATOM | 1579 | CD1 | LEU | H | 68 | 13.204 | 17.495 | 5.901 | 1.00 | 14.52 | H | C |
| ATOM | 1580 | CD2 | LEU | H | 68 | 13.645 | 17.729 | 3.445 | 1.00 | 12.56 | H | C |
| ATOM | 1581 | N | GLY | H | 69 | 10.098 | 14.593 | 6.047 | 1.00 | 13.97 | H | N |
| ATOM | 1582 | CA | GLY | H | 69 | 8.890 | 13.951 | 6.547 | 1.00 | 13.77 | H | C |
| ATOM | 1583 | C | GLY | H | 69 | 8.913 | 12.438 | 6.465 | 1.00 | 17.11 | H | C |
| ATOM | 1584 | O | GLY | H | 69 | 7.886 | 11.774 | 6.637 | 1.00 | 17.76 | H | O |
| ATOM | 1585 | N | GLU | H | 70 | 10.096 | 11.889 | 6.211 | 1.00 | 16.90 | H | N |
| ATOM | 1586 | CA | GLU | H | 70 | 10.275 | 10.454 | 6.101 | 1.00 | 16.57 | H | C |
| ATOM | 1587 | C | GLU | H | 70 | 10.245 | 9.800 | 7.491 | 1.00 | 16.50 | H | C |
| ATOM | 1588 | O | GLU | H | 70 | 10.567 | 10.437 | 8.494 | 1.00 | 15.98 | H | O |
| ATOM | 1589 | CB | GLU | H | 70 | 11.602 | 10.174 | 5.387 | 1.00 | 19.03 | H | C |
| ATOM | 1590 | CG | GLU | H | 70 | 11.865 | 8.726 | 5.080 | 1.00 | 22.67 | H | C |
| ATOM | 1591 | CD | GLU | H | 70 | 10.684 | 8.066 | 4.398 | 1.00 | 25.35 | H | C |
| ATOM | 1592 | OE1 | GLU | H | 70 | 10.563 | 8.141 | 3.189 | 1.00 | 24.42 | H | O |
| ATOM | 1593 | OE2 | GLU | H | 70 | 9.892 | 7.495 | 5.098 | 1.00 | 23.25 | H | O |
| ATOM | 1594 | N | HIS | H | 71 | 9.813 | 8.544 | 7.546 | 1.00 | 12.74 | H | N |
| ATOM | 1595 | CA | HIS | H | 71 | 9.761 | 7.801 | 8.799 | 1.00 | 13.45 | H | C |
| ATOM | 1596 | C | HIS | H | 71 | 10.080 | 6.321 | 8.586 | 1.00 | 12.69 | H | C |
| ATOM | 1597 | O | HIS | H | 71 | 11.080 | 5.815 | 9.091 | 1.00 | 11.97 | H | O |
| ATOM | 1598 | CB | HIS | H | 71 | 8.380 | 7.919 | 9.455 | 1.00 | 12.65 | H | C |
| ATOM | 1599 | CG | HIS | H | 71 | 8.219 | 7.045 | 10.659 | 1.00 | 14.72 | H | C |
| ATOM | 1600 | ND1 | HIS | H | 71 | 8.933 | 7.245 | 11.821 | 1.00 | 15.86 | H | N |
| ATOM | 1601 | CD2 | HIS | H | 71 | 7.488 | 5.922 | 10.857 | 1.00 | 15.60 | H | C |
| ATOM | 1602 | CE1 | HIS | H | 71 | 8.652 | 6.281 | 12.680 | 1.00 | 15.50 | H | C |
| ATOM | 1603 | NE2 | HIS | H | 71 | 7.778 | 5.465 | 12.119 | 1.00 | 16.25 | H | N |
| ATOM | 1604 | N | ASP | H | 72 | 9.214 | 5.642 | 7.836 | 1.00 | 12.78 | H | N |
| ATOM | 1605 | CA | ASP | H | 72 | 9.340 | 4.213 | 7.543 | 1.00 | 14.80 | H | C |
| ATOM | 1606 | C | ASP | H | 72 | 9.726 | 4.058 | 6.078 | 1.00 | 14.88 | H | C |
| ATOM | 1607 | O | ASP | H | 72 | 8.931 | 4.350 | 5.200 | 1.00 | 14.21 | H | O |
| ATOM | 1608 | CB | ASP | H | 72 | 7.988 | 3.539 | 7.798 | 1.00 | 17.28 | H | C |
| ATOM | 1609 | CG | ASP | H | 72 | 8.012 | 2.046 | 7.555 | 1.00 | 20.88 | H | C |
| ATOM | 1610 | OD1 | ASP | H | 72 | 8.887 | 1.559 | 6.837 | 1.00 | 18.95 | H | O |
| ATOM | 1611 | OD2 | ASP | H | 72 | 7.134 | 1.377 | 8.082 | 1.00 | 22.75 | H | O |
| ATOM | 1612 | N | LEU | H | 73 | 10.936 | 3.587 | 5.805 | 1.00 | 16.56 | H | N |
| ATOM | 1613 | CA | LEU | H | 73 | 11.385 | 3.443 | 4.423 | 1.00 | 16.35 | H | C |
| ATOM | 1614 | C | LEU | H | 73 | 10.650 | 2.377 | 3.596 | 1.00 | 18.34 | H | C |
| ATOM | 1615 | O | LEU | H | 73 | 10.858 | 2.282 | 2.385 | 1.00 | 19.52 | H | O |
| ATOM | 1616 | CB | LEU | H | 73 | 12.895 | 3.171 | 4.397 | 1.00 | 16.77 | H | C |
| ATOM | 1617 | CG | LEU | H | 73 | 13.769 | 4.110 | 5.247 | 1.00 | 17.81 | H | C |
| ATOM | 1618 | CD1 | LEU | H | 73 | 15.230 | 3.720 | 5.100 | 1.00 | 15.70 | H | C |
| ATOM | 1619 | CD2 | LEU | H | 73 | 13.555 | 5.549 | 4.823 | 1.00 | 16.14 | H | C |

| | | | | | -continued | | | | | |
|---|---|---|---|---|---|---|---|---|---|---|
| ATOM | 1620 | N | SER | H | 74 | 9.790 | 1.590 | 4.234 | 1.00 | 19.10 | H | N |
| ATOM | 1621 | CA | SER | H | 74 | 9.043 | 0.548 | 3.531 | 1.00 | 21.62 | H | C |
| ATOM | 1622 | C | SER | H | 74 | 7.575 | 0.880 | 3.242 | 1.00 | 23.33 | H | O |
| ATOM | 1623 | O | SER | H | 74 | 6.867 | 0.078 | 2.625 | 1.00 | 22.33 | H | O |
| ATOM | 1624 | CB | SER | H | 74 | 9.114 | −0.769 | 4.308 | 1.00 | 20.45 | H | O |
| ATOM | 1625 | OG | SER | H | 74 | 8.439 | −0.675 | 5.547 | 1.00 | 22.87 | H | O |
| ATOM | 1626 | N | GLU | H | 75 | 7.117 | 2.053 | 3.677 | 1.00 | 22.57 | H | N |
| ATOM | 1627 | CA | GLU | H | 75 | 5.732 | 2.466 | 3.449 | 1.00 | 24.78 | H | C |
| ATOM | 1628 | C | GLU | H | 75 | 5.688 | 3.934 | 3.040 | 1.00 | 25.10 | H | C |
| ATOM | 1629 | O | GLU | H | 75 | 6.318 | 4.749 | 3.678 | 1.00 | 25.82 | H | O |
| ATOM | 1630 | CB | GLU | H | 75 | 4.911 | 2.301 | 4.730 | 1.00 | 26.53 | H | C |
| ATOM | 1631 | CG | GLU | H | 75 | 4.714 | 0.873 | 5.205 | 1.00 | 31.89 | H | C |
| ATOM | 1632 | CD | GLU | H | 75 | 3.839 | 0.065 | 4.270 | 1.00 | 33.67 | H | C |
| ATOM | 1633 | OE1 | GLU | H | 75 | 2.831 | 0.603 | 3.814 | 1.00 | 35.97 | H | O |
| ATOM | 1634 | OE2 | GLU | H | 75 | 4.162 | −1.102 | 4.013 | 1.00 | 36.04 | H | O |
| ATOM | 1635 | N | HIS | H | 76 | 4.934 | 4.275 | 2.000 | 1.00 | 24.98 | H | N |
| ATOM | 1636 | CA | HIS | H | 76 | 4.830 | 5.668 | 1.558 | 1.00 | 24.23 | H | C |
| ATOM | 1637 | C | HIS | H | 76 | 3.569 | 6.338 | 2.106 | 1.00 | 23.39 | H | C |
| ATOM | 1638 | O | HIS | H | 76 | 2.514 | 5.706 | 2.166 | 1.00 | 23.35 | H | O |
| ATOM | 1639 | CB | HIS | H | 76 | 4.760 | 5.749 | 0.026 | 1.00 | 25.80 | H | C |
| ATOM | 1640 | CG | HIS | H | 76 | 6.056 | 5.469 | −0.671 | 1.00 | 29.25 | H | C |
| ATOM | 1641 | ND1 | HIS | H | 76 | 7.159 | 6.288 | −0.554 | 1.00 | 28.58 | H | N |
| ATOM | 1642 | CD2 | HIS | H | 76 | 6.408 | 4.488 | −1.538 | 1.00 | 28.86 | H | C |
| ATOM | 1643 | CE1 | HIS | H | 76 | 8.132 | 5.827 | −1.321 | 1.00 | 29.52 | H | C |
| ATOM | 1644 | NE2 | HIS | H | 76 | 7.701 | 4.736 | −1.929 | 1.00 | 28.15 | H | N |
| ATOM | 1645 | N | ASP | H | 77 | 3.677 | 7.607 | 2.510 | 1.00 | 20.79 | H | N |
| ATOM | 1646 | CA | ASP | H | 77 | 2.509 | 8.359 | 2.973 | 1.00 | 19.38 | H | C |
| ATOM | 1647 | C | ASP | H | 77 | 2.621 | 9.817 | 2.533 | 1.00 | 18.66 | H | C |
| ATOM | 1648 | O | ASP | H | 77 | 3.651 | 10.230 | 2.004 | 1.00 | 21.60 | H | O |
| ATOM | 1649 | CB | ASP | H | 77 | 2.299 | 8.257 | 4.499 | 1.00 | 18.12 | H | C |
| ATOM | 1650 | CG | ASP | H | 77 | 3.384 | 8.946 | 5.308 | 1.00 | 19.27 | H | C |
| ATOM | 1651 | OD1 | ASP | H | 77 | 3.954 | 9.946 | 4.848 | 1.00 | 19.03 | H | O |
| ATOM | 1652 | OD2 | ASP | H | 77 | 3.635 | 8.490 | 6.418 | 1.00 | 17.06 | H | O |
| ATOM | 1653 | N | GLY | H | 78 | 1.566 | 10.592 | 2.755 | 1.00 | 18.19 | H | N |
| ATOM | 1654 | CA | GLY | H | 78 | 1.545 | 11.980 | 2.326 | 1.00 | 18.10 | H | C |
| ATOM | 1655 | C | GLY | H | 78 | 2.371 | 13.025 | 3.054 | 1.00 | 18.55 | H | C |
| ATOM | 1656 | O | GLY | H | 78 | 2.352 | 14.197 | 2.675 | 1.00 | 16.08 | H | O |
| ATOM | 1657 | N | ASP | H | 79 | 3.095 | 12.625 | 4.091 | 1.00 | 19.01 | H | N |
| ATOM | 1658 | CA | ASP | H | 79 | 3.910 | 13.580 | 4.827 | 1.00 | 18.79 | H | C |
| ATOM | 1659 | C | ASP | H | 79 | 5.297 | 13.730 | 4.227 | 1.00 | 18.30 | H | C |
| ATOM | 1660 | O | ASP | H | 79 | 6.014 | 14.676 | 4.543 | 1.00 | 18.65 | H | O |
| ATOM | 1661 | CB | ASP | H | 79 | 4.034 | 13.164 | 6.295 | 1.00 | 19.58 | H | C |
| ATOM | 1662 | CG | ASP | H | 79 | 2.696 | 13.111 | 6.996 | 1.00 | 21.14 | H | C |
| ATOM | 1663 | OD1 | ASP | H | 79 | 1.909 | 14.047 | 6.832 | 1.00 | 22.87 | H | O |
| ATOM | 1664 | OD2 | ASP | H | 79 | 2.450 | 12.148 | 7.704 | 1.00 | 20.28 | H | O |
| ATOM | 1665 | N | GLU | H | 80 | 5.685 | 12.799 | 3.364 | 1.00 | 19.12 | H | N |
| ATOM | 1666 | CA | GLU | H | 80 | 7.003 | 12.873 | 2.758 | 1.00 | 20.29 | H | C |
| ATOM | 1667 | C | GLU | H | 80 | 7.062 | 13.811 | 1.563 | 1.00 | 19.63 | H | C |
| ATOM | 1668 | O | GLU | H | 80 | 6.185 | 13.815 | 0.699 | 1.00 | 19.10 | H | O |
| ATOM | 1669 | CB | GLU | H | 80 | 7.491 | 11.472 | 2.380 | 1.00 | 22.03 | H | C |
| ATOM | 1670 | CG | GLU | H | 80 | 6.528 | 10.659 | 1.571 | 1.00 | 29.30 | H | C |
| ATOM | 1671 | CD | GLU | H | 80 | 6.895 | 9.188 | 1.567 | 1.00 | 29.90 | H | C |
| ATOM | 1672 | OE1 | GLU | H | 80 | 6.763 | 8.547 | 2.597 | 1.00 | 27.84 | H | O |
| ATOM | 1673 | OE2 | GLU | H | 80 | 7.315 | 8.707 | 0.544 | 1.00 | 32.19 | H | O |
| ATOM | 1674 | N | GLN | H | 81 | 8.110 | 14.625 | 1.541 | 1.00 | 18.82 | H | N |
| ATOM | 1675 | CA | GLN | H | 81 | 8.324 | 15.592 | 0.482 | 1.00 | 17.15 | H | C |
| ATOM | 1676 | C | GLN | H | 81 | 9.723 | 15.373 | −0.065 | 1.00 | 18.57 | H | C |
| ATOM | 1677 | O | GLN | H | 81 | 10.689 | 15.277 | 0.691 | 1.00 | 18.79 | H | O |
| ATOM | 1678 | CB | GLN | H | 81 | 8.202 | 17.004 | 1.037 | 1.00 | 16.07 | H | C |
| ATOM | 1679 | CG | GLN | H | 81 | 6.873 | 17.277 | 1.709 | 1.00 | 15.69 | H | C |
| ATOM | 1680 | CD | GLN | H | 81 | 6.792 | 18.684 | 2.237 | 1.00 | 13.45 | H | C |
| ATOM | 1681 | OE1 | GLN | H | 81 | 6.982 | 19.630 | 1.493 | 1.00 | 12.22 | H | O |
| ATOM | 1682 | NE2 | GLN | H | 81 | 6.516 | 18.828 | 3.530 | 1.00 | 12.50 | H | N |
| ATOM | 1683 | N | SER | H | 82 | 9.829 | 15.313 | −1.384 | 1.00 | 17.31 | H | N |
| ATOM | 1684 | CA | SER | H | 82 | 11.105 | 15.072 | −2.029 | 1.00 | 18.12 | H | C |
| ATOM | 1685 | C | SER | H | 82 | 11.576 | 16.299 | −2.799 | 1.00 | 17.87 | H | C |
| ATOM | 1686 | O | SER | H | 82 | 10.778 | 16.996 | −3.428 | 1.00 | 17.54 | H | O |
| ATOM | 1687 | CB | SER | H | 82 | 10.965 | 13.867 | −2.960 | 1.00 | 16.29 | H | C |
| ATOM | 1688 | OG | SER | H | 82 | 12.222 | 13.446 | −3.436 | 1.00 | 28.10 | H | O |
| ATOM | 1689 | N | ARG | H | 83 | 12.878 | 16.563 | −2.750 | 1.00 | 18.40 | H | N |
| ATOM | 1690 | CA | ARG | H | 83 | 13.447 | 17.717 | −3.443 | 1.00 | 18.45 | H | C |
| ATOM | 1691 | C | ARG | H | 83 | 14.830 | 17.401 | −3.998 | 1.00 | 20.13 | H | C |
| ATOM | 1692 | O | ARG | H | 83 | 15.629 | 16.715 | −3.354 | 1.00 | 21.06 | H | O |
| ATOM | 1693 | CB | ARG | H | 83 | 13.572 | 18.906 | −2.486 | 1.00 | 18.69 | H | C |
| ATOM | 1694 | CG | ARG | H | 83 | 12.253 | 19.439 | −1.927 | 1.00 | 19.20 | H | C |
| ATOM | 1695 | CD | ARG | H | 83 | 11.544 | 20.319 | −2.947 | 1.00 | 17.18 | H | C |
| ATOM | 1696 | NE | ARG | H | 83 | 10.393 | 21.010 | −2.378 | 1.00 | 14.55 | H | N |
| ATOM | 1697 | CZ | ARG | H | 83 | 9.214 | 20.444 | −2.131 | 1.00 | 16.58 | H | C |
| ATOM | 1698 | NH1 | ARG | H | 83 | 9.004 | 19.159 | −2.401 | 1.00 | 13.28 | H | N |

-continued

| | | | | | | | | | | | |
|---|---|---|---|---|---|---|---|---|---|---|---|
| ATOM | 1699 | NH2 | ARG | H | 83 | 8.241 | 21.170 | −1.603 | 1.00 | 16.69 | H N |
| ATOM | 1700 | N | ARG | H | 84 | 15.116 | 17.902 | −5.194 | 1.00 | 19.27 | H N |
| ATOM | 1701 | CA | ARG | H | 84 | 16.426 | 17.697 | −5.788 | 1.00 | 20.61 | H C |
| ATOM | 1702 | C | ARG | H | 84 | 17.392 | 18.641 | −5.075 | 1.00 | 18.87 | H C |
| ATOM | 1703 | O | ARG | H | 84 | 17.015 | 19.746 | −4.689 | 1.00 | 16.00 | H O |
| ATOM | 1704 | CB | ARG | H | 84 | 16.414 | 18.037 | −7.283 | 1.00 | 23.54 | H C |
| ATOM | 1705 | CG | ARG | H | 84 | 15.483 | 17.186 | −8.127 | 1.00 | 29.19 | H C |
| ATOM | 1706 | CD | ARG | H | 84 | 15.845 | 17.288 | −9.604 | 1.00 | 34.52 | H C |
| ATOM | 1707 | NE | ARG | H | 84 | 14.872 | 16.600 | −10.451 | 1.00 | 40.99 | H N |
| ATOM | 1708 | CZ | ARG | H | 84 | 15.065 | 16.298 | −11.733 | 1.00 | 44.71 | H C |
| ATOM | 1709 | NH1 | ARG | H | 84 | 16.206 | 16.614 | −12.337 | 1.00 | 46.58 | H N |
| ATOM | 1710 | NH2 | ARG | H | 84 | 14.110 | 15.682 | −12.417 | 1.00 | 46.99 | H N |
| ATOM | 1711 | N | VAL | H | 85 | 18.629 | 18.203 | −4.888 | 1.00 | 17.74 | H N |
| ATOM | 1712 | CA | VAL | H | 85 | 19.622 | 19.049 | −4.243 | 1.00 | 16.85 | H C |
| ATOM | 1713 | C | VAL | H | 85 | 20.229 | 19.920 | −5.341 | 1.00 | 17.99 | H C |
| ATOM | 1714 | O | VAL | H | 85 | 20.877 | 19.416 | −6.259 | 1.00 | 17.19 | H O |
| ATOM | 1715 | CB | VAL | H | 85 | 20.732 | 18.207 | −3.557 | 1.00 | 16.36 | H C |
| ATOM | 1716 | CG1 | VAL | H | 85 | 21.763 | 19.123 | −2.907 | 1.00 | 14.96 | H C |
| ATOM | 1717 | CG2 | VAL | H | 85 | 20.117 | 17.289 | −2.507 | 1.00 | 13.28 | H C |
| ATOM | 1718 | N | ALA | H | 86 | 19.992 | 21.227 | −5.251 | 1.00 | 18.63 | H N |
| ATOM | 1719 | CA | ALA | H | 86 | 20.504 | 22.181 | −6.231 | 1.00 | 18.54 | H C |
| ATOM | 1720 | C | ALA | H | 86 | 21.974 | 22.513 | −6.000 | 1.00 | 19.52 | H C |
| ATOM | 1721 | O | ALA | H | 86 | 22.692 | 22.847 | −6.942 | 1.00 | 20.09 | H O |
| ATOM | 1722 | CB | ALA | H | 86 | 19.671 | 23.471 | −6.193 | 1.00 | 16.39 | H C |
| ATOM | 1723 | N | GLN | H | 87 | 22.424 | 22.426 | −4.752 | 1.00 | 18.48 | H N |
| ATOM | 1724 | CA | GLN | H | 87 | 23.812 | 22.739 | −4.443 | 1.00 | 19.14 | H C |
| ATOM | 1725 | C | GLN | H | 87 | 24.330 | 22.107 | −3.149 | 1.00 | 17.00 | H C |
| ATOM | 1726 | O | GLN | H | 87 | 23.620 | 22.030 | −2.149 | 1.00 | 17.11 | H O |
| ATOM | 1727 | CB | GLN | H | 87 | 23.986 | 24.259 | −4.376 | 1.00 | 20.74 | H C |
| ATOM | 1728 | CG | GLN | H | 87 | 25.425 | 24.729 | −4.330 | 1.00 | 23.25 | H C |
| ATOM | 1729 | CD | GLN | H | 87 | 25.587 | 26.134 | −4.886 | 1.00 | 28.67 | H C |
| ATOM | 1730 | OE1 | GLN | H | 87 | 25.068 | 27.099 | −4.328 | 1.00 | 31.99 | H O |
| ATOM | 1731 | NE2 | GLN | H | 87 | 26.305 | 26.250 | −5.999 | 1.00 | 30.93 | H N |
| ATOM | 1732 | N | VAL | H | 88 | 25.574 | 21.645 | −3.196 | 1.00 | 14.74 | H N |
| ATOM | 1733 | CA | VAL | H | 88 | 26.239 | 21.047 | −2.047 | 1.00 | 14.64 | H C |
| ATOM | 1734 | C | VAL | H | 88 | 27.465 | 21.920 | −1.772 | 1.00 | 15.48 | H C |
| ATOM | 1735 | O | VAL | H | 88 | 28.404 | 21.946 | −2.562 | 1.00 | 17.00 | H O |
| ATOM | 1736 | CB | VAL | H | 88 | 26.705 | 19.606 | −2.347 | 1.00 | 14.89 | H C |
| ATOM | 1737 | CG1 | VAL | H | 88 | 27.474 | 19.046 | −1.155 | 1.00 | 14.11 | H C |
| ATOM | 1738 | CG2 | VAL | H | 88 | 25.506 | 18.726 | −2.680 | 1.00 | 14.41 | H C |
| ATOM | 1739 | N | ILE | H | 89 | 27.443 | 22.646 | −0.662 | 1.00 | 15.46 | H N |
| ATOM | 1740 | CA | ILE | H | 89 | 28.545 | 23.523 | −0.300 | 1.00 | 14.42 | H C |
| ATOM | 1741 | C | ILE | H | 89 | 29.390 | 22.884 | 0.794 | 1.00 | 15.81 | H C |
| ATOM | 1742 | O | ILE | H | 89 | 28.897 | 22.549 | 1.876 | 1.00 | 16.16 | H O |
| ATOM | 1743 | CB | ILE | H | 89 | 28.030 | 24.884 | 0.190 | 1.00 | 13.77 | H C |
| ATOM | 1744 | CG1 | ILE | H | 89 | 27.072 | 25.485 | −0.847 | 1.00 | 14.85 | H C |
| ATOM | 1745 | CG2 | ILE | H | 89 | 29.209 | 25.829 | 0.413 | 1.00 | 14.01 | H C |
| ATOM | 1746 | CD1 | ILE | H | 89 | 26.360 | 26.755 | −0.384 | 1.00 | 13.34 | H C |
| ATOM | 1747 | N | ILE | H | 90 | 30.674 | 22.724 | 0.500 | 1.00 | 15.61 | H N |
| ATOM | 1748 | CA | ILE | H | 90 | 31.619 | 22.110 | 1.421 | 1.00 | 15.21 | H C |
| ATOM | 1749 | C | ILE | H | 90 | 32.777 | 23.066 | 1.691 | 1.00 | 15.60 | H C |
| ATOM | 1750 | O | ILE | H | 90 | 33.197 | 23.804 | 0.802 | 1.00 | 16.74 | H O |
| ATOM | 1751 | CB | ILE | H | 90 | 32.151 | 20.789 | 0.802 | 1.00 | 15.99 | H C |
| ATOM | 1752 | CG1 | ILE | H | 90 | 31.018 | 19.759 | 0.760 | 1.00 | 15.68 | H C |
| ATOM | 1753 | CG2 | ILE | H | 90 | 33.339 | 20.254 | 1.590 | 1.00 | 17.02 | H C |
| ATOM | 1754 | CD1 | ILE | H | 90 | 31.365 | 18.486 | 0.005 | 1.00 | 19.51 | H C |
| ATOM | 1755 | N | PRO | H | 91 | 33.297 | 23.081 | 2.931 | 1.00 | 16.87 | H N |
| ATOM | 1756 | CA | PRO | H | 91 | 34.415 | 23.971 | 3.259 | 1.00 | 14.80 | H C |
| ATOM | 1757 | C | PRO | H | 91 | 35.627 | 23.649 | 2.384 | 1.00 | 15.40 | H C |
| ATOM | 1758 | O | PRO | H | 91 | 35.917 | 22.480 | 2.120 | 1.00 | 12.85 | H O |
| ATOM | 1759 | CB | PRO | H | 91 | 34.692 | 23.657 | 4.728 | 1.00 | 15.20 | H C |
| ATOM | 1760 | CG | PRO | H | 91 | 33.360 | 23.185 | 5.241 | 1.00 | 16.50 | H C |
| ATOM | 1761 | CD | PRO | H | 91 | 32.867 | 22.319 | 4.118 | 1.00 | 15.23 | H C |
| ATOM | 1762 | N | SER | H | 92 | 36.336 | 24.681 | 1.939 | 1.00 | 14.94 | H N |
| ATOM | 1763 | CA | SER | H | 92 | 37.521 | 24.471 | 1.114 | 1.00 | 15.06 | H C |
| ATOM | 1764 | C | SER | H | 92 | 38.598 | 23.704 | 1.888 | 1.00 | 14.20 | H C |
| ATOM | 1765 | O | SER | H | 92 | 39.489 | 23.117 | 1.289 | 1.00 | 15.42 | H O |
| ATOM | 1766 | CB | SER | H | 92 | 38.084 | 25.813 | 0.643 | 1.00 | 14.89 | H C |
| ATOM | 1767 | OG | SER | H | 92 | 37.144 | 26.502 | −0.166 | 1.00 | 15.02 | H O |
| ATOM | 1768 | N | THR | H | 93 | 38.497 | 23.701 | 3.214 | 1.00 | 12.98 | H N |
| ATOM | 1769 | CA | THR | H | 93 | 39.461 | 23.020 | 4.072 | 1.00 | 13.34 | H C |
| ATOM | 1770 | C | THR | H | 93 | 39.182 | 21.531 | 4.309 | 1.00 | 14.82 | H C |
| ATOM | 1771 | O | THR | H | 93 | 39.994 | 20.840 | 4.916 | 1.00 | 15.40 | H O |
| ATOM | 1772 | CB | THR | H | 93 | 39.556 | 23.716 | 5.448 | 1.00 | 14.87 | H C |
| ATOM | 1773 | OG1 | THR | H | 93 | 38.249 | 23.788 | 6.033 | 1.00 | 11.15 | H O |
| ATOM | 1774 | CG2 | THR | H | 93 | 40.133 | 25.140 | 5.302 | 1.00 | 11.43 | H C |
| ATOM | 1775 | N | TYR | H | 94 | 38.040 | 21.033 | 3.847 | 1.00 | 14.91 | H N |
| ATOM | 1776 | CA | TYR | H | 94 | 37.724 | 19.618 | 4.024 | 1.00 | 14.16 | H C |
| ATOM | 1777 | C | TYR | H | 94 | 38.482 | 18.783 | 2.989 | 1.00 | 14.17 | H C |

-continued

| | | | | | | | | | | |
|---|---|---|---|---|---|---|---|---|---|---|
| ATOM | 1778 O | TYR | H | 94 | 38.558 | 19.151 | 1.822 | 1.00 | 14.26 | H O |
| ATOM | 1779 CB | TYR | H | 94 | 36.220 | 19.366 | 3.862 | 1.00 | 12.83 | H C |
| ATOM | 1780 CG | TYR | H | 94 | 35.874 | 17.888 | 3.785 | 1.00 | 11.02 | H C |
| ATOM | 1781 CD1 | TYR | H | 94 | 35.851 | 17.101 | 4.931 | 1.00 | 9.72 | H C |
| ATOM | 1782 CD2 | TYR | H | 94 | 35.656 | 17.264 | 2.552 | 1.00 | 11.67 | H C |
| ATOM | 1783 CE1 | TYR | H | 94 | 35.629 | 15.728 | 4.858 | 1.00 | 8.62 | H C |
| ATOM | 1784 CE2 | TYR | H | 94 | 35.433 | 15.888 | 2.467 | 1.00 | 8.29 | H C |
| ATOM | 1785 CZ | TYR | H | 94 | 35.424 | 15.130 | 3.631 | 1.00 | 9.43 | H C |
| ATOM | 1786 OH | TYR | H | 94 | 35.222 | 13.773 | 3.574 | 1.00 | 11.83 | H O |
| ATOM | 1787 N | VAL | H | 95 | 39.048 | 17.664 | 3.423 | 1.00 | 13.98 | H N |
| ATOM | 1788 CA | VAL | H | 95 | 39.771 | 16.775 | 2.519 | 1.00 | 13.14 | H C |
| ATOM | 1789 C | VAL | H | 95 | 39.041 | 15.431 | 2.436 | 1.00 | 12.82 | H C |
| ATOM | 1790 O | VAL | H | 95 | 38.845 | 14.761 | 3.444 | 1.00 | 13.46 | H O |
| ATOM | 1791 CB | VAL | H | 95 | 41.219 | 16.517 | 3.006 | 1.00 | 11.88 | H C |
| ATOM | 1792 CG1 | VAL | H | 95 | 41.922 | 15.540 | 2.062 | 1.00 | 10.92 | H C |
| ATOM | 1793 CG2 | VAL | H | 95 | 41.992 | 17.826 | 3.065 | 1.00 | 11.07 | H C |
| ATOM | 1794 N | PRO | H | 96 | 38.624 | 15.025 | 1.229 | 1.00 | 12.92 | H N |
| ATOM | 1795 CA | PRO | H | 96 | 37.922 | 13.749 | 1.062 | 1.00 | 11.72 | H C |
| ATOM | 1796 C | PRO | H | 96 | 38.730 | 12.604 | 1.675 | 1.00 | 13.96 | H C |
| ATOM | 1797 O | PRO | H | 96 | 39.957 | 12.548 | 1.525 | 1.00 | 15.05 | H O |
| ATOM | 1798 CB | PRO | H | 96 | 37.809 | 13.620 | −0.453 | 1.00 | 9.89 | H C |
| ATOM | 1799 CG | PRO | H | 96 | 37.671 | 15.048 | −0.885 | 1.00 | 12.78 | H C |
| ATOM | 1800 CD | PRO | H | 96 | 38.742 | 15.730 | −0.060 | 1.00 | 12.59 | H C |
| ATOM | 1801 N | GLY | H | 97 | 38.038 | 11.697 | 2.354 | 1.00 | 12.86 | H N |
| ATOM | 1802 CA | GLY | H | 97 | 38.698 | 10.574 | 2.986 | 1.00 | 13.45 | H C |
| ATOM | 1803 C | GLY | H | 97 | 39.107 | 10.871 | 4.418 | 1.00 | 15.29 | H C |
| ATOM | 1804 O | GLY | H | 97 | 39.539 | 9.967 | 5.131 | 1.00 | 15.13 | H O |
| ATOM | 1805 N | THR | H | 98 | 38.972 | 12.127 | 4.846 | 1.00 | 15.09 | H N |
| ATOM | 1806 CA | THR | H | 98 | 39.356 | 12.509 | 6.202 | 1.00 | 15.44 | H C |
| ATOM | 1807 C | THR | H | 98 | 38.173 | 12.924 | 7.082 | 1.00 | 15.39 | H C |
| ATOM | 1808 O | THR | H | 98 | 37.014 | 12.798 | 6.679 | 1.00 | 15.40 | H O |
| ATOM | 1809 CB | THR | H | 98 | 40.417 | 13.631 | 6.185 | 1.00 | 16.79 | H C |
| ATOM | 1810 OG1 | THR | H | 98 | 39.864 | 14.813 | 5.605 | 1.00 | 16.68 | H O |
| ATOM | 1811 CG2 | THR | H | 98 | 41.631 | 13.193 | 5.375 | 1.00 | 17.03 | H C |
| ATOM | 1812 N | THR | H | 99 | 38.469 | 13.433 | 8.275 | 1.00 | 14.02 | H N |
| ATOM | 1813 CA | THR | H | 99 | 37.429 | 13.783 | 9.236 | 1.00 | 14.07 | H C |
| ATOM | 1814 C | THR | H | 99 | 37.206 | 15.251 | 9.633 | 1.00 | 14.00 | H C |
| ATOM | 1815 O | THR | H | 99 | 36.111 | 15.605 | 10.086 | 1.00 | 11.58 | H O |
| ATOM | 1816 CB | THR | H | 99 | 37.643 | 12.963 | 10.532 | 1.00 | 16.74 | H C |
| ATOM | 1817 OG1 | THR | H | 99 | 38.973 | 13.187 | 11.022 | 1.00 | 17.73 | H O |
| ATOM | 1818 CG2 | THR | H | 99 | 37.468 | 11.465 | 10.265 | 1.00 | 15.58 | H C |
| ATOM | 1819 N | ASN | H | 100 | 38.219 | 16.102 | 9.473 | 1.00 | 11.56 | H N |
| ATOM | 1820 CA | ASN | H | 100 | 38.097 | 17.512 | 9.859 | 1.00 | 11.57 | H C |
| ATOM | 1821 C | ASN | H | 100 | 37.189 | 18.315 | 8.927 | 1.00 | 9.66 | H C |
| ATOM | 1822 O | ASN | H | 100 | 37.165 | 18.086 | 7.719 | 1.00 | 11.07 | H O |
| ATOM | 1823 CB | ASN | H | 100 | 39.485 | 18.181 | 9.911 | 1.00 | 9.81 | H C |
| ATOM | 1824 CG | ASN | H | 100 | 39.576 | 19.288 | 10.966 | 1.00 | 12.61 | H C |
| ATOM | 1825 OD1 | ASN | H | 100 | 40.498 | 20.112 | 10.939 | 1.00 | 15.96 | H O |
| ATOM | 1826 ND2 | ASN | H | 100 | 38.633 | 19.300 | 11.908 | 1.00 | 7.34 | H N |
| ATOM | 1827 N | HIS | H | 101 | 36.455 | 19.264 | 9.500 | 1.00 | 9.02 | H N |
| ATOM | 1828 CA | HIS | H | 101 | 35.552 | 20.124 | 8.738 | 1.00 | 10.03 | H C |
| ATOM | 1829 C | HIS | H | 101 | 34.503 | 19.292 | 8.017 | 1.00 | 9.38 | H C |
| ATOM | 1830 O | HIS | H | 101 | 34.188 | 19.544 | 6.857 | 1.00 | 8.47 | H O |
| ATOM | 1831 CB | HIS | H | 101 | 36.347 | 20.953 | 7.724 | 1.00 | 11.39 | H C |
| ATOM | 1832 CG | HIS | H | 101 | 37.353 | 21.868 | 8.352 | 1.00 | 16.40 | H C |
| ATOM | 1833 ND1 | HIS | H | 101 | 36.997 | 22.895 | 9.200 | 1.00 | 18.05 | H N |
| ATOM | 1834 CD2 | HIS | H | 101 | 38.705 | 21.882 | 8.293 | 1.00 | 17.22 | H C |
| ATOM | 1835 CE1 | HIS | H | 101 | 38.086 | 23.501 | 9.639 | 1.00 | 18.13 | H C |
| ATOM | 1836 NE2 | HIS | H | 101 | 39.137 | 22.906 | 9.103 | 1.00 | 17.47 | H N |
| ATOM | 1837 N | ASP | H | 102 | 33.958 | 18.305 | 8.720 | 1.00 | 8.97 | H N |
| ATOM | 1838 CA | ASP | H | 102 | 32.967 | 17.407 | 8.148 | 1.00 | 10.95 | H C |
| ATOM | 1839 C | ASP | H | 102 | 31.567 | 18.022 | 8.153 | 1.00 | 10.99 | H C |
| ATOM | 1840 O | ASP | H | 102 | 30.699 | 17.621 | 8.935 | 1.00 | 10.41 | H O |
| ATOM | 1841 CB | ASP | H | 102 | 32.971 | 16.092 | 8.928 | 1.00 | 9.16 | H C |
| ATOM | 1842 CG | ASP | H | 102 | 32.360 | 14.959 | 8.147 | 1.00 | 12.94 | H C |
| ATOM | 1843 OD1 | ASP | H | 102 | 32.039 | 15.173 | 6.976 | 1.00 | 11.04 | H O |
| ATOM | 1844 OD2 | ASP | H | 102 | 32.216 | 13.870 | 8.703 | 1.00 | 12.25 | H O |
| ATOM | 1845 N | ILE | H | 103 | 31.351 | 18.993 | 7.271 | 1.00 | 10.37 | H N |
| ATOM | 1846 CA | ILE | H | 103 | 30.061 | 19.672 | 7.192 | 1.00 | 8.57 | H C |
| ATOM | 1847 C | ILE | H | 103 | 29.730 | 20.071 | 5.760 | 1.00 | 9.30 | H C |
| ATOM | 1848 O | ILE | H | 103 | 30.621 | 20.374 | 4.962 | 1.00 | 8.92 | H O |
| ATOM | 1849 CB | ILE | H | 103 | 30.058 | 20.941 | 8.084 | 1.00 | 10.09 | H C |
| ATOM | 1850 CG1 | ILE | H | 103 | 28.677 | 21.607 | 8.072 | 1.00 | 7.85 | H C |
| ATOM | 1851 CG2 | ILE | H | 103 | 31.120 | 21.923 | 7.591 | 1.00 | 9.32 | H C |
| ATOM | 1852 CD1 | ILE | H | 103 | 28.502 | 22.665 | 9.152 | 1.00 | 11.15 | H C |
| ATOM | 1853 N | ALA | H | 104 | 28.442 | 20.055 | 5.437 | 1.00 | 9.70 | H N |
| ATOM | 1854 CA | ALA | H | 104 | 27.970 | 20.445 | 4.114 | 1.00 | 10.78 | H C |
| ATOM | 1855 C | ALA | H | 104 | 26.639 | 21.173 | 4.248 | 1.00 | 12.66 | H C |
| ATOM | 1856 O | ALA | H | 104 | 25.789 | 20.804 | 5.063 | 1.00 | 11.86 | H O |

-continued

| | | | | | | | | | | | |
|---|---|---|---|---|---|---|---|---|---|---|---|
| ATOM | 1857 | CB | ALA | H | 104 | 27.807 | 19.217 | 3.216 | 1.00 | 7.13 | H | C |
| ATOM | 1858 | N | LEU | H | 105 | 26.482 | 22.226 | 3.454 | 1.00 | 14.56 | H | N |
| ATOM | 1859 | CA | LEU | H | 105 | 25.258 | 23.016 | 3.426 | 1.00 | 12.91 | H | C |
| ATOM | 1860 | C | LEU | H | 105 | 24.640 | 22.753 | 2.057 | 1.00 | 12.76 | H | C |
| ATOM | 1861 | O | LEU | H | 105 | 25.243 | 23.065 | 1.029 | 1.00 | 12.63 | H | O |
| ATOM | 1862 | CB | LEU | H | 105 | 25.580 | 24.504 | 3.576 | 1.00 | 12.35 | H | C |
| ATOM | 1863 | CG | LEU | H | 105 | 24.389 | 25.466 | 3.494 | 1.00 | 12.09 | H | C |
| ATOM | 1864 | CD1 | LEU | H | 105 | 23.413 | 25.197 | 4.641 | 1.00 | 9.27 | H | C |
| ATOM | 1865 | CD2 | LEU | H | 105 | 24.903 | 26.892 | 3.560 | 1.00 | 9.24 | H | C |
| ATOM | 1866 | N | LEU | H | 106 | 23.445 | 22.172 | 2.046 | 1.00 | 12.35 | H | N |
| ATOM | 1867 | CA | LEU | H | 106 | 22.758 | 21.837 | 0.803 | 1.00 | 11.43 | H | C |
| ATOM | 1868 | C | LEU | H | 106 | 21.564 | 22.748 | 0.515 | 1.00 | 12.98 | H | C |
| ATOM | 1869 | O | LEU | H | 106 | 20.726 | 22.978 | 1.384 | 1.00 | 12.54 | H | O |
| ATOM | 1870 | CB | LEU | H | 106 | 22.285 | 20.380 | 0.859 | 1.00 | 12.53 | H | C |
| ATOM | 1871 | CG | LEU | H | 106 | 23.263 | 19.202 | 0.659 | 1.00 | 14.01 | H | C |
| ATOM | 1872 | CD1 | LEU | H | 106 | 24.503 | 19.322 | 1.539 | 1.00 | 12.26 | H | C |
| ATOM | 1873 | CD2 | LEU | H | 106 | 22.519 | 17.906 | 0.983 | 1.00 | 12.82 | H | C |
| ATOM | 1874 | N | ARG | H | 107 | 21.492 | 23.278 | −0.703 | 1.00 | 14.02 | H | N |
| ATOM | 1875 | CA | ARG | H | 107 | 20.370 | 24.128 | −1.077 | 1.00 | 16.64 | H | C |
| ATOM | 1876 | C | ARG | H | 107 | 19.397 | 23.266 | −1.873 | 1.00 | 16.72 | H | C |
| ATOM | 1877 | O | ARG | H | 107 | 19.791 | 22.591 | −2.819 | 1.00 | 18.56 | H | O |
| ATOM | 1878 | CB | ARG | H | 107 | 20.822 | 25.313 | −1.942 | 1.00 | 18.34 | H | C |
| ATOM | 1879 | CG | ARG | H | 107 | 19.754 | 26.410 | −2.081 | 1.00 | 20.80 | H | C |
| ATOM | 1880 | CD | ARG | H | 107 | 19.992 | 27.301 | −3.302 | 1.00 | 26.37 | H | C |
| ATOM | 1881 | NE | ARG | H | 107 | 21.234 | 28.069 | −3.224 | 1.00 | 29.38 | H | N |
| ATOM | 1882 | CZ | ARG | H | 107 | 21.321 | 29.337 | −2.827 | 1.00 | 30.69 | H | C |
| ATOM | 1883 | NH1 | ARG | H | 107 | 20.233 | 30.007 | −2.463 | 1.00 | 31.39 | H | N |
| ATOM | 1884 | NH2 | ARG | H | 107 | 22.503 | 29.940 | −2.798 | 1.00 | 29.68 | H | N |
| ATOM | 1885 | N | LEU | H | 108 | 18.131 | 23.280 | −1.480 | 1.00 | 16.62 | H | N |
| ATOM | 1886 | CA | LEU | H | 108 | 17.114 | 22.500 | −2.170 | 1.00 | 17.28 | H | C |
| ATOM | 1887 | C | LEU | H | 108 | 16.608 | 23.281 | −3.385 | 1.00 | 18.87 | H | C |
| ATOM | 1888 | O | LEU | H | 108 | 16.532 | 24.510 | −3.349 | 1.00 | 18.26 | H | O |
| ATOM | 1889 | CB | LEU | H | 108 | 15.962 | 22.188 | −1.208 | 1.00 | 15.65 | H | C |
| ATOM | 1890 | CG | LEU | H | 108 | 16.352 | 21.391 | 0.050 | 1.00 | 14.18 | H | C |
| ATOM | 1891 | CD1 | LEU | H | 108 | 15.134 | 21.191 | 0.953 | 1.00 | 10.37 | H | C |
| ATOM | 1892 | CD2 | LEU | H | 108 | 16.942 | 20.041 | −0.361 | 1.00 | 11.86 | H | C |
| ATOM | 1893 | N | HIS | H | 109 | 16.273 | 22.568 | −4.457 | 1.00 | 20.64 | H | N |
| ATOM | 1894 | CA | HIS | H | 109 | 15.790 | 23.205 | −5.683 | 1.00 | 22.07 | H | C |
| ATOM | 1895 | C | HIS | H | 109 | 14.546 | 24.054 | −5.430 | 1.00 | 21.71 | H | C |
| ATOM | 1896 | O | HIS | H | 109 | 14.399 | 25.139 | −5.986 | 1.00 | 21.72 | H | O |
| ATOM | 1897 | CB | HIS | H | 109 | 15.467 | 22.155 | −6.746 | 1.00 | 24.90 | H | C |
| ATOM | 1898 | CG | HIS | H | 109 | 15.022 | 22.742 | −8.048 | 1.00 | 28.69 | H | C |
| ATOM | 1899 | ND1 | HIS | H | 109 | 13.921 | 22.279 | −8.738 | 1.00 | 31.80 | H | N |
| ATOM | 1900 | CD2 | HIS | H | 109 | 15.525 | 23.762 | −8.784 | 1.00 | 30.89 | H | C |
| ATOM | 1901 | CE1 | HIS | H | 109 | 13.766 | 22.989 | −9.842 | 1.00 | 31.18 | H | C |
| ATOM | 1902 | NE2 | HIS | H | 109 | 14.726 | 23.895 | −9.894 | 1.00 | 30.63 | H | N |
| ATOM | 1903 | N | GLN | H | 110 | 13.647 | 23.541 | −4.603 | 1.00 | 19.28 | H | N |
| ATOM | 1904 | CA | GLN | H | 110 | 12.430 | 24.252 | −4.258 | 1.00 | 21.37 | H | C |
| ATOM | 1905 | C | GLN | H | 110 | 12.219 | 24.059 | −2.766 | 1.00 | 19.91 | H | C |
| ATOM | 1906 | O | GLN | H | 110 | 12.566 | 23.014 | −2.210 | 1.00 | 19.14 | H | O |
| ATOM | 1907 | CB | GLN | H | 110 | 11.230 | 23.689 | −5.030 | 1.00 | 24.70 | H | C |
| ATOM | 1908 | CG | GLN | H | 110 | 11.340 | 23.814 | −6.551 | 1.00 | 33.11 | H | C |
| ATOM | 1909 | CD | GLN | H | 110 | 11.188 | 25.245 | −7.075 | 1.00 | 37.50 | H | C |
| ATOM | 1910 | OE1 | GLN | H | 110 | 11.434 | 25.505 | −8.254 | 1.00 | 42.27 | H | O |
| ATOM | 1911 | NE2 | GLN | H | 110 | 10.772 | 26.168 | −6.212 | 1.00 | 40.37 | H | N |
| ATOM | 1912 | N | PRO | H | 111 | 11.643 | 25.062 | −2.096 | 1.00 | 17.61 | H | N |
| ATOM | 1913 | CA | PRO | H | 111 | 11.406 | 24.959 | −0.657 | 1.00 | 18.39 | H | C |
| ATOM | 1914 | C | PRO | H | 111 | 10.409 | 23.869 | −0.306 | 1.00 | 18.13 | H | C |
| ATOM | 1915 | O | PRO | H | 111 | 9.472 | 23.615 | −1.056 | 1.00 | 18.29 | H | O |
| ATOM | 1916 | CB | PRO | H | 111 | 10.882 | 26.348 | −0.299 | 1.00 | 18.48 | H | C |
| ATOM | 1917 | CG | PRO | H | 111 | 10.127 | 26.733 | −1.540 | 1.00 | 17.21 | H | C |
| ATOM | 1918 | CD | PRO | H | 111 | 11.091 | 26.319 | −2.632 | 1.00 | 15.77 | H | C |
| ATOM | 1919 | N | VAL | H | 112 | 10.624 | 23.215 | 0.831 | 1.00 | 17.13 | H | N |
| ATOM | 1920 | CA | VAL | H | 112 | 9.700 | 22.189 | 1.286 | 1.00 | 17.69 | H | C |
| ATOM | 1921 | C | VAL | H | 112 | 8.573 | 22.915 | 2.013 | 1.00 | 16.47 | H | C |
| ATOM | 1922 | O | VAL | H | 112 | 8.708 | 24.088 | 2.364 | 1.00 | 15.80 | H | O |
| ATOM | 1923 | CB | VAL | H | 112 | 10.371 | 21.195 | 2.261 | 1.00 | 17.46 | H | C |
| ATOM | 1924 | CG1 | VAL | H | 112 | 11.412 | 20.374 | 1.526 | 1.00 | 19.26 | H | C |
| ATOM | 1925 | CG2 | VAL | H | 112 | 10.996 | 21.945 | 3.419 | 1.00 | 15.83 | H | C |
| ATOM | 1926 | N | VAL | H | 113 | 7.463 | 22.222 | 2.228 | 1.00 | 15.47 | H | N |
| ATOM | 1927 | CA | VAL | H | 113 | 6.316 | 22.806 | 2.912 | 1.00 | 13.75 | H | C |
| ATOM | 1928 | C | VAL | H | 113 | 6.395 | 22.459 | 4.394 | 1.00 | 14.36 | H | C |
| ATOM | 1929 | O | VAL | H | 113 | 6.542 | 21.290 | 4.759 | 1.00 | 12.82 | H | O |
| ATOM | 1930 | CB | VAL | H | 113 | 4.983 | 22.247 | 2.353 | 1.00 | 13.88 | H | C |
| ATOM | 1931 | CG1 | VAL | H | 113 | 3.808 | 22.974 | 2.993 | 1.00 | 10.56 | H | C |
| ATOM | 1932 | CG2 | VAL | H | 113 | 4.951 | 22.381 | 0.821 | 1.00 | 12.19 | H | C |
| ATOM | 1933 | N | LEU | H | 114 | 6.305 | 23.467 | 5.253 | 1.00 | 13.94 | H | N |
| ATOM | 1934 | CA | LEU | H | 114 | 6.363 | 23.199 | 6.679 | 1.00 | 15.06 | H | C |
| ATOM | 1935 | C | LEU | H | 114 | 5.017 | 22.632 | 7.122 | 1.00 | 15.96 | H | C |

-continued

| | | | | | | | | | | | |
|---|---|---|---|---|---|---|---|---|---|---|---|
| ATOM | 1936 | O | LEU | H | 114 | 3.968 | 23.236 | 6.898 | 1.00 | 15.97 | H | O |
| ATOM | 1937 | CB | LEU | H | 114 | 6.710 | 24.475 | 7.454 | 1.00 | 13.15 | H | C |
| ATOM | 1938 | CG | LEU | H | 114 | 8.090 | 25.081 | 7.135 | 1.00 | 15.88 | H | C |
| ATOM | 1939 | CD1 | LEU | H | 114 | 8.406 | 26.194 | 8.129 | 1.00 | 13.86 | H | C |
| ATOM | 1940 | CD2 | LEU | H | 114 | 9.173 | 23.999 | 7.194 | 1.00 | 11.78 | H | C |
| ATOM | 1941 | N | THR | H | 115 | 5.057 | 21.453 | 7.732 | 1.00 | 14.58 | H | N |
| ATOM | 1942 | CA | THR | H | 115 | 3.846 | 20.791 | 8.197 | 1.00 | 15.14 | H | C |
| ATOM | 1943 | C | THR | H | 115 | 4.087 | 20.219 | 9.591 | 1.00 | 14.81 | H | C |
| ATOM | 1944 | O | THR | H | 115 | 5.158 | 20.404 | 10.168 | 1.00 | 15.34 | H | O |
| ATOM | 1945 | CB | THR | H | 115 | 3.462 | 19.627 | 7.268 | 1.00 | 14.99 | H | C |
| ATOM | 1946 | OG1 | THR | H | 115 | 4.431 | 18.580 | 7.406 | 1.00 | 15.74 | H | O |
| ATOM | 1947 | CG2 | THR | H | 115 | 3.419 | 20.084 | 5.805 | 1.00 | 13.98 | H | C |
| ATOM | 1948 | N | ASP | H | 116 | 3.094 | 19.523 | 10.130 | 1.00 | 15.45 | H | N |
| ATOM | 1949 | CA | ASP | H | 116 | 3.244 | 18.904 | 11.437 | 1.00 | 16.55 | H | C |
| ATOM | 1950 | C | ASP | H | 116 | 4.359 | 17.849 | 11.416 | 1.00 | 17.00 | H | C |
| ATOM | 1951 | O | ASP | H | 116 | 4.913 | 17.519 | 12.460 | 1.00 | 16.90 | H | O |
| ATOM | 1952 | CB | ASP | H | 116 | 1.934 | 18.244 | 11.883 | 1.00 | 18.41 | H | C |
| ATOM | 1953 | CG | ASP | H | 116 | 0.866 | 19.254 | 12.283 | 1.00 | 20.47 | H | C |
| ATOM | 1954 | OD1 | ASP | H | 116 | 1.166 | 20.431 | 12.388 | 1.00 | 20.75 | H | O |
| ATOM | 1955 | OD2 | ASP | H | 116 | −0.270 | 18.844 | 12.496 | 1.00 | 23.70 | H | O |
| ATOM | 1956 | N | HIS | H | 117 | 4.687 | 17.326 | 10.233 | 1.00 | 15.90 | H | N |
| ATOM | 1957 | CA | HIS | H | 117 | 5.733 | 16.307 | 10.105 | 1.00 | 16.55 | H | C |
| ATOM | 1958 | C | HIS | H | 117 | 7.041 | 16.802 | 9.492 | 1.00 | 16.30 | H | C |
| ATOM | 1959 | O | HIS | H | 117 | 8.001 | 16.040 | 9.372 | 1.00 | 15.70 | H | O |
| ATOM | 1960 | CB | HIS | H | 117 | 5.217 | 15.115 | 9.297 | 1.00 | 16.16 | H | C |
| ATOM | 1961 | CG | HIS | H | 117 | 4.102 | 14.384 | 9.970 | 1.00 | 19.31 | H | C |
| ATOM | 1962 | ND1 | HIS | H | 117 | 2.808 | 14.857 | 9.986 | 1.00 | 18.50 | H | N |
| ATOM | 1963 | CD2 | HIS | H | 117 | 4.103 | 13.259 | 10.723 | 1.00 | 17.50 | H | C |
| ATOM | 1964 | CE1 | HIS | H | 117 | 2.059 | 14.056 | 10.723 | 1.00 | 21.07 | H | C |
| ATOM | 1965 | NE2 | HIS | H | 117 | 2.821 | 13.080 | 11.182 | 1.00 | 20.92 | H | N |
| ATOM | 1966 | N | VAL | H | 118 | 7.078 | 18.072 | 9.103 | 1.00 | 15.64 | H | N |
| ATOM | 1967 | CA | VAL | H | 118 | 8.276 | 18.655 | 8.511 | 1.00 | 14.14 | H | C |
| ATOM | 1968 | C | VAL | H | 118 | 8.493 | 20.041 | 9.095 | 1.00 | 14.78 | H | C |
| ATOM | 1969 | O | VAL | H | 118 | 7.784 | 20.984 | 8.762 | 1.00 | 14.27 | H | O |
| ATOM | 1970 | CB | VAL | H | 118 | 8.148 | 18.761 | 6.990 | 1.00 | 14.64 | H | C |
| ATOM | 1971 | CG1 | VAL | H | 118 | 9.381 | 19.463 | 6.413 | 1.00 | 12.73 | H | C |
| ATOM | 1972 | CG2 | VAL | H | 118 | 7.983 | 17.367 | 6.393 | 1.00 | 12.56 | H | C |
| ATOM | 1973 | N | VAL | H | 119 | 9.486 | 20.147 | 9.970 | 1.00 | 15.25 | H | N |
| ATOM | 1974 | CA | VAL | H | 119 | 9.808 | 21.394 | 10.653 | 1.00 | 13.86 | H | C |
| ATOM | 1975 | C | VAL | H | 119 | 11.329 | 21.501 | 10.766 | 1.00 | 14.17 | H | C |
| ATOM | 1976 | O | VAL | H | 119 | 12.017 | 20.499 | 10.956 | 1.00 | 13.56 | H | O |
| ATOM | 1977 | CB | VAL | H | 119 | 9.177 | 21.390 | 12.081 | 1.00 | 15.77 | H | C |
| ATOM | 1978 | CG1 | VAL | H | 119 | 9.570 | 22.641 | 12.856 | 1.00 | 16.33 | H | C |
| ATOM | 1979 | CG2 | VAL | H | 119 | 7.656 | 21.285 | 11.974 | 1.00 | 16.16 | H | C |
| ATOM | 1980 | N | PRO | H | 120 | 11.875 | 22.718 | 10.644 | 1.00 | 13.65 | H | N |
| ATOM | 1981 | CA | PRO | H | 120 | 13.325 | 22.881 | 10.746 | 1.00 | 12.56 | H | C |
| ATOM | 1982 | C | PRO | H | 120 | 13.817 | 22.966 | 12.189 | 1.00 | 13.87 | H | C |
| ATOM | 1983 | O | PRO | H | 120 | 13.085 | 23.398 | 13.086 | 1.00 | 11.70 | H | O |
| ATOM | 1984 | CB | PRO | H | 120 | 13.573 | 24.172 | 9.981 | 1.00 | 12.13 | H | C |
| ATOM | 1985 | CG | PRO | H | 120 | 12.355 | 24.978 | 10.315 | 1.00 | 15.18 | H | C |
| ATOM | 1986 | CD | PRO | H | 120 | 11.230 | 23.971 | 10.203 | 1.00 | 14.55 | H | C |
| ATOM | 1987 | N | LEU | H | 121 | 15.054 | 22.521 | 12.403 | 1.00 | 12.25 | H | N |
| ATOM | 1988 | CA | LEU | H | 121 | 15.688 | 22.577 | 13.713 | 1.00 | 11.41 | H | C |
| ATOM | 1989 | C | LEU | H | 121 | 16.359 | 23.944 | 13.719 | 1.00 | 12.91 | H | C |
| ATOM | 1990 | O | LEU | H | 121 | 16.826 | 24.394 | 12.676 | 1.00 | 12.87 | H | O |
| ATOM | 1991 | CB | LEU | H | 121 | 16.747 | 21.472 | 13.838 | 1.00 | 10.88 | H | C |
| ATOM | 1992 | CG | LEU | H | 121 | 17.592 | 21.380 | 15.124 | 1.00 | 9.26 | H | C |
| ATOM | 1993 | CD1 | LEU | H | 121 | 16.692 | 21.104 | 16.320 | 1.00 | 7.01 | H | C |
| ATOM | 1994 | CD2 | LEU | H | 121 | 18.640 | 20.259 | 14.978 | 1.00 | 7.10 | H | C |
| ATOM | 1995 | N | CYS | H | 122 | 16.409 | 24.610 | 14.867 | 1.00 | 13.27 | H | N |
| ATOM | 1996 | CA | CYS | H | 122 | 17.034 | 25.932 | 14.925 | 1.00 | 15.06 | H | C |
| ATOM | 1997 | C | CYS | H | 122 | 18.556 | 25.919 | 14.874 | 1.00 | 15.31 | H | C |
| ATOM | 1998 | O | CYS | H | 122 | 19.202 | 25.139 | 15.571 | 1.00 | 16.54 | H | O |
| ATOM | 1999 | CB | CYS | H | 122 | 16.657 | 26.684 | 16.205 | 1.00 | 15.03 | H | C |
| ATOM | 2000 | SG | CYS | H | 122 | 14.893 | 26.918 | 16.573 | 1.00 | 16.60 | H | S |
| ATOM | 2001 | N | LEU | H | 123 | 19.119 | 26.793 | 14.046 | 1.00 | 14.53 | H | N |
| ATOM | 2002 | CA | LEU | H | 123 | 20.560 | 26.955 | 13.970 | 1.00 | 12.48 | H | C |
| ATOM | 2003 | C | LEU | H | 123 | 20.747 | 28.048 | 15.018 | 1.00 | 12.30 | H | C |
| ATOM | 2004 | O | LEU | H | 123 | 20.207 | 29.149 | 14.876 | 1.00 | 13.28 | H | O |
| ATOM | 2005 | CB | LEU | H | 123 | 20.991 | 27.466 | 12.590 | 1.00 | 11.93 | H | C |
| ATOM | 2006 | CG | LEU | H | 123 | 22.513 | 27.606 | 12.445 | 1.00 | 12.58 | H | C |
| ATOM | 2007 | CD1 | LEU | H | 123 | 23.142 | 26.211 | 12.479 | 1.00 | 9.53 | H | C |
| ATOM | 2008 | CD2 | LEU | H | 123 | 22.865 | 28.312 | 11.147 | 1.00 | 10.47 | H | C |
| ATOM | 2009 | N | PRO | H | 124 | 21.497 | 27.762 | 16.093 | 1.00 | 12.74 | H | N |
| ATOM | 2010 | CA | PRO | H | 124 | 21.708 | 28.760 | 17.149 | 1.00 | 12.16 | H | C |
| ATOM | 2011 | C | PRO | H | 124 | 22.827 | 29.747 | 16.881 | 1.00 | 13.37 | H | C |
| ATOM | 2012 | O | PRO | H | 124 | 23.639 | 29.535 | 15.984 | 1.00 | 13.97 | H | O |
| ATOM | 2013 | CB | PRO | H | 124 | 22.031 | 27.897 | 18.356 | 1.00 | 10.72 | H | C |
| ATOM | 2014 | CG | PRO | H | 124 | 22.924 | 26.839 | 17.730 | 1.00 | 12.77 | H | C |

| | | | | -continued | | | | | | | |
|---|---|---|---|---|---|---|---|---|---|---|---|
| ATOM | 2015 | CD | PRO | H | 124 | 22.205 | 26.505 | 16.408 | 1.00 | 10.59 | H | C |
| ATOM | 2016 | N | GLU | H | 125 | 22.860 | 30.831 | 17.657 | 1.00 | 13.81 | H | N |
| ATOM | 2017 | CA | GLU | H | 125 | 23.947 | 31.800 | 17.533 | 1.00 | 14.83 | H | C |
| ATOM | 2018 | C | GLU | H | 125 | 25.145 | 31.082 | 18.149 | 1.00 | 14.18 | H | C |
| ATOM | 2019 | O | GLU | H | 125 | 24.975 | 30.182 | 18.972 | 1.00 | 13.59 | H | O |
| ATOM | 2020 | CB | GLU | H | 125 | 23.656 | 33.085 | 18.319 | 1.00 | 15.94 | H | C |
| ATOM | 2021 | CG | GLU | H | 125 | 22.528 | 33.918 | 17.745 | 1.00 | 20.23 | H | C |
| ATOM | 2022 | CD | GLU | H | 125 | 22.427 | 35.292 | 18.380 | 1.00 | 23.56 | H | C |
| ATOM | 2023 | OE1 | GLU | H | 125 | 22.850 | 35.449 | 19.526 | 1.00 | 21.49 | H | O |
| ATOM | 2024 | OE2 | GLU | H | 125 | 21.912 | 36.198 | 17.728 | 1.00 | 25.49 | H | O |
| ATOM | 2025 | N | ARG | H | 126 | 26.350 | 31.477 | 17.759 | 1.00 | 15.26 | H | N |
| ATOM | 2026 | CA | ARG | H | 126 | 27.557 | 30.836 | 18.258 | 1.00 | 16.72 | H | C |
| ATOM | 2027 | C | ARG | H | 126 | 27.793 | 30.894 | 19.772 | 1.00 | 16.72 | H | C |
| ATOM | 2028 | O | ARG | H | 126 | 28.012 | 29.854 | 20.397 | 1.00 | 15.77 | H | O |
| ATOM | 2029 | CB | ARG | H | 126 | 28.787 | 31.399 | 17.550 | 1.00 | 18.05 | H | C |
| ATOM | 2030 | CG | ARG | H | 126 | 30.075 | 30.784 | 18.054 | 1.00 | 23.13 | H | C |
| ATOM | 2031 | CD | ARG | H | 126 | 31.236 | 31.724 | 17.874 | 1.00 | 28.03 | H | C |
| ATOM | 2032 | NE | ARG | H | 126 | 31.769 | 31.681 | 16.524 | 1.00 | 30.56 | H | N |
| ATOM | 2033 | CZ | ARG | H | 126 | 32.772 | 30.897 | 16.141 | 1.00 | 33.42 | H | C |
| ATOM | 2034 | NH1 | ARG | H | 126 | 33.356 | 30.081 | 17.011 | 1.00 | 33.03 | H | N |
| ATOM | 2035 | NH2 | ARG | H | 126 | 33.199 | 30.945 | 14.886 | 1.00 | 33.65 | H | N |
| ATOM | 2036 | N | THR | H | 127 | 27.764 | 32.086 | 20.365 | 1.00 | 15.89 | H | N |
| ATOM | 2037 | CA | THR | H | 127 | 28.020 | 32.191 | 21.803 | 1.00 | 16.74 | H | C |
| ATOM | 2038 | C | THR | H | 127 | 26.976 | 31.448 | 22.634 | 1.00 | 15.42 | H | C |
| ATOM | 2039 | O | THR | H | 127 | 27.320 | 30.816 | 23.630 | 1.00 | 15.65 | H | O |
| ATOM | 2040 | CB | THR | H | 127 | 28.124 | 33.669 | 22.277 | 1.00 | 19.12 | H | C |
| ATOM | 2041 | OG1 | THR | H | 127 | 26.860 | 34.323 | 22.127 | 1.00 | 23.54 | H | O |
| ATOM | 2042 | CG2 | THR | H | 127 | 29.175 | 34.413 | 21.461 | 1.00 | 18.93 | H | C |
| ATOM | 2043 | N | PHE | H | 128 | 25.710 | 31.522 | 22.234 | 1.00 | 12.93 | H | N |
| ATOM | 2044 | CA | PHE | H | 128 | 24.650 | 30.798 | 22.938 | 1.00 | 12.70 | H | C |
| ATOM | 2045 | C | PHE | H | 128 | 25.006 | 29.307 | 22.929 | 1.00 | 11.77 | H | C |
| ATOM | 2046 | O | PHE | H | 128 | 24.971 | 28.643 | 23.963 | 1.00 | 11.84 | H | O |
| ATOM | 2047 | CB | PHE | H | 128 | 23.300 | 31.019 | 22.232 | 1.00 | 11.78 | H | C |
| ATOM | 2048 | CG | PHE | H | 128 | 22.186 | 30.092 | 22.694 | 1.00 | 11.98 | H | C |
| ATOM | 2049 | CD1 | PHE | H | 128 | 21.783 | 30.057 | 24.026 | 1.00 | 13.78 | H | C |
| ATOM | 2050 | CD2 | PHE | H | 128 | 21.498 | 29.306 | 21.773 | 1.00 | 9.96 | H | C |
| ATOM | 2051 | CE1 | PHE | H | 128 | 20.704 | 29.256 | 24.437 | 1.00 | 12.05 | H | C |
| ATOM | 2052 | CE2 | PHE | H | 128 | 20.423 | 28.504 | 22.163 | 1.00 | 10.60 | H | C |
| ATOM | 2053 | CZ | PHE | H | 128 | 20.021 | 28.480 | 23.503 | 1.00 | 12.84 | H | C |
| ATOM | 2054 | N | SER | H | 129 | 25.364 | 28.792 | 21.757 | 1.00 | 11.50 | H | N |
| ATOM | 2055 | CA | SER | H | 129 | 25.712 | 27.383 | 21.622 | 1.00 | 12.61 | H | C |
| ATOM | 2056 | C | SER | H | 129 | 26.962 | 26.998 | 22.417 | 1.00 | 12.76 | H | C |
| ATOM | 2057 | O | SER | H | 129 | 27.008 | 25.929 | 23.023 | 1.00 | 12.80 | H | O |
| ATOM | 2058 | CB | SER | H | 129 | 25.908 | 27.029 | 20.145 | 1.00 | 12.21 | H | C |
| ATOM | 2059 | OG | SER | H | 129 | 26.052 | 25.624 | 19.977 | 1.00 | 17.13 | H | O |
| ATOM | 2060 | N | GLU | H | 129A | 27.969 | 27.868 | 22.420 | 1.00 | 13.31 | H | N |
| ATOM | 2061 | CA | GLU | H | 129A | 29.217 | 27.603 | 23.136 | 1.00 | 14.09 | H | C |
| ATOM | 2062 | C | GLU | H | 129A | 29.128 | 27.730 | 24.657 | 1.00 | 14.85 | H | C |
| ATOM | 2063 | O | GLU | H | 129A | 29.707 | 26.921 | 25.382 | 1.00 | 14.98 | H | O |
| ATOM | 2064 | CB | GLU | H | 129A | 30.328 | 28.542 | 22.639 | 1.00 | 14.74 | H | C |
| ATOM | 2065 | CG | GLU | H | 129A | 30.715 | 28.369 | 21.172 | 1.00 | 14.19 | H | C |
| ATOM | 2066 | CD | GLU | H | 129A | 31.780 | 29.367 | 20.745 | 1.00 | 16.54 | H | C |
| ATOM | 2067 | OE1 | GLU | H | 129A | 31.941 | 30.368 | 21.432 | 1.00 | 16.37 | H | O |
| ATOM | 2068 | OE2 | GLU | H | 129A | 32.431 | 29.146 | 19.728 | 1.00 | 17.94 | H | O |
| ATOM | 2069 | N | ARG | H | 129B | 28.410 | 28.739 | 25.145 | 1.00 | 15.04 | H | N |
| ATOM | 2070 | CA | ARG | H | 129B | 28.310 | 28.957 | 26.589 | 1.00 | 16.21 | H | C |
| ATOM | 2071 | C | ARG | H | 129B | 27.114 | 28.309 | 27.267 | 1.00 | 14.62 | H | C |
| ATOM | 2072 | O | ARG | H | 129B | 27.124 | 28.110 | 28.479 | 1.00 | 14.82 | H | O |
| ATOM | 2073 | CB | ARG | H | 129B | 28.296 | 30.460 | 26.904 | 1.00 | 19.47 | H | C |
| ATOM | 2074 | CG | ARG | H | 129B | 27.031 | 31.161 | 26.451 | 1.00 | 28.02 | H | C |
| ATOM | 2075 | CD | ARG | H | 129B | 26.919 | 32.605 | 26.946 | 1.00 | 33.00 | H | C |
| ATOM | 2076 | NE | ARG | H | 129B | 27.978 | 33.478 | 26.447 | 1.00 | 36.47 | H | N |
| ATOM | 2077 | CZ | ARG | H | 129B | 27.822 | 34.777 | 26.197 | 1.00 | 38.35 | H | C |
| ATOM | 2078 | NH1 | ARG | H | 129B | 26.645 | 35.360 | 26.391 | 1.00 | 38.64 | H | N |
| ATOM | 2079 | NH2 | ARG | H | 129B | 28.845 | 35.500 | 25.757 | 1.00 | 36.71 | H | N |
| ATOM | 2080 | N | THR | H | 129C | 26.079 | 27.984 | 26.503 | 1.00 | 13.48 | H | N |
| ATOM | 2081 | CA | THR | H | 129C | 24.897 | 27.378 | 27.094 | 1.00 | 12.08 | H | C |
| ATOM | 2082 | C | THR | H | 129C | 24.611 | 25.974 | 26.574 | 1.00 | 12.22 | H | C |
| ATOM | 2083 | O | THR | H | 129C | 24.631 | 25.021 | 27.344 | 1.00 | 12.56 | H | O |
| ATOM | 2084 | CB | THR | H | 129C | 23.643 | 28.263 | 26.872 | 1.00 | 13.41 | H | C |
| ATOM | 2085 | OG1 | THR | H | 129C | 23.841 | 29.541 | 27.496 | 1.00 | 12.83 | H | O |
| ATOM | 2086 | CG2 | THR | H | 129C | 22.411 | 27.604 | 27.472 | 1.00 | 13.85 | H | C |
| ATOM | 2087 | N | LEU | H | 129D | 24.358 | 25.839 | 25.273 | 1.00 | 9.80 | H | N |
| ATOM | 2088 | CA | LEU | H | 129D | 24.043 | 24.533 | 24.706 | 1.00 | 9.83 | H | C |
| ATOM | 2089 | C | LEU | H | 129D | 25.121 | 23.466 | 24.903 | 1.00 | 10.51 | H | C |
| ATOM | 2090 | O | LEU | H | 129D | 24.802 | 22.292 | 25.092 | 1.00 | 9.04 | H | O |
| ATOM | 2091 | CB | LEU | H | 129D | 23.717 | 24.661 | 23.215 | 1.00 | 9.11 | H | C |
| ATOM | 2092 | CG | LEU | H | 129D | 22.473 | 25.482 | 22.856 | 1.00 | 10.88 | H | C |
| ATOM | 2093 | CD1 | LEU | H | 129D | 22.268 | 25.452 | 21.349 | 1.00 | 7.76 | H | C |

-continued

| | | | | | | | | | | | |
|---|---|---|---|---|---|---|---|---|---|---|---|
| ATOM | 2094 | CD2 | LEU | H | 129D | 21.249 | 24.927 | 23.580 | 1.00 | 8.60 | H | C |
| ATOM | 2095 | N | ALA | H | 129E | 26.388 | 23.871 | 24.874 | 1.00 | 9.50 | H | N |
| ATOM | 2096 | CA | ALA | H | 129E | 27.495 | 22.929 | 25.038 | 1.00 | 11.11 | H | C |
| ATOM | 2097 | C | ALA | H | 129E | 27.527 | 22.284 | 26.417 | 1.00 | 12.05 | H | C |
| ATOM | 2098 | O | ALA | H | 129E | 28.209 | 21.277 | 26.614 | 1.00 | 14.06 | H | O |
| ATOM | 2099 | CB | ALA | H | 129E | 28.828 | 23.627 | 24.768 | 1.00 | 8.33 | H | C |
| ATOM | 2100 | N | PHE | H | 129F | 26.794 | 22.848 | 27.372 | 1.00 | 11.37 | H | N |
| ATOM | 2101 | CA | PHE | H | 129F | 26.793 | 22.291 | 28.714 | 1.00 | 11.44 | H | C |
| ATOM | 2102 | C | PHE | H | 129F | 25.513 | 21.561 | 29.108 | 1.00 | 11.62 | H | C |
| ATOM | 2103 | O | PHE | H | 129F | 25.328 | 21.163 | 30.260 | 1.00 | 10.42 | H | O |
| ATOM | 2104 | CB | PHE | H | 129F | 27.180 | 23.386 | 29.714 | 1.00 | 13.71 | H | C |
| ATOM | 2105 | CG | PHE | H | 129F | 28.562 | 23.937 | 29.469 | 1.00 | 12.82 | H | C |
| ATOM | 2106 | CD1 | PHE | H | 129F | 29.669 | 23.090 | 29.491 | 1.00 | 13.92 | H | C |
| ATOM | 2107 | CD2 | PHE | H | 129F | 28.749 | 25.275 | 29.148 | 1.00 | 13.07 | H | C |
| ATOM | 2108 | CE1 | PHE | H | 129F | 30.944 | 23.567 | 29.190 | 1.00 | 15.14 | H | C |
| ATOM | 2109 | CE2 | PHE | H | 129F | 30.017 | 25.765 | 28.844 | 1.00 | 13.32 | H | C |
| ATOM | 2110 | CZ | PHE | H | 129F | 31.118 | 24.911 | 28.863 | 1.00 | 14.84 | H | C |
| ATOM | 2111 | N | VAL | H | 129G | 24.633 | 21.380 | 28.132 | 1.00 | 11.71 | H | N |
| ATOM | 2112 | CA | VAL | H | 129G | 23.418 | 20.617 | 28.339 | 1.00 | 10.87 | H | C |
| ATOM | 2113 | C | VAL | H | 129G | 23.969 | 19.201 | 28.125 | 1.00 | 12.85 | H | C |
| ATOM | 2114 | O | VAL | H | 129G | 24.514 | 18.886 | 27.062 | 1.00 | 12.09 | H | O |
| ATOM | 2115 | CB | VAL | H | 129G | 22.344 | 20.956 | 27.271 | 1.00 | 10.74 | H | C |
| ATOM | 2116 | CG1 | VAL | H | 129G | 21.203 | 19.946 | 27.329 | 1.00 | 8.96 | H | C |
| ATOM | 2117 | CG2 | VAL | H | 129G | 21.806 | 22.372 | 27.510 | 1.00 | 9.81 | H | C |
| ATOM | 2118 | N | ARG | H | 134 | 23.847 | 18.367 | 29.147 | 1.00 | 12.84 | H | N |
| ATOM | 2119 | CA | ARG | H | 134 | 24.368 | 17.008 | 29.114 | 1.00 | 14.10 | H | C |
| ATOM | 2120 | C | ARG | H | 134 | 23.977 | 16.147 | 27.909 | 1.00 | 14.87 | H | C |
| ATOM | 2121 | O | ARG | H | 134 | 24.831 | 15.767 | 27.104 | 1.00 | 14.59 | H | O |
| ATOM | 2122 | CB | ARG | H | 134 | 23.960 | 16.281 | 30.400 | 1.00 | 14.36 | H | C |
| ATOM | 2123 | CG | ARG | H | 134 | 24.450 | 14.840 | 30.485 | 1.00 | 17.60 | H | C |
| ATOM | 2124 | CD | ARG | H | 134 | 25.916 | 14.769 | 30.854 | 1.00 | 20.10 | H | C |
| ATOM | 2125 | NE | ARG | H | 134 | 26.154 | 15.328 | 32.182 | 1.00 | 21.14 | H | N |
| ATOM | 2126 | CZ | ARG | H | 134 | 27.311 | 15.262 | 32.832 | 1.00 | 19.89 | H | C |
| ATOM | 2127 | NH1 | ARG | H | 134 | 28.356 | 14.659 | 32.287 | 1.00 | 20.58 | H | N |
| ATOM | 2128 | NH2 | ARG | H | 134 | 27.419 | 15.795 | 34.035 | 1.00 | 20.22 | H | N |
| ATOM | 2129 | N | PHE | H | 135 | 22.687 | 15.844 | 27.801 | 1.00 | 12.87 | H | N |
| ATOM | 2130 | CA | PHE | H | 135 | 22.164 | 14.986 | 26.745 | 1.00 | 12.91 | H | C |
| ATOM | 2131 | C | PHE | H | 135 | 21.591 | 15.697 | 25.521 | 1.00 | 13.23 | H | C |
| ATOM | 2132 | O | PHE | H | 135 | 21.053 | 16.799 | 25.609 | 1.00 | 15.91 | H | O |
| ATOM | 2133 | CB | PHE | H | 135 | 21.089 | 14.054 | 27.340 | 1.00 | 11.61 | H | C |
| ATOM | 2134 | CG | PHE | H | 135 | 21.640 | 12.996 | 28.259 | 1.00 | 11.27 | H | C |
| ATOM | 2135 | CD1 | PHE | H | 135 | 22.119 | 11.794 | 27.752 | 1.00 | 12.29 | H | C |
| ATOM | 2136 | CD2 | PHE | H | 135 | 21.694 | 13.205 | 29.631 | 1.00 | 12.45 | H | C |
| ATOM | 2137 | CE1 | PHE | H | 135 | 22.648 | 10.812 | 28.602 | 1.00 | 11.52 | H | C |
| ATOM | 2138 | CE2 | PHE | H | 135 | 22.219 | 12.235 | 30.485 | 1.00 | 13.43 | H | C |
| ATOM | 2139 | CZ | PHE | H | 135 | 22.699 | 11.035 | 29.966 | 1.00 | 10.85 | H | C |
| ATOM | 2140 | N | SER | H | 136 | 21.718 | 15.030 | 24.378 | 1.00 | 13.39 | H | N |
| ATOM | 2141 | CA | SER | H | 136 | 21.209 | 15.499 | 23.095 | 1.00 | 13.57 | H | C |
| ATOM | 2142 | C | SER | H | 136 | 20.797 | 14.259 | 22.305 | 1.00 | 13.47 | H | C |
| ATOM | 2143 | O | SER | H | 136 | 21.293 | 13.160 | 22.559 | 1.00 | 11.08 | H | O |
| ATOM | 2144 | CB | SER | H | 136 | 22.285 | 16.249 | 22.307 | 1.00 | 13.40 | H | C |
| ATOM | 2145 | OG | SER | H | 136 | 22.576 | 17.513 | 22.881 | 1.00 | 14.55 | H | O |
| ATOM | 2146 | N | LEU | H | 137 | 19.903 | 14.441 | 21.341 | 1.00 | 12.22 | H | N |
| ATOM | 2147 | CA | LEU | H | 137 | 19.429 | 13.331 | 20.519 | 1.00 | 13.36 | H | C |
| ATOM | 2148 | C | LEU | H | 137 | 20.157 | 13.217 | 19.187 | 1.00 | 13.34 | H | C |
| ATOM | 2149 | O | LEU | H | 137 | 20.391 | 14.216 | 18.509 | 1.00 | 12.33 | H | O |
| ATOM | 2150 | CB | LEU | H | 137 | 17.938 | 13.486 | 20.228 | 1.00 | 13.15 | H | C |
| ATOM | 2151 | CG | LEU | H | 137 | 16.941 | 13.480 | 21.385 | 1.00 | 15.66 | H | C |
| ATOM | 2152 | CD1 | LEU | H | 137 | 15.532 | 13.692 | 20.815 | 1.00 | 14.08 | H | C |
| ATOM | 2153 | CD2 | LEU | H | 137 | 17.026 | 12.158 | 22.157 | 1.00 | 14.11 | H | C |
| ATOM | 2154 | N | VAL | H | 138 | 20.524 | 11.991 | 18.827 | 1.00 | 12.73 | H | N |
| ATOM | 2155 | CA | VAL | H | 138 | 21.170 | 11.715 | 17.550 | 1.00 | 12.09 | H | C |
| ATOM | 2156 | C | VAL | H | 138 | 20.216 | 10.733 | 16.870 | 1.00 | 12.01 | H | C |
| ATOM | 2157 | O | VAL | H | 138 | 19.675 | 9.836 | 17.513 | 1.00 | 12.12 | H | O |
| ATOM | 2158 | CB | VAL | H | 138 | 22.585 | 11.077 | 17.720 | 1.00 | 13.28 | H | C |
| ATOM | 2159 | CG1 | VAL | H | 138 | 23.551 | 12.094 | 18.330 | 1.00 | 8.61 | H | C |
| ATOM | 2160 | CG2 | VAL | H | 138 | 22.506 | 9.842 | 18.600 | 1.00 | 11.66 | H | C |
| ATOM | 2161 | N | SER | H | 139 | 20.002 | 10.897 | 15.573 | 1.00 | 12.22 | H | N |
| ATOM | 2162 | CA | SER | H | 139 | 19.061 | 10.041 | 14.869 | 1.00 | 11.00 | H | C |
| ATOM | 2163 | C | SER | H | 139 | 19.462 | 9.715 | 13.437 | 1.00 | 10.54 | H | C |
| ATOM | 2164 | O | SER | H | 139 | 20.324 | 10.378 | 12.856 | 1.00 | 11.74 | H | O |
| ATOM | 2165 | CB | SER | H | 139 | 17.693 | 10.722 | 14.870 | 1.00 | 11.90 | H | C |
| ATOM | 2166 | OG | SER | H | 139 | 17.823 | 12.060 | 14.405 | 1.00 | 9.32 | H | O |
| ATOM | 2167 | N | GLY | H | 140 | 18.818 | 8.690 | 12.881 | 1.00 | 9.70 | H | N |
| ATOM | 2168 | CA | GLY | H | 140 | 19.084 | 8.269 | 11.516 | 1.00 | 9.30 | H | C |
| ATOM | 2169 | C | GLY | H | 140 | 18.579 | 6.864 | 11.200 | 1.00 | 9.94 | H | C |
| ATOM | 2170 | O | GLY | H | 140 | 18.082 | 6.147 | 12.076 | 1.00 | 9.85 | H | O |
| ATOM | 2171 | N | TRP | H | 141 | 18.698 | 6.479 | 9.935 | 1.00 | 10.84 | H | N |
| ATOM | 2172 | CA | TRP | H | 141 | 18.299 | 5.149 | 9.471 | 1.00 | 13.57 | H | C |

-continued

| | | | | | | | | | | | |
|---|---|---|---|---|---|---|---|---|---|---|---|
| ATOM | 2173 | C | TRP | H | 141 | 19.547 | 4.284 | 9.307 | 1.00 | 14.42 | H | C |
| ATOM | 2174 | O | TRP | H | 141 | 19.559 | 3.338 | 8.518 | 1.00 | 14.11 | H | O |
| ATOM | 2175 | CB | TRP | H | 141 | 17.585 | 5.251 | 8.119 | 1.00 | 11.62 | H | C |
| ATOM | 2176 | CG | TRP | H | 141 | 16.213 | 5.852 | 8.198 | 1.00 | 9.53 | H | C |
| ATOM | 2177 | CD1 | TRP | H | 141 | 15.042 | 5.194 | 8.451 | 1.00 | 7.95 | H | C |
| ATOM | 2178 | CD2 | TRP | H | 141 | 15.868 | 7.227 | 7.992 | 1.00 | 9.12 | H | C |
| ATOM | 2179 | NE1 | TRP | H | 141 | 13.987 | 6.076 | 8.407 | 1.00 | 10.35 | H | N |
| ATOM | 2180 | CE2 | TRP | H | 141 | 14.465 | 7.330 | 8.131 | 1.00 | 9.30 | H | C |
| ATOM | 2181 | CE3 | TRP | H | 141 | 16.609 | 8.381 | 7.700 | 1.00 | 6.96 | H | C |
| ATOM | 2182 | CZ2 | TRP | H | 141 | 13.784 | 8.547 | 7.992 | 1.00 | 9.43 | H | C |
| ATOM | 2183 | CZ3 | TRP | H | 141 | 15.934 | 9.590 | 7.559 | 1.00 | 8.75 | H | C |
| ATOM | 2184 | CH2 | TRP | H | 141 | 14.531 | 9.662 | 7.707 | 1.00 | 9.90 | H | C |
| ATOM | 2185 | N | GLY | H | 142 | 20.591 | 4.623 | 10.059 | 1.00 | 16.02 | H | N |
| ATOM | 2186 | CA | GLY | H | 142 | 21.848 | 3.898 | 9.988 | 1.00 | 15.99 | H | C |
| ATOM | 2187 | C | GLY | H | 142 | 21.825 | 2.514 | 10.589 | 1.00 | 15.07 | H | C |
| ATOM | 2188 | O | GLY | H | 142 | 20.767 | 2.010 | 10.972 | 1.00 | 15.13 | H | O |
| ATOM | 2189 | N | GLN | H | 143 | 23.006 | 1.904 | 10.672 | 1.00 | 16.63 | H | N |
| ATOM | 2190 | CA | GLN | H | 143 | 23.162 | 0.556 | 11.212 | 1.00 | 17.93 | H | C |
| ATOM | 2191 | C | GLN | H | 143 | 22.665 | 0.409 | 12.640 | 1.00 | 20.58 | H | C |
| ATOM | 2192 | O | GLN | H | 143 | 22.882 | 1.278 | 13.489 | 1.00 | 18.31 | H | O |
| ATOM | 2193 | CB | GLN | H | 143 | 24.628 | 0.110 | 11.167 | 1.00 | 18.10 | H | C |
| ATOM | 2194 | CG | GLN | H | 143 | 25.228 | −0.100 | 9.770 | 1.00 | 19.46 | H | C |
| ATOM | 2195 | CD | GLN | H | 143 | 25.525 | 1.199 | 9.043 | 1.00 | 21.99 | H | C |
| ATOM | 2196 | OE1 | GLN | H | 143 | 25.714 | 2.242 | 9.669 | 1.00 | 20.13 | H | O |
| ATOM | 2197 | NE2 | GLN | H | 143 | 25.588 | 1.137 | 7.712 | 1.00 | 20.26 | H | N |
| ATOM | 2198 | N | LEU | H | 144 | 22.003 | −0.714 | 12.898 | 1.00 | 21.01 | H | N |
| ATOM | 2199 | CA | LEU | H | 144 | 21.481 | −1.012 | 14.221 | 1.00 | 23.46 | H | C |
| ATOM | 2200 | C | LEU | H | 144 | 22.573 | −1.658 | 15.069 | 1.00 | 25.89 | H | C |
| ATOM | 2201 | O | LEU | H | 144 | 22.507 | −1.642 | 16.298 | 1.00 | 25.66 | H | O |
| ATOM | 2202 | CB | LEU | H | 144 | 20.269 | −1.944 | 14.101 | 1.00 | 21.41 | H | C |
| ATOM | 2203 | CG | LEU | H | 144 | 19.080 | −1.313 | 13.367 | 1.00 | 19.40 | H | C |
| ATOM | 2204 | CD1 | LEU | H | 144 | 17.980 | −2.352 | 13.121 | 1.00 | 21.44 | H | C |
| ATOM | 2205 | CD2 | LEU | H | 144 | 18.551 | −0.157 | 14.199 | 1.00 | 14.43 | H | C |
| ATOM | 2206 | N | LEU | H | 145 | 23.574 | −2.226 | 14.400 | 1.00 | 27.35 | H | N |
| ATOM | 2207 | CA | LEU | H | 145 | 24.700 | −2.875 | 15.067 | 1.00 | 32.19 | H | C |
| ATOM | 2208 | C | LEU | H | 145 | 25.976 | −2.620 | 14.267 | 1.00 | 32.79 | H | C |
| ATOM | 2209 | O | LEU | H | 145 | 25.916 | −2.351 | 13.067 | 1.00 | 33.17 | H | O |
| ATOM | 2210 | CB | LEU | H | 145 | 24.470 | −4.391 | 15.186 | 1.00 | 33.26 | H | C |
| ATOM | 2211 | CG | LEU | H | 145 | 23.588 | −4.949 | 16.311 | 1.00 | 35.26 | H | C |
| ATOM | 2212 | CD1 | LEU | H | 145 | 22.133 | −4.554 | 16.123 | 1.00 | 37.31 | H | C |
| ATOM | 2213 | CD2 | LEU | H | 145 | 23.704 | −6.456 | 16.313 | 1.00 | 36.17 | H | C |
| ATOM | 2214 | N | ASP | H | 146 | 27.124 | −2.694 | 14.934 | 1.00 | 33.83 | H | N |
| ATOM | 2215 | CA | ASP | H | 146 | 28.404 | −2.483 | 14.266 | 1.00 | 35.01 | H | C |
| ATOM | 2216 | C | ASP | H | 146 | 28.493 | −3.449 | 13.091 | 1.00 | 36.95 | H | C |
| ATOM | 2217 | O | ASP | H | 146 | 28.380 | −4.661 | 13.268 | 1.00 | 36.80 | H | O |
| ATOM | 2218 | CB | ASP | H | 146 | 29.562 | −2.750 | 15.232 | 1.00 | 35.30 | H | C |
| ATOM | 2219 | CG | ASP | H | 146 | 30.922 | −2.459 | 14.612 | 1.00 | 35.18 | H | C |
| ATOM | 2220 | OD1 | ASP | H | 146 | 31.245 | −1.297 | 14.431 | 1.00 | 33.00 | H | O |
| ATOM | 2221 | OD2 | ASP | H | 146 | 31.652 | −3.406 | 14.310 | 1.00 | 36.91 | H | O |
| ATOM | 2222 | N | ARG | H | 147 | 28.679 | −2.906 | 11.893 | 1.00 | 38.24 | H | N |
| ATOM | 2223 | CA | ARG | H | 147 | 28.782 | −3.719 | 10.686 | 1.00 | 40.29 | H | C |
| ATOM | 2224 | C | ARG | H | 147 | 27.507 | −4.535 | 10.434 | 1.00 | 39.24 | H | C |
| ATOM | 2225 | O | ARG | H | 147 | 27.550 | −5.613 | 9.842 | 1.00 | 40.33 | H | O |
| ATOM | 2226 | CB | ARG | H | 147 | 29.995 | −4.651 | 10.797 | 1.00 | 43.36 | H | C |
| ATOM | 2227 | CG | ARG | H | 147 | 30.348 | −5.385 | 9.516 | 1.00 | 48.53 | H | C |
| ATOM | 2228 | CD | ARG | H | 147 | 31.593 | −6.237 | 9.698 | 1.00 | 54.02 | H | C |
| ATOM | 2229 | NE | ARG | H | 147 | 31.930 | −6.977 | 8.484 | 1.00 | 56.36 | H | N |
| ATOM | 2230 | CZ | ARG | H | 147 | 32.980 | −7.784 | 8.361 | 1.00 | 58.31 | H | C |
| ATOM | 2231 | NH1 | ARG | H | 147 | 33.811 | −7.965 | 9.381 | 1.00 | 58.01 | H | N |
| ATOM | 2232 | NH2 | ARG | H | 147 | 33.199 | −8.414 | 7.215 | 1.00 | 58.04 | H | N |
| ATOM | 2233 | N | GLY | H | 149 | 26.372 | −4.009 | 10.883 | 1.00 | 36.85 | H | N |
| ATOM | 2234 | CA | GLY | H | 149 | 25.109 | −4.696 | 10.697 | 1.00 | 33.07 | H | C |
| ATOM | 2235 | C | GLY | H | 149 | 24.277 | −4.049 | 9.610 | 1.00 | 30.38 | H | C |
| ATOM | 2236 | O | GLY | H | 149 | 24.782 | −3.246 | 8.826 | 1.00 | 29.52 | H | O |
| ATOM | 2237 | N | ALA | H | 150 | 22.997 | −4.398 | 9.562 | 1.00 | 28.41 | H | N |
| ATOM | 2238 | CA | ALA | H | 150 | 22.091 | −3.846 | 8.561 | 1.00 | 26.03 | H | C |
| ATOM | 2239 | C | ALA | H | 150 | 21.468 | −2.542 | 9.048 | 1.00 | 23.50 | H | C |
| ATOM | 2240 | O | ALA | H | 150 | 21.415 | −2.283 | 10.249 | 1.00 | 21.67 | H | O |
| ATOM | 2241 | CB | ALA | H | 150 | 21.005 | −4.850 | 8.248 | 1.00 | 27.18 | H | C |
| ATOM | 2242 | N | THR | H | 151 | 20.986 | −1.732 | 8.112 | 1.00 | 22.99 | H | N |
| ATOM | 2243 | CA | THR | H | 151 | 20.374 | −0.455 | 8.458 | 1.00 | 22.82 | H | C |
| ATOM | 2244 | C | THR | H | 151 | 18.923 | −0.593 | 8.925 | 1.00 | 22.79 | H | C |
| ATOM | 2245 | O | THR | H | 151 | 18.302 | −1.651 | 8.783 | 1.00 | 21.21 | H | O |
| ATOM | 2246 | CB | THR | H | 151 | 20.450 | 0.538 | 7.278 | 1.00 | 23.93 | H | C |
| ATOM | 2247 | OG1 | THR | H | 151 | 19.822 | −0.027 | 6.122 | 1.00 | 22.56 | H | O |
| ATOM | 2248 | CG2 | THR | H | 151 | 21.903 | 0.865 | 6.956 | 1.00 | 22.44 | H | C |
| ATOM | 2249 | N | ALA | H | 152 | 18.389 | 0.484 | 9.493 | 1.00 | 20.52 | H | N |
| ATOM | 2250 | CA | ALA | H | 152 | 17.025 | 0.474 | 10.005 | 1.00 | 18.60 | H | C |
| ATOM | 2251 | C | ALA | H | 152 | 15.979 | 0.962 | 9.011 | 1.00 | 16.25 | H | C |

-continued

| | | | | | | | | | | | |
|---|---|---|---|---|---|---|---|---|---|---|---|
| ATOM | 2252 | O | ALA | H | 152 | 16.218 | 1.883 | 8.237 | 1.00 | 16.12 | H | O |
| ATOM | 2253 | CB | ALA | H | 152 | 16.951 | 1.303 | 11.280 | 1.00 | 18.25 | H | C |
| ATOM | 2254 | N | LEU | H | 153 | 14.811 | 0.332 | 9.045 | 1.00 | 15.23 | H | N |
| ATOM | 2255 | CA | LEU | H | 153 | 13.713 | 0.707 | 8.169 | 1.00 | 15.57 | H | C |
| ATOM | 2256 | C | LEU | H | 153 | 12.954 | 1.881 | 8.754 | 1.00 | 14.76 | H | C |
| ATOM | 2257 | O | LEU | H | 153 | 12.443 | 2.720 | 8.021 | 1.00 | 17.16 | H | O |
| ATOM | 2258 | CB | LEU | H | 153 | 12.770 | −0.479 | 7.962 | 1.00 | 15.57 | H | C |
| ATOM | 2259 | CG | LEU | H | 153 | 13.349 | −1.531 | 7.015 | 1.00 | 16.60 | H | C |
| ATOM | 2260 | CD1 | LEU | H | 153 | 12.575 | −2.847 | 7.125 | 1.00 | 16.63 | H | C |
| ATOM | 2261 | CD2 | LEU | H | 153 | 13.302 | −0.978 | 5.602 | 1.00 | 15.24 | H | C |
| ATOM | 2262 | N | GLU | H | 154 | 12.871 | 1.933 | 10.079 | 1.00 | 15.00 | H | N |
| ATOM | 2263 | CA | GLU | H | 154 | 12.182 | 3.025 | 10.755 | 1.00 | 15.61 | H | C |
| ATOM | 2264 | C | GLU | H | 154 | 13.198 | 3.936 | 11.431 | 1.00 | 14.97 | H | C |
| ATOM | 2265 | O | GLU | H | 154 | 14.143 | 3.465 | 12.070 | 1.00 | 15.21 | H | O |
| ATOM | 2266 | CB | GLU | H | 154 | 11.201 | 2.482 | 11.789 | 1.00 | 14.17 | H | C |
| ATOM | 2267 | CG | GLU | H | 154 | 9.877 | 2.027 | 11.206 | 1.00 | 20.51 | H | C |
| ATOM | 2268 | CD | GLU | H | 154 | 8.914 | 1.551 | 12.274 | 1.00 | 23.96 | H | C |
| ATOM | 2269 | OE1 | GLU | H | 154 | 9.164 | 0.504 | 12.851 | 1.00 | 23.53 | H | O |
| ATOM | 2270 | OE2 | GLU | H | 154 | 7.919 | 2.249 | 12.535 | 1.00 | 27.22 | H | O |
| ATOM | 2271 | N | LEU | H | 155 | 13.000 | 5.241 | 11.279 | 1.00 | 14.72 | H | N |
| ATOM | 2272 | CA | LEU | H | 155 | 13.900 | 6.234 | 11.864 | 1.00 | 13.82 | H | C |
| ATOM | 2273 | C | LEU | H | 155 | 14.157 | 5.954 | 13.336 | 1.00 | 12.35 | H | C |
| ATOM | 2274 | O | LEU | H | 155 | 13.223 | 5.883 | 14.127 | 1.00 | 13.95 | H | O |
| ATOM | 2275 | CB | LEU | H | 155 | 13.304 | 7.635 | 11.725 | 1.00 | 14.43 | H | C |
| ATOM | 2276 | CG | LEU | H | 155 | 14.144 | 8.775 | 12.315 | 1.00 | 13.63 | H | C |
| ATOM | 2277 | CD1 | LEU | H | 155 | 15.464 | 8.868 | 11.565 | 1.00 | 13.84 | H | C |
| ATOM | 2278 | CD2 | LEU | H | 155 | 13.380 | 10.088 | 12.210 | 1.00 | 13.06 | H | C |
| ATOM | 2279 | N | MET | H | 156 | 15.424 | 5.805 | 13.701 | 1.00 | 12.83 | H | N |
| ATOM | 2280 | CA | MET | H | 156 | 15.798 | 5.542 | 15.087 | 1.00 | 12.93 | H | C |
| ATOM | 2281 | C | MET | H | 156 | 16.366 | 6.812 | 15.739 | 1.00 | 12.73 | H | C |
| ATOM | 2282 | O | MET | H | 156 | 16.871 | 7.700 | 15.054 | 1.00 | 13.04 | H | O |
| ATOM | 2283 | CB | MET | H | 156 | 16.841 | 4.421 | 15.150 | 1.00 | 12.00 | H | C |
| ATOM | 2284 | CG | MET | H | 156 | 16.461 | 3.125 | 14.429 | 1.00 | 12.49 | H | C |
| ATOM | 2285 | SD | MET | H | 156 | 15.054 | 2.200 | 15.133 | 1.00 | 13.73 | H | S |
| ATOM | 2286 | CE | MET | H | 156 | 15.766 | 1.648 | 16.690 | 1.00 | 12.82 | H | C |
| ATOM | 2287 | N | VAL | H | 157 | 16.292 | 6.883 | 17.066 | 1.00 | 12.85 | H | N |
| ATOM | 2288 | CA | VAL | H | 157 | 16.779 | 8.037 | 17.813 | 1.00 | 11.88 | H | C |
| ATOM | 2289 | C | VAL | H | 157 | 17.463 | 7.558 | 19.098 | 1.00 | 13.44 | H | C |
| ATOM | 2290 | O | VAL | H | 157 | 17.127 | 6.499 | 19.642 | 1.00 | 12.26 | H | O |
| ATOM | 2291 | CB | VAL | H | 157 | 15.606 | 9.020 | 18.126 | 1.00 | 9.61 | H | C |
| ATOM | 2292 | CG1 | VAL | H | 157 | 14.621 | 8.382 | 19.074 | 1.00 | 9.52 | H | C |
| ATOM | 2293 | CG2 | VAL | H | 157 | 16.142 | 10.337 | 18.685 | 1.00 | 11.73 | H | C |
| ATOM | 2294 | N | LEU | H | 158 | 18.425 | 8.343 | 19.574 | 1.00 | 12.79 | H | N |
| ATOM | 2295 | CA | LEU | H | 158 | 19.202 | 7.999 | 20.758 | 1.00 | 11.41 | H | C |
| ATOM | 2296 | C | LEU | H | 158 | 19.660 | 9.223 | 21.545 | 1.00 | 13.56 | H | C |
| ATOM | 2297 | O | LEU | H | 158 | 20.119 | 10.215 | 20.963 | 1.00 | 10.13 | H | O |
| ATOM | 2298 | CB | LEU | H | 158 | 20.444 | 7.215 | 20.331 | 1.00 | 12.58 | H | C |
| ATOM | 2299 | CG | LEU | H | 158 | 21.465 | 6.879 | 21.414 | 1.00 | 11.97 | H | C |
| ATOM | 2300 | CD1 | LEU | H | 158 | 20.871 | 5.843 | 22.360 | 1.00 | 11.50 | H | C |
| ATOM | 2301 | CD2 | LEU | H | 158 | 22.740 | 6.350 | 20.770 | 1.00 | 11.54 | H | C |
| ATOM | 2302 | N | ASN | H | 159 | 19.547 | 9.138 | 22.869 | 1.00 | 11.48 | H | N |
| ATOM | 2303 | CA | ASN | H | 159 | 19.973 | 10.216 | 23.749 | 1.00 | 13.66 | H | C |
| ATOM | 2304 | C | ASN | H | 159 | 21.419 | 9.908 | 24.142 | 1.00 | 12.37 | H | C |
| ATOM | 2305 | O | ASN | H | 159 | 21.701 | 8.835 | 24.673 | 1.00 | 13.12 | H | O |
| ATOM | 2306 | CB | ASN | H | 159 | 19.092 | 10.254 | 25.004 | 1.00 | 15.32 | H | C |
| ATOM | 2307 | CG | ASN | H | 159 | 19.000 | 11.643 | 25.621 | 1.00 | 18.58 | H | C |
| ATOM | 2308 | OD1 | ASN | H | 159 | 18.609 | 11.791 | 26.783 | 1.00 | 19.52 | H | O |
| ATOM | 2309 | ND2 | ASN | H | 159 | 19.341 | 12.668 | 24.843 | 1.00 | 17.35 | H | N |
| ATOM | 2310 | N | VAL | H | 160 | 22.331 | 10.835 | 23.867 | 1.00 | 11.23 | H | N |
| ATOM | 2311 | CA | VAL | H | 160 | 23.741 | 10.644 | 24.196 | 1.00 | 10.26 | H | C |
| ATOM | 2312 | C | VAL | H | 160 | 24.309 | 11.844 | 24.952 | 1.00 | 11.62 | H | C |
| ATOM | 2313 | O | VAL | H | 160 | 23.965 | 12.989 | 24.658 | 1.00 | 11.36 | H | O |
| ATOM | 2314 | CB | VAL | H | 160 | 24.608 | 10.425 | 22.926 | 1.00 | 11.37 | H | C |
| ATOM | 2315 | CG1 | VAL | H | 160 | 24.175 | 9.147 | 22.200 | 1.00 | 9.21 | H | C |
| ATOM | 2316 | CG2 | VAL | H | 160 | 24.506 | 11.650 | 21.989 | 1.00 | 7.47 | H | C |
| ATOM | 2317 | N | PRO | H | 161 | 25.183 | 11.590 | 25.947 | 1.00 | 10.82 | H | N |
| ATOM | 2318 | CA | PRO | H | 161 | 25.804 | 12.652 | 26.746 | 1.00 | 11.11 | H | C |
| ATOM | 2319 | C | PRO | H | 161 | 27.055 | 13.199 | 26.058 | 1.00 | 10.16 | H | C |
| ATOM | 2320 | O | PRO | H | 161 | 27.822 | 12.458 | 25.445 | 1.00 | 9.67 | H | O |
| ATOM | 2321 | CB | PRO | H | 161 | 26.129 | 11.944 | 28.058 | 1.00 | 10.26 | H | C |
| ATOM | 2322 | CG | PRO | H | 161 | 26.562 | 10.594 | 27.575 | 1.00 | 10.20 | H | C |
| ATOM | 2323 | CD | PRO | H | 161 | 25.505 | 10.264 | 26.511 | 1.00 | 11.31 | H | C |
| ATOM | 2324 | N | ARG | H | 162 | 27.268 | 14.499 | 26.185 | 1.00 | 10.55 | H | N |
| ATOM | 2325 | CA | ARG | H | 162 | 28.411 | 15.145 | 25.560 | 1.00 | 10.54 | H | C |
| ATOM | 2326 | C | ARG | H | 162 | 29.639 | 15.171 | 26.474 | 1.00 | 11.25 | H | C |
| ATOM | 2327 | O | ARG | H | 162 | 29.515 | 15.158 | 27.701 | 1.00 | 13.29 | H | O |
| ATOM | 2328 | CB | ARG | H | 162 | 28.004 | 16.564 | 25.152 | 1.00 | 11.25 | H | C |
| ATOM | 2329 | CG | ARG | H | 162 | 29.082 | 17.391 | 24.464 | 1.00 | 12.83 | H | C |
| ATOM | 2330 | CD | ARG | H | 162 | 28.483 | 18.669 | 23.889 | 1.00 | 9.42 | H | C |

-continued

| | | | | | | | | | | | |
|---|---|---|---|---|---|---|---|---|---|---|---|
| ATOM | 2331 | NE | ARG | H | 162 | 29.498 | 19.534 | 23.303 | 1.00 | 9.59 | H | N |
| ATOM | 2332 | CZ | ARG | H | 162 | 29.236 | 20.576 | 22.520 | 1.00 | 11.68 | H | C |
| ATOM | 2333 | NH1 | ARG | H | 162 | 27.979 | 20.886 | 22.217 | 1.00 | 11.81 | H | N |
| ATOM | 2334 | NH2 | ARG | H | 162 | 30.232 | 21.318 | 22.047 | 1.00 | 12.43 | H | N |
| ATOM | 2335 | N | LEU | H | 163 | 30.825 | 15.178 | 25.872 | 1.00 | 9.08 | H | N |
| ATOM | 2336 | CA | LEU | H | 163 | 32.062 | 15.230 | 26.636 | 1.00 | 10.57 | H | C |
| ATOM | 2337 | C | LEU | H | 163 | 32.991 | 16.323 | 26.127 | 1.00 | 11.95 | H | C |
| ATOM | 2338 | O | LEU | H | 163 | 33.074 | 16.570 | 24.923 | 1.00 | 10.27 | H | O |
| ATOM | 2339 | CB | LEU | H | 163 | 32.835 | 13.907 | 26.548 | 1.00 | 12.13 | H | C |
| ATOM | 2340 | CG | LEU | H | 163 | 32.369 | 12.650 | 27.278 | 1.00 | 12.88 | H | C |
| ATOM | 2341 | CD1 | LEU | H | 163 | 31.177 | 12.034 | 26.547 | 1.00 | 12.78 | H | C |
| ATOM | 2342 | CD2 | LEU | H | 163 | 33.540 | 11.658 | 27.336 | 1.00 | 14.29 | H | C |
| ATOM | 2343 | N | MET | H | 164 | 33.677 | 16.990 | 27.047 | 1.00 | 11.82 | H | N |
| ATOM | 2344 | CA | MET | H | 164 | 34.654 | 17.980 | 26.633 | 1.00 | 12.80 | H | C |
| ATOM | 2345 | C | MET | H | 164 | 35.782 | 17.109 | 26.081 | 1.00 | 12.63 | H | C |
| ATOM | 2346 | O | MET | H | 164 | 35.980 | 15.977 | 26.532 | 1.00 | 10.67 | H | O |
| ATOM | 2347 | CB | MET | H | 164 | 35.107 | 18.825 | 27.822 | 1.00 | 14.08 | H | C |
| ATOM | 2348 | CG | MET | H | 164 | 34.020 | 19.805 | 28.259 | 1.00 | 18.16 | H | C |
| ATOM | 2349 | SD | MET | H | 164 | 34.564 | 21.069 | 29.400 | 1.00 | 22.97 | H | S |
| ATOM | 2350 | CE | MET | H | 164 | 35.402 | 22.150 | 28.252 | 1.00 | 19.99 | H | C |
| ATOM | 2351 | N | THR | H | 165 | 36.504 | 17.621 | 25.095 | 1.00 | 12.59 | H | N |
| ATOM | 2352 | CA | THR | H | 165 | 37.554 | 16.849 | 24.451 | 1.00 | 15.62 | H | C |
| ATOM | 2353 | C | THR | H | 165 | 38.629 | 16.275 | 25.375 | 1.00 | 16.25 | H | C |
| ATOM | 2354 | O | THR | H | 165 | 39.064 | 15.143 | 25.186 | 1.00 | 15.20 | H | O |
| ATOM | 2355 | CB | THR | H | 165 | 38.172 | 17.679 | 23.320 | 1.00 | 17.38 | H | C |
| ATOM | 2356 | OG1 | THR | H | 165 | 37.112 | 18.103 | 22.452 | 1.00 | 17.32 | H | O |
| ATOM | 2357 | CG2 | THR | H | 165 | 39.175 | 16.855 | 22.510 | 1.00 | 14.61 | H | C |
| ATOM | 2358 | N | GLN | H | 166 | 39.048 | 17.036 | 26.378 | 1.00 | 16.53 | H | N |
| ATOM | 2359 | CA | GLN | H | 166 | 40.055 | 16.541 | 27.310 | 1.00 | 17.06 | H | C |
| ATOM | 2360 | C | GLN | H | 166 | 39.549 | 15.231 | 27.923 | 1.00 | 17.05 | H | C |
| ATOM | 2361 | O | GLN | H | 166 | 40.284 | 14.250 | 28.008 | 1.00 | 16.97 | H | O |
| ATOM | 2362 | CB | GLN | H | 166 | 40.316 | 17.585 | 28.400 | 1.00 | 16.34 | H | C |
| ATOM | 2363 | CG | GLN | H | 166 | 41.362 | 17.196 | 29.432 | 1.00 | 18.36 | H | C |
| ATOM | 2364 | CD | GLN | H | 166 | 41.681 | 18.350 | 30.373 | 1.00 | 18.67 | H | C |
| ATOM | 2365 | OE1 | GLN | H | 166 | 42.310 | 19.329 | 29.973 | 1.00 | 22.60 | H | O |
| ATOM | 2366 | NE2 | GLN | H | 166 | 41.228 | 18.249 | 31.618 | 1.00 | 14.45 | H | N |
| ATOM | 2367 | N | ASP | H | 167 | 38.290 | 15.217 | 28.347 | 1.00 | 17.30 | H | N |
| ATOM | 2368 | CA | ASP | H | 167 | 37.707 | 14.010 | 28.916 | 1.00 | 17.76 | H | C |
| ATOM | 2369 | C | ASP | H | 167 | 37.628 | 12.893 | 27.876 | 1.00 | 17.98 | H | C |
| ATOM | 2370 | O | ASP | H | 167 | 37.922 | 11.739 | 28.182 | 1.00 | 18.09 | H | O |
| ATOM | 2371 | CB | ASP | H | 167 | 36.302 | 14.282 | 29.456 | 1.00 | 18.74 | H | C |
| ATOM | 2372 | CG | ASP | H | 167 | 36.313 | 15.086 | 30.729 | 1.00 | 18.60 | H | C |
| ATOM | 2373 | OD1 | ASP | H | 167 | 37.056 | 14.726 | 31.625 | 1.00 | 19.37 | H | O |
| ATOM | 2374 | OD2 | ASP | H | 167 | 35.569 | 16.071 | 30.818 | 1.00 | 20.49 | H | O |
| ATOM | 2375 | N | CYS | H | 168 | 37.226 | 13.227 | 26.651 | 1.00 | 17.56 | H | N |
| ATOM | 2376 | CA | CYS | H | 168 | 37.114 | 12.210 | 25.608 | 1.00 | 18.06 | H | C |
| ATOM | 2377 | C | CYS | H | 168 | 38.449 | 11.496 | 25.398 | 1.00 | 18.33 | H | C |
| ATOM | 2378 | O | CYS | H | 168 | 38.508 | 10.270 | 25.404 | 1.00 | 17.46 | H | O |
| ATOM | 2379 | CB | CYS | H | 168 | 36.658 | 12.829 | 24.281 | 1.00 | 17.54 | H | C |
| ATOM | 2380 | SG | CYS | H | 168 | 36.253 | 11.592 | 23.003 | 1.00 | 18.27 | H | S |
| ATOM | 2381 | N | LEU | H | 169 | 39.511 | 12.271 | 25.202 | 1.00 | 18.38 | H | N |
| ATOM | 2382 | CA | LEU | H | 169 | 40.843 | 11.711 | 24.990 | 1.00 | 22.32 | H | C |
| ATOM | 2383 | C | LEU | H | 169 | 41.294 | 10.864 | 26.175 | 1.00 | 23.09 | H | C |
| ATOM | 2384 | O | LEU | H | 169 | 41.797 | 9.757 | 25.995 | 1.00 | 23.96 | H | O |
| ATOM | 2385 | CB | LEU | H | 169 | 41.861 | 12.830 | 24.748 | 1.00 | 22.08 | H | C |
| ATOM | 2386 | CG | LEU | H | 169 | 41.665 | 13.649 | 23.471 | 1.00 | 24.49 | H | C |
| ATOM | 2387 | CD1 | LEU | H | 169 | 42.705 | 14.766 | 23.403 | 1.00 | 24.94 | H | C |
| ATOM | 2388 | CD2 | LEU | H | 169 | 41.779 | 12.733 | 22.260 | 1.00 | 23.41 | H | C |
| ATOM | 2389 | N | GLN | H | 170 | 41.103 | 11.377 | 27.386 | 1.00 | 22.94 | H | N |
| ATOM | 2390 | CA | GLN | H | 170 | 41.508 | 10.651 | 28.584 | 1.00 | 24.75 | H | C |
| ATOM | 2391 | C | GLN | H | 170 | 40.732 | 9.350 | 28.756 | 1.00 | 26.16 | H | C |
| ATOM | 2392 | O | GLN | H | 170 | 41.298 | 8.337 | 29.161 | 1.00 | 26.39 | H | O |
| ATOM | 2393 | CB | GLN | H | 170 | 41.333 | 11.532 | 29.837 | 1.00 | 21.09 | H | C |
| ATOM | 2394 | CG | GLN | H | 170 | 42.137 | 12.840 | 29.793 | 1.00 | 20.61 | H | C |
| ATOM | 2395 | CD | GLN | H | 170 | 42.114 | 13.623 | 31.103 | 1.00 | 19.91 | H | C |
| ATOM | 2396 | OE1 | GLN | H | 170 | 41.153 | 13.560 | 31.874 | 1.00 | 19.12 | H | O |
| ATOM | 2397 | NE2 | GLN | H | 170 | 43.174 | 14.382 | 31.348 | 1.00 | 16.44 | H | N |
| ATOM | 2398 | N | GLN | H | 170A | 39.442 | 9.379 | 28.432 | 1.00 | 26.53 | H | N |
| ATOM | 2399 | CA | GLN | H | 170A | 38.576 | 8.210 | 28.572 | 1.00 | 26.34 | H | C |
| ATOM | 2400 | C | GLN | H | 170A | 38.536 | 7.266 | 27.371 | 1.00 | 26.09 | H | C |
| ATOM | 2401 | O | GLN | H | 170A | 37.795 | 6.288 | 27.386 | 1.00 | 26.50 | H | O |
| ATOM | 2402 | CB | GLN | H | 170A | 37.146 | 8.655 | 28.884 | 1.00 | 28.29 | H | C |
| ATOM | 2403 | CG | GLN | H | 170A | 36.957 | 9.298 | 30.236 | 1.00 | 30.52 | H | C |
| ATOM | 2404 | CD | GLN | H | 170A | 35.513 | 9.682 | 30.478 | 1.00 | 34.79 | H | C |
| ATOM | 2405 | OE1 | GLN | H | 170A | 34.602 | 8.867 | 30.290 | 1.00 | 37.17 | H | O |
| ATOM | 2406 | NE2 | GLN | H | 170A | 35.290 | 10.921 | 30.904 | 1.00 | 34.78 | H | N |
| ATOM | 2407 | N | SER | H | 170B | 39.317 | 7.549 | 26.336 | 1.00 | 26.18 | H | N |
| ATOM | 2408 | CA | SER | H | 170B | 39.317 | 6.696 | 25.159 | 1.00 | 28.66 | H | C |
| ATOM | 2409 | C | SER | H | 170B | 40.585 | 5.848 | 25.055 | 1.00 | 31.18 | H | C |

-continued

| | | | | | | | | | | | |
|---|---|---|---|---|---|---|---|---|---|---|---|
| ATOM | 2410 | O | SER | H | 170B | 41.643 | 6.231 | 25.552 | 1.00 | 29.81 | H | O |
| ATOM | 2411 | CB | SER | H | 170B | 39.153 | 7.544 | 23.890 | 1.00 | 27.91 | H | C |
| ATOM | 2412 | OG | SER | H | 170B | 37.912 | 8.239 | 23.886 | 1.00 | 24.13 | H | O |
| ATOM | 2413 | N | ARG | H | 170C | 40.459 | 4.688 | 24.417 | 1.00 | 33.34 | H | N |
| ATOM | 2414 | CA | ARG | H | 170C | 41.579 | 3.777 | 24.211 | 1.00 | 36.91 | H | C |
| ATOM | 2415 | C | ARG | H | 170C | 42.471 | 4.323 | 23.102 | 1.00 | 38.48 | H | C |
| ATOM | 2416 | O | ARG | H | 170C | 42.078 | 4.341 | 21.939 | 1.00 | 39.23 | H | O |
| ATOM | 2417 | CB | ARG | H | 170C | 41.059 | 2.395 | 23.805 | 1.00 | 37.94 | H | C |
| ATOM | 2418 | CG | ARG | H | 170C | 40.558 | 1.530 | 24.947 | 1.00 | 38.36 | H | C |
| ATOM | 2419 | CD | ARG | H | 170C | 41.710 | 0.756 | 25.572 | 1.00 | 39.49 | H | C |
| ATOM | 2420 | NE | ARG | H | 170C | 42.369 | −0.108 | 24.592 | 1.00 | 39.64 | H | N |
| ATOM | 2421 | CZ | ARG | H | 170C | 41.864 | −1.246 | 24.122 | 1.00 | 40.03 | H | C |
| ATOM | 2422 | NH1 | ARG | H | 170C | 40.684 | −1.686 | 24.540 | 1.00 | 41.69 | H | N |
| ATOM | 2423 | NH2 | ARG | H | 170C | 42.540 | −1.941 | 23.217 | 1.00 | 41.52 | H | N |
| ATOM | 2424 | N | LYS | H | 170D | 43.670 | 4.765 | 23.459 | 1.00 | 41.25 | H | N |
| ATOM | 2425 | CA | LYS | H | 170D | 44.605 | 5.306 | 22.472 | 1.00 | 43.27 | H | C |
| ATOM | 2426 | C | LYS | H | 170D | 44.971 | 4.266 | 21.415 | 1.00 | 44.63 | H | C |
| ATOM | 2427 | O | LYS | H | 170D | 45.314 | 3.137 | 21.752 | 1.00 | 45.60 | H | O |
| ATOM | 2428 | CB | LYS | H | 170D | 45.876 | 5.790 | 23.170 | 1.00 | 44.06 | H | C |
| ATOM | 2429 | CG | LYS | H | 170D | 45.660 | 6.974 | 24.098 | 1.00 | 43.63 | H | C |
| ATOM | 2430 | CD | LYS | H | 170D | 45.336 | 8.243 | 23.320 | 1.00 | 43.73 | H | C |
| ATOM | 2431 | CE | LYS | H | 170D | 44.179 | 8.998 | 23.957 | 1.00 | 42.88 | H | C |
| ATOM | 2432 | NZ | LYS | H | 170D | 42.919 | 8.196 | 23.891 | 1.00 | 44.55 | H | N |
| ATOM | 2433 | N | VAL | H | 170E | 44.897 | 4.647 | 20.141 | 1.00 | 45.92 | H | N |
| ATOM | 2434 | CA | VAL | H | 170E | 45.229 | 3.737 | 19.050 | 1.00 | 47.38 | H | C |
| ATOM | 2435 | C | VAL | H | 170E | 46.174 | 4.403 | 18.038 | 1.00 | 48.37 | H | C |
| ATOM | 2436 | O | VAL | H | 170E | 46.307 | 5.628 | 18.008 | 1.00 | 48.59 | H | O |
| ATOM | 2437 | CB | VAL | H | 170E | 43.955 | 3.237 | 18.317 | 1.00 | 48.27 | H | C |
| ATOM | 2438 | CG1 | VAL | H | 170E | 43.053 | 2.478 | 19.283 | 1.00 | 48.47 | H | C |
| ATOM | 2439 | CG2 | VAL | H | 170E | 43.195 | 4.398 | 17.721 | 1.00 | 50.40 | H | C |
| ATOM | 2440 | N | GLY | H | 170F | 46.828 | 3.580 | 17.220 | 1.00 | 49.26 | H | N |
| ATOM | 2441 | CA | GLY | H | 170F | 47.778 | 4.055 | 16.227 | 1.00 | 49.68 | H | C |
| ATOM | 2442 | C | GLY | H | 170F | 47.456 | 5.293 | 15.409 | 1.00 | 49.19 | H | C |
| ATOM | 2443 | O | GLY | H | 170F | 47.643 | 6.420 | 15.869 | 1.00 | 49.83 | H | O |
| ATOM | 2444 | N | ASP | H | 170G | 46.988 | 5.081 | 14.181 | 1.00 | 49.28 | H | N |
| ATOM | 2445 | CA | ASP | H | 170G | 46.666 | 6.176 | 13.262 | 1.00 | 48.00 | H | C |
| ATOM | 2446 | C | ASP | H | 170G | 45.293 | 6.803 | 13.484 | 1.00 | 44.35 | H | C |
| ATOM | 2447 | O | ASP | H | 170G | 44.613 | 7.177 | 12.527 | 1.00 | 44.28 | H | O |
| ATOM | 2448 | CB | ASP | H | 170G | 46.771 | 5.684 | 11.815 | 1.00 | 52.87 | H | C |
| ATOM | 2449 | CG | ASP | H | 170G | 48.206 | 5.571 | 11.341 | 1.00 | 56.19 | H | C |
| ATOM | 2450 | OD1 | ASP | H | 170G | 48.987 | 4.862 | 11.981 | 1.00 | 59.14 | H | O |
| ATOM | 2451 | OD2 | ASP | H | 170G | 48.545 | 6.193 | 10.325 | 1.00 | 58.70 | H | O |
| ATOM | 2452 | N | SER | H | 170H | 44.899 | 6.933 | 14.745 | 1.00 | 39.99 | H | N |
| ATOM | 2453 | CA | SER | H | 170H | 43.613 | 7.524 | 15.084 | 1.00 | 36.53 | H | C |
| ATOM | 2454 | C | SER | H | 170H | 43.583 | 9.003 | 14.727 | 1.00 | 32.15 | H | C |
| ATOM | 2455 | O | SER | H | 170H | 44.501 | 9.747 | 15.056 | 1.00 | 31.87 | H | O |
| ATOM | 2456 | CB | SER | H | 170H | 43.337 | 7.364 | 16.579 | 1.00 | 37.95 | H | C |
| ATOM | 2457 | OG | SER | H | 170H | 42.120 | 7.987 | 16.949 | 1.00 | 42.60 | H | O |
| ATOM | 2458 | N | PRO | H | 170I | 42.529 | 9.442 | 14.026 | 1.00 | 28.54 | H | N |
| ATOM | 2459 | CA | PRO | H | 170I | 42.433 | 10.856 | 13.660 | 1.00 | 26.44 | H | C |
| ATOM | 2460 | C | PRO | H | 170I | 42.405 | 11.701 | 14.931 | 1.00 | 25.04 | H | C |
| ATOM | 2461 | O | PRO | H | 170I | 41.964 | 11.239 | 15.981 | 1.00 | 24.79 | H | O |
| ATOM | 2462 | CB | PRO | H | 170I | 41.112 | 10.921 | 12.900 | 1.00 | 24.88 | H | C |
| ATOM | 2463 | CG | PRO | H | 170I | 41.032 | 9.575 | 12.255 | 1.00 | 26.28 | H | C |
| ATOM | 2464 | CD | PRO | H | 170I | 41.466 | 8.658 | 13.376 | 1.00 | 26.49 | H | C |
| ATOM | 2465 | N | ASN | H | 175 | 42.890 | 12.930 | 14.842 | 1.00 | 24.55 | H | N |
| ATOM | 2466 | CA | ASN | H | 175 | 42.884 | 13.820 | 15.994 | 1.00 | 24.55 | H | C |
| ATOM | 2467 | C | ASN | H | 175 | 41.484 | 14.376 | 16.174 | 1.00 | 21.18 | H | C |
| ATOM | 2468 | O | ASN | H | 175 | 40.733 | 14.509 | 15.211 | 1.00 | 19.35 | H | O |
| ATOM | 2469 | CB | ASN | H | 175 | 43.839 | 15.004 | 15.788 | 1.00 | 26.79 | H | C |
| ATOM | 2470 | CG | ASN | H | 175 | 45.269 | 14.576 | 15.576 | 1.00 | 30.83 | H | C |
| ATOM | 2471 | OD1 | ASN | H | 175 | 45.829 | 13.823 | 16.370 | 1.00 | 32.43 | H | O |
| ATOM | 2472 | ND2 | ASN | H | 175 | 45.876 | 15.064 | 14.499 | 1.00 | 33.68 | H | N |
| ATOM | 2473 | N | ILE | H | 176 | 41.140 | 14.695 | 17.414 | 1.00 | 18.30 | H | N |
| ATOM | 2474 | CA | ILE | H | 176 | 39.852 | 15.290 | 17.716 | 1.00 | 17.01 | H | C |
| ATOM | 2475 | C | ILE | H | 176 | 40.181 | 16.773 | 17.786 | 1.00 | 17.25 | H | C |
| ATOM | 2476 | O | ILE | H | 176 | 40.800 | 17.232 | 18.740 | 1.00 | 18.43 | H | O |
| ATOM | 2477 | CB | ILE | H | 176 | 39.306 | 14.807 | 19.077 | 1.00 | 16.65 | H | C |
| ATOM | 2478 | CG1 | ILE | H | 176 | 39.186 | 13.277 | 19.073 | 1.00 | 15.60 | H | C |
| ATOM | 2479 | CG2 | ILE | H | 176 | 37.935 | 15.437 | 19.343 | 1.00 | 13.67 | H | C |
| ATOM | 2480 | CD1 | ILE | H | 176 | 38.827 | 12.685 | 20.411 | 1.00 | 17.27 | H | C |
| ATOM | 2481 | N | THR | H | 177 | 39.784 | 17.521 | 16.764 | 1.00 | 16.30 | H | N |
| ATOM | 2482 | CA | THR | H | 177 | 40.094 | 18.945 | 16.712 | 1.00 | 15.04 | H | C |
| ATOM | 2483 | C | THR | H | 177 | 39.060 | 19.829 | 17.400 | 1.00 | 14.07 | H | C |
| ATOM | 2484 | O | THR | H | 177 | 38.107 | 19.344 | 18.006 | 1.00 | 13.41 | H | O |
| ATOM | 2485 | CB | THR | H | 177 | 40.227 | 19.419 | 15.258 | 1.00 | 16.10 | H | C |
| ATOM | 2486 | OG1 | THR | H | 177 | 38.926 | 19.445 | 14.655 | 1.00 | 16.94 | H | O |
| ATOM | 2487 | CG2 | THR | H | 177 | 41.149 | 18.479 | 14.460 | 1.00 | 12.71 | H | C |
| ATOM | 2488 | N | GLU | H | 178 | 39.266 | 21.138 | 17.305 | 1.00 | 13.19 | H | N |

-continued

| | | | | | | | | | | | |
|---|---|---|---|---|---|---|---|---|---|---|---|
| ATOM | 2489 | CA | GLU | H | 178 | 38.351 | 22.106 | 17.893 | 1.00 | 14.78 | H | C |
| ATOM | 2490 | C | GLU | H | 178 | 37.062 | 22.188 | 17.074 | 1.00 | 13.86 | H | C |
| ATOM | 2491 | O | GLU | H | 178 | 36.104 | 22.847 | 17.478 | 1.00 | 12.84 | H | O |
| ATOM | 2492 | CB | GLU | H | 178 | 39.009 | 23.490 | 17.955 | 1.00 | 18.37 | H | C |
| ATOM | 2493 | CG | GLU | H | 178 | 39.254 | 24.129 | 16.596 | 1.00 | 20.75 | H | C |
| ATOM | 2494 | CD | GLU | H | 178 | 40.674 | 23.943 | 16.096 | 1.00 | 27.62 | H | C |
| ATOM | 2495 | OE1 | GLU | H | 178 | 41.148 | 22.778 | 16.008 | 1.00 | 27.54 | H | O |
| ATOM | 2496 | OE2 | GLU | H | 178 | 41.317 | 24.969 | 15.785 | 1.00 | 30.43 | H | O |
| ATOM | 2497 | N | TYR | H | 179 | 37.044 | 21.524 | 15.921 | 1.00 | 12.57 | H | N |
| ATOM | 2498 | CA | TYR | H | 179 | 35.868 | 21.517 | 15.056 | 1.00 | 11.69 | H | C |
| ATOM | 2499 | C | TYR | H | 179 | 35.042 | 20.248 | 15.265 | 1.00 | 11.04 | H | C |
| ATOM | 2500 | O | TYR | H | 179 | 34.189 | 19.910 | 14.444 | 1.00 | 11.12 | H | O |
| ATOM | 2501 | CB | TYR | H | 179 | 36.317 | 21.637 | 13.594 | 1.00 | 12.21 | H | C |
| ATOM | 2502 | CG | TYR | H | 179 | 37.076 | 22.924 | 13.342 | 1.00 | 15.01 | H | C |
| ATOM | 2503 | CD1 | TYR | H | 179 | 36.406 | 24.148 | 13.311 | 1.00 | 13.28 | H | C |
| ATOM | 2504 | CD2 | TYR | H | 179 | 38.466 | 22.927 | 13.211 | 1.00 | 13.16 | H | C |
| ATOM | 2505 | CE1 | TYR | H | 179 | 37.090 | 25.344 | 13.163 | 1.00 | 15.33 | H | C |
| ATOM | 2506 | CE2 | TYR | H | 179 | 39.169 | 24.124 | 13.062 | 1.00 | 16.25 | H | C |
| ATOM | 2507 | CZ | TYR | H | 179 | 38.468 | 25.329 | 13.043 | 1.00 | 17.14 | H | C |
| ATOM | 2508 | OH | TYR | H | 179 | 39.134 | 26.519 | 12.935 | 1.00 | 17.38 | H | O |
| ATOM | 2509 | N | MET | H | 180 | 35.289 | 19.567 | 16.383 | 1.00 | 11.28 | H | N |
| ATOM | 2510 | CA | MET | H | 180 | 34.607 | 18.319 | 16.711 | 1.00 | 10.08 | H | C |
| ATOM | 2511 | C | MET | H | 180 | 34.345 | 18.230 | 18.210 | 1.00 | 10.42 | H | C |
| ATOM | 2512 | O | MET | H | 180 | 34.873 | 19.014 | 18.992 | 1.00 | 11.63 | H | O |
| ATOM | 2513 | CB | MET | H | 180 | 35.498 | 17.122 | 16.359 | 1.00 | 10.13 | H | C |
| ATOM | 2514 | CG | MET | H | 180 | 36.249 | 17.191 | 15.046 | 1.00 | 11.90 | H | C |
| ATOM | 2515 | SD | MET | H | 180 | 37.417 | 15.806 | 14.948 | 1.00 | 13.02 | H | S |
| ATOM | 2516 | CE | MET | H | 180 | 38.056 | 16.055 | 13.327 | 1.00 | 10.31 | H | C |
| ATOM | 2517 | N | PHE | H | 181 | 33.544 | 17.246 | 18.603 | 1.00 | 10.40 | H | N |
| ATOM | 2518 | CA | PHE | H | 181 | 33.276 | 16.987 | 20.012 | 1.00 | 10.41 | H | C |
| ATOM | 2519 | C | PHE | H | 181 | 32.745 | 15.564 | 20.107 | 1.00 | 11.92 | H | C |
| ATOM | 2520 | O | PHE | H | 181 | 32.119 | 15.070 | 19.167 | 1.00 | 11.21 | H | O |
| ATOM | 2521 | CB | PHE | H | 181 | 32.293 | 18.010 | 20.600 | 1.00 | 10.04 | H | C |
| ATOM | 2522 | CG | PHE | H | 181 | 30.857 | 17.822 | 20.179 | 1.00 | 11.23 | H | C |
| ATOM | 2523 | CD1 | PHE | H | 181 | 30.057 | 16.852 | 20.784 | 1.00 | 9.00 | H | C |
| ATOM | 2524 | CD2 | PHE | H | 181 | 30.292 | 18.650 | 19.210 | 1.00 | 10.30 | H | C |
| ATOM | 2525 | CE1 | PHE | H | 181 | 28.712 | 16.711 | 20.434 | 1.00 | 10.61 | H | C |
| ATOM | 2526 | CE2 | PHE | H | 181 | 28.941 | 18.518 | 18.848 | 1.00 | 9.40 | H | C |
| ATOM | 2527 | CZ | PHE | H | 181 | 28.152 | 17.548 | 19.464 | 1.00 | 9.56 | H | C |
| ATOM | 2528 | N | CYS | H | 182 | 33.030 | 14.892 | 21.217 | 1.00 | 11.17 | H | N |
| ATOM | 2529 | CA | CYS | H | 182 | 32.576 | 13.525 | 21.408 | 1.00 | 13.43 | H | C |
| ATOM | 2530 | C | CYS | H | 182 | 31.306 | 13.494 | 22.220 | 1.00 | 12.56 | H | C |
| ATOM | 2531 | O | CYS | H | 182 | 31.047 | 14.379 | 23.040 | 1.00 | 13.75 | H | O |
| ATOM | 2532 | CB | CYS | H | 182 | 33.605 | 12.685 | 22.166 | 1.00 | 14.35 | H | C |
| ATOM | 2533 | SG | CYS | H | 182 | 35.315 | 12.691 | 21.563 | 1.00 | 16.95 | H | S |
| ATOM | 2534 | N | ALA | H | 183 | 30.530 | 12.445 | 22.005 | 1.00 | 10.97 | H | N |
| ATOM | 2535 | CA | ALA | H | 183 | 29.290 | 12.254 | 22.731 | 1.00 | 12.15 | H | C |
| ATOM | 2536 | C | ALA | H | 183 | 28.980 | 10.769 | 22.670 | 1.00 | 11.48 | H | C |
| ATOM | 2537 | O | ALA | H | 183 | 29.325 | 10.102 | 21.696 | 1.00 | 13.04 | H | O |
| ATOM | 2538 | CB | ALA | H | 183 | 28.166 | 13.066 | 22.088 | 1.00 | 10.31 | H | C |
| ATOM | 2539 | N | GLY | H | 184A | 28.352 | 10.244 | 23.714 | 1.00 | 11.66 | H | N |
| ATOM | 2540 | CA | GLY | H | 184A | 28.016 | 8.835 | 23.712 | 1.00 | 12.38 | H | C |
| ATOM | 2541 | C | GLY | H | 184A | 28.474 | 8.038 | 24.916 | 1.00 | 13.73 | H | C |
| ATOM | 2542 | O | GLY | H | 184A | 28.543 | 8.545 | 26.041 | 1.00 | 13.45 | H | O |
| ATOM | 2543 | N | TYR | H | 184 | 28.793 | 6.773 | 24.667 | 1.00 | 14.78 | H | N |
| ATOM | 2544 | CA | TYR | H | 184 | 29.217 | 5.864 | 25.720 | 1.00 | 14.94 | H | C |
| ATOM | 2545 | C | TYR | H | 184 | 30.395 | 5.029 | 25.250 | 1.00 | 15.46 | H | C |
| ATOM | 2546 | O | TYR | H | 184 | 30.509 | 4.702 | 24.070 | 1.00 | 16.06 | H | O |
| ATOM | 2547 | CB | TYR | H | 184 | 28.065 | 4.935 | 26.112 | 1.00 | 16.53 | H | C |
| ATOM | 2548 | CG | TYR | H | 184 | 26.792 | 5.637 | 26.533 | 1.00 | 18.74 | H | C |
| ATOM | 2549 | CD1 | TYR | H | 184 | 25.937 | 6.206 | 25.589 | 1.00 | 18.37 | H | C |
| ATOM | 2550 | CD2 | TYR | H | 184 | 26.443 | 5.731 | 27.878 | 1.00 | 20.30 | H | C |
| ATOM | 2551 | CE1 | TYR | H | 184 | 24.772 | 6.847 | 25.973 | 1.00 | 19.02 | H | C |
| ATOM | 2552 | CE2 | TYR | H | 184 | 25.277 | 6.371 | 28.273 | 1.00 | 19.18 | H | C |
| ATOM | 2553 | CZ | TYR | H | 184 | 24.448 | 6.925 | 27.317 | 1.00 | 19.19 | H | C |
| ATOM | 2554 | OH | TYR | H | 184 | 23.285 | 7.542 | 27.699 | 1.00 | 21.68 | H | O |
| ATOM | 2555 | N | SER | H | 185 | 31.267 | 4.681 | 26.185 | 1.00 | 15.70 | H | N |
| ATOM | 2556 | CA | SER | H | 185 | 32.450 | 3.891 | 25.882 | 1.00 | 15.49 | H | C |
| ATOM | 2557 | C | SER | H | 185 | 32.314 | 2.426 | 26.309 | 1.00 | 16.42 | H | C |
| ATOM | 2558 | O | SER | H | 185 | 33.294 | 1.680 | 26.293 | 1.00 | 16.49 | H | O |
| ATOM | 2559 | CB | SER | H | 185 | 33.655 | 4.506 | 26.579 | 1.00 | 15.34 | H | C |
| ATOM | 2560 | OG | SER | H | 185 | 33.478 | 4.459 | 27.984 | 1.00 | 15.56 | H | O |
| ATOM | 2561 | N | ASP | H | 186 | 31.110 | 2.013 | 26.691 | 1.00 | 17.79 | H | N |
| ATOM | 2562 | CA | ASP | H | 186 | 30.898 | 0.633 | 27.116 | 1.00 | 20.64 | H | C |
| ATOM | 2563 | C | ASP | H | 186 | 30.358 | −0.274 | 26.006 | 1.00 | 20.60 | H | C |
| ATOM | 2564 | O | ASP | H | 186 | 29.934 | −1.397 | 26.268 | 1.00 | 20.87 | H | O |
| ATOM | 2565 | CB | ASP | H | 186 | 29.962 | 0.589 | 28.330 | 1.00 | 20.43 | H | C |
| ATOM | 2566 | CG | ASP | H | 186 | 28.576 | 1.098 | 28.019 | 1.00 | 21.02 | H | C |
| ATOM | 2567 | OD1 | ASP | H | 186 | 28.330 | 1.483 | 26.884 | 1.00 | 21.60 | H | O |

-continued

| | | | | | | | | | | | |
|---|---|---|---|---|---|---|---|---|---|---|---|
| ATOM | 2568 | OD2 | ASP | H | 186 | 27.750 | 1.103 | 28.921 | 1.00 | 21.42 | H | O |
| ATOM | 2569 | N | GLY | H | 187 | 30.373 | 0.230 | 24.773 | 1.00 | 21.14 | H | N |
| ATOM | 2570 | CA | GLY | H | 187 | 29.914 | −0.531 | 23.625 | 1.00 | 20.04 | H | C |
| ATOM | 2571 | C | GLY | H | 187 | 28.424 | −0.780 | 23.493 | 1.00 | 21.04 | H | C |
| ATOM | 2572 | O | GLY | H | 187 | 28.022 | −1.702 | 22.789 | 1.00 | 22.73 | H | O |
| ATOM | 2573 | N | SER | H | 188A | 27.597 | 0.046 | 24.126 | 1.00 | 20.16 | H | N |
| ATOM | 2574 | CA | SER | H | 188A | 26.153 | −0.151 | 24.068 | 1.00 | 18.78 | H | C |
| ATOM | 2575 | C | SER | H | 188A | 25.337 | 0.830 | 23.225 | 1.00 | 17.55 | H | C |
| ATOM | 2576 | O | SER | H | 188A | 24.298 | 0.457 | 22.686 | 1.00 | 18.92 | H | O |
| ATOM | 2577 | CB | SER | H | 188A | 25.582 | −0.127 | 25.482 | 1.00 | 18.59 | H | C |
| ATOM | 2578 | OG | SER | H | 188A | 25.675 | 1.186 | 26.011 | 1.00 | 20.17 | H | O |
| ATOM | 2579 | N | LYS | H | 188 | 25.786 | 2.076 | 23.118 | 1.00 | 17.33 | H | N |
| ATOM | 2580 | CA | LYS | H | 188 | 25.020 | 3.091 | 22.390 | 1.00 | 15.93 | H | C |
| ATOM | 2581 | C | LYS | H | 188 | 25.889 | 4.084 | 21.610 | 1.00 | 15.78 | H | C |
| ATOM | 2582 | O | LYS | H | 188 | 26.883 | 4.596 | 22.133 | 1.00 | 14.09 | H | O |
| ATOM | 2583 | CB | LYS | H | 188 | 24.140 | 3.847 | 23.388 | 1.00 | 15.97 | H | C |
| ATOM | 2584 | CG | LYS | H | 188 | 23.127 | 2.967 | 24.114 | 1.00 | 17.40 | H | C |
| ATOM | 2585 | CD | LYS | H | 188 | 22.386 | 3.732 | 25.199 | 1.00 | 18.22 | H | C |
| ATOM | 2586 | CE | LYS | H | 188 | 23.253 | 3.944 | 26.424 | 1.00 | 19.93 | H | C |
| ATOM | 2587 | NZ | LYS | H | 188 | 23.548 | 2.666 | 27.142 | 1.00 | 23.44 | H | N |
| ATOM | 2588 | N | ASP | H | 189 | 25.487 | 4.381 | 20.375 | 1.00 | 14.78 | H | N |
| ATOM | 2589 | CA | ASP | H | 189 | 26.254 | 5.283 | 19.517 | 1.00 | 14.89 | H | C |
| ATOM | 2590 | C | ASP | H | 189 | 25.516 | 5.427 | 18.179 | 1.00 | 15.27 | H | C |
| ATOM | 2591 | O | ASP | H | 189 | 24.557 | 4.698 | 17.911 | 1.00 | 12.95 | H | O |
| ATOM | 2592 | CB | ASP | H | 189 | 27.639 | 4.640 | 19.305 | 1.00 | 15.17 | H | C |
| ATOM | 2593 | CG | ASP | H | 189 | 28.650 | 5.548 | 18.606 | 1.00 | 14.51 | H | C |
| ATOM | 2594 | OD1 | ASP | H | 189 | 28.434 | 6.750 | 18.465 | 1.00 | 13.62 | H | O |
| ATOM | 2595 | OD2 | ASP | H | 189 | 29.685 | 5.019 | 18.219 | 1.00 | 13.36 | H | O |
| ATOM | 2596 | N | SER | H | 190 | 25.930 | 6.393 | 17.363 | 1.00 | 12.60 | H | N |
| ATOM | 2597 | CA | SER | H | 190 | 25.358 | 6.542 | 16.036 | 1.00 | 12.63 | H | C |
| ATOM | 2598 | C | SER | H | 190 | 26.323 | 5.715 | 15.176 | 1.00 | 14.47 | H | C |
| ATOM | 2599 | O | SER | H | 190 | 27.309 | 5.184 | 15.697 | 1.00 | 14.59 | H | O |
| ATOM | 2600 | CB | SER | H | 190 | 25.337 | 8.012 | 15.595 | 1.00 | 12.32 | H | C |
| ATOM | 2601 | OG | SER | H | 190 | 26.590 | 8.641 | 15.775 | 1.00 | 16.00 | H | O |
| ATOM | 2602 | N | CYS | H | 191 | 26.063 | 5.592 | 13.879 | 1.00 | 16.70 | H | N |
| ATOM | 2603 | CA | CYS | H | 191 | 26.932 | 4.786 | 13.023 | 1.00 | 18.01 | H | C |
| ATOM | 2604 | C | CYS | H | 191 | 27.094 | 5.424 | 11.651 | 1.00 | 18.15 | H | C |
| ATOM | 2605 | O | CYS | H | 191 | 26.502 | 6.469 | 11.374 | 1.00 | 18.84 | H | O |
| ATOM | 2606 | CB | CYS | H | 191 | 26.336 | 3.376 | 12.898 | 1.00 | 21.90 | H | C |
| ATOM | 2607 | SG | CYS | H | 191 | 27.470 | 2.046 | 12.380 | 1.00 | 30.15 | H | S |
| ATOM | 2608 | N | LYS | H | 192 | 27.898 | 4.791 | 10.800 | 1.00 | 16.09 | H | N |
| ATOM | 2609 | CA | LYS | H | 192 | 28.172 | 5.271 | 9.446 | 1.00 | 17.53 | H | C |
| ATOM | 2610 | C | LYS | H | 192 | 26.934 | 5.717 | 8.668 | 1.00 | 15.62 | H | C |
| ATOM | 2611 | O | LYS | H | 192 | 26.914 | 6.803 | 8.097 | 1.00 | 13.65 | H | O |
| ATOM | 2612 | CB | LYS | H | 192 | 28.898 | 4.186 | 8.638 | 1.00 | 21.05 | H | C |
| ATOM | 2613 | CG | LYS | H | 192 | 30.199 | 3.698 | 9.262 | 1.00 | 26.03 | H | C |
| ATOM | 2614 | CD | LYS | H | 192 | 30.964 | 2.766 | 8.330 | 1.00 | 30.74 | H | C |
| ATOM | 2615 | CE | LYS | H | 192 | 30.199 | 1.481 | 8.048 | 1.00 | 35.28 | H | C |
| ATOM | 2616 | NZ | LYS | H | 192 | 30.941 | 0.599 | 7.093 | 1.00 | 36.87 | H | N |
| ATOM | 2617 | N | GLY | H | 193 | 25.910 | 4.872 | 8.635 | 1.00 | 15.41 | H | N |
| ATOM | 2618 | CA | GLY | H | 193 | 24.698 | 5.207 | 7.912 | 1.00 | 14.29 | H | C |
| ATOM | 2619 | C | GLY | H | 193 | 23.928 | 6.392 | 8.471 | 1.00 | 14.66 | H | C |
| ATOM | 2620 | O | GLY | H | 193 | 23.014 | 6.898 | 7.822 | 1.00 | 13.96 | H | O |
| ATOM | 2621 | N | ASP | H | 194 | 24.287 | 6.836 | 9.673 | 1.00 | 13.02 | H | N |
| ATOM | 2622 | CA | ASP | H | 194 | 23.627 | 7.976 | 10.304 | 1.00 | 11.92 | H | C |
| ATOM | 2623 | C | ASP | H | 194 | 24.319 | 9.299 | 9.972 | 1.00 | 11.87 | H | C |
| ATOM | 2624 | O | ASP | H | 194 | 23.795 | 10.379 | 10.273 | 1.00 | 10.97 | H | O |
| ATOM | 2625 | CB | ASP | H | 194 | 23.585 | 7.780 | 11.821 | 1.00 | 11.84 | H | C |
| ATOM | 2626 | CG | ASP | H | 194 | 22.824 | 6.530 | 12.223 | 1.00 | 12.55 | H | C |
| ATOM | 2627 | OD1 | ASP | H | 194 | 21.676 | 6.411 | 11.836 | 1.00 | 11.16 | H | O |
| ATOM | 2628 | OD2 | ASP | H | 194 | 23.389 | 5.684 | 12.923 | 1.00 | 10.92 | H | O |
| ATOM | 2629 | N | SER | H | 195 | 25.492 | 9.201 | 9.348 | 1.00 | 10.97 | H | N |
| ATOM | 2630 | CA | SER | H | 195 | 26.290 | 10.359 | 8.945 | 1.00 | 11.04 | H | C |
| ATOM | 2631 | C | SER | H | 195 | 25.454 | 11.500 | 8.379 | 1.00 | 11.57 | H | C |
| ATOM | 2632 | O | SER | H | 195 | 24.571 | 11.285 | 7.545 | 1.00 | 10.28 | H | O |
| ATOM | 2633 | CB | SER | H | 195 | 27.316 | 9.943 | 7.890 | 1.00 | 9.93 | H | C |
| ATOM | 2634 | OG | SER | H | 195 | 28.260 | 9.039 | 8.425 | 1.00 | 14.11 | H | O |
| ATOM | 2635 | N | GLY | H | 196 | 25.753 | 12.717 | 8.824 | 1.00 | 12.35 | H | N |
| ATOM | 2636 | CA | GLY | H | 196 | 25.028 | 13.884 | 8.348 | 1.00 | 12.23 | H | C |
| ATOM | 2637 | C | GLY | H | 196 | 23.805 | 14.182 | 9.189 | 1.00 | 13.45 | H | C |
| ATOM | 2638 | O | GLY | H | 196 | 23.259 | 15.286 | 9.146 | 1.00 | 13.77 | H | O |
| ATOM | 2639 | N | GLY | H | 197 | 23.383 | 13.187 | 9.962 | 1.00 | 13.04 | H | N |
| ATOM | 2640 | CA | GLY | H | 197 | 22.222 | 13.334 | 10.807 | 1.00 | 13.77 | H | C |
| ATOM | 2641 | C | GLY | H | 197 | 22.427 | 14.322 | 11.934 | 1.00 | 14.43 | H | C |
| ATOM | 2642 | O | GLY | H | 197 | 23.558 | 14.645 | 12.302 | 1.00 | 15.21 | H | O |
| ATOM | 2643 | N | PRO | H | 198 | 21.327 | 14.806 | 12.516 | 1.00 | 13.56 | H | N |
| ATOM | 2644 | CA | PRO | H | 198 | 21.315 | 15.772 | 13.615 | 1.00 | 13.40 | H | C |
| ATOM | 2645 | C | PRO | H | 198 | 21.761 | 15.263 | 14.981 | 1.00 | 11.88 | H | C |
| ATOM | 2646 | O | PRO | H | 198 | 21.559 | 14.102 | 15.330 | 1.00 | 11.73 | H | O |

-continued

| | | | | | | | | | | | |
|---|---|---|---|---|---|---|---|---|---|---|---|
| ATOM | 2647 | CB | PRO | H | 198 | 19.847 | 16.220 | 13.688 | 1.00 | 12.32 | H | C |
| ATOM | 2648 | CG | PRO | H | 198 | 19.183 | 15.624 | 12.464 | 1.00 | 16.84 | H | C |
| ATOM | 2649 | CD | PRO | H | 198 | 19.960 | 14.396 | 12.164 | 1.00 | 14.30 | H | C |
| ATOM | 2650 | N | HIS | H | 199 | 22.378 | 16.166 | 15.730 | 1.00 | 10.39 | H | N |
| ATOM | 2651 | CA | HIS | H | 199 | 22.775 | 15.954 | 17.116 | 1.00 | 10.13 | H | C |
| ATOM | 2652 | C | HIS | H | 199 | 22.028 | 17.189 | 17.599 | 1.00 | 10.86 | H | C |
| ATOM | 2653 | O | HIS | H | 199 | 22.509 | 18.312 | 17.426 | 1.00 | 10.19 | H | O |
| ATOM | 2654 | CB | HIS | H | 199 | 24.284 | 16.121 | 17.322 | 1.00 | 11.26 | H | C |
| ATOM | 2655 | CG | HIS | H | 199 | 24.698 | 16.134 | 18.765 | 1.00 | 9.49 | H | C |
| ATOM | 2656 | ND1 | HIS | H | 199 | 24.605 | 17.258 | 19.556 | 1.00 | 7.80 | H | N |
| ATOM | 2657 | CD2 | HIS | H | 199 | 25.174 | 15.151 | 19.567 | 1.00 | 9.62 | H | C |
| ATOM | 2658 | CE1 | HIS | H | 199 | 25.006 | 16.970 | 20.782 | 1.00 | 9.46 | H | C |
| ATOM | 2659 | NE2 | HIS | H | 199 | 25.356 | 15.698 | 20.816 | 1.00 | 10.16 | H | N |
| ATOM | 2660 | N | ALA | H | 200 | 20.826 | 16.979 | 18.140 | 1.00 | 11.28 | H | N |
| ATOM | 2661 | CA | ALA | H | 200 | 19.964 | 18.076 | 18.578 | 1.00 | 11.42 | H | C |
| ATOM | 2662 | C | ALA | H | 200 | 19.879 | 18.243 | 20.085 | 1.00 | 10.13 | H | C |
| ATOM | 2663 | O | ALA | H | 200 | 19.714 | 17.281 | 20.819 | 1.00 | 8.59 | H | O |
| ATOM | 2664 | CB | ALA | H | 200 | 18.567 | 17.893 | 17.991 | 1.00 | 8.70 | H | C |
| ATOM | 2665 | N | THR | H | 201 | 19.968 | 19.488 | 20.531 | 1.00 | 10.27 | H | N |
| ATOM | 2666 | CA | THR | H | 201 | 19.943 | 19.795 | 21.950 | 1.00 | 11.65 | H | C |
| ATOM | 2667 | C | THR | H | 201 | 18.690 | 20.573 | 22.350 | 1.00 | 12.35 | H | C |
| ATOM | 2668 | O | THR | H | 201 | 18.358 | 21.590 | 21.753 | 1.00 | 12.80 | H | O |
| ATOM | 2669 | CB | THR | H | 201 | 21.189 | 20.616 | 22.322 | 1.00 | 10.77 | H | C |
| ATOM | 2670 | OG1 | THR | H | 201 | 22.354 | 19.955 | 21.814 | 1.00 | 9.62 | H | O |
| ATOM | 2671 | CG2 | THR | H | 201 | 21.307 | 20.769 | 23.823 | 1.00 | 5.98 | H | C |
| ATOM | 2672 | N | HIS | H | 202 | 18.012 | 20.084 | 23.379 | 1.00 | 12.93 | H | N |
| ATOM | 2673 | CA | HIS | H | 202 | 16.799 | 20.709 | 23.889 | 1.00 | 14.16 | H | C |
| ATOM | 2674 | C | HIS | H | 202 | 17.182 | 21.718 | 24.972 | 1.00 | 13.17 | H | C |
| ATOM | 2675 | O | HIS | H | 202 | 17.953 | 21.406 | 25.877 | 1.00 | 11.26 | H | O |
| ATOM | 2676 | CB | HIS | H | 202 | 15.883 | 19.630 | 24.487 | 1.00 | 15.77 | H | C |
| ATOM | 2677 | CG | HIS | H | 202 | 14.461 | 20.062 | 24.661 | 1.00 | 19.01 | H | C |
| ATOM | 2678 | ND1 | HIS | H | 202 | 13.551 | 19.330 | 25.399 | 1.00 | 20.89 | H | N |
| ATOM | 2679 | CD2 | HIS | H | 202 | 13.778 | 21.124 | 24.172 | 1.00 | 17.67 | H | C |
| ATOM | 2680 | CE1 | HIS | H | 202 | 12.374 | 19.925 | 25.356 | 1.00 | 18.13 | H | C |
| ATOM | 2681 | NE2 | HIS | H | 202 | 12.484 | 21.016 | 24.617 | 1.00 | 20.03 | H | N |
| ATOM | 2682 | N | TYR | H | 203 | 16.654 | 22.932 | 24.878 | 1.00 | 13.14 | H | N |
| ATOM | 2683 | CA | TYR | H | 203 | 16.949 | 23.947 | 25.882 | 1.00 | 14.38 | H | C |
| ATOM | 2684 | C | TYR | H | 203 | 15.762 | 24.872 | 26.070 | 1.00 | 15.63 | H | C |
| ATOM | 2685 | O | TYR | H | 203 | 15.399 | 25.617 | 25.160 | 1.00 | 17.55 | H | O |
| ATOM | 2686 | CB | TYR | H | 203 | 18.170 | 24.788 | 25.495 | 1.00 | 11.34 | H | C |
| ATOM | 2687 | CG | TYR | H | 203 | 18.555 | 25.767 | 26.587 | 1.00 | 13.03 | H | C |
| ATOM | 2688 | CD1 | TYR | H | 203 | 19.202 | 25.328 | 27.741 | 1.00 | 11.89 | H | C |
| ATOM | 2689 | CD2 | TYR | H | 203 | 18.224 | 27.118 | 26.494 | 1.00 | 11.33 | H | C |
| ATOM | 2690 | CE1 | TYR | H | 203 | 19.510 | 26.208 | 28.775 | 1.00 | 15.40 | H | C |
| ATOM | 2691 | CE2 | TYR | H | 203 | 18.520 | 28.006 | 27.523 | 1.00 | 13.47 | H | C |
| ATOM | 2692 | CZ | TYR | H | 203 | 19.163 | 27.544 | 28.660 | 1.00 | 15.28 | H | C |
| ATOM | 2693 | OH | TYR | H | 203 | 19.449 | 28.406 | 29.689 | 1.00 | 17.54 | H | O |
| ATOM | 2694 | N | ARG | H | 204 | 15.162 | 24.817 | 27.254 | 1.00 | 17.36 | H | N |
| ATOM | 2695 | CA | ARG | H | 204 | 14.019 | 25.654 | 27.590 | 1.00 | 16.44 | H | C |
| ATOM | 2696 | C | ARG | H | 204 | 12.928 | 25.702 | 26.523 | 1.00 | 18.12 | H | C |
| ATOM | 2697 | O | ARG | H | 204 | 12.544 | 26.774 | 26.054 | 1.00 | 19.33 | H | O |
| ATOM | 2698 | CB | ARG | H | 204 | 14.507 | 27.068 | 27.931 | 1.00 | 18.74 | H | C |
| ATOM | 2699 | CG | ARG | H | 204 | 15.268 | 27.102 | 29.256 | 1.00 | 21.03 | H | C |
| ATOM | 2700 | CD | ARG | H | 204 | 15.852 | 28.461 | 29.633 | 1.00 | 23.39 | H | C |
| ATOM | 2701 | NE | ARG | H | 204 | 16.460 | 28.378 | 30.965 | 1.00 | 29.04 | H | N |
| ATOM | 2702 | CZ | ARG | H | 204 | 17.208 | 29.320 | 31.536 | 1.00 | 29.55 | H | C |
| ATOM | 2703 | NH1 | ARG | H | 204 | 17.473 | 30.455 | 30.906 | 1.00 | 29.68 | H | N |
| ATOM | 2704 | NH2 | ARG | H | 204 | 17.698 | 29.120 | 32.753 | 1.00 | 30.72 | H | N |
| ATOM | 2705 | N | GLY | H | 205 | 12.437 | 24.528 | 26.135 | 1.00 | 18.15 | H | N |
| ATOM | 2706 | CA | GLY | H | 205 | 11.366 | 24.455 | 25.158 | 1.00 | 18.43 | H | C |
| ATOM | 2707 | C | GLY | H | 205 | 11.688 | 24.465 | 23.672 | 1.00 | 17.94 | H | C |
| ATOM | 2708 | O | GLY | H | 205 | 10.773 | 24.325 | 22.859 | 1.00 | 20.84 | H | O |
| ATOM | 2709 | N | THR | H | 206 | 12.957 | 24.613 | 23.302 | 1.00 | 17.15 | H | N |
| ATOM | 2710 | CA | THR | H | 206 | 13.334 | 24.651 | 21.889 | 1.00 | 16.34 | H | C |
| ATOM | 2711 | C | THR | H | 206 | 14.556 | 23.786 | 21.587 | 1.00 | 15.73 | H | C |
| ATOM | 2712 | O | THR | H | 206 | 15.485 | 23.715 | 22.389 | 1.00 | 16.49 | H | O |
| ATOM | 2713 | CB | THR | H | 206 | 13.608 | 26.111 | 21.451 | 1.00 | 16.85 | H | C |
| ATOM | 2714 | OG1 | THR | H | 206 | 12.396 | 26.859 | 21.558 | 1.00 | 20.04 | H | O |
| ATOM | 2715 | CG2 | THR | H | 206 | 14.112 | 26.181 | 20.008 | 1.00 | 15.79 | H | C |
| ATOM | 2716 | N | TRP | H | 207 | 14.544 | 23.136 | 20.424 | 1.00 | 14.13 | H | N |
| ATOM | 2717 | CA | TRP | H | 207 | 15.639 | 22.270 | 19.995 | 1.00 | 11.78 | H | C |
| ATOM | 2718 | C | TRP | H | 207 | 16.582 | 23.008 | 19.051 | 1.00 | 11.84 | H | C |
| ATOM | 2719 | O | TRP | H | 207 | 16.138 | 23.745 | 18.174 | 1.00 | 10.36 | H | O |
| ATOM | 2720 | CB | TRP | H | 207 | 15.089 | 21.025 | 19.297 | 1.00 | 10.05 | H | C |
| ATOM | 2721 | CG | TRP | H | 207 | 14.342 | 20.115 | 20.205 | 1.00 | 12.23 | H | C |
| ATOM | 2722 | CD1 | TRP | H | 207 | 13.032 | 20.210 | 20.573 | 1.00 | 11.57 | H | C |
| ATOM | 2723 | CD2 | TRP | H | 207 | 14.871 | 18.974 | 20.891 | 1.00 | 12.27 | H | C |
| ATOM | 2724 | NE1 | TRP | H | 207 | 12.711 | 19.197 | 21.446 | 1.00 | 10.79 | H | N |
| ATOM | 2725 | CE2 | TRP | H | 207 | 13.821 | 18.425 | 21.659 | 1.00 | 11.69 | H | C |

-continued

| | | | | | | | | | | | |
|---|---|---|---|---|---|---|---|---|---|---|---|
| ATOM | 2726 | CE3 | TRP | H | 207 | 16.130 | 18.362 | 20.927 | 1.00 | 10.32 | H | C |
| ATOM | 2727 | CZ2 | TRP | H | 207 | 13.994 | 17.292 | 22.460 | 1.00 | 12.43 | H | C |
| ATOM | 2728 | CZ3 | TRP | H | 207 | 16.303 | 17.233 | 21.722 | 1.00 | 13.70 | H | C |
| ATOM | 2729 | CH2 | TRP | H | 207 | 15.239 | 16.710 | 22.478 | 1.00 | 12.06 | H | C |
| ATOM | 2730 | N | TYR | H | 208 | 17.881 | 22.785 | 19.226 | 1.00 | 11.22 | H | N |
| ATOM | 2731 | CA | TYR | H | 208 | 18.909 | 23.446 | 18.421 | 1.00 | 12.37 | H | C |
| ATOM | 2732 | C | TYR | H | 208 | 19.912 | 22.457 | 17.832 | 1.00 | 12.09 | H | C |
| ATOM | 2733 | O | TYR | H | 208 | 20.175 | 21.413 | 18.422 | 1.00 | 11.35 | H | O |
| ATOM | 2734 | CB | TYR | H | 208 | 19.679 | 24.457 | 19.281 | 1.00 | 10.64 | H | C |
| ATOM | 2735 | CG | TYR | H | 208 | 18.818 | 25.521 | 19.927 | 1.00 | 11.14 | H | C |
| ATOM | 2736 | CD1 | TYR | H | 208 | 18.192 | 25.297 | 21.155 | 1.00 | 10.27 | H | C |
| ATOM | 2737 | CD2 | TYR | H | 208 | 18.622 | 26.756 | 19.302 | 1.00 | 9.96 | H | C |
| ATOM | 2738 | CE1 | TYR | H | 208 | 17.391 | 26.279 | 21.746 | 1.00 | 9.89 | H | C |
| ATOM | 2739 | CE2 | TYR | H | 208 | 17.823 | 27.739 | 19.881 | 1.00 | 11.17 | H | C |
| ATOM | 2740 | CZ | TYR | H | 208 | 17.211 | 27.496 | 21.102 | 1.00 | 11.59 | H | C |
| ATOM | 2741 | OH | TYR | H | 208 | 16.417 | 28.471 | 21.667 | 1.00 | 14.79 | H | O |
| ATOM | 2742 | N | LEU | H | 209 | 20.479 | 22.803 | 16.676 | 1.00 | 11.60 | H | N |
| ATOM | 2743 | CA | LEU | H | 209 | 21.473 | 21.956 | 16.019 | 1.00 | 10.61 | H | C |
| ATOM | 2744 | C | LEU | H | 209 | 22.838 | 22.217 | 16.655 | 1.00 | 11.52 | H | C |
| ATOM | 2745 | O | LEU | H | 209 | 23.372 | 23.328 | 16.572 | 1.00 | 9.17 | H | O |
| ATOM | 2746 | CB | LEU | H | 209 | 21.538 | 22.275 | 14.519 | 1.00 | 11.62 | H | C |
| ATOM | 2747 | CG | LEU | H | 209 | 22.533 | 21.438 | 13.703 | 1.00 | 10.56 | H | C |
| ATOM | 2748 | CD1 | LEU | H | 209 | 22.154 | 19.964 | 13.799 | 1.00 | 9.75 | H | C |
| ATOM | 2749 | CD2 | LEU | H | 209 | 22.530 | 21.888 | 12.253 | 1.00 | 11.64 | H | C |
| ATOM | 2750 | N | THR | H | 210 | 23.401 | 21.203 | 17.301 | 1.00 | 11.36 | H | N |
| ATOM | 2751 | CA | THR | H | 210 | 24.703 | 21.362 | 17.945 | 1.00 | 12.32 | H | C |
| ATOM | 2752 | C | THR | H | 210 | 25.788 | 20.487 | 17.322 | 1.00 | 11.28 | H | C |
| ATOM | 2753 | O | THR | H | 210 | 26.970 | 20.801 | 17.411 | 1.00 | 11.33 | H | O |
| ATOM | 2754 | CB | THR | H | 210 | 24.631 | 21.051 | 19.464 | 1.00 | 11.07 | H | C |
| ATOM | 2755 | OG1 | THR | H | 210 | 23.797 | 19.907 | 19.681 | 1.00 | 12.24 | H | O |
| ATOM | 2756 | CG2 | THR | H | 210 | 24.069 | 22.232 | 20.227 | 1.00 | 11.51 | H | C |
| ATOM | 2757 | N | GLY | H | 211 | 25.392 | 19.396 | 16.685 | 1.00 | 11.49 | H | N |
| ATOM | 2758 | CA | GLY | H | 211 | 26.385 | 18.527 | 16.085 | 1.00 | 12.62 | H | C |
| ATOM | 2759 | C | GLY | H | 211 | 25.899 | 17.781 | 14.861 | 1.00 | 12.53 | H | C |
| ATOM | 2760 | O | GLY | H | 211 | 24.709 | 17.781 | 14.540 | 1.00 | 10.55 | H | O |
| ATOM | 2761 | N | ILE | H | 212 | 26.842 | 17.147 | 14.174 | 1.00 | 12.70 | H | N |
| ATOM | 2762 | CA | ILE | H | 212 | 26.545 | 16.371 | 12.976 | 1.00 | 11.37 | H | C |
| ATOM | 2763 | C | ILE | H | 212 | 27.240 | 15.016 | 13.116 | 1.00 | 12.64 | H | C |
| ATOM | 2764 | O | ILE | H | 212 | 28.424 | 14.961 | 13.451 | 1.00 | 11.86 | H | O |
| ATOM | 2765 | CB | ILE | H | 212 | 27.094 | 17.076 | 11.716 | 1.00 | 10.36 | H | C |
| ATOM | 2766 | CG1 | ILE | H | 212 | 26.527 | 18.498 | 11.619 | 1.00 | 9.87 | H | C |
| ATOM | 2767 | CG2 | ILE | H | 212 | 26.758 | 16.270 | 10.485 | 1.00 | 7.55 | H | C |
| ATOM | 2768 | CD1 | ILE | H | 212 | 27.194 | 19.343 | 10.538 | 1.00 | 10.68 | H | C |
| ATOM | 2769 | N | VAL | H | 213 | 26.503 | 13.930 | 12.890 | 1.00 | 11.61 | H | N |
| ATOM | 2770 | CA | VAL | H | 213 | 27.086 | 12.591 | 12.969 | 1.00 | 10.63 | H | C |
| ATOM | 2771 | C | VAL | H | 213 | 28.248 | 12.608 | 11.976 | 1.00 | 10.32 | H | C |
| ATOM | 2772 | O | VAL | H | 213 | 28.032 | 12.764 | 10.773 | 1.00 | 10.80 | H | O |
| ATOM | 2773 | CB | VAL | H | 213 | 26.054 | 11.512 | 12.562 | 1.00 | 8.77 | H | C |
| ATOM | 2774 | CG1 | VAL | H | 213 | 26.686 | 10.123 | 12.627 | 1.00 | 7.54 | H | C |
| ATOM | 2775 | CG2 | VAL | H | 213 | 24.850 | 11.575 | 13.486 | 1.00 | 9.35 | H | C |
| ATOM | 2776 | N | SER | H | 214 | 29.476 | 12.465 | 12.473 | 1.00 | 10.48 | H | N |
| ATOM | 2777 | CA | SER | H | 214 | 30.654 | 12.533 | 11.601 | 1.00 | 10.02 | H | C |
| ATOM | 2778 | C | SER | H | 214 | 31.527 | 11.288 | 11.510 | 1.00 | 10.29 | H | C |
| ATOM | 2779 | O | SER | H | 214 | 31.662 | 10.694 | 10.436 | 1.00 | 10.45 | H | O |
| ATOM | 2780 | CB | SER | H | 214 | 31.525 | 13.725 | 12.015 | 1.00 | 10.33 | H | C |
| ATOM | 2781 | OG | SER | H | 214 | 32.650 | 13.856 | 11.166 | 1.00 | 14.56 | H | O |
| ATOM | 2782 | N | TRP | H | 215 | 32.144 | 10.894 | 12.616 | 1.00 | 9.38 | H | N |
| ATOM | 2783 | CA | TRP | H | 215 | 32.996 | 9.715 | 12.571 | 1.00 | 9.84 | H | C |
| ATOM | 2784 | C | TRP | H | 215 | 33.186 | 9.044 | 13.919 | 1.00 | 11.40 | H | C |
| ATOM | 2785 | O | TRP | H | 215 | 32.595 | 9.440 | 14.925 | 1.00 | 10.83 | H | O |
| ATOM | 2786 | CB | TRP | H | 215 | 34.372 | 10.077 | 11.979 | 1.00 | 11.73 | H | C |
| ATOM | 2787 | CG | TRP | H | 215 | 35.189 | 11.045 | 12.802 | 1.00 | 11.28 | H | C |
| ATOM | 2788 | CD1 | TRP | H | 215 | 35.054 | 12.405 | 12.851 | 1.00 | 12.73 | H | C |
| ATOM | 2789 | CD2 | TRP | H | 215 | 36.286 | 10.720 | 13.670 | 1.00 | 12.20 | H | C |
| ATOM | 2790 | NE1 | TRP | H | 215 | 36.002 | 12.949 | 13.690 | 1.00 | 12.73 | H | N |
| ATOM | 2791 | CE2 | TRP | H | 215 | 36.770 | 11.937 | 14.206 | 1.00 | 13.66 | H | C |
| ATOM | 2792 | CE3 | TRP | H | 215 | 36.907 | 9.520 | 14.044 | 1.00 | 11.80 | H | C |
| ATOM | 2793 | CZ2 | TRP | H | 215 | 37.852 | 11.986 | 15.100 | 1.00 | 11.52 | H | C |
| ATOM | 2794 | CZ3 | TRP | H | 215 | 37.986 | 9.569 | 14.936 | 1.00 | 11.59 | H | C |
| ATOM | 2795 | CH2 | TRP | H | 215 | 38.445 | 10.796 | 15.451 | 1.00 | 12.21 | H | C |
| ATOM | 2796 | N | GLY | H | 216 | 34.029 | 8.020 | 13.928 | 1.00 | 12.15 | H | N |
| ATOM | 2797 | CA | GLY | H | 216 | 34.308 | 7.298 | 15.151 | 1.00 | 14.20 | H | C |
| ATOM | 2798 | C | GLY | H | 216 | 34.988 | 6.002 | 14.792 | 1.00 | 15.78 | H | C |
| ATOM | 2799 | O | GLY | H | 216 | 35.124 | 5.684 | 13.611 | 1.00 | 17.05 | H | O |
| ATOM | 2800 | N | GLN | H | 217 | 35.435 | 5.255 | 15.792 | 1.00 | 17.07 | H | N |
| ATOM | 2801 | CA | GLN | H | 217 | 36.081 | 3.982 | 15.521 | 1.00 | 19.04 | H | C |
| ATOM | 2802 | C | GLN | H | 217 | 34.986 | 2.937 | 15.544 | 1.00 | 17.72 | H | C |
| ATOM | 2803 | O | GLN | H | 217 | 34.486 | 2.579 | 16.606 | 1.00 | 19.73 | H | O |
| ATOM | 2804 | CB | GLN | H | 217 | 37.136 | 3.683 | 16.579 | 1.00 | 22.69 | H | C |

-continued

| | | | | | | | | | | | |
|---|---|---|---|---|---|---|---|---|---|---|---|
| ATOM | 2805 | CG  | GLN | H | 217  | 37.813 | 2.342  | 16.395 | 1.00 | 27.55 | H | C |
| ATOM | 2806 | CD  | GLN | H | 217  | 39.254 | 2.360  | 16.845 | 1.00 | 33.39 | H | C |
| ATOM | 2807 | OE1 | GLN | H | 217  | 39.613 | 3.063  | 17.791 | 1.00 | 34.21 | H | O |
| ATOM | 2808 | NE2 | GLN | H | 217  | 40.092 | 1.576  | 16.173 | 1.00 | 37.35 | H | N |
| ATOM | 2809 | N   | GLY | H | 219  | 34.606 | 2.458  | 14.364 | 1.00 | 18.12 | H | N |
| ATOM | 2810 | CA  | GLY | H | 219  | 33.539 | 1.482  | 14.279 | 1.00 | 17.60 | H | C |
| ATOM | 2811 | C   | GLY | H | 219  | 32.283 | 2.125  | 14.835 | 1.00 | 20.54 | H | C |
| ATOM | 2812 | O   | GLY | H | 219  | 32.135 | 3.347  | 14.788 | 1.00 | 20.64 | H | O |
| ATOM | 2813 | N   | CYS | H | 220  | 31.381 | 1.311  | 15.372 | 1.00 | 21.24 | H | N |
| ATOM | 2814 | CA  | CYS | H | 220  | 30.145 | 1.824  | 15.943 | 1.00 | 23.06 | H | C |
| ATOM | 2815 | C   | CYS | H | 220  | 29.893 | 1.193  | 17.310 | 1.00 | 22.01 | H | C |
| ATOM | 2816 | O   | CYS | H | 220  | 29.765 | −0.028 | 17.432 | 1.00 | 22.87 | H | O |
| ATOM | 2817 | CB  | CYS | H | 220  | 28.981 | 1.549  | 14.983 | 1.00 | 23.60 | H | C |
| ATOM | 2818 | SG  | CYS | H | 220  | 29.194 | 2.422  | 13.398 | 1.00 | 28.32 | H | S |
| ATOM | 2819 | N   | ALA | H | 221A | 29.830 | 2.039  | 18.333 | 1.00 | 21.07 | H | N |
| ATOM | 2820 | CA  | ALA | H | 221A | 29.613 | 1.586  | 19.704 | 1.00 | 21.19 | H | C |
| ATOM | 2821 | C   | ALA | H | 221A | 30.719 | 0.615  | 20.102 | 1.00 | 20.46 | H | C |
| ATOM | 2822 | O   | ALA | H | 221A | 30.463 | −0.454 | 20.660 | 1.00 | 21.19 | H | O |
| ATOM | 2823 | CB  | ALA | H | 221A | 28.245 | 0.916  | 19.833 | 1.00 | 20.81 | H | C |
| ATOM | 2824 | N   | THR | H | 221  | 31.953 | 0.992  | 19.797 | 1.00 | 20.10 | H | N |
| ATOM | 2825 | CA  | THR | H | 221  | 33.109 | 0.173  | 20.121 | 1.00 | 19.79 | H | C |
| ATOM | 2826 | C   | THR | H | 221  | 33.530 | 0.484  | 21.551 | 1.00 | 18.64 | H | C |
| ATOM | 2827 | O   | THR | H | 221  | 33.610 | 1.647  | 21.943 | 1.00 | 17.97 | H | O |
| ATOM | 2828 | CB  | THR | H | 221  | 34.273 | 0.467  | 19.151 | 1.00 | 20.35 | H | C |
| ATOM | 2829 | OG1 | THR | H | 221  | 33.854 | 0.169  | 17.815 | 1.00 | 22.66 | H | O |
| ATOM | 2830 | CG2 | THR | H | 221  | 35.492 | −0.386 | 19.485 | 1.00 | 22.20 | H | C |
| ATOM | 2831 | N   | VAL | H | 222  | 33.776 | −0.560 | 22.332 | 1.00 | 16.93 | H | N |
| ATOM | 2832 | CA  | VAL | H | 222  | 34.186 | −0.402 | 23.721 | 1.00 | 16.22 | H | C |
| ATOM | 2833 | C   | VAL | H | 222  | 35.458 | 0.437  | 23.788 | 1.00 | 16.60 | H | C |
| ATOM | 2834 | O   | VAL | H | 222  | 36.424 | 0.173  | 23.077 | 1.00 | 16.78 | H | O |
| ATOM | 2835 | CB  | VAL | H | 222  | 34.444 | −1.783 | 24.388 | 1.00 | 15.57 | H | C |
| ATOM | 2836 | CG1 | VAL | H | 222  | 34.994 | −1.596 | 25.802 | 1.00 | 15.54 | H | C |
| ATOM | 2837 | CG2 | VAL | H | 222  | 33.147 | −2.589 | 24.433 | 1.00 | 12.31 | H | C |
| ATOM | 2838 | N   | GLY | H | 223  | 35.444 | 1.458  | 24.639 | 1.00 | 18.10 | H | N |
| ATOM | 2839 | CA  | GLY | H | 223  | 36.603 | 2.322  | 24.785 | 1.00 | 17.10 | H | C |
| ATOM | 2840 | C   | GLY | H | 223  | 36.607 | 3.503  | 23.834 | 1.00 | 16.65 | H | C |
| ATOM | 2841 | O   | GLY | H | 223  | 37.602 | 4.221  | 23.749 | 1.00 | 16.09 | H | O |
| ATOM | 2842 | N   | HIS | H | 224  | 35.501 | 3.716  | 23.122 | 1.00 | 14.21 | H | N |
| ATOM | 2843 | CA  | HIS | H | 224  | 35.418 | 4.817  | 22.172 | 1.00 | 14.13 | H | C |
| ATOM | 2844 | C   | HIS | H | 224  | 34.054 | 5.490  | 22.169 | 1.00 | 13.03 | H | C |
| ATOM | 2845 | O   | HIS | H | 224  | 33.043 | 4.883  | 22.523 | 1.00 | 12.79 | H | O |
| ATOM | 2846 | CB  | HIS | H | 224  | 35.772 | 4.324  | 20.768 | 1.00 | 14.15 | H | C |
| ATOM | 2847 | CG  | HIS | H | 224  | 37.163 | 3.786  | 20.665 | 1.00 | 18.68 | H | C |
| ATOM | 2848 | ND1 | HIS | H | 224  | 38.273 | 4.602  | 20.632 | 1.00 | 22.89 | H | N |
| ATOM | 2849 | CD2 | HIS | H | 224  | 37.630 | 2.516  | 20.690 | 1.00 | 18.87 | H | C |
| ATOM | 2850 | CE1 | HIS | H | 224  | 39.365 | 3.859  | 20.645 | 1.00 | 20.95 | H | C |
| ATOM | 2851 | NE2 | HIS | H | 224  | 39.002 | 2.590  | 20.682 | 1.00 | 24.07 | H | N |
| ATOM | 2852 | N   | PHE | H | 225  | 34.059 | 6.758  | 21.772 | 1.00 | 12.58 | H | N |
| ATOM | 2853 | CA  | PHE | H | 225  | 32.870 | 7.597  | 21.709 | 1.00 | 13.20 | H | C |
| ATOM | 2854 | C   | PHE | H | 225  | 32.638 | 8.059  | 20.270 | 1.00 | 14.27 | H | C |
| ATOM | 2855 | O   | PHE | H | 225  | 33.567 | 8.102  | 19.459 | 1.00 | 13.13 | H | O |
| ATOM | 2856 | CB  | PHE | H | 225  | 33.070 | 8.857  | 22.566 | 1.00 | 12.36 | H | C |
| ATOM | 2857 | CG  | PHE | H | 225  | 33.176 | 8.599  | 24.041 | 1.00 | 13.26 | H | C |
| ATOM | 2858 | CD1 | PHE | H | 225  | 32.034 | 8.486  | 24.826 | 1.00 | 10.55 | H | C |
| ATOM | 2859 | CD2 | PHE | H | 225  | 34.422 | 8.496  | 24.655 | 1.00 | 12.18 | H | C |
| ATOM | 2860 | CE1 | PHE | H | 225  | 32.132 | 8.275  | 26.197 | 1.00 | 11.54 | H | C |
| ATOM | 2861 | CE2 | PHE | H | 225  | 34.528 | 8.284  | 26.024 | 1.00 | 11.28 | H | C |
| ATOM | 2862 | CZ  | PHE | H | 225  | 33.383 | 8.173  | 26.797 | 1.00 | 11.86 | H | C |
| ATOM | 2863 | N   | GLY | H | 226  | 31.401 | 8.423  | 19.954 | 1.00 | 11.84 | H | N |
| ATOM | 2864 | CA  | GLY | H | 226  | 31.141 | 8.930  | 18.622 | 1.00 | 11.14 | H | C |
| ATOM | 2865 | C   | GLY | H | 226  | 31.706 | 10.345 | 18.564 | 1.00 | 11.37 | H | C |
| ATOM | 2866 | O   | GLY | H | 226  | 31.783 | 11.018 | 19.593 | 1.00 | 9.76  | H | O |
| ATOM | 2867 | N   | VAL | H | 227  | 32.124 | 10.789 | 17.383 | 1.00 | 10.30 | H | N |
| ATOM | 2868 | CA  | VAL | H | 227  | 32.664 | 12.137 | 17.217 | 1.00 | 11.99 | H | C |
| ATOM | 2869 | C   | VAL | H | 227  | 31.711 | 12.893 | 16.279 | 1.00 | 12.30 | H | C |
| ATOM | 2870 | O   | VAL | H | 227  | 31.308 | 12.376 | 15.236 | 1.00 | 11.88 | H | O |
| ATOM | 2871 | CB  | VAL | H | 227  | 34.096 | 12.119 | 16.597 | 1.00 | 13.42 | H | C |
| ATOM | 2872 | CG1 | VAL | H | 227  | 34.725 | 13.503 | 16.711 | 1.00 | 10.66 | H | C |
| ATOM | 2873 | CG2 | VAL | H | 227  | 34.977 | 11.081 | 17.304 | 1.00 | 11.39 | H | C |
| ATOM | 2874 | N   | TYR | H | 228  | 31.360 | 14.117 | 16.651 | 1.00 | 11.76 | H | N |
| ATOM | 2875 | CA  | TYR | H | 228  | 30.424 | 14.913 | 15.868 | 1.00 | 11.60 | H | C |
| ATOM | 2876 | C   | TYR | H | 228  | 31.040 | 16.251 | 15.458 | 1.00 | 11.78 | H | C |
| ATOM | 2877 | O   | TYR | H | 228  | 31.870 | 16.798 | 16.176 | 1.00 | 12.87 | H | O |
| ATOM | 2878 | CB  | TYR | H | 228  | 29.147 | 15.158 | 16.692 | 1.00 | 12.02 | H | C |
| ATOM | 2879 | CG  | TYR | H | 228  | 28.446 | 13.883 | 17.159 | 1.00 | 13.58 | H | C |
| ATOM | 2880 | CD1 | TYR | H | 228  | 28.956 | 13.112 | 18.211 | 1.00 | 15.38 | H | C |
| ATOM | 2881 | CD2 | TYR | H | 228  | 27.302 | 13.425 | 16.515 | 1.00 | 12.87 | H | C |
| ATOM | 2882 | CE1 | TYR | H | 228  | 28.334 | 11.908 | 18.599 | 1.00 | 13.68 | H | C |
| ATOM | 2883 | CE2 | TYR | H | 228  | 26.680 | 12.235 | 16.894 | 1.00 | 11.86 | H | C |

-continued

| | | | | | | | | | | |
|---|---|---|---|---|---|---|---|---|---|---|
| ATOM | 2884 | CZ | TYR | H | 228 | 27.198 | 11.484 | 17.931 | 1.00 | 13.33 | H | C |
| ATOM | 2885 | OH | TYR | H | 228 | 26.570 | 10.310 | 18.293 | 1.00 | 13.39 | H | O |
| ATOM | 2886 | N | THR | H | 229 | 30.649 | 16.767 | 14.296 | 1.00 | 10.21 | H | N |
| ATOM | 2887 | CA | THR | H | 229 | 31.158 | 18.056 | 13.840 | 1.00 | 9.23 | H | C |
| ATOM | 2888 | C | THR | H | 229 | 30.612 | 19.105 | 14.817 | 1.00 | 9.22 | H | C |
| ATOM | 2889 | O | THR | H | 229 | 29.422 | 19.093 | 15.133 | 1.00 | 9.33 | H | O |
| ATOM | 2890 | CB | THR | H | 229 | 30.656 | 18.383 | 12.420 | 1.00 | 11.04 | H | C |
| ATOM | 2891 | OG1 | THR | H | 229 | 31.037 | 17.334 | 11.519 | 1.00 | 10.26 | H | O |
| ATOM | 2892 | CG2 | THR | H | 229 | 31.246 | 19.712 | 11.935 | 1.00 | 8.87 | H | C |
| ATOM | 2893 | N | ARG | H | 230 | 31.473 | 19.993 | 15.309 | 1.00 | 7.76 | H | N |
| ATOM | 2894 | CA | ARG | H | 230 | 31.051 | 21.026 | 16.257 | 1.00 | 7.07 | H | C |
| ATOM | 2895 | C | ARG | H | 230 | 30.444 | 22.197 | 15.487 | 1.00 | 7.98 | H | C |
| ATOM | 2896 | O | ARG | H | 230 | 31.150 | 23.158 | 15.134 | 1.00 | 6.49 | H | O |
| ATOM | 2897 | CB | ARG | H | 230 | 32.251 | 21.505 | 17.093 | 1.00 | 8.54 | H | C |
| ATOM | 2898 | CG | ARG | H | 230 | 31.885 | 22.461 | 18.238 | 1.00 | 11.66 | H | C |
| ATOM | 2899 | CD | ARG | H | 230 | 33.104 | 22.903 | 19.054 | 1.00 | 14.39 | H | C |
| ATOM | 2900 | NE | ARG | H | 230 | 33.846 | 21.777 | 19.631 | 1.00 | 14.90 | H | N |
| ATOM | 2901 | CZ | ARG | H | 230 | 33.986 | 21.545 | 20.937 | 1.00 | 19.51 | H | C |
| ATOM | 2902 | NH1 | ARG | H | 230 | 33.434 | 22.355 | 21.835 | 1.00 | 18.42 | H | N |
| ATOM | 2903 | NH2 | ARG | H | 230 | 34.694 | 20.503 | 21.356 | 1.00 | 18.54 | H | N |
| ATOM | 2904 | N | VAL | H | 231 | 29.134 | 22.115 | 15.243 | 1.00 | 7.40 | H | N |
| ATOM | 2905 | CA | VAL | H | 231 | 28.396 | 23.132 | 14.485 | 1.00 | 8.02 | H | C |
| ATOM | 2906 | C | VAL | H | 231 | 28.582 | 24.590 | 14.906 | 1.00 | 8.03 | H | C |
| ATOM | 2907 | O | VAL | H | 231 | 28.522 | 25.478 | 14.063 | 1.00 | 11.15 | H | O |
| ATOM | 2908 | CB | VAL | H | 231 | 26.869 | 22.813 | 14.453 | 1.00 | 8.34 | H | C |
| ATOM | 2909 | CG1 | VAL | H | 231 | 26.091 | 23.963 | 13.789 | 1.00 | 6.76 | H | C |
| ATOM | 2910 | CG2 | VAL | H | 231 | 26.631 | 21.536 | 13.663 | 1.00 | 6.77 | H | C |
| ATOM | 2911 | N | SER | H | 232 | 28.812 | 24.846 | 16.191 | 1.00 | 9.98 | H | N |
| ATOM | 2912 | CA | SER | H | 232 | 28.999 | 26.216 | 16.665 | 1.00 | 10.61 | H | C |
| ATOM | 2913 | C | SER | H | 232 | 30.141 | 26.942 | 15.951 | 1.00 | 11.51 | H | C |
| ATOM | 2914 | O | SER | H | 232 | 30.116 | 28.162 | 15.815 | 1.00 | 13.83 | H | O |
| ATOM | 2915 | CB | SER | H | 232 | 29.253 | 26.225 | 18.172 | 1.00 | 9.74 | H | C |
| ATOM | 2916 | OG | SER | H | 232 | 30.328 | 25.366 | 18.508 | 1.00 | 9.99 | H | O |
| ATOM | 2917 | N | GLN | H | 233 | 31.138 | 26.192 | 15.500 | 1.00 | 10.91 | H | N |
| ATOM | 2918 | CA | GLN | H | 233 | 32.282 | 26.758 | 14.790 | 1.00 | 12.68 | H | C |
| ATOM | 2919 | C | GLN | H | 233 | 31.957 | 27.212 | 13.365 | 1.00 | 12.56 | H | C |
| ATOM | 2920 | O | GLN | H | 233 | 32.715 | 27.973 | 12.755 | 1.00 | 10.39 | H | O |
| ATOM | 2921 | CB | GLN | H | 233 | 33.410 | 25.725 | 14.738 | 1.00 | 14.26 | H | C |
| ATOM | 2922 | CG | GLN | H | 233 | 33.859 | 25.290 | 16.109 | 1.00 | 17.78 | H | C |
| ATOM | 2923 | CD | GLN | H | 233 | 34.180 | 26.481 | 16.983 | 1.00 | 23.92 | H | C |
| ATOM | 2924 | OE1 | GLN | H | 233 | 35.120 | 27.221 | 16.702 | 1.00 | 22.25 | H | O |
| ATOM | 2925 | NE2 | GLN | H | 233 | 33.383 | 26.687 | 18.045 | 1.00 | 25.97 | H | N |
| ATOM | 2926 | N | TYR | H | 234 | 30.815 | 26.765 | 12.851 | 1.00 | 10.53 | H | N |
| ATOM | 2927 | CA | TYR | H | 234 | 30.401 | 27.072 | 11.485 | 1.00 | 10.91 | H | C |
| ATOM | 2928 | C | TYR | H | 234 | 29.164 | 27.970 | 11.338 | 1.00 | 11.10 | H | C |
| ATOM | 2929 | O | TYR | H | 234 | 28.663 | 28.137 | 10.232 | 1.00 | 12.26 | H | O |
| ATOM | 2930 | CB | TYR | H | 234 | 30.145 | 25.748 | 10.752 | 1.00 | 11.97 | H | C |
| ATOM | 2931 | CG | TYR | H | 234 | 31.359 | 24.833 | 10.717 | 1.00 | 10.28 | H | C |
| ATOM | 2932 | CD1 | TYR | H | 234 | 32.363 | 25.018 | 9.765 | 1.00 | 9.58 | H | C |
| ATOM | 2933 | CD2 | TYR | H | 234 | 31.526 | 23.826 | 11.661 | 1.00 | 8.26 | H | C |
| ATOM | 2934 | CE1 | TYR | H | 234 | 33.501 | 24.231 | 9.756 | 1.00 | 10.13 | H | C |
| ATOM | 2935 | CE2 | TYR | H | 234 | 32.673 | 23.022 | 11.665 | 1.00 | 10.83 | H | C |
| ATOM | 2936 | CZ | TYR | H | 234 | 33.653 | 23.236 | 10.707 | 1.00 | 10.93 | H | C |
| ATOM | 2937 | OH | TYR | H | 234 | 34.782 | 22.464 | 10.691 | 1.00 | 11.60 | H | O |
| ATOM | 2938 | N | ILE | H | 235 | 28.670 | 28.549 | 12.428 | 1.00 | 10.49 | H | N |
| ATOM | 2939 | CA | ILE | H | 235 | 27.473 | 29.389 | 12.341 | 1.00 | 12.21 | H | C |
| ATOM | 2940 | C | ILE | H | 235 | 27.624 | 30.539 | 11.343 | 1.00 | 13.01 | H | C |
| ATOM | 2941 | O | ILE | H | 235 | 26.790 | 30.710 | 10.455 | 1.00 | 13.67 | H | O |
| ATOM | 2942 | CB | ILE | H | 235 | 27.076 | 29.971 | 13.725 | 1.00 | 12.39 | H | C |
| ATOM | 2943 | CG1 | ILE | H | 235 | 26.910 | 28.842 | 14.746 | 1.00 | 13.92 | H | C |
| ATOM | 2944 | CG2 | ILE | H | 235 | 25.759 | 30.764 | 13.601 | 1.00 | 14.14 | H | C |
| ATOM | 2945 | CD1 | ILE | H | 235 | 25.923 | 27.750 | 14.319 | 1.00 | 11.48 | H | C |
| ATOM | 2946 | N | GLU | H | 236 | 28.680 | 31.331 | 11.493 | 1.00 | 15.53 | H | N |
| ATOM | 2947 | CA | GLU | H | 236 | 28.931 | 32.449 | 10.582 | 1.00 | 16.27 | H | C |
| ATOM | 2948 | C | GLU | H | 236 | 29.116 | 31.967 | 9.143 | 1.00 | 15.01 | H | C |
| ATOM | 2949 | O | GLU | H | 236 | 28.608 | 32.575 | 8.199 | 1.00 | 15.26 | H | O |
| ATOM | 2950 | CB | GLU | H | 236 | 30.178 | 33.222 | 11.023 | 1.00 | 20.86 | H | C |
| ATOM | 2951 | CG | GLU | H | 236 | 30.002 | 34.066 | 12.278 | 1.00 | 28.52 | H | C |
| ATOM | 2952 | CD | GLU | H | 236 | 29.769 | 33.243 | 13.535 | 1.00 | 35.96 | H | C |
| ATOM | 2953 | OE1 | GLU | H | 236 | 30.614 | 32.384 | 13.848 | 1.00 | 39.48 | H | O |
| ATOM | 2954 | OE2 | GLU | H | 236 | 28.742 | 33.466 | 14.205 | 1.00 | 39.32 | H | O |
| ATOM | 2955 | N | TRP | H | 237 | 29.848 | 30.873 | 8.979 | 1.00 | 13.41 | H | N |
| ATOM | 2956 | CA | TRP | H | 237 | 30.098 | 30.298 | 7.660 | 1.00 | 12.55 | H | C |
| ATOM | 2957 | C | TRP | H | 237 | 28.759 | 29.950 | 7.000 | 1.00 | 13.34 | H | C |
| ATOM | 2958 | O | TRP | H | 237 | 28.524 | 30.268 | 5.828 | 1.00 | 12.48 | H | O |
| ATOM | 2959 | CB | TRP | H | 237 | 30.950 | 29.023 | 7.807 | 1.00 | 12.29 | H | C |
| ATOM | 2960 | CG | TRP | H | 237 | 31.424 | 28.400 | 6.509 | 1.00 | 10.83 | H | C |
| ATOM | 2961 | CD1 | TRP | H | 237 | 32.421 | 28.860 | 5.690 | 1.00 | 11.49 | H | C |
| ATOM | 2962 | CD2 | TRP | H | 237 | 30.927 | 27.196 | 5.897 | 1.00 | 11.56 | H | C |

-continued

| | | | | | | | | | | | |
|---|---|---|---|---|---|---|---|---|---|---|---|
| ATOM | 2963 | NE1 | TRP | H | 237 | 32.577 | 28.019 | 4.612 | 1.00 | 11.23 | H | N |
| ATOM | 2964 | CE2 | TRP | H | 237 | 31.675 | 26.993 | 4.711 | 1.00 | 10.61 | H | C |
| ATOM | 2965 | CE3 | TRP | H | 237 | 29.922 | 26.276 | 6.232 | 1.00 | 11.81 | H | C |
| ATOM | 2966 | CZ2 | TRP | H | 237 | 31.448 | 25.903 | 3.856 | 1.00 | 10.86 | H | C |
| ATOM | 2967 | CZ3 | TRP | H | 237 | 29.695 | 25.186 | 5.379 | 1.00 | 13.69 | H | C |
| ATOM | 2968 | CH2 | TRP | H | 237 | 30.459 | 25.013 | 4.202 | 1.00 | 11.69 | H | C |
| ATOM | 2969 | N | LEU | H | 238 | 27.890 | 29.289 | 7.762 | 1.00 | 11.93 | H | N |
| ATOM | 2970 | CA | LEU | H | 238 | 26.577 | 28.876 | 7.272 | 1.00 | 13.74 | H | C |
| ATOM | 2971 | C | LEU | H | 238 | 25.660 | 30.064 | 6.976 | 1.00 | 14.26 | H | C |
| ATOM | 2972 | O | LEU | H | 238 | 25.006 | 30.106 | 5.937 | 1.00 | 15.47 | H | O |
| ATOM | 2973 | CB | LEU | H | 238 | 25.906 | 27.948 | 8.296 | 1.00 | 11.48 | H | C |
| ATOM | 2974 | CG | LEU | H | 238 | 26.619 | 26.607 | 8.530 | 1.00 | 12.33 | H | C |
| ATOM | 2975 | CD1 | LEU | H | 238 | 26.127 | 25.955 | 9.816 | 1.00 | 9.88 | H | C |
| ATOM | 2976 | CD2 | LEU | H | 238 | 26.393 | 25.696 | 7.330 | 1.00 | 11.54 | H | C |
| ATOM | 2977 | N | GLN | H | 239 | 25.614 | 31.029 | 7.887 | 1.00 | 16.12 | H | N |
| ATOM | 2978 | CA | GLN | H | 239 | 24.761 | 32.202 | 7.696 | 1.00 | 18.31 | H | C |
| ATOM | 2979 | C | GLN | H | 239 | 25.149 | 33.011 | 6.463 | 1.00 | 17.63 | H | C |
| ATOM | 2980 | O | GLN | H | 239 | 24.289 | 33.448 | 5.705 | 1.00 | 17.31 | H | O |
| ATOM | 2981 | CB | GLN | H | 239 | 24.809 | 33.099 | 8.930 | 1.00 | 16.56 | H | C |
| ATOM | 2982 | CG | GLN | H | 239 | 24.263 | 32.442 | 10.176 | 1.00 | 22.50 | H | C |
| ATOM | 2983 | CD | GLN | H | 239 | 24.217 | 33.393 | 11.348 | 1.00 | 24.81 | H | C |
| ATOM | 2984 | OE1 | GLN | H | 239 | 25.143 | 34.179 | 11.563 | 1.00 | 28.05 | H | O |
| ATOM | 2985 | NE2 | GLN | H | 239 | 23.144 | 33.321 | 12.124 | 1.00 | 28.34 | H | N |
| ATOM | 2986 | N | LYS | H | 240 | 26.446 | 33.205 | 6.268 | 1.00 | 19.23 | H | N |
| ATOM | 2987 | CA | LYS | H | 240 | 26.944 | 33.958 | 5.125 | 1.00 | 20.76 | H | C |
| ATOM | 2988 | C | LYS | H | 240 | 26.544 | 33.269 | 3.816 | 1.00 | 20.55 | H | C |
| ATOM | 2989 | O | LYS | H | 240 | 26.068 | 33.915 | 2.884 | 1.00 | 20.97 | H | O |
| ATOM | 2990 | CB | LYS | H | 240 | 28.467 | 34.072 | 5.218 | 1.00 | 23.48 | H | C |
| ATOM | 2991 | CG | LYS | H | 240 | 29.082 | 35.190 | 4.391 | 1.00 | 30.47 | H | C |
| ATOM | 2992 | CD | LYS | H | 240 | 29.016 | 34.913 | 2.900 | 1.00 | 34.65 | H | C |
| ATOM | 2993 | CE | LYS | H | 240 | 29.606 | 36.071 | 2.101 | 1.00 | 38.36 | H | C |
| ATOM | 2994 | NZ | LYS | H | 240 | 31.028 | 36.326 | 2.469 | 1.00 | 39.99 | H | N |
| ATOM | 2995 | N | LEU | H | 241 | 26.733 | 31.954 | 3.754 | 1.00 | 20.03 | H | N |
| ATOM | 2996 | CA | LEU | H | 241 | 26.398 | 31.187 | 2.560 | 1.00 | 19.49 | H | C |
| ATOM | 2997 | C | LEU | H | 241 | 24.900 | 31.140 | 2.256 | 1.00 | 19.86 | H | C |
| ATOM | 2998 | O | LEU | H | 241 | 24.508 | 31.126 | 1.094 | 1.00 | 18.70 | H | O |
| ATOM | 2999 | CB | LEU | H | 241 | 26.948 | 29.763 | 2.680 | 1.00 | 19.02 | H | C |
| ATOM | 3000 | CG | LEU | H | 241 | 28.473 | 29.630 | 2.647 | 1.00 | 19.62 | H | C |
| ATOM | 3001 | CD1 | LEU | H | 241 | 28.870 | 28.191 | 2.990 | 1.00 | 18.89 | H | C |
| ATOM | 3002 | CD2 | LEU | H | 241 | 29.001 | 30.032 | 1.273 | 1.00 | 14.59 | H | C |
| ATOM | 3003 | N | MET | H | 242 | 24.058 | 31.106 | 3.287 | 1.00 | 21.92 | H | N |
| ATOM | 3004 | CA | MET | H | 242 | 22.615 | 31.081 | 3.051 | 1.00 | 24.59 | H | C |
| ATOM | 3005 | C | MET | H | 242 | 22.142 | 32.421 | 2.477 | 1.00 | 27.60 | H | C |
| ATOM | 3006 | O | MET | H | 242 | 21.097 | 32.497 | 1.834 | 1.00 | 27.62 | H | O |
| ATOM | 3007 | CB | MET | H | 242 | 21.854 | 30.746 | 4.341 | 1.00 | 21.21 | H | C |
| ATOM | 3008 | CG | MET | H | 242 | 22.003 | 29.283 | 4.768 | 1.00 | 20.37 | H | C |
| ATOM | 3009 | SD | MET | H | 242 | 21.011 | 28.815 | 6.206 | 1.00 | 18.95 | H | S |
| ATOM | 3010 | CE | MET | H | 242 | 21.948 | 29.603 | 7.540 | 1.00 | 14.65 | H | C |
| ATOM | 3011 | N | ARG | H | 243 | 22.924 | 33.472 | 2.703 | 1.00 | 30.45 | H | N |
| ATOM | 3012 | CA | ARG | H | 243 | 22.595 | 34.795 | 2.187 | 1.00 | 34.75 | H | C |
| ATOM | 3013 | C | ARG | H | 243 | 23.270 | 35.048 | 0.840 | 1.00 | 37.34 | H | C |
| ATOM | 3014 | O | ARG | H | 243 | 23.277 | 36.176 | 0.351 | 1.00 | 39.24 | H | O |
| ATOM | 3015 | CB | ARG | H | 243 | 23.048 | 35.868 | 3.170 | 1.00 | 35.66 | H | C |
| ATOM | 3016 | CG | ARG | H | 243 | 22.216 | 35.976 | 4.429 | 1.00 | 37.59 | H | C |
| ATOM | 3017 | CD | ARG | H | 243 | 23.094 | 36.381 | 5.600 | 1.00 | 42.39 | H | C |
| ATOM | 3018 | NE | ARG | H | 243 | 24.090 | 37.380 | 5.218 | 1.00 | 45.18 | H | N |
| ATOM | 3019 | CZ | ARG | H | 243 | 25.137 | 37.722 | 5.965 | 1.00 | 46.96 | H | C |
| ATOM | 3020 | NH1 | ARG | H | 243 | 25.335 | 37.148 | 7.147 | 1.00 | 45.77 | H | N |
| ATOM | 3021 | NH2 | ARG | H | 243 | 25.997 | 38.631 | 5.519 | 1.00 | 47.07 | H | N |
| ATOM | 3022 | N | SER | H | 244 | 23.836 | 34.002 | 0.245 | 1.00 | 39.09 | H | N |
| ATOM | 3023 | CA | SER | H | 244 | 24.522 | 34.130 | −1.034 | 1.00 | 40.99 | H | C |
| ATOM | 3024 | C | SER | H | 244 | 23.684 | 33.644 | −2.208 | 1.00 | 42.62 | H | C |
| ATOM | 3025 | O | SER | H | 244 | 22.743 | 32.867 | −2.042 | 1.00 | 41.83 | H | O |
| ATOM | 3026 | CB | SER | H | 244 | 25.845 | 33.363 | −0.994 | 1.00 | 41.34 | H | C |
| ATOM | 3027 | OG | SER | H | 244 | 26.705 | 33.895 | −0.001 | 1.00 | 43.40 | H | O |
| ATOM | 3028 | N | GLU | H | 245 | 24.038 | 34.113 | −3.400 | 1.00 | 44.75 | H | N |
| ATOM | 3029 | CA | GLU | H | 245 | 23.330 | 33.737 | −4.615 | 1.00 | 46.58 | H | C |
| ATOM | 3030 | C | GLU | H | 245 | 23.882 | 32.431 | −5.165 | 1.00 | 46.31 | H | C |
| ATOM | 3031 | O | GLU | H | 245 | 25.076 | 32.157 | −5.057 | 1.00 | 46.57 | H | O |
| ATOM | 3032 | CB | GLU | H | 245 | 23.470 | 34.833 | −5.672 | 1.00 | 49.32 | H | C |
| ATOM | 3033 | CG | GLU | H | 245 | 22.851 | 36.164 | −5.282 | 1.00 | 53.68 | H | C |
| ATOM | 3034 | CD | GLU | H | 245 | 22.994 | 37.212 | −6.369 | 1.00 | 56.49 | H | C |
| ATOM | 3035 | OE1 | GLU | H | 245 | 22.529 | 38.339 | −6.166 | 1.00 | 58.31 | H | O |
| ATOM | 3036 | OE2 | GLU | H | 245 | 23.571 | 36.900 | −7.417 | 1.00 | 57.52 | H | O |
| ATOM | 3037 | N | PRO | H | 246 | 23.013 | 31.605 | −5.765 | 1.00 | 46.06 | H | N |
| ATOM | 3038 | CA | PRO | H | 246 | 23.430 | 30.323 | −6.334 | 1.00 | 46.49 | H | C |
| ATOM | 3039 | C | PRO | H | 246 | 24.612 | 30.488 | −7.287 | 1.00 | 46.82 | H | C |
| ATOM | 3040 | O | PRO | H | 246 | 24.884 | 31.588 | −7.770 | 1.00 | 47.98 | H | O |
| ATOM | 3041 | CB | PRO | H | 246 | 22.174 | 29.846 | −7.055 | 1.00 | 46.60 | H | C |

-continued

| | | | | | | | | | | | |
|---|---|---|---|---|---|---|---|---|---|---|---|
| ATOM | 3042 | CG | PRO | H | 246 | 21.081 | 30.401 | −6.206 | 1.00 | 46.59 | H | C |
| ATOM | 3043 | CD | PRO | H | 246 | 21.563 | 31.803 | −5.932 | 1.00 | 45.49 | H | C |
| ATOM | 3044 | N | ARG | H | 247 | 25.316 | 29.393 | −7.545 | 1.00 | 45.68 | H | N |
| ATOM | 3045 | CA | ARG | H | 247 | 26.455 | 29.420 | −8.449 | 1.00 | 45.13 | H | C |
| ATOM | 3046 | C | ARG | H | 247 | 26.391 | 28.204 | −9.360 | 1.00 | 43.90 | H | C |
| ATOM | 3047 | O | ARG | H | 247 | 26.012 | 27.114 | −8.930 | 1.00 | 43.91 | H | O |
| ATOM | 3048 | CB | ARG | H | 247 | 27.772 | 29.416 | −7.665 | 1.00 | 46.78 | H | C |
| ATOM | 3049 | CG | ARG | H | 247 | 27.999 | 30.655 | −6.806 | 1.00 | 48.61 | H | C |
| ATOM | 3050 | CD | ARG | H | 247 | 29.351 | 30.585 | −6.107 | 1.00 | 50.94 | H | C |
| ATOM | 3051 | NE | ARG | H | 247 | 29.547 | 31.650 | −5.121 | 1.00 | 52.94 | H | N |
| ATOM | 3052 | CZ | ARG | H | 247 | 28.897 | 31.748 | −3.962 | 1.00 | 53.90 | H | C |
| ATOM | 3053 | NH1 | ARG | H | 247 | 27.988 | 30.846 | −3.611 | 1.00 | 53.30 | H | N |
| ATOM | 3054 | NH2 | ARG | H | 247 | 29.164 | 32.756 | −3.142 | 1.00 | 54.90 | H | N |
| ATOM | 3055 | N | PRO | H | 248 | 26.754 | 28.378 | −10.639 | 1.00 | 42.02 | H | N |
| ATOM | 3056 | CA | PRO | H | 248 | 26.725 | 27.268 | −11.595 | 1.00 | 40.10 | H | C |
| ATOM | 3057 | C | PRO | H | 248 | 27.396 | 26.040 | −10.999 | 1.00 | 36.76 | H | C |
| ATOM | 3058 | O | PRO | H | 248 | 28.348 | 26.168 | −10.238 | 1.00 | 37.56 | H | O |
| ATOM | 3059 | CB | PRO | H | 248 | 27.495 | 27.826 | −12.786 | 1.00 | 40.68 | H | C |
| ATOM | 3060 | CG | PRO | H | 248 | 27.146 | 29.282 | −12.741 | 1.00 | 43.23 | H | C |
| ATOM | 3061 | CD | PRO | H | 248 | 27.282 | 29.600 | −11.269 | 1.00 | 41.68 | H | C |
| ATOM | 3062 | N | GLY | H | 249 | 26.897 | 24.858 | −11.341 | 1.00 | 33.94 | H | N |
| ATOM | 3063 | CA | GLY | H | 249 | 27.483 | 23.636 | −10.818 | 1.00 | 30.93 | H | C |
| ATOM | 3064 | C | GLY | H | 249 | 27.004 | 23.304 | −9.416 | 1.00 | 27.97 | H | C |
| ATOM | 3065 | O | GLY | H | 249 | 26.983 | 24.164 | −8.536 | 1.00 | 28.75 | H | O |
| ATOM | 3066 | N | VAL | H | 250 | 26.627 | 22.047 | −9.210 | 1.00 | 25.90 | H | N |
| ATOM | 3067 | CA | VAL | H | 250 | 26.137 | 21.584 | −7.916 | 1.00 | 22.51 | H | C |
| ATOM | 3068 | C | VAL | H | 250 | 27.154 | 21.751 | −6.785 | 1.00 | 20.73 | H | C |
| ATOM | 3069 | O | VAL | H | 250 | 26.866 | 22.406 | −5.783 | 1.00 | 19.56 | H | O |
| ATOM | 3070 | CB | VAL | H | 250 | 25.708 | 20.091 | −7.989 | 1.00 | 22.46 | H | C |
| ATOM | 3071 | CG1 | VAL | H | 250 | 25.243 | 19.603 | −6.616 | 1.00 | 21.14 | H | C |
| ATOM | 3072 | CG2 | VAL | H | 250 | 24.588 | 19.924 | −9.000 | 1.00 | 22.82 | H | C |
| ATOM | 3073 | N | LEU | H | 251 | 28.337 | 21.165 | −6.950 | 1.00 | 18.48 | H | N |
| ATOM | 3074 | CA | LEU | H | 251 | 29.380 | 21.230 | −5.929 | 1.00 | 18.83 | H | C |
| ATOM | 3075 | C | LEU | H | 251 | 30.070 | 22.588 | −5.808 | 1.00 | 19.13 | H | C |
| ATOM | 3076 | O | LEU | H | 251 | 30.520 | 23.164 | −6.790 | 1.00 | 18.06 | H | O |
| ATOM | 3077 | CB | LEU | H | 251 | 30.431 | 20.146 | −6.192 | 1.00 | 16.90 | H | C |
| ATOM | 3078 | CG | LEU | H | 251 | 31.581 | 20.002 | −5.186 | 1.00 | 17.64 | H | C |
| ATOM | 3079 | CD1 | LEU | H | 251 | 31.029 | 19.732 | −3.787 | 1.00 | 15.90 | H | C |
| ATOM | 3080 | CD2 | LEU | H | 251 | 32.504 | 18.862 | −5.628 | 1.00 | 16.46 | H | C |
| ATOM | 3081 | N | LEU | H | 252 | 30.151 | 23.096 | −4.586 | 1.00 | 19.09 | H | N |
| ATOM | 3082 | CA | LEU | H | 252 | 30.808 | 24.369 | −4.342 | 1.00 | 18.91 | H | C |
| ATOM | 3083 | C | LEU | H | 252 | 31.699 | 24.284 | −3.109 | 1.00 | 19.51 | H | C |
| ATOM | 3084 | O | LEU | H | 252 | 31.261 | 23.835 | −2.054 | 1.00 | 20.28 | H | O |
| ATOM | 3085 | CB | LEU | H | 252 | 29.777 | 25.476 | −4.129 | 1.00 | 19.71 | H | C |
| ATOM | 3086 | CG | LEU | H | 252 | 30.362 | 26.831 | −3.726 | 1.00 | 21.00 | H | C |
| ATOM | 3087 | CD1 | LEU | H | 252 | 31.252 | 27.360 | −4.845 | 1.00 | 21.46 | H | C |
| ATOM | 3088 | CD2 | LEU | H | 252 | 29.237 | 27.808 | −3.431 | 1.00 | 21.39 | H | C |
| ATOM | 3089 | N | ARG | H | 253 | 32.951 | 24.703 | −3.247 | 1.00 | 17.62 | H | N |
| ATOM | 3090 | CA | ARG | H | 253 | 33.869 | 24.704 | −2.119 | 1.00 | 17.97 | H | C |
| ATOM | 3091 | C | ARG | H | 253 | 34.015 | 26.150 | −1.688 | 1.00 | 17.05 | H | C |
| ATOM | 3092 | O | ARG | H | 253 | 34.559 | 26.970 | −2.426 | 1.00 | 15.25 | H | O |
| ATOM | 3093 | CB | ARG | H | 253 | 35.230 | 24.123 | −2.511 | 1.00 | 18.44 | H | C |
| ATOM | 3094 | CG | ARG | H | 253 | 35.358 | 22.635 | −2.232 | 1.00 | 20.42 | H | C |
| ATOM | 3095 | CD | ARG | H | 253 | 34.282 | 21.846 | −2.952 | 1.00 | 21.21 | H | C |
| ATOM | 3096 | NE | ARG | H | 253 | 34.476 | 21.856 | −4.397 | 1.00 | 21.18 | H | N |
| ATOM | 3097 | CZ | ARG | H | 253 | 35.307 | 21.047 | −5.047 | 1.00 | 22.46 | H | C |
| ATOM | 3098 | NH1 | ARG | H | 253 | 36.028 | 20.152 | −4.380 | 1.00 | 23.51 | H | N |
| ATOM | 3099 | NH2 | ARG | H | 253 | 35.414 | 21.126 | −6.367 | 1.00 | 19.08 | H | N |
| ATOM | 3100 | N | ALA | H | 254 | 33.499 | 26.458 | −0.501 | 1.00 | 16.11 | H | N |
| ATOM | 3101 | CA | ALA | H | 254 | 33.542 | 27.815 | 0.028 | 1.00 | 15.47 | H | C |
| ATOM | 3102 | C | ALA | H | 254 | 34.658 | 27.919 | 1.047 | 1.00 | 16.28 | H | C |
| ATOM | 3103 | O | ALA | H | 254 | 34.879 | 27.003 | 1.843 | 1.00 | 15.62 | H | O |
| ATOM | 3104 | CB | ALA | H | 254 | 32.205 | 28.179 | 0.664 | 1.00 | 13.69 | H | C |
| ATOM | 3105 | N | PRO | H | 255 | 35.381 | 29.044 | 1.039 | 1.00 | 15.40 | H | N |
| ATOM | 3106 | CA | PRO | H | 255 | 36.475 | 29.191 | 1.994 | 1.00 | 14.78 | H | C |
| ATOM | 3107 | C | PRO | H | 255 | 36.048 | 29.162 | 3.445 | 1.00 | 14.38 | H | C |
| ATOM | 3108 | O | PRO | H | 255 | 34.935 | 29.556 | 3.798 | 1.00 | 13.71 | H | O |
| ATOM | 3109 | CB | PRO | H | 255 | 37.116 | 30.526 | 1.594 | 1.00 | 15.88 | H | C |
| ATOM | 3110 | CG | PRO | H | 255 | 35.987 | 31.294 | 0.995 | 1.00 | 15.99 | H | C |
| ATOM | 3111 | CD | PRO | H | 255 | 35.233 | 30.249 | 0.200 | 1.00 | 16.40 | H | C |
| ATOM | 3112 | N | PHE | H | 256 | 36.943 | 28.663 | 4.281 | 1.00 | 13.80 | H | N |
| ATOM | 3113 | CA | PHE | H | 256 | 36.701 | 28.616 | 5.706 | 1.00 | 16.87 | H | C |
| ATOM | 3114 | C | PHE | H | 256 | 38.005 | 28.945 | 6.408 | 1.00 | 17.50 | H | C |
| ATOM | 3115 | O | PHE | H | 256 | 39.049 | 28.394 | 6.067 | 1.00 | 18.45 | H | O |
| ATOM | 3116 | CB | PHE | H | 256 | 36.243 | 27.240 | 6.174 | 1.00 | 14.38 | H | C |
| ATOM | 3117 | CG | PHE | H | 256 | 35.955 | 27.201 | 7.641 | 1.00 | 16.91 | H | C |
| ATOM | 3118 | CD1 | PHE | H | 256 | 34.773 | 27.744 | 8.141 | 1.00 | 16.40 | H | C |
| ATOM | 3119 | CD2 | PHE | H | 256 | 36.909 | 26.729 | 8.538 | 1.00 | 16.52 | H | C |
| ATOM | 3120 | CE1 | PHE | H | 256 | 34.546 | 27.828 | 9.509 | 1.00 | 17.72 | H | C |

-continued

| | | | | | | | | | | | |
|---|---|---|---|---|---|---|---|---|---|---|---|
| ATOM | 3121 | CE2 | PHE | H | 256 | 36.692 | 26.809 | 9.911 | 1.00 | 17.93 | H | C |
| ATOM | 3122 | CZ | PHE | H | 256 | 35.510 | 27.362 | 10.398 | 1.00 | 18.72 | H | C |
| ATOM | 3123 | N | PRO | H | 257 | 37.960 | 29.830 | 7.413 | 1.00 | 18.95 | H | N |
| ATOM | 3124 | CA | PRO | H | 257 | 36.765 | 30.512 | 7.921 | 1.00 | 20.37 | H | C |
| ATOM | 3125 | C | PRO | H | 257 | 36.095 | 31.426 | 6.893 | 1.00 | 22.86 | H | C |
| ATOM | 3126 | O | PRO | H | 257 | 34.888 | 31.666 | 7.011 | 1.00 | 23.60 | H | O |
| ATOM | 3127 | CB | PRO | H | 257 | 37.299 | 31.268 | 9.136 | 1.00 | 20.14 | H | C |
| ATOM | 3128 | CG | PRO | H | 257 | 38.684 | 31.608 | 8.721 | 1.00 | 20.11 | H | C |
| ATOM | 3129 | CD | PRO | H | 257 | 39.167 | 30.315 | 8.104 | 1.00 | 18.62 | H | C |
| ATOM | 3130 | OT | PRO | H | 257 | 36.786 | 31.886 | 6.001 | 1.00 | 26.65 | H | O |
| ATOM | 3131 | N | THR | T | 6 | 48.678 | 29.980 | 30.872 | 1.00 | 39.18 | T | N |
| ATOM | 3132 | CA | THR | T | 6 | 47.791 | 29.559 | 31.995 | 1.00 | 38.59 | T | C |
| ATOM | 3133 | C | THR | T | 6 | 47.976 | 28.083 | 32.299 | 1.00 | 36.71 | T | C |
| ATOM | 3134 | O | THR | T | 6 | 48.275 | 27.290 | 31.410 | 1.00 | 37.09 | T | O |
| ATOM | 3135 | CB | THR | T | 6 | 46.308 | 29.771 | 31.656 | 1.00 | 40.14 | T | C |
| ATOM | 3136 | OG1 | THR | T | 6 | 45.930 | 28.877 | 30.600 | 1.00 | 41.93 | T | O |
| ATOM | 3137 | CG2 | THR | T | 6 | 46.064 | 31.202 | 31.212 | 1.00 | 42.09 | T | C |
| ATOM | 3138 | N | VAL | T | 7 | 47.790 | 27.721 | 33.562 | 1.00 | 35.02 | T | N |
| ATOM | 3139 | CA | VAL | T | 7 | 47.919 | 26.335 | 33.987 | 1.00 | 33.21 | T | C |
| ATOM | 3140 | C | VAL | T | 7 | 46.611 | 25.871 | 34.613 | 1.00 | 31.57 | T | C |
| ATOM | 3141 | O | VAL | T | 7 | 45.876 | 26.663 | 35.211 | 1.00 | 31.61 | T | O |
| ATOM | 3142 | CB | VAL | T | 7 | 49.054 | 26.155 | 35.019 | 1.00 | 32.59 | T | C |
| ATOM | 3143 | CG1 | VAL | T | 7 | 50.380 | 26.620 | 34.422 | 1.00 | 31.03 | T | C |
| ATOM | 3144 | CG2 | VAL | T | 7 | 48.731 | 26.920 | 36.288 | 1.00 | 31.27 | T | C |
| ATOM | 3145 | N | ALA | T | 8 | 46.320 | 24.587 | 34.468 | 1.00 | 29.98 | T | N |
| ATOM | 3146 | CA | ALA | T | 8 | 45.101 | 24.023 | 35.023 | 1.00 | 29.21 | T | C |
| ATOM | 3147 | C | ALA | T | 8 | 45.239 | 23.892 | 36.531 | 1.00 | 28.58 | T | C |
| ATOM | 3148 | O | ALA | T | 8 | 46.342 | 23.743 | 37.055 | 1.00 | 28.70 | T | O |
| ATOM | 3149 | CB | ALA | T | 8 | 44.828 | 22.660 | 34.402 | 1.00 | 28.98 | T | C |
| ATOM | 3150 | N | ALA | T | 9 | 44.115 | 23.964 | 37.230 | 1.00 | 25.62 | T | N |
| ATOM | 3151 | CA | ALA | T | 9 | 44.121 | 23.828 | 38.673 | 1.00 | 25.80 | T | C |
| ATOM | 3152 | C | ALA | T | 9 | 44.490 | 22.387 | 39.016 | 1.00 | 26.18 | T | C |
| ATOM | 3153 | O | ALA | T | 9 | 44.425 | 21.501 | 38.161 | 1.00 | 25.07 | T | O |
| ATOM | 3154 | CB | ALA | T | 9 | 42.744 | 24.162 | 39.233 | 1.00 | 22.93 | T | C |
| ATOM | 3155 | N | TYR | T | 10 | 44.886 | 22.157 | 40.263 | 1.00 | 24.93 | T | N |
| ATOM | 3156 | CA | TYR | T | 10 | 45.240 | 20.815 | 40.701 | 1.00 | 25.50 | T | C |
| ATOM | 3157 | C | TYR | T | 10 | 44.978 | 20.661 | 42.186 | 1.00 | 25.20 | T | C |
| ATOM | 3158 | O | TYR | T | 10 | 44.754 | 21.641 | 42.896 | 1.00 | 23.18 | T | O |
| ATOM | 3159 | CB | TYR | T | 10 | 46.706 | 20.493 | 40.367 | 1.00 | 27.61 | T | C |
| ATOM | 3160 | CG | TYR | T | 10 | 47.724 | 21.429 | 40.975 | 1.00 | 27.41 | T | C |
| ATOM | 3161 | CD1 | TYR | T | 10 | 48.245 | 21.199 | 42.248 | 1.00 | 28.54 | T | C |
| ATOM | 3162 | CD2 | TYR | T | 10 | 48.160 | 22.554 | 40.277 | 1.00 | 28.91 | T | C |
| ATOM | 3163 | CE1 | TYR | T | 10 | 49.183 | 22.072 | 42.810 | 1.00 | 28.45 | T | C |
| ATOM | 3164 | CE2 | TYR | T | 10 | 49.090 | 23.429 | 40.827 | 1.00 | 29.62 | T | C |
| ATOM | 3165 | CZ | TYR | T | 10 | 49.595 | 23.184 | 42.088 | 1.00 | 29.24 | T | C |
| ATOM | 3166 | OH | TYR | T | 10 | 50.506 | 24.061 | 42.626 | 1.00 | 33.96 | T | O |
| ATOM | 3167 | N | ASN | T | 11 | 44.992 | 19.418 | 42.647 | 1.00 | 25.50 | T | N |
| ATOM | 3168 | CA | ASN | T | 11 | 44.729 | 19.119 | 44.045 | 1.00 | 25.22 | T | C |
| ATOM | 3169 | C | ASN | T | 11 | 43.354 | 19.624 | 44.466 | 1.00 | 23.78 | T | C |
| ATOM | 3170 | O | ASN | T | 11 | 43.197 | 20.179 | 45.553 | 1.00 | 20.92 | T | O |
| ATOM | 3171 | CB | ASN | T | 11 | 45.812 | 19.735 | 44.944 | 1.00 | 29.09 | T | C |
| ATOM | 3172 | CG | ASN | T | 11 | 47.105 | 18.924 | 44.954 | 1.00 | 31.48 | T | C |
| ATOM | 3173 | OD1 | ASN | T | 11 | 48.090 | 19.321 | 45.578 | 1.00 | 34.70 | T | O |
| ATOM | 3174 | ND2 | ASN | T | 11 | 47.105 | 17.784 | 44.270 | 1.00 | 32.60 | T | N |
| ATOM | 3175 | N | LEU | T | 12 | 42.356 | 19.441 | 43.602 | 1.00 | 23.43 | T | N |
| ATOM | 3176 | CA | LEU | T | 12 | 41.003 | 19.868 | 43.939 | 1.00 | 22.96 | T | C |
| ATOM | 3177 | C | LEU | T | 12 | 40.594 | 19.011 | 45.126 | 1.00 | 22.88 | T | C |
| ATOM | 3178 | O | LEU | T | 12 | 40.726 | 17.792 | 45.084 | 1.00 | 24.43 | T | O |
| ATOM | 3179 | CB | LEU | T | 12 | 40.043 | 19.652 | 42.763 | 1.00 | 21.46 | T | C |
| ATOM | 3180 | CG | LEU | T | 12 | 40.003 | 20.731 | 41.671 | 1.00 | 20.61 | T | C |
| ATOM | 3181 | CD1 | LEU | T | 12 | 41.321 | 20.784 | 40.921 | 1.00 | 19.28 | T | C |
| ATOM | 3182 | CD2 | LEU | T | 12 | 38.859 | 20.437 | 40.712 | 1.00 | 17.88 | T | C |
| ATOM | 3183 | N | THR | T | 13 | 40.097 | 19.651 | 46.178 | 1.00 | 22.51 | T | N |
| ATOM | 3184 | CA | THR | T | 13 | 39.719 | 18.946 | 47.394 | 1.00 | 22.60 | T | C |
| ATOM | 3185 | C | THR | T | 13 | 38.387 | 19.434 | 47.936 | 1.00 | 21.35 | T | C |
| ATOM | 3186 | O | THR | T | 13 | 38.106 | 20.622 | 47.904 | 1.00 | 22.14 | T | O |
| ATOM | 3187 | CB | THR | T | 13 | 40.786 | 19.172 | 48.494 | 1.00 | 24.31 | T | C |
| ATOM | 3188 | OG1 | THR | T | 13 | 42.087 | 18.887 | 47.965 | 1.00 | 28.20 | T | O |
| ATOM | 3189 | CG2 | THR | T | 13 | 40.524 | 18.276 | 49.695 | 1.00 | 25.13 | T | C |
| ATOM | 3190 | N | TRP | T | 14 | 37.570 | 18.517 | 48.442 | 1.00 | 20.93 | T | N |
| ATOM | 3191 | CA | TRP | T | 14 | 36.290 | 18.896 | 49.022 | 1.00 | 21.26 | T | C |
| ATOM | 3192 | C | TRP | T | 14 | 36.445 | 19.101 | 50.527 | 1.00 | 21.82 | T | C |
| ATOM | 3193 | O | TRP | T | 14 | 37.003 | 18.250 | 51.221 | 1.00 | 22.88 | T | O |
| ATOM | 3194 | CB | TRP | T | 14 | 35.233 | 17.816 | 48.775 | 1.00 | 21.62 | T | C |
| ATOM | 3195 | CG | TRP | T | 14 | 34.895 | 17.603 | 47.331 | 1.00 | 20.57 | T | C |
| ATOM | 3196 | CD1 | TRP | T | 14 | 35.525 | 16.769 | 46.450 | 1.00 | 19.07 | T | C |
| ATOM | 3197 | CD2 | TRP | T | 14 | 33.843 | 18.238 | 46.602 | 1.00 | 18.11 | T | C |
| ATOM | 3198 | NE1 | TRP | T | 14 | 34.925 | 16.845 | 45.215 | 1.00 | 19.68 | T | N |
| ATOM | 3199 | CE2 | TRP | T | 14 | 33.889 | 17.741 | 45.281 | 1.00 | 20.45 | T | C |

-continued

| ATOM | 3200 | CE3 | TRP | T | 14 | 32.863 | 19.180 | 46.936 | 1.00 | 20.85 | T | C |
|---|---|---|---|---|---|---|---|---|---|---|---|---|
| ATOM | 3201 | CZ2 | TRP | T | 14 | 32.989 | 18.155 | 44.292 | 1.00 | 20.30 | T | C |
| ATOM | 3202 | CZ3 | TRP | T | 14 | 31.964 | 19.592 | 45.953 | 1.00 | 20.57 | T | C |
| ATOM | 3203 | CH2 | TRP | T | 14 | 32.037 | 19.077 | 44.646 | 1.00 | 20.36 | T | C |
| ATOM | 3204 | N | LYS | T | 15 | 35.968 | 20.240 | 51.016 | 1.00 | 21.08 | T | N |
| ATOM | 3205 | CA | LYS | T | 15 | 36.005 | 20.568 | 52.439 | 1.00 | 20.11 | T | C |
| ATOM | 3206 | C | LYS | T | 15 | 34.534 | 20.651 | 52.818 | 1.00 | 19.45 | T | C |
| ATOM | 3207 | O | LYS | T | 15 | 33.862 | 21.632 | 52.510 | 1.00 | 20.83 | T | O |
| ATOM | 3208 | CB | LYS | T | 15 | 36.700 | 21.918 | 52.663 | 1.00 | 21.44 | T | C |
| ATOM | 3209 | CG | LYS | T | 15 | 38.162 | 21.933 | 52.228 | 1.00 | 23.27 | T | C |
| ATOM | 3210 | CD | LYS | T | 15 | 38.990 | 20.995 | 53.097 | 1.00 | 28.61 | T | C |
| ATOM | 3211 | CE | LYS | T | 15 | 40.296 | 20.589 | 52.427 | 1.00 | 31.74 | T | C |
| ATOM | 3212 | NZ | LYS | T | 15 | 41.190 | 21.741 | 52.152 | 1.00 | 36.85 | T | N |
| ATOM | 3213 | N | SER | T | 16 | 34.035 | 19.613 | 53.478 | 1.00 | 17.55 | T | N |
| ATOM | 3214 | CA | SER | T | 16 | 32.628 | 19.556 | 53.832 | 1.00 | 17.18 | T | C |
| ATOM | 3215 | C | SER | T | 16 | 32.363 | 19.073 | 55.255 | 1.00 | 18.04 | T | C |
| ATOM | 3216 | O | SER | T | 16 | 32.859 | 18.021 | 55.671 | 1.00 | 16.19 | T | O |
| ATOM | 3217 | CB | SER | T | 16 | 31.906 | 18.639 | 52.831 | 1.00 | 17.42 | T | C |
| ATOM | 3218 | OG | SER | T | 16 | 30.500 | 18.633 | 53.032 | 1.00 | 16.16 | T | O |
| ATOM | 3219 | N | THR | T | 17 | 31.572 | 19.851 | 55.988 | 1.00 | 17.33 | T | N |
| ATOM | 3220 | CA | THR | T | 17 | 31.199 | 19.523 | 57.360 | 1.00 | 17.85 | T | C |
| ATOM | 3221 | C | THR | T | 17 | 29.735 | 19.890 | 57.527 | 1.00 | 17.66 | T | C |
| ATOM | 3222 | O | THR | T | 17 | 29.345 | 21.033 | 57.293 | 1.00 | 17.63 | T | O |
| ATOM | 3223 | CB | THR | T | 17 | 32.031 | 20.322 | 58.385 | 1.00 | 16.36 | T | C |
| ATOM | 3224 | OG1 | THR | T | 17 | 33.414 | 19.996 | 58.231 | 1.00 | 18.91 | T | O |
| ATOM | 3225 | CG2 | THR | T | 17 | 31.596 | 19.990 | 59.799 | 1.00 | 17.35 | T | C |
| ATOM | 3226 | N | ASN | T | 18 | 28.922 | 18.922 | 57.935 | 1.00 | 18.02 | T | N |
| ATOM | 3227 | CA | ASN | T | 18 | 27.493 | 19.160 | 58.103 | 1.00 | 19.26 | T | C |
| ATOM | 3228 | C | ASN | T | 18 | 26.901 | 19.764 | 56.837 | 1.00 | 18.10 | T | C |
| ATOM | 3229 | O | ASN | T | 18 | 26.039 | 20.643 | 56.886 | 1.00 | 18.37 | T | O |
| ATOM | 3230 | CB | ASN | T | 18 | 27.238 | 20.073 | 59.301 | 1.00 | 20.54 | T | C |
| ATOM | 3231 | CG | ASN | T | 18 | 27.792 | 19.494 | 60.579 | 1.00 | 23.12 | T | C |
| ATOM | 3232 | OD1 | ASN | T | 18 | 27.706 | 18.288 | 60.804 | 1.00 | 22.01 | T | O |
| ATOM | 3233 | ND2 | ASN | T | 18 | 28.368 | 20.346 | 61.423 | 1.00 | 26.13 | T | N |
| ATOM | 3234 | N | PHE | T | 19 | 27.394 | 19.269 | 55.706 | 1.00 | 18.27 | T | N |
| ATOM | 3235 | CA | PHE | T | 19 | 26.959 | 19.672 | 54.383 | 1.00 | 19.15 | T | C |
| ATOM | 3236 | C | PHE | T | 19 | 27.453 | 21.022 | 53.869 | 1.00 | 20.26 | T | C |
| ATOM | 3237 | O | PHE | T | 19 | 27.200 | 21.369 | 52.715 | 1.00 | 20.39 | T | O |
| ATOM | 3238 | CB | PHE | T | 19 | 25.441 | 19.539 | 54.305 | 1.00 | 20.26 | T | C |
| ATOM | 3239 | CG | PHE | T | 19 | 24.965 | 18.124 | 54.530 | 1.00 | 21.59 | T | C |
| ATOM | 3240 | CD1 | PHE | T | 19 | 25.184 | 17.144 | 53.565 | 1.00 | 21.66 | T | C |
| ATOM | 3241 | CD2 | PHE | T | 19 | 24.371 | 17.755 | 55.731 | 1.00 | 22.37 | T | C |
| ATOM | 3242 | CE1 | PHE | T | 19 | 24.823 | 15.819 | 53.790 | 1.00 | 21.75 | T | C |
| ATOM | 3243 | CE2 | PHE | T | 19 | 24.003 | 16.425 | 55.970 | 1.00 | 24.36 | T | C |
| ATOM | 3244 | CZ | PHE | T | 19 | 24.232 | 15.456 | 54.995 | 1.00 | 22.96 | T | C |
| ATOM | 3245 | N | LYS | T | 20 | 28.162 | 21.779 | 54.706 | 1.00 | 19.77 | T | N |
| ATOM | 3246 | CA | LYS | T | 20 | 28.737 | 23.044 | 54.252 | 1.00 | 18.78 | T | C |
| ATOM | 3247 | C | LYS | T | 20 | 29.855 | 22.526 | 53.362 | 1.00 | 18.12 | T | C |
| ATOM | 3248 | O | LYS | T | 20 | 30.848 | 21.993 | 53.853 | 1.00 | 19.69 | T | O |
| ATOM | 3249 | CB | LYS | T | 20 | 29.326 | 23.831 | 55.414 | 1.00 | 20.11 | T | C |
| ATOM | 3250 | CG | LYS | T | 20 | 28.777 | 25.232 | 55.535 | 1.00 | 22.19 | T | C |
| ATOM | 3251 | CD | LYS | T | 20 | 29.115 | 26.090 | 54.338 | 1.00 | 21.31 | T | C |
| ATOM | 3252 | CE | LYS | T | 20 | 28.434 | 27.437 | 54.474 | 1.00 | 21.39 | T | C |
| ATOM | 3253 | NZ | LYS | T | 20 | 28.973 | 28.453 | 53.548 | 1.00 | 23.07 | T | N |
| ATOM | 3254 | N | THR | T | 21 | 29.692 | 22.684 | 52.056 | 1.00 | 16.64 | T | N |
| ATOM | 3255 | CA | THR | T | 21 | 30.643 | 22.143 | 51.100 | 1.00 | 16.45 | T | C |
| ATOM | 3256 | C | THR | T | 21 | 31.364 | 23.167 | 50.243 | 1.00 | 18.19 | T | C |
| ATOM | 3257 | O | THR | T | 21 | 30.749 | 23.879 | 49.453 | 1.00 | 17.44 | T | O |
| ATOM | 3258 | CB | THR | T | 21 | 29.911 | 21.151 | 50.192 | 1.00 | 15.26 | T | C |
| ATOM | 3259 | OG1 | THR | T | 21 | 29.179 | 20.236 | 51.016 | 1.00 | 16.35 | T | O |
| ATOM | 3260 | CG2 | THR | T | 21 | 30.885 | 20.380 | 49.320 | 1.00 | 16.11 | T | C |
| ATOM | 3261 | N | ILE | T | 22 | 32.682 | 23.215 | 50.394 | 1.00 | 19.00 | T | N |
| ATOM | 3262 | CA | ILE | T | 22 | 33.511 | 24.146 | 49.648 | 1.00 | 19.12 | T | C |
| ATOM | 3263 | C | ILE | T | 22 | 34.603 | 23.396 | 48.896 | 1.00 | 18.47 | T | C |
| ATOM | 3264 | O | ILE | T | 22 | 35.326 | 22.588 | 49.477 | 1.00 | 18.08 | T | O |
| ATOM | 3265 | CB | ILE | T | 22 | 34.180 | 25.169 | 50.597 | 1.00 | 20.41 | T | C |
| ATOM | 3266 | CG1 | ILE | T | 22 | 33.108 | 25.959 | 51.353 | 1.00 | 21.22 | T | C |
| ATOM | 3267 | CG2 | ILE | T | 22 | 35.075 | 26.121 | 49.804 | 1.00 | 19.96 | T | C |
| ATOM | 3268 | CD1 | ILE | T | 22 | 33.673 | 26.948 | 52.352 | 1.00 | 21.24 | T | C |
| ATOM | 3269 | N | LEU | T | 23 | 34.711 | 23.658 | 47.599 | 1.00 | 17.48 | T | N |
| ATOM | 3270 | CA | LEU | T | 23 | 35.738 | 23.029 | 46.783 | 1.00 | 18.70 | T | C |
| ATOM | 3271 | C | LEU | T | 23 | 36.967 | 23.925 | 46.847 | 1.00 | 17.68 | T | C |
| ATOM | 3272 | O | LEU | T | 23 | 36.859 | 25.141 | 46.691 | 1.00 | 18.29 | T | O |
| ATOM | 3273 | CB | LEU | T | 23 | 35.275 | 22.905 | 45.329 | 1.00 | 19.42 | T | C |
| ATOM | 3274 | CG | LEU | T | 23 | 36.258 | 22.183 | 44.399 | 1.00 | 21.43 | T | C |
| ATOM | 3275 | CD1 | LEU | T | 23 | 36.325 | 20.714 | 44.790 | 1.00 | 19.69 | T | C |
| ATOM | 3276 | CD2 | LEU | T | 23 | 35.820 | 22.334 | 42.944 | 1.00 | 17.72 | T | C |
| ATOM | 3277 | N | GLU | T | 24 | 38.129 | 23.334 | 47.093 | 1.00 | 16.78 | T | N |
| ATOM | 3278 | CA | GLU | T | 24 | 39.367 | 24.102 | 47.165 | 1.00 | 18.87 | T | C |

-continued

| | | | | | | | | | | |
|---|---|---|---|---|---|---|---|---|---|---|
| ATOM | 3279 | C | GLU | T | 24 | 40.354 | 23.566 | 46.146 | 1.00 | 20.20 | T | C |
| ATOM | 3280 | O | GLU | T | 24 | 40.262 | 22.411 | 45.735 | 1.00 | 20.83 | T | O |
| ATOM | 3281 | CB | GLU | T | 24 | 39.968 | 24.025 | 48.575 | 1.00 | 18.72 | T | C |
| ATOM | 3282 | CG | GLU | T | 24 | 39.349 | 25.019 | 49.553 | 1.00 | 21.38 | T | C |
| ATOM | 3283 | CD | GLU | T | 24 | 39.777 | 24.789 | 50.988 | 1.00 | 23.65 | T | C |
| ATOM | 3284 | OE1 | GLU | T | 24 | 40.878 | 24.291 | 51.202 | 1.00 | 25.81 | T | O |
| ATOM | 3285 | OE2 | GLU | T | 24 | 39.008 | 25.125 | 51.887 | 1.00 | 26.26 | T | O |
| ATOM | 3286 | N | TRP | T | 25 | 41.300 | 24.401 | 45.735 | 1.00 | 19.89 | T | N |
| ATOM | 3287 | CA | TRP | T | 25 | 42.280 | 23.965 | 44.759 | 1.00 | 20.95 | T | C |
| ATOM | 3288 | C | TRP | T | 25 | 43.524 | 24.843 | 44.721 | 1.00 | 22.24 | T | C |
| ATOM | 3289 | O | TRP | T | 25 | 43.635 | 25.829 | 45.451 | 1.00 | 23.01 | T | O |
| ATOM | 3290 | CB | TRP | T | 25 | 41.629 | 23.912 | 43.366 | 1.00 | 18.38 | T | C |
| ATOM | 3291 | CG | TRP | T | 25 | 41.213 | 25.252 | 42.815 | 1.00 | 16.29 | T | C |
| ATOM | 3292 | CD1 | TRP | T | 25 | 41.994 | 26.133 | 42.115 | 1.00 | 16.76 | T | C |
| ATOM | 3293 | CD2 | TRP | T | 25 | 39.917 | 25.856 | 42.911 | 1.00 | 14.79 | T | C |
| ATOM | 3294 | NE1 | TRP | T | 25 | 41.260 | 27.246 | 41.765 | 1.00 | 13.11 | T | N |
| ATOM | 3295 | CE2 | TRP | T | 25 | 39.984 | 27.102 | 42.242 | 1.00 | 14.48 | T | C |
| ATOM | 3296 | CE3 | TRP | T | 25 | 38.704 | 25.466 | 43.498 | 1.00 | 15.24 | T | C |
| ATOM | 3297 | CZ2 | TRP | T | 25 | 38.882 | 27.960 | 42.141 | 1.00 | 14.18 | T | C |
| ATOM | 3298 | CZ3 | TRP | T | 25 | 37.606 | 26.320 | 43.399 | 1.00 | 14.21 | T | C |
| ATOM | 3299 | CH2 | TRP | T | 25 | 37.705 | 27.554 | 42.725 | 1.00 | 15.19 | T | C |
| ATOM | 3300 | N | GLU | T | 26 | 44.455 | 24.449 | 43.862 | 1.00 | 24.44 | T | N |
| ATOM | 3301 | CA | GLU | T | 26 | 45.713 | 25.148 | 43.644 | 1.00 | 27.06 | T | C |
| ATOM | 3302 | C | GLU | T | 26 | 45.713 | 25.499 | 42.159 | 1.00 | 28.34 | T | C |
| ATOM | 3303 | O | GLU | T | 26 | 44.953 | 24.918 | 41.384 | 1.00 | 26.89 | T | O |
| ATOM | 3304 | CB | GLU | T | 26 | 46.889 | 24.214 | 43.939 | 1.00 | 28.64 | T | C |
| ATOM | 3305 | CG | GLU | T | 26 | 46.993 | 23.741 | 45.376 | 1.00 | 34.94 | T | C |
| ATOM | 3306 | CD | GLU | T | 26 | 47.761 | 24.705 | 46.253 | 1.00 | 39.39 | T | C |
| ATOM | 3307 | OE1 | GLU | T | 26 | 47.870 | 24.444 | 47.440 | 1.00 | 42.73 | T | O |
| ATOM | 3308 | OE2 | GLU | T | 26 | 48.255 | 25.713 | 45.739 | 1.00 | 42.24 | T | O |
| ATOM | 3309 | N | PRO | T | 27 | 46.567 | 26.445 | 41.737 | 1.00 | 30.61 | T | N |
| ATOM | 3310 | CA | PRO | T | 27 | 47.516 | 27.202 | 42.550 | 1.00 | 33.08 | T | C |
| ATOM | 3311 | C | PRO | T | 27 | 47.039 | 28.646 | 42.694 | 1.00 | 36.39 | T | C |
| ATOM | 3312 | O | PRO | T | 27 | 45.969 | 29.008 | 42.204 | 1.00 | 37.38 | T | O |
| ATOM | 3313 | CB | PRO | T | 27 | 48.781 | 27.116 | 41.722 | 1.00 | 31.05 | T | C |
| ATOM | 3314 | CG | PRO | T | 27 | 48.232 | 27.369 | 40.350 | 1.00 | 29.94 | T | C |
| ATOM | 3315 | CD | PRO | T | 27 | 46.943 | 26.535 | 40.312 | 1.00 | 29.62 | T | C |
| ATOM | 3316 | N | LYS | T | 28 | 47.844 | 29.469 | 43.354 | 1.00 | 40.49 | T | N |
| ATOM | 3317 | CA | LYS | T | 28 | 47.509 | 30.874 | 43.534 | 1.00 | 44.79 | T | C |
| ATOM | 3318 | C | LYS | T | 28 | 47.525 | 31.555 | 42.169 | 1.00 | 46.88 | T | C |
| ATOM | 3319 | O | LYS | T | 28 | 48.585 | 31.737 | 41.566 | 1.00 | 47.96 | T | O |
| ATOM | 3320 | CB | LYS | T | 28 | 48.518 | 31.537 | 44.472 | 1.00 | 45.11 | T | C |
| ATOM | 3321 | CG | LYS | T | 28 | 48.533 | 30.923 | 45.859 | 1.00 | 46.65 | T | C |
| ATOM | 3322 | CD | LYS | T | 28 | 47.146 | 30.969 | 46.483 | 1.00 | 47.76 | T | C |
| ATOM | 3323 | CE | LYS | T | 28 | 47.120 | 30.295 | 47.843 | 1.00 | 49.21 | T | C |
| ATOM | 3324 | NZ | LYS | T | 28 | 45.769 | 30.375 | 48.468 | 1.00 | 50.84 | T | N |
| ATOM | 3325 | N | PRO | T | 29 | 46.342 | 31.942 | 41.667 | 1.00 | 47.94 | T | N |
| ATOM | 3326 | CA | PRO | T | 29 | 46.170 | 32.602 | 40.371 | 1.00 | 48.83 | T | C |
| ATOM | 3327 | C | PRO | T | 29 | 47.026 | 33.841 | 40.130 | 1.00 | 49.78 | T | C |
| ATOM | 3328 | O | PRO | T | 29 | 46.997 | 34.802 | 40.899 | 1.00 | 49.58 | T | O |
| ATOM | 3329 | CB | PRO | T | 29 | 44.677 | 32.914 | 40.339 | 1.00 | 48.24 | T | C |
| ATOM | 3330 | CG | PRO | T | 29 | 44.346 | 33.102 | 41.778 | 1.00 | 47.36 | T | C |
| ATOM | 3331 | CD | PRO | T | 29 | 45.074 | 31.952 | 42.417 | 1.00 | 48.57 | T | C |
| ATOM | 3332 | N | VAL | T | 30 | 47.790 | 33.795 | 39.044 | 1.00 | 50.46 | T | N |
| ATOM | 3333 | CA | VAL | T | 30 | 48.656 | 34.894 | 38.640 | 1.00 | 51.62 | T | C |
| ATOM | 3334 | C | VAL | T | 30 | 48.245 | 35.208 | 37.210 | 1.00 | 51.40 | T | C |
| ATOM | 3335 | O | VAL | T | 30 | 48.602 | 34.479 | 36.283 | 1.00 | 51.31 | T | O |
| ATOM | 3336 | CB | VAL | T | 30 | 50.138 | 34.482 | 38.664 | 1.00 | 51.98 | T | C |
| ATOM | 3337 | CG1 | VAL | T | 30 | 51.002 | 35.657 | 38.258 | 1.00 | 52.42 | T | C |
| ATOM | 3338 | CG2 | VAL | T | 30 | 50.523 | 33.993 | 40.055 | 1.00 | 51.87 | T | C |
| ATOM | 3339 | N | ASN | T | 31 | 47.491 | 36.291 | 37.033 | 1.00 | 50.80 | T | N |
| ATOM | 3340 | CA | ASN | T | 31 | 46.994 | 36.652 | 35.709 | 1.00 | 49.64 | T | C |
| ATOM | 3341 | C | ASN | T | 31 | 46.213 | 35.437 | 35.222 | 1.00 | 46.82 | T | C |
| ATOM | 3342 | O | ASN | T | 31 | 46.349 | 35.007 | 34.077 | 1.00 | 46.96 | T | O |
| ATOM | 3343 | CB | ASN | T | 31 | 48.155 | 36.952 | 34.760 | 1.00 | 52.08 | T | C |
| ATOM | 3344 | CG | ASN | T | 31 | 48.857 | 38.249 | 35.095 | 1.00 | 54.19 | T | C |
| ATOM | 3345 | OD1 | ASN | T | 31 | 48.257 | 39.322 | 35.032 | 1.00 | 56.94 | T | O |
| ATOM | 3346 | ND2 | ASN | T | 31 | 50.131 | 38.160 | 35.457 | 1.00 | 54.94 | T | N |
| ATOM | 3347 | N | GLN | T | 32 | 45.392 | 34.897 | 36.118 | 1.00 | 44.02 | T | N |
| ATOM | 3348 | CA | GLN | T | 32 | 44.597 | 33.711 | 35.845 | 1.00 | 39.84 | T | C |
| ATOM | 3349 | C | GLN | T | 32 | 43.356 | 33.696 | 36.732 | 1.00 | 36.22 | T | C |
| ATOM | 3350 | O | GLN | T | 32 | 43.450 | 33.789 | 37.956 | 1.00 | 36.42 | T | O |
| ATOM | 3351 | CB | GLN | T | 32 | 45.457 | 32.474 | 36.107 | 1.00 | 40.02 | T | C |
| ATOM | 3352 | CG | GLN | T | 32 | 44.756 | 31.141 | 35.996 | 1.00 | 38.97 | T | C |
| ATOM | 3353 | CD | GLN | T | 32 | 45.743 | 29.991 | 36.046 | 1.00 | 37.53 | T | C |
| ATOM | 3354 | OE1 | GLN | T | 32 | 46.616 | 29.880 | 35.189 | 1.00 | 36.12 | T | O |
| ATOM | 3355 | NE2 | GLN | T | 32 | 45.614 | 29.136 | 37.053 | 1.00 | 35.32 | T | N |
| ATOM | 3356 | N | VAL | T | 33 | 42.192 | 33.578 | 36.104 | 1.00 | 31.20 | T | N |
| ATOM | 3357 | CA | VAL | T | 33 | 40.930 | 33.555 | 36.824 | 1.00 | 26.24 | T | C |

-continued

| | | | | | | | | | | | |
|---|---|---|---|---|---|---|---|---|---|---|---|
| ATOM | 3358 | C | VAL | T | 33 | 40.280 | 32.178 | 36.683 | 1.00 | 24.67 | T | C |
| ATOM | 3359 | O | VAL | T | 33 | 40.698 | 31.375 | 35.851 | 1.00 | 23.37 | T | O |
| ATOM | 3360 | CB | VAL | T | 33 | 39.986 | 34.658 | 36.296 | 1.00 | 25.12 | T | C |
| ATOM | 3361 | CG1 | VAL | T | 33 | 40.676 | 36.014 | 36.410 | 1.00 | 23.86 | T | C |
| ATOM | 3362 | CG2 | VAL | T | 33 | 39.603 | 34.385 | 34.854 | 1.00 | 26.27 | T | C |
| ATOM | 3363 | N | TYR | T | 34 | 39.260 | 31.911 | 37.493 | 1.00 | 21.25 | T | N |
| ATOM | 3364 | CA | TYR | T | 34 | 38.589 | 30.615 | 37.473 | 1.00 | 19.35 | T | C |
| ATOM | 3365 | C | TYR | T | 34 | 37.070 | 30.677 | 37.428 | 1.00 | 18.92 | T | C |
| ATOM | 3366 | O | TYR | T | 34 | 36.454 | 31.670 | 37.801 | 1.00 | 18.57 | T | O |
| ATOM | 3367 | CB | TYR | T | 34 | 38.947 | 29.816 | 38.728 | 1.00 | 18.40 | T | C |
| ATOM | 3368 | CG | TYR | T | 34 | 40.416 | 29.582 | 38.957 | 1.00 | 20.44 | T | C |
| ATOM | 3369 | CD1 | TYR | T | 34 | 41.125 | 28.667 | 38.182 | 1.00 | 18.46 | T | C |
| ATOM | 3370 | CD2 | TYR | T | 34 | 41.096 | 30.259 | 39.971 | 1.00 | 19.10 | T | C |
| ATOM | 3371 | CE1 | TYR | T | 34 | 42.475 | 28.424 | 38.412 | 1.00 | 19.96 | T | C |
| ATOM | 3372 | CE2 | TYR | T | 34 | 42.447 | 30.021 | 40.207 | 1.00 | 20.05 | T | C |
| ATOM | 3373 | CZ | TYR | T | 34 | 43.126 | 29.102 | 39.426 | 1.00 | 20.10 | T | C |
| ATOM | 3374 | OH | TYR | T | 34 | 44.454 | 28.848 | 39.669 | 1.00 | 24.65 | T | O |
| ATOM | 3375 | N | THR | T | 35 | 36.478 | 29.581 | 36.974 | 1.00 | 16.56 | T | N |
| ATOM | 3376 | CA | THR | T | 35 | 35.034 | 29.429 | 36.956 | 1.00 | 16.37 | T | C |
| ATOM | 3377 | C | THR | T | 35 | 34.831 | 27.950 | 37.233 | 1.00 | 15.30 | T | C |
| ATOM | 3378 | O | THR | T | 35 | 35.490 | 27.103 | 36.634 | 1.00 | 18.13 | T | O |
| ATOM | 3379 | CB | THR | T | 35 | 34.390 | 29.799 | 35.608 | 1.00 | 15.23 | T | C |
| ATOM | 3380 | OG1 | THR | T | 35 | 34.409 | 31.222 | 35.438 | 1.00 | 15.18 | T | O |
| ATOM | 3381 | CG2 | THR | T | 35 | 32.941 | 29.336 | 35.581 | 1.00 | 16.79 | T | C |
| ATOM | 3382 | N | VAL | T | 36 | 33.940 | 27.647 | 38.163 | 1.00 | 15.22 | T | N |
| ATOM | 3383 | CA | VAL | T | 36 | 33.669 | 26.271 | 38.543 | 1.00 | 14.65 | T | C |
| ATOM | 3384 | C | VAL | T | 36 | 32.340 | 25.787 | 37.974 | 1.00 | 14.97 | T | C |
| ATOM | 3385 | O | VAL | T | 36 | 31.405 | 26.568 | 37.816 | 1.00 | 15.99 | T | O |
| ATOM | 3386 | CB | VAL | T | 36 | 33.638 | 26.153 | 40.086 | 1.00 | 12.56 | T | C |
| ATOM | 3387 | CG1 | VAL | T | 36 | 33.230 | 24.751 | 40.517 | 1.00 | 14.14 | T | C |
| ATOM | 3388 | CG2 | VAL | T | 36 | 35.019 | 26.496 | 40.652 | 1.00 | 13.80 | T | C |
| ATOM | 3389 | N | GLN | T | 37 | 32.278 | 24.507 | 37.624 | 1.00 | 14.43 | T | N |
| ATOM | 3390 | CA | GLN | T | 37 | 31.045 | 23.903 | 37.136 | 1.00 | 14.45 | T | C |
| ATOM | 3391 | C | GLN | T | 37 | 30.796 | 22.668 | 37.990 | 1.00 | 14.47 | T | C |
| ATOM | 3392 | O | GLN | T | 37 | 31.733 | 21.976 | 38.381 | 1.00 | 14.12 | T | O |
| ATOM | 3393 | CB | GLN | T | 37 | 31.152 | 23.468 | 35.671 | 1.00 | 14.86 | T | C |
| ATOM | 3394 | CG | GLN | T | 37 | 31.085 | 24.583 | 34.637 | 1.00 | 14.48 | T | C |
| ATOM | 3395 | CD | GLN | T | 37 | 30.857 | 24.037 | 33.234 | 1.00 | 13.74 | T | C |
| ATOM | 3396 | OE1 | GLN | T | 37 | 31.300 | 22.940 | 32.912 | 1.00 | 13.95 | T | O |
| ATOM | 3397 | NE2 | GLN | T | 37 | 30.175 | 24.807 | 32.393 | 1.00 | 10.80 | T | N |
| ATOM | 3398 | N | ILE | T | 38 | 29.533 | 22.399 | 38.287 | 1.00 | 14.90 | T | N |
| ATOM | 3399 | CA | ILE | T | 38 | 29.176 | 21.231 | 39.070 | 1.00 | 14.60 | T | C |
| ATOM | 3400 | C | ILE | T | 38 | 27.965 | 20.576 | 38.417 | 1.00 | 16.38 | T | C |
| ATOM | 3401 | O | ILE | T | 38 | 27.150 | 21.252 | 37.788 | 1.00 | 17.10 | T | O |
| ATOM | 3402 | CB | ILE | T | 38 | 28.829 | 21.617 | 40.521 | 1.00 | 15.19 | T | C |
| ATOM | 3403 | CG1 | ILE | T | 38 | 28.607 | 20.351 | 41.358 | 1.00 | 14.88 | T | C |
| ATOM | 3404 | CG2 | ILE | T | 38 | 27.601 | 22.530 | 40.539 | 1.00 | 10.78 | T | C |
| ATOM | 3405 | CD1 | ILE | T | 38 | 28.402 | 20.620 | 42.845 | 1.00 | 14.77 | T | C |
| ATOM | 3406 | N | SER | T | 39 | 27.857 | 19.260 | 38.557 | 1.00 | 16.00 | T | N |
| ATOM | 3407 | CA | SER | T | 39 | 26.737 | 18.529 | 37.989 | 1.00 | 15.27 | T | C |
| ATOM | 3408 | C | SER | T | 39 | 26.642 | 17.157 | 38.622 | 1.00 | 15.45 | T | C |
| ATOM | 3409 | O | SER | T | 39 | 27.511 | 16.748 | 39.382 | 1.00 | 16.91 | T | O |
| ATOM | 3410 | CB | SER | T | 39 | 26.948 | 18.327 | 36.491 | 1.00 | 12.90 | T | C |
| ATOM | 3411 | OG | SER | T | 39 | 27.999 | 17.389 | 36.285 | 1.00 | 12.71 | T | O |
| ATOM | 3412 | N | THR | T | 40 | 25.569 | 16.453 | 38.295 | 1.00 | 17.91 | T | N |
| ATOM | 3413 | CA | THR | T | 40 | 25.381 | 15.088 | 38.745 | 1.00 | 18.74 | T | C |
| ATOM | 3414 | C | THR | T | 40 | 25.637 | 14.283 | 37.480 | 1.00 | 21.10 | T | C |
| ATOM | 3415 | O | THR | T | 40 | 25.606 | 14.839 | 36.378 | 1.00 | 20.86 | T | O |
| ATOM | 3416 | CB | THR | T | 40 | 23.947 | 14.834 | 39.245 | 1.00 | 19.11 | T | C |
| ATOM | 3417 | OG1 | THR | T | 40 | 23.002 | 15.399 | 38.325 | 1.00 | 17.75 | T | O |
| ATOM | 3418 | CG2 | THR | T | 40 | 23.755 | 15.448 | 40.620 | 1.00 | 17.44 | T | C |
| ATOM | 3419 | N | LYS | T | 41 | 25.896 | 12.989 | 37.639 | 1.00 | 24.75 | T | N |
| ATOM | 3420 | CA | LYS | T | 41 | 26.183 | 12.079 | 36.527 | 1.00 | 26.61 | T | C |
| ATOM | 3421 | C | LYS | T | 41 | 25.427 | 12.345 | 35.224 | 1.00 | 26.89 | T | C |
| ATOM | 3422 | O | LYS | T | 41 | 26.032 | 12.422 | 34.154 | 1.00 | 27.99 | T | O |
| ATOM | 3423 | CB | LYS | T | 41 | 25.922 | 10.637 | 36.970 | 1.00 | 31.82 | T | C |
| ATOM | 3424 | CG | LYS | T | 41 | 26.089 | 9.598 | 35.873 | 1.00 | 37.07 | T | C |
| ATOM | 3425 | CD | LYS | T | 41 | 25.717 | 8.204 | 36.371 | 1.00 | 39.57 | T | C |
| ATOM | 3426 | CE | LYS | T | 41 | 25.812 | 7.175 | 35.253 | 1.00 | 40.27 | T | C |
| ATOM | 3427 | NZ | LYS | T | 41 | 25.454 | 5.808 | 35.729 | 1.00 | 43.52 | T | N |
| ATOM | 3428 | N | SER | T | 42 | 24.108 | 12.473 | 35.303 | 1.00 | 24.42 | T | N |
| ATOM | 3429 | CA | SER | T | 42 | 23.324 | 12.711 | 34.105 | 1.00 | 24.61 | T | C |
| ATOM | 3430 | C | SER | T | 42 | 22.618 | 14.066 | 34.081 | 1.00 | 22.94 | T | C |
| ATOM | 3431 | O | SER | T | 42 | 21.641 | 14.244 | 33.360 | 1.00 | 25.38 | T | O |
| ATOM | 3432 | CB | SER | T | 42 | 22.299 | 11.588 | 33.926 | 1.00 | 26.04 | T | C |
| ATOM | 3433 | OG | SER | T | 42 | 21.442 | 11.505 | 35.048 | 1.00 | 31.07 | T | O |
| ATOM | 3434 | N | GLY | T | 43 | 23.114 | 15.017 | 34.866 | 1.00 | 19.49 | T | N |
| ATOM | 3435 | CA | GLY | T | 43 | 22.513 | 16.338 | 34.898 | 1.00 | 18.07 | T | C |
| ATOM | 3436 | C | GLY | T | 43 | 23.352 | 17.340 | 34.125 | 1.00 | 15.78 | T | C |

-continued

| ATOM | 3437 | O | GLY | T | 43 | 24.494 | 17.058 | 33.774 | 1.00 | 15.61 | T | O |
| ATOM | 3438 | N | ASP | T | 44 | 22.787 | 18.508 | 33.852 | 1.00 | 15.33 | T | N |
| ATOM | 3439 | CA | ASP | T | 44 | 23.500 | 19.543 | 33.119 | 1.00 | 15.18 | T | C |
| ATOM | 3440 | C | ASP | T | 44 | 24.586 | 20.168 | 33.991 | 1.00 | 15.75 | T | C |
| ATOM | 3441 | O | ASP | T | 44 | 24.536 | 20.085 | 35.220 | 1.00 | 14.67 | T | O |
| ATOM | 3442 | CB | ASP | T | 44 | 22.532 | 20.645 | 32.664 | 1.00 | 14.49 | T | C |
| ATOM | 3443 | CG | ASP | T | 44 | 21.512 | 20.163 | 31.635 | 1.00 | 15.31 | T | C |
| ATOM | 3444 | OD1 | ASP | T | 44 | 21.724 | 19.121 | 31.012 | 1.00 | 11.39 | T | O |
| ATOM | 3445 | OD2 | ASP | T | 44 | 20.500 | 20.857 | 31.448 | 1.00 | 16.14 | T | O |
| ATOM | 3446 | N | TRP | T | 45 | 25.570 | 20.794 | 33.356 | 1.00 | 15.26 | T | N |
| ATOM | 3447 | CA | TRP | T | 45 | 26.632 | 21.449 | 34.104 | 1.00 | 16.12 | T | C |
| ATOM | 3448 | C | TRP | T | 45 | 26.155 | 22.832 | 34.532 | 1.00 | 16.65 | T | C |
| ATOM | 3449 | O | TRP | T | 45 | 25.592 | 23.575 | 33.738 | 1.00 | 17.64 | T | O |
| ATOM | 3450 | CB | TRP | T | 45 | 27.895 | 21.576 | 33.259 | 1.00 | 14.65 | T | C |
| ATOM | 3451 | CG | TRP | T | 45 | 28.542 | 20.254 | 32.967 | 1.00 | 16.11 | T | C |
| ATOM | 3452 | CD1 | TRP | T | 45 | 28.359 | 19.476 | 31.859 | 1.00 | 14.82 | T | C |
| ATOM | 3453 | CD2 | TRP | T | 45 | 29.469 | 19.550 | 33.804 | 1.00 | 15.28 | T | C |
| ATOM | 3454 | NE1 | TRP | T | 45 | 29.119 | 18.332 | 31.951 | 1.00 | 14.03 | T | N |
| ATOM | 3455 | CE2 | TRP | T | 45 | 29.812 | 18.352 | 33.135 | 1.00 | 15.34 | T | C |
| ATOM | 3456 | CE3 | TRP | T | 45 | 30.044 | 19.814 | 35.056 | 1.00 | 17.68 | T | C |
| ATOM | 3457 | CZ2 | TRP | T | 45 | 30.708 | 17.420 | 33.672 | 1.00 | 14.08 | T | C |
| ATOM | 3458 | CZ3 | TRP | T | 45 | 30.938 | 18.884 | 35.595 | 1.00 | 15.15 | T | C |
| ATOM | 3459 | CH2 | TRP | T | 45 | 31.260 | 17.703 | 34.899 | 1.00 | 15.49 | T | C |
| ATOM | 3460 | N | LYS | T | 46 | 26.374 | 23.165 | 35.795 | 1.00 | 16.58 | T | N |
| ATOM | 3461 | CA | LYS | T | 46 | 25.960 | 24.455 | 36.323 | 1.00 | 17.49 | T | C |
| ATOM | 3462 | C | LYS | T | 46 | 27.218 | 25.240 | 36.702 | 1.00 | 16.41 | T | C |
| ATOM | 3463 | O | LYS | T | 46 | 28.109 | 24.704 | 37.358 | 1.00 | 17.90 | T | O |
| ATOM | 3464 | CB | LYS | T | 46 | 25.070 | 24.223 | 37.545 | 1.00 | 18.63 | T | C |
| ATOM | 3465 | CG | LYS | T | 46 | 24.011 | 25.285 | 37.794 | 1.00 | 25.36 | T | C |
| ATOM | 3466 | CD | LYS | T | 46 | 24.421 | 26.245 | 38.886 | 1.00 | 27.44 | T | C |
| ATOM | 3467 | CE | LYS | T | 46 | 23.245 | 27.096 | 39.336 | 1.00 | 30.02 | T | C |
| ATOM | 3468 | NZ | LYS | T | 46 | 22.215 | 26.308 | 40.063 | 1.00 | 30.73 | T | N |
| ATOM | 3469 | N | SER | T | 47 | 27.299 | 26.499 | 36.276 | 1.00 | 16.11 | T | N |
| ATOM | 3470 | CA | SER | T | 47 | 28.460 | 27.334 | 36.582 | 1.00 | 14.72 | T | C |
| ATOM | 3471 | C | SER | T | 47 | 28.330 | 28.031 | 37.928 | 1.00 | 13.96 | T | C |
| ATOM | 3472 | O | SER | T | 47 | 27.244 | 28.454 | 38.319 | 1.00 | 13.03 | T | O |
| ATOM | 3473 | CB | SER | T | 47 | 28.678 | 28.386 | 35.488 | 1.00 | 11.64 | T | C |
| ATOM | 3474 | OG | SER | T | 47 | 29.306 | 27.819 | 34.350 | 1.00 | 15.92 | T | O |
| ATOM | 3475 | N | LYS | T | 48 | 29.456 | 28.163 | 38.619 | 1.00 | 13.74 | T | N |
| ATOM | 3476 | CA | LYS | T | 48 | 29.503 | 28.794 | 39.935 | 1.00 | 15.63 | T | C |
| ATOM | 3477 | C | LYS | T | 48 | 30.801 | 29.581 | 40.095 | 1.00 | 15.18 | T | C |
| ATOM | 3478 | O | LYS | T | 48 | 31.774 | 29.346 | 39.376 | 1.00 | 14.77 | T | O |
| ATOM | 3479 | CB | LYS | T | 48 | 29.447 | 27.724 | 41.033 | 1.00 | 13.97 | T | C |
| ATOM | 3480 | CG | LYS | T | 48 | 28.293 | 26.747 | 40.906 | 1.00 | 15.98 | T | C |
| ATOM | 3481 | CD | LYS | T | 48 | 27.363 | 26.832 | 42.093 | 1.00 | 19.94 | T | C |
| ATOM | 3482 | CE | LYS | T | 48 | 26.789 | 28.221 | 42.253 | 1.00 | 19.83 | T | C |
| ATOM | 3483 | NZ | LYS | T | 48 | 25.892 | 28.306 | 43.425 | 1.00 | 18.63 | T | N |
| ATOM | 3484 | N | CYS | T | 49 | 30.806 | 30.508 | 41.046 | 1.00 | 16.26 | T | N |
| ATOM | 3485 | CA | CYS | T | 49 | 31.993 | 31.308 | 41.339 | 1.00 | 17.07 | T | C |
| ATOM | 3486 | C | CYS | T | 49 | 32.635 | 31.844 | 40.058 | 1.00 | 17.80 | T | C |
| ATOM | 3487 | O | CYS | T | 49 | 33.815 | 31.627 | 39.784 | 1.00 | 17.68 | T | O |
| ATOM | 3488 | CB | CYS | T | 49 | 32.975 | 30.448 | 42.144 | 1.00 | 15.94 | T | C |
| ATOM | 3489 | SG | CYS | T | 49 | 32.249 | 29.824 | 43.705 | 1.00 | 18.32 | T | S |
| ATOM | 3490 | N | PHE | T | 50 | 31.826 | 32.568 | 39.293 | 1.00 | 19.09 | T | N |
| ATOM | 3491 | CA | PHE | T | 50 | 32.208 | 33.145 | 38.006 | 1.00 | 19.69 | T | C |
| ATOM | 3492 | C | PHE | T | 50 | 33.438 | 34.046 | 38.020 | 1.00 | 18.93 | T | C |
| ATOM | 3493 | O | PHE | T | 50 | 33.462 | 35.073 | 38.687 | 1.00 | 19.65 | T | O |
| ATOM | 3494 | CB | PHE | T | 50 | 31.018 | 33.925 | 37.437 | 1.00 | 21.03 | T | C |
| ATOM | 3495 | CG | PHE | T | 50 | 29.705 | 33.212 | 37.598 | 1.00 | 22.82 | T | C |
| ATOM | 3496 | CD1 | PHE | T | 50 | 29.410 | 32.090 | 36.834 | 1.00 | 23.21 | T | C |
| ATOM | 3497 | CD2 | PHE | T | 50 | 28.791 | 33.626 | 38.562 | 1.00 | 24.00 | T | C |
| ATOM | 3498 | CE1 | PHE | T | 50 | 28.225 | 31.388 | 37.031 | 1.00 | 22.86 | T | C |
| ATOM | 3499 | CE2 | PHE | T | 50 | 27.604 | 32.929 | 38.768 | 1.00 | 24.77 | T | C |
| ATOM | 3500 | CZ | PHE | T | 50 | 27.324 | 31.808 | 38.000 | 1.00 | 24.10 | T | C |
| ATOM | 3501 | N | TYR | T | 51 | 34.454 | 33.646 | 37.264 | 1.00 | 19.61 | T | N |
| ATOM | 3502 | CA | TYR | T | 51 | 35.694 | 34.404 | 37.135 | 1.00 | 19.80 | T | C |
| ATOM | 3503 | C | TYR | T | 51 | 36.262 | 34.886 | 38.459 | 1.00 | 20.72 | T | C |
| ATOM | 3504 | O | TYR | T | 51 | 36.662 | 36.043 | 38.590 | 1.00 | 20.88 | T | O |
| ATOM | 3505 | CB | TYR | T | 51 | 35.470 | 35.601 | 36.212 | 1.00 | 20.21 | T | C |
| ATOM | 3506 | CG | TYR | T | 51 | 34.778 | 35.245 | 34.915 | 1.00 | 21.19 | T | C |
| ATOM | 3507 | CD1 | TYR | T | 51 | 35.358 | 34.354 | 34.011 | 1.00 | 20.94 | T | C |
| ATOM | 3508 | CD2 | TYR | T | 51 | 33.536 | 35.795 | 34.596 | 1.00 | 22.01 | T | C |
| ATOM | 3509 | CE1 | TYR | T | 51 | 34.717 | 34.021 | 32.820 | 1.00 | 23.56 | T | C |
| ATOM | 3510 | CE2 | TYR | T | 51 | 32.888 | 35.471 | 33.409 | 1.00 | 23.16 | T | C |
| ATOM | 3511 | CZ | TYR | T | 51 | 33.481 | 34.586 | 32.527 | 1.00 | 25.31 | T | C |
| ATOM | 3512 | OH | TYR | T | 51 | 32.835 | 34.271 | 31.353 | 1.00 | 29.02 | T | O |
| ATOM | 3513 | N | THR | T | 52 | 36.300 | 33.989 | 39.436 | 1.00 | 20.20 | T | N |
| ATOM | 3514 | CA | THR | T | 52 | 36.828 | 34.301 | 40.754 | 1.00 | 19.96 | T | C |
| ATOM | 3515 | C | THR | T | 52 | 38.348 | 34.188 | 40.741 | 1.00 | 20.71 | T | C |

-continued

| | | | | | | | | | | | |
|---|---|---|---|---|---|---|---|---|---|---|---|
| ATOM | 3516 | O | THR | T | 52 | 38.916 | 33.409 | 39.970 | 1.00 | 19.97 | T | O |
| ATOM | 3517 | CB | THR | T | 52 | 36.283 | 33.317 | 41.816 | 1.00 | 19.38 | T | C |
| ATOM | 3518 | OG1 | THR | T | 52 | 36.848 | 33.631 | 43.094 | 1.00 | 18.27 | T | O |
| ATOM | 3519 | CG2 | THR | T | 52 | 36.651 | 31.878 | 41.452 | 1.00 | 20.27 | T | C |
| ATOM | 3520 | N | THR | T | 53 | 39.007 | 34.973 | 41.585 | 1.00 | 20.41 | T | N |
| ATOM | 3521 | CA | THR | T | 53 | 40.460 | 34.911 | 41.688 | 1.00 | 22.43 | T | C |
| ATOM | 3522 | C | THR | T | 53 | 40.862 | 34.112 | 42.934 | 1.00 | 23.31 | T | C |
| ATOM | 3523 | O | THR | T | 53 | 42.042 | 33.872 | 43.178 | 1.00 | 24.50 | T | O |
| ATOM | 3524 | CB | THR | T | 53 | 41.094 | 36.318 | 41.751 | 1.00 | 21.43 | T | C |
| ATOM | 3525 | OG1 | THR | T | 53 | 40.475 | 37.077 | 42.793 | 1.00 | 23.60 | T | O |
| ATOM | 3526 | CG2 | THR | T | 53 | 40.919 | 37.039 | 40.423 | 1.00 | 20.43 | T | C |
| ATOM | 3527 | N | ASP | T | 54 | 39.878 | 33.701 | 43.727 | 1.00 | 24.66 | T | N |
| ATOM | 3528 | CA | ASP | T | 54 | 40.170 | 32.907 | 44.910 | 1.00 | 24.86 | T | C |
| ATOM | 3529 | C | ASP | T | 54 | 40.341 | 31.467 | 44.447 | 1.00 | 24.57 | T | C |
| ATOM | 3530 | O | ASP | T | 54 | 39.991 | 31.124 | 43.311 | 1.00 | 23.26 | T | O |
| ATOM | 3531 | CB | ASP | T | 54 | 39.027 | 32.991 | 45.920 | 1.00 | 28.59 | T | C |
| ATOM | 3532 | CG | ASP | T | 54 | 38.695 | 34.418 | 46.307 | 1.00 | 31.77 | T | C |
| ATOM | 3533 | OD1 | ASP | T | 54 | 39.607 | 35.179 | 46.642 | 1.00 | 35.02 | T | O |
| ATOM | 3534 | OD2 | ASP | T | 54 | 37.529 | 34.759 | 46.279 | 1.00 | 36.17 | T | O |
| ATOM | 3535 | N | THR | T | 55 | 40.888 | 30.625 | 45.316 | 1.00 | 20.61 | T | N |
| ATOM | 3536 | CA | THR | T | 55 | 41.088 | 29.230 | 44.969 | 1.00 | 18.26 | T | C |
| ATOM | 3537 | C | THR | T | 55 | 40.114 | 28.339 | 45.741 | 1.00 | 18.54 | T | C |
| ATOM | 3538 | O | THR | T | 55 | 40.483 | 27.264 | 46.222 | 1.00 | 16.66 | T | O |
| ATOM | 3539 | CB | THR | T | 55 | 42.526 | 28.806 | 45.266 | 1.00 | 17.06 | T | C |
| ATOM | 3540 | OG1 | THR | T | 55 | 42.852 | 29.159 | 46.612 | 1.00 | 17.45 | T | O |
| ATOM | 3541 | CG2 | THR | T | 55 | 43.488 | 29.500 | 44.321 | 1.00 | 19.50 | T | C |
| ATOM | 3542 | N | GLU | T | 56 | 38.871 | 28.804 | 45.857 | 1.00 | 15.86 | T | N |
| ATOM | 3543 | CA | GLU | T | 56 | 37.822 | 28.072 | 46.553 | 1.00 | 17.50 | T | C |
| ATOM | 3544 | C | GLU | T | 56 | 36.462 | 28.477 | 45.999 | 1.00 | 16.59 | T | C |
| ATOM | 3545 | O | GLU | T | 56 | 36.294 | 29.576 | 45.475 | 1.00 | 15.56 | T | O |
| ATOM | 3546 | CB | GLU | T | 56 | 37.837 | 28.387 | 48.053 | 1.00 | 17.92 | T | C |
| ATOM | 3547 | CG | GLU | T | 56 | 37.396 | 29.809 | 48.374 | 1.00 | 20.51 | T | C |
| ATOM | 3548 | CD | GLU | T | 56 | 37.265 | 30.061 | 49.859 | 1.00 | 24.03 | T | C |
| ATOM | 3549 | OE1 | GLU | T | 56 | 38.221 | 29.802 | 50.582 | 1.00 | 26.81 | T | O |
| ATOM | 3550 | OE2 | GLU | T | 56 | 36.205 | 30.518 | 50.287 | 1.00 | 26.27 | T | O |
| ATOM | 3551 | N | CYS | T | 57 | 35.490 | 27.586 | 46.129 | 1.00 | 16.04 | T | N |
| ATOM | 3552 | CA | CYS | T | 57 | 34.147 | 27.870 | 45.665 | 1.00 | 16.17 | T | C |
| ATOM | 3553 | C | CYS | T | 57 | 33.140 | 27.164 | 46.552 | 1.00 | 15.98 | T | C |
| ATOM | 3554 | O | CYS | T | 57 | 33.225 | 25.954 | 46.754 | 1.00 | 14.72 | T | O |
| ATOM | 3555 | CB | CYS | T | 57 | 33.963 | 27.403 | 44.219 | 1.00 | 17.24 | T | C |
| ATOM | 3556 | SG | CYS | T | 57 | 32.314 | 27.793 | 43.557 | 1.00 | 17.97 | T | S |
| ATOM | 3557 | N | ASP | T | 58 | 32.187 | 27.918 | 47.084 | 1.00 | 14.99 | T | N |
| ATOM | 3558 | CA | ASP | T | 58 | 31.172 | 27.326 | 47.934 | 1.00 | 15.94 | T | C |
| ATOM | 3559 | C | ASP | T | 58 | 30.115 | 26.677 | 47.061 | 1.00 | 16.95 | T | C |
| ATOM | 3560 | O | ASP | T | 58 | 29.477 | 27.340 | 46.244 | 1.00 | 17.86 | T | O |
| ATOM | 3561 | CB | ASP | T | 58 | 30.526 | 28.385 | 48.829 | 1.00 | 16.18 | T | C |
| ATOM | 3562 | CG | ASP | T | 58 | 29.436 | 27.806 | 49.715 | 1.00 | 17.55 | T | C |
| ATOM | 3563 | OD1 | ASP | T | 58 | 29.529 | 26.636 | 50.053 | 1.00 | 15.23 | T | O |
| ATOM | 3564 | OD2 | ASP | T | 58 | 28.502 | 28.531 | 50.073 | 1.00 | 18.41 | T | O |
| ATOM | 3565 | N | LEU | T | 59 | 29.939 | 25.373 | 47.227 | 1.00 | 16.87 | T | N |
| ATOM | 3566 | CA | LEU | T | 59 | 28.951 | 24.643 | 46.449 | 1.00 | 16.97 | T | C |
| ATOM | 3567 | C | LEU | T | 59 | 27.832 | 24.092 | 47.331 | 1.00 | 17.59 | T | C |
| ATOM | 3568 | O | LEU | T | 59 | 27.077 | 23.218 | 46.916 | 1.00 | 19.55 | T | O |
| ATOM | 3569 | CB | LEU | T | 59 | 29.638 | 23.513 | 45.682 | 1.00 | 14.54 | T | C |
| ATOM | 3570 | CG | LEU | T | 59 | 30.694 | 24.010 | 44.686 | 1.00 | 16.18 | T | C |
| ATOM | 3571 | CD1 | LEU | T | 59 | 31.435 | 22.828 | 44.072 | 1.00 | 13.02 | T | C |
| ATOM | 3572 | CD2 | LEU | T | 59 | 30.019 | 24.850 | 43.606 | 1.00 | 14.07 | T | C |
| ATOM | 3573 | N | THR | T | 60 | 27.718 | 24.630 | 48.541 | 1.00 | 18.48 | T | N |
| ATOM | 3574 | CA | THR | T | 60 | 26.701 | 24.199 | 49.495 | 1.00 | 20.05 | T | C |
| ATOM | 3575 | C | THR | T | 60 | 25.274 | 24.228 | 48.952 | 1.00 | 20.61 | T | C |
| ATOM | 3576 | O | THR | T | 60 | 24.558 | 23.230 | 49.030 | 1.00 | 20.04 | T | O |
| ATOM | 3577 | CB | THR | T | 60 | 26.748 | 25.062 | 50.779 | 1.00 | 20.92 | T | C |
| ATOM | 3578 | OG1 | THR | T | 60 | 28.024 | 24.909 | 51.415 | 1.00 | 21.02 | T | O |
| ATOM | 3579 | CG2 | THR | T | 60 | 25.654 | 24.647 | 51.747 | 1.00 | 19.78 | T | C |
| ATOM | 3580 | N | ASP | T | 61 | 24.859 | 25.368 | 48.405 | 1.00 | 20.95 | T | N |
| ATOM | 3581 | CA | ASP | T | 61 | 23.500 | 25.507 | 47.884 | 1.00 | 22.33 | T | C |
| ATOM | 3582 | C | ASP | T | 61 | 23.142 | 24.529 | 46.778 | 1.00 | 21.88 | T | C |
| ATOM | 3583 | O | ASP | T | 61 | 21.967 | 24.220 | 46.574 | 1.00 | 23.89 | T | O |
| ATOM | 3584 | CB | ASP | T | 61 | 23.252 | 26.934 | 47.391 | 1.00 | 23.16 | T | C |
| ATOM | 3585 | CG | ASP | T | 61 | 23.321 | 27.947 | 48.507 | 1.00 | 26.60 | T | C |
| ATOM | 3586 | OD1 | ASP | T | 61 | 23.175 | 27.550 | 49.659 | 1.00 | 28.12 | T | O |
| ATOM | 3587 | OD2 | ASP | T | 61 | 23.511 | 29.127 | 48.221 | 1.00 | 31.54 | T | O |
| ATOM | 3588 | N | GLU | T | 62 | 24.146 | 24.042 | 46.060 | 1.00 | 20.11 | T | N |
| ATOM | 3589 | CA | GLU | T | 62 | 23.890 | 23.102 | 44.986 | 1.00 | 21.57 | T | C |
| ATOM | 3590 | C | GLU | T | 62 | 23.774 | 21.671 | 45.504 | 1.00 | 21.37 | T | C |
| ATOM | 3591 | O | GLU | T | 62 | 22.848 | 20.950 | 45.130 | 1.00 | 22.03 | T | O |
| ATOM | 3592 | CB | GLU | T | 62 | 24.996 | 23.179 | 43.925 | 1.00 | 20.82 | T | C |
| ATOM | 3593 | CG | GLU | T | 62 | 25.211 | 24.565 | 43.313 | 1.00 | 22.54 | T | C |
| ATOM | 3594 | CD | GLU | T | 62 | 23.923 | 25.198 | 42.794 | 1.00 | 26.23 | T | C |

-continued

| | | | | | | | | | | | |
|---|---|---|---|---|---|---|---|---|---|---|---|
| ATOM | 3595 | OE1 | GLU | T | 62 | 23.135 | 24.492 | 42.164 | 1.00 | 25.97 | T | O |
| ATOM | 3596 | OE2 | GLU | T | 62 | 23.717 | 26.403 | 43.012 | 1.00 | 24.60 | T | O |
| ATOM | 3597 | N | ILE | T | 63 | 24.693 | 21.257 | 46.375 | 1.00 | 19.96 | T | N |
| ATOM | 3598 | CA | ILE | T | 63 | 24.656 | 19.887 | 46.878 | 1.00 | 20.43 | T | C |
| ATOM | 3599 | C | ILE | T | 63 | 23.529 | 19.576 | 47.870 | 1.00 | 20.80 | T | C |
| ATOM | 3600 | O | ILE | T | 63 | 23.082 | 18.434 | 47.951 | 1.00 | 19.50 | T | O |
| ATOM | 3601 | CB | ILE | T | 63 | 26.035 | 19.460 | 47.477 | 1.00 | 20.40 | T | C |
| ATOM | 3602 | CG1 | ILE | T | 63 | 26.424 | 20.356 | 48.654 | 1.00 | 19.56 | T | C |
| ATOM | 3603 | CG2 | ILE | T | 63 | 27.105 | 19.513 | 46.398 | 1.00 | 18.09 | T | C |
| ATOM | 3604 | CD1 | ILE | T | 63 | 25.877 | 19.894 | 49.986 | 1.00 | 19.86 | T | C |
| ATOM | 3605 | N | VAL | T | 64 | 23.047 | 20.576 | 48.603 | 1.00 | 20.09 | T | N |
| ATOM | 3606 | CA | VAL | T | 64 | 21.967 | 20.334 | 49.558 | 1.00 | 20.98 | T | C |
| ATOM | 3607 | C | VAL | T | 64 | 20.614 | 20.092 | 48.875 | 1.00 | 23.72 | T | C |
| ATOM | 3608 | O | VAL | T | 64 | 19.638 | 19.736 | 49.537 | 1.00 | 21.27 | T | O |
| ATOM | 3609 | CB | VAL | T | 64 | 21.804 | 21.501 | 50.568 | 1.00 | 20.02 | T | C |
| ATOM | 3610 | CG1 | VAL | T | 64 | 23.093 | 21.690 | 51.358 | 1.00 | 20.46 | T | C |
| ATOM | 3611 | CG2 | VAL | T | 64 | 21.405 | 22.775 | 49.842 | 1.00 | 20.60 | T | C |
| ATOM | 3612 | N | LYS | T | 65 | 20.553 | 20.294 | 47.559 | 1.00 | 25.22 | T | N |
| ATOM | 3613 | CA | LYS | T | 65 | 19.318 | 20.065 | 46.809 | 1.00 | 28.22 | T | C |
| ATOM | 3614 | C | LYS | T | 65 | 18.978 | 18.574 | 46.822 | 1.00 | 27.08 | T | C |
| ATOM | 3615 | O | LYS | T | 65 | 17.812 | 18.194 | 46.764 | 1.00 | 28.54 | T | O |
| ATOM | 3616 | CB | LYS | T | 65 | 19.466 | 20.565 | 45.366 | 1.00 | 30.57 | T | C |
| ATOM | 3617 | CG | LYS | T | 65 | 19.579 | 22.081 | 45.256 | 1.00 | 32.86 | T | C |
| ATOM | 3618 | CD | LYS | T | 65 | 19.681 | 22.544 | 43.811 | 1.00 | 35.41 | T | C |
| ATOM | 3619 | CE | LYS | T | 65 | 19.767 | 24.064 | 43.735 | 1.00 | 37.84 | T | C |
| ATOM | 3620 | NZ | LYS | T | 65 | 19.813 | 24.564 | 42.334 | 1.00 | 39.60 | T | N |
| ATOM | 3621 | N | ASP | T | 66 | 20.014 | 17.742 | 46.879 | 1.00 | 26.86 | T | N |
| ATOM | 3622 | CA | ASP | T | 66 | 19.877 | 16.291 | 46.956 | 1.00 | 24.78 | T | C |
| ATOM | 3623 | C | ASP | T | 66 | 21.205 | 15.780 | 47.494 | 1.00 | 23.00 | T | C |
| ATOM | 3624 | O | ASP | T | 66 | 22.125 | 15.490 | 46.734 | 1.00 | 21.38 | T | O |
| ATOM | 3625 | CB | ASP | T | 66 | 19.609 | 15.669 | 45.586 | 1.00 | 26.36 | T | C |
| ATOM | 3626 | CG | ASP | T | 66 | 19.251 | 14.188 | 45.680 | 1.00 | 29.40 | T | C |
| ATOM | 3627 | OD1 | ASP | T | 66 | 19.538 | 13.568 | 46.722 | 1.00 | 28.55 | T | O |
| ATOM | 3628 | OD2 | ASP | T | 66 | 18.695 | 13.648 | 44.717 | 1.00 | 31.14 | T | O |
| ATOM | 3629 | N | VAL | T | 67 | 21.300 | 15.672 | 48.814 | 1.00 | 22.91 | T | N |
| ATOM | 3630 | CA | VAL | T | 67 | 22.530 | 15.221 | 49.452 | 1.00 | 22.94 | T | C |
| ATOM | 3631 | C | VAL | T | 67 | 22.927 | 13.783 | 49.125 | 1.00 | 24.63 | T | C |
| ATOM | 3632 | O | VAL | T | 67 | 24.071 | 13.390 | 49.356 | 1.00 | 24.10 | T | O |
| ATOM | 3633 | CB | VAL | T | 67 | 22.449 | 15.384 | 50.992 | 1.00 | 22.47 | T | C |
| ATOM | 3634 | CG1 | VAL | T | 67 | 22.180 | 16.846 | 51.350 | 1.00 | 17.69 | T | C |
| ATOM | 3635 | CG2 | VAL | T | 67 | 21.364 | 14.488 | 51.563 | 1.00 | 19.93 | T | C |
| ATOM | 3636 | N | LYS | T | 68 | 21.998 | 13.003 | 48.578 | 1.00 | 26.06 | T | N |
| ATOM | 3637 | CA | LYS | T | 68 | 22.284 | 11.608 | 48.239 | 1.00 | 27.04 | T | C |
| ATOM | 3638 | C | LYS | T | 68 | 22.873 | 11.395 | 46.850 | 1.00 | 26.31 | T | C |
| ATOM | 3639 | O | LYS | T | 68 | 23.342 | 10.304 | 46.531 | 1.00 | 24.28 | T | O |
| ATOM | 3640 | CB | LYS | T | 68 | 21.024 | 10.759 | 48.401 | 1.00 | 28.46 | T | C |
| ATOM | 3641 | CG | LYS | T | 68 | 20.634 | 10.547 | 49.850 | 1.00 | 30.19 | T | C |
| ATOM | 3642 | CD | LYS | T | 68 | 19.389 | 9.699 | 49.975 | 1.00 | 32.33 | T | C |
| ATOM | 3643 | CE | LYS | T | 68 | 19.115 | 9.356 | 51.425 | 1.00 | 34.80 | T | C |
| ATOM | 3644 | NZ | LYS | T | 68 | 20.235 | 8.569 | 52.002 | 1.00 | 38.91 | T | N |
| ATOM | 3645 | N | GLN | T | 69 | 22.848 | 12.436 | 46.025 | 1.00 | 26.68 | T | N |
| ATOM | 3646 | CA | GLN | T | 69 | 23.404 | 12.351 | 44.681 | 1.00 | 24.77 | T | C |
| ATOM | 3647 | C | GLN | T | 69 | 24.924 | 12.389 | 44.739 | 1.00 | 23.29 | T | C |
| ATOM | 3648 | O | GLN | T | 69 | 25.501 | 12.750 | 45.762 | 1.00 | 22.51 | T | O |
| ATOM | 3649 | CB | GLN | T | 69 | 22.901 | 13.519 | 43.829 | 1.00 | 27.54 | T | C |
| ATOM | 3650 | CG | GLN | T | 69 | 21.556 | 13.274 | 43.173 | 1.00 | 32.96 | T | C |
| ATOM | 3651 | CD | GLN | T | 69 | 21.628 | 12.171 | 42.135 | 1.00 | 35.85 | T | C |
| ATOM | 3652 | OE1 | GLN | T | 69 | 22.338 | 12.292 | 41.138 | 1.00 | 37.60 | T | O |
| ATOM | 3653 | NE2 | GLN | T | 69 | 20.901 | 11.084 | 42.369 | 1.00 | 39.16 | T | N |
| ATOM | 3654 | N | THR | T | 70 | 25.562 | 11.995 | 43.640 | 1.00 | 21.11 | T | N |
| ATOM | 3655 | CA | THR | T | 70 | 27.013 | 12.016 | 43.531 | 1.00 | 20.59 | T | C |
| ATOM | 3656 | C | THR | T | 70 | 27.345 | 13.152 | 42.570 | 1.00 | 20.22 | T | C |
| ATOM | 3657 | O | THR | T | 70 | 26.917 | 13.149 | 41.414 | 1.00 | 19.62 | T | O |
| ATOM | 3658 | CB | THR | T | 70 | 27.570 | 10.687 | 42.978 | 1.00 | 19.99 | T | C |
| ATOM | 3659 | OG1 | THR | T | 70 | 27.344 | 9.643 | 43.931 | 1.00 | 21.36 | T | O |
| ATOM | 3660 | CG2 | THR | T | 70 | 29.067 | 10.802 | 42.728 | 1.00 | 18.95 | T | C |
| ATOM | 3661 | N | TYR | T | 71 | 28.102 | 14.127 | 43.061 | 1.00 | 18.76 | T | N |
| ATOM | 3662 | CA | TYR | T | 71 | 28.462 | 15.292 | 42.271 | 1.00 | 17.58 | T | C |
| ATOM | 3663 | C | TYR | T | 71 | 29.885 | 15.284 | 41.752 | 1.00 | 17.20 | T | C |
| ATOM | 3664 | O | TYR | T | 71 | 30.786 | 14.721 | 42.366 | 1.00 | 17.10 | T | O |
| ATOM | 3665 | CB | TYR | T | 71 | 28.263 | 16.572 | 43.095 | 1.00 | 15.82 | T | C |
| ATOM | 3666 | CG | TYR | T | 71 | 26.852 | 16.779 | 43.587 | 1.00 | 15.19 | T | C |
| ATOM | 3667 | CD1 | TYR | T | 71 | 26.381 | 16.119 | 44.729 | 1.00 | 15.57 | T | C |
| ATOM | 3668 | CD2 | TYR | T | 71 | 25.967 | 17.598 | 42.887 | 1.00 | 14.29 | T | C |
| ATOM | 3669 | CE1 | TYR | T | 71 | 25.065 | 16.268 | 45.155 | 1.00 | 14.24 | T | C |
| ATOM | 3670 | CE2 | TYR | T | 71 | 24.649 | 17.752 | 43.302 | 1.00 | 14.12 | T | C |
| ATOM | 3671 | CZ | TYR | T | 71 | 24.205 | 17.083 | 44.435 | 1.00 | 15.17 | T | C |
| ATOM | 3672 | OH | TYR | T | 71 | 22.901 | 17.226 | 44.844 | 1.00 | 13.94 | T | O |
| ATOM | 3673 | N | LEU | T | 72 | 30.077 | 15.926 | 40.609 | 1.00 | 17.96 | T | N |

| | | | | | | | | | | | |
|---|---|---|---|---|---|---|---|---|---|---|---|
| ATOM | 3674 | CA | LEU | T | 72 | 31.397 | 16.052 | 40.017 | 1.00 | 18.23 | T | C |
| ATOM | 3675 | C | LEU | T | 72 | 31.517 | 17.536 | 39.729 | 1.00 | 17.51 | T | C |
| ATOM | 3676 | O | LEU | T | 72 | 30.556 | 18.179 | 39.300 | 1.00 | 17.06 | T | O |
| ATOM | 3677 | CB | LEU | T | 72 | 31.500 | 15.256 | 38.712 | 1.00 | 22.12 | T | C |
| ATOM | 3678 | CG | LEU | T | 72 | 32.895 | 14.972 | 38.119 | 1.00 | 26.17 | T | C |
| ATOM | 3679 | CD1 | LEU | T | 72 | 33.519 | 16.243 | 37.563 | 1.00 | 28.99 | T | C |
| ATOM | 3680 | CD2 | LEU | T | 72 | 33.792 | 14.356 | 39.182 | 1.00 | 25.19 | T | C |
| ATOM | 3681 | N | ALA | T | 73 | 32.686 | 18.089 | 40.003 | 1.00 | 17.91 | T | N |
| ATOM | 3682 | CA | ALA | T | 73 | 32.928 | 19.496 | 39.751 | 1.00 | 16.95 | T | C |
| ATOM | 3683 | C | ALA | T | 73 | 34.197 | 19.592 | 38.922 | 1.00 | 16.12 | T | C |
| ATOM | 3684 | O | ALA | T | 73 | 34.947 | 18.624 | 38.809 | 1.00 | 18.51 | T | O |
| ATOM | 3685 | CB | ALA | T | 73 | 33.092 | 20.240 | 41.065 | 1.00 | 15.74 | T | C |
| ATOM | 3686 | N | ARG | T | 74 | 34.415 | 20.746 | 38.312 | 1.00 | 15.02 | T | N |
| ATOM | 3687 | CA | ARG | T | 74 | 35.613 | 20.966 | 37.524 | 1.00 | 14.43 | T | C |
| ATOM | 3688 | C | ARG | T | 74 | 35.926 | 22.453 | 37.535 | 1.00 | 14.10 | T | C |
| ATOM | 3689 | O | ARG | T | 74 | 35.024 | 23.293 | 37.512 | 1.00 | 13.27 | T | O |
| ATOM | 3690 | CB | ARG | T | 74 | 35.444 | 20.438 | 36.090 | 1.00 | 13.57 | T | C |
| ATOM | 3691 | CG | ARG | T | 74 | 34.246 | 20.969 | 35.312 | 1.00 | 15.95 | T | C |
| ATOM | 3692 | CD | ARG | T | 74 | 34.070 | 20.161 | 34.015 | 1.00 | 15.26 | T | C |
| ATOM | 3693 | NE | ARG | T | 74 | 32.983 | 20.658 | 33.173 | 1.00 | 11.15 | T | N |
| ATOM | 3694 | CZ | ARG | T | 74 | 32.545 | 20.051 | 32.071 | 1.00 | 13.10 | T | C |
| ATOM | 3695 | NH1 | ARG | T | 74 | 33.093 | 18.910 | 31.661 | 1.00 | 9.53 | T | N |
| ATOM | 3696 | NH2 | ARG | T | 74 | 31.562 | 20.594 | 31.364 | 1.00 | 10.82 | T | N |
| ATOM | 3697 | N | VAL | T | 75 | 37.211 | 22.767 | 37.599 | 1.00 | 14.14 | T | N |
| ATOM | 3698 | CA | VAL | T | 75 | 37.672 | 24.147 | 37.643 | 1.00 | 15.10 | T | C |
| ATOM | 3699 | C | VAL | T | 75 | 38.307 | 24.589 | 36.333 | 1.00 | 16.01 | T | C |
| ATOM | 3700 | O | VAL | T | 75 | 39.301 | 24.016 | 35.896 | 1.00 | 14.34 | T | O |
| ATOM | 3701 | CB | VAL | T | 75 | 38.708 | 24.336 | 38.773 | 1.00 | 15.28 | T | C |
| ATOM | 3702 | CG1 | VAL | T | 75 | 39.280 | 25.747 | 38.731 | 1.00 | 13.98 | T | C |
| ATOM | 3703 | CG2 | VAL | T | 75 | 38.058 | 24.065 | 40.122 | 1.00 | 14.39 | T | C |
| ATOM | 3704 | N | PHE | T | 76 | 37.722 | 25.604 | 35.708 | 1.00 | 18.72 | T | N |
| ATOM | 3705 | CA | PHE | T | 76 | 38.247 | 26.140 | 34.460 | 1.00 | 21.14 | T | C |
| ATOM | 3706 | C | PHE | T | 76 | 39.211 | 27.272 | 34.780 | 1.00 | 22.66 | T | C |
| ATOM | 3707 | O | PHE | T | 76 | 38.992 | 28.035 | 35.723 | 1.00 | 23.68 | T | O |
| ATOM | 3708 | CB | PHE | T | 76 | 37.112 | 26.668 | 33.583 | 1.00 | 23.60 | T | C |
| ATOM | 3709 | CG | PHE | T | 76 | 36.199 | 25.596 | 33.062 | 1.00 | 28.84 | T | C |
| ATOM | 3710 | CD1 | PHE | T | 76 | 36.660 | 24.654 | 32.152 | 1.00 | 31.44 | T | C |
| ATOM | 3711 | CD2 | PHE | T | 76 | 34.880 | 25.521 | 33.486 | 1.00 | 31.69 | T | C |
| ATOM | 3712 | CE1 | PHE | T | 76 | 35.818 | 23.652 | 31.671 | 1.00 | 33.34 | T | C |
| ATOM | 3713 | CE2 | PHE | T | 76 | 34.034 | 24.522 | 33.008 | 1.00 | 34.41 | T | C |
| ATOM | 3714 | CZ | PHE | T | 76 | 34.505 | 23.589 | 32.101 | 1.00 | 30.45 | T | C |
| ATOM | 3715 | N | SER | T | 77 | 40.282 | 27.369 | 34.000 | 1.00 | 24.37 | T | N |
| ATOM | 3716 | CA | SER | T | 77 | 41.287 | 28.410 | 34.182 | 1.00 | 25.59 | T | C |
| ATOM | 3717 | C | SER | T | 77 | 41.337 | 29.303 | 32.953 | 1.00 | 27.03 | T | C |
| ATOM | 3718 | O | SER | T | 77 | 41.322 | 28.817 | 31.823 | 1.00 | 25.41 | T | O |
| ATOM | 3719 | CB | SER | T | 77 | 42.668 | 27.793 | 34.401 | 1.00 | 26.08 | T | C |
| ATOM | 3720 | OG | SER | T | 77 | 42.714 | 27.056 | 35.604 | 1.00 | 28.24 | T | O |
| ATOM | 3721 | N | TYR | T | 78 | 41.398 | 30.610 | 33.188 | 1.00 | 29.89 | T | N |
| ATOM | 3722 | CA | TYR | T | 78 | 41.465 | 31.601 | 32.119 | 1.00 | 31.65 | T | C |
| ATOM | 3723 | C | TYR | T | 78 | 42.636 | 32.537 | 32.414 | 1.00 | 33.58 | T | C |
| ATOM | 3724 | O | TYR | T | 78 | 43.009 | 32.726 | 33.572 | 1.00 | 34.76 | T | O |
| ATOM | 3725 | CB | TYR | T | 78 | 40.173 | 32.413 | 32.073 | 1.00 | 31.59 | T | C |
| ATOM | 3726 | CG | TYR | T | 78 | 38.919 | 31.579 | 31.943 | 1.00 | 31.52 | T | C |
| ATOM | 3727 | CD1 | TYR | T | 78 | 38.505 | 31.093 | 30.706 | 1.00 | 29.66 | T | C |
| ATOM | 3728 | CD2 | TYR | T | 78 | 38.147 | 31.274 | 33.062 | 1.00 | 30.05 | T | C |
| ATOM | 3729 | CE1 | TYR | T | 78 | 37.352 | 30.331 | 30.587 | 1.00 | 30.62 | T | C |
| ATOM | 3730 | CE2 | TYR | T | 78 | 36.998 | 30.512 | 32.955 | 1.00 | 30.31 | T | C |
| ATOM | 3731 | CZ | TYR | T | 78 | 36.604 | 30.044 | 31.716 | 1.00 | 30.37 | T | C |
| ATOM | 3732 | OH | TYR | T | 78 | 35.458 | 29.296 | 31.607 | 1.00 | 31.28 | T | O |
| ATOM | 3733 | N | PRO | T | 79 | 43.236 | 33.132 | 31.372 | 1.00 | 35.05 | T | N |
| ATOM | 3734 | CA | PRO | T | 79 | 44.365 | 34.047 | 31.573 | 1.00 | 35.74 | T | C |
| ATOM | 3735 | C | PRO | T | 79 | 43.914 | 35.395 | 32.139 | 1.00 | 36.81 | T | C |
| ATOM | 3736 | O | PRO | T | 79 | 43.932 | 35.611 | 33.352 | 1.00 | 37.66 | T | O |
| ATOM | 3737 | CB | PRO | T | 79 | 44.949 | 34.178 | 30.173 | 1.00 | 35.23 | T | C |
| ATOM | 3738 | CG | PRO | T | 79 | 43.723 | 34.105 | 29.313 | 1.00 | 35.61 | T | C |
| ATOM | 3739 | CD | PRO | T | 79 | 42.960 | 32.951 | 29.935 | 1.00 | 35.09 | T | C |
| ATOM | 3740 | N | GLU | T | 91 | 38.161 | 24.891 | 23.662 | 1.00 | 26.53 | T | N |
| ATOM | 3741 | CA | GLU | T | 91 | 37.694 | 24.757 | 25.073 | 1.00 | 26.00 | T | C |
| ATOM | 3742 | C | GLU | T | 91 | 38.810 | 25.160 | 26.043 | 1.00 | 26.45 | T | C |
| ATOM | 3743 | O | GLU | T | 91 | 39.991 | 24.986 | 25.748 | 1.00 | 24.05 | T | O |
| ATOM | 3744 | CB | GLU | T | 91 | 37.238 | 23.315 | 25.331 | 1.00 | 24.69 | T | C |
| ATOM | 3745 | CG | GLU | T | 91 | 36.117 | 22.857 | 24.384 | 1.00 | 22.94 | T | C |
| ATOM | 3746 | CD | GLU | T | 91 | 35.711 | 21.405 | 24.588 | 1.00 | 20.53 | T | C |
| ATOM | 3747 | OE1 | GLU | T | 91 | 36.581 | 20.582 | 24.780 | 1.00 | 21.42 | T | O |
| ATOM | 3748 | OE2 | GLU | T | 91 | 34.525 | 21.111 | 24.538 | 1.00 | 21.55 | T | O |
| ATOM | 3749 | N | PRO | T | 92 | 38.443 | 25.714 | 27.212 | 1.00 | 27.49 | T | N |
| ATOM | 3750 | CA | PRO | T | 92 | 39.402 | 26.153 | 28.232 | 1.00 | 28.13 | T | C |
| ATOM | 3751 | C | PRO | T | 92 | 40.087 | 25.028 | 28.998 | 1.00 | 27.90 | T | C |
| ATOM | 3752 | O | PRO | T | 92 | 39.618 | 23.893 | 29.012 | 1.00 | 28.67 | T | O |

-continued

| | | | | | | | | | | | |
|---|---|---|---|---|---|---|---|---|---|---|---|
| ATOM | 3753 | CB | PRO | T | 92 | 38.545 | 27.016 | 29.148 | 1.00 | 29.05 | T | C |
| ATOM | 3754 | CG | PRO | T | 92 | 37.243 | 26.282 | 29.135 | 1.00 | 30.13 | T | C |
| ATOM | 3755 | CD | PRO | T | 92 | 37.063 | 25.993 | 27.650 | 1.00 | 28.84 | T | C |
| ATOM | 3756 | N | LEU | T | 93 | 41.199 | 25.361 | 29.642 | 1.00 | 28.40 | T | N |
| ATOM | 3757 | CA | LEU | T | 93 | 41.944 | 24.392 | 30.435 | 1.00 | 27.14 | T | C |
| ATOM | 3758 | C | LEU | T | 93 | 41.152 | 24.159 | 31.710 | 1.00 | 24.86 | T | C |
| ATOM | 3759 | O | LEU | T | 93 | 40.576 | 25.094 | 32.268 | 1.00 | 23.66 | T | O |
| ATOM | 3760 | CB | LEU | T | 93 | 43.327 | 24.936 | 30.797 | 1.00 | 29.29 | T | C |
| ATOM | 3761 | CG | LEU | T | 93 | 44.208 | 25.476 | 29.665 | 1.00 | 33.20 | T | C |
| ATOM | 3762 | CD1 | LEU | T | 93 | 45.541 | 25.928 | 30.247 | 1.00 | 34.70 | T | C |
| ATOM | 3763 | CD2 | LEU | T | 93 | 44.426 | 24.412 | 28.604 | 1.00 | 34.85 | T | C |
| ATOM | 3764 | N | TYR | T | 94 | 41.108 | 22.912 | 32.162 | 1.00 | 23.07 | T | N |
| ATOM | 3765 | CA | TYR | T | 94 | 40.379 | 22.584 | 33.379 | 1.00 | 20.97 | T | C |
| ATOM | 3766 | C | TYR | T | 94 | 40.878 | 21.296 | 34.007 | 1.00 | 19.78 | T | C |
| ATOM | 3767 | O | TYR | T | 94 | 41.676 | 20.562 | 33.422 | 1.00 | 18.62 | T | O |
| ATOM | 3768 | CB | TYR | T | 94 | 38.875 | 22.454 | 33.104 | 1.00 | 20.47 | T | C |
| ATOM | 3769 | CG | TYR | T | 94 | 38.496 | 21.246 | 32.272 | 1.00 | 21.39 | T | C |
| ATOM | 3770 | CD1 | TYR | T | 94 | 38.595 | 21.268 | 30.877 | 1.00 | 20.22 | T | C |
| ATOM | 3771 | CD2 | TYR | T | 94 | 38.054 | 20.071 | 32.883 | 1.00 | 19.95 | T | C |
| ATOM | 3772 | CE1 | TYR | T | 94 | 38.266 | 20.149 | 30.113 | 1.00 | 20.60 | T | C |
| ATOM | 3773 | CE2 | TYR | T | 94 | 37.719 | 18.947 | 32.128 | 1.00 | 20.65 | T | C |
| ATOM | 3774 | CZ | TYR | T | 94 | 37.828 | 18.993 | 30.747 | 1.00 | 21.30 | T | C |
| ATOM | 3775 | OH | TYR | T | 94 | 37.508 | 17.881 | 30.004 | 1.00 | 21.41 | T | O |
| ATOM | 3776 | N | GLU | T | 95 | 40.380 | 21.035 | 35.207 | 1.00 | 18.35 | T | N |
| ATOM | 3777 | CA | GLU | T | 95 | 40.733 | 19.857 | 35.976 | 1.00 | 19.30 | T | C |
| ATOM | 3778 | C | GLU | T | 95 | 39.452 | 19.393 | 36.660 | 1.00 | 18.34 | T | C |
| ATOM | 3779 | O | GLU | T | 95 | 38.667 | 20.216 | 37.133 | 1.00 | 17.95 | T | O |
| ATOM | 3780 | CB | GLU | T | 95 | 41.782 | 20.231 | 37.028 | 1.00 | 22.02 | T | C |
| ATOM | 3781 | CG | GLU | T | 95 | 42.241 | 19.097 | 37.936 | 1.00 | 28.22 | T | C |
| ATOM | 3782 | CD | GLU | T | 95 | 43.004 | 18.024 | 37.189 | 1.00 | 30.84 | T | C |
| ATOM | 3783 | OE1 | GLU | T | 95 | 43.404 | 18.269 | 36.044 | 1.00 | 34.07 | T | O |
| ATOM | 3784 | OE2 | GLU | T | 95 | 43.205 | 16.957 | 37.753 | 1.00 | 31.49 | T | O |
| ATOM | 3785 | N | ASN | T | 96 | 39.233 | 18.084 | 36.697 | 1.00 | 15.73 | T | N |
| ATOM | 3786 | CA | ASN | T | 96 | 38.052 | 17.537 | 37.348 | 1.00 | 16.84 | T | C |
| ATOM | 3787 | C | ASN | T | 96 | 38.375 | 17.281 | 38.815 | 1.00 | 16.63 | T | C |
| ATOM | 3788 | O | ASN | T | 96 | 39.526 | 17.045 | 39.172 | 1.00 | 17.38 | T | O |
| ATOM | 3789 | CB | ASN | T | 96 | 37.623 | 16.211 | 36.703 | 1.00 | 15.17 | T | C |
| ATOM | 3790 | CG | ASN | T | 96 | 37.110 | 16.381 | 35.279 | 1.00 | 18.47 | T | C |
| ATOM | 3791 | OD1 | ASN | T | 96 | 36.458 | 17.371 | 34.957 | 1.00 | 16.54 | T | O |
| ATOM | 3792 | ND2 | ASN | T | 96 | 37.384 | 15.394 | 34.425 | 1.00 | 16.63 | T | N |
| ATOM | 3793 | N | SER | T | 97 | 37.355 | 17.335 | 39.660 | 1.00 | 15.24 | T | N |
| ATOM | 3794 | CA | SER | T | 97 | 37.523 | 17.068 | 41.082 | 1.00 | 17.45 | T | C |
| ATOM | 3795 | C | SER | T | 97 | 37.125 | 15.613 | 41.313 | 1.00 | 18.06 | T | C |
| ATOM | 3796 | O | SER | T | 97 | 36.594 | 14.958 | 40.419 | 1.00 | 18.60 | T | O |
| ATOM | 3797 | CB | SER | T | 97 | 36.575 | 17.935 | 41.893 | 1.00 | 16.21 | T | C |
| ATOM | 3798 | OG | SER | T | 97 | 35.238 | 17.519 | 41.660 | 1.00 | 15.25 | T | O |
| ATOM | 3799 | N | PRO | T | 98 | 37.402 | 15.076 | 42.508 | 1.00 | 19.40 | T | N |
| ATOM | 3800 | CA | PRO | T | 98 | 36.991 | 13.686 | 42.710 | 1.00 | 19.93 | T | C |
| ATOM | 3801 | C | PRO | T | 98 | 35.478 | 13.714 | 42.878 | 1.00 | 19.53 | T | C |
| ATOM | 3802 | O | PRO | T | 98 | 34.907 | 14.767 | 43.139 | 1.00 | 20.13 | T | O |
| ATOM | 3803 | CB | PRO | T | 98 | 37.716 | 13.289 | 43.997 | 1.00 | 22.25 | T | C |
| ATOM | 3804 | CG | PRO | T | 98 | 37.885 | 14.595 | 44.720 | 1.00 | 22.51 | T | C |
| ATOM | 3805 | CD | PRO | T | 98 | 38.269 | 15.537 | 43.606 | 1.00 | 21.78 | T | C |
| ATOM | 3806 | N | GLU | T | 99 | 34.819 | 12.579 | 42.708 | 1.00 | 19.80 | T | N |
| ATOM | 3807 | CA | GLU | T | 99 | 33.378 | 12.555 | 42.872 | 1.00 | 20.54 | T | C |
| ATOM | 3808 | C | GLU | T | 99 | 33.076 | 12.827 | 44.334 | 1.00 | 20.49 | T | C |
| ATOM | 3809 | O | GLU | T | 99 | 33.882 | 12.511 | 45.210 | 1.00 | 20.71 | T | O |
| ATOM | 3810 | CB | GLU | T | 99 | 32.819 | 11.198 | 42.464 | 1.00 | 23.90 | T | C |
| ATOM | 3811 | CG | GLU | T | 99 | 33.062 | 10.850 | 41.009 | 1.00 | 30.24 | T | C |
| ATOM | 3812 | CD | GLU | T | 99 | 32.382 | 9.561 | 40.609 | 1.00 | 34.08 | T | C |
| ATOM | 3813 | OE1 | GLU | T | 99 | 32.625 | 8.547 | 41.256 | 1.00 | 39.49 | T | O |
| ATOM | 3814 | OE2 | GLU | T | 99 | 31.619 | 9.578 | 39.661 | 1.00 | 37.57 | T | O |
| ATOM | 3815 | N | PHE | T | 100 | 31.921 | 13.422 | 44.603 | 1.00 | 19.39 | T | N |
| ATOM | 3816 | CA | PHE | T | 100 | 31.552 | 13.723 | 45.974 | 1.00 | 20.04 | T | C |
| ATOM | 3817 | C | PHE | T | 100 | 30.099 | 13.404 | 46.279 | 1.00 | 19.86 | T | C |
| ATOM | 3818 | O | PHE | T | 100 | 29.195 | 13.977 | 45.684 | 1.00 | 22.07 | T | O |
| ATOM | 3819 | CB | PHE | T | 100 | 31.810 | 15.202 | 46.285 | 1.00 | 18.94 | T | C |
| ATOM | 3820 | CG | PHE | T | 100 | 31.554 | 15.570 | 47.721 | 1.00 | 17.26 | T | C |
| ATOM | 3821 | CD1 | PHE | T | 100 | 32.348 | 15.051 | 48.734 | 1.00 | 17.16 | T | C |
| ATOM | 3822 | CD2 | PHE | T | 100 | 30.506 | 16.417 | 48.063 | 1.00 | 17.80 | T | C |
| ATOM | 3823 | CE1 | PHE | T | 100 | 32.102 | 15.369 | 50.072 | 1.00 | 18.82 | T | C |
| ATOM | 3824 | CE2 | PHE | T | 100 | 30.252 | 16.739 | 49.402 | 1.00 | 18.00 | T | C |
| ATOM | 3825 | CZ | PHE | T | 100 | 31.053 | 16.212 | 50.405 | 1.00 | 14.11 | T | C |
| ATOM | 3826 | N | THR | T | 101 | 29.880 | 12.486 | 47.213 | 1.00 | 19.96 | T | N |
| ATOM | 3827 | CA | THR | T | 101 | 28.529 | 12.125 | 47.618 | 1.00 | 19.19 | T | C |
| ATOM | 3828 | C | THR | T | 101 | 28.359 | 12.669 | 49.032 | 1.00 | 19.73 | T | C |
| ATOM | 3829 | O | THR | T | 101 | 28.774 | 12.041 | 50.005 | 1.00 | 19.00 | T | O |
| ATOM | 3830 | CB | THR | T | 101 | 28.339 | 10.602 | 47.616 | 1.00 | 19.88 | T | C |
| ATOM | 3831 | OG1 | THR | T | 101 | 28.767 | 10.075 | 46.353 | 1.00 | 19.78 | T | O |

-continued

| | | | | | | | | | | | |
|---|---|---|---|---|---|---|---|---|---|---|---|
| ATOM | 3832 | CG2 | THR | T | 101 | 26.869 | 10.252 | 47.842 | 1.00 | 16.06 | T | C |
| ATOM | 3833 | N | PRO | T | 102 | 27.740 | 13.851 | 49.159 | 1.00 | 20.90 | T | N |
| ATOM | 3834 | CA | PRO | T | 102 | 27.512 | 14.514 | 50.450 | 1.00 | 20.65 | T | C |
| ATOM | 3835 | C | PRO | T | 102 | 27.112 | 13.595 | 51.599 | 1.00 | 21.85 | T | C |
| ATOM | 3836 | O | PRO | T | 102 | 27.826 | 13.483 | 52.594 | 1.00 | 22.55 | T | O |
| ATOM | 3837 | CB | PRO | T | 102 | 26.426 | 15.539 | 50.126 | 1.00 | 20.56 | T | C |
| ATOM | 3838 | CG | PRO | T | 102 | 26.710 | 15.892 | 48.691 | 1.00 | 19.84 | T | C |
| ATOM | 3839 | CD | PRO | T | 102 | 27.008 | 14.540 | 48.079 | 1.00 | 20.33 | T | C |
| ATOM | 3840 | N | TYR | T | 103 | 25.964 | 12.946 | 51.458 | 1.00 | 21.87 | T | N |
| ATOM | 3841 | CA | TYR | T | 103 | 25.441 | 12.050 | 52.484 | 1.00 | 22.45 | T | C |
| ATOM | 3842 | C | TYR | T | 103 | 26.464 | 11.034 | 53.003 | 1.00 | 22.95 | T | C |
| ATOM | 3843 | O | TYR | T | 103 | 26.534 | 10.774 | 54.200 | 1.00 | 23.24 | T | O |
| ATOM | 3844 | CB | TYR | T | 103 | 24.222 | 11.308 | 51.936 | 1.00 | 23.18 | T | C |
| ATOM | 3845 | CG | TYR | T | 103 | 23.404 | 10.588 | 52.983 | 1.00 | 23.57 | T | C |
| ATOM | 3846 | CD1 | TYR | T | 103 | 22.458 | 11.272 | 53.747 | 1.00 | 23.47 | T | C |
| ATOM | 3847 | CD2 | TYR | T | 103 | 23.559 | 9.220 | 53.197 | 1.00 | 22.61 | T | C |
| ATOM | 3848 | CE1 | TYR | T | 103 | 21.684 | 10.612 | 54.693 | 1.00 | 23.51 | T | C |
| ATOM | 3849 | CE2 | TYR | T | 103 | 22.785 | 8.548 | 54.145 | 1.00 | 23.64 | T | C |
| ATOM | 3850 | CZ | TYR | T | 103 | 21.852 | 9.251 | 54.885 | 1.00 | 23.20 | T | C |
| ATOM | 3851 | OH | TYR | T | 103 | 21.089 | 8.602 | 55.824 | 1.00 | 24.87 | T | O |
| ATOM | 3852 | N | LEU | T | 104 | 27.256 | 10.465 | 52.101 | 1.00 | 23.67 | T | N |
| ATOM | 3853 | CA | LEU | T | 104 | 28.250 | 9.468 | 52.474 | 1.00 | 22.89 | T | C |
| ATOM | 3854 | C | LEU | T | 104 | 29.579 | 10.006 | 53.000 | 1.00 | 23.88 | T | C |
| ATOM | 3855 | O | LEU | T | 104 | 30.272 | 9.307 | 53.743 | 1.00 | 23.44 | T | O |
| ATOM | 3856 | CB | LEU | T | 104 | 28.546 | 8.550 | 51.285 | 1.00 | 22.13 | T | C |
| ATOM | 3857 | CG | LEU | T | 104 | 27.414 | 7.715 | 50.680 | 1.00 | 23.01 | T | C |
| ATOM | 3858 | CD1 | LEU | T | 104 | 27.973 | 6.885 | 49.531 | 1.00 | 20.25 | T | C |
| ATOM | 3859 | CD2 | LEU | T | 104 | 26.797 | 6.808 | 51.747 | 1.00 | 20.91 | T | C |
| ATOM | 3860 | N | GLU | T | 105 | 29.957 | 11.225 | 52.627 | 1.00 | 23.91 | T | N |
| ATOM | 3861 | CA | GLU | T | 105 | 31.243 | 11.733 | 53.092 | 1.00 | 25.61 | T | C |
| ATOM | 3862 | C | GLU | T | 105 | 31.364 | 13.110 | 53.752 | 1.00 | 24.53 | T | C |
| ATOM | 3863 | O | GLU | T | 105 | 32.473 | 13.529 | 54.080 | 1.00 | 24.54 | T | O |
| ATOM | 3864 | CB | GLU | T | 105 | 32.281 | 11.599 | 51.967 | 1.00 | 26.37 | T | C |
| ATOM | 3865 | CG | GLU | T | 105 | 31.867 | 12.121 | 50.611 | 1.00 | 28.41 | T | C |
| ATOM | 3866 | CD | GLU | T | 105 | 32.602 | 11.421 | 49.471 | 1.00 | 27.99 | T | C |
| ATOM | 3867 | OE1 | GLU | T | 105 | 33.821 | 11.326 | 49.516 | 1.00 | 27.95 | T | O |
| ATOM | 3868 | OE2 | GLU | T | 105 | 31.950 | 10.979 | 48.543 | 1.00 | 27.09 | T | O |
| ATOM | 3869 | N | THR | T | 106 | 30.258 | 13.813 | 53.973 | 1.00 | 23.46 | T | N |
| ATOM | 3870 | CA | THR | T | 106 | 30.367 | 15.112 | 54.632 | 1.00 | 22.92 | T | C |
| ATOM | 3871 | C | THR | T | 106 | 30.738 | 14.856 | 56.091 | 1.00 | 24.04 | T | C |
| ATOM | 3872 | O | THR | T | 106 | 30.143 | 14.002 | 56.752 | 1.00 | 22.58 | T | O |
| ATOM | 3873 | CB | THR | T | 106 | 29.052 | 15.919 | 54.586 | 1.00 | 21.63 | T | C |
| ATOM | 3874 | OG1 | THR | T | 106 | 29.308 | 17.265 | 55.010 | 1.00 | 21.19 | T | O |
| ATOM | 3875 | CG2 | THR | T | 106 | 28.009 | 15.312 | 55.506 | 1.00 | 21.52 | T | C |
| ATOM | 3876 | N | ASN | T | 107 | 31.728 | 15.587 | 56.588 | 1.00 | 22.90 | T | N |
| ATOM | 3877 | CA | ASN | T | 107 | 32.171 | 15.417 | 57.965 | 1.00 | 24.07 | T | C |
| ATOM | 3878 | C | ASN | T | 107 | 31.108 | 15.795 | 58.978 | 1.00 | 24.33 | T | C |
| ATOM | 3879 | O | ASN | T | 107 | 30.380 | 16.773 | 58.799 | 1.00 | 24.71 | T | O |
| ATOM | 3880 | CB | ASN | T | 107 | 33.424 | 16.252 | 58.232 | 1.00 | 24.30 | T | C |
| ATOM | 3881 | CG | ASN | T | 107 | 34.633 | 15.725 | 57.507 | 1.00 | 25.25 | T | C |
| ATOM | 3882 | OD1 | ASN | T | 107 | 35.037 | 14.582 | 57.707 | 1.00 | 29.41 | T | O |
| ATOM | 3883 | ND2 | ASN | T | 107 | 35.223 | 16.553 | 56.657 | 1.00 | 28.39 | T | N |
| ATOM | 3884 | N | LEU | T | 108 | 31.017 | 15.006 | 60.041 | 1.00 | 24.30 | T | N |
| ATOM | 3885 | CA | LEU | T | 108 | 30.068 | 15.279 | 61.110 | 1.00 | 24.22 | T | C |
| ATOM | 3886 | C | LEU | T | 108 | 30.744 | 16.309 | 62.007 | 1.00 | 22.82 | T | C |
| ATOM | 3887 | O | LEU | T | 108 | 31.870 | 16.105 | 62.452 | 1.00 | 21.51 | T | O |
| ATOM | 3888 | CB | LEU | T | 108 | 29.772 | 13.998 | 61.890 | 1.00 | 25.35 | T | C |
| ATOM | 3889 | CG | LEU | T | 108 | 29.094 | 12.904 | 61.062 | 1.00 | 27.74 | T | C |
| ATOM | 3890 | CD1 | LEU | T | 108 | 29.156 | 11.562 | 61.786 | 1.00 | 27.60 | T | C |
| ATOM | 3891 | CD2 | LEU | T | 108 | 27.659 | 13.318 | 60.786 | 1.00 | 28.49 | T | C |
| ATOM | 3892 | N | GLY | T | 109 | 30.066 | 17.425 | 62.252 | 1.00 | 23.68 | T | N |
| ATOM | 3893 | CA | GLY | T | 109 | 30.648 | 18.461 | 63.084 | 1.00 | 22.92 | T | C |
| ATOM | 3894 | C | GLY | T | 109 | 30.829 | 18.004 | 64.520 | 1.00 | 23.12 | T | C |
| ATOM | 3895 | O | GLY | T | 109 | 30.240 | 17.003 | 64.927 | 1.00 | 21.62 | T | O |
| ATOM | 3896 | N | GLN | T | 110 | 31.656 | 18.718 | 65.281 | 1.00 | 21.54 | T | N |
| ATOM | 3897 | CA | GLN | T | 110 | 31.869 | 18.378 | 66.683 | 1.00 | 21.94 | T | C |
| ATOM | 3898 | C | GLN | T | 110 | 30.527 | 18.570 | 67.381 | 1.00 | 21.65 | T | C |
| ATOM | 3899 | O | GLN | T | 110 | 29.916 | 19.630 | 67.276 | 1.00 | 21.94 | T | O |
| ATOM | 3900 | CB | GLN | T | 110 | 32.919 | 19.304 | 67.313 | 1.00 | 21.36 | T | C |
| ATOM | 3901 | CG | GLN | T | 110 | 33.166 | 19.045 | 68.802 | 1.00 | 21.01 | T | C |
| ATOM | 3902 | CD | GLN | T | 110 | 34.203 | 19.979 | 69.398 | 1.00 | 21.94 | T | C |
| ATOM | 3903 | OE1 | GLN | T | 110 | 34.139 | 21.189 | 69.207 | 1.00 | 24.10 | T | O |
| ATOM | 3904 | NE2 | GLN | T | 110 | 35.162 | 19.419 | 70.132 | 1.00 | 21.56 | T | N |
| ATOM | 3905 | N | PRO | T | 111 | 30.045 | 17.542 | 68.094 | 1.00 | 23.09 | T | N |
| ATOM | 3906 | CA | PRO | T | 111 | 28.762 | 17.651 | 68.790 | 1.00 | 22.88 | T | C |
| ATOM | 3907 | C | PRO | T | 111 | 28.920 | 18.496 | 70.043 | 1.00 | 24.37 | T | C |
| ATOM | 3908 | O | PRO | T | 111 | 30.032 | 18.876 | 70.408 | 1.00 | 24.44 | T | O |
| ATOM | 3909 | CB | PRO | T | 111 | 28.418 | 16.198 | 69.141 | 1.00 | 23.56 | T | C |
| ATOM | 3910 | CG | PRO | T | 111 | 29.425 | 15.358 | 68.352 | 1.00 | 23.39 | T | C |

|      |      |     |     |   |     |        |        |        |      |       |   |   |
|------|------|-----|-----|---|-----|--------|--------|--------|------|-------|---|---|
| ATOM | 3911 | CD  | PRO | T | 111 | 30.641 | 16.217 | 68.322 | 1.00 | 22.94 | T | C |
| ATOM | 3912 | N   | THR | T | 112 | 27.797 | 18.769 | 70.697 | 1.00 | 25.07 | T | N |
| ATOM | 3913 | CA  | THR | T | 112 | 27.762 | 19.552 | 71.918 | 1.00 | 25.43 | T | C |
| ATOM | 3914 | C   | THR | T | 112 | 26.764 | 18.915 | 72.880 | 1.00 | 26.70 | T | C |
| ATOM | 3915 | O   | THR | T | 112 | 25.616 | 18.681 | 72.512 | 1.00 | 26.69 | T | O |
| ATOM | 3916 | CB  | THR | T | 112 | 27.295 | 21.001 | 71.645 | 1.00 | 27.11 | T | C |
| ATOM | 3917 | OG1 | THR | T | 112 | 28.261 | 21.673 | 70.830 | 1.00 | 29.22 | T | O |
| ATOM | 3918 | CG2 | THR | T | 112 | 27.114 | 21.765 | 72.955 | 1.00 | 26.39 | T | C |
| ATOM | 3919 | N   | ILE | T | 113 | 27.202 | 18.626 | 74.102 | 1.00 | 26.55 | T | N |
| ATOM | 3920 | CA  | ILE | T | 113 | 26.314 | 18.057 | 75.111 | 1.00 | 27.02 | T | C |
| ATOM | 3921 | C   | ILE | T | 113 | 25.371 | 19.181 | 75.536 | 1.00 | 28.66 | T | C |
| ATOM | 3922 | O   | ILE | T | 113 | 25.811 | 20.228 | 76.010 | 1.00 | 29.26 | T | O |
| ATOM | 3923 | CB  | ILE | T | 113 | 27.117 | 17.541 | 76.337 | 1.00 | 26.73 | T | C |
| ATOM | 3924 | CG1 | ILE | T | 113 | 27.926 | 16.305 | 75.935 | 1.00 | 24.38 | T | C |
| ATOM | 3925 | CG2 | ILE | T | 113 | 26.179 | 17.208 | 77.490 | 1.00 | 25.10 | T | C |
| ATOM | 3926 | CD1 | ILE | T | 113 | 28.821 | 15.766 | 77.021 | 1.00 | 27.02 | T | C |
| ATOM | 3927 | N   | GLN | T | 114 | 24.073 | 18.967 | 75.347 | 1.00 | 30.54 | T | N |
| ATOM | 3928 | CA  | GLN | T | 114 | 23.069 | 19.967 | 75.690 | 1.00 | 31.98 | T | C |
| ATOM | 3929 | C   | GLN | T | 114 | 22.772 | 20.033 | 77.185 | 1.00 | 33.02 | T | C |
| ATOM | 3930 | O   | GLN | T | 114 | 22.588 | 21.119 | 77.739 | 1.00 | 33.20 | T | O |
| ATOM | 3931 | CB  | GLN | T | 114 | 21.773 | 19.688 | 74.926 | 1.00 | 32.72 | T | C |
| ATOM | 3932 | CG  | GLN | T | 114 | 20.714 | 20.773 | 75.070 | 1.00 | 34.48 | T | C |
| ATOM | 3933 | CD  | GLN | T | 114 | 19.499 | 20.516 | 74.199 | 1.00 | 36.97 | T | C |
| ATOM | 3934 | OE1 | GLN | T | 114 | 18.648 | 19.686 | 74.523 | 1.00 | 39.79 | T | O |
| ATOM | 3935 | NE2 | GLN | T | 114 | 19.421 | 21.218 | 73.077 | 1.00 | 37.84 | T | N |
| ATOM | 3936 | N   | SER | T | 115 | 22.721 | 18.873 | 77.833 | 1.00 | 34.02 | T | N |
| ATOM | 3937 | CA  | SER | T | 115 | 22.442 | 18.810 | 79.262 | 1.00 | 34.71 | T | C |
| ATOM | 3938 | C   | SER | T | 115 | 22.528 | 17.392 | 79.811 | 1.00 | 36.31 | T | C |
| ATOM | 3939 | O   | SER | T | 115 | 22.729 | 16.429 | 79.072 | 1.00 | 34.54 | T | O |
| ATOM | 3940 | CB  | SER | T | 115 | 21.041 | 19.350 | 79.544 | 1.00 | 34.16 | T | C |
| ATOM | 3941 | OG  | SER | T | 115 | 20.056 | 18.493 | 78.989 | 1.00 | 34.47 | T | O |
| ATOM | 3942 | N   | PHE | T | 116 | 22.384 | 17.286 | 81.126 | 1.00 | 39.39 | T | N |
| ATOM | 3943 | CA  | PHE | T | 116 | 22.391 | 16.006 | 81.814 | 1.00 | 43.50 | T | C |
| ATOM | 3944 | C   | PHE | T | 116 | 21.700 | 16.155 | 83.160 | 1.00 | 45.33 | T | C |
| ATOM | 3945 | O   | PHE | T | 116 | 22.130 | 16.930 | 84.013 | 1.00 | 46.10 | T | O |
| ATOM | 3946 | CB  | PHE | T | 116 | 23.816 | 15.449 | 81.990 | 1.00 | 43.81 | T | C |
| ATOM | 3947 | CG  | PHE | T | 116 | 24.829 | 16.456 | 82.449 | 1.00 | 44.31 | T | C |
| ATOM | 3948 | CD1 | PHE | T | 116 | 25.669 | 17.079 | 81.532 | 1.00 | 46.06 | T | C |
| ATOM | 3949 | CD2 | PHE | T | 116 | 24.976 | 16.753 | 83.797 | 1.00 | 45.66 | T | C |
| ATOM | 3950 | CE1 | PHE | T | 116 | 26.643 | 17.977 | 81.949 | 1.00 | 45.84 | T | C |
| ATOM | 3951 | CE2 | PHE | T | 116 | 25.946 | 17.651 | 84.227 | 1.00 | 46.21 | T | C |
| ATOM | 3952 | CZ  | PHE | T | 116 | 26.783 | 18.264 | 83.299 | 1.00 | 47.39 | T | C |
| ATOM | 3953 | N   | GLU | T | 117 | 20.609 | 15.416 | 83.331 | 1.00 | 47.44 | T | N |
| ATOM | 3954 | CA  | GLU | T | 117 | 19.832 | 15.465 | 84.561 | 1.00 | 50.33 | T | C |
| ATOM | 3955 | C   | GLU | T | 117 | 19.909 | 14.160 | 85.340 | 1.00 | 51.09 | T | C |
| ATOM | 3956 | O   | GLU | T | 117 | 19.858 | 13.073 | 84.765 | 1.00 | 50.21 | T | O |
| ATOM | 3957 | CB  | GLU | T | 117 | 18.368 | 15.770 | 84.239 | 1.00 | 52.68 | T | C |
| ATOM | 3958 | CG  | GLU | T | 117 | 17.499 | 16.012 | 85.462 | 1.00 | 54.67 | T | C |
| ATOM | 3959 | CD  | GLU | T | 117 | 16.035 | 16.159 | 85.114 | 1.00 | 56.19 | T | C |
| ATOM | 3960 | OE1 | GLU | T | 117 | 15.263 | 16.548 | 85.987 | 1.00 | 58.48 | T | O |
| ATOM | 3961 | OE2 | GLU | T | 117 | 15.671 | 15.878 | 83.971 | 1.00 | 57.72 | T | O |
| ATOM | 3962 | N   | GLN | T | 118 | 20.026 | 14.278 | 86.657 | 1.00 | 52.53 | T | N |
| ATOM | 3963 | CA  | GLN | T | 118 | 20.091 | 13.113 | 87.524 | 1.00 | 53.52 | T | C |
| ATOM | 3964 | C   | GLN | T | 118 | 18.790 | 12.987 | 88.307 | 1.00 | 53.74 | T | C |
| ATOM | 3965 | O   | GLN | T | 118 | 18.292 | 13.967 | 88.863 | 1.00 | 52.43 | T | O |
| ATOM | 3966 | CB  | GLN | T | 118 | 21.268 | 13.237 | 88.495 | 1.00 | 55.69 | T | C |
| ATOM | 3967 | CG  | GLN | T | 118 | 21.248 | 14.505 | 89.345 | 1.00 | 58.28 | T | C |
| ATOM | 3968 | CD  | GLN | T | 118 | 22.398 | 14.581 | 90.341 | 1.00 | 59.98 | T | C |
| ATOM | 3969 | OE1 | GLN | T | 118 | 22.559 | 15.585 | 91.038 | 1.00 | 60.49 | T | O |
| ATOM | 3970 | NE2 | GLN | T | 118 | 23.198 | 13.520 | 90.417 | 1.00 | 59.89 | T | N |
| ATOM | 3971 | N   | VAL | T | 119 | 18.236 | 11.780 | 88.336 | 1.00 | 54.32 | T | N |
| ATOM | 3972 | CA  | VAL | T | 119 | 16.999 | 11.527 | 89.064 | 1.00 | 55.20 | T | C |
| ATOM | 3973 | C   | VAL | T | 119 | 17.342 | 10.874 | 90.400 | 1.00 | 55.28 | T | C |
| ATOM | 3974 | O   | VAL | T | 119 | 17.050 | 11.421 | 91.465 | 1.00 | 55.61 | T | O |
| ATOM | 3975 | CB  | VAL | T | 119 | 16.056 | 10.592 | 88.270 | 1.00 | 55.27 | T | C |
| ATOM | 3976 | CG1 | VAL | T | 119 | 14.808 | 10.294 | 89.089 | 1.00 | 55.95 | T | C |
| ATOM | 3977 | CG2 | VAL | T | 119 | 15.675 | 11.239 | 86.948 | 1.00 | 55.25 | T | C |
| ATOM | 3978 | N   | GLY | T | 120 | 17.968 | 9.705  | 90.330 | 1.00 | 54.96 | T | N |
| ATOM | 3979 | CA  | GLY | T | 120 | 18.357 | 8.992  | 91.531 | 1.00 | 55.01 | T | C |
| ATOM | 3980 | C   | GLY | T | 120 | 19.681 | 8.294  | 91.305 | 1.00 | 55.06 | T | C |
| ATOM | 3981 | O   | GLY | T | 120 | 20.739 | 8.802  | 91.681 | 1.00 | 54.95 | T | O |
| ATOM | 3982 | N   | THR | T | 121 | 19.622 | 7.124  | 90.680 | 1.00 | 54.66 | T | N |
| ATOM | 3983 | CA  | THR | T | 121 | 20.824 | 6.356  | 90.388 | 1.00 | 54.74 | T | C |
| ATOM | 3984 | C   | THR | T | 121 | 21.039 | 6.232  | 88.876 | 1.00 | 53.59 | T | C |
| ATOM | 3985 | O   | THR | T | 121 | 21.706 | 5.311  | 88.406 | 1.00 | 53.56 | T | O |
| ATOM | 3986 | CB  | THR | T | 121 | 20.743 | 4.945  | 91.010 | 1.00 | 55.32 | T | C |
| ATOM | 3987 | OG1 | THR | T | 121 | 21.985 | 4.259  | 90.805 | 1.00 | 56.26 | T | O |
| ATOM | 3988 | CG2 | THR | T | 121 | 19.607 | 4.145  | 90.379 | 1.00 | 55.25 | T | C |
| ATOM | 3989 | N   | LYS | T | 122 | 20.474 | 7.171  | 88.122 | 1.00 | 52.48 | T | N |

-continued

| | | | | | | | | | | |
|---|---|---|---|---|---|---|---|---|---|---|
| ATOM | 3990 | CA | LYS | T | 122 | 20.599 | 7.178 | 86.669 | 1.00 | 51.79 | T | C |
| ATOM | 3991 | C | LYS | T | 122 | 20.720 | 8.611 | 86.155 | 1.00 | 50.74 | T | C |
| ATOM | 3992 | O | LYS | T | 122 | 20.121 | 9.532 | 86.713 | 1.00 | 50.69 | T | O |
| ATOM | 3993 | CB | LYS | T | 122 | 19.385 | 6.493 | 86.038 | 1.00 | 52.21 | T | C |
| ATOM | 3994 | CG | LYS | T | 122 | 19.206 | 5.042 | 86.475 | 1.00 | 53.53 | T | C |
| ATOM | 3995 | CD | LYS | T | 122 | 17.813 | 4.797 | 87.036 | 1.00 | 55.85 | T | C |
| ATOM | 3996 | CE | LYS | T | 122 | 17.508 | 5.721 | 88.216 | 1.00 | 57.36 | T | C |
| ATOM | 3997 | NZ | LYS | T | 122 | 16.108 | 5.599 | 88.713 | 1.00 | 55.80 | T | N |
| ATOM | 3998 | N | VAL | T | 123 | 21.498 | 8.792 | 85.091 | 1.00 | 48.62 | T | N |
| ATOM | 3999 | CA | VAL | T | 123 | 21.712 | 10.111 | 84.504 | 1.00 | 46.58 | T | C |
| ATOM | 4000 | C | VAL | T | 123 | 21.280 | 10.170 | 83.040 | 1.00 | 44.65 | T | C |
| ATOM | 4001 | O | VAL | T | 123 | 21.533 | 9.248 | 82.267 | 1.00 | 45.12 | T | O |
| ATOM | 4002 | CB | VAL | T | 123 | 23.207 | 10.519 | 84.597 | 1.00 | 46.69 | T | C |
| ATOM | 4003 | CG1 | VAL | T | 123 | 23.439 | 11.859 | 83.907 | 1.00 | 46.11 | T | C |
| ATOM | 4004 | CG2 | VAL | T | 123 | 23.630 | 10.599 | 86.055 | 1.00 | 46.67 | T | C |
| ATOM | 4005 | N | ASN | T | 124 | 20.622 | 11.261 | 82.670 | 1.00 | 42.65 | T | N |
| ATOM | 4006 | CA | ASN | T | 124 | 20.171 | 11.456 | 81.301 | 1.00 | 41.30 | T | C |
| ATOM | 4007 | C | ASN | T | 124 | 21.069 | 12.470 | 80.604 | 1.00 | 38.83 | T | C |
| ATOM | 4008 | O | ASN | T | 124 | 21.026 | 13.655 | 80.915 | 1.00 | 38.66 | T | O |
| ATOM | 4009 | CB | ASN | T | 124 | 18.725 | 11.957 | 81.282 | 1.00 | 42.92 | T | C |
| ATOM | 4010 | CG | ASN | T | 124 | 18.287 | 12.420 | 79.904 | 1.00 | 45.20 | T | C |
| ATOM | 4011 | OD1 | ASN | T | 124 | 18.444 | 11.703 | 78.917 | 1.00 | 47.86 | T | O |
| ATOM | 4012 | ND2 | ASN | T | 124 | 17.728 | 13.623 | 79.833 | 1.00 | 46.71 | T | N |
| ATOM | 4013 | N | VAL | T | 125 | 21.892 | 11.999 | 79.674 | 1.00 | 35.58 | T | N |
| ATOM | 4014 | CA | VAL | T | 125 | 22.779 | 12.890 | 78.934 | 1.00 | 34.22 | T | C |
| ATOM | 4015 | C | VAL | T | 125 | 22.150 | 13.178 | 77.576 | 1.00 | 32.94 | T | C |
| ATOM | 4016 | O | VAL | T | 125 | 21.938 | 12.273 | 76.776 | 1.00 | 32.50 | T | O |
| ATOM | 4017 | CB | VAL | T | 125 | 24.180 | 12.264 | 78.723 | 1.00 | 33.64 | T | C |
| ATOM | 4018 | CG1 | VAL | T | 125 | 25.051 | 13.205 | 77.897 | 1.00 | 33.24 | T | C |
| ATOM | 4019 | CG2 | VAL | T | 125 | 24.840 | 11.994 | 80.069 | 1.00 | 31.46 | T | C |
| ATOM | 4020 | N | THR | T | 126 | 21.835 | 14.442 | 77.332 | 1.00 | 31.93 | T | N |
| ATOM | 4021 | CA | THR | T | 126 | 21.225 | 14.847 | 76.078 | 1.00 | 31.44 | T | C |
| ATOM | 4022 | C | THR | T | 126 | 22.246 | 15.541 | 75.181 | 1.00 | 30.53 | T | C |
| ATOM | 4023 | O | THR | T | 126 | 22.995 | 16.406 | 75.631 | 1.00 | 30.92 | T | O |
| ATOM | 4024 | CB | THR | T | 126 | 20.035 | 15.801 | 76.333 | 1.00 | 32.80 | T | C |
| ATOM | 4025 | OG1 | THR | T | 126 | 19.046 | 15.126 | 77.123 | 1.00 | 34.45 | T | O |
| ATOM | 4026 | CG2 | THR | T | 126 | 19.404 | 16.248 | 75.018 | 1.00 | 33.11 | T | C |
| ATOM | 4027 | N | VAL | T | 127 | 22.273 | 15.144 | 73.915 | 1.00 | 28.54 | T | N |
| ATOM | 4028 | CA | VAL | T | 127 | 23.181 | 15.720 | 72.931 | 1.00 | 28.68 | T | C |
| ATOM | 4029 | C | VAL | T | 127 | 22.381 | 16.700 | 72.074 | 1.00 | 29.29 | T | C |
| ATOM | 4030 | O | VAL | T | 127 | 21.293 | 16.376 | 71.596 | 1.00 | 28.57 | T | O |
| ATOM | 4031 | CB | VAL | T | 127 | 23.776 | 14.631 | 72.009 | 1.00 | 27.25 | T | C |
| ATOM | 4032 | CG1 | VAL | T | 127 | 24.740 | 15.260 | 71.013 | 1.00 | 28.11 | T | C |
| ATOM | 4033 | CG2 | VAL | T | 127 | 24.478 | 13.567 | 72.837 | 1.00 | 26.10 | T | C |
| ATOM | 4034 | N | GLU | T | 128 | 22.923 | 17.896 | 71.880 | 1.00 | 30.12 | T | N |
| ATOM | 4035 | CA | GLU | T | 128 | 22.248 | 18.920 | 71.094 | 1.00 | 32.79 | T | C |
| ATOM | 4036 | C | GLU | T | 128 | 22.060 | 18.489 | 69.642 | 1.00 | 33.25 | T | C |
| ATOM | 4037 | O | GLU | T | 128 | 23.005 | 18.051 | 68.987 | 1.00 | 32.52 | T | O |
| ATOM | 4038 | CB | GLU | T | 128 | 23.049 | 20.222 | 71.146 | 1.00 | 35.07 | T | C |
| ATOM | 4039 | CG | GLU | T | 128 | 22.327 | 21.419 | 70.558 | 1.00 | 39.25 | T | C |
| ATOM | 4040 | CD | GLU | T | 128 | 23.162 | 22.681 | 70.624 | 1.00 | 42.60 | T | C |
| ATOM | 4041 | OE1 | GLU | T | 128 | 24.132 | 22.785 | 69.872 | 1.00 | 42.38 | T | O |
| ATOM | 4042 | OE2 | GLU | T | 128 | 22.842 | 23.549 | 71.436 | 1.00 | 44.49 | T | O |
| ATOM | 4043 | N | ASP | T | 129 | 20.834 | 18.602 | 69.146 | 1.00 | 34.87 | T | N |
| ATOM | 4044 | CA | ASP | T | 129 | 20.543 | 18.234 | 67.765 | 1.00 | 38.67 | T | C |
| ATOM | 4045 | C | ASP | T | 129 | 21.016 | 19.404 | 66.908 | 1.00 | 39.15 | T | C |
| ATOM | 4046 | O | ASP | T | 129 | 20.271 | 20.355 | 66.684 | 1.00 | 40.95 | T | O |
| ATOM | 4047 | CB | ASP | T | 129 | 19.038 | 18.020 | 67.571 | 1.00 | 41.05 | T | C |
| ATOM | 4048 | CG | ASP | T | 129 | 18.721 | 17.167 | 66.354 | 1.00 | 44.26 | T | C |
| ATOM | 4049 | OD1 | ASP | T | 129 | 19.421 | 17.291 | 65.355 | 1.00 | 45.06 | T | O |
| ATOM | 4050 | OD2 | ASP | T | 129 | 17.768 | 16.387 | 66.411 | 1.00 | 46.55 | T | O |
| ATOM | 4051 | N | GLU | T | 130 | 22.259 | 19.328 | 66.442 | 1.00 | 39.21 | T | N |
| ATOM | 4052 | CA | GLU | T | 130 | 22.859 | 20.388 | 65.639 | 1.00 | 39.23 | T | C |
| ATOM | 4053 | C | GLU | T | 130 | 22.242 | 20.531 | 64.257 | 1.00 | 37.36 | T | C |
| ATOM | 4054 | O | GLU | T | 130 | 21.867 | 19.548 | 63.627 | 1.00 | 35.82 | T | O |
| ATOM | 4055 | CB | GLU | T | 130 | 24.362 | 20.145 | 65.485 | 1.00 | 43.16 | T | C |
| ATOM | 4056 | CG | GLU | T | 130 | 25.175 | 21.419 | 65.294 | 1.00 | 46.75 | T | C |
| ATOM | 4057 | CD | GLU | T | 130 | 26.607 | 21.139 | 64.891 | 1.00 | 48.44 | T | C |
| ATOM | 4058 | OE1 | GLU | T | 130 | 26.819 | 20.722 | 63.766 | 1.00 | 52.82 | T | O |
| ATOM | 4059 | OE2 | GLU | T | 130 | 27.496 | 21.331 | 65.701 | 1.00 | 49.66 | T | O |
| ATOM | 4060 | N | ARG | T | 131 | 22.151 | 21.768 | 63.785 | 1.00 | 36.07 | T | N |
| ATOM | 4061 | CA | ARG | T | 131 | 21.590 | 22.024 | 62.473 | 1.00 | 34.72 | T | C |
| ATOM | 4062 | C | ARG | T | 131 | 22.631 | 21.836 | 61.377 | 1.00 | 32.32 | T | C |
| ATOM | 4063 | O | ARG | T | 131 | 23.838 | 21.925 | 61.612 | 1.00 | 30.97 | T | O |
| ATOM | 4064 | CB | ARG | T | 131 | 21.000 | 23.436 | 62.402 | 1.00 | 37.34 | T | C |
| ATOM | 4065 | CG | ARG | T | 131 | 21.948 | 24.547 | 62.807 | 1.00 | 41.83 | T | C |
| ATOM | 4066 | CD | ARG | T | 131 | 21.330 | 25.901 | 62.509 | 1.00 | 43.91 | T | C |
| ATOM | 4067 | NE | ARG | T | 131 | 22.022 | 26.999 | 63.178 | 1.00 | 45.56 | T | N |
| ATOM | 4068 | CZ | ARG | T | 131 | 21.691 | 28.280 | 63.048 | 1.00 | 45.22 | T | C |

-continued

| | | | | | | | | | | | |
|---|---|---|---|---|---|---|---|---|---|---|---|
| ATOM | 4069 | NH1 | ARG | T | 131 | 20.679 | 28.634 | 62.265 | 1.00 | 44.75 | T | N |
| ATOM | 4070 | NH2 | ARG | T | 131 | 22.362 | 29.208 | 63.715 | 1.00 | 46.22 | T | N |
| ATOM | 4071 | N | THR | T | 132 | 22.141 | 21.556 | 60.177 | 1.00 | 29.36 | T | N |
| ATOM | 4072 | CA | THR | T | 132 | 22.989 | 21.343 | 59.013 | 1.00 | 25.98 | T | C |
| ATOM | 4073 | C | THR | T | 132 | 22.664 | 22.438 | 58.008 | 1.00 | 26.04 | T | C |
| ATOM | 4074 | O | THR | T | 132 | 21.750 | 23.236 | 58.220 | 1.00 | 25.67 | T | O |
| ATOM | 4075 | CB | THR | T | 132 | 22.689 | 19.986 | 58.351 | 1.00 | 24.12 | T | C |
| ATOM | 4076 | OG1 | THR | T | 132 | 21.425 | 20.061 | 57.680 | 1.00 | 19.80 | T | O |
| ATOM | 4077 | CG2 | THR | T | 132 | 22.621 | 18.874 | 59.403 | 1.00 | 22.09 | T | C |
| ATOM | 4078 | N | LEU | T | 133 | 23.410 | 22.471 | 56.912 | 1.00 | 26.23 | T | N |
| ATOM | 4079 | CA | LEU | T | 133 | 23.181 | 23.459 | 55.867 | 1.00 | 28.66 | T | C |
| ATOM | 4080 | C | LEU | T | 133 | 22.060 | 23.029 | 54.922 | 1.00 | 31.07 | T | C |
| ATOM | 4081 | O | LEU | T | 133 | 21.664 | 23.788 | 54.038 | 1.00 | 31.66 | T | O |
| ATOM | 4082 | CB | LEU | T | 133 | 24.466 | 23.700 | 55.069 | 1.00 | 25.94 | T | C |
| ATOM | 4083 | CG | LEU | T | 133 | 25.457 | 24.719 | 55.645 | 1.00 | 24.82 | T | C |
| ATOM | 4084 | CD1 | LEU | T | 133 | 24.818 | 26.095 | 55.618 | 1.00 | 23.33 | T | C |
| ATOM | 4085 | CD2 | LEU | T | 133 | 25.873 | 24.336 | 57.068 | 1.00 | 23.50 | T | C |
| ATOM | 4086 | N | VAL | T | 134 | 21.553 | 21.812 | 55.104 | 1.00 | 32.72 | T | N |
| ATOM | 4087 | CA | VAL | T | 134 | 20.475 | 21.309 | 54.260 | 1.00 | 35.27 | T | C |
| ATOM | 4088 | C | VAL | T | 134 | 19.203 | 22.086 | 54.557 | 1.00 | 37.69 | T | C |
| ATOM | 4089 | O | VAL | T | 134 | 18.691 | 22.045 | 55.671 | 1.00 | 37.30 | T | O |
| ATOM | 4090 | CB | VAL | T | 134 | 20.207 | 19.803 | 54.508 | 1.00 | 33.94 | T | C |
| ATOM | 4091 | CG1 | VAL | T | 134 | 19.038 | 19.335 | 53.652 | 1.00 | 31.92 | T | C |
| ATOM | 4092 | CG2 | VAL | T | 134 | 21.453 | 18.992 | 54.189 | 1.00 | 30.88 | T | C |
| ATOM | 4093 | N | ARG | T | 135 | 18.702 | 22.803 | 53.558 | 1.00 | 42.86 | T | N |
| ATOM | 4094 | CA | ARG | T | 135 | 17.485 | 23.587 | 53.720 | 1.00 | 48.17 | T | C |
| ATOM | 4095 | C | ARG | T | 135 | 16.268 | 22.895 | 53.123 | 1.00 | 51.28 | T | C |
| ATOM | 4096 | O | ARG | T | 135 | 16.332 | 22.333 | 52.031 | 1.00 | 52.30 | T | O |
| ATOM | 4097 | CB | ARG | T | 135 | 17.636 | 24.960 | 53.063 | 1.00 | 48.77 | T | C |
| ATOM | 4098 | CG | ARG | T | 135 | 17.844 | 26.107 | 54.032 | 1.00 | 51.28 | T | C |
| ATOM | 4099 | CD | ARG | T | 135 | 17.150 | 27.366 | 53.522 | 1.00 | 53.42 | T | C |
| ATOM | 4100 | NE | ARG | T | 135 | 17.342 | 28.513 | 54.408 | 1.00 | 54.39 | T | N |
| ATOM | 4101 | CZ | ARG | T | 135 | 18.442 | 29.260 | 54.454 | 1.00 | 54.74 | T | C |
| ATOM | 4102 | NH1 | ARG | T | 135 | 19.473 | 28.995 | 53.659 | 1.00 | 53.86 | T | N |
| ATOM | 4103 | NH2 | ARG | T | 135 | 18.512 | 30.276 | 55.303 | 1.00 | 55.25 | T | N |
| ATOM | 4104 | N | ARG | T | 136 | 15.161 | 22.938 | 53.855 | 1.00 | 55.32 | T | N |
| ATOM | 4105 | CA | ARG | T | 136 | 13.905 | 22.355 | 53.401 | 1.00 | 59.86 | T | C |
| ATOM | 4106 | C | ARG | T | 136 | 12.764 | 23.218 | 53.912 | 1.00 | 60.84 | T | C |
| ATOM | 4107 | O | ARG | T | 136 | 12.685 | 23.514 | 55.105 | 1.00 | 60.73 | T | O |
| ATOM | 4108 | CB | ARG | T | 136 | 13.740 | 20.917 | 53.903 | 1.00 | 62.06 | T | C |
| ATOM | 4109 | CG | ARG | T | 136 | 14.704 | 19.926 | 53.266 | 1.00 | 65.96 | T | C |
| ATOM | 4110 | CD | ARG | T | 136 | 14.066 | 18.552 | 53.079 | 1.00 | 68.51 | T | C |
| ATOM | 4111 | NE | ARG | T | 136 | 13.514 | 18.011 | 54.320 | 1.00 | 71.12 | T | N |
| ATOM | 4112 | CZ | ARG | T | 136 | 13.019 | 16.784 | 54.453 | 1.00 | 72.57 | T | C |
| ATOM | 4113 | NH1 | ARG | T | 136 | 12.999 | 15.951 | 53.420 | 1.00 | 73.26 | T | N |
| ATOM | 4114 | NH2 | ARG | T | 136 | 12.542 | 16.387 | 55.625 | 1.00 | 73.03 | T | N |
| ATOM | 4115 | N | ASN | T | 137 | 11.888 | 23.623 | 52.998 | 1.00 | 62.35 | T | N |
| ATOM | 4116 | CA | ASN | T | 137 | 10.751 | 24.473 | 53.330 | 1.00 | 63.21 | T | C |
| ATOM | 4117 | C | ASN | T | 137 | 11.254 | 25.891 | 53.602 | 1.00 | 62.33 | T | C |
| ATOM | 4118 | O | ASN | T | 137 | 11.409 | 26.685 | 52.674 | 1.00 | 63.22 | T | O |
| ATOM | 4119 | CB | ASN | T | 137 | 10.001 | 23.924 | 54.552 | 1.00 | 65.32 | T | C |
| ATOM | 4120 | CG | ASN | T | 137 | 9.422 | 22.542 | 54.311 | 1.00 | 67.61 | T | C |
| ATOM | 4121 | OD1 | ASN | T | 137 | 10.147 | 21.596 | 54.002 | 1.00 | 69.63 | T | O |
| ATOM | 4122 | ND2 | ASN | T | 137 | 8.108 | 22.419 | 54.456 | 1.00 | 69.48 | T | N |
| ATOM | 4123 | N | ASN | T | 138 | 11.518 | 26.205 | 54.867 | 1.00 | 60.71 | T | N |
| ATOM | 4124 | CA | ASN | T | 138 | 12.003 | 27.531 | 55.234 | 1.00 | 58.80 | T | C |
| ATOM | 4125 | C | ASN | T | 138 | 12.940 | 27.486 | 56.445 | 1.00 | 56.17 | T | C |
| ATOM | 4126 | O | ASN | T | 138 | 13.061 | 28.467 | 57.179 | 1.00 | 56.57 | T | O |
| ATOM | 4127 | CB | ASN | T | 138 | 10.823 | 28.464 | 55.542 | 1.00 | 60.66 | T | C |
| ATOM | 4128 | CG | ASN | T | 138 | 9.842 | 28.582 | 54.381 | 1.00 | 62.38 | T | C |
| ATOM | 4129 | OD1 | ASN | T | 138 | 9.132 | 27.631 | 54.049 | 1.00 | 62.68 | T | O |
| ATOM | 4130 | ND2 | ASN | T | 138 | 9.801 | 29.756 | 53.760 | 1.00 | 63.11 | T | N |
| ATOM | 4131 | N | THR | T | 139 | 13.606 | 26.352 | 56.649 | 1.00 | 52.17 | T | N |
| ATOM | 4132 | CA | THR | T | 139 | 14.520 | 26.197 | 57.777 | 1.00 | 48.11 | T | C |
| ATOM | 4133 | C | THR | T | 139 | 15.641 | 25.203 | 57.483 | 1.00 | 43.77 | T | C |
| ATOM | 4134 | O | THR | T | 139 | 15.649 | 24.548 | 56.442 | 1.00 | 43.95 | T | O |
| ATOM | 4135 | CB | THR | T | 139 | 13.772 | 25.709 | 59.040 | 1.00 | 49.28 | T | C |
| ATOM | 4136 | OG1 | THR | T | 139 | 13.085 | 24.486 | 58.745 | 1.00 | 48.22 | T | O |
| ATOM | 4137 | CG2 | THR | T | 139 | 12.771 | 26.755 | 59.516 | 1.00 | 49.39 | T | C |
| ATOM | 4138 | N | PHE | T | 140 | 16.586 | 25.102 | 58.412 | 1.00 | 39.50 | T | N |
| ATOM | 4139 | CA | PHE | T | 140 | 17.713 | 24.184 | 58.284 | 1.00 | 34.81 | T | C |
| ATOM | 4140 | C | PHE | T | 140 | 17.369 | 22.876 | 58.987 | 1.00 | 33.69 | T | C |
| ATOM | 4141 | O | PHE | T | 140 | 16.857 | 22.884 | 60.107 | 1.00 | 33.95 | T | O |
| ATOM | 4142 | CB | PHE | T | 140 | 18.968 | 24.782 | 58.924 | 1.00 | 31.68 | T | C |
| ATOM | 4143 | CG | PHE | T | 140 | 19.538 | 25.956 | 58.177 | 1.00 | 29.78 | T | C |
| ATOM | 4144 | CD1 | PHE | T | 140 | 20.222 | 25.772 | 56.980 | 1.00 | 28.87 | T | C |
| ATOM | 4145 | CD2 | PHE | T | 140 | 19.404 | 27.247 | 58.679 | 1.00 | 29.29 | T | C |
| ATOM | 4146 | CE1 | PHE | T | 140 | 20.770 | 26.856 | 56.293 | 1.00 | 27.26 | T | C |
| ATOM | 4147 | CE2 | PHE | T | 140 | 19.948 | 28.341 | 57.999 | 1.00 | 28.58 | T | C |

-continued

| ATOM | 4148 | CZ | PHE | T | 140 | 20.634 | 28.142 | 56.803 | 1.00 | 26.93 | T | C |
|---|---|---|---|---|---|---|---|---|---|---|---|---|
| ATOM | 4149 | N | LEU | T | 141 | 17.648 | 21.758 | 58.325 | 1.00 | 31.02 | T | N |
| ATOM | 4150 | CA | LEU | T | 141 | 17.374 | 20.446 | 58.890 | 1.00 | 29.31 | T | C |
| ATOM | 4151 | C | LEU | T | 141 | 18.484 | 20.056 | 59.849 | 1.00 | 28.67 | T | C |
| ATOM | 4152 | O | LEU | T | 141 | 19.654 | 20.369 | 59.623 | 1.00 | 27.90 | T | O |
| ATOM | 4153 | CB | LEU | T | 141 | 17.285 | 19.389 | 57.788 | 1.00 | 28.83 | T | C |
| ATOM | 4154 | CG | LEU | T | 141 | 16.220 | 19.545 | 56.706 | 1.00 | 29.79 | T | C |
| ATOM | 4155 | CD1 | LEU | T | 141 | 16.308 | 18.356 | 55.761 | 1.00 | 27.88 | T | C |
| ATOM | 4156 | CD2 | LEU | T | 141 | 14.836 | 19.634 | 57.340 | 1.00 | 29.65 | T | C |
| ATOM | 4157 | N | SER | T | 142 | 18.116 | 19.359 | 60.916 | 1.00 | 26.59 | T | N |
| ATOM | 4158 | CA | SER | T | 142 | 19.095 | 18.930 | 61.900 | 1.00 | 25.72 | T | C |
| ATOM | 4159 | C | SER | T | 142 | 19.815 | 17.689 | 61.389 | 1.00 | 25.43 | T | C |
| ATOM | 4160 | O | SER | T | 142 | 19.422 | 17.099 | 60.380 | 1.00 | 24.69 | T | O |
| ATOM | 4161 | CB | SER | T | 142 | 18.405 | 18.617 | 63.225 | 1.00 | 24.53 | T | C |
| ATOM | 4162 | OG | SER | T | 142 | 17.693 | 17.393 | 63.142 | 1.00 | 27.31 | T | O |
| ATOM | 4163 | N | LEU | T | 143 | 20.866 | 17.287 | 62.095 | 1.00 | 25.42 | T | N |
| ATOM | 4164 | CA | LEU | T | 143 | 21.632 | 16.117 | 61.700 | 1.00 | 26.13 | T | C |
| ATOM | 4165 | C | LEU | T | 143 | 20.765 | 14.862 | 61.714 | 1.00 | 27.25 | T | C |
| ATOM | 4166 | O | LEU | T | 143 | 20.931 | 13.973 | 60.875 | 1.00 | 27.17 | T | O |
| ATOM | 4167 | CB | LEU | T | 143 | 22.830 | 15.936 | 62.630 | 1.00 | 28.10 | T | C |
| ATOM | 4168 | CG | LEU | T | 143 | 23.975 | 15.082 | 62.080 | 1.00 | 29.38 | T | C |
| ATOM | 4169 | CD1 | LEU | T | 143 | 24.572 | 15.759 | 60.854 | 1.00 | 30.74 | T | C |
| ATOM | 4170 | CD2 | LEU | T | 143 | 25.041 | 14.903 | 63.153 | 1.00 | 33.30 | T | C |
| ATOM | 4171 | N | ARG | T | 144 | 19.837 | 14.778 | 62.662 | 1.00 | 28.42 | T | N |
| ATOM | 4172 | CA | ARG | T | 144 | 18.973 | 13.609 | 62.721 | 1.00 | 29.34 | T | C |
| ATOM | 4173 | C | ARG | T | 144 | 17.850 | 13.700 | 61.687 | 1.00 | 29.34 | T | C |
| ATOM | 4174 | O | ARG | T | 144 | 17.338 | 12.676 | 61.244 | 1.00 | 30.63 | T | O |
| ATOM | 4175 | CB | ARG | T | 144 | 18.403 | 13.411 | 64.127 | 1.00 | 28.19 | T | C |
| ATOM | 4176 | CG | ARG | T | 144 | 17.727 | 12.059 | 64.285 | 1.00 | 29.87 | T | C |
| ATOM | 4177 | CD | ARG | T | 144 | 17.594 | 11.638 | 65.736 | 1.00 | 29.47 | T | C |
| ATOM | 4178 | NE | ARG | T | 144 | 18.861 | 11.246 | 66.358 | 1.00 | 29.59 | T | N |
| ATOM | 4179 | CZ | ARG | T | 144 | 19.587 | 10.183 | 66.017 | 1.00 | 28.70 | T | C |
| ATOM | 4180 | NH1 | ARG | T | 144 | 19.195 | 9.378 | 65.039 | 1.00 | 28.08 | T | N |
| ATOM | 4181 | NH2 | ARG | T | 144 | 20.699 | 9.904 | 66.682 | 1.00 | 27.54 | T | N |
| ATOM | 4182 | N | ASP | T | 145 | 17.469 | 14.918 | 61.301 | 1.00 | 29.51 | T | N |
| ATOM | 4183 | CA | ASP | T | 145 | 16.438 | 15.093 | 60.275 | 1.00 | 30.78 | T | C |
| ATOM | 4184 | C | ASP | T | 145 | 16.940 | 14.472 | 58.970 | 1.00 | 29.67 | T | C |
| ATOM | 4185 | O | ASP | T | 145 | 16.195 | 13.793 | 58.263 | 1.00 | 30.38 | T | O |
| ATOM | 4186 | CB | ASP | T | 145 | 16.147 | 16.578 | 60.007 | 1.00 | 31.56 | T | C |
| ATOM | 4187 | CG | ASP | T | 145 | 15.239 | 17.204 | 61.048 | 1.00 | 33.74 | T | C |
| ATOM | 4188 | OD1 | ASP | T | 145 | 14.327 | 16.520 | 61.530 | 1.00 | 37.12 | T | O |
| ATOM | 4189 | OD2 | ASP | T | 145 | 15.430 | 18.385 | 61.356 | 1.00 | 31.92 | T | O |
| ATOM | 4190 | N | VAL | T | 146 | 18.215 | 14.719 | 58.670 | 1.00 | 27.99 | T | N |
| ATOM | 4191 | CA | VAL | T | 146 | 18.871 | 14.231 | 57.459 | 1.00 | 25.95 | T | C |
| ATOM | 4192 | C | VAL | T | 146 | 19.245 | 12.750 | 57.474 | 1.00 | 26.46 | T | C |
| ATOM | 4193 | O | VAL | T | 146 | 18.922 | 12.024 | 56.541 | 1.00 | 27.73 | T | O |
| ATOM | 4194 | CB | VAL | T | 146 | 20.168 | 15.048 | 57.164 | 1.00 | 24.95 | T | C |
| ATOM | 4195 | CG1 | VAL | T | 146 | 20.901 | 14.461 | 55.960 | 1.00 | 20.92 | T | C |
| ATOM | 4196 | CG2 | VAL | T | 146 | 19.823 | 16.519 | 56.916 | 1.00 | 20.74 | T | C |
| ATOM | 4197 | N | PHE | T | 147 | 19.929 | 12.305 | 58.524 | 1.00 | 26.36 | T | N |
| ATOM | 4198 | CA | PHE | T | 147 | 20.369 | 10.912 | 58.619 | 1.00 | 25.98 | T | C |
| ATOM | 4199 | C | PHE | T | 147 | 19.379 | 9.919 | 59.236 | 1.00 | 27.12 | T | C |
| ATOM | 4200 | O | PHE | T | 147 | 19.536 | 8.708 | 59.084 | 1.00 | 25.23 | T | O |
| ATOM | 4201 | CB | PHE | T | 147 | 21.689 | 10.844 | 59.389 | 1.00 | 24.48 | T | C |
| ATOM | 4202 | CG | PHE | T | 147 | 22.844 | 11.465 | 58.662 | 1.00 | 25.86 | T | C |
| ATOM | 4203 | CD1 | PHE | T | 147 | 23.388 | 10.848 | 57.546 | 1.00 | 25.81 | T | C |
| ATOM | 4204 | CD2 | PHE | T | 147 | 23.377 | 12.681 | 59.082 | 1.00 | 26.68 | T | C |
| ATOM | 4205 | CE1 | PHE | T | 147 | 24.450 | 11.429 | 56.852 | 1.00 | 27.09 | T | C |
| ATOM | 4206 | CE2 | PHE | T | 147 | 24.435 | 13.267 | 58.398 | 1.00 | 26.05 | T | C |
| ATOM | 4207 | CZ | PHE | T | 147 | 24.972 | 12.639 | 57.280 | 1.00 | 25.43 | T | C |
| ATOM | 4208 | N | GLY | T | 148 | 18.368 | 10.421 | 59.930 | 1.00 | 27.07 | T | N |
| ATOM | 4209 | CA | GLY | T | 148 | 17.406 | 9.526 | 60.542 | 1.00 | 30.74 | T | C |
| ATOM | 4210 | C | GLY | T | 148 | 18.079 | 8.427 | 61.347 | 1.00 | 31.38 | T | C |
| ATOM | 4211 | O | GLY | T | 148 | 18.894 | 8.710 | 62.227 | 1.00 | 31.75 | T | O |
| ATOM | 4212 | N | LYS | T | 149 | 17.757 | 7.174 | 61.033 | 1.00 | 31.90 | T | N |
| ATOM | 4213 | CA | LYS | T | 149 | 18.319 | 6.024 | 61.745 | 1.00 | 30.48 | T | C |
| ATOM | 4214 | C | LYS | T | 149 | 19.784 | 5.707 | 61.448 | 1.00 | 29.20 | T | C |
| ATOM | 4215 | O | LYS | T | 149 | 20.391 | 4.894 | 62.143 | 1.00 | 28.53 | T | O |
| ATOM | 4216 | CB | LYS | T | 149 | 17.480 | 4.771 | 61.475 | 1.00 | 32.10 | T | C |
| ATOM | 4217 | CG | LYS | T | 149 | 17.526 | 4.284 | 60.036 | 1.00 | 34.68 | T | C |
| ATOM | 4218 | CD | LYS | T | 149 | 16.654 | 3.045 | 59.849 | 1.00 | 38.94 | T | C |
| ATOM | 4219 | CE | LYS | T | 149 | 16.596 | 2.617 | 58.390 | 1.00 | 39.85 | T | C |
| ATOM | 4220 | NZ | LYS | T | 149 | 17.943 | 2.260 | 57.865 | 1.00 | 42.88 | T | N |
| ATOM | 4221 | N | ASP | T | 150 | 20.356 | 6.318 | 60.416 | 1.00 | 28.28 | T | N |
| ATOM | 4222 | CA | ASP | T | 150 | 21.763 | 6.060 | 60.103 | 1.00 | 27.67 | T | C |
| ATOM | 4223 | C | ASP | T | 150 | 22.698 | 6.678 | 61.142 | 1.00 | 26.20 | T | C |
| ATOM | 4224 | O | ASP | T | 150 | 23.859 | 6.283 | 61.257 | 1.00 | 26.29 | T | O |
| ATOM | 4225 | CB | ASP | T | 150 | 22.137 | 6.620 | 58.727 | 1.00 | 28.41 | T | C |
| ATOM | 4226 | CG | ASP | T | 150 | 21.631 | 5.765 | 57.592 | 1.00 | 30.84 | T | C |

-continued

| | | | | | | | | | | | |
|---|---|---|---|---|---|---|---|---|---|---|---|
| ATOM | 4227 | OD1 | ASP | T | 150 | 21.557 | 4.547 | 57.765 | 1.00 | 30.37 | T | O |
| ATOM | 4228 | OD2 | ASP | T | 150 | 21.330 | 6.319 | 56.530 | 1.00 | 31.25 | T | O |
| ATOM | 4229 | N | LEU | T | 151 | 22.186 | 7.645 | 61.897 | 1.00 | 24.20 | T | N |
| ATOM | 4230 | CA | LEU | T | 151 | 22.978 | 8.342 | 62.901 | 1.00 | 24.32 | T | C |
| ATOM | 4231 | C | LEU | T | 151 | 22.800 | 7.847 | 64.333 | 1.00 | 23.19 | T | C |
| ATOM | 4232 | O | LEU | T | 151 | 21.681 | 7.654 | 64.805 | 1.00 | 23.35 | T | O |
| ATOM | 4233 | CB | LEU | T | 151 | 22.651 | 9.839 | 62.858 | 1.00 | 23.48 | T | C |
| ATOM | 4234 | CG | LEU | T | 151 | 23.299 | 10.741 | 63.916 | 1.00 | 24.55 | T | C |
| ATOM | 4235 | CD1 | LEU | T | 151 | 24.791 | 10.863 | 63.649 | 1.00 | 21.55 | T | C |
| ATOM | 4236 | CD2 | LEU | T | 151 | 22.638 | 12.117 | 63.885 | 1.00 | 24.04 | T | C |
| ATOM | 4237 | N | ILE | T | 152 | 23.917 | 7.639 | 65.020 | 1.00 | 23.69 | T | N |
| ATOM | 4238 | CA | ILE | T | 152 | 23.882 | 7.235 | 66.419 | 1.00 | 23.13 | T | C |
| ATOM | 4239 | C | ILE | T | 152 | 24.886 | 8.111 | 67.154 | 1.00 | 23.28 | T | C |
| ATOM | 4240 | O | ILE | T | 152 | 25.736 | 8.752 | 66.537 | 1.00 | 24.54 | T | O |
| ATOM | 4241 | CB | ILE | T | 152 | 24.287 | 5.747 | 66.643 | 1.00 | 22.81 | T | C |
| ATOM | 4242 | CG1 | ILE | T | 152 | 25.799 | 5.584 | 66.493 | 1.00 | 22.58 | T | C |
| ATOM | 4243 | CG2 | ILE | T | 152 | 23.534 | 4.839 | 65.672 | 1.00 | 23.41 | T | C |
| ATOM | 4244 | CD1 | ILE | T | 152 | 26.322 | 4.228 | 66.945 | 1.00 | 22.76 | T | C |
| ATOM | 4245 | N | TYR | T | 153 | 24.779 | 8.150 | 68.472 | 1.00 | 23.49 | T | N |
| ATOM | 4246 | CA | TYR | T | 153 | 25.711 | 8.920 | 69.271 | 1.00 | 24.51 | T | C |
| ATOM | 4247 | C | TYR | T | 153 | 26.359 | 7.984 | 70.274 | 1.00 | 24.18 | T | C |
| ATOM | 4248 | O | TYR | T | 153 | 25.715 | 7.078 | 70.802 | 1.00 | 24.71 | T | O |
| ATOM | 4249 | CB | TYR | T | 153 | 24.995 | 10.067 | 69.984 | 1.00 | 23.68 | T | C |
| ATOM | 4250 | CG | TYR | T | 153 | 24.745 | 11.256 | 69.081 | 1.00 | 23.64 | T | C |
| ATOM | 4251 | CD1 | TYR | T | 153 | 25.805 | 12.036 | 68.623 | 1.00 | 23.71 | T | C |
| ATOM | 4252 | CD2 | TYR | T | 153 | 23.454 | 11.597 | 68.677 | 1.00 | 22.84 | T | C |
| ATOM | 4253 | CE1 | TYR | T | 153 | 25.590 | 13.130 | 67.786 | 1.00 | 21.55 | T | C |
| ATOM | 4254 | CE2 | TYR | T | 153 | 23.226 | 12.690 | 67.839 | 1.00 | 22.98 | T | C |
| ATOM | 4255 | CZ | TYR | T | 153 | 24.301 | 13.450 | 67.399 | 1.00 | 22.00 | T | C |
| ATOM | 4256 | OH | TYR | T | 153 | 24.092 | 14.527 | 66.575 | 1.00 | 21.50 | T | O |
| ATOM | 4257 | N | THR | T | 154 | 27.647 | 8.193 | 70.506 | 1.00 | 23.44 | T | N |
| ATOM | 4258 | CA | THR | T | 154 | 28.403 | 7.381 | 71.438 | 1.00 | 23.84 | T | C |
| ATOM | 4259 | C | THR | T | 154 | 28.830 | 8.250 | 72.615 | 1.00 | 25.48 | T | C |
| ATOM | 4260 | O | THR | T | 154 | 29.260 | 9.387 | 72.431 | 1.00 | 25.59 | T | O |
| ATOM | 4261 | CB | THR | T | 154 | 29.640 | 6.783 | 70.741 | 1.00 | 24.28 | T | C |
| ATOM | 4262 | OG1 | THR | T | 154 | 29.212 | 5.846 | 69.742 | 1.00 | 24.66 | T | O |
| ATOM | 4263 | CG2 | THR | T | 154 | 30.540 | 6.081 | 71.740 | 1.00 | 27.90 | T | C |
| ATOM | 4264 | N | LEU | T | 155 | 28.685 | 7.715 | 73.822 | 1.00 | 26.46 | T | N |
| ATOM | 4265 | CA | LEU | T | 155 | 29.056 | 8.428 | 75.036 | 1.00 | 29.00 | T | C |
| ATOM | 4266 | C | LEU | T | 155 | 30.286 | 7.788 | 75.670 | 1.00 | 31.35 | T | C |
| ATOM | 4267 | O | LEU | T | 155 | 30.356 | 6.570 | 75.831 | 1.00 | 33.70 | T | O |
| ATOM | 4268 | CB | LEU | T | 155 | 27.894 | 8.416 | 76.039 | 1.00 | 26.23 | T | C |
| ATOM | 4269 | CG | LEU | T | 155 | 28.112 | 9.127 | 77.381 | 1.00 | 26.86 | T | C |
| ATOM | 4270 | CD1 | LEU | T | 155 | 28.263 | 10.620 | 77.155 | 1.00 | 25.42 | T | C |
| ATOM | 4271 | CD2 | LEU | T | 155 | 26.941 | 8.851 | 78.307 | 1.00 | 24.97 | T | C |
| ATOM | 4272 | N | TYR | T | 156 | 31.254 | 8.625 | 76.014 | 1.00 | 33.72 | T | N |
| ATOM | 4273 | CA | TYR | T | 156 | 32.494 | 8.198 | 76.649 | 1.00 | 36.80 | T | C |
| ATOM | 4274 | C | TYR | T | 156 | 32.466 | 8.870 | 78.016 | 1.00 | 37.49 | T | C |
| ATOM | 4275 | O | TYR | T | 156 | 32.747 | 10.061 | 78.125 | 1.00 | 37.28 | T | O |
| ATOM | 4276 | CB | TYR | T | 156 | 33.690 | 8.703 | 75.835 | 1.00 | 39.78 | T | C |
| ATOM | 4277 | CG | TYR | T | 156 | 35.056 | 8.392 | 76.413 | 1.00 | 44.27 | T | C |
| ATOM | 4278 | CD1 | TYR | T | 156 | 35.633 | 7.130 | 76.262 | 1.00 | 45.90 | T | C |
| ATOM | 4279 | CD2 | TYR | T | 156 | 35.787 | 9.374 | 77.085 | 1.00 | 46.33 | T | C |
| ATOM | 4280 | CE1 | TYR | T | 156 | 36.908 | 6.856 | 76.762 | 1.00 | 46.82 | T | C |
| ATOM | 4281 | CE2 | TYR | T | 156 | 37.060 | 9.110 | 77.590 | 1.00 | 46.50 | T | C |
| ATOM | 4282 | CZ | TYR | T | 156 | 37.614 | 7.851 | 77.424 | 1.00 | 47.92 | T | C |
| ATOM | 4283 | OH | TYR | T | 156 | 38.875 | 7.593 | 77.914 | 1.00 | 48.85 | T | O |
| ATOM | 4284 | N | TYR | T | 157 | 32.098 | 8.113 | 79.047 | 1.00 | 38.10 | T | N |
| ATOM | 4285 | CA | TYR | T | 157 | 32.017 | 8.650 | 80.404 | 1.00 | 39.51 | T | C |
| ATOM | 4286 | C | TYR | T | 157 | 32.911 | 7.927 | 81.407 | 1.00 | 41.43 | T | C |
| ATOM | 4287 | O | TYR | T | 157 | 33.153 | 6.729 | 81.286 | 1.00 | 41.55 | T | O |
| ATOM | 4288 | CB | TYR | T | 157 | 30.566 | 8.627 | 80.905 | 1.00 | 37.07 | T | C |
| ATOM | 4289 | CG | TYR | T | 157 | 29.924 | 7.255 | 81.019 | 1.00 | 36.59 | T | C |
| ATOM | 4290 | CD1 | TYR | T | 157 | 29.578 | 6.520 | 79.884 | 1.00 | 36.61 | T | C |
| ATOM | 4291 | CD2 | TYR | T | 157 | 29.622 | 6.712 | 82.269 | 1.00 | 36.44 | T | C |
| ATOM | 4292 | CE1 | TYR | T | 157 | 28.942 | 5.282 | 79.990 | 1.00 | 36.96 | T | C |
| ATOM | 4293 | CE2 | TYR | T | 157 | 28.989 | 5.478 | 82.388 | 1.00 | 36.19 | T | C |
| ATOM | 4294 | CZ | TYR | T | 157 | 28.649 | 4.768 | 81.247 | 1.00 | 37.43 | T | C |
| ATOM | 4295 | OH | TYR | T | 157 | 28.011 | 3.554 | 81.362 | 1.00 | 35.29 | T | O |
| ATOM | 4296 | N | TRP | T | 158 | 33.393 | 8.666 | 82.402 | 1.00 | 44.59 | T | N |
| ATOM | 4297 | CA | TRP | T | 158 | 34.266 | 8.101 | 83.423 | 1.00 | 48.36 | T | C |
| ATOM | 4298 | C | TRP | T | 158 | 33.941 | 8.612 | 84.822 | 1.00 | 50.71 | T | C |
| ATOM | 4299 | O | TRP | T | 158 | 33.389 | 9.700 | 84.989 | 1.00 | 50.01 | T | O |
| ATOM | 4300 | CB | TRP | T | 158 | 35.727 | 8.414 | 83.092 | 1.00 | 48.77 | T | C |
| ATOM | 4301 | CG | TRP | T | 158 | 36.071 | 9.873 | 83.156 | 1.00 | 50.02 | T | C |
| ATOM | 4302 | CD1 | TRP | T | 158 | 36.242 | 10.631 | 84.281 | 1.00 | 50.16 | T | C |
| ATOM | 4303 | CD2 | TRP | T | 158 | 36.291 | 10.752 | 82.045 | 1.00 | 50.25 | T | C |
| ATOM | 4304 | NE1 | TRP | T | 158 | 36.557 | 11.924 | 83.940 | 1.00 | 50.45 | T | N |
| ATOM | 4305 | CE2 | TRP | T | 158 | 36.595 | 12.027 | 82.574 | 1.00 | 49.97 | T | C |

-continued

| | | | | | | | | | | | |
|---|---|---|---|---|---|---|---|---|---|---|---|
| ATOM | 4306 | CE3 | TRP | T | 158 | 36.262 | 10.585 | 80.653 | 1.00 | 50.09 | T | C |
| ATOM | 4307 | CZ2 | TRP | T | 158 | 36.869 | 13.131 | 81.760 | 1.00 | 49.43 | T | C |
| ATOM | 4308 | CZ3 | TRP | T | 158 | 36.534 | 11.685 | 79.843 | 1.00 | 50.00 | T | C |
| ATOM | 4309 | CH2 | TRP | T | 158 | 36.834 | 12.941 | 80.402 | 1.00 | 50.53 | T | C |
| ATOM | 4310 | N | LYS | T | 159 | 34.295 | 7.815 | 85.826 | 1.00 | 54.36 | T | N |
| ATOM | 4311 | CA | LYS | T | 159 | 34.053 | 8.167 | 87.220 | 1.00 | 57.78 | T | C |
| ATOM | 4312 | C | LYS | T | 159 | 35.218 | 9.024 | 87.735 | 1.00 | 58.65 | T | C |
| ATOM | 4313 | O | LYS | T | 159 | 35.371 | 10.173 | 87.325 | 1.00 | 60.01 | T | O |
| ATOM | 4314 | CB | LYS | T | 159 | 33.911 | 6.887 | 88.053 | 1.00 | 59.26 | T | C |
| ATOM | 4315 | CG | LYS | T | 159 | 33.266 | 7.081 | 89.416 | 1.00 | 61.42 | T | C |
| ATOM | 4316 | CD | LYS | T | 159 | 33.503 | 5.877 | 90.322 | 1.00 | 63.98 | T | C |
| ATOM | 4317 | CE | LYS | T | 159 | 32.979 | 4.584 | 89.712 | 1.00 | 65.42 | T | C |
| ATOM | 4318 | NZ | LYS | T | 159 | 31.501 | 4.599 | 89.542 | 1.00 | 67.11 | T | N |
| ATOM | 4319 | N | SER | T | 160 | 36.035 | 8.460 | 88.622 | 1.00 | 60.77 | T | N |
| ATOM | 4320 | CA | SER | T | 160 | 37.188 | 9.152 | 89.198 | 1.00 | 62.01 | T | C |
| ATOM | 4321 | C | SER | T | 160 | 37.933 | 8.228 | 90.157 | 1.00 | 62.68 | T | C |
| ATOM | 4322 | O | SER | T | 160 | 37.520 | 8.043 | 91.303 | 1.00 | 63.75 | T | O |
| ATOM | 4323 | CB | SER | T | 160 | 36.751 | 10.413 | 89.952 | 1.00 | 62.64 | T | C |
| ATOM | 4324 | OG | SER | T | 160 | 36.348 | 11.441 | 89.063 | 1.00 | 63.25 | T | O |
| ATOM | 4325 | N | GLY | T | 164 | 39.552 | 4.169 | 84.389 | 1.00 | 46.65 | T | N |
| ATOM | 4326 | CA | GLY | T | 164 | 38.188 | 3.681 | 84.302 | 1.00 | 46.62 | T | C |
| ATOM | 4327 | C | GLY | T | 164 | 37.414 | 4.314 | 83.161 | 1.00 | 45.68 | T | C |
| ATOM | 4328 | O | GLY | T | 164 | 36.884 | 5.415 | 83.296 | 1.00 | 45.48 | T | O |
| ATOM | 4329 | N | LYS | T | 165 | 37.347 | 3.611 | 82.036 | 1.00 | 45.62 | T | N |
| ATOM | 4330 | CA | LYS | T | 165 | 36.635 | 4.100 | 80.859 | 1.00 | 44.77 | T | C |
| ATOM | 4331 | C | LYS | T | 165 | 35.296 | 3.385 | 80.697 | 1.00 | 42.99 | T | C |
| ATOM | 4332 | O | LYS | T | 165 | 35.198 | 2.178 | 80.921 | 1.00 | 43.15 | T | O |
| ATOM | 4333 | CB | LYS | T | 165 | 37.480 | 3.885 | 79.593 | 1.00 | 47.71 | T | C |
| ATOM | 4334 | CG | LYS | T | 165 | 38.658 | 4.851 | 79.404 | 1.00 | 51.07 | T | C |
| ATOM | 4335 | CD | LYS | T | 165 | 39.777 | 4.652 | 80.424 | 1.00 | 53.07 | T | C |
| ATOM | 4336 | CE | LYS | T | 165 | 40.370 | 3.252 | 80.348 | 1.00 | 55.53 | T | C |
| ATOM | 4337 | NZ | LYS | T | 165 | 40.940 | 2.954 | 79.005 | 1.00 | 58.19 | T | N |
| ATOM | 4338 | N | LYS | T | 166 | 34.269 | 4.135 | 80.309 | 1.00 | 40.32 | T | N |
| ATOM | 4339 | CA | LYS | T | 166 | 32.937 | 3.573 | 80.103 | 1.00 | 38.29 | T | C |
| ATOM | 4340 | C | LYS | T | 166 | 32.325 | 4.137 | 78.818 | 1.00 | 36.09 | T | C |
| ATOM | 4341 | O | LYS | T | 166 | 32.609 | 5.268 | 78.427 | 1.00 | 32.41 | T | O |
| ATOM | 4342 | CB | LYS | T | 166 | 32.032 | 3.892 | 81.297 | 1.00 | 40.50 | T | C |
| ATOM | 4343 | CG | LYS | T | 166 | 32.510 | 3.306 | 82.617 | 1.00 | 43.96 | T | C |
| ATOM | 4344 | CD | LYS | T | 166 | 31.622 | 3.752 | 83.767 | 1.00 | 45.60 | T | C |
| ATOM | 4345 | CE | LYS | T | 166 | 32.151 | 3.265 | 85.107 | 1.00 | 47.87 | T | C |
| ATOM | 4346 | NZ | LYS | T | 166 | 31.334 | 3.791 | 86.239 | 1.00 | 49.02 | T | N |
| ATOM | 4347 | N | THR | T | 167 | 31.475 | 3.347 | 78.172 | 1.00 | 33.24 | T | N |
| ATOM | 4348 | CA | THR | T | 167 | 30.851 | 3.771 | 76.926 | 1.00 | 32.13 | T | C |
| ATOM | 4349 | C | THR | T | 167 | 29.386 | 3.355 | 76.799 | 1.00 | 30.44 | T | C |
| ATOM | 4350 | O | THR | T | 167 | 28.969 | 2.318 | 77.316 | 1.00 | 29.24 | T | O |
| ATOM | 4351 | CB | THR | T | 167 | 31.623 | 3.205 | 75.719 | 1.00 | 33.05 | T | C |
| ATOM | 4352 | OG1 | THR | T | 167 | 31.000 | 3.632 | 74.502 | 1.00 | 34.90 | T | O |
| ATOM | 4353 | CG2 | THR | T | 167 | 31.633 | 1.686 | 75.767 | 1.00 | 34.83 | T | C |
| ATOM | 4354 | N | ALA | T | 168 | 28.616 | 4.184 | 76.102 | 1.00 | 27.66 | T | N |
| ATOM | 4355 | CA | ALA | T | 168 | 27.201 | 3.934 | 75.866 | 1.00 | 27.24 | T | C |
| ATOM | 4356 | C | ALA | T | 168 | 26.887 | 4.359 | 74.434 | 1.00 | 26.54 | T | C |
| ATOM | 4357 | O | ALA | T | 168 | 27.614 | 5.159 | 73.853 | 1.00 | 26.79 | T | O |
| ATOM | 4358 | CB | ALA | T | 168 | 26.356 | 4.738 | 76.847 | 1.00 | 25.11 | T | C |
| ATOM | 4359 | N | LYS | T | 169 | 25.815 | 3.818 | 73.864 | 1.00 | 25.71 | T | N |
| ATOM | 4360 | CA | LYS | T | 169 | 25.421 | 4.174 | 72.503 | 1.00 | 24.30 | T | C |
| ATOM | 4361 | C | LYS | T | 169 | 23.912 | 4.341 | 72.416 | 1.00 | 23.34 | T | C |
| ATOM | 4362 | O | LYS | T | 169 | 23.165 | 3.613 | 73.056 | 1.00 | 25.30 | T | O |
| ATOM | 4363 | CB | LYS | T | 169 | 25.898 | 3.108 | 71.519 | 1.00 | 25.23 | T | C |
| ATOM | 4364 | CG | LYS | T | 169 | 27.401 | 2.925 | 71.531 | 1.00 | 24.44 | T | C |
| ATOM | 4365 | CD | LYS | T | 169 | 27.864 | 1.937 | 70.489 | 1.00 | 25.08 | T | C |
| ATOM | 4366 | CE | LYS | T | 169 | 29.368 | 1.780 | 70.552 | 1.00 | 22.30 | T | C |
| ATOM | 4367 | NZ | LYS | T | 169 | 29.879 | 1.009 | 69.398 | 1.00 | 25.32 | T | N |
| ATOM | 4368 | N | THR | T | 170 | 23.467 | 5.309 | 71.625 | 1.00 | 24.63 | T | N |
| ATOM | 4369 | CA | THR | T | 170 | 22.040 | 5.574 | 71.475 | 1.00 | 24.26 | T | C |
| ATOM | 4370 | C | THR | T | 170 | 21.680 | 5.871 | 70.023 | 1.00 | 26.19 | T | C |
| ATOM | 4371 | O | THR | T | 170 | 22.491 | 6.408 | 69.269 | 1.00 | 26.16 | T | O |
| ATOM | 4372 | CB | THR | T | 170 | 21.607 | 6.783 | 72.335 | 1.00 | 22.44 | T | C |
| ATOM | 4373 | OG1 | THR | T | 170 | 20.202 | 7.008 | 72.178 | 1.00 | 21.98 | T | O |
| ATOM | 4374 | CG2 | THR | T | 170 | 22.361 | 8.040 | 71.907 | 1.00 | 20.38 | T | C |
| ATOM | 4375 | N | ASN | T | 171 | 20.463 | 5.518 | 69.631 | 1.00 | 27.31 | T | N |
| ATOM | 4376 | CA | ASN | T | 171 | 20.018 | 5.777 | 68.272 | 1.00 | 29.89 | T | C |
| ATOM | 4377 | C | ASN | T | 171 | 19.207 | 7.071 | 68.202 | 1.00 | 28.86 | T | C |
| ATOM | 4378 | O | ASN | T | 171 | 18.659 | 7.416 | 67.158 | 1.00 | 30.77 | T | O |
| ATOM | 4379 | CB | ASN | T | 171 | 19.201 | 4.596 | 67.744 | 1.00 | 34.19 | T | C |
| ATOM | 4380 | CG | ASN | T | 171 | 17.917 | 4.401 | 68.497 | 1.00 | 38.11 | T | C |
| ATOM | 4381 | OD1 | ASN | T | 171 | 17.919 | 4.219 | 69.714 | 1.00 | 43.07 | T | O |
| ATOM | 4382 | ND2 | ASN | T | 171 | 16.803 | 4.433 | 67.778 | 1.00 | 42.28 | T | N |
| ATOM | 4383 | N | THR | T | 172 | 19.129 | 7.781 | 69.324 | 1.00 | 27.79 | T | N |
| ATOM | 4384 | CA | THR | T | 172 | 18.432 | 9.063 | 69.385 | 1.00 | 27.05 | T | C |

-continued

| | | | | | | | | | | | |
|---|---|---|---|---|---|---|---|---|---|---|---|
| ATOM | 4385 | C | THR | T | 172 | 19.487 | 10.072 | 69.863 | 1.00 | 26.35 | T | C |
| ATOM | 4386 | O | THR | T | 172 | 20.678 | 9.898 | 69.593 | 1.00 | 24.98 | T | O |
| ATOM | 4387 | CB | THR | T | 172 | 17.242 | 9.030 | 70.381 | 1.00 | 26.35 | T | C |
| ATOM | 4388 | OG1 | THR | T | 172 | 17.732 | 8.790 | 71.704 | 1.00 | 29.03 | T | O |
| ATOM | 4389 | CG2 | THR | T | 172 | 16.258 | 7.930 | 70.009 | 1.00 | 26.97 | T | C |
| ATOM | 4390 | N | ASN | T | 173 | 19.065 | 11.119 | 70.559 | 1.00 | 24.76 | T | N |
| ATOM | 4391 | CA | ASN | T | 173 | 20.008 | 12.112 | 71.061 | 1.00 | 26.67 | T | C |
| ATOM | 4392 | C | ASN | T | 173 | 20.147 | 12.074 | 72.578 | 1.00 | 26.96 | T | C |
| ATOM | 4393 | O | ASN | T | 173 | 20.741 | 12.974 | 73.167 | 1.00 | 26.63 | T | O |
| ATOM | 4394 | CB | ASN | T | 173 | 19.583 | 13.517 | 70.632 | 1.00 | 27.09 | T | C |
| ATOM | 4395 | CG | ASN | T | 173 | 19.974 | 13.829 | 69.206 | 1.00 | 27.88 | T | C |
| ATOM | 4396 | OD1 | ASN | T | 173 | 19.682 | 13.064 | 68.291 | 1.00 | 28.96 | T | O |
| ATOM | 4397 | ND2 | ASN | T | 173 | 20.642 | 14.960 | 69.009 | 1.00 | 29.78 | T | N |
| ATOM | 4398 | N | GLU | T | 174 | 19.617 | 11.028 | 73.206 | 1.00 | 26.96 | T | N |
| ATOM | 4399 | CA | GLU | T | 174 | 19.680 | 10.906 | 74.659 | 1.00 | 28.12 | T | C |
| ATOM | 4400 | C | GLU | T | 174 | 20.340 | 9.619 | 75.143 | 1.00 | 26.22 | T | C |
| ATOM | 4401 | O | GLU | T | 174 | 20.215 | 8.569 | 74.523 | 1.00 | 26.38 | T | O |
| ATOM | 4402 | CB | GLU | T | 174 | 18.268 | 11.012 | 75.241 | 1.00 | 32.01 | T | C |
| ATOM | 4403 | CG | GLU | T | 174 | 17.604 | 12.365 | 74.996 | 1.00 | 39.60 | T | C |
| ATOM | 4404 | CD | GLU | T | 174 | 16.095 | 12.313 | 75.150 | 1.00 | 45.20 | T | C |
| ATOM | 4405 | OE1 | GLU | T | 174 | 15.439 | 11.627 | 74.350 | 1.00 | 47.98 | T | O |
| ATOM | 4406 | OE2 | GLU | T | 174 | 15.575 | 12.951 | 76.068 | 1.00 | 49.78 | T | O |
| ATOM | 4407 | N | PHE | T | 175 | 21.047 | 9.722 | 76.262 | 1.00 | 26.73 | T | N |
| ATOM | 4408 | CA | PHE | T | 175 | 21.730 | 8.591 | 76.877 | 1.00 | 26.52 | T | C |
| ATOM | 4409 | C | PHE | T | 175 | 21.161 | 8.402 | 78.280 | 1.00 | 29.29 | T | C |
| ATOM | 4410 | O | PHE | T | 175 | 21.052 | 9.367 | 79.037 | 1.00 | 29.51 | T | O |
| ATOM | 4411 | CB | PHE | T | 175 | 23.228 | 8.873 | 77.012 | 1.00 | 23.85 | T | C |
| ATOM | 4412 | CG | PHE | T | 175 | 23.968 | 8.919 | 75.710 | 1.00 | 23.33 | T | C |
| ATOM | 4413 | CD1 | PHE | T | 175 | 24.315 | 7.743 | 75.051 | 1.00 | 22.59 | T | C |
| ATOM | 4414 | CD2 | PHE | T | 175 | 24.345 | 10.139 | 75.154 | 1.00 | 21.95 | T | C |
| ATOM | 4415 | CE1 | PHE | T | 175 | 25.034 | 7.780 | 73.851 | 1.00 | 24.26 | T | C |
| ATOM | 4416 | CE2 | PHE | T | 175 | 25.063 | 10.189 | 73.956 | 1.00 | 23.03 | T | C |
| ATOM | 4417 | CZ | PHE | T | 175 | 25.408 | 9.006 | 73.304 | 1.00 | 22.27 | T | C |
| ATOM | 4418 | N | LEU | T | 176 | 20.791 | 7.171 | 78.622 | 1.00 | 31.93 | T | N |
| ATOM | 4419 | CA | LEU | T | 176 | 20.276 | 6.873 | 79.959 | 1.00 | 34.35 | T | C |
| ATOM | 4420 | C | LEU | T | 176 | 21.250 | 5.879 | 80.574 | 1.00 | 35.33 | T | C |
| ATOM | 4421 | O | LEU | T | 176 | 21.255 | 4.705 | 80.211 | 1.00 | 36.35 | T | O |
| ATOM | 4422 | CB | LEU | T | 176 | 18.876 | 6.254 | 79.890 | 1.00 | 34.93 | T | C |
| ATOM | 4423 | CG | LEU | T | 176 | 18.220 | 5.937 | 81.243 | 1.00 | 36.34 | T | C |
| ATOM | 4424 | CD1 | LEU | T | 176 | 18.026 | 7.218 | 82.039 | 1.00 | 36.74 | T | C |
| ATOM | 4425 | CD2 | LEU | T | 176 | 16.876 | 5.250 | 81.022 | 1.00 | 37.90 | T | C |
| ATOM | 4426 | N | ILE | T | 177 | 22.083 | 6.355 | 81.494 | 1.00 | 36.14 | T | N |
| ATOM | 4427 | CA | ILE | T | 177 | 23.080 | 5.500 | 82.125 | 1.00 | 38.18 | T | C |
| ATOM | 4428 | C | ILE | T | 177 | 22.968 | 5.430 | 83.643 | 1.00 | 39.89 | T | C |
| ATOM | 4429 | O | ILE | T | 177 | 22.350 | 6.284 | 84.274 | 1.00 | 38.85 | T | O |
| ATOM | 4430 | CB | ILE | T | 177 | 24.510 | 5.974 | 81.795 | 1.00 | 38.42 | T | C |
| ATOM | 4431 | CG1 | ILE | T | 177 | 24.750 | 7.358 | 82.407 | 1.00 | 38.45 | T | C |
| ATOM | 4432 | CG2 | ILE | T | 177 | 24.712 | 6.009 | 80.288 | 1.00 | 38.52 | T | C |
| ATOM | 4433 | CD1 | ILE | T | 177 | 26.208 | 7.791 | 82.420 | 1.00 | 39.58 | T | C |
| ATOM | 4434 | N | ASP | T | 178 | 23.589 | 4.403 | 84.215 | 1.00 | 42.03 | T | N |
| ATOM | 4435 | CA | ASP | T | 178 | 23.602 | 4.192 | 85.657 | 1.00 | 45.50 | T | C |
| ATOM | 4436 | C | ASP | T | 178 | 24.802 | 4.914 | 86.259 | 1.00 | 47.95 | T | C |
| ATOM | 4437 | O | ASP | T | 178 | 25.866 | 4.984 | 85.645 | 1.00 | 48.69 | T | O |
| ATOM | 4438 | CB | ASP | T | 178 | 23.704 | 2.699 | 85.969 | 1.00 | 45.09 | T | C |
| ATOM | 4439 | CG | ASP | T | 178 | 22.462 | 1.935 | 85.572 | 1.00 | 45.52 | T | C |
| ATOM | 4440 | OD1 | ASP | T | 178 | 22.561 | 0.737 | 85.367 | 1.00 | 46.53 | T | O |
| ATOM | 4441 | OD2 | ASP | T | 178 | 21.402 | 2.543 | 85.480 | 1.00 | 47.77 | T | O |
| ATOM | 4442 | N | VAL | T | 179 | 24.630 | 5.447 | 87.463 | 1.00 | 51.00 | T | N |
| ATOM | 4443 | CA | VAL | T | 179 | 25.709 | 6.158 | 88.138 | 1.00 | 54.37 | T | C |
| ATOM | 4444 | C | VAL | T | 179 | 25.697 | 5.894 | 89.638 | 1.00 | 57.41 | T | C |
| ATOM | 4445 | O | VAL | T | 179 | 24.634 | 5.808 | 90.257 | 1.00 | 58.33 | T | O |
| ATOM | 4446 | CB | VAL | T | 179 | 25.610 | 7.684 | 87.912 | 1.00 | 53.68 | T | C |
| ATOM | 4447 | CG1 | VAL | T | 179 | 25.755 | 8.002 | 86.434 | 1.00 | 54.55 | T | C |
| ATOM | 4448 | CG2 | VAL | T | 179 | 24.285 | 8.206 | 88.445 | 1.00 | 53.15 | T | C |
| ATOM | 4449 | N | ASP | T | 180 | 26.884 | 5.760 | 90.218 | 1.00 | 60.20 | T | N |
| ATOM | 4450 | CA | ASP | T | 180 | 27.008 | 5.526 | 91.649 | 1.00 | 63.22 | T | C |
| ATOM | 4451 | C | ASP | T | 180 | 26.787 | 6.854 | 92.363 | 1.00 | 64.55 | T | C |
| ATOM | 4452 | O | ASP | T | 180 | 27.554 | 7.800 | 92.178 | 1.00 | 64.55 | T | O |
| ATOM | 4453 | CB | ASP | T | 180 | 28.398 | 4.974 | 91.981 | 1.00 | 65.14 | T | C |
| ATOM | 4454 | CG | ASP | T | 180 | 28.659 | 3.620 | 91.339 | 1.00 | 67.56 | T | C |
| ATOM | 4455 | OD1 | ASP | T | 180 | 28.706 | 3.545 | 90.113 | 1.00 | 69.02 | T | O |
| ATOM | 4456 | OD2 | ASP | T | 180 | 28.812 | 2.641 | 92.072 | 1.00 | 69.35 | T | O |
| ATOM | 4457 | N | LYS | T | 181 | 25.730 | 6.924 | 93.169 | 1.00 | 66.14 | T | N |
| ATOM | 4458 | CA | LYS | T | 181 | 25.400 | 8.145 | 93.900 | 1.00 | 66.70 | T | C |
| ATOM | 4459 | C | LYS | T | 181 | 26.589 | 8.693 | 94.679 | 1.00 | 66.19 | T | C |
| ATOM | 4460 | O | LYS | T | 181 | 27.464 | 7.941 | 95.110 | 1.00 | 66.44 | T | O |
| ATOM | 4461 | CB | LYS | T | 181 | 24.230 | 7.895 | 94.858 | 1.00 | 68.20 | T | C |
| ATOM | 4462 | CG | LYS | T | 181 | 22.910 | 7.573 | 94.166 | 1.00 | 70.66 | T | C |
| ATOM | 4463 | CD | LYS | T | 181 | 21.747 | 7.534 | 95.154 | 1.00 | 71.98 | T | C |

-continued

| | | | | | | | | | | | |
|---|---|---|---|---|---|---|---|---|---|---|---|
| ATOM | 4464 | CE | LYS | T | 181 | 21.915 | 6.434 | 96.194 | 1.00 | 73.05 | T | C |
| ATOM | 4465 | NZ | LYS | T | 181 | 21.906 | 5.071 | 95.589 | 1.00 | 74.30 | T | N |
| ATOM | 4466 | N | GLY | T | 182 | 26.613 | 10.011 | 94.851 | 1.00 | 65.88 | T | N |
| ATOM | 4467 | CA | GLY | T | 182 | 27.698 | 10.647 | 95.578 | 1.00 | 65.07 | T | C |
| ATOM | 4468 | C | GLY | T | 182 | 29.030 | 10.580 | 94.856 | 1.00 | 64.52 | T | C |
| ATOM | 4469 | O | GLY | T | 182 | 30.085 | 10.552 | 95.488 | 1.00 | 64.76 | T | O |
| ATOM | 4470 | N | GLU | T | 183 | 28.985 | 10.558 | 93.528 | 1.00 | 63.96 | T | N |
| ATOM | 4471 | CA | GLU | T | 183 | 30.197 | 10.496 | 92.722 | 1.00 | 63.00 | T | C |
| ATOM | 4472 | C | GLU | T | 183 | 30.012 | 11.349 | 91.471 | 1.00 | 60.60 | T | C |
| ATOM | 4473 | O | GLU | T | 183 | 28.948 | 11.336 | 90.854 | 1.00 | 60.74 | T | O |
| ATOM | 4474 | CB | GLU | T | 183 | 30.493 | 9.047 | 92.333 | 1.00 | 65.51 | T | C |
| ATOM | 4475 | CG | GLU | T | 183 | 31.877 | 8.829 | 91.749 | 1.00 | 69.10 | T | C |
| ATOM | 4476 | CD | GLU | T | 183 | 32.986 | 9.080 | 92.755 | 1.00 | 70.99 | T | C |
| ATOM | 4477 | OE1 | GLU | T | 183 | 33.103 | 10.209 | 93.234 | 1.00 | 72.19 | T | O |
| ATOM | 4478 | OE2 | GLU | T | 183 | 33.730 | 8.143 | 93.056 | 1.00 | 71.72 | T | O |
| ATOM | 4479 | N | ASN | T | 184 | 31.052 | 12.089 | 91.100 | 1.00 | 57.69 | T | N |
| ATOM | 4480 | CA | ASN | T | 184 | 30.987 | 12.959 | 89.933 | 1.00 | 54.65 | T | C |
| ATOM | 4481 | C | ASN | T | 184 | 31.475 | 12.282 | 88.654 | 1.00 | 51.10 | T | C |
| ATOM | 4482 | O | ASN | T | 184 | 32.494 | 11.589 | 88.647 | 1.00 | 49.50 | T | O |
| ATOM | 4483 | CB | ASN | T | 184 | 31.797 | 14.236 | 90.185 | 1.00 | 57.28 | T | C |
| ATOM | 4484 | CG | ASN | T | 184 | 31.324 | 14.996 | 91.415 | 1.00 | 59.82 | T | C |
| ATOM | 4485 | OD1 | ASN | T | 184 | 31.448 | 14.517 | 92.545 | 1.00 | 62.30 | T | O |
| ATOM | 4486 | ND2 | ASN | T | 184 | 30.775 | 16.187 | 91.200 | 1.00 | 60.42 | T | N |
| ATOM | 4487 | N | TYR | T | 185 | 30.733 | 12.492 | 87.572 | 1.00 | 46.87 | T | N |
| ATOM | 4488 | CA | TYR | T | 185 | 31.072 | 11.919 | 86.276 | 1.00 | 43.13 | T | C |
| ATOM | 4489 | C | TYR | T | 185 | 31.282 | 13.009 | 85.232 | 1.00 | 40.25 | T | C |
| ATOM | 4490 | O | TYR | T | 185 | 30.614 | 14.042 | 85.257 | 1.00 | 38.63 | T | O |
| ATOM | 4491 | CB | TYR | T | 185 | 29.955 | 10.999 | 85.772 | 1.00 | 42.93 | T | C |
| ATOM | 4492 | CG | TYR | T | 185 | 29.806 | 9.679 | 86.491 | 1.00 | 43.09 | T | C |
| ATOM | 4493 | CD1 | TYR | T | 185 | 29.313 | 9.618 | 87.794 | 1.00 | 43.56 | T | C |
| ATOM | 4494 | CD2 | TYR | T | 185 | 30.126 | 8.483 | 85.852 | 1.00 | 42.77 | T | C |
| ATOM | 4495 | CE1 | TYR | T | 185 | 29.137 | 8.400 | 88.441 | 1.00 | 44.38 | T | C |
| ATOM | 4496 | CE2 | TYR | T | 185 | 29.955 | 7.260 | 86.489 | 1.00 | 44.41 | T | C |
| ATOM | 4497 | CZ | TYR | T | 185 | 29.459 | 7.225 | 87.784 | 1.00 | 44.61 | T | C |
| ATOM | 4498 | OH | TYR | T | 185 | 29.273 | 6.016 | 88.413 | 1.00 | 46.20 | T | O |
| ATOM | 4499 | N | CYS | T | 186 | 32.215 | 12.773 | 84.318 | 1.00 | 37.22 | T | N |
| ATOM | 4500 | CA | CYS | T | 186 | 32.469 | 13.711 | 83.233 | 1.00 | 35.28 | T | C |
| ATOM | 4501 | C | CYS | T | 186 | 32.033 | 12.986 | 81.964 | 1.00 | 33.69 | T | C |
| ATOM | 4502 | O | CYS | T | 186 | 32.113 | 11.757 | 81.884 | 1.00 | 33.01 | T | O |
| ATOM | 4503 | CB | CYS | T | 186 | 33.948 | 14.084 | 83.145 | 1.00 | 34.62 | T | C |
| ATOM | 4504 | SG | CYS | T | 186 | 34.609 | 15.088 | 84.517 | 1.00 | 35.26 | T | S |
| ATOM | 4505 | N | PHE | T | 187 | 31.579 | 13.745 | 80.974 | 1.00 | 31.82 | T | N |
| ATOM | 4506 | CA | PHE | T | 187 | 31.085 | 13.164 | 79.737 | 1.00 | 29.80 | T | C |
| ATOM | 4507 | C | PHE | T | 187 | 31.657 | 13.778 | 78.465 | 1.00 | 28.26 | T | C |
| ATOM | 4508 | O | PHE | T | 187 | 32.121 | 14.918 | 78.451 | 1.00 | 25.87 | T | O |
| ATOM | 4509 | CB | PHE | T | 187 | 29.559 | 13.280 | 79.711 | 1.00 | 31.70 | T | C |
| ATOM | 4510 | CG | PHE | T | 187 | 28.892 | 12.750 | 80.950 | 1.00 | 32.92 | T | C |
| ATOM | 4511 | CD1 | PHE | T | 187 | 28.783 | 11.381 | 81.167 | 1.00 | 32.88 | T | C |
| ATOM | 4512 | CD2 | PHE | T | 187 | 28.401 | 13.623 | 81.919 | 1.00 | 34.37 | T | C |
| ATOM | 4513 | CE1 | PHE | T | 187 | 28.196 | 10.887 | 82.330 | 1.00 | 32.44 | T | C |
| ATOM | 4514 | CE2 | PHE | T | 187 | 27.812 | 13.137 | 83.088 | 1.00 | 33.58 | T | C |
| ATOM | 4515 | CZ | PHE | T | 187 | 27.711 | 11.767 | 83.292 | 1.00 | 33.15 | T | C |
| ATOM | 4516 | N | SER | T | 188 | 31.612 | 12.992 | 77.397 | 1.00 | 27.99 | T | N |
| ATOM | 4517 | CA | SER | T | 188 | 32.079 | 13.406 | 76.083 | 1.00 | 26.65 | T | C |
| ATOM | 4518 | C | SER | T | 188 | 31.324 | 12.557 | 75.071 | 1.00 | 26.06 | T | C |
| ATOM | 4519 | O | SER | T | 188 | 31.268 | 11.335 | 75.203 | 1.00 | 25.10 | T | O |
| ATOM | 4520 | CB | SER | T | 188 | 33.580 | 13.165 | 75.941 | 1.00 | 27.85 | T | C |
| ATOM | 4521 | OG | SER | T | 188 | 34.034 | 13.597 | 74.670 | 1.00 | 28.63 | T | O |
| ATOM | 4522 | N | VAL | T | 189 | 30.737 | 13.200 | 74.068 | 1.00 | 25.94 | T | N |
| ATOM | 4523 | CA | VAL | T | 189 | 29.977 | 12.476 | 73.056 | 1.00 | 25.53 | T | C |
| ATOM | 4524 | C | VAL | T | 189 | 30.585 | 12.579 | 71.667 | 1.00 | 26.44 | T | C |
| ATOM | 4525 | O | VAL | T | 189 | 31.397 | 13.462 | 71.381 | 1.00 | 27.25 | T | O |
| ATOM | 4526 | CB | VAL | T | 189 | 28.510 | 12.967 | 72.986 | 1.00 | 26.62 | T | C |
| ATOM | 4527 | CG1 | VAL | T | 189 | 27.850 | 12.822 | 74.353 | 1.00 | 23.61 | T | C |
| ATOM | 4528 | CG2 | VAL | T | 189 | 28.459 | 14.412 | 72.503 | 1.00 | 25.43 | T | C |
| ATOM | 4529 | N | GLN | T | 190 | 30.160 | 11.677 | 70.794 | 1.00 | 26.03 | T | N |
| ATOM | 4530 | CA | GLN | T | 190 | 30.670 | 11.627 | 69.438 | 1.00 | 25.75 | T | C |
| ATOM | 4531 | C | GLN | T | 190 | 29.562 | 11.173 | 68.495 | 1.00 | 24.90 | T | C |
| ATOM | 4532 | O | GLN | T | 190 | 28.825 | 10.238 | 68.803 | 1.00 | 24.21 | T | O |
| ATOM | 4533 | CB | GLN | T | 190 | 31.845 | 10.651 | 69.415 | 1.00 | 27.57 | T | C |
| ATOM | 4534 | CG | GLN | T | 190 | 32.563 | 10.466 | 68.103 | 1.00 | 29.40 | T | C |
| ATOM | 4535 | CD | GLN | T | 190 | 33.803 | 9.605 | 68.276 | 1.00 | 31.44 | T | C |
| ATOM | 4536 | OE1 | GLN | T | 190 | 33.738 | 8.525 | 68.864 | 1.00 | 32.92 | T | O |
| ATOM | 4537 | NE2 | GLN | T | 190 | 34.937 | 10.079 | 67.770 | 1.00 | 29.76 | T | N |
| ATOM | 4538 | N | ALA | T | 191 | 29.428 | 11.854 | 67.361 | 1.00 | 23.85 | T | N |
| ATOM | 4539 | CA | ALA | T | 191 | 28.415 | 11.496 | 66.374 | 1.00 | 22.47 | T | C |
| ATOM | 4540 | C | ALA | T | 191 | 29.016 | 10.401 | 65.504 | 1.00 | 22.81 | T | C |
| ATOM | 4541 | O | ALA | T | 191 | 30.212 | 10.424 | 65.214 | 1.00 | 22.19 | T | O |
| ATOM | 4542 | CB | ALA | T | 191 | 28.051 | 12.702 | 65.529 | 1.00 | 20.37 | T | C |

-continued

| | | | | | | | | | | | |
|---|---|---|---|---|---|---|---|---|---|---|---|
| ATOM | 4543 | N | VAL | T | 192 | 28.195 | 9.438 | 65.099 | 1.00 | 22.78 | T | N |
| ATOM | 4544 | CA | VAL | T | 192 | 28.684 | 8.332 | 64.286 | 1.00 | 23.06 | T | C |
| ATOM | 4545 | C | VAL | T | 192 | 27.636 | 7.854 | 63.285 | 1.00 | 25.12 | T | C |
| ATOM | 4546 | O | VAL | T | 192 | 26.435 | 7.911 | 63.549 | 1.00 | 25.90 | T | O |
| ATOM | 4547 | CB | VAL | T | 192 | 29.080 | 7.124 | 65.182 | 1.00 | 24.31 | T | C |
| ATOM | 4548 | CG1 | VAL | T | 192 | 29.694 | 6.023 | 64.347 | 1.00 | 23.66 | T | C |
| ATOM | 4549 | CG2 | VAL | T | 192 | 30.051 | 7.564 | 66.272 | 1.00 | 23.45 | T | C |
| ATOM | 4550 | N | ILE | T | 193 | 28.102 | 7.409 | 62.125 | 1.00 | 25.32 | T | N |
| ATOM | 4551 | CA | ILE | T | 193 | 27.233 | 6.856 | 61.098 | 1.00 | 27.61 | T | C |
| ATOM | 4552 | C | ILE | T | 193 | 27.881 | 5.519 | 60.772 | 1.00 | 29.11 | T | C |
| ATOM | 4553 | O | ILE | T | 193 | 28.734 | 5.429 | 59.887 | 1.00 | 31.58 | T | O |
| ATOM | 4554 | CB | ILE | T | 193 | 27.188 | 7.746 | 59.845 | 1.00 | 28.18 | T | C |
| ATOM | 4555 | CG1 | ILE | T | 193 | 26.516 | 9.078 | 60.190 | 1.00 | 27.35 | T | C |
| ATOM | 4556 | CG2 | ILE | T | 193 | 26.420 | 7.039 | 58.734 | 1.00 | 26.33 | T | C |
| ATOM | 4557 | CD1 | ILE | T | 193 | 26.511 | 10.072 | 59.058 | 1.00 | 31.00 | T | C |
| ATOM | 4558 | N | PRO | T | 194 | 27.496 | 4.462 | 61.506 | 1.00 | 29.13 | T | N |
| ATOM | 4559 | CA | PRO | T | 194 | 28.006 | 3.091 | 61.360 | 1.00 | 30.19 | T | C |
| ATOM | 4560 | C | PRO | T | 194 | 28.153 | 2.557 | 59.940 | 1.00 | 29.68 | T | C |
| ATOM | 4561 | O | PRO | T | 194 | 29.168 | 1.954 | 59.605 | 1.00 | 30.22 | T | O |
| ATOM | 4562 | CB | PRO | T | 194 | 27.020 | 2.268 | 62.187 | 1.00 | 29.86 | T | C |
| ATOM | 4563 | CG | PRO | T | 194 | 26.631 | 3.224 | 63.273 | 1.00 | 30.63 | T | C |
| ATOM | 4564 | CD | PRO | T | 194 | 26.402 | 4.501 | 62.493 | 1.00 | 28.23 | T | C |
| ATOM | 4565 | N | SER | T | 195 | 27.142 | 2.773 | 59.109 | 1.00 | 31.11 | T | N |
| ATOM | 4566 | CA | SER | T | 195 | 27.172 | 2.294 | 57.732 | 1.00 | 33.61 | T | C |
| ATOM | 4567 | C | SER | T | 195 | 28.304 | 2.882 | 56.894 | 1.00 | 36.37 | T | C |
| ATOM | 4568 | O | SER | T | 195 | 28.653 | 2.331 | 55.848 | 1.00 | 37.68 | T | O |
| ATOM | 4569 | CB | SER | T | 195 | 25.841 | 2.594 | 57.049 | 1.00 | 33.34 | T | C |
| ATOM | 4570 | OG | SER | T | 195 | 25.592 | 3.987 | 57.025 | 1.00 | 33.89 | T | O |
| ATOM | 4571 | N | ARG | T | 196 | 28.876 | 3.994 | 57.350 | 1.00 | 37.43 | T | N |
| ATOM | 4572 | CA | ARG | T | 196 | 29.956 | 4.654 | 56.626 | 1.00 | 38.17 | T | C |
| ATOM | 4573 | C | ARG | T | 196 | 31.279 | 3.915 | 56.617 | 1.00 | 40.14 | T | C |
| ATOM | 4574 | O | ARG | T | 196 | 31.567 | 3.104 | 57.497 | 1.00 | 39.73 | T | O |
| ATOM | 4575 | CB | ARG | T | 196 | 30.201 | 6.055 | 57.181 | 1.00 | 36.13 | T | C |
| ATOM | 4576 | CG | ARG | T | 196 | 29.241 | 7.107 | 56.686 | 1.00 | 34.25 | T | C |
| ATOM | 4577 | CD | ARG | T | 196 | 29.764 | 8.479 | 57.042 | 1.00 | 33.30 | T | C |
| ATOM | 4578 | NE | ARG | T | 196 | 28.936 | 9.540 | 56.486 | 1.00 | 32.53 | T | N |
| ATOM | 4579 | CZ | ARG | T | 196 | 29.210 | 10.835 | 56.592 | 1.00 | 33.06 | T | C |
| ATOM | 4580 | NH1 | ARG | T | 196 | 30.299 | 11.234 | 57.238 | 1.00 | 30.86 | T | N |
| ATOM | 4581 | NH2 | ARG | T | 196 | 28.397 | 11.730 | 56.048 | 1.00 | 29.51 | T | N |
| ATOM | 4582 | N | THR | T | 197 | 32.082 | 4.227 | 55.604 | 1.00 | 42.50 | T | N |
| ATOM | 4583 | CA | THR | T | 197 | 33.405 | 3.645 | 55.435 | 1.00 | 43.94 | T | C |
| ATOM | 4584 | C | THR | T | 197 | 34.437 | 4.714 | 55.802 | 1.00 | 43.45 | T | C |
| ATOM | 4585 | O | THR | T | 197 | 35.368 | 4.458 | 56.567 | 1.00 | 43.73 | T | O |
| ATOM | 4586 | CB | THR | T | 197 | 33.623 | 3.181 | 53.976 | 1.00 | 45.61 | T | C |
| ATOM | 4587 | OG1 | THR | T | 197 | 33.452 | 4.291 | 53.086 | 1.00 | 48.03 | T | O |
| ATOM | 4588 | CG2 | THR | T | 197 | 32.618 | 2.094 | 53.608 | 1.00 | 46.03 | T | C |
| ATOM | 4589 | N | VAL | T | 198 | 34.254 | 5.917 | 55.263 | 1.00 | 42.98 | T | N |
| ATOM | 4590 | CA | VAL | T | 198 | 35.149 | 7.039 | 55.546 | 1.00 | 41.57 | T | C |
| ATOM | 4591 | C | VAL | T | 198 | 34.383 | 8.062 | 56.371 | 1.00 | 38.54 | T | C |
| ATOM | 4592 | O | VAL | T | 198 | 33.159 | 8.109 | 56.308 | 1.00 | 38.93 | T | O |
| ATOM | 4593 | CB | VAL | T | 198 | 35.641 | 7.720 | 54.250 | 1.00 | 42.24 | T | C |
| ATOM | 4594 | CG1 | VAL | T | 198 | 36.388 | 6.713 | 53.390 | 1.00 | 43.81 | T | C |
| ATOM | 4595 | CG2 | VAL | T | 198 | 34.461 | 8.318 | 53.490 | 1.00 | 41.73 | T | C |
| ATOM | 4596 | N | ASN | T | 199 | 35.104 | 8.882 | 57.133 | 1.00 | 36.53 | T | N |
| ATOM | 4597 | CA | ASN | T | 199 | 34.483 | 9.898 | 57.985 | 1.00 | 34.68 | T | C |
| ATOM | 4598 | C | ASN | T | 199 | 33.289 | 9.315 | 58.741 | 1.00 | 32.52 | T | C |
| ATOM | 4599 | O | ASN | T | 199 | 32.201 | 9.884 | 58.732 | 1.00 | 31.11 | T | O |
| ATOM | 4600 | CB | ASN | T | 199 | 34.016 | 11.092 | 57.147 | 1.00 | 36.34 | T | C |
| ATOM | 4601 | CG | ASN | T | 199 | 35.137 | 11.723 | 56.352 | 1.00 | 38.20 | T | C |
| ATOM | 4602 | OD1 | ASN | T | 199 | 36.227 | 11.962 | 56.872 | 1.00 | 39.82 | T | O |
| ATOM | 4603 | ND2 | ASN | T | 199 | 34.871 | 12.012 | 55.083 | 1.00 | 38.88 | T | N |
| ATOM | 4604 | N | ARG | T | 200 | 33.497 | 8.183 | 59.404 | 1.00 | 32.29 | T | N |
| ATOM | 4605 | CA | ARG | T | 200 | 32.422 | 7.528 | 60.137 | 1.00 | 32.10 | T | C |
| ATOM | 4606 | C | ARG | T | 200 | 32.098 | 8.205 | 61.459 | 1.00 | 29.78 | T | C |
| ATOM | 4607 | O | ARG | T | 200 | 30.988 | 8.077 | 61.968 | 1.00 | 29.26 | T | O |
| ATOM | 4608 | CB | ARG | T | 200 | 32.769 | 6.053 | 60.390 | 1.00 | 34.20 | T | C |
| ATOM | 4609 | CG | ARG | T | 200 | 33.974 | 5.832 | 61.294 | 1.00 | 40.10 | T | C |
| ATOM | 4610 | CD | ARG | T | 200 | 34.403 | 4.361 | 61.385 | 1.00 | 44.11 | T | C |
| ATOM | 4611 | NE | ARG | T | 200 | 33.484 | 3.524 | 62.159 | 1.00 | 46.39 | T | N |
| ATOM | 4612 | CZ | ARG | T | 200 | 32.419 | 2.896 | 61.665 | 1.00 | 46.92 | T | C |
| ATOM | 4613 | NH1 | ARG | T | 200 | 32.113 | 2.992 | 60.378 | 1.00 | 46.68 | T | N |
| ATOM | 4614 | NH2 | ARG | T | 200 | 31.656 | 2.161 | 62.465 | 1.00 | 47.08 | T | N |
| ATOM | 4615 | N | LYS | T | 201 | 33.053 | 8.942 | 62.008 | 1.00 | 28.96 | T | N |
| ATOM | 4616 | CA | LYS | T | 201 | 32.831 | 9.589 | 63.292 | 1.00 | 28.86 | T | C |
| ATOM | 4617 | C | LYS | T | 201 | 33.277 | 11.042 | 63.325 | 1.00 | 26.57 | T | C |
| ATOM | 4618 | O | LYS | T | 201 | 34.194 | 11.441 | 62.611 | 1.00 | 26.41 | T | O |
| ATOM | 4619 | CB | LYS | T | 201 | 33.576 | 8.814 | 64.384 | 1.00 | 30.67 | T | C |
| ATOM | 4620 | CG | LYS | T | 201 | 33.328 | 7.319 | 64.358 | 1.00 | 33.65 | T | C |
| ATOM | 4621 | CD | LYS | T | 201 | 34.438 | 6.565 | 65.065 | 1.00 | 38.71 | T | C |

-continued

| | | | | | | | | | | | |
|---|---|---|---|---|---|---|---|---|---|---|---|
| ATOM | 4622 | CE | LYS | T | 201 | 34.446 | 6.850 | 66.550 | 1.00 | 42.37 | T | C |
| ATOM | 4623 | NZ | LYS | T | 201 | 33.187 | 6.371 | 67.184 | 1.00 | 45.63 | T | N |
| ATOM | 4624 | N | SER | T | 202 | 32.614 | 11.830 | 64.161 | 1.00 | 25.68 | T | N |
| ATOM | 4625 | CA | SER | T | 202 | 32.967 | 13.233 | 64.326 | 1.00 | 26.09 | T | C |
| ATOM | 4626 | C | SER | T | 202 | 34.038 | 13.257 | 65.415 | 1.00 | 25.74 | T | C |
| ATOM | 4627 | O | SER | T | 202 | 34.424 | 12.212 | 65.929 | 1.00 | 25.97 | T | O |
| ATOM | 4628 | CB | SER | T | 202 | 31.754 | 14.033 | 64.803 | 1.00 | 25.44 | T | C |
| ATOM | 4629 | OG | SER | T | 202 | 31.439 | 13.699 | 66.145 | 1.00 | 24.76 | T | O |
| ATOM | 4630 | N | THR | T | 203 | 34.523 | 14.441 | 65.764 | 1.00 | 25.64 | T | N |
| ATOM | 4631 | CA | THR | T | 203 | 35.507 | 14.545 | 66.829 | 1.00 | 26.70 | T | C |
| ATOM | 4632 | C | THR | T | 203 | 34.734 | 14.575 | 68.150 | 1.00 | 26.56 | T | C |
| ATOM | 4633 | O | THR | T | 203 | 33.542 | 14.890 | 68.170 | 1.00 | 26.32 | T | O |
| ATOM | 4634 | CB | THR | T | 203 | 36.333 | 15.839 | 66.709 | 1.00 | 27.27 | T | C |
| ATOM | 4635 | OG1 | THR | T | 203 | 35.447 | 16.964 | 66.678 | 1.00 | 29.25 | T | O |
| ATOM | 4636 | CG2 | THR | T | 203 | 37.178 | 15.821 | 65.441 | 1.00 | 26.74 | T | C |
| ATOM | 4637 | N | ASP | T | 204 | 35.407 | 14.244 | 69.247 | 1.00 | 26.24 | T | N |
| ATOM | 4638 | CA | ASP | T | 204 | 34.775 | 14.245 | 70.561 | 1.00 | 25.07 | T | C |
| ATOM | 4639 | C | ASP | T | 204 | 34.287 | 15.648 | 70.904 | 1.00 | 23.20 | T | C |
| ATOM | 4640 | O | ASP | T | 204 | 34.926 | 16.638 | 70.557 | 1.00 | 22.85 | T | O |
| ATOM | 4641 | CB | ASP | T | 204 | 35.774 | 13.781 | 71.629 | 1.00 | 26.47 | T | C |
| ATOM | 4642 | CG | ASP | T | 204 | 36.322 | 12.384 | 71.360 | 1.00 | 28.96 | T | C |
| ATOM | 4643 | OD1 | ASP | T | 204 | 35.559 | 11.414 | 71.438 | 1.00 | 28.17 | T | O |
| ATOM | 4644 | OD2 | ASP | T | 204 | 37.515 | 12.269 | 71.071 | 1.00 | 31.64 | T | O |
| ATOM | 4645 | N | SER | T | 205 | 33.147 | 15.728 | 71.580 | 1.00 | 22.21 | T | N |
| ATOM | 4646 | CA | SER | T | 205 | 32.580 | 17.009 | 71.994 | 1.00 | 21.13 | T | C |
| ATOM | 4647 | C | SER | T | 205 | 33.383 | 17.532 | 73.179 | 1.00 | 20.53 | T | C |
| ATOM | 4648 | O | SER | T | 205 | 34.233 | 16.828 | 73.720 | 1.00 | 21.01 | T | O |
| ATOM | 4649 | CB | SER | T | 205 | 31.136 | 16.818 | 72.458 | 1.00 | 24.15 | T | C |
| ATOM | 4650 | OG | SER | T | 205 | 31.104 | 16.109 | 73.694 | 1.00 | 22.18 | T | O |
| ATOM | 4651 | N | PRO | T | 206 | 33.141 | 18.786 | 73.583 | 1.00 | 20.24 | T | N |
| ATOM | 4652 | CA | PRO | T | 206 | 33.893 | 19.294 | 74.733 | 1.00 | 21.58 | T | C |
| ATOM | 4653 | C | PRO | T | 206 | 33.465 | 18.464 | 75.947 | 1.00 | 23.90 | T | C |
| ATOM | 4654 | O | PRO | T | 206 | 32.334 | 17.971 | 75.998 | 1.00 | 23.99 | T | O |
| ATOM | 4655 | CB | PRO | T | 206 | 33.426 | 20.740 | 74.840 | 1.00 | 19.27 | T | C |
| ATOM | 4656 | CG | PRO | T | 206 | 33.146 | 21.107 | 73.403 | 1.00 | 20.23 | T | C |
| ATOM | 4657 | CD | PRO | T | 206 | 32.434 | 19.875 | 72.884 | 1.00 | 18.56 | T | C |
| ATOM | 4658 | N | VAL | T | 207 | 34.360 | 18.302 | 76.912 | 1.00 | 24.52 | T | N |
| ATOM | 4659 | CA | VAL | T | 207 | 34.052 | 17.528 | 78.109 | 1.00 | 26.63 | T | C |
| ATOM | 4660 | C | VAL | T | 207 | 33.169 | 18.319 | 79.072 | 1.00 | 28.46 | T | C |
| ATOM | 4661 | O | VAL | T | 207 | 33.402 | 19.499 | 79.320 | 1.00 | 29.61 | T | O |
| ATOM | 4662 | CB | VAL | T | 207 | 35.348 | 17.108 | 78.851 | 1.00 | 25.30 | T | C |
| ATOM | 4663 | CG1 | VAL | T | 207 | 35.004 | 16.306 | 80.105 | 1.00 | 25.46 | T | C |
| ATOM | 4664 | CG2 | VAL | T | 207 | 36.235 | 16.283 | 77.930 | 1.00 | 23.54 | T | C |
| ATOM | 4665 | N | GLU | T | 208 | 32.144 | 17.660 | 79.598 | 1.00 | 31.26 | T | N |
| ATOM | 4666 | CA | GLU | T | 208 | 31.231 | 18.269 | 80.556 | 1.00 | 32.65 | T | C |
| ATOM | 4667 | C | GLU | T | 208 | 31.174 | 17.371 | 81.785 | 1.00 | 34.52 | T | C |
| ATOM | 4668 | O | GLU | T | 208 | 31.032 | 16.161 | 81.662 | 1.00 | 33.84 | T | O |
| ATOM | 4669 | CB | GLU | T | 208 | 29.832 | 18.407 | 79.953 | 1.00 | 33.49 | T | C |
| ATOM | 4670 | CG | GLU | T | 208 | 29.728 | 19.482 | 78.893 | 1.00 | 37.75 | T | C |
| ATOM | 4671 | CD | GLU | T | 208 | 30.128 | 20.844 | 79.422 | 1.00 | 40.28 | T | C |
| ATOM | 4672 | OE1 | GLU | T | 208 | 29.501 | 21.309 | 80.373 | 1.00 | 42.72 | T | O |
| ATOM | 4673 | OE2 | GLU | T | 208 | 31.067 | 21.435 | 78.887 | 1.00 | 42.16 | T | O |
| ATOM | 4674 | N | CYS | T | 209 | 31.296 | 17.957 | 82.970 | 1.00 | 36.17 | T | N |
| ATOM | 4675 | CA | CYS | T | 209 | 31.252 | 17.170 | 84.196 | 1.00 | 38.20 | T | C |
| ATOM | 4676 | C | CYS | T | 209 | 30.084 | 17.610 | 85.068 | 1.00 | 39.82 | T | C |
| ATOM | 4677 | O | CYS | T | 209 | 29.734 | 18.790 | 85.110 | 1.00 | 39.53 | T | O |
| ATOM | 4678 | CB | CYS | T | 209 | 32.555 | 17.323 | 84.984 | 1.00 | 37.29 | T | C |
| ATOM | 4679 | SG | CYS | T | 209 | 34.098 | 17.006 | 84.069 | 1.00 | 36.18 | T | S |
| ATOM | 4680 | N | MET | T | 210 | 29.481 | 16.656 | 85.767 | 1.00 | 42.37 | T | N |
| ATOM | 4681 | CA | MET | T | 210 | 28.354 | 16.964 | 86.635 | 1.00 | 44.92 | T | C |
| ATOM | 4682 | C | MET | T | 210 | 28.859 | 17.451 | 87.987 | 1.00 | 46.67 | T | C |
| ATOM | 4683 | O | MET | T | 210 | 28.359 | 18.480 | 88.460 | 1.00 | 48.11 | T | O |
| ATOM | 4684 | CB | MET | T | 210 | 27.463 | 15.730 | 86.805 | 1.00 | 46.14 | T | C |
| ATOM | 4685 | CG | MET | T | 210 | 28.119 | 14.558 | 87.511 | 1.00 | 48.38 | T | C |
| ATOM | 4686 | SD | MET | T | 210 | 27.134 | 13.050 | 87.366 | 1.00 | 51.31 | T | S |
| ATOM | 4687 | CE | MET | T | 210 | 25.678 | 13.526 | 88.260 | 1.00 | 50.81 | T | C |
| ATOM | 4688 | OT | MET | T | 210 | 29.743 | 16.798 | 88.541 | 1.00 | 47.67 | T | O |
| ATOM | 4689 | CA | CA | C | 1 | 8.112 | 6.415 | 3.761 | 1.00 | 33.86 | C | C |
| ATOM | 4690 | CA | CA | C | 2 | 36.518 | 26.475 | 68.287 | 1.00 | 30.83 | C | C |
| ATOM | 4691 | CA | CA | C | 3 | 48.458 | 24.377 | 90.635 | 1.00 | 32.15 | C | C |
| ATOM | 4692 | CA | CA | C | 4 | 44.635 | 23.829 | 91.244 | 1.00 | 29.14 | C | C |
| ATOM | 4693 | CA | CA | C | 5 | 43.916 | 27.507 | 90.375 | 1.00 | 26.38 | C | C |
| ATOM | 4694 | CA | CA | C | 6 | 41.663 | 30.293 | 91.119 | 1.00 | 31.82 | C | C |
| ATOM | 4695 | CA | CA | C | 7 | 29.812 | 29.126 | 89.307 | 1.00 | 52.40 | C | C |
| ATOM | 4696 | CA | CA | C | 8 | 37.684 | 33.223 | 91.461 | 1.00 | 43.18 | C | C |
| ATOM | 4697 | CA | CA | C | 9 | 50.866 | 20.912 | 89.468 | 1.00 | 40.17 | C | C |
| ATOM | 4698 | C11 | 267 | I | 1 | 35.873 | 7.021 | 10.051 | 1.00 | 13.34 | I | C |
| ATOM | 4699 | O2 | 267 | I | 1 | 35.030 | 7.274 | 10.906 | 1.00 | 12.12 | I | O |
| ATOM | 4700 | N4 | 267 | I | 1 | 35.755 | 7.412 | 8.778 | 1.00 | 14.34 | I | N |

-continued

| | | | | | | | | | | | |
|---|---|---|---|---|---|---|---|---|---|---|---|
| ATOM | 4701 | C10 | 267 | I | 1 | 34.583 | 8.190 | 8.382 | 1.00 | 15.61 | I | C |
| ATOM | 4702 | C13 | 267 | I | 1 | 34.631 | 8.529 | 6.895 | 1.00 | 13.61 | I | C |
| ATOM | 4703 | C14 | 267 | I | 1 | 35.845 | 9.376 | 6.522 | 1.00 | 13.67 | I | C |
| ATOM | 4704 | C9 | 267 | I | 1 | 33.296 | 7.419 | 8.715 | 1.00 | 14.50 | I | C |
| ATOM | 4705 | O1 | 267 | I | 1 | 33.219 | 6.200 | 8.578 | 1.00 | 14.69 | I | O |
| ATOM | 4706 | N3 | 267 | I | 1 | 32.293 | 8.206 | 9.171 | 1.00 | 12.44 | I | N |
| ATOM | 4707 | C8 | 267 | I | 1 | 31.028 | 7.571 | 9.430 | 1.00 | 10.00 | I | C |
| ATOM | 4708 | C6 | 267 | I | 1 | 31.561 | 6.344 | 11.579 | 1.00 | 10.55 | I | C |
| ATOM | 4709 | C7 | 267 | I | 1 | 31.365 | 6.163 | 12.955 | 1.00 | 12.08 | I | C |
| ATOM | 4710 | C2 | 267 | I | 1 | 30.416 | 6.941 | 13.646 | 1.00 | 12.47 | I | C |
| ATOM | 4711 | C3 | 267 | I | 1 | 29.621 | 7.867 | 12.916 | 1.00 | 12.14 | I | C |
| ATOM | 4712 | C4 | 267 | I | 1 | 29.820 | 8.053 | 11.556 | 1.00 | 10.96 | I | C |
| ATOM | 4713 | C5 | 267 | I | 1 | 30.798 | 7.306 | 10.882 | 1.00 | 12.08 | I | C |
| ATOM | 4714 | C1 | 267 | I | 1 | 30.241 | 6.805 | 15.109 | 1.00 | 12.72 | I | C |
| ATOM | 4715 | N1 | 267 | I | 1 | 30.857 | 5.861 | 15.820 | 1.00 | 11.13 | I | N |
| ATOM | 4716 | C15 | 267 | I | 1 | 35.718 | 9.758 | 5.051 | 1.00 | 12.95 | I | C |
| ATOM | 4717 | O5 | 267 | I | 1 | 35.473 | 8.916 | 4.192 | 1.00 | 17.02 | I | O |
| ATOM | 4718 | N6 | 267 | I | 1 | 35.851 | 11.064 | 4.801 | 1.00 | 14.07 | I | N |
| ATOM | 4719 | C16 | 267 | I | 1 | 38.333 | 7.104 | 10.843 | 1.00 | 14.85 | I | C |
| ATOM | 4720 | N5 | 267 | I | 1 | 36.894 | 5.189 | 11.391 | 1.00 | 13.27 | I | N |
| ATOM | 4721 | C12 | 267 | I | 1 | 37.171 | 6.192 | 10.381 | 1.00 | 15.61 | I | C |
| ATOM | 4722 | S1 | 267 | I | 1 | 36.148 | 3.708 | 10.947 | 1.00 | 18.24 | I | S |
| ATOM | 4723 | O4 | 267 | I | 1 | 36.273 | 2.919 | 12.112 | 1.00 | 17.08 | I | O |
| ATOM | 4724 | O3 | 267 | I | 1 | 36.874 | 3.315 | 9.787 | 1.00 | 17.15 | I | O |
| ATOM | 4725 | C25 | 267 | I | 1 | 34.411 | 3.917 | 10.599 | 1.00 | 17.32 | I | C |
| ATOM | 4726 | C26 | 267 | I | 1 | 33.721 | 2.520 | 10.336 | 1.00 | 16.35 | I | C |
| ATOM | 4727 | N2 | 267 | I | 1 | 29.433 | 7.615 | 15.770 | 1.00 | 11.70 | I | N |
| ATOM | 4728 | O6 | 267 | I | 1 | 32.719 | 2.228 | 10.988 | 0.00 | 16.69 | I | O |
| ATOM | 4729 | O7 | 267 | I | 1 | 34.205 | 1.773 | 9.486 | 0.00 | 16.69 | I | O |
| ATOM | 4730 | C21 | 267 | I | 1 | 41.910 | 4.359 | 13.982 | 0.00 | 15.00 | I | C |
| ATOM | 4731 | C22 | 267 | I | 1 | 42.331 | 4.560 | 12.625 | 0.00 | 14.96 | I | C |
| ATOM | 4732 | C23 | 267 | I | 1 | 41.530 | 5.218 | 11.673 | 0.00 | 14.93 | I | C |
| ATOM | 4733 | C18 | 267 | I | 1 | 40.239 | 5.718 | 12.078 | 0.00 | 14.96 | I | C |
| ATOM | 4734 | C19 | 267 | I | 1 | 39.817 | 5.521 | 13.406 | 0.00 | 14.96 | I | C |
| ATOM | 4735 | C20 | 267 | I | 1 | 40.627 | 4.846 | 14.378 | 0.00 | 14.99 | I | C |
| ATOM | 4736 | N7 | 267 | I | 1 | 41.683 | 5.545 | 10.332 | 0.00 | 14.91 | I | N |
| ATOM | 4737 | C24 | 267 | I | 1 | 40.585 | 6.212 | 9.888 | 0.00 | 14.90 | I | C |
| ATOM | 4738 | C17 | 267 | I | 1 | 39.655 | 6.359 | 10.924 | 0.00 | 15.02 | I | C |
| ATOM | 4739 | OH2 | WAT | W | 1 | 9.820 | 12.056 | 12.743 | 1.00 | 14.47 | W | O |
| ATOM | 4740 | OH2 | WAT | W | 2 | 21.093 | 10.398 | 10.275 | 1.00 | 7.31 | W | O |
| ATOM | 4741 | OH2 | WAT | W | 3 | 32.300 | 19.309 | 24.267 | 1.00 | 9.92 | W | O |
| ATOM | 4742 | OH2 | WAT | W | 4 | 24.662 | 17.645 | 24.602 | 1.00 | 12.63 | W | O |
| ATOM | 4743 | OH2 | WAT | W | 5 | 10.321 | 9.426 | 13.052 | 1.00 | 13.81 | W | O |
| ATOM | 4744 | OH2 | WAT | W | 6 | 12.733 | 19.635 | −6.440 | 1.00 | 7.53 | W | O |
| ATOM | 4745 | OH2 | WAT | W | 7 | 33.048 | 14.954 | 0.011 | 1.00 | 12.00 | W | O |
| ATOM | 4746 | OH2 | WAT | W | 8 | 27.807 | 23.167 | 18.401 | 1.00 | 6.67 | W | O |
| ATOM | 4747 | OH2 | WAT | W | 9 | 29.296 | 10.590 | 15.340 | 1.00 | 10.47 | W | O |
| ATOM | 4748 | OH2 | WAT | W | 10 | 6.543 | 11.732 | 8.949 | 1.00 | 8.19 | W | O |
| ATOM | 4749 | OH2 | WAT | W | 11 | 34.705 | 16.831 | 33.297 | 1.00 | 18.07 | W | O |
| ATOM | 4750 | OH2 | WAT | W | 12 | 27.522 | 23.545 | 21.120 | 1.00 | 12.95 | W | O |
| ATOM | 4751 | OH2 | WAT | W | 13 | 41.017 | 11.884 | 9.347 | 1.00 | 16.81 | W | O |
| ATOM | 4752 | OH2 | WAT | W | 14 | 29.276 | 13.613 | 29.743 | 1.00 | 19.27 | W | O |
| ATOM | 4753 | OH2 | WAT | W | 15 | 40.567 | 16.246 | 35.000 | 1.00 | 18.02 | W | O |
| ATOM | 4754 | OH2 | WAT | W | 16 | 25.516 | 15.164 | 23.686 | 1.00 | 10.81 | W | O |
| ATOM | 4755 | OH2 | WAT | W | 17 | 41.029 | 15.604 | 9.020 | 1.00 | 16.62 | W | O |
| ATOM | 4756 | OH2 | WAT | W | 18 | 8.271 | 20.932 | 21.125 | 1.00 | 20.96 | W | O |
| ATOM | 4757 | OH2 | WAT | W | 19 | 34.181 | 16.292 | 63.608 | 1.00 | 25.92 | W | O |
| ATOM | 4758 | OH2 | WAT | W | 20 | 34.774 | 18.566 | 11.988 | 1.00 | 9.54 | W | O |
| ATOM | 4759 | OH2 | WAT | W | 21 | 14.232 | 27.939 | 10.813 | 1.00 | 20.22 | W | O |
| ATOM | 4760 | OH2 | WAT | W | 22 | 25.655 | 24.820 | 17.299 | 1.00 | 8.83 | W | O |
| ATOM | 4761 | OH2 | WAT | W | 23 | 33.138 | 16.360 | 29.823 | 1.00 | 14.28 | W | O |
| ATOM | 4762 | OH2 | WAT | W | 24 | 7.284 | 23.996 | 14.905 | 1.00 | 15.88 | W | O |
| ATOM | 4763 | OH2 | WAT | W | 25 | 22.950 | 17.820 | 10.222 | 1.00 | 11.07 | W | O |
| ATOM | 4764 | OH2 | WAT | W | 26 | 6.303 | 9.578 | 6.184 | 1.00 | 13.56 | W | O |
| ATOM | 4765 | OH2 | WAT | W | 27 | 20.934 | 2.177 | 72.570 | 1.00 | 20.66 | W | O |
| ATOM | 4766 | OH2 | WAT | W | 28 | 5.602 | 17.093 | 14.953 | 1.00 | 13.98 | W | O |
| ATOM | 4767 | OH2 | WAT | W | 29 | 25.530 | 19.981 | 23.409 | 1.00 | 11.61 | W | O |
| ATOM | 4768 | OH2 | WAT | W | 30 | 36.724 | 8.439 | 21.083 | 1.00 | 16.21 | W | O |
| ATOM | 4769 | OH2 | WAT | W | 31 | 5.701 | 26.405 | 4.405 | 1.00 | 23.01 | W | O |
| ATOM | 4770 | OH2 | WAT | W | 32 | 6.195 | 19.147 | −1.275 | 1.00 | 25.93 | W | O |
| ATOM | 4771 | OH2 | WAT | W | 33 | 27.238 | 18.873 | 27.707 | 1.00 | 12.95 | W | O |
| ATOM | 4772 | OH2 | WAT | W | 34 | 10.019 | 19.300 | 22.404 | 1.00 | 20.89 | W | O |
| ATOM | 4773 | OH2 | WAT | W | 35 | 18.660 | 17.642 | 24.646 | 1.00 | 12.31 | W | O |
| ATOM | 4774 | OH2 | WAT | W | 36 | 27.000 | 8.766 | −7.917 | 1.00 | 12.95 | W | O |
| ATOM | 4775 | OH2 | WAT | W | 37 | 20.499 | 17.083 | 29.622 | 1.00 | 11.97 | W | O |
| ATOM | 4776 | OH2 | WAT | W | 38 | 37.642 | 19.584 | 20.497 | 1.00 | 7.27 | W | O |
| ATOM | 4777 | OH2 | WAT | W | 39 | 28.905 | 6.346 | 21.635 | 1.00 | 15.10 | W | O |
| ATOM | 4778 | OH2 | WAT | W | 40 | 19.368 | 3.656 | 12.781 | 1.00 | 8.09 | W | O |
| ATOM | 4779 | OH2 | WAT | W | 41 | 29.481 | 7.328 | 6.028 | 1.00 | 18.76 | W | O |

-continued

| | | | | | | | | | | | |
|---|---|---|---|---|---|---|---|---|---|---|---|
| ATOM | 4780 | OH2 | WAT | W | 42 | 31.853 | 30.028 | 11.019 | 1.00 | 11.55 | W | O |
| ATOM | 4781 | OH2 | WAT | W | 43 | 30.815 | 5.845 | 28.771 | 1.00 | 18.94 | W | O |
| ATOM | 4782 | OH2 | WAT | W | 44 | 7.816 | 13.593 | 10.596 | 1.00 | 12.04 | W | O |
| ATOM | 4783 | OH2 | WAT | W | 45 | 20.264 | 8.396 | 8.487 | 1.00 | 14.53 | W | O |
| ATOM | 4784 | OH2 | WAT | W | 46 | 12.987 | 12.795 | 6.319 | 1.00 | 13.34 | W | O |
| ATOM | 4785 | OH2 | WAT | W | 47 | 23.619 | 18.649 | 37.291 | 1.00 | 20.21 | W | O |
| ATOM | 4786 | OH2 | WAT | W | 48 | 18.254 | 6.979 | 24.266 | 1.00 | 20.22 | W | O |
| ATOM | 4787 | OH2 | WAT | W | 49 | 25.729 | 5.521 | 54.904 | 1.00 | 29.74 | W | O |
| ATOM | 4788 | OH2 | WAT | W | 50 | 33.846 | 31.445 | 49.694 | 1.00 | 24.01 | W | O |
| ATOM | 4789 | OH2 | WAT | W | 51 | 1.203 | 22.687 | 6.517 | 1.00 | 15.75 | W | O |
| ATOM | 4790 | OH2 | WAT | W | 52 | 18.931 | 1.545 | 17.773 | 1.00 | 11.88 | W | O |
| ATOM | 4791 | OH2 | WAT | W | 53 | 39.260 | 17.313 | 6.209 | 1.00 | 11.31 | W | O |
| ATOM | 4792 | OH2 | WAT | W | 54 | 11.858 | 29.857 | 13.454 | 1.00 | 17.79 | W | O |
| ATOM | 4793 | OH2 | WAT | W | 55 | 39.076 | 22.410 | −1.485 | 1.00 | 9.18 | W | O |
| ATOM | 4794 | OH2 | WAT | W | 56 | 26.485 | 33.714 | 15.886 | 1.00 | 19.67 | W | O |
| ATOM | 4795 | OH2 | WAT | W | 57 | 37.050 | 20.790 | 0.260 | 1.00 | 15.14 | W | O |
| ATOM | 4796 | OH2 | WAT | W | 58 | 27.797 | 26.672 | 32.268 | 1.00 | 28.03 | W | O |
| ATOM | 4797 | OH2 | WAT | W | 59 | 18.324 | 13.670 | 16.592 | 1.00 | 14.91 | W | O |
| ATOM | 4798 | OH2 | WAT | W | 60 | 17.408 | 28.124 | 11.960 | 1.00 | 22.12 | W | O |
| ATOM | 4799 | OH2 | WAT | W | 61 | 30.927 | 20.411 | 26.562 | 1.00 | 11.62 | W | O |
| ATOM | 4800 | OH2 | WAT | W | 62 | 9.546 | 29.554 | 23.251 | 1.00 | 25.92 | W | O |
| ATOM | 4801 | OH2 | WAT | W | 63 | 19.679 | 15.880 | 80.100 | 1.00 | 32.98 | W | O |
| ATOM | 4802 | OH2 | WAT | W | 64 | 32.325 | 25.087 | 22.495 | 1.00 | 35.63 | W | O |
| ATOM | 4803 | OH2 | WAT | W | 65 | 30.276 | 24.296 | 21.082 | 1.00 | 13.13 | W | O |
| ATOM | 4804 | OH2 | WAT | W | 66 | 13.503 | −0.011 | 12.178 | 1.00 | 16.78 | W | O |
| ATOM | 4805 | OH2 | WAT | W | 67 | 32.301 | 3.759 | 18.886 | 1.00 | 15.31 | W | O |
| ATOM | 4806 | OH2 | WAT | W | 68 | 17.841 | 15.087 | 24.535 | 1.00 | 17.04 | W | O |
| ATOM | 4807 | OH2 | WAT | W | 69 | 32.212 | −1.864 | 17.231 | 1.00 | 33.57 | W | O |
| ATOM | 4808 | OH2 | WAT | W | 70 | 31.942 | 25.422 | 24.949 | 1.00 | 14.32 | W | O |
| ATOM | 4809 | OH2 | WAT | W | 71 | 41.741 | 24.676 | 35.656 | 1.00 | 25.77 | W | O |
| ATOM | 4810 | OH2 | WAT | W | 72 | 7.065 | 7.005 | 6.381 | 1.00 | 22.12 | W | O |
| ATOM | 4811 | OH2 | WAT | W | 73 | 30.082 | 19.209 | 75.060 | 1.00 | 21.78 | W | O |
| ATOM | 4812 | OH2 | WAT | W | 74 | 4.031 | 12.254 | −0.177 | 1.00 | 19.44 | W | O |
| ATOM | 4813 | OH2 | WAT | W | 75 | 35.845 | 17.333 | 53.696 | 1.00 | 21.03 | W | O |
| ATOM | 4814 | OH2 | WAT | W | 76 | 36.526 | 20.255 | 76.854 | 1.00 | 17.50 | W | O |
| ATOM | 4815 | OH2 | WAT | W | 77 | 31.251 | 2.379 | 23.047 | 1.00 | 17.45 | W | O |
| ATOM | 4816 | OH2 | WAT | W | 78 | 21.143 | 15.514 | 65.628 | 1.00 | 35.20 | W | O |
| ATOM | 4817 | OH2 | WAT | W | 79 | 25.623 | 18.283 | 68.925 | 1.00 | 23.69 | W | O |
| ATOM | 4818 | OH2 | WAT | W | 80 | 31.465 | 30.948 | −2.078 | 1.00 | 41.37 | W | O |
| ATOM | 4819 | OH2 | WAT | W | 81 | 24.891 | 29.425 | 38.535 | 1.00 | 32.19 | W | O |
| ATOM | 4820 | OH2 | WAT | W | 82 | 26.966 | 27.373 | 47.300 | 1.00 | 31.18 | W | O |
| ATOM | 4821 | OH2 | WAT | W | 83 | 29.620 | 34.079 | −0.291 | 1.00 | 38.61 | W | O |
| ATOM | 4822 | OH2 | WAT | W | 84 | 33.991 | 16.748 | −1.768 | 1.00 | 21.41 | W | O |
| ATOM | 4823 | OH2 | WAT | W | 85 | 36.100 | 19.081 | −1.640 | 1.00 | 18.06 | W | O |
| ATOM | 4824 | OH2 | WAT | W | 86 | 37.135 | 37.881 | 40.383 | 1.00 | 20.11 | W | O |
| ATOM | 4825 | OH2 | WAT | W | 87 | 11.337 | 15.166 | 8.469 | 1.00 | 15.10 | W | O |
| ATOM | 4826 | OH2 | WAT | W | 88 | 38.668 | 19.971 | 26.489 | 1.00 | 15.24 | W | O |
| ATOM | 4827 | OH2 | WAT | W | 89 | 34.405 | 15.814 | 12.156 | 1.00 | 10.82 | W | O |
| ATOM | 4828 | OH2 | WAT | W | 90 | 27.246 | 34.729 | 18.461 | 1.00 | 22.71 | W | O |
| ATOM | 4829 | OH2 | WAT | W | 91 | 27.552 | 8.778 | 20.143 | 1.00 | 13.91 | W | O |
| ATOM | 4830 | OH2 | WAT | W | 92 | 18.593 | 17.220 | 27.671 | 1.00 | 20.14 | W | O |
| ATOM | 4831 | OH2 | WAT | W | 93 | 36.799 | 17.534 | 73.777 | 1.00 | 30.67 | W | O |
| ATOM | 4832 | OH2 | WAT | W | 94 | 9.790 | 29.242 | 2.101 | 1.00 | 22.36 | W | O |
| ATOM | 4833 | OH2 | WAT | W | 95 | 24.239 | 29.551 | 51.184 | 1.00 | 26.73 | W | O |
| ATOM | 4834 | OH2 | WAT | W | 96 | 29.035 | 29.710 | 45.452 | 1.00 | 17.18 | W | O |
| ATOM | 4835 | OH2 | WAT | W | 97 | 34.661 | 16.311 | 23.110 | 1.00 | 15.24 | W | O |
| ATOM | 4836 | OH2 | WAT | W | 98 | 21.314 | 17.064 | −7.614 | 1.00 | 27.82 | W | O |
| ATOM | 4837 | OH2 | WAT | W | 99 | 30.880 | 19.181 | 28.970 | 1.00 | 18.73 | W | O |
| ATOM | 4838 | OH2 | WAT | W | 100 | 28.850 | 17.366 | 29.169 | 1.00 | 18.53 | W | O |
| ATOM | 4839 | OH2 | WAT | W | 101 | 42.030 | 21.777 | 13.248 | 1.00 | 26.15 | W | O |
| ATOM | 4840 | OH2 | WAT | W | 102 | 3.956 | 12.762 | −2.958 | 1.00 | 27.96 | W | O |
| ATOM | 4841 | OH2 | WAT | W | 103 | 16.051 | 15.146 | 16.848 | 1.00 | 14.41 | W | O |
| ATOM | 4842 | OH2 | WAT | W | 104 | 27.365 | 17.435 | 64.773 | 1.00 | 38.96 | W | O |
| ATOM | 4843 | OH2 | WAT | W | 105 | 17.747 | 1.507 | 5.871 | 1.00 | 23.60 | W | O |
| ATOM | 4844 | OH2 | WAT | W | 106 | 37.627 | 37.114 | 42.976 | 1.00 | 24.96 | W | O |
| ATOM | 4845 | OH2 | WAT | W | 107 | 24.719 | 4.196 | 59.681 | 1.00 | 32.55 | W | O |
| ATOM | 4846 | OH2 | WAT | W | 108 | 17.686 | 33.626 | 13.933 | 1.00 | 20.39 | W | O |
| ATOM | 4847 | OH2 | WAT | W | 109 | −0.184 | 23.823 | 13.296 | 1.00 | 46.49 | W | O |
| ATOM | 4848 | OH2 | WAT | W | 110 | 15.373 | 35.019 | 25.333 | 1.00 | 21.46 | W | O |
| ATOM | 4849 | OH2 | WAT | W | 111 | 30.768 | 14.093 | 34.177 | 1.00 | 33.90 | W | O |
| ATOM | 4850 | OH2 | WAT | W | 112 | 25.218 | 27.843 | 34.700 | 1.00 | 33.99 | W | O |
| ATOM | 4851 | OH2 | WAT | W | 113 | 7.403 | 26.902 | 1.736 | 1.00 | 32.04 | W | O |
| ATOM | 4852 | OH2 | WAT | W | 114 | 20.038 | 32.869 | 15.272 | 1.00 | 23.28 | W | O |
| ATOM | 4853 | OH2 | WAT | W | 115 | 15.360 | 28.092 | 24.066 | 1.00 | 16.94 | W | O |
| ATOM | 4854 | OH2 | WAT | W | 116 | 19.926 | 37.657 | 60.577 | 1.00 | 40.46 | W | O |
| ATOM | 4855 | OH2 | WAT | W | 117 | 32.502 | 22.719 | 25.889 | 1.00 | 19.53 | W | O |
| ATOM | 4856 | OH2 | WAT | W | 118 | 30.616 | 31.722 | 4.387 | 1.00 | 18.60 | W | O |
| ATOM | 4857 | OH2 | WAT | W | 119 | 26.479 | 8.176 | 55.645 | 1.00 | 36.63 | W | O |
| ATOM | 4858 | OH2 | WAT | W | 120 | 22.372 | 22.465 | 40.919 | 1.00 | 40.52 | W | O |

-continued

| | | | | | | | | | | | |
|---|---|---|---|---|---|---|---|---|---|---|---|
| ATOM | 4859 | OH2 | WAT | W | 121 | 39.623 | 15.685 | 32.220 | 1.00 | 28.34 | W O |
| ATOM | 4860 | OH2 | WAT | W | 122 | 48.066 | 29.461 | 95.001 | 1.00 | 27.75 | W O |
| ATOM | 4861 | OH2 | WAT | W | 123 | 31.897 | 32.419 | 0.487 | 1.00 | 30.32 | W O |
| ATOM | 4862 | OH2 | WAT | W | 124 | 20.734 | −1.804 | 18.413 | 1.00 | 26.72 | W O |
| ATOM | 4863 | OH2 | WAT | W | 125 | 31.094 | 6.561 | 53.456 | 1.00 | 25.11 | W O |
| ATOM | 4864 | OH2 | WAT | W | 126 | 45.312 | 37.218 | 40.612 | 1.00 | 33.55 | W O |
| ATOM | 4865 | OH2 | WAT | W | 127 | 1.538 | 17.016 | 8.474 | 1.00 | 19.86 | W O |
| ATOM | 4866 | OH2 | WAT | W | 128 | 29.731 | 9.406 | −1.174 | 1.00 | 20.25 | W O |
| ATOM | 4867 | OH2 | WAT | W | 129 | 27.305 | 38.491 | 25.414 | 1.00 | 28.22 | W O |
| ATOM | 4868 | OH2 | WAT | W | 130 | 28.077 | 29.238 | 30.743 | 1.00 | 23.73 | W O |
| ATOM | 4869 | OH2 | WAT | W | 131 | 26.574 | 28.140 | 51.775 | 1.00 | 15.37 | W O |
| ATOM | 4870 | OH2 | WAT | W | 132 | 19.946 | 5.062 | 76.332 | 1.00 | 36.71 | W O |
| ATOM | 4871 | OH2 | WAT | W | 133 | 10.627 | 12.756 | 10.004 | 1.00 | 22.21 | W O |
| ATOM | 4872 | OH2 | WAT | W | 134 | 11.190 | −1.258 | 13.067 | 1.00 | 23.85 | W O |
| ATOM | 4873 | OH2 | WAT | W | 135 | 3.651 | 9.620 | 16.508 | 1.00 | 29.13 | W O |
| ATOM | 4874 | OH2 | WAT | W | 136 | 24.584 | 34.295 | 21.191 | 1.00 | 23.76 | W O |
| ATOM | 4875 | OH2 | WAT | W | 137 | 24.301 | 30.242 | 41.148 | 1.00 | 33.00 | W O |
| ATOM | 4876 | OH2 | WAT | W | 138 | 19.879 | 15.502 | 31.848 | 1.00 | 24.77 | W O |
| ATOM | 4877 | OH2 | WAT | W | 139 | 31.486 | 28.385 | 56.405 | 1.00 | 20.53 | W O |
| ATOM | 4878 | OH2 | WAT | W | 140 | 15.743 | 41.487 | 27.914 | 1.00 | 25.39 | W O |
| ATOM | 4879 | OH2 | WAT | W | 141 | 35.109 | 22.703 | 77.680 | 1.00 | 41.76 | W O |
| ATOM | 4880 | OH2 | WAT | W | 142 | 22.799 | 24.131 | 34.328 | 1.00 | 24.16 | W O |
| ATOM | 4881 | OH2 | WAT | W | 143 | 19.856 | 25.294 | 47.782 | 1.00 | 36.17 | W O |
| ATOM | 4882 | OH2 | WAT | W | 144 | 7.019 | 28.800 | 5.810 | 1.00 | 26.61 | W O |
| ATOM | 4883 | OH2 | WAT | W | 145 | 35.707 | 19.657 | 90.022 | 1.00 | 34.12 | W O |
| ATOM | 4884 | OH2 | WAT | W | 146 | 29.118 | 8.498 | 28.737 | 1.00 | 16.55 | W O |
| ATOM | 4885 | OH2 | WAT | W | 147 | 25.461 | 2.178 | 29.528 | 1.00 | 31.87 | W O |
| ATOM | 4886 | OH2 | WAT | W | 148 | 29.591 | 2.587 | 66.923 | 1.00 | 38.76 | W O |
| ATOM | 4887 | OH2 | WAT | W | 149 | 38.299 | 31.491 | 93.878 | 1.00 | 37.57 | W O |
| ATOM | 4888 | OH2 | WAT | W | 150 | 16.338 | 23.326 | 29.568 | 1.00 | 28.12 | W O |
| ATOM | 4889 | OH2 | WAT | W | 151 | 50.138 | 29.041 | 96.866 | 1.00 | 27.78 | W O |
| ATOM | 4890 | OH2 | WAT | W | 152 | 22.910 | 21.458 | 38.404 | 1.00 | 25.84 | W O |
| ATOM | 4891 | OH2 | WAT | W | 153 | 21.563 | 31.334 | 13.807 | 1.00 | 35.91 | W O |
| ATOM | 4892 | OH2 | WAT | W | 154 | 47.345 | 32.238 | 87.047 | 1.00 | 33.44 | W O |
| ATOM | 4893 | OH2 | WAT | W | 155 | 33.641 | 15.072 | −3.898 | 1.00 | 34.95 | W O |
| ATOM | 4894 | OH2 | WAT | W | 156 | 21.869 | 28.002 | 43.965 | 1.00 | 32.96 | W O |
| ATOM | 4895 | OH2 | WAT | W | 157 | 31.608 | 14.352 | 30.918 | 1.00 | 27.70 | W O |
| ATOM | 4896 | OH2 | WAT | W | 158 | 22.471 | 6.040 | 5.325 | 1.00 | 25.62 | W O |
| ATOM | 4897 | OH2 | WAT | W | 159 | 8.576 | 2.761 | 0.289 | 1.00 | 33.92 | W O |
| ATOM | 4898 | OH2 | WAT | W | 160 | 40.895 | 14.749 | 12.622 | 1.00 | 23.15 | W O |
| ATOM | 4899 | OH2 | WAT | W | 161 | 29.005 | 28.427 | 68.038 | 1.00 | 30.48 | W O |
| ATOM | 4900 | OH2 | WAT | W | 162 | 22.507 | 4.454 | 76.352 | 1.00 | 33.53 | W O |
| ATOM | 4901 | OH2 | WAT | W | 163 | 44.106 | 37.763 | 35.688 | 1.00 | 48.32 | W O |
| ATOM | 4902 | OH2 | WAT | W | 164 | 26.450 | 3.355 | 5.768 | 1.00 | 28.13 | W O |
| ATOM | 4903 | OH2 | WAT | W | 165 | 4.723 | 30.331 | 5.955 | 1.00 | 44.11 | W O |
| ATOM | 4904 | OH2 | WAT | W | 166 | 35.185 | 27.903 | −4.961 | 1.00 | 27.15 | W O |
| ATOM | 4905 | OH2 | WAT | W | 167 | 18.473 | 10.311 | −5.754 | 1.00 | 31.75 | W O |
| ATOM | 4906 | OH2 | WAT | W | 168 | 31.008 | 4.482 | 21.032 | 1.00 | 44.53 | W O |
| ATOM | 4907 | OH2 | WAT | W | 169 | 38.894 | 15.944 | 48.372 | 1.00 | 38.35 | W O |
| ATOM | 4908 | OH2 | WAT | W | 170 | 34.331 | 25.697 | 20.938 | 1.00 | 21.61 | W O |
| ATOM | 4909 | OH2 | WAT | W | 171 | 49.199 | 26.268 | 86.643 | 1.00 | 30.58 | W O |
| ATOM | 4910 | OH2 | WAT | W | 172 | 5.127 | 9.693 | −0.969 | 1.00 | 34.66 | W O |
| ATOM | 4911 | OH2 | WAT | W | 173 | −0.373 | 13.989 | 8.086 | 1.00 | 34.97 | W O |
| ATOM | 4912 | OH2 | WAT | W | 174 | 16.470 | −0.001 | 3.800 | 1.00 | 32.29 | W O |
| ATOM | 4913 | OH2 | WAT | W | 175 | 18.074 | 31.513 | 1.418 | 1.00 | 34.23 | W O |
| ATOM | 4914 | OH2 | WAT | W | 176 | 38.094 | 40.562 | 31.950 | 1.00 | 29.70 | W O |
| ATOM | 4915 | OH2 | WAT | W | 177 | 40.881 | 31.784 | 48.268 | 1.00 | 38.43 | W O |
| ATOM | 4916 | OH2 | WAT | W | 178 | 33.053 | 31.307 | 3.076 | 1.00 | 21.18 | W O |
| ATOM | 4917 | OH2 | WAT | W | 179 | 5.567 | 14.818 | −1.815 | 1.00 | 30.86 | W O |
| ATOM | 4918 | OH2 | WAT | W | 180 | 31.429 | 9.957 | 46.073 | 1.00 | 34.20 | W O |
| ATOM | 4919 | OH2 | WAT | W | 181 | 11.917 | 28.333 | 8.565 | 1.00 | 16.99 | W O |
| ATOM | 4920 | OH2 | WAT | W | 182 | 36.688 | 10.228 | 42.234 | 1.00 | 32.93 | W O |
| ATOM | 4921 | OH2 | WAT | W | 183 | 3.251 | 31.546 | 9.757 | 1.00 | 29.65 | W O |
| ATOM | 4922 | OH2 | WAT | W | 184 | 18.321 | 2.574 | −0.484 | 1.00 | 32.80 | W O |
| ATOM | 4923 | OH2 | WAT | W | 185 | 5.637 | 5.762 | 14.955 | 1.00 | 32.54 | W O |
| ATOM | 4924 | OH2 | WAT | W | 186 | 15.673 | 14.210 | 25.757 | 1.00 | 34.67 | W O |
| ATOM | 4925 | OH2 | WAT | W | 187 | 40.626 | 21.784 | 27.626 | 1.00 | 32.36 | W O |
| ATOM | 4926 | OH2 | WAT | W | 188 | 42.987 | 22.261 | 89.602 | 1.00 | 27.87 | W O |
| ATOM | 4927 | OH2 | WAT | W | 189 | 14.638 | 39.203 | 19.516 | 1.00 | 32.86 | W O |
| ATOM | 4928 | OH2 | WAT | W | 190 | 11.036 | 30.934 | 11.072 | 1.00 | 31.17 | W O |
| ATOM | 4929 | OH2 | WAT | W | 191 | 33.710 | 31.642 | 9.747 | 1.00 | 31.14 | W O |
| ATOM | 4930 | OH2 | WAT | W | 192 | 20.870 | 6.918 | 26.506 | 1.00 | 33.93 | W O |
| ATOM | 4931 | OH2 | WAT | W | 193 | 28.954 | 1.020 | 74.566 | 1.00 | 34.78 | W O |
| ATOM | 4932 | OH2 | WAT | W | 194 | 37.700 | 14.002 | 57.999 | 1.00 | 52.48 | W O |
| ATOM | 4933 | OH2 | WAT | W | 195 | 2.310 | 11.077 | 13.236 | 1.00 | 36.20 | W O |
| ATOM | 4934 | OH2 | WAT | W | 196 | 29.084 | −0.199 | 11.021 | 1.00 | 39.14 | W O |
| ATOM | 4935 | OH2 | WAT | W | 197 | 41.032 | 19.200 | 6.700 | 1.00 | 29.69 | W O |
| ATOM | 4936 | OH2 | WAT | W | 198 | 12.343 | 28.516 | 23.498 | 1.00 | 25.52 | W O |
| ATOM | 4937 | OH2 | WAT | W | 199 | 28.735 | 31.233 | 43.028 | 1.00 | 25.67 | W O |

-continued

| | | | | | | | | | | | |
|---|---|---|---|---|---|---|---|---|---|---|---|
| ATOM | 4938 | OH2 | WAT | W | 200 | 44.326 | 3.129 | 25.867 | 1.00 | 53.38 | W O |
| ATOM | 4939 | OH2 | WAT | W | 201 | 28.603 | 7.431 | −2.611 | 1.00 | 30.58 | W O |
| ATOM | 4940 | OH2 | WAT | W | 202 | 33.156 | 26.217 | 56.692 | 1.00 | 26.48 | W O |
| ATOM | 4941 | OH2 | WAT | W | 203 | 36.278 | 15.450 | −4.311 | 1.00 | 26.09 | W O |
| ATOM | 4942 | OH2 | WAT | W | 204 | 38.154 | 8.018 | 19.062 | 1.00 | 37.43 | W O |
| ATOM | 4943 | OH2 | WAT | W | 205 | 9.837 | 28.610 | 10.272 | 1.00 | 31.67 | W O |
| ATOM | 4944 | OH2 | WAT | W | 206 | 14.373 | 16.403 | 26.718 | 1.00 | 36.07 | W O |
| ATOM | 4945 | OH2 | WAT | W | 207 | 37.593 | 16.593 | 70.391 | 1.00 | 29.23 | W O |
| ATOM | 4946 | OH2 | WAT | W | 208 | 0.132 | 11.716 | 9.251 | 1.00 | 33.00 | W O |
| ATOM | 4947 | OH2 | WAT | W | 209 | 25.144 | 28.339 | 31.889 | 1.00 | 49.28 | W O |
| ATOM | 4948 | OH2 | WAT | W | 210 | 7.440 | 16.389 | −2.874 | 1.00 | 20.15 | W O |
| ATOM | 4949 | OH2 | WAT | W | 211 | 7.530 | 29.833 | 8.482 | 1.00 | 30.21 | W O |
| ATOM | 4950 | OH2 | WAT | W | 212 | 21.589 | 17.888 | 38.999 | 1.00 | 33.78 | W O |
| ATOM | 4951 | OH2 | WAT | W | 213 | 42.227 | 19.920 | 8.912 | 1.00 | 24.14 | W O |
| ATOM | 4952 | OH2 | WAT | W | 214 | 18.081 | 13.134 | 53.952 | 1.00 | 46.05 | W O |
| ATOM | 4953 | OH2 | WAT | W | 215 | 28.604 | 36.515 | 31.266 | 1.00 | 35.94 | W O |
| ATOM | 4954 | OH2 | WAT | W | 216 | 21.979 | 38.636 | 47.184 | 1.00 | 45.57 | W O |
| ATOM | 4955 | OH2 | WAT | W | 217 | 37.628 | 28.720 | 13.544 | 1.00 | 35.13 | W O |
| ATOM | 4956 | OH2 | WAT | W | 218 | 13.553 | 15.154 | 18.167 | 1.00 | 30.54 | W O |
| ATOM | 4957 | OH2 | WAT | W | 219 | 32.654 | 30.845 | 47.076 | 1.00 | 25.26 | W O |
| ATOM | 4958 | OH2 | WAT | W | 220 | −2.842 | 14.831 | 8.115 | 1.00 | 33.07 | W O |
| ATOM | 4959 | OH2 | WAT | W | 221 | 18.483 | 15.571 | −7.984 | 1.00 | 30.86 | W O |
| ATOM | 4960 | OH2 | WAT | W | 222 | 3.270 | 25.714 | 5.665 | 1.00 | 26.54 | W O |
| ATOM | 4961 | OH2 | WAT | W | 223 | 50.144 | 24.757 | 82.596 | 1.00 | 34.50 | W O |
| ATOM | 4962 | OH2 | WAT | W | 224 | 26.242 | 11.203 | 31.526 | 1.00 | 30.44 | W O |
| ATOM | 4963 | OH2 | WAT | W | 225 | 18.073 | −1.159 | 18.149 | 1.00 | 34.58 | W O |
| ATOM | 4964 | OH2 | WAT | W | 226 | 47.321 | 29.376 | 85.710 | 1.00 | 34.51 | W O |
| ATOM | 4965 | OH2 | WAT | W | 227 | 22.195 | 20.381 | 42.496 | 1.00 | 30.12 | W O |
| ATOM | 4966 | OH2 | WAT | W | 228 | 3.659 | 2.259 | 0.190 | 1.00 | 34.67 | W O |
| ATOM | 4967 | OH2 | WAT | W | 229 | 40.557 | 0.237 | 20.769 | 1.00 | 28.72 | W O |
| ATOM | 4968 | OH2 | WAT | W | 230 | 21.900 | 26.386 | 53.079 | 1.00 | 26.13 | W O |
| ATOM | 4969 | OH2 | WAT | W | 231 | 7.647 | 31.085 | 26.330 | 1.00 | 35.78 | W O |
| ATOM | 4970 | OH2 | WAT | W | 232 | 13.007 | 21.995 | 27.742 | 1.00 | 38.60 | W O |
| ATOM | 4971 | OH2 | WAT | W | 233 | 45.245 | 0.872 | 24.555 | 1.00 | 46.33 | W O |
| ATOM | 4972 | OH2 | WAT | W | 234 | 18.696 | 16.785 | 50.319 | 1.00 | 37.87 | W O |
| ATOM | 4973 | OH2 | WAT | W | 235 | 31.471 | 4.379 | 68.498 | 1.00 | 43.22 | W O |
| ATOM | 4974 | OH2 | WAT | W | 236 | 44.018 | 19.076 | 33.450 | 1.00 | 32.66 | W O |
| ATOM | 4975 | OH2 | WAT | W | 237 | 23.071 | 24.930 | 30.360 | 1.00 | 23.93 | W O |
| ATOM | 4976 | OH2 | WAT | W | 238 | 35.628 | 33.217 | 93.628 | 1.00 | 33.30 | W O |
| ATOM | 4977 | OH2 | WAT | W | 239 | 35.847 | 25.095 | 70.900 | 1.00 | 44.01 | W O |
| ATOM | 4978 | OH2 | WAT | W | 240 | 22.701 | 20.328 | 82.692 | 1.00 | 39.98 | W O |
| ATOM | 4979 | OH2 | WAT | W | 241 | 7.838 | 12.303 | −1.787 | 1.00 | 34.86 | W O |
| ATOM | 4980 | OH2 | WAT | W | 242 | 28.268 | 21.326 | 68.248 | 1.00 | 31.86 | W O |
| ATOM | 4981 | OH2 | WAT | W | 243 | −0.770 | 24.146 | 8.061 | 1.00 | 34.90 | W O |
| ATOM | 4982 | OH2 | WAT | W | 244 | 38.119 | 6.075 | 7.064 | 1.00 | 31.06 | W O |
| ATOM | 4983 | OH2 | WAT | W | 245 | 23.502 | 28.608 | 54.003 | 1.00 | 28.10 | W O |
| ATOM | 4984 | OH2 | WAT | W | 246 | 34.476 | 12.129 | 8.573 | 1.00 | 22.78 | W O |
| ATOM | 4985 | OH2 | WAT | W | 247 | 11.730 | 40.646 | 20.091 | 1.00 | 43.62 | W O |
| ATOM | 4986 | OH2 | WAT | W | 248 | 20.358 | 23.090 | 67.179 | 1.00 | 43.07 | W O |
| ATOM | 4987 | OH2 | WAT | W | 249 | 33.233 | 30.859 | 32.765 | 1.00 | 29.52 | W O |
| ATOM | 4988 | OH2 | WAT | W | 250 | 34.971 | 29.300 | 13.451 | 1.00 | 24.97 | W O |
| ATOM | 4989 | OH2 | WAT | W | 251 | 21.456 | 30.121 | 50.897 | 1.00 | 51.79 | W O |
| ATOM | 4990 | OH2 | WAT | W | 252 | 38.432 | 11.736 | 55.327 | 1.00 | 41.69 | W O |
| ATOM | 4991 | OH2 | WAT | W | 253 | 42.192 | 23.969 | 9.558 | 1.00 | 58.78 | W O |
| ATOM | 4992 | OH2 | WAT | W | 254 | 45.254 | 27.469 | 47.916 | 1.00 | 33.81 | W O |
| ATOM | 4993 | OH2 | WAT | W | 255 | 34.867 | 39.746 | 60.424 | 1.00 | 51.82 | W O |
| ATOM | 4994 | OH2 | WAT | W | 256 | 7.714 | 11.590 | 23.225 | 1.00 | 47.38 | W O |
| ATOM | 4995 | OH2 | WAT | W | 257 | 11.234 | 37.040 | 13.444 | 1.00 | 45.19 | W O |
| ATOM | 4996 | OH2 | WAT | W | 258 | 5.250 | 24.259 | 16.611 | 1.00 | 35.12 | W O |
| ATOM | 4997 | OH2 | WAT | W | 259 | 30.634 | 7.333 | 46.566 | 1.00 | 64.60 | W O |
| ATOM | 4998 | OH2 | WAT | W | 260 | 41.043 | 28.449 | 49.954 | 1.00 | 34.29 | W O |
| ATOM | 4999 | OH2 | WAT | W | 261 | 27.833 | 42.178 | 56.031 | 1.00 | 38.43 | W O |
| ATOM | 5000 | OH2 | WAT | W | 262 | 36.007 | 23.861 | 20.102 | 1.00 | 26.54 | W O |
| ATOM | 5001 | OH2 | WAT | W | 263 | 47.752 | 24.361 | 74.233 | 1.00 | 52.97 | W O |
| ATOM | 5002 | OH2 | WAT | W | 264 | 20.405 | 19.480 | −9.352 | 1.00 | 39.53 | W O |
| ATOM | 5003 | OH2 | WAT | W | 265 | 27.553 | 31.025 | 88.317 | 1.00 | 52.14 | W O |
| ATOM | 5004 | OH2 | WAT | W | 266 | 27.439 | 6.871 | 2.671 | 1.00 | 33.49 | W O |
| ATOM | 5005 | OH2 | WAT | W | 267 | 28.522 | 39.164 | 45.564 | 1.00 | 34.68 | W O |
| ATOM | 5006 | OH2 | WAT | W | 268 | 43.870 | 22.301 | 47.233 | 1.00 | 40.78 | W O |
| ATOM | 5007 | OH2 | WAT | W | 269 | 35.079 | 36.340 | 52.168 | 1.00 | 44.82 | W O |
| ATOM | 5008 | OH2 | WAT | W | 270 | 23.451 | 34.163 | 23.718 | 1.00 | 27.05 | W O |
| ATOM | 5009 | OH2 | WAT | W | 271 | 30.957 | 22.554 | 71.076 | 1.00 | 42.91 | W O |
| ATOM | 5010 | OH2 | WAT | W | 272 | 38.744 | 7.564 | 80.920 | 1.00 | 40.95 | W O |
| ATOM | 5011 | OH2 | WAT | W | 273 | 13.936 | 30.988 | 30.446 | 1.00 | 41.06 | W O |
| ATOM | 5012 | OH2 | WAT | W | 274 | 23.419 | 17.708 | 86.267 | 1.00 | 59.87 | W O |
| ATOM | 5013 | OH2 | WAT | W | 275 | 21.017 | 0.277 | 3.695 | 1.00 | 50.07 | W O |
| ATOM | 5014 | OH2 | WAT | W | 276 | 21.549 | 22.757 | 36.427 | 1.00 | 45.15 | W O |
| ATOM | 5015 | OH2 | WAT | W | 277 | 37.355 | 12.567 | 39.061 | 1.00 | 34.74 | W O |
| ATOM | 5016 | OH2 | WAT | W | 278 | 2.783 | 23.907 | 15.169 | 1.00 | 48.05 | W O |

-continued

| | | | | | | | | | | | |
|---|---|---|---|---|---|---|---|---|---|---|---|
| ATOM | 5017 | OH2 | WAT | W | 279 | 32.292 | 35.378 | 41.347 | 1.00 | 45.51 | W | O |
| ATOM | 5018 | OH2 | WAT | W | 280 | 24.285 | 8.129 | 48.241 | 1.00 | 36.55 | W | O |
| ATOM | 5019 | OH2 | WAT | W | 281 | 9.135 | 10.036 | −0.985 | 1.00 | 36.77 | W | O |
| ATOM | 5020 | OH2 | WAT | W | 282 | 9.648 | 4.536 | 20.435 | 1.00 | 35.26 | W | O |
| ATOM | 5021 | OH2 | WAT | W | 283 | 37.143 | 14.114 | 86.099 | 1.00 | 40.95 | W | O |
| ATOM | 5022 | OH2 | WAT | W | 284 | 9.020 | 35.287 | 33.571 | 1.00 | 41.52 | W | O |
| ATOM | 5023 | OH2 | WAT | W | 285 | −1.612 | 10.514 | 3.421 | 1.00 | 51.78 | W | O |
| ATOM | 5024 | OH2 | WAT | W | 286 | 42.982 | 17.337 | 41.377 | 1.00 | 38.67 | W | O |
| ATOM | 5025 | OH2 | WAT | W | 287 | 34.957 | 31.854 | 45.389 | 1.00 | 25.75 | W | O |
| ATOM | 5026 | OH2 | WAT | W | 288 | 3.170 | 28.704 | 16.548 | 1.00 | 47.39 | W | O |
| ATOM | 5027 | OH2 | WAT | W | 289 | 4.236 | 26.437 | 18.194 | 1.00 | 40.60 | W | O |
| ATOM | 5028 | OH2 | WAT | W | 290 | 11.780 | 0.909 | 19.173 | 1.00 | 31.13 | W | O |
| ATOM | 5029 | OH2 | WAT | W | 291 | 35.076 | 18.990 | 60.316 | 1.00 | 38.09 | W | O |
| ATOM | 5030 | OH2 | WAT | W | 292 | −0.662 | 15.295 | 21.926 | 1.00 | 52.48 | W | O |
| ATOM | 5031 | OH2 | WAT | W | 293 | 42.355 | 22.441 | 69.467 | 1.00 | 43.05 | W | O |
| ATOM | 5032 | OH2 | WAT | W | 294 | 36.115 | 8.550 | 0.838 | 1.00 | 34.86 | W | O |
| ATOM | 5033 | OH2 | WAT | W | 295 | 5.539 | 38.578 | 29.277 | 1.00 | 41.01 | W | O |
| ATOM | 5034 | OH2 | WAT | W | 296 | −0.774 | 16.342 | 12.374 | 1.00 | 44.15 | W | O |
| ATOM | 5035 | OH2 | WAT | W | 297 | 20.248 | 19.074 | 34.881 | 1.00 | 32.08 | W | O |
| ATOM | 5036 | OH2 | WAT | W | 298 | 22.485 | 11.810 | 37.890 | 1.00 | 40.55 | W | O |
| ATOM | 5037 | OH2 | WAT | W | 299 | 42.707 | 16.687 | 11.459 | 1.00 | 42.38 | W | O |
| ATOM | 5038 | OH2 | WAT | W | 300 | 40.839 | 15.634 | 41.011 | 1.00 | 38.21 | W | O |
| ATOM | 5039 | OH2 | WAT | W | 301 | 20.094 | 24.068 | 71.878 | 1.00 | 70.09 | W | O |
| ATOM | 5040 | OH2 | WAT | W | 302 | 31.865 | −0.414 | 10.192 | 1.00 | 41.10 | W | O |
| ATOM | 5041 | OH2 | WAT | W | 303 | 20.743 | 26.537 | 50.189 | 1.00 | 45.73 | W | O |
| ATOM | 5042 | OH2 | WAT | W | 304 | 44.143 | 13.662 | 12.378 | 1.00 | 40.41 | W | O |
| ATOM | 5043 | OH2 | WAT | W | 305 | 40.498 | 25.176 | 54.332 | 1.00 | 46.48 | W | O |
| ATOM | 5044 | OH2 | WAT | W | 306 | 35.746 | 6.890 | 18.386 | 1.00 | 32.88 | W | O |
| ATOM | 5045 | OH2 | WAT | W | 307 | 14.855 | 41.757 | 31.970 | 1.00 | 44.75 | W | O |
| ATOM | 5046 | OH2 | WAT | W | 308 | 18.143 | −0.909 | 20.903 | 1.00 | 45.80 | W | O |
| ATOM | 5047 | OH2 | WAT | W | 309 | 27.593 | 7.517 | −5.357 | 1.00 | 51.75 | W | O |
| ATOM | 5048 | OH2 | WAT | W | 310 | 29.441 | 20.038 | −9.566 | 1.00 | 48.48 | W | O |
| ATOM | 5049 | OH2 | WAT | W | 311 | 33.031 | 8.376 | 2.930 | 1.00 | 37.72 | W | O |
| ATOM | 5050 | OH2 | WAT | W | 312 | 28.826 | 12.995 | 39.392 | 1.00 | 28.46 | W | O |
| ATOM | 5051 | OH2 | WAT | W | 313 | 19.453 | 26.455 | 33.576 | 1.00 | 49.37 | W | O |
| ATOM | 5052 | OH2 | WAT | W | 314 | 32.900 | 12.710 | 60.296 | 1.00 | 43.04 | W | O |
| ATOM | 5053 | OH2 | WAT | W | 315 | 35.171 | 34.093 | 47.106 | 1.00 | 46.97 | W | O |
| ATOM | 5054 | OH2 | WAT | W | 316 | 42.577 | 27.086 | 48.235 | 1.00 | 40.03 | W | O |
| ATOM | 5055 | OH2 | WAT | W | 317 | 8.900 | 30.335 | 4.530 | 1.00 | 36.15 | W | O |
| ATOM | 5056 | OH2 | WAT | W | 318 | 30.817 | 33.985 | 69.076 | 1.00 | 46.39 | W | O |
| ATOM | 5057 | OH2 | WAT | W | 319 | 19.929 | 3.244 | 55.862 | 1.00 | 64.48 | W | O |
| ATOM | 5058 | OH2 | WAT | W | 320 | 23.376 | 1.981 | 90.249 | 1.00 | 39.58 | W | O |
| ATOM | 5059 | OH2 | WAT | W | 321 | 40.437 | 5.728 | 17.654 | 1.00 | 39.03 | W | O |
| ATOM | 5060 | OH2 | WAT | W | 322 | 9.640 | 35.993 | 11.234 | 1.00 | 42.42 | W | O |
| ATOM | 5061 | OH2 | WAT | W | 323 | 16.153 | 42.346 | 23.466 | 1.00 | 34.97 | W | O |
| ATOM | 5062 | OH2 | WAT | W | 324 | 35.436 | 19.673 | 64.215 | 1.00 | 57.86 | W | O |
| ATOM | 5063 | OH2 | WAT | W | 325 | 4.918 | 16.942 | 5.288 | 1.00 | 10.46 | W | O |
| ATOM | 5064 | OH2 | WAT | W | 326 | 18.390 | 21.278 | −9.254 | 1.00 | 31.50 | W | O |
| ATOM | 5065 | OH2 | WAT | W | 327 | 1.490 | 16.464 | 5.809 | 1.00 | 20.84 | W | O |
| ATOM | 5066 | OH2 | WAT | W | 328 | 2.997 | 16.779 | 3.328 | 1.00 | 19.39 | W | O |
| ATOM | 5067 | OH2 | WAT | W | 329 | 6.139 | 1.050 | −0.292 | 1.00 | 48.96 | W | O |
| ATOM | 5068 | OH2 | WAT | W | 330 | 35.510 | 12.689 | 47.619 | 1.00 | 31.05 | W | O |
| ATOM | 5069 | OH2 | WAT | W | 331 | 27.536 | 5.618 | −0.676 | 1.00 | 54.07 | W | O |
| ATOM | 5070 | OH2 | WAT | W | 332 | 43.643 | 19.826 | 17.185 | 1.00 | 59.51 | W | O |
| ATOM | 5071 | OH2 | WAT | W | 333 | 19.184 | 30.073 | 10.467 | 1.00 | 46.29 | W | O |
| ATOM | 5072 | OH2 | WAT | W | 334 | 31.305 | 28.910 | 32.552 | 1.00 | 37.09 | W | O |
| ATOM | 5073 | OH2 | WAT | W | 335 | 9.970 | 0.903 | −1.332 | 1.00 | 48.94 | W | O |
| ATOM | 5074 | OH2 | WAT | W | 336 | 42.603 | 21.451 | 5.443 | 1.00 | 46.05 | W | O |
| ATOM | 5075 | OH2 | WAT | W | 337 | 25.589 | 37.355 | 19.101 | 1.00 | 50.70 | W | O |
| ATOM | 5076 | OH2 | WAT | W | 338 | 16.211 | 15.273 | 77.481 | 1.00 | 45.46 | W | O |
| ATOM | 5077 | OH2 | WAT | W | 339 | 4.566 | 4.778 | 9.222 | 1.00 | 38.08 | W | O |
| ATOM | 5078 | OH2 | WAT | W | 340 | 24.583 | 13.388 | −12.370 | 1.00 | 38.31 | W | O |
| ATOM | 5079 | OH2 | WAT | W | 341 | 41.377 | 15.443 | 47.138 | 1.00 | 42.95 | W | O |
| ATOM | 5080 | OH2 | WAT | W | 342 | 46.584 | 22.712 | 72.438 | 1.00 | 50.39 | W | O |
| ATOM | 5081 | OH2 | WAT | W | 343 | 37.742 | −1.808 | 21.784 | 1.00 | 43.11 | W | O |
| ATOM | 5082 | OH2 | WAT | W | 344 | 19.595 | 0.633 | 24.707 | 1.00 | 42.68 | W | O |
| ATOM | 5083 | OH2 | WAT | W | 345 | 20.648 | 23.506 | 31.934 | 1.00 | 41.44 | W | O |
| ATOM | 5084 | OH2 | WAT | W | 346 | 5.215 | 28.843 | 9.509 | 1.00 | 27.51 | W | O |
| ATOM | 5085 | OH2 | WAT | W | 347 | −1.391 | 17.437 | 9.148 | 1.00 | 44.39 | W | O |
| ATOM | 5086 | OH2 | WAT | W | 348 | 37.699 | 11.902 | 32.487 | 1.00 | 31.25 | W | O |
| ATOM | 5087 | OH2 | WAT | W | 349 | 21.639 | 34.577 | 35.581 | 1.00 | 39.86 | W | O |
| ATOM | 5088 | OH2 | WAT | W | 350 | 19.819 | 24.919 | 38.691 | 1.00 | 51.89 | W | O |
| ATOM | 5089 | OH2 | WAT | W | 351 | 34.940 | 35.726 | 43.895 | 1.00 | 60.97 | W | O |
| ATOM | 5090 | OH2 | WAT | W | 352 | 37.201 | 17.622 | 58.850 | 1.00 | 43.91 | W | O |
| ATOM | 5091 | OH2 | WAT | W | 353 | 29.384 | 35.815 | 62.018 | 1.00 | 33.90 | W | O |
| ATOM | 5092 | OH2 | WAT | W | 354 | 34.042 | 37.937 | 56.652 | 1.00 | 31.53 | W | O |
| ATOM | 5093 | OH2 | WAT | W | 355 | 18.864 | −1.487 | 3.101 | 1.00 | 49.21 | W | O |
| ATOM | 5094 | OH2 | WAT | W | 356 | 45.897 | 16.661 | 41.685 | 1.00 | 45.52 | W | O |
| ATOM | 5095 | OH2 | WAT | W | 357 | 46.644 | 36.386 | 90.281 | 1.00 | 51.76 | W | O |

-continued

| | | | | | | | | | | | | |
|---|---|---|---|---|---|---|---|---|---|---|---|---|
| ATOM | 5096 | OH2 | WAT | W | 358 | 25.350 | 25.538 | 31.973 | 1.00 | 43.63 | W | O |
| ATOM | 5097 | OH2 | WAT | W | 359 | 34.925 | 5.802 | 29.713 | 1.00 | 38.77 | W | O |
| ATOM | 5098 | OH2 | WAT | W | 360 | 33.389 | 12.245 | −5.833 | 1.00 | 38.52 | W | O |
| ATOM | 5099 | OH2 | WAT | W | 361 | 13.401 | 36.615 | 6.966 | 1.00 | 60.27 | W | O |
| ATOM | 5100 | OH2 | WAT | W | 362 | 29.038 | 14.217 | 36.874 | 1.00 | 43.15 | W | O |
| ATOM | 5101 | OH2 | WAT | W | 363 | 43.754 | 18.992 | 93.095 | 1.00 | 43.98 | W | O |
| ATOM | 5102 | OH2 | WAT | W | 364 | 24.549 | 4.764 | 4.197 | 1.00 | 50.16 | W | O |
| ATOM | 5103 | OH2 | WAT | W | 365 | 43.227 | 13.919 | 19.497 | 1.00 | 58.10 | W | O |
| ATOM | 5104 | OH2 | WAT | W | 366 | 10.214 | 33.407 | 9.945 | 1.00 | 50.53 | W | O |
| ATOM | 5105 | OH2 | WAT | W | 367 | 17.413 | 19.604 | 27.704 | 1.00 | 31.46 | W | O |
| ATOM | 5106 | OH2 | WAT | W | 368 | 28.562 | 31.651 | 91.027 | 1.00 | 58.48 | W | O |
| ATOM | 5107 | OH2 | WAT | W | 369 | 39.915 | 9.085 | 8.229 | 1.00 | 51.34 | W | O |
| ATOM | 5108 | OH2 | WAT | W | 370 | 37.715 | 6.403 | 1.728 | 1.00 | 49.76 | W | O |
| ATOM | 5109 | OH2 | WAT | W | 371 | 45.177 | 11.389 | 17.053 | 1.00 | 38.62 | W | O |
| ATOM | 5110 | OH2 | WAT | W | 372 | −1.495 | 16.407 | 5.919 | 1.00 | 24.58 | W | O |
| ATOM | 5111 | OH2 | WAT | W | 373 | 17.928 | 10.777 | −8.990 | 1.00 | 48.78 | W | O |
| ATOM | 5112 | OH2 | WAT | W | 374 | 49.671 | 41.399 | 35.418 | 1.00 | 39.49 | W | O |
| ATOM | 5113 | OH2 | WAT | W | 375 | −2.896 | 22.960 | 9.444 | 1.00 | 64.43 | W | O |
| ATOM | 5114 | OH2 | WAT | W | 376 | 44.242 | 20.119 | 13.114 | 1.00 | 43.91 | W | O |
| ATOM | 5115 | OH2 | WAT | W | 377 | 45.998 | 27.498 | 65.911 | 1.00 | 52.62 | W | O |
| ATOM | 5116 | OH2 | WAT | W | 378 | 54.712 | 25.922 | 87.283 | 1.00 | 44.48 | W | O |
| ATOM | 5117 | OH2 | WAT | W | 379 | 9.336 | 21.221 | 24.256 | 1.00 | 39.28 | W | O |
| ATOM | 5118 | OH2 | WAT | W | 380 | 5.711 | 10.622 | 25.188 | 1.00 | 45.01 | W | O |
| ATOM | 5119 | OH2 | WAT | W | 381 | 22.065 | 36.408 | 12.747 | 1.00 | 59.06 | W | O |
| ATOM | 5120 | OH2 | WAT | W | 382 | 16.957 | 10.821 | 43.808 | 1.00 | 40.75 | W | O |
| ATOM | 5121 | OH2 | WAT | W | 383 | 39.595 | 1.633 | 12.436 | 1.00 | 49.31 | W | O |
| ATOM | 5122 | OH2 | WAT | W | 384 | 11.084 | 30.834 | 0.209 | 1.00 | 39.09 | W | O |
| ATOM | 5123 | OH2 | WAT | W | 385 | 16.720 | 27.264 | −4.002 | 1.00 | 41.06 | W | O |
| ATOM | 5124 | OH2 | WAT | W | 386 | 31.056 | 0.281 | 79.010 | 1.00 | 38.99 | W | O |
| ATOM | 5125 | OH2 | WAT | W | 387 | 19.887 | 9.930 | 45.039 | 1.00 | 49.86 | W | O |
| ATOM | 5126 | OH2 | WAT | W | 388 | 36.655 | 37.162 | 45.509 | 1.00 | 47.87 | W | O |
| ATOM | 5127 | OH2 | WAT | W | 389 | 27.630 | 7.903 | 30.948 | 1.00 | 41.08 | W | O |
| ATOM | 5128 | OH2 | WAT | W | 390 | 22.128 | 23.087 | −9.666 | 1.00 | 41.60 | W | O |
| ATOM | 5129 | OH2 | WAT | W | 391 | 16.596 | 34.405 | 7.509 | 1.00 | 52.09 | W | O |
| ATOM | 5130 | OH2 | WAT | W | 392 | 18.187 | 37.051 | 16.426 | 1.00 | 58.25 | W | O |
| ATOM | 5131 | OH2 | WAT | W | 393 | 20.557 | 35.471 | 15.670 | 1.00 | 30.35 | W | O |
| ATOM | 5132 | OH2 | WAT | W | 394 | 38.852 | 10.942 | 68.815 | 1.00 | 56.37 | W | O |
| ATOM | 5133 | OH2 | WAT | W | 395 | 14.789 | 20.103 | 63.603 | 1.00 | 69.08 | W | O |
| ATOM | 5134 | OH2 | WAT | W | 396 | 35.781 | 9.917 | 61.122 | 1.00 | 45.92 | W | O |
| ATOM | 5135 | OH2 | WAT | W | 397 | 32.425 | 7.986 | 44.362 | 1.00 | 50.04 | W | O |
| ATOM | 5136 | OH2 | WAT | W | 398 | 39.173 | 29.239 | 58.940 | 1.00 | 46.65 | W | O |
| ATOM | 5137 | OH2 | WAT | W | 399 | 33.925 | 28.356 | 71.709 | 1.00 | 46.27 | W | O |
| ATOM | 5138 | OH2 | WAT | W | 400 | 26.195 | 11.085 | 39.837 | 1.00 | 37.48 | W | O |
| ATOM | 5139 | OH2 | WAT | W | 401 | 40.425 | 2.450 | 9.983 | 1.00 | 44.75 | W | O |
| ATOM | 5140 | OH2 | WAT | W | 402 | 28.452 | −1.394 | 7.667 | 1.00 | 56.86 | W | O |
| ATOM | 5141 | OH2 | WAT | W | 403 | 22.460 | 2.393 | 0.537 | 1.00 | 46.38 | W | O |
| ATOM | 5142 | OH2 | WAT | W | 404 | 20.613 | 0.672 | −0.814 | 1.00 | 61.12 | W | O |
| END | | | | | | | | | | | | |

Table 37 Coordinate data of the complex between Compound (2) and human factor VIIa/soluble tissue factor (around the inhibitor)

| | | | | | | | | | | | | |
|---|---|---|---|---|---|---|---|---|---|---|---|---|
| CRYST1 | 71.280 | 82.320 | 123.380 | 90.00 | 90.00 | 90.00 P212121 | | | | | | |
| ATOM | 1 | N | ILE | H | 16 | 22.059 | 3.893 | 14.020 | 1.00 | 5.70 | H | N |
| ATOM | 2 | CA | ILE | H | 16 | 21.957 | 4.124 | 15.491 | 1.00 | 6.52 | H | C |
| ATOM | 3 | C | ILE | H | 16 | 22.005 | 2.782 | 16.220 | 1.00 | 7.66 | H | C |
| ATOM | 4 | O | ILE | H | 16 | 21.209 | 1.883 | 15.942 | 1.00 | 8.62 | H | O |
| ATOM | 5 | CB | ILE | H | 16 | 20.628 | 4.834 | 15.856 | 1.00 | 7.20 | H | C |
| ATOM | 6 | CG1 | ILE | H | 16 | 20.515 | 6.174 | 15.119 | 1.00 | 6.97 | H | C |
| ATOM | 7 | CG2 | ILE | H | 16 | 20.545 | 5.036 | 17.365 | 1.00 | 7.03 | H | C |
| ATOM | 8 | CD1 | ILE | H | 16 | 21.554 | 7.217 | 15.521 | 1.00 | 6.54 | H | C |
| ATOM | 9 | N | VAL | H | 17 | 22.947 | 2.646 | 17.144 | 1.00 | 8.63 | H | N |
| ATOM | 10 | CA | VAL | H | 17 | 23.087 | 1.417 | 17.916 | 1.00 | 9.50 | H | C |
| ATOM | 11 | C | VAL | H | 17 | 22.570 | 1.634 | 19.338 | 1.00 | 9.85 | H | C |
| ATOM | 12 | O | VAL | H | 17 | 23.002 | 2.553 | 20.026 | 1.00 | 10.72 | H | O |
| ATOM | 13 | CB | VAL | H | 17 | 24.566 | 0.964 | 18.008 | 1.00 | 9.85 | H | C |
| ATOM | 14 | CG1 | VAL | H | 17 | 24.659 | −0.327 | 18.813 | 1.00 | 10.27 | H | C |
| ATOM | 15 | CG2 | VAL | H | 17 | 25.148 | 0.754 | 16.613 | 1.00 | 9.47 | H | C |
| ATOM | 16 | N | LEU | H | 41 | 22.072 | 7.406 | 1.097 | 1.00 | 11.66 | H | N |
| ATOM | 17 | CA | LEU | H | 41 | 23.440 | 7.899 | 1.213 | 1.00 | 11.08 | H | C |
| ATOM | 18 | C | LEU | H | 41 | 23.808 | 8.366 | 2.624 | 1.00 | 10.34 | H | C |
| ATOM | 19 | O | LEU | H | 41 | 24.765 | 7.871 | 3.224 | 1.00 | 10.61 | H | O |

-continued

| | | | | | | | | | | | | |
|---|---|---|---|---|---|---|---|---|---|---|---|---|
| ATOM | 20 | CB | LEU | H | 41 | 23.657 | 9.058 | 0.226 | 1.00 | 10.87 | H | C |
| ATOM | 21 | CG | LEU | H | 41 | 25.000 | 9.801 | 0.273 | 1.00 | 11.44 | H | C |
| ATOM | 22 | CD1 | LEU | H | 41 | 26.115 | 8.893 | −0.221 | 1.00 | 11.67 | H | C |
| ATOM | 23 | CD2 | LEU | H | 41 | 24.921 | 11.048 | −0.582 | 1.00 | 11.04 | H | C |
| ATOM | 24 | N | CYS | H | 42 | 23.032 | 9.307 | 3.153 | 1.00 | 8.47 | H | N |
| ATOM | 25 | CA | CYS | H | 42 | 23.314 | 9.885 | 4.457 | 1.00 | 6.60 | H | C |
| ATOM | 26 | C | CYS | H | 42 | 22.102 | 10.577 | 5.061 | 1.00 | 6.35 | H | C |
| ATOM | 27 | O | CYS | H | 42 | 21.038 | 10.660 | 4.448 | 1.00 | 8.58 | H | O |
| ATOM | 28 | CB | CYS | H | 42 | 24.421 | 10.935 | 4.309 | 1.00 | 6.00 | H | C |
| ATOM | 29 | SG | CYS | H | 42 | 26.138 | 10.338 | 4.348 | 1.00 | 7.26 | H | S |
| ATOM | 30 | N | GLY | H | 43 | 22.291 | 11.087 | 6.272 | 1.00 | 4.57 | H | N |
| ATOM | 31 | CA | GLY | H | 43 | 21.248 | 11.827 | 6.949 | 1.00 | 3.67 | H | C |
| ATOM | 32 | C | GLY | H | 43 | 21.549 | 13.308 | 6.764 | 1.00 | 3.89 | H | C |
| ATOM | 33 | O | GLY | H | 43 | 22.525 | 13.686 | 6.104 | 1.00 | 3.28 | H | O |
| ATOM | 34 | N | ALA | H | 55 | 26.992 | 16.158 | 6.411 | 1.00 | 5.39 | H | N |
| ATOM | 35 | CA | ALA | H | 55 | 28.424 | 15.958 | 6.611 | 1.00 | 5.45 | H | C |
| ATOM | 36 | C | ALA | H | 55 | 29.160 | 15.980 | 5.277 | 1.00 | 6.95 | H | C |
| ATOM | 37 | O | ALA | H | 55 | 28.674 | 15.441 | 4.279 | 1.00 | 6.34 | H | O |
| ATOM | 38 | CB | ALA | H | 55 | 28.681 | 14.624 | 7.326 | 1.00 | 4.19 | H | C |
| ATOM | 39 | N | ALA | H | 56 | 30.333 | 16.606 | 5.265 | 1.00 | 6.14 | H | N |
| ATOM | 40 | CA | ALA | H | 56 | 31.142 | 16.694 | 4.053 | 1.00 | 7.74 | H | C |
| ATOM | 41 | C | ALA | H | 56 | 31.552 | 15.332 | 3.488 | 1.00 | 6.96 | H | C |
| ATOM | 42 | O | ALA | H | 56 | 31.487 | 15.118 | 2.276 | 1.00 | 8.41 | H | O |
| ATOM | 43 | CB | ALA | H | 56 | 32.399 | 17.532 | 4.319 | 1.00 | 6.48 | H | C |
| ATOM | 44 | N | HIS | H | 57 | 31.971 | 14.412 | 4.355 | 1.00 | 5.95 | H | N |
| ATOM | 45 | CA | HIS | H | 57 | 32.419 | 13.103 | 3.889 | 1.00 | 6.77 | H | C |
| ATOM | 46 | C | HIS | H | 57 | 31.358 | 12.282 | 3.151 | 1.00 | 8.28 | H | C |
| ATOM | 47 | O | HIS | H | 57 | 31.685 | 11.304 | 2.476 | 1.00 | 8.26 | H | O |
| ATOM | 48 | CB | HIS | H | 57 | 33.021 | 12.288 | 5.046 | 1.00 | 5.22 | H | C |
| ATOM | 49 | CG | HIS | H | 57 | 32.022 | 11.512 | 5.846 | 1.00 | 4.67 | H | C |
| ATOM | 50 | ND1 | HIS | H | 57 | 31.558 | 11.936 | 7.074 | 1.00 | 2.15 | H | N |
| ATOM | 51 | CD2 | HIS | H | 57 | 31.432 | 10.314 | 5.613 | 1.00 | 3.66 | H | C |
| ATOM | 52 | CE1 | HIS | H | 57 | 30.730 | 11.032 | 7.564 | 1.00 | 2.30 | H | C |
| ATOM | 53 | NE2 | HIS | H | 57 | 30.636 | 10.038 | 6.698 | 1.00 | 3.94 | H | N |
| ATOM | 54 | N | CYS | H | 58 | 30.096 | 12.686 | 3.267 | 1.00 | 7.28 | H | N |
| ATOM | 55 | CA | CYS | H | 58 | 29.008 | 11.999 | 2.584 | 1.00 | 8.91 | H | C |
| ATOM | 56 | C | CYS | H | 58 | 29.128 | 12.140 | 1.069 | 1.00 | 9.73 | H | C |
| ATOM | 57 | O | CYS | H | 58 | 28.496 | 11.407 | 0.317 | 1.00 | 7.76 | H | O |
| ATOM | 58 | CB | CYS | H | 58 | 27.660 | 12.578 | 3.035 | 1.00 | 7.86 | H | C |
| ATOM | 59 | SG | CYS | H | 58 | 27.176 | 12.043 | 4.706 | 1.00 | 6.38 | H | S |
| ATOM | 60 | N | PHE | H | 59 | 29.962 | 13.074 | 0.628 | 1.00 | 10.76 | H | N |
| ATOM | 61 | CA | PHE | H | 59 | 30.114 | 13.347 | −0.790 | 1.00 | 9.91 | H | C |
| ATOM | 62 | C | PHE | H | 59 | 31.481 | 12.971 | −1.364 | 1.00 | 9.71 | H | C |
| ATOM | 63 | O | PHE | H | 59 | 31.804 | 13.337 | −2.496 | 1.00 | 8.14 | H | O |
| ATOM | 64 | CB | PHE | H | 59 | 29.804 | 14.832 | −1.020 | 1.00 | 9.77 | H | C |
| ATOM | 65 | CG | PHE | H | 59 | 28.484 | 15.267 | −0.422 | 1.00 | 10.32 | H | C |
| ATOM | 66 | CD1 | PHE | H | 59 | 27.287 | 15.011 | −1.083 | 1.00 | 7.39 | H | C |
| ATOM | 67 | CD2 | PHE | H | 59 | 28.436 | 15.845 | 0.846 | 1.00 | 11.05 | H | C |
| ATOM | 68 | CE1 | PHE | H | 59 | 26.061 | 15.314 | −0.493 | 1.00 | 9.49 | H | C |
| ATOM | 69 | CE2 | PHE | H | 59 | 27.214 | 16.151 | 1.447 | 1.00 | 11.89 | H | C |
| ATOM | 70 | CZ | PHE | H | 59 | 26.023 | 15.884 | 0.776 | 1.00 | 10.25 | H | C |
| ATOM | 71 | N | ASP | H | 60 | 32.273 | 12.230 | −0.591 | 1.00 | 8.71 | H | N |
| ATOM | 72 | CA | ASP | H | 60 | 33.596 | 11.796 | −1.041 | 1.00 | 11.41 | H | C |
| ATOM | 73 | C | ASP | H | 60 | 33.570 | 11.036 | −2.370 | 1.00 | 13.85 | H | C |
| ATOM | 74 | O | ASP | H | 60 | 34.394 | 11.286 | −3.250 | 1.00 | 13.33 | H | O |
| ATOM | 75 | CB | ASP | H | 60 | 34.255 | 10.904 | 0.016 | 1.00 | 9.72 | H | C |
| ATOM | 76 | CG | ASP | H | 60 | 34.855 | 11.694 | 1.157 | 1.00 | 10.46 | H | C |
| ATOM | 77 | OD1 | ASP | H | 60 | 34.672 | 12.930 | 1.191 | 1.00 | 8.35 | H | O |
| ATOM | 78 | OD2 | ASP | H | 60 | 35.514 | 11.074 | 2.020 | 1.00 | 9.24 | H | O |
| ATOM | 79 | N | LYS | H | 60A | 32.634 | 10.105 | −2.522 | 1.00 | 15.64 | H | N |
| ATOM | 80 | CA | LYS | H | 60A | 32.579 | 9.330 | −3.755 | 1.00 | 19.34 | H | C |
| ATOM | 81 | C | LYS | H | 60A | 31.407 | 9.614 | −4.690 | 1.00 | 19.44 | H | C |
| ATOM | 82 | O | LYS | H | 60A | 30.971 | 8.728 | −5.420 | 1.00 | 19.48 | H | O |
| ATOM | 83 | CB | LYS | H | 60A | 32.624 | 7.830 | −3.441 | 1.00 | 21.25 | H | C |
| ATOM | 84 | CG | LYS | H | 60A | 34.024 | 7.315 | −3.136 | 1.00 | 25.19 | H | C |
| ATOM | 85 | CD | LYS | H | 60A | 34.292 | 7.216 | −1.650 | 1.00 | 28.66 | H | C |
| ATOM | 86 | CE | LYS | H | 60A | 33.594 | 6.006 | −1.041 | 1.00 | 31.51 | H | C |
| ATOM | 87 | NZ | LYS | H | 60A | 33.915 | 5.848 | 0.412 | 1.00 | 35.53 | H | N |
| ATOM | 88 | N | ILE | H | 90 | 30.977 | 22.763 | 0.695 | 1.00 | 7.99 | H | N |
| ATOM | 89 | CA | ILE | H | 90 | 31.915 | 22.141 | 1.623 | 1.00 | 7.65 | H | C |
| ATOM | 90 | C | ILE | H | 90 | 33.092 | 23.074 | 1.866 | 1.00 | 7.29 | H | C |
| ATOM | 91 | O | ILE | H | 90 | 33.544 | 23.761 | 0.953 | 1.00 | 9.45 | H | O |
| ATOM | 92 | CB | ILE | H | 90 | 32.422 | 20.804 | 1.016 | 1.00 | 7.65 | H | C |
| ATOM | 93 | CG1 | ILE | H | 90 | 31.298 | 19.767 | 1.061 | 1.00 | 8.19 | H | C |
| ATOM | 94 | CG2 | ILE | H | 90 | 33.667 | 20.313 | 1.732 | 1.00 | 8.25 | H | C |
| ATOM | 95 | CD1 | ILE | H | 90 | 31.620 | 18.477 | 0.319 | 1.00 | 9.60 | H | C |
| ATOM | 96 | N | TYR | H | 94 | 38.317 | 21.049 | 3.982 | 1.00 | 8.73 | H | N |
| ATOM | 97 | CA | TYR | H | 94 | 37.972 | 19.637 | 4.148 | 1.00 | 7.55 | H | C |
| ATOM | 98 | C | TYR | H | 94 | 38.721 | 18.785 | 3.130 | 1.00 | 7.26 | H | C |

-continued

| | | | | | | | | | | | |
|---|---|---|---|---|---|---|---|---|---|---|---|
| ATOM | 99  | O   | TYR | H | 94  | 38.805 | 19.138 | 1.959  | 1.00 | 6.40  | H | O |
| ATOM | 100 | CB  | TYR | H | 94  | 36.464 | 19.404 | 3.969  | 1.00 | 5.85  | H | C |
| ATOM | 101 | CG  | TYR | H | 94  | 36.110 | 17.927 | 3.920  | 1.00 | 4.59  | H | C |
| ATOM | 102 | CD1 | TYR | H | 94  | 36.088 | 17.157 | 5.082  | 1.00 | 4.45  | H | C |
| ATOM | 103 | CD2 | TYR | H | 94  | 35.884 | 17.281 | 2.700  | 1.00 | 4.26  | H | C |
| ATOM | 104 | CE1 | TYR | H | 94  | 35.859 | 15.780 | 5.035  | 1.00 | 2.80  | H | C |
| ATOM | 105 | CE2 | TYR | H | 94  | 35.653 | 15.907 | 2.642  | 1.00 | 3.12  | H | C |
| ATOM | 106 | CZ  | TYR | H | 94  | 35.646 | 15.163 | 3.814  | 1.00 | 1.93  | H | C |
| ATOM | 107 | OH  | TYR | H | 94  | 35.462 | 13.796 | 3.767  | 1.00 | 5.06  | H | O |
| ATOM | 108 | N   | VAL | H | 95  | 39.254 | 17.656 | 3.584  | 1.00 | 8.23  | H | N |
| ATOM | 109 | CA  | VAL | H | 95  | 39.989 | 16.748 | 2.713  | 1.00 | 8.13  | H | C |
| ATOM | 110 | C   | VAL | H | 95  | 39.293 | 15.393 | 2.622  | 1.00 | 9.13  | H | C |
| ATOM | 111 | O   | VAL | H | 95  | 39.141 | 14.692 | 3.625  | 1.00 | 8.17  | H | O |
| ATOM | 112 | CB  | VAL | H | 95  | 41.428 | 16.523 | 3.225  | 1.00 | 8.63  | H | C |
| ATOM | 113 | CG1 | VAL | H | 95  | 42.160 | 15.530 | 2.315  | 1.00 | 7.79  | H | C |
| ATOM | 114 | CG2 | VAL | H | 95  | 42.173 | 17.848 | 3.271  | 1.00 | 9.62  | H | C |
| ATOM | 115 | N   | PRO | H | 96  | 38.863 | 15.005 | 1.410  | 1.00 | 10.15 | H | N |
| ATOM | 116 | CA  | PRO | H | 96  | 38.187 | 13.716 | 1.237  | 1.00 | 10.07 | H | C |
| ATOM | 117 | C   | PRO | H | 96  | 38.988 | 12.623 | 1.928  | 1.00 | 9.71  | H | C |
| ATOM | 118 | O   | PRO | H | 96  | 40.221 | 12.655 | 1.917  | 1.00 | 10.21 | H | O |
| ATOM | 119 | CB  | PRO | H | 96  | 38.171 | 13.536 | −0.279 | 1.00 | 9.81  | H | C |
| ATOM | 120 | CG  | PRO | H | 96  | 38.070 | 14.949 | −0.776 | 1.00 | 9.61  | H | C |
| ATOM | 121 | CD  | PRO | H | 96  | 39.062 | 15.673 | 0.110  | 1.00 | 8.77  | H | C |
| ATOM | 122 | N   | GLY | H | 97  | 38.280 | 11.675 | 2.534  | 1.00 | 7.35  | H | N |
| ATOM | 123 | CA  | GLY | H | 97  | 38.928 | 10.571 | 3.222  | 1.00 | 7.72  | H | C |
| ATOM | 124 | C   | GLY | H | 97  | 39.292 | 10.853 | 4.670  | 1.00 | 8.31  | H | C |
| ATOM | 125 | O   | GLY | H | 97  | 39.656 | 9.934  | 5.404  | 1.00 | 5.90  | H | O |
| ATOM | 126 | N   | THR | H | 98  | 39.187 | 12.112 | 5.091  | 1.00 | 8.38  | H | N |
| ATOM | 127 | CA  | THR | H | 98  | 39.543 | 12.474 | 6.456  | 1.00 | 8.75  | H | C |
| ATOM | 128 | C   | THR | H | 98  | 38.347 | 12.901 | 7.301  | 1.00 | 9.32  | H | C |
| ATOM | 129 | O   | THR | H | 98  | 37.197 | 12.726 | 6.888  | 1.00 | 9.82  | H | O |
| ATOM | 130 | CB  | THR | H | 98  | 40.639 | 13.572 | 6.474  | 1.00 | 10.03 | H | C |
| ATOM | 131 | OG1 | THR | H | 98  | 40.118 | 14.798 | 5.939  | 1.00 | 9.30  | H | O |
| ATOM | 132 | CG2 | THR | H | 98  | 41.841 | 13.123 | 5.636  | 1.00 | 7.92  | H | C |
| ATOM | 133 | N   | THR | H | 99  | 38.622 | 13.478 | 8.470  | 1.00 | 6.94  | H | N |
| ATOM | 134 | CA  | THR | H | 99  | 37.576 | 13.853 | 9.411  | 1.00 | 7.19  | H | C |
| ATOM | 135 | C   | THR | H | 99  | 37.371 | 15.330 | 9.811  | 1.00 | 7.60  | H | C |
| ATOM | 136 | O   | THR | H | 99  | 36.267 | 15.704 | 10.221 | 1.00 | 4.56  | H | O |
| ATOM | 137 | CB  | THR | H | 99  | 37.761 | 13.028 | 10.697 | 1.00 | 9.01  | H | C |
| ATOM | 138 | OG1 | THR | H | 99  | 39.126 | 13.133 | 11.128 | 1.00 | 8.28  | H | O |
| ATOM | 139 | CG2 | THR | H | 99  | 37.434 | 11.556 | 10.444 | 1.00 | 8.22  | H | C |
| ATOM | 140 | N   | ASN | H | 100 | 38.405 | 16.163 | 9.703  | 1.00 | 4.83  | H | N |
| ATOM | 141 | CA  | ASN | H | 100 | 38.280 | 17.573 | 10.093 | 1.00 | 6.56  | H | C |
| ATOM | 142 | C   | ASN | H | 100 | 37.359 | 18.369 | 9.157  | 1.00 | 6.18  | H | C |
| ATOM | 143 | O   | ASN | H | 100 | 37.299 | 18.109 | 7.957  | 1.00 | 6.48  | H | O |
| ATOM | 144 | CB  | ASN | H | 100 | 39.669 | 18.244 | 10.151 | 1.00 | 3.59  | H | C |
| ATOM | 145 | CG  | ASN | H | 100 | 39.760 | 19.337 | 11.227 | 1.00 | 7.18  | H | C |
| ATOM | 146 | OD1 | ASN | H | 100 | 40.685 | 20.162 | 11.222 | 1.00 | 9.38  | H | O |
| ATOM | 147 | ND2 | ASN | H | 100 | 38.809 | 19.340 | 12.156 | 1.00 | 1.98  | H | N |
| ATOM | 148 | N   | HIS | H | 101 | 36.638 | 19.338 | 9.718  | 1.00 | 6.06  | H | N |
| ATOM | 149 | CA  | HIS | H | 101 | 35.725 | 20.178 | 8.940  | 1.00 | 6.01  | H | C |
| ATOM | 150 | C   | HIS | H | 101 | 34.705 | 19.325 | 8.198  | 1.00 | 6.65  | H | C |
| ATOM | 151 | O   | HIS | H | 101 | 34.433 | 19.562 | 7.017  | 1.00 | 6.05  | H | O |
| ATOM | 152 | CB  | HIS | H | 101 | 36.510 | 21.018 | 7.927  | 1.00 | 6.18  | H | C |
| ATOM | 153 | CG  | HIS | H | 101 | 37.589 | 21.853 | 8.541  | 1.00 | 9.14  | H | C |
| ATOM | 154 | ND1 | HIS | H | 101 | 37.331 | 22.852 | 9.456  | 1.00 | 10.10 | H | N |
| ATOM | 155 | CD2 | HIS | H | 101 | 38.935 | 21.824 | 8.387  | 1.00 | 8.84  | H | C |
| ATOM | 156 | CE1 | HIS | H | 101 | 38.470 | 23.401 | 9.839  | 1.00 | 9.36  | H | C |
| ATOM | 157 | NE2 | HIS | H | 101 | 39.458 | 22.795 | 9.206  | 1.00 | 5.86  | H | N |
| ATOM | 158 | N   | ASP | H | 102 | 34.136 | 18.341 | 8.891  | 1.00 | 4.35  | H | N |
| ATOM | 159 | CA  | ASP | H | 102 | 33.170 | 17.436 | 8.279  | 1.00 | 4.62  | H | C |
| ATOM | 160 | C   | ASP | H | 102 | 31.773 | 18.055 | 8.310  | 1.00 | 5.36  | H | C |
| ATOM | 161 | O   | ASP | H | 102 | 30.936 | 17.713 | 9.154  | 1.00 | 5.27  | H | O |
| ATOM | 162 | CB  | ASP | H | 102 | 33.188 | 16.095 | 9.016  | 1.00 | 1.00  | H | C |
| ATOM | 163 | CG  | ASP | H | 102 | 32.509 | 14.992 | 8.238  | 1.00 | 3.93  | H | C |
| ATOM | 164 | OD1 | ASP | H | 102 | 32.142 | 15.219 | 7.067  | 1.00 | 5.39  | H | O |
| ATOM | 165 | OD2 | ASP | H | 102 | 32.352 | 13.889 | 8.794  | 1.00 | 2.41  | H | O |
| ATOM | 166 | N   | ILE | H | 103 | 31.529 | 18.972 | 7.381  | 1.00 | 5.02  | H | N |
| ATOM | 167 | CA  | ILE | H | 103 | 30.248 | 19.659 | 7.309  | 1.00 | 3.77  | H | C |
| ATOM | 168 | C   | ILE | H | 103 | 29.945 | 20.059 | 5.874  | 1.00 | 4.55  | H | C |
| ATOM | 169 | O   | ILE | H | 103 | 30.851 | 20.349 | 5.094  | 1.00 | 4.54  | H | O |
| ATOM | 170 | CB  | ILE | H | 103 | 30.266 | 20.931 | 8.201  | 1.00 | 4.83  | H | C |
| ATOM | 171 | CG1 | ILE | H | 103 | 28.873 | 21.570 | 8.259  | 1.00 | 2.69  | H | C |
| ATOM | 172 | CG2 | ILE | H | 103 | 31.288 | 21.931 | 7.664  | 1.00 | 2.18  | H | C |
| ATOM | 173 | CD1 | ILE | H | 103 | 28.770 | 22.730 | 9.246  | 1.00 | 1.00  | H | C |
| ATOM | 174 | N   | VAL | H | 138 | 20.653 | 12.090 | 18.785 | 1.00 | 5.55  | H | N |
| ATOM | 175 | CA  | VAL | H | 138 | 21.298 | 11.812 | 17.509 | 1.00 | 6.30  | H | C |
| ATOM | 176 | C   | VAL | H | 138 | 20.336 | 10.842 | 16.823 | 1.00 | 6.56  | H | C |
| ATOM | 177 | O   | VAL | H | 138 | 19.741 | 9.990  | 17.479 | 1.00 | 7.54  | H | O |

-continued

| | | | | | | | | | | | |
|---|---|---|---|---|---|---|---|---|---|---|---|
| ATOM | 178 | CB | VAL | H | 138 | 22.704 | 11.165 | 17.677 | 1.00 | 6.77 | H | C |
| ATOM | 179 | CG1 | VAL | H | 138 | 23.664 | 12.166 | 18.324 | 1.00 | 3.97 | H | C |
| ATOM | 180 | CG2 | VAL | H | 138 | 22.614 | 9.906 | 18.515 | 1.00 | 5.04 | H | C |
| ATOM | 181 | N | SER | H | 139 | 20.172 | 10.967 | 15.512 | 1.00 | 6.69 | H | N |
| ATOM | 182 | CA | SER | H | 139 | 19.227 | 10.114 | 14.805 | 1.00 | 5.72 | H | C |
| ATOM | 183 | C | SER | H | 139 | 19.611 | 9.790 | 13.370 | 1.00 | 6.17 | H | C |
| ATOM | 184 | O | SER | H | 139 | 20.485 | 10.431 | 12.787 | 1.00 | 5.98 | H | O |
| ATOM | 185 | CB | SER | H | 139 | 17.850 | 10.786 | 14.815 | 1.00 | 6.76 | H | C |
| ATOM | 186 | OG | SER | H | 139 | 17.944 | 12.120 | 14.327 | 1.00 | 4.59 | H | O |
| ATOM | 187 | N | GLY | H | 142 | 20.741 | 4.754 | 9.987 | 1.00 | 8.09 | H | N |
| ATOM | 188 | CA | GLY | H | 142 | 21.997 | 4.032 | 9.902 | 1.00 | 6.84 | H | C |
| ATOM | 189 | C | GLY | H | 142 | 21.957 | 2.626 | 10.456 | 1.00 | 7.70 | H | C |
| ATOM | 190 | O | GLY | H | 142 | 20.900 | 2.125 | 10.850 | 1.00 | 7.86 | H | O |
| ATOM | 191 | N | GLN | H | 143 | 23.126 | 1.993 | 10.480 | 1.00 | 9.91 | H | N |
| ATOM | 192 | CA | GLN | H | 143 | 23.278 | 0.628 | 10.976 | 1.00 | 11.50 | H | C |
| ATOM | 193 | C | GLN | H | 143 | 22.843 | 0.499 | 12.425 | 1.00 | 11.62 | H | C |
| ATOM | 194 | O | GLN | H | 143 | 23.133 | 1.360 | 13.255 | 1.00 | 10.73 | H | O |
| ATOM | 195 | CB | GLN | H | 143 | 24.737 | 0.158 | 10.868 | 1.00 | 10.78 | H | C |
| ATOM | 196 | CG | GLN | H | 143 | 25.309 | 0.056 | 9.452 | 1.00 | 13.60 | H | C |
| ATOM | 197 | CD | GLN | H | 143 | 25.651 | 1.411 | 8.850 | 1.00 | 16.26 | H | C |
| ATOM | 198 | OE1 | GLN | H | 143 | 25.652 | 2.430 | 9.542 | 1.00 | 13.61 | H | O |
| ATOM | 199 | NE2 | GLN | H | 143 | 25.952 | 1.425 | 7.555 | 1.00 | 15.87 | H | N |
| ATOM | 200 | N | LEU | H | 145 | 23.813 | −2.024 | 14.132 | 1.00 | 17.85 | H | N |
| ATOM | 201 | CA | LEU | H | 145 | 24.999 | −2.630 | 14.718 | 1.00 | 21.26 | H | C |
| ATOM | 202 | C | LEU | H | 145 | 26.174 | −2.317 | 13.805 | 1.00 | 22.23 | H | C |
| ATOM | 203 | O | LEU | H | 145 | 25.998 | −2.080 | 12.610 | 1.00 | 20.28 | H | O |
| ATOM | 204 | CB | LEU | H | 145 | 24.848 | −4.149 | 14.816 | 1.00 | 21.41 | H | C |
| ATOM | 205 | CG | LEU | H | 145 | 23.756 | −4.748 | 15.699 | 1.00 | 24.05 | H | C |
| ATOM | 206 | CD1 | LEU | H | 145 | 23.709 | −6.251 | 15.465 | 1.00 | 22.91 | H | C |
| ATOM | 207 | CD2 | LEU | H | 145 | 24.029 | −4.437 | 17.166 | 1.00 | 24.83 | H | C |
| ATOM | 208 | N | ASP | H | 146 | 27.371 | −2.314 | 14.374 | 1.00 | 24.68 | H | N |
| ATOM | 209 | CA | ASP | H | 146 | 28.569 | −2.054 | 13.600 | 1.00 | 28.79 | H | C |
| ATOM | 210 | C | ASP | H | 146 | 28.701 | −3.221 | 12.634 | 1.00 | 30.65 | H | C |
| ATOM | 211 | O | ASP | H | 146 | 28.649 | −4.379 | 13.046 | 1.00 | 29.72 | H | O |
| ATOM | 212 | CB | ASP | H | 146 | 29.781 | −1.974 | 14.534 | 1.00 | 30.17 | H | C |
| ATOM | 213 | CG | ASP | H | 146 | 31.076 | −1.707 | 13.795 | 1.00 | 31.88 | H | C |
| ATOM | 214 | OD1 | ASP | H | 146 | 31.050 | −0.995 | 12.767 | 1.00 | 32.57 | H | O |
| ATOM | 215 | OD2 | ASP | H | 146 | 32.128 | −2.199 | 14.257 | 1.00 | 35.02 | H | O |
| ATOM | 216 | N | ARG | H | 147 | 28.838 | −2.918 | 11.348 | 1.00 | 34.10 | H | N |
| ATOM | 217 | CA | ARG | H | 147 | 28.968 | −3.964 | 10.338 | 1.00 | 37.74 | H | C |
| ATOM | 218 | C | ARG | H | 147 | 27.620 | −4.672 | 10.137 | 1.00 | 36.36 | H | C |
| ATOM | 219 | O | ARG | H | 147 | 27.580 | −5.856 | 9.805 | 1.00 | 38.70 | H | O |
| ATOM | 220 | CB | ARG | H | 147 | 30.023 | −4.977 | 10.794 | 1.00 | 41.63 | H | C |
| ATOM | 221 | CG | ARG | H | 147 | 30.984 | −5.462 | 9.731 | 1.00 | 48.94 | H | C |
| ATOM | 222 | CD | ARG | H | 147 | 32.085 | −6.279 | 10.395 | 1.00 | 55.34 | H | C |
| ATOM | 223 | NE | ARG | H | 147 | 33.126 | −6.706 | 9.465 | 1.00 | 60.79 | H | N |
| ATOM | 224 | CZ | ARG | H | 147 | 34.228 | −7.360 | 9.826 | 1.00 | 63.32 | H | C |
| ATOM | 225 | NH1 | ARG | H | 147 | 34.439 | −7.667 | 11.100 | 1.00 | 64.90 | H | N |
| ATOM | 226 | NH2 | ARG | H | 147 | 35.122 | −7.708 | 8.912 | 1.00 | 64.23 | H | N |
| ATOM | 227 | N | LEU | H | 158 | 18.599 | 8.382 | 19.520 | 1.00 | 8.74 | H | N |
| ATOM | 228 | CA | LEU | H | 158 | 19.340 | 8.024 | 20.727 | 1.00 | 7.23 | H | C |
| ATOM | 229 | C | LEU | H | 158 | 19.751 | 9.261 | 21.527 | 1.00 | 8.93 | H | C |
| ATOM | 230 | O | LEU | H | 158 | 20.116 | 10.290 | 20.953 | 1.00 | 8.07 | H | O |
| ATOM | 231 | CB | LEU | H | 158 | 20.603 | 7.253 | 20.336 | 1.00 | 6.49 | H | C |
| ATOM | 232 | CG | LEU | H | 158 | 21.572 | 6.875 | 21.454 | 1.00 | 6.44 | H | C |
| ATOM | 233 | CD1 | LEU | H | 158 | 20.931 | 5.804 | 22.334 | 1.00 | 7.20 | H | C |
| ATOM | 234 | CD2 | LEU | H | 158 | 22.886 | 6.374 | 20.853 | 1.00 | 6.24 | H | C |
| ATOM | 235 | N | VAL | H | 160 | 22.440 | 10.884 | 23.870 | 1.00 | 6.69 | H | N |
| ATOM | 236 | CA | VAL | H | 160 | 23.841 | 10.699 | 24.231 | 1.00 | 5.16 | H | C |
| ATOM | 237 | C | VAL | H | 160 | 24.363 | 11.899 | 25.015 | 1.00 | 6.46 | H | C |
| ATOM | 238 | O | VAL | H | 160 | 23.972 | 13.038 | 24.761 | 1.00 | 6.24 | H | O |
| ATOM | 239 | CB | VAL | H | 160 | 24.748 | 10.493 | 22.977 | 1.00 | 4.79 | H | C |
| ATOM | 240 | CG1 | VAL | H | 160 | 24.364 | 9.202 | 22.248 | 1.00 | 2.87 | H | C |
| ATOM | 241 | CG2 | VAL | H | 160 | 24.636 | 11.690 | 22.033 | 1.00 | 4.14 | H | C |
| ATOM | 242 | N | ARG | H | 170C | 40.277 | 4.649 | 25.092 | 1.00 | 26.96 | H | N |
| ATOM | 243 | CA | ARG | H | 170C | 41.408 | 3.742 | 25.040 | 1.00 | 30.88 | H | C |
| ATOM | 244 | C | ARG | H | 170C | 42.455 | 4.322 | 24.096 | 1.00 | 33.02 | H | C |
| ATOM | 245 | O | ARG | H | 170C | 42.180 | 4.560 | 22.920 | 1.00 | 32.09 | H | O |
| ATOM | 246 | CB | ARG | H | 170C | 40.952 | 2.368 | 24.546 | 1.00 | 32.33 | H | C |
| ATOM | 247 | CG | ARG | H | 170C | 42.066 | 1.343 | 24.417 | 1.00 | 36.16 | H | C |
| ATOM | 248 | CD | ARG | H | 170C | 41.510 | −0.012 | 24.014 | 1.00 | 39.39 | H | C |
| ATOM | 249 | NE | ARG | H | 170C | 42.563 | −0.955 | 23.649 | 1.00 | 41.61 | H | N |
| ATOM | 250 | CZ | ARG | H | 170C | 42.345 | −2.177 | 23.169 | 1.00 | 44.13 | H | C |
| ATOM | 251 | NH1 | ARG | H | 170C | 41.105 | −2.617 | 22.992 | 1.00 | 45.02 | H | N |
| ATOM | 252 | NH2 | ARG | H | 170C | 43.370 | −2.959 | 22.859 | 1.00 | 45.11 | H | N |
| ATOM | 253 | N | LYS | H | 170D | 43.650 | 4.565 | 24.622 | 1.00 | 36.30 | H | N |
| ATOM | 254 | CA | LYS | H | 170D | 44.737 | 5.114 | 23.820 | 1.00 | 39.96 | H | C |
| ATOM | 255 | C | LYS | H | 170D | 45.045 | 4.165 | 22.667 | 1.00 | 39.79 | H | C |
| ATOM | 256 | O | LYS | H | 170D | 45.328 | 2.986 | 22.881 | 1.00 | 39.51 | H | O |

-continued

| | | | | | | | | | | | |
|---|---|---|---|---|---|---|---|---|---|---|---|
| ATOM | 257 | CB | LYS | H | 170D | 45.986 | 5.302 | 24.685 | 1.00 | 43.00 | H | C |
| ATOM | 258 | CG | LYS | H | 170D | 47.201 | 5.802 | 23.921 | 1.00 | 47.37 | H | C |
| ATOM | 259 | CD | LYS | H | 170D | 48.433 | 5.842 | 24.812 | 1.00 | 51.67 | H | C |
| ATOM | 260 | CE | LYS | H | 170D | 49.673 | 6.249 | 24.028 | 1.00 | 54.05 | H | C |
| ATOM | 261 | NZ | LYS | H | 170D | 49.975 | 5.293 | 22.924 | 1.00 | 55.60 | H | N |
| ATOM | 262 | N | VAL | H | 170E | 44.983 | 4.679 | 21.445 | 1.00 | 39.89 | H | N |
| ATOM | 263 | CA | VAL | H | 170E | 45.250 | 3.860 | 20.269 | 1.00 | 40.30 | H | C |
| ATOM | 264 | C | VAL | H | 170E | 46.447 | 4.372 | 19.472 | 1.00 | 41.06 | H | C |
| ATOM | 265 | O | VAL | H | 170E | 47.128 | 5.312 | 19.888 | 1.00 | 41.71 | H | O |
| ATOM | 266 | CB | VAL | H | 170E | 44.015 | 3.799 | 19.340 | 1.00 | 40.64 | H | C |
| ATOM | 267 | CG1 | VAL | H | 170E | 42.876 | 3.065 | 20.034 | 1.00 | 40.47 | H | C |
| ATOM | 268 | CG2 | VAL | H | 170E | 43.582 | 5.199 | 18.958 | 1.00 | 40.92 | H | C |
| ATOM | 269 | N | GLY | H | 170F | 46.700 | 3.741 | 18.330 | 1.00 | 40.52 | H | N |
| ATOM | 270 | CA | GLY | H | 170F | 47.814 | 4.140 | 17.492 | 1.00 | 39.24 | H | C |
| ATOM | 271 | C | GLY | H | 170F | 47.649 | 5.534 | 16.920 | 1.00 | 38.47 | H | C |
| ATOM | 272 | O | GLY | H | 170F | 47.270 | 6.468 | 17.630 | 1.00 | 38.87 | H | O |
| ATOM | 273 | N | ASP | H | 170G | 47.932 | 5.672 | 15.629 | 1.00 | 36.20 | H | N |
| ATOM | 274 | CA | ASP | H | 170G | 47.823 | 6.955 | 14.951 | 1.00 | 34.41 | H | C |
| ATOM | 275 | C | ASP | H | 170G | 46.433 | 7.192 | 14.370 | 1.00 | 31.26 | H | C |
| ATOM | 276 | O | ASP | H | 170G | 46.265 | 7.306 | 13.155 | 1.00 | 30.19 | H | O |
| ATOM | 277 | CB | ASP | H | 170G | 48.869 | 7.049 | 13.839 | 1.00 | 38.35 | H | C |
| ATOM | 278 | CG | ASP | H | 170G | 50.282 | 7.112 | 14.377 | 1.00 | 42.44 | H | C |
| ATOM | 279 | OD1 | ASP | H | 170G | 50.595 | 8.077 | 15.111 | 1.00 | 43.77 | H | O |
| ATOM | 280 | OD2 | ASP | H | 170G | 51.080 | 6.200 | 14.069 | 1.00 | 44.37 | H | O |
| ATOM | 281 | N | SER | H | 170H | 45.438 | 7.265 | 15.245 | 1.00 | 27.38 | H | N |
| ATOM | 282 | CA | SER | H | 170H | 44.066 | 7.501 | 14.822 | 1.00 | 23.64 | H | C |
| ATOM | 283 | C | SER | H | 170H | 43.830 | 9.008 | 14.677 | 1.00 | 20.46 | H | C |
| ATOM | 284 | O | SER | H | 170H | 44.628 | 9.817 | 15.149 | 1.00 | 19.96 | H | O |
| ATOM | 285 | CB | SER | H | 170H | 43.096 | 6.902 | 15.846 | 1.00 | 24.30 | H | C |
| ATOM | 286 | OG | SER | H | 170H | 43.323 | 7.430 | 17.142 | 1.00 | 24.12 | H | O |
| ATOM | 287 | N | PRO | H | 170I | 42.733 | 9.403 | 14.013 | 1.00 | 17.84 | H | N |
| ATOM | 288 | CA | PRO | H | 170I | 42.432 | 10.826 | 13.826 | 1.00 | 15.01 | H | C |
| ATOM | 289 | C | PRO | H | 170I | 42.402 | 11.597 | 15.146 | 1.00 | 13.81 | H | C |
| ATOM | 290 | O | PRO | H | 170I | 41.933 | 11.090 | 16.162 | 1.00 | 11.82 | H | O |
| ATOM | 291 | CB | PRO | H | 170I | 41.066 | 10.798 | 13.142 | 1.00 | 14.13 | H | C |
| ATOM | 292 | CG | PRO | H | 170I | 41.112 | 9.519 | 12.359 | 1.00 | 15.60 | H | C |
| ATOM | 293 | CD | PRO | H | 170I | 41.716 | 8.562 | 13.358 | 1.00 | 16.03 | H | C |
| ATOM | 294 | N | ASN | H | 175 | 42.918 | 12.819 | 15.137 | 1.00 | 13.26 | H | N |
| ATOM | 295 | CA | ASN | H | 175 | 42.911 | 13.627 | 16.347 | 1.00 | 15.22 | H | C |
| ATOM | 296 | C | ASN | H | 175 | 41.540 | 14.261 | 16.497 | 1.00 | 12.70 | 11 | C |
| ATOM | 297 | O | ASN | H | 175 | 40.813 | 14.420 | 15.520 | 1.00 | 9.75 | H | O |
| ATOM | 298 | CB | ASN | H | 175 | 43.964 | 14.744 | 16.280 | 1.00 | 19.16 | H | C |
| ATOM | 299 | CG | ASN | H | 175 | 45.367 | 14.217 | 16.081 | 1.00 | 22.90 | H | C |
| ATOM | 300 | OD1 | ASN | H | 175 | 45.726 | 13.159 | 16.597 | 1.00 | 28.38 | H | O |
| ATOM | 301 | ND2 | ASN | H | 175 | 46.178 | 14.963 | 15.338 | 1.00 | 26.32 | H | N |
| ATOM | 302 | N | ILE | H | 176 | 41.190 | 14.609 | 17.729 | 1.00 | 12.09 | H | N |
| ATOM | 303 | CA | ILE | H | 176 | 39.922 | 15.270 | 18.015 | 1.00 | 10.80 | H | C |
| ATOM | 304 | C | ILE | H | 176 | 40.253 | 16.759 | 18.040 | 1.00 | 9.92 | H | C |
| ATOM | 305 | O | ILE | H | 176 | 40.856 | 17.248 | 18.992 | 1.00 | 8.78 | H | O |
| ATOM | 306 | CB | ILE | H | 176 | 39.373 | 14.856 | 19.391 | 1.00 | 10.52 | H | C |
| ATOM | 307 | CG1 | ILE | H | 176 | 39.207 | 13.335 | 19.451 | 1.00 | 11.68 | H | C |
| ATOM | 308 | CG2 | ILE | H | 176 | 38.032 | 15.533 | 19.636 | 1.00 | 7.09 | H | C |
| ATOM | 309 | CD1 | ILE | H | 176 | 38.867 | 12.816 | 20.830 | 1.00 | 15.04 | H | C |
| ATOM | 310 | N | MET | H | 180 | 35.459 | 19.555 | 16.502 | 1.00 | 3.00 | H | N |
| ATOM | 311 | CA | MET | H | 180 | 34.757 | 18.321 | 16.843 | 1.00 | 3.79 | H | C |
| ATOM | 312 | C | MET | H | 180 | 34.487 | 18.263 | 18.344 | 1.00 | 4.77 | H | C |
| ATOM | 313 | O | MET | H | 180 | 35.007 | 19.075 | 19.114 | 1.00 | 6.30 | H | O |
| ATOM | 314 | CB | MET | H | 180 | 35.625 | 17.105 | 16.499 | 1.00 | 3.93 | H | C |
| ATOM | 315 | CG | MET | H | 180 | 36.365 | 17.162 | 15.169 | 1.00 | 5.58 | H | C |
| ATOM | 316 | SD | MET | H | 180 | 37.565 | 15.805 | 15.057 | 1.00 | 6.35 | H | S |
| ATOM | 317 | CE | MET | H | 180 | 38.175 | 16.035 | 13.399 | 1.00 | 4.33 | H | C |
| ATOM | 318 | N | PHE | H | 181 | 33.677 | 17.288 | 18.745 | 1.00 | 3.48 | H | N |
| ATOM | 319 | CA | PHE | H | 181 | 33.379 | 17.034 | 20.151 | 1.00 | 3.80 | H | C |
| ATOM | 320 | C | PHE | H | 181 | 32.851 | 15.608 | 20.242 | 1.00 | 4.05 | H | C |
| ATOM | 321 | O | PHE | H | 181 | 32.219 | 15.111 | 19.304 | 1.00 | 3.48 | H | O |
| ATOM | 322 | CB | PHE | H | 181 | 32.371 | 18.051 | 20.719 | 1.00 | 4.63 | H | C |
| ATOM | 323 | CG | PHE | H | 181 | 30.939 | 17.853 | 20.273 | 1.00 | 6.12 | H | C |
| ATOM | 324 | CD1 | PHE | H | 181 | 30.134 | 16.881 | 20.863 | 1.00 | 3.60 | H | C |
| ATOM | 325 | CD2 | PHE | H | 181 | 30.370 | 18.706 | 19.323 | 1.00 | 4.58 | H | C |
| ATOM | 326 | CE1 | PHE | H | 181 | 28.777 | 16.767 | 20.519 | 1.00 | 4.70 | H | C |
| ATOM | 327 | CE2 | PHE | H | 181 | 29.018 | 18.601 | 18.973 | 1.00 | 2.41 | H | C |
| ATOM | 328 | CZ | PHE | H | 181 | 28.220 | 17.634 | 19.572 | 1.00 | 4.06 | H | C |
| ATOM | 329 | N | CYS | H | 182 | 33.142 | 14.938 | 21.349 | 1.00 | 3.27 | H | N |
| ATOM | 330 | CA | CYS | H | 182 | 32.684 | 13.571 | 21.539 | 1.00 | 4.42 | H | C |
| ATOM | 331 | C | CYS | H | 182 | 31.373 | 13.550 | 22.298 | 1.00 | 3.93 | H | C |
| ATOM | 332 | O | CYS | H | 182 | 31.061 | 14.473 | 23.047 | 1.00 | 4.77 | H | O |
| ATOM | 333 | CB | CYS | H | 182 | 33.685 | 12.758 | 22.352 | 1.00 | 5.96 | H | C |
| ATOM | 334 | SG | CYS | H | 182 | 35.402 | 12.734 | 21.771 | 1.00 | 5.85 | H | S |
| ATOM | 335 | N | ALA | H | 183 | 30.619 | 12.476 | 22.112 | 1.00 | 3.91 | H | N |

-continued

| | | | | | | | | | | | |
|---|---|---|---|---|---|---|---|---|---|---|---|
| ATOM | 336 | CA | ALA | H | 183 | 29.356 | 12.290 | 22.810 | 1.00 | 5.23 | H | C |
| ATOM | 337 | C | ALA | H | 183 | 29.000 | 10.813 | 22.723 | 1.00 | 5.27 | H | C |
| ATOM | 338 | O | ALA | H | 183 | 29.318 | 10.150 | 21.740 | 1.00 | 7.26 | H | O |
| ATOM | 339 | CB | ALA | H | 183 | 28.254 | 13.152 | 22.178 | 1.00 | 2.74 | H | C |
| ATOM | 340 | N | GLY | H | 184A | 28.361 | 10.289 | 23.760 | 1.00 | 7.33 | H | N |
| ATOM | 341 | CA | GLY | H | 184A | 27.986 | 8.890 | 23.741 | 1.00 | 6.69 | H | C |
| ATOM | 342 | C | GLY | H | 184A | 28.482 | 8.101 | 24.936 | 1.00 | 8.17 | H | C |
| ATOM | 343 | O | GLY | H | 184A | 28.615 | 8.634 | 26.042 | 1.00 | 6.87 | H | O |
| ATOM | 344 | N | TYR | H | 184 | 28.771 | 6.825 | 24.699 | 1.00 | 7.70 | H | N |
| ATOM | 345 | CA | TYR | H | 184 | 29.224 | 5.921 | 25.750 | 1.00 | 8.19 | H | C |
| ATOM | 346 | C | TYR | H | 184 | 30.406 | 5.068 | 25.288 | 1.00 | 7.75 | H | C |
| ATOM | 347 | O | TYR | H | 184 | 30.506 | 4.712 | 24.114 | 1.00 | 6.46 | H | O |
| ATOM | 348 | CB | TYR | H | 184 | 28.074 | 5.004 | 26.176 | 1.00 | 8.95 | H | C |
| ATOM | 349 | CG | TYR | H | 184 | 26.813 | 5.725 | 26.615 | 1.00 | 10.41 | H | C |
| ATOM | 350 | CD1 | TYR | H | 184 | 25.924 | 6.256 | 25.681 | 1.00 | 10.78 | H | C |
| ATOM | 351 | CD2 | TYR | H | 184 | 26.515 | 5.881 | 27.967 | 1.00 | 10.54 | H | C |
| ATOM | 352 | CE1 | TYR | H | 184 | 24.771 | 6.923 | 26.080 | 1.00 | 12.32 | H | C |
| ATOM | 353 | CE2 | TYR | H | 184 | 25.369 | 6.542 | 28.378 | 1.00 | 12.08 | H | C |
| ATOM | 354 | CZ | TYR | H | 184 | 24.500 | 7.061 | 27.429 | 1.00 | 13.74 | H | C |
| ATOM | 355 | OH | TYR | H | 184 | 23.357 | 7.705 | 27.829 | 1.00 | 15.66 | H | O |
| ATOM | 356 | N | LYS | H | 188 | 25.832 | 2.110 | 23.136 | 1.00 | 8.03 | H | N |
| ATOM | 357 | CA | LYS | H | 188 | 25.079 | 3.077 | 22.349 | 1.00 | 7.40 | H | C |
| ATOM | 358 | C | LYS | H | 188 | 25.957 | 4.081 | 21.605 | 1.00 | 9.19 | H | C |
| ATOM | 359 | O | LYS | H | 188 | 26.946 | 4.585 | 22.143 | 1.00 | 7.00 | H | O |
| ATOM | 360 | CB | LYS | H | 188 | 24.123 | 3.820 | 23.283 | 1.00 | 8.96 | H | C |
| ATOM | 361 | CG | LYS | H | 188 | 23.123 | 2.911 | 24.006 | 1.00 | 9.81 | H | C |
| ATOM | 362 | CD | LYS | H | 188 | 22.325 | 3.672 | 25.051 | 1.00 | 11.33 | H | C |
| ATOM | 363 | CE | LYS | H | 188 | 23.157 | 3.965 | 26.292 | 1.00 | 14.58 | H | C |
| ATOM | 364 | NZ | LYS | H | 188 | 23.504 | 2.721 | 27.048 | 1.00 | 14.57 | H | N |
| ATOM | 365 | N | ASP | H | 189 | 25.570 | 4.397 | 20.373 | 1.00 | 6.80 | H | N |
| ATOM | 366 | CA | ASP | H | 189 | 26.350 | 5.319 | 19.560 | 1.00 | 8.44 | H | C |
| ATOM | 367 | C | ASP | H | 189 | 25.650 | 5.465 | 18.209 | 1.00 | 8.51 | H | C |
| ATOM | 368 | O | ASP | H | 189 | 24.752 | 4.686 | 17.886 | 1.00 | 7.47 | H | O |
| ATOM | 369 | CB | ASP | H | 189 | 27.755 | 4.705 | 19.393 | 1.00 | 9.61 | H | C |
| ATOM | 370 | CG | ASP | H | 189 | 28.738 | 5.610 | 18.677 | 1.00 | 8.64 | H | C |
| ATOM | 371 | OD1 | ASP | H | 189 | 28.457 | 6.811 | 18.489 | 1.00 | 9.82 | H | O |
| ATOM | 372 | OD2 | ASP | H | 189 | 29.819 | 5.098 | 18.313 | 1.00 | 6.31 | H | O |
| ATOM | 373 | N | SER | H | 190 | 26.013 | 6.486 | 17.441 | 1.00 | 6.24 | H | N |
| ATOM | 374 | CA | SER | H | 190 | 25.450 | 6.628 | 16.106 | 1.00 | 6.22 | H | C |
| ATOM | 375 | C | SER | H | 190 | 26.395 | 5.773 | 15.249 | 1.00 | 7.07 | H | C |
| ATOM | 376 | O | SER | H | 190 | 27.367 | 5.221 | 15.775 | 1.00 | 5.91 | H | O |
| ATOM | 377 | CB | SER | H | 190 | 25.450 | 8.101 | 15.658 | 1.00 | 4.21 | H | C |
| ATOM | 378 | OG | SER | H | 190 | 26.703 | 8.733 | 15.861 | 1.00 | 4.59 | H | O |
| ATOM | 379 | N | CYS | H | 191 | 26.128 | 5.641 | 13.953 | 1.00 | 8.36 | H | N |
| ATOM | 380 | CA | CYS | H | 191 | 26.992 | 4.823 | 13.099 | 1.00 | 7.99 | H | C |
| ATOM | 381 | C | CYS | H | 191 | 27.131 | 5.428 | 11.698 | 1.00 | 8.96 | H | C |
| ATOM | 382 | O | CYS | H | 191 | 26.507 | 6.442 | 11.388 | 1.00 | 8.95 | H | O |
| ATOM | 383 | CB | CYS | H | 191 | 26.446 | 3.384 | 13.036 | 1.00 | 8.01 | H | C |
| ATOM | 384 | SG | CYS | H | 191 | 27.624 | 2.081 | 12.512 | 1.00 | 11.48 | H | S |
| ATOM | 385 | N | LYS | H | 192 | 27.955 | 4.804 | 10.861 | 1.00 | 9.23 | H | N |
| ATOM | 386 | CA | LYS | H | 192 | 28.232 | 5.291 | 9.508 | 1.00 | 10.49 | H | C |
| ATOM | 387 | C | LYS | H | 192 | 27.042 | 5.787 | 8.691 | 1.00 | 9.74 | H | C |
| ATOM | 388 | O | LYS | H | 192 | 27.089 | 6.885 | 8.131 | 1.00 | 9.42 | H | O |
| ATOM | 389 | CB | LYS | H | 192 | 28.996 | 4.221 | 8.720 | 1.00 | 12.99 | H | C |
| ATOM | 390 | CG | LYS | H | 192 | 30.288 | 3.788 | 9.406 | 1.00 | 17.47 | H | C |
| ATOM | 391 | CD | LYS | H | 192 | 31.180 | 2.948 | 8.509 | 1.00 | 21.20 | H | C |
| ATOM | 392 | CE | LYS | H | 192 | 32.448 | 2.535 | 9.258 | 1.00 | 25.68 | H | C |
| ATOM | 393 | NZ | LYS | H | 192 | 33.427 | 1.809 | 8.395 | 1.00 | 28.01 | H | N |
| ATOM | 394 | N | GLY | H | 193 | 25.983 | 4.989 | 8.623 | 1.00 | 9.29 | H | N |
| ATOM | 395 | CA | GLY | H | 193 | 24.806 | 5.380 | 7.863 | 1.00 | 9.11 | H | C |
| ATOM | 396 | C | GLY | H | 193 | 24.059 | 6.573 | 8.433 | 1.00 | 10.62 | H | C |
| ATOM | 397 | O | GLY | H | 193 | 23.188 | 7.141 | 7.774 | 1.00 | 12.70 | H | O |
| ATOM | 398 | N | ASP | H | 194 | 24.386 | 6.959 | 9.662 | 1.00 | 8.84 | H | N |
| ATOM | 399 | CA | ASP | H | 194 | 23.744 | 8.108 | 10.289 | 1.00 | 7.33 | H | C |
| ATOM | 400 | C | ASP | H | 194 | 24.475 | 9.412 | 9.972 | 1.00 | 7.03 | H | C |
| ATOM | 401 | O | ASP | H | 194 | 23.989 | 10.492 | 10.312 | 1.00 | 7.04 | H | O |
| ATOM | 402 | CB | ASP | H | 194 | 23.688 | 7.917 | 11.802 | 1.00 | 5.37 | H | C |
| ATOM | 403 | CG | ASP | H | 194 | 22.927 | 6.671 | 12.195 | 1.00 | 7.85 | H | C |
| ATOM | 404 | OD1 | ASP | H | 194 | 21.737 | 6.572 | 11.833 | 1.00 | 6.73 | H | O |
| ATOM | 405 | OD2 | ASP | H | 194 | 23.519 | 5.794 | 12.857 | 1.00 | 4.09 | H | O |
| ATOM | 406 | N | SER | H | 195 | 25.634 | 9.301 | 9.324 | 1.00 | 5.06 | H | N |
| ATOM | 407 | CA | SER | H | 195 | 26.449 | 10.454 | 8.960 | 1.00 | 5.57 | H | C |
| ATOM | 408 | C | SER | H | 195 | 25.629 | 11.601 | 8.387 | 1.00 | 6.98 | H | C |
| ATOM | 409 | O | SER | H | 195 | 24.730 | 11.391 | 7.573 | 1.00 | 4.66 | H | O |
| ATOM | 410 | CB | SER | H | 195 | 27.521 | 10.050 | 7.939 | 1.00 | 4.83 | H | C |
| ATOM | 411 | OG | SER | H | 195 | 28.461 | 9.156 | 8.509 | 1.00 | 2.83 | H | O |
| ATOM | 412 | N | GLY | H | 196 | 25.958 | 12.817 | 8.816 | 1.00 | 7.56 | H | N |
| ATOM | 413 | CA | GLY | H | 196 | 25.253 | 13.994 | 8.337 | 1.00 | 7.44 | H | C |
| ATOM | 414 | C | GLY | H | 196 | 24.032 | 14.324 | 9.174 | 1.00 | 7.23 | H | C |

-continued

| | | | | | | | | | | | |
|---|---|---|---|---|---|---|---|---|---|---|---|
| ATOM | 415 | O | GLY | H | 196 | 23.564 | 15.460 | 9.178 | 1.00 | 7.34 | H | O |
| ATOM | 416 | N | GLY | H | 197 | 23.520 | 13.325 | 9.888 | 1.00 | 7.25 | H | N |
| ATOM | 417 | CA | GLY | H | 197 | 22.351 | 13.517 | 10.721 | 1.00 | 5.90 | H | C |
| ATOM | 418 | C | GLY | H | 197 | 22.572 | 14.494 | 11.858 | 1.00 | 6.34 | H | C |
| ATOM | 419 | O | GLY | H | 197 | 23.707 | 14.824 | 12.195 | 1.00 | 7.23 | H | O |
| ATOM | 420 | N | HIS | H | 199 | 22.592 | 16.228 | 15.752 | 1.00 | 4.66 | H | N |
| ATOM | 421 | CA | HIS | H | 199 | 22.920 | 16.007 | 17.151 | 1.00 | 2.68 | H | C |
| ATOM | 422 | C | HIS | H | 199 | 22.168 | 17.243 | 17.628 | 1.00 | 3.98 | H | C |
| ATOM | 423 | O | HIS | H | 199 | 22.668 | 18.366 | 17.497 | 1.00 | 4.27 | H | O |
| ATOM | 424 | CB | HIS | H | 199 | 24.424 | 16.155 | 17.391 | 1.00 | 4.75 | H | C |
| ATOM | 425 | CG | HIS | H | 199 | 24.812 | 16.159 | 18.838 | 1.00 | 3.77 | H | C |
| ATOM | 426 | ND1 | HIS | H | 199 | 24.693 | 17.275 | 19.636 | 1.00 | 1.00 | H | N |
| ATOM | 427 | CD2 | HIS | H | 199 | 25.308 | 15.179 | 19.633 | 1.00 | 4.02 | H | C |
| ATOM | 428 | CE1 | HIS | H | 199 | 25.103 | 16.987 | 20.858 | 1.00 | 2.26 | H | C |
| ATOM | 429 | NE2 | HIS | H | 199 | 25.481 | 15.721 | 20.883 | 1.00 | 2.92 | H | N |
| ATOM | 430 | N | ILE | H | 212 | 26.974 | 17.242 | 14.214 | 1.00 | 5.45 | H | N |
| ATOM | 431 | CA | ILE | H | 212 | 26.692 | 16.454 | 13.021 | 1.00 | 5.68 | H | C |
| ATOM | 432 | C | ILE | H | 212 | 27.372 | 15.092 | 13.160 | 1.00 | 6.39 | H | C |
| ATOM | 433 | O | ILE | H | 212 | 28.561 | 15.029 | 13.458 | 1.00 | 7.22 | H | O |
| ATOM | 434 | CB | ILE | H | 212 | 27.265 | 17.133 | 11.753 | 1.00 | 5.98 | H | C |
| ATOM | 435 | CG1 | ILE | H | 212 | 26.699 | 18.545 | 11.606 | 1.00 | 4.14 | H | C |
| ATOM | 436 | CG2 | ILE | H | 212 | 26.943 | 16.296 | 10.522 | 1.00 | 5.31 | H | C |
| ATOM | 437 | CD1 | ILE | H | 212 | 27.426 | 19.368 | 10.561 | 1.00 | 3.83 | H | C |
| ATOM | 438 | N | VAL | H | 213 | 26.620 | 14.010 | 12.962 | 1.00 | 6.29 | H | N |
| ATOM | 439 | CA | VAL | H | 213 | 27.187 | 12.661 | 13.039 | 1.00 | 3.02 | H | C |
| ATOM | 440 | C | VAL | H | 213 | 28.340 | 12.692 | 12.046 | 1.00 | 3.61 | H | C |
| ATOM | 441 | O | VAL | H | 213 | 28.130 | 12.905 | 10.846 | 1.00 | 3.84 | H | O |
| ATOM | 442 | CB | VAL | H | 213 | 26.149 | 11.581 | 12.617 | 1.00 | 1.61 | H | C |
| ATOM | 443 | CG1 | VAL | H | 213 | 26.792 | 10.194 | 12.636 | 1.00 | 1.00 | H | C |
| ATOM | 444 | CG2 | VAL | H | 213 | 24.959 | 11.599 | 13.578 | 1.00 | 1.00 | H | C |
| ATOM | 445 | N | SER | H | 214 | 29.557 | 12.491 | 12.540 | 1.00 | 4.04 | H | N |
| ATOM | 446 | CA | SER | H | 214 | 30.728 | 12.582 | 11.675 | 1.00 | 5.26 | H | C |
| ATOM | 447 | C | SER | H | 214 | 31.619 | 11.349 | 11.577 | 1.00 | 3.67 | H | C |
| ATOM | 448 | O | SER | H | 214 | 31.766 | 10.778 | 10.497 | 1.00 | 3.00 | H | O |
| ATOM | 449 | CB | SER | H | 214 | 31.561 | 13.794 | 12.101 | 1.00 | 4.06 | H | C |
| ATOM | 450 | OG | SER | H | 214 | 32.746 | 13.898 | 11.343 | 1.00 | 7.47 | H | O |
| ATOM | 451 | N | TRP | H | 215 | 32.225 | 10.946 | 12.689 | 1.00 | 2.06 | H | N |
| ATOM | 452 | CA | TRP | H | 215 | 33.094 | 9.779 | 12.667 | 1.00 | 4.11 | H | C |
| ATOM | 453 | C | TRP | H | 215 | 33.247 | 9.099 | 14.018 | 1.00 | 5.89 | H | C |
| ATOM | 454 | O | TRP | H | 215 | 32.628 | 9.491 | 15.007 | 1.00 | 5.44 | H | O |
| ATOM | 455 | CB | TRP | H | 215 | 34.489 | 10.148 | 12.120 | 1.00 | 5.71 | H | C |
| ATOM | 456 | CG | TRP | H | 215 | 35.298 | 11.099 | 12.983 | 1.00 | 6.60 | H | C |
| ATOM | 457 | CD1 | TRP | H | 215 | 35.174 | 12.459 | 13.046 | 1.00 | 8.26 | H | C |
| ATOM | 458 | CD2 | TRP | H | 215 | 36.374 | 10.755 | 13.870 | 1.00 | 7.17 | H | C |
| ATOM | 459 | NE1 | TRP | H | 215 | 36.106 | 12.985 | 13.910 | 1.00 | 6.83 | H | N |
| ATOM | 460 | CE2 | TRP | H | 215 | 36.855 | 11.962 | 14.433 | 1.00 | 7.22 | H | C |
| ATOM | 461 | CE3 | TRP | H | 215 | 36.979 | 9.546 | 14.244 | 1.00 | 6.60 | H | C |
| ATOM | 462 | CZ2 | TRP | H | 215 | 37.912 | 11.996 | 15.351 | 1.00 | 4.55 | H | C |
| ATOM | 463 | CZ3 | TRP | H | 215 | 38.035 | 9.578 | 15.161 | 1.00 | 7.36 | H | C |
| ATOM | 464 | CH2 | TRP | H | 215 | 38.488 | 10.799 | 15.703 | 1.00 | 6.87 | H | C |
| ATOM | 465 | N | GLY | H | 216 | 34.086 | 8.070 | 14.043 | 1.00 | 6.33 | H | N |
| ATOM | 466 | CA | GLY | H | 216 | 34.336 | 7.332 | 15.265 | 1.00 | 8.66 | H | C |
| ATOM | 467 | C | GLY | H | 216 | 35.004 | 6.017 | 14.932 | 1.00 | 9.66 | H | C |
| ATOM | 468 | O | GLY | H | 216 | 34.914 | 5.543 | 13.795 | 1.00 | 9.71 | H | O |
| ATOM | 469 | N | GLN | H | 217 | 35.684 | 5.422 | 15.906 | 1.00 | 10.43 | H | N |
| ATOM | 470 | CA | GLN | H | 217 | 36.346 | 4.148 | 15.669 | 1.00 | 10.60 | H | C |
| ATOM | 471 | C | GLN | H | 217 | 35.284 | 3.065 | 15.765 | 1.00 | 10.61 | H | C |
| ATOM | 472 | O | GLN | H | 217 | 34.858 | 2.695 | 16.858 | 1.00 | 13.71 | H | O |
| ATOM | 473 | CB | GLN | H | 217 | 37.449 | 3.919 | 16.701 | 1.00 | 12.43 | H | C |
| ATOM | 474 | CG | GLN | H | 217 | 38.205 | 2.612 | 16.498 | 1.00 | 14.99 | H | C |
| ATOM | 475 | CD | GLN | H | 217 | 39.564 | 2.605 | 17.171 | 1.00 | 18.06 | H | C |
| ATOM | 476 | OE1 | GLN | H | 217 | 40.134 | 1.540 | 17.427 | 1.00 | 19.54 | H | O |
| ATOM | 477 | NE2 | GLN | H | 217 | 40.103 | 3.794 | 17.443 | 1.00 | 13.50 | H | N |
| ATOM | 478 | N | GLY | H | 219 | 34.854 | 2.563 | 14.612 | 1.00 | 10.68 | H | N |
| ATOM | 479 | CA | GLY | H | 219 | 33.803 | 1.563 | 14.596 | 1.00 | 11.37 | H | C |
| ATOM | 480 | C | GLY | H | 219 | 32.536 | 2.218 | 15.126 | 1.00 | 11.52 | H | C |
| ATOM | 481 | O | GLY | H | 219 | 32.436 | 3.446 | 15.163 | 1.00 | 11.41 | H | O |
| ATOM | 482 | N | CYS | H | 220 | 31.569 | 1.410 | 15.542 | 1.00 | 11.97 | H | N |
| ATOM | 483 | CA | CYS | H | 220 | 30.317 | 1.934 | 16.077 | 1.00 | 11.90 | H | C |
| ATOM | 484 | C | CYS | H | 220 | 30.052 | 1.266 | 17.420 | 1.00 | 11.82 | H | C |
| ATOM | 485 | O | CYS | H | 220 | 29.975 | 0.037 | 17.508 | 1.00 | 12.68 | H | O |
| ATOM | 486 | CB | CYS | H | 220 | 29.170 | 1.658 | 15.099 | 1.00 | 11.56 | H | C |
| ATOM | 487 | SG | CYS | H | 220 | 29.346 | 2.521 | 13.505 | 1.00 | 8.67 | H | S |
| ATOM | 488 | N | ALA | H | 221A | 29.916 | 2.084 | 18.462 | 1.00 | 10.74 | H | N |
| ATOM | 489 | CA | ALA | H | 221A | 29.691 | 1.588 | 19.817 | 1.00 | 10.47 | H | C |
| ATOM | 490 | C | ALA | H | 221A | 30.806 | 0.616 | 20.198 | 1.00 | 10.93 | H | C |
| ATOM | 491 | O | ALA | H | 221A | 30.547 | −0.493 | 20.677 | 1.00 | 11.08 | H | O |
| ATOM | 492 | CB | ALA | H | 221A | 28.336 | 0.901 | 19.914 | 1.00 | 11.15 | H | C |
| ATOM | 493 | N | THR | H | 221 | 32.046 | 1.045 | 19.968 | 1.00 | 9.44 | H | N |

-continued

| | | | | | | | | | | | |
|---|---|---|---|---|---|---|---|---|---|---|---|
| ATOM | 494 | CA | THR | H | 221 | 33.237 | 0.249 | 20.274 | 1.00 | 8.66 | H | C |
| ATOM | 495 | C | THR | H | 221 | 33.708 | 0.543 | 21.695 | 1.00 | 8.04 | H | C |
| ATOM | 496 | O | THR | H | 221 | 33.859 | 1.706 | 22.075 | 1.00 | 7.03 | H | O |
| ATOM | 497 | CB | THR | H | 221 | 34.391 | 0.578 | 19.289 | 1.00 | 8.20 | H | C |
| ATOM | 498 | OG1 | THR | H | 221 | 33.983 | 0.265 | 17.951 | 1.00 | 10.25 | H | O |
| ATOM | 499 | CG2 | THR | H | 221 | 35.634 | −0.225 | 19.623 | 1.00 | 11.22 | H | C |
| ATOM | 500 | N | VAL | H | 222 | 33.926 | −0.508 | 22.480 | 1.00 | 7.75 | H | N |
| ATOM | 501 | CA | VAL | H | 222 | 34.386 | −0.361 | 23.862 | 1.00 | 7.14 | H | C |
| ATOM | 502 | C | VAL | H | 222 | 35.637 | 0.508 | 23.904 | 1.00 | 7.56 | H | C |
| ATOM | 503 | O | VAL | H | 222 | 36.567 | 0.304 | 23.132 | 1.00 | 7.65 | H | O |
| ATOM | 504 | CB | VAL | H | 222 | 34.705 | −1.745 | 24.507 | 1.00 | 6.51 | H | C |
| ATOM | 505 | CG1 | VAL | H | 222 | 35.329 | −1.558 | 25.893 | 1.00 | 6.03 | H | C |
| ATOM | 506 | CG2 | VAL | H | 222 | 33.426 | −2.564 | 24.629 | 1.00 | 4.73 | H | C |
| ATOM | 507 | N | HIS | H | 224 | 35.632 | 3.718 | 23.234 | 1.00 | 6.63 | H | N |
| ATOM | 508 | CA | HIS | H | 224 | 35.512 | 4.808 | 22.269 | 1.00 | 7.22 | H | C |
| ATOM | 509 | C | HIS | H | 224 | 34.148 | 5.500 | 22.271 | 1.00 | 7.59 | H | C |
| ATOM | 510 | O | HIS | H | 224 | 33.127 | 4.906 | 22.618 | 1.00 | 8.49 | H | O |
| ATOM | 511 | CB | HIS | H | 224 | 35.840 | 4.300 | 20.862 | 1.00 | 8.31 | H | C |
| ATOM | 512 | CG | HIS | H | 224 | 37.279 | 3.936 | 20.682 | 1.00 | 10.98 | H | C |
| ATOM | 513 | ND1 | HIS | H | 224 | 38.276 | 4.881 | 20.572 | 1.00 | 10.97 | H | N |
| ATOM | 514 | CD2 | HIS | H | 224 | 37.899 | 2.731 | 20.668 | 1.00 | 12.41 | H | C |
| ATOM | 515 | CE1 | HIS | H | 224 | 39.448 | 4.277 | 20.501 | 1.00 | 11.73 | H | C |
| ATOM | 516 | NE2 | HIS | H | 224 | 39.247 | 2.973 | 20.557 | 1.00 | 14.76 | H | N |
| ATOM | 517 | N | PHE | H | 225 | 34.157 | 6.770 | 21.881 | 1.00 | 7.18 | H | N |
| ATOM | 518 | CA | PHE | H | 225 | 32.960 | 7.596 | 21.822 | 1.00 | 6.04 | H | C |
| ATOM | 519 | C | PHE | H | 225 | 32.725 | 8.038 | 20.381 | 1.00 | 7.09 | H | C |
| ATOM | 520 | O | PHE | H | 225 | 33.657 | 8.075 | 19.573 | 1.00 | 9.02 | H | O |
| ATOM | 521 | CB | PHE | H | 225 | 33.151 | 8.870 | 22.659 | 1.00 | 5.47 | H | C |
| ATOM | 522 | CG | PHE | H | 225 | 33.293 | 8.634 | 24.136 | 1.00 | 6.44 | H | C |
| ATOM | 523 | CD1 | PHE | H | 225 | 32.171 | 8.572 | 24.954 | 1.00 | 2.41 | H | C |
| ATOM | 524 | CD2 | PHE | H | 225 | 34.554 | 8.511 | 24.716 | 1.00 | 4.55 | H | C |
| ATOM | 525 | CE1 | PHE | H | 225 | 32.303 | 8.397 | 26.333 | 1.00 | 5.42 | H | C |
| ATOM | 526 | CE2 | PHE | H | 225 | 34.694 | 8.335 | 26.089 | 1.00 | 5.19 | H | C |
| ATOM | 527 | CZ | PHE | H | 225 | 33.565 | 8.280 | 26.900 | 1.00 | 3.44 | H | C |
| ATOM | 528 | N | GLY | H | 226 | 31.485 | 8.392 | 20.065 | 1.00 | 5.55 | H | N |
| ATOM | 529 | CA | GLY | H | 226 | 31.197 | 8.893 | 18.734 | 1.00 | 5.48 | H | C |
| ATOM | 530 | C | GLY | H | 226 | 31.753 | 10.313 | 18.667 | 1.00 | 5.81 | H | C |
| ATOM | 531 | O | GLY | H | 226 | 31.837 | 10.990 | 19.695 | 1.00 | 4.00 | H | O |
| ATOM | 532 | N | VAL | H | 227 | 32.151 | 10.760 | 17.479 | 1.00 | 3.76 | H | N |
| ATOM | 533 | CA | VAL | H | 227 | 32.693 | 12.107 | 17.312 | 1.00 | 5.52 | H | C |
| ATOM | 534 | C | VAL | H | 227 | 31.800 | 12.883 | 16.347 | 1.00 | 5.53 | H | C |
| ATOM | 535 | O | VAL | H | 227 | 31.436 | 12.389 | 15.277 | 1.00 | 3.89 | H | O |
| ATOM | 536 | CB | VAL | H | 227 | 34.142 | 12.088 | 16.764 | 1.00 | 5.30 | H | C |
| ATOM | 537 | CG1 | VAL | H | 227 | 34.725 | 13.500 | 16.812 | 1.00 | 3.32 | H | C |
| ATOM | 538 | CG2 | VAL | H | 227 | 35.000 | 11.126 | 17.576 | 1.00 | 1.00 | H | C |
| ATOM | 539 | N | TYR | H | 228 | 31.467 | 14.108 | 16.734 | 1.00 | 5.76 | H | N |
| ATOM | 540 | CA | TYR | H | 228 | 30.566 | 14.947 | 15.959 | 1.00 | 5.23 | H | C |
| ATOM | 541 | C | TYR | H | 228 | 31.190 | 16.277 | 15.556 | 1.00 | 4.97 | H | C |
| ATOM | 542 | O | TYR | H | 228 | 32.007 | 16.833 | 16.282 | 1.00 | 4.90 | H | O |
| ATOM | 543 | CB | TYR | H | 228 | 29.291 | 15.203 | 16.781 | 1.00 | 6.48 | H | C |
| ATOM | 544 | CG | TYR | H | 228 | 28.564 | 13.935 | 17.216 | 1.00 | 7.32 | H | C |
| ATOM | 545 | CD1 | TYR | H | 228 | 29.046 | 13.138 | 18.264 | 1.00 | 8.15 | H | C |
| ATOM | 546 | CD2 | TYR | H | 228 | 27.432 | 13.500 | 16.531 | 1.00 | 6.35 | H | C |
| ATOM | 547 | CE1 | TYR | H | 228 | 28.408 | 11.929 | 18.603 | 1.00 | 9.05 | H | C |
| ATOM | 548 | CE2 | TYR | H | 228 | 26.801 | 12.316 | 16.857 | 1.00 | 7.95 | H | C |
| ATOM | 549 | CZ | TYR | H | 228 | 27.287 | 11.532 | 17.885 | 1.00 | 8.70 | H | C |
| ATOM | 550 | OH | TYR | H | 228 | 26.647 | 10.347 | 18.158 | 1.00 | 8.64 | H | O |
| ATOM | 551 | N | THR | H | 229 | 30.807 | 16.784 | 14.389 | 1.00 | 4.04 | H | N |
| ATOM | 552 | CA | THR | H | 229 | 31.329 | 18.067 | 13.929 | 1.00 | 4.70 | H | C |
| ATOM | 553 | C | THR | H | 229 | 30.782 | 19.121 | 14.900 | 1.00 | 3.38 | H | C |
| ATOM | 554 | O | THR | H | 229 | 29.590 | 19.133 | 15.181 | 1.00 | 3.30 | H | O |
| ATOM | 555 | CB | THR | H | 229 | 30.836 | 18.381 | 12.504 | 1.00 | 5.34 | H | C |
| ATOM | 556 | OG1 | THR | H | 229 | 31.188 | 17.301 | 11.627 | 1.00 | 6.83 | H | O |
| ATOM | 557 | CG2 | THR | H | 229 | 31.461 | 19.668 | 11.998 | 1.00 | 2.01 | H | C |
| ATOM | 558 | C11 | 142 | I | 1 | 35.781 | 7.018 | 10.285 | 1.00 | 12.37 | I | C |
| ATOM | 559 | O2 | 142 | I | 1 | 34.889 | 7.239 | 11.100 | 1.00 | 10.13 | I | O |
| ATOM | 560 | N4 | 142 | I | 1 | 35.803 | 7.455 | 9.001 | 1.00 | 10.92 | I | N |
| ATOM | 561 | C10 | 142 | I | 1 | 34.710 | 8.250 | 8.481 | 1.00 | 9.56 | I | C |
| ATOM | 562 | C13 | 142 | I | 1 | 34.848 | 8.535 | 6.994 | 1.00 | 8.40 | I | C |
| ATOM | 563 | C14 | 142 | I | 1 | 36.165 | 9.222 | 6.602 | 1.00 | 6.40 | I | C |
| ATOM | 564 | C9 | 142 | I | 1 | 33.397 | 7.494 | 8.773 | 1.00 | 10.00 | I | C |
| ATOM | 565 | O1 | 142 | I | 1 | 33.289 | 6.279 | 8.607 | 1.00 | 8.42 | I | O |
| ATOM | 566 | N3 | 142 | I | 1 | 32.427 | 8.295 | 9.230 | 1.00 | 8.14 | I | N |
| ATOM | 567 | C8 | 142 | I | 1 | 31.166 | 7.668 | 9.494 | 1.00 | 7.12 | I | C |
| ATOM | 568 | C6 | 142 | I | 1 | 31.799 | 6.529 | 11.670 | 1.00 | 3.93 | I | C |
| ATOM | 569 | C7 | 142 | I | 1 | 31.539 | 6.286 | 13.035 | 1.00 | 6.62 | I | C |
| ATOM | 570 | C2 | 142 | I | 1 | 30.475 | 6.947 | 13.697 | 1.00 | 4.23 | I | C |
| ATOM | 571 | C3 | 142 | I | 1 | 29.626 | 7.773 | 12.954 | 1.00 | 3.55 | I | C |
| ATOM | 572 | C4 | 142 | I | 1 | 29.868 | 7.994 | 11.603 | 1.00 | 5.96 | I | C |

-continued

| | | | | | | | | | | | | |
|---|---|---|---|---|---|---|---|---|---|---|---|---|
| ATOM | 573 | C5 | 142 | I | 1 | 30.952 | 7.384 | 10.951 | 1.00 | 6.87 | I | C |
| ATOM | 574 | C1 | 142 | I | 1 | 30.247 | 6.782 | 15.131 | 1.00 | 4.86 | I | C |
| ATOM | 575 | N1 | 142 | I | 1 | 30.808 | 5.783 | 15.789 | 1.00 | 2.27 | I | N |
| ATOM | 576 | C15 | 142 | I | 1 | 36.036 | 9.591 | 5.142 | 1.00 | 7.71 | I | C |
| ATOM | 577 | O5 | 142 | I | 1 | 35.840 | 8.729 | 4.291 | 1.00 | 11.38 | I | O |
| ATOM | 578 | N6 | 142 | I | 1 | 36.066 | 10.898 | 4.897 | 1.00 | 6.65 | I | N |
| ATOM | 579 | C16 | 142 | I | 1 | 37.992 | 7.122 | 11.404 | 1.00 | 12.61 | I | C |
| ATOM | 580 | N5 | 142 | I | 1 | 36.563 | 5.104 | 11.541 | 1.00 | 16.04 | I | N |
| ATOM | 581 | C12 | 142 | I | 1 | 37.009 | 6.187 | 10.696 | 1.00 | 13.72 | I | C |
| ATOM | 582 | S1 | 142 | I | 1 | 36.372 | 3.520 | 10.904 | 1.00 | 19.57 | I | S |
| ATOM | 583 | O4 | 142 | I | 1 | 35.680 | 3.703 | 9.668 | 1.00 | 20.77 | I | O |
| ATOM | 584 | O3 | 142 | I | 1 | 35.734 | 2.849 | 11.987 | 1.00 | 18.06 | I | O |
| ATOM | 585 | C29 | 142 | I | 1 | 37.958 | 2.804 | 10.578 | 1.00 | 19.56 | I | C |
| ATOM | 586 | C30 | 142 | I | 1 | 38.640 | 3.369 | 9.320 | 1.00 | 26.52 | I | C |
| ATOM | 587 | N2 | 142 | I | 1 | 29.435 | 7.589 | 15.802 | 1.00 | 2.52 | I | N |
| ATOM | 588 | C22 | 142 | I | 1 | 40.253 | 6.007 | 11.120 | 1.00 | 13.78 | I | C |
| ATOM | 589 | C17 | 142 | I | 1 | 39.172 | 6.378 | 11.945 | 1.00 | 12.60 | I | C |
| ATOM | 590 | C18 | 142 | I | 1 | 39.260 | 5.996 | 13.297 | 1.00 | 13.94 | I | C |
| ATOM | 591 | C19 | 142 | I | 1 | 40.362 | 5.257 | 13.785 | 1.00 | 14.86 | I | C |
| ATOM | 592 | C20 | 142 | I | 1 | 41.430 | 4.868 | 12.954 | 1.00 | 14.31 | 1 | C |
| ATOM | 593 | C21 | 142 | I | 1 | 41.350 | 5.273 | 11.615 | 1.00 | 12.85 | I | C |
| ATOM | 594 | C27 | 142 | I | 1 | 45.001 | 3.681 | 13.710 | 1.00 | 18.09 | I | C |
| ATOM | 595 | C28 | 142 | I | 1 | 43.904 | 4.357 | 13.114 | 1.00 | 16.71 | I | C |
| ATOM | 596 | C23 | 142 | I | 1 | 42.573 | 4.077 | 13.477 | 1.00 | 15.00 | I | C |
| ATOM | 597 | C24 | 142 | I | 1 | 42.385 | 3.038 | 14.411 | 1.00 | 17.61 | I | C |
| ATOM | 598 | C25 | 142 | I | 1 | 43.473 | 2.352 | 15.002 | 1.00 | 18.20 | I | C |
| ATOM | 599 | C26 | 142 | I | 1 | 44.803 | 2.684 | 14.686 | 1.00 | 18.30 | I | C |
| ATOM | 600 | OH2 | WAT | W | 2 | 21.173 | 10.598 | 10.229 | 1.00 | 2.46 | W | O |
| ATOM | 601 | OH2 | WAT | W | 3 | 41.236 | 15.367 | 9.038 | 1.00 | 9.89 | W | O |
| ATOM | 602 | OH2 | WAT | W | 11 | 39.351 | 17.218 | 6.324 | 1.00 | 2.98 | W | O |
| ATOM | 603 | OH2 | WAT | W | 16 | 28.951 | 6.415 | 21.747 | 1.00 | 8.07 | W | O |
| ATOM | 604 | OH2 | WAT | W | 17 | 36.844 | 8.297 | 21.377 | 1.00 | 8.16 | W | O |
| ATOM | 605 | OH2 | WAT | W | 19 | 29.393 | 7.360 | 5.894 | 1.00 | 10.69 | W | O |
| ATOM | 606 | OH2 | WAT | W | 22 | 40.618 | 0.517 | 20.963 | 1.00 | 12.88 | W | O |
| ATOM | 607 | OH2 | WAT | W | 41 | 20.474 | 8.594 | 8.383 | 1.00 | 2.92 | W | O |
| ATOM | 608 | OH2 | WAT | W | 43 | 33.354 | 15.140 | 0.160 | 1.00 | 4.35 | W | O |
| ATOM | 609 | OH2 | WAT | W | 52 | 41.064 | 11.721 | 9.444 | 1.00 | 11.25 | W | O |
| ATOM | 610 | OH2 | WAT | W | 55 | 31.078 | 4.628 | 20.839 | 1.00 | 19.21 | W | O |
| ATOM | 611 | OH2 | WAT | W | 73 | 31.424 | 2.387 | 23.087 | 1.00 | 16.83 | W | O |
| ATOM | 612 | OH2 | WAT | W | 90 | 34.297 | 16.904 | −1.657 | 1.00 | 8.85 | W | O |
| ATOM | 613 | OH2 | WAT | W | 92 | 34.705 | 15.756 | 12.306 | 1.00 | 4.39 | W | O |
| ATOM | 614 | OH2 | WAT | W | 97 | 32.609 | 3.792 | 18.618 | 1.00 | 10.06 | W | O |
| ATOM | 615 | OH2 | WAT | W | 113 | 29.869 | 9.653 | −1.073 | 1.00 | 13.89 | W | O |
| ATOM | 616 | OH2 | WAT | W | 115 | 27.599 | 8.830 | 20.107 | 1.00 | 6.50 | W | O |
| ATOM | 617 | OH2 | WAT | W | 119 | 35.741 | 6.643 | 18.640 | 1.00 | 13.65 | W | O |
| ATOM | 618 | OH2 | WAT | W | 132 | 38.202 | 7.871 | 19.316 | 1.00 | 21.67 | W | O |
| ATOM | 619 | OH2 | WAT | W | 133 | 39.823 | 6.712 | 17.466 | 1.00 | 16.74 | W | O |
| ATOM | 620 | OH2 | WAT | W | 167 | 45.149 | 0.561 | 24.578 | 1.00 | 31.52 | W | O |
| ATOM | 621 | OH2 | WAT | W | 169 | 26.773 | 3.657 | 5.750 | 1.00 | 20.71 | W | O |
| ATOM | 622 | OH2 | WAT | W | 179 | 33.910 | 15.111 | −3.886 | 1.00 | 26.31 | W | O |
| ATOM | 623 | OH2 | WAT | W | 183 | 22.630 | 6.394 | 5.218 | 1.00 | 17.19 | W | O |
| ATOM | 624 | OH2 | WAT | W | 190 | 41.408 | 8.993 | 17.609 | 1.00 | 38.16 | W | O |
| ATOM | 625 | OH2 | WAT | W | 208 | 28.879 | 7.652 | −2.728 | 1.00 | 25.34 | W | O |
| ATOM | 626 | OH2 | WAT | W | 211 | 40.187 | 8.447 | 20.906 | 1.00 | 29.06 | W | O |
| ATOM | 627 | OH2 | WAT | W | 223 | 41.040 | 14.573 | 12.781 | 1.00 | 21.90 | W | O |
| ATOM | 628 | OH2 | WAT | W | 279 | 28.609 | −2.348 | 19.633 | 1.00 | 16.06 | W | O |
| ATOM | 629 | OH2 | WAT | W | 287 | 27.925 | −2.786 | 17.100 | 1.00 | 28.20 | W | O |
| ATOM | 630 | OH2 | WAT | W | 292 | 29.248 | 10.608 | 15.460 | 1.00 | 4.55 | W | O |
| ATOM | 631 | OH2 | WAT | W | 294 | 34.711 | 11.933 | 8.259 | 1.00 | 18.60 | W | O |
| ATOM | 632 | OH2 | WAT | W | 296 | 36.499 | 8.641 | 1.251 | 1.00 | 16.68 | W | O |
| ATOM | 633 | OH2 | WAT | W | 302 | 33.346 | 8.640 | 3.104 | 1.00 | 31.25 | W | O |
| ATOM | 634 | OH2 | WAT | W | 314 | 38.929 | −1.342 | 19.839 | 1.00 | 27.36 | W | O |
| ATOM | 635 | OH2 | WAT | W | 319 | 24.988 | 4.849 | 4.100 | 1.00 | 39.67 | W | O |
| ATOM | 636 | OH2 | WAT | W | 321 | 38.601 | −1.114 | 16.775 | 1.00 | 24.51 | W | O |
| ATOM | 637 | OH2 | WAT | W | 327 | 39.896 | 8.788 | 8.314 | 1.00 | 40.66 | W | O |
| ATOM | 638 | OH2 | WAT | W | 335 | 44.187 | 13.742 | 12.663 | 1.00 | 29.57 | W | O |
| ATOM | 639 | OH2 | WAT | W | 337 | 27.275 | 6.739 | 2.616 | 1.00 | 23.30 | W | O |
| ATOM | 640 | OH2 | WAT | W | 343 | 34.463 | 4.647 | 6.797 | 1.00 | 34.65 | W | O |
| ATOM | 641 | OH2 | WAT | W | 358 | 35.750 | −0.120 | 8.819 | 1.00 | 35.63 | W | O |
| ATOM | 642 | OH2 | WAT | W | 370 | 38.235 | 6.328 | 7.390 | 1.00 | 28.92 | W | O |
| ATOM | 643 | OH2 | WAT | W | 388 | 42.864 | 7.185 | 8.805 | 1.00 | 39.53 | W | O |
| ATOM | 644 | OH2 | WAT | W | 390 | 31.573 | 8.191 | 0.869 | 1.00 | 38.78 | W | O |
| ATOM | 645 | OH2 | WAT | W | 401 | 41.353 | 4.533 | 8.074 | 1.00 | 36.07 | W | O |
| ATOM | 646 | OH2 | WAT | W | 402 | 29.643 | −0.022 | 10.304 | 1.00 | 38.02 | W | O |
| ATOM | 647 | OH2 | WAT | W | 433 | 44.330 | 8.280 | 11.373 | 1.00 | 43.93 | W | O |
| ATOM | 648 | OH2 | WAT | W | 440 | 29.301 | −0.100 | 7.598 | 1.00 | 43.24 | W | O |
| ATOM | 649 | OH2 | WAT | W | 446 | 38.570 | 9.454 | −0.831 | 1.00 | 41.14 | W | O |
| ATOM | 650 | OH2 | WAT | W | 447 | 42.864 | 11.302 | 1.981 | 1.00 | 29.17 | W | O |
| ATOM | 651 | OH2 | WAT | W | 448 | 44.322 | 12.556 | 8.806 | 1.00 | 50.64 | W | O |

-continued

| ATOM | 652 | OH2 | WAT | W | 452 | 41.748 | 10.947 | 19.697 | 1.00 | 41.61 | W | O |
| ATOM | 653 | OH2 | WAT | W | 454 | 38.170 | 6.670 | 2.158 | 1.00 | 38.30 | W | O |
| END | | | | | | | | | | | | |

What is claimed is:

1. A compound of Formula (1):

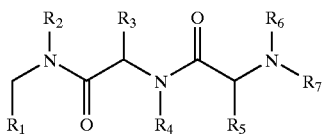

(1)

wherein $R_1$ represents a group selected from the following formulae:

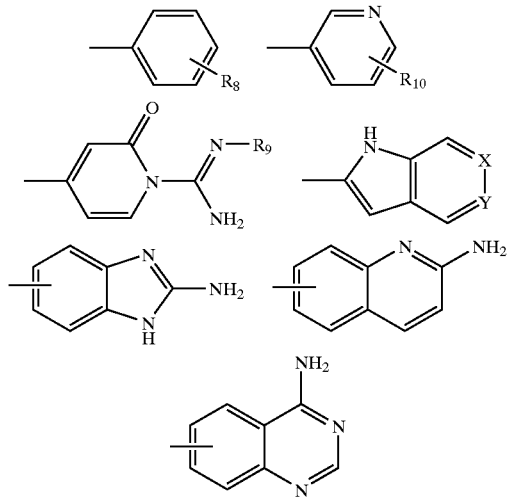

wherein $R_8$ represents an amino group, an aminomethyl group or

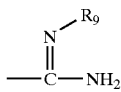

(wherein $R_9$ represents a hydrogen atom, an amino group, a hydroxy group, an acyl group or an alkoxycarbonyl group having an optionally substituted linear or branched $C_1$–$C_6$ alkyl as its alkyl moiety, $R_{10}$ represents an amino group, one of X and Y represents =CH— and the other represents =N—);

$R_2$ represents a hydrogen atom or a linear or branched $C_1$–$C_6$ alkyl group;

$R_3$ represents:

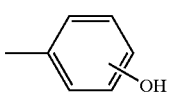

or

—(CH$_2$)$_m$—R$_{11}$ wherein m represents an integer of 1 to 6, and $R_{11}$ represents:

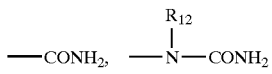

(wherein $R_{12}$ represents a hydrogen atom or a linear or branched $C_1$–$C_3$ alkyl group) or

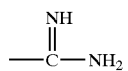

$R_4$ represents a hydrogen atom or a linear or branched $C_1$–$C_6$ alkyl group;

$R_5$ represents a linear or branched $C_1$–$C_6$ alkyl group or —CH$_2$—R$_{13}$ (wherein $R_{13}$ represents an optionally substituted aryl group or an optionally substituted heterocyclic group);

$R_6$ represents a hydrogen atom or a linear or branched $C_1$–$C_6$ alkyl group; and $R_7$ represents an optionally substituted linear or branched $C_1$–$C_6$ alkyl group or —SO$_2$—R$_{14}$ (wherein $R_{14}$ represents an optionally substituted linear or branched $C_1$–$C_8$ alkyl group)

or a tautomer or enantiomer of the compound, or a hydrate or pharmaceutically acceptable salt thereof.

2. The compound according to claim 1, wherein $R_5$ in Formula (1) is a linear or branched $C_1$–$C_6$ alkyl group or —CH$_2$—R$_{13}$, in which $R_{13}$ represents a group selected from the following formulae:

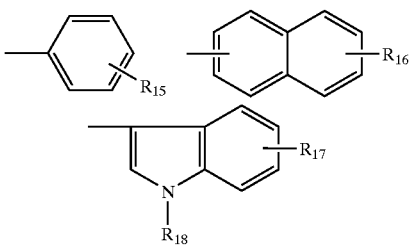

wherein $R_{15}$ represents a hydrogen atom, an optionally substituted aryl group, a $C_1$–$C_3$ alkyl group which may be substituted with a halogen atom, a linear or branched $C_1$–$C_3$ alkoxy group, a halogen atom, an arylcarbonyl group, an alkylcarbonyl group having a linear or branched $C_1$–$C_3$ alkyl as its alkyl moiety, a nitro group, or an amino group;

$R_{16}$ represents a hydrogen atom or a linear or branched $C_1$–$C_6$ alkyl group;

$R_{17}$ represents a hydrogen atom, a hydroxy group, a linear or branched $C_1$–$C_6$ alkyl group, a linear or branched $C_1$–$C_6$ alkoxy group, —O—(CH$_2$)$_n$—OH (wherein n represents an integer of 1 to 5), —O—(CH$_2$)$_p$—COOH (wherein p represents an integer of 1 to 5), —O—(CH$_2$)$_q$—NH$_2$ (wherein q represents an integer of 1 to 5),

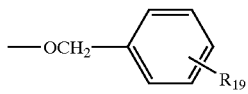

(wherein $R_{19}$ represents a hydrogen atom, a hydroxy group, a carboxyl group, a linear or branched $C_1$–$C_6$ alkyl group, a halogen atom, a linear or branched $C_1$–$C_6$ alkoxy group, or an alkoxycarbonyl group having a linear or branched $C_1$–$C_3$ alkyl as its alkyl moiety), or —$OSO_2$—$R_{20}$ (wherein $R_{20}$ represents a linear or branched $C_1$–$C_6$ alkyl group or a benzyl group); and $R_{18}$ represents a hydrogen atom, a linear or branched $C_1$–$C_6$ alkyl group, a linear or branched $C_1$–$C_6$ alkylsulfonyl group, or an optionally substituted arylsulfonyl group.

3. The compound according to claim 1, wherein $R_7$ in Formula (1) is a linear or branched $C_1$–$C_6$ alkyl substituted linear alkyl group or a group of the following formula:

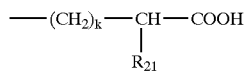

wherein k represents an integer of 0 to 3, and $R_{21}$ represents a hydrogen atom or —$NHR_{22}$ (wherein $R_{22}$ represents a linear or branched $C_1$–$C_3$ alkyl group or an alkylcarbonyl group having a linear or branched $C_1$–$C_3$ alkyl as its alkyl moiety) or

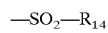

wherein $R_{14}$ represents:

(i) an optionally substituted linear or branched $C_1$–$C_6$ alkyl group (wherein said alkyl group may be substituted with a carboxyl group or an alkoxycarbonyl group having a linear or branched $C_1$–$C_3$ alkyl as its alkyl moiety); or (ii) —$CH_2$—$R_{23}$ (wherein $R_{23}$ represents an optionally substituted phenyl group).

4. The compound according to claim 1, wherein $R_3$ in Formula (1) is a group of the following formula:

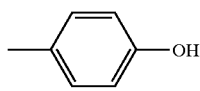

or

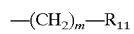

wherein m represents an integer of 1 to 3, and $R_{11}$ represents:

—$CONH_2$,

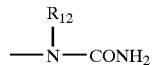

(wherein $R_{12}$ represents a hydrogen atom or a methyl group) or

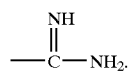

5. The compound according to claim 1, wherein $R_1$ in Formula (1) is a group selected from the following formulae:

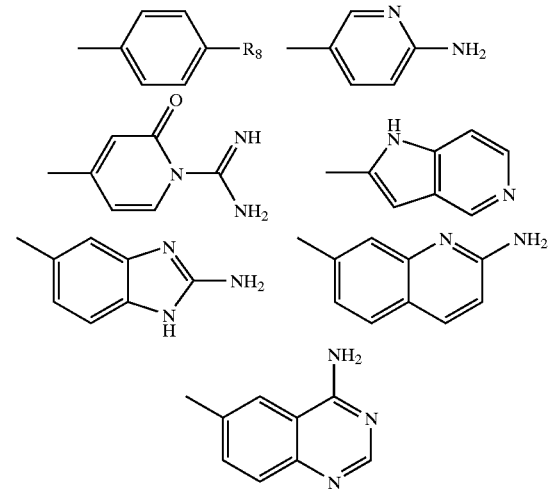

wherein $R_8$ represents:

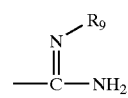

(wherein $R_9$ represents a hydrogen atom, an amino group, a hydroxy group, an acyl group, or an alkoxycarbonyl group having an optionally substituted linear or branched $C_1$–$C_6$ alkyl as its alkyl moiety).

6. The compound according to claim 1, wherein $R_2$ in Formula (1) is a hydrogen atom or a linear or branched $C_1$–$C_3$ alkyl group.

7. The compound according to claim 1, wherein $R_4$ in Formula (1) is a hydrogen atom or a linear or branched $C_1$–$C_3$ alkyl group.

8. The compound according to claim 1, wherein $R_6$ in Formula (1) is a hydrogen atom or a linear or branched $C_1$–$C_3$ alkyl group.

9. The compound according to claim 1, wherein $R_3$ in Formula (1) is —$(CH_2)_m$—$R_{11}$ (wherein m and $R_{11}$ are as defined in claim 1).

10. The compound according to claim 1, wherein in Formula (1), $R_3$ is a group of the following formula:

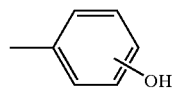

and $R_7$ is —$SO_2$—$R_{14}$ (wherein $R_{14}$ is as defined in claim 1).

11. The compound according to claim 1, wherein in Formula (1), $R_1$ is a group selected from the following formulae:

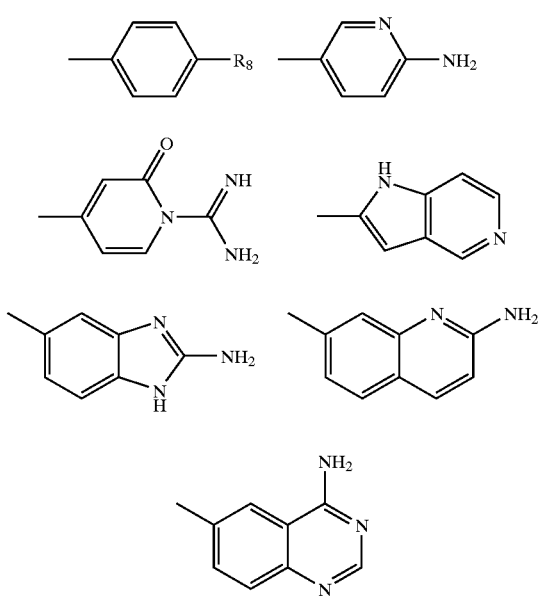

wherein $R_8$ represents:

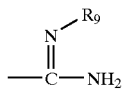

(wherein $R_9$ represents a hydrogen atom, an amino group, a hydroxy group, an acetyl group, a propionyl group, a butyryl group, an isobutyryl group, an isovaleryl group, a methoxycarbonyl group, an ethoxycarbonyl group, a t-butoxycarbonyl group or a benzyloxycarbonyl group);

$R_2$ is a hydrogen atom or a methyl group;

$R_3$ is a group of the following formula:

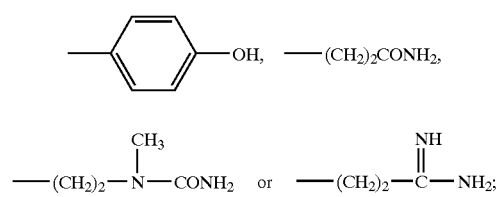

$R_4$ is a hydrogen atom or a methyl group;

$R_5$ is a linear or branched $C_1$–$C_4$ alkyl group or —$CH_2$—$R_{13}$ wherein $R_{13}$ represents a group selected from the following formulae:

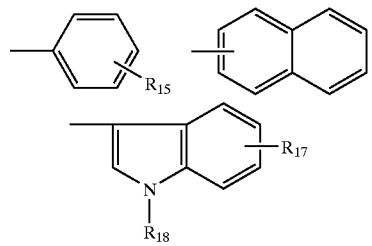

(wherein $R_{15}$ represents a hydrogen atom, a t-butyl group, a methoxy group, a bromine atom, a chlorine atom, a benzoyl group, or a phenyl group which may be substituted with a methoxy group or a trifluoromethyl group or a nitro group or an amino group;

$R_{17}$ represents a hydrogen atom, a hydroxy group, a methyl group, a linear or branched $C_1$–$C_3$ alkoxy group, —O—$(CH_2)_n$—OH (wherein n represents an integer of 1 to 3), —O—$(CH_2)_p$—COOH (wherein p represents an integer of 1 to 3), —O—$(CH_2)_q$—$NH_2$ (wherein q represents an integer of 1 to 3), —$OSO_2$—$R_{20}$ (wherein $R_{20}$ represents an ethyl group, an n-propyl group, an i-propyl group or a benzyl group), a benzyloxy group, a 3- or 4-hydroxybenzyloxy group, or a 3- or 4-carboxybenzyloxy group; and $R_{18}$ represents a hydrogen atom, a methyl group, a methanesulfonyl group or a benzenesulfonyl group);

$R_6$ is a hydrogen atom or a methyl group; and $R_7$ is a linear or branched $C_1$–$C_4$ alkyl group or a group of the following formula:

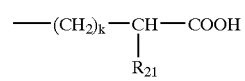

wherein k represents an integer of 0 to 2, and $R_{21}$ represents a hydrogen atom or —$NHR_{22}$ (wherein $R_{22}$ represents a methyl group or an acetyl group) or

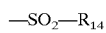

wherein $R_{14}$ represents a benzyl group, a 2-, 3- or 4-carboxybenzyl group, or an optionally substituted linear or branched $C_1$–$C_4$ alkyl group (wherein said alkyl group may be substituted with a carboxyl group or an alkoxycarbonyl group having a linear or branched $C_1$–$C_3$ alkyl as its alkyl moiety).

12. The compound according to claim 1, which is selected from the following formulae:

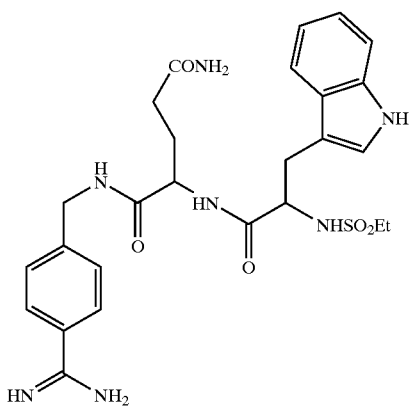

349
-continued
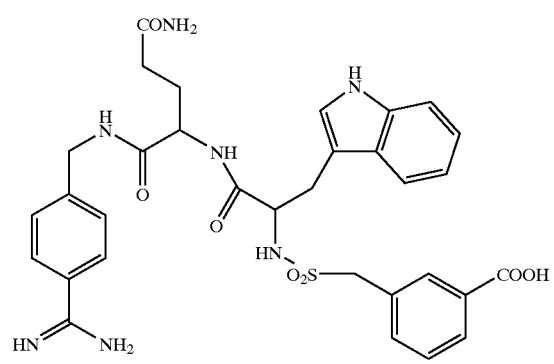
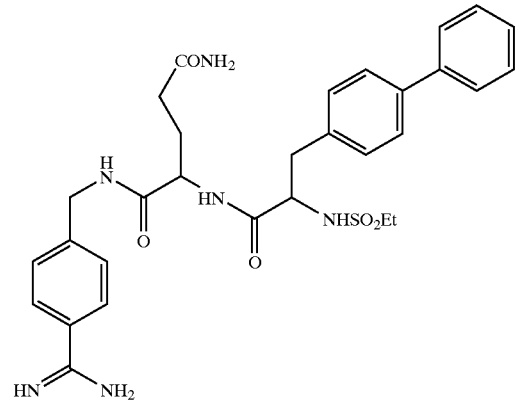
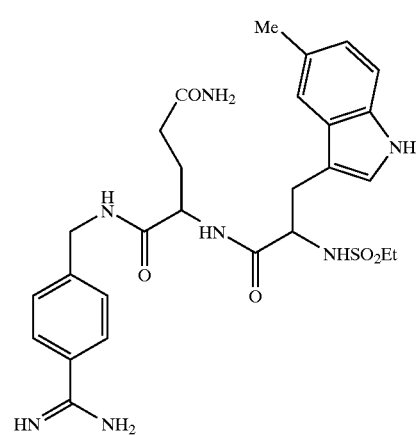
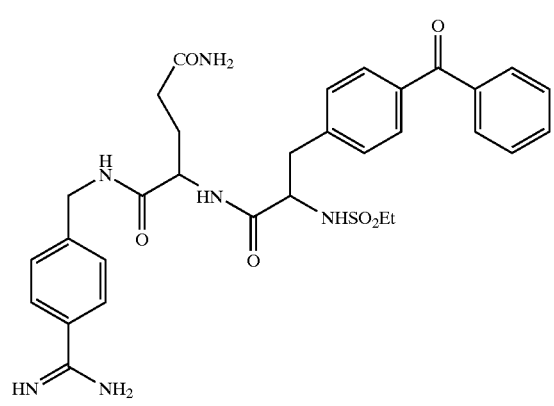
350
-continued
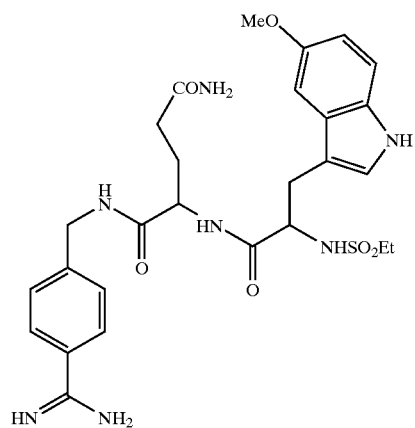
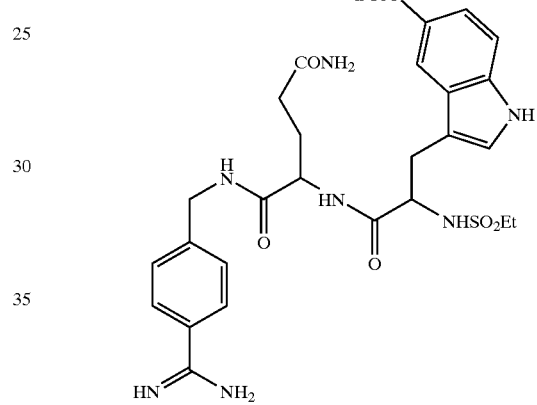
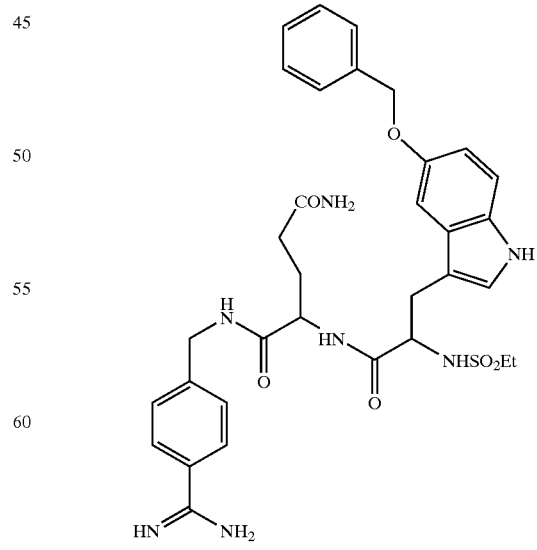

351
-continued
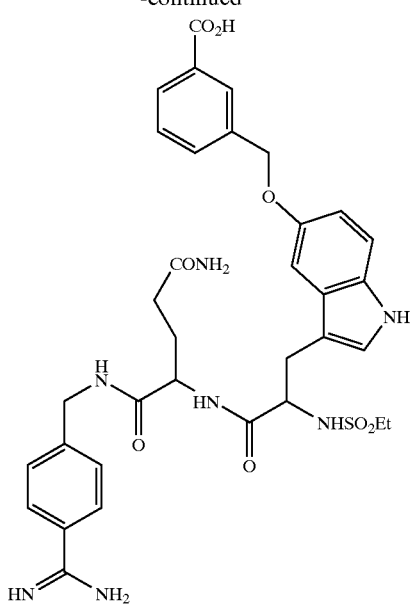
352
-continued
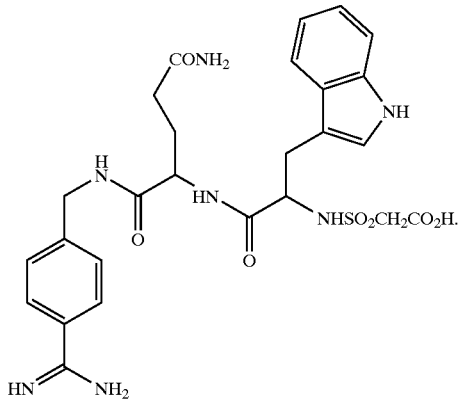
13. A pharmaceutical composition comprising the compound according to claim 1.
* * * * *